US009682123B2

(12) United States Patent
Leibel et al.

(10) Patent No.: US 9,682,123 B2
(45) Date of Patent: Jun. 20, 2017

(54) METHODS OF TREATING METABOLIC DISEASE

(71) Applicant: THE TRUSTEES OF COLUMBIA UNIVERSITY IN THE CITY OF NEW YORK, New York, NY (US)

(72) Inventors: Rudolph L. Leibel, New York, NY (US); Kazuhisa Watanabe, Shimotsuke (JP); Wendy K. Chung, Hackensack, NJ (US); Stuart G. Fischer, New Rochelle, NY (US); Charles Leduc, Hackensack, NJ (US); Elizabeth Watson, New York, NY (US); Maria Laura Cremona, Englewood, NJ (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 0 days.

(21) Appl. No.: 14/579,913

(22) Filed: Dec. 22, 2014

(65) Prior Publication Data

US 2015/0190466 A1 Jul. 9, 2015

Related U.S. Application Data

(60) Provisional application No. 61/919,367, filed on Dec. 20, 2013.

(51) Int. Cl.

| | |
|---|---|
| ***A61K 48/00*** | (2006.01) |
| ***A61K 38/17*** | (2006.01) |
| ***A61K 31/00*** | (2006.01) |
| ***C07K 14/705*** | (2006.01) |
| ***A01K 67/027*** | (2006.01) |
| ***A61K 45/06*** | (2006.01) |
| ***A61K 31/7105*** | (2006.01) |
| ***A61K 31/713*** | (2006.01) |

(52) U.S. Cl.

CPC ...... *A61K 38/1774* (2013.01); *A01K 67/0276* (2013.01); *A61K 31/00* (2013.01); *A61K 31/713* (2013.01); *A61K 31/7105* (2013.01); *A61K 45/06* (2013.01); *C07K 14/70503* (2013.01); *A01K 2217/075* (2013.01); *A01K 2217/206* (2013.01); *A01K 2227/105* (2013.01); *A01K 2267/0362* (2013.01); *A61K 48/00* (2013.01)

(58) Field of Classification Search

CPC .............................. A61K 48/00; A61K 48/005
See application file for complete search history.

(56) References Cited

U.S. PATENT DOCUMENTS

| | | | |
|---|---|---|---|
| 3,536,809 | A | 10/1970 | Applezweig |
| 3,598,123 | A | 8/1971 | Zaffaroni |
| 3,845,770 | A | 11/1974 | Theeuwes et al. |
| 3,916,899 | A | 11/1975 | Theeuwes et al. |
| 4,008,719 | A | 2/1977 | Theeuwes et al. |
| 4,683,195 | A | 7/1987 | Mullis et al. |
| 4,683,202 | A | 7/1987 | Mullis |
| 4,710,384 | A | 12/1987 | Rotman |
| 5,059,595 | A | 10/1991 | Le Grazie |
| 5,073,543 | A | 12/1991 | Marshall et al. |
| 5,120,548 | A | 6/1992 | McClelland et al. |
| 5,223,408 | A | 6/1993 | Goeddel et al. |
| 5,236,838 | A | 8/1993 | Rasmussen et al. |
| 5,252,479 | A | 10/1993 | Srivastava |
| 5,328,470 | A | 7/1994 | Nabel et al. |
| 5,354,556 | A | 10/1994 | Sparks et al. |
| 5,539,084 | A | 7/1996 | Geysen |
| 5,580,757 | A | 12/1996 | Desnick et al. |
| 5,591,767 | A | 1/1997 | Mohr et al. |
| 5,625,048 | A | 4/1997 | Tsien et al. |
| 5,639,476 | A | 6/1997 | Oshlack et al. |
| 5,674,533 | A | 10/1997 | Santus et al. |
| 5,741,668 | A | 4/1998 | Ward et al. |
| 5,747,469 | A | 5/1998 | Roth et al. |
| 5,777,079 | A | 7/1998 | Tsien et al. |
| 5,783,674 | A | 7/1998 | Geysen |
| 5,804,387 | A | 9/1998 | Cormack et al. |
| 5,866,341 | A | 2/1999 | Spinella et al. |

(Continued)

FOREIGN PATENT DOCUMENTS

| | | |
|---|---|---|
| WO | WO-99/07409 | 2/1999 |
| WO | WO-99/32619 A1 | 7/1999 |

(Continued)

OTHER PUBLICATIONS

Verma et al. Gene therapy—promises, problems and prospects. Nature, vol. 389, pp. 239-242, 1997.*
Palù et al. In pursuit of new developments for gene therapy of human diseases. Journal of Biotechnology. vol. 68, pp. 1-13, 1999.*
Luo et al. Synthetic DNA delivery systems. Nature Biotechnology, vol. 18, pp. 33-37, 2000.*
Verma et al. Gene Therapy: Twenty-first century medicine. Annual Review of Biochemistry, vol. 74, pp. 711-738, 2005.*
Domvri et al. Gene therapy in liver diseases: State-of-the-art and future perspectives. Current Gene Therapy, vol. 12, pp. 463-483, Dec. 2012.*

(Continued)

*Primary Examiner* — Jennifer Dunston
(74) *Attorney, Agent, or Firm* — Wilmer Cutler Pickering Hale and Dorr LLP

(57) ABSTRACT

The invention provides methods for treating metabolic disease in a subject and methods for increasing the expression of ILDR2 in a subject. The invention further provides a method for identifying an agent which modulates expression of an Ildr2 RNA comprising contacting a cell with an agent; determining expression of the Ildr2 RNA in the presence and the absence of the agent; and comparing expression of the Ildr2 RNA in the presence and the absence of the agent, wherein a change in the expression of the Ildr2 RNA in the presence of the agent is indicative of an agent which modulates the level of expression of the RNA.

15 Claims, 86 Drawing Sheets
(74 of 86 Drawing Sheet(s) Filed in Color)

(56) References Cited

U.S. PATENT DOCUMENTS

| | | | |
|---|---|---|---|
| 5,874,304 | A | 2/1999 | Zolotukhin et al. |
| 5,876,969 | A | 3/1999 | Fleer et al. |
| 5,879,680 | A | 3/1999 | Ginns et al. |
| 5,968,750 | A | 10/1999 | Zolotukhin et al. |
| 6,017,524 | A | 1/2000 | Roth et al. |
| 6,027,881 | A | 2/2000 | Pavlakis et al. |
| 6,054,321 | A | 4/2000 | Tsien et al. |
| 6,066,476 | A | 5/2000 | Tsien et al. |
| 6,083,725 | A | 7/2000 | Selden et al. |
| 6,090,919 | A | 7/2000 | Cormack et al. |
| 6,096,865 | A | 8/2000 | Michaels |
| 6,124,128 | A | 9/2000 | Tsien et al. |
| 6,143,290 | A | 11/2000 | Zhang et al. |
| 6,188,045 | B1 | 2/2001 | Hansen et al. |
| 6,190,619 | B1 | 2/2001 | Kilcoin et al. |
| 6,194,612 | B1 | 2/2001 | Boger et al. |
| 6,210,666 | B1 | 4/2001 | Miyamura |
| 6,395,884 | B1 | 5/2002 | Selden et al. |
| 6,410,010 | B1 | 6/2002 | Zhang et al. |
| 6,451,600 | B1 | 9/2002 | Rasmussen et al. |
| 6,458,574 | B1 | 10/2002 | Selden et al. |
| 6,461,609 | B1 | 10/2002 | Calhoun et al. |
| 6,511,847 | B1 | 1/2003 | Zhang et al. |
| 6,656,467 | B2 | 12/2003 | Young et al. |
| 7,148,342 | B2 | 12/2006 | Tolentino et al. |
| 7,291,709 | B2 | 11/2007 | Bihain et al. |
| 7,294,504 | B1 | 11/2007 | Wang |
| 7,422,896 | B1 | 9/2008 | Wang |
| 8,263,662 | B2 | 9/2012 | Dohil et al. |
| 2002/0077313 | A1 | 6/2002 | Clayman |
| 2002/0164326 | A1 | 11/2002 | Young et al. |
| 2002/0173478 | A1 | 11/2002 | Gewirtz |
| 2004/0110226 | A1 | 6/2004 | Lazar et al. |
| 2006/0121042 | A1 | 6/2006 | Dall'Acqua et al. |
| 2007/0072204 | A1 | 3/2007 | Hannon et al. |
| 2008/0194575 | A1 | 8/2008 | Beraza et al. |
| 2011/0287974 | A1 | 11/2011 | Benvenisty et al. |
| 2011/0318738 | A1 | 12/2011 | Jones et al. |
| 2012/0134997 | A1 | 5/2012 | Levine et al. |
| 2012/0231471 | A1 | 9/2012 | Sato et al. |
| 2012/0264824 | A1 | 10/2012 | Mizuguchi et al. |

FOREIGN PATENT DOCUMENTS

| | | | |
|---|---|---|---|
| WO | WO-00/01846 | 1/2000 | |
| WO | WO-00/44895 | 8/2000 | |
| WO | WO-00/44914 | 8/2000 | |
| WO | WO-01/29058 A1 | 4/2001 | |
| WO | WO-01/36646 | 5/2001 | |
| WO | WO-02/21139 A2 | 3/2002 | |
| WO | WO 2009076651 A2 * | 6/2009 | ........... C07K 14/705 |

OTHER PUBLICATIONS

Edelstein et al. Gene therapy clinical trials worldwide 1989-2004—an overview. Journal of Gene Medicine, vol. 6, pp. 597-602, 2004.*

Watanabe et al. ILDR2: An endoplasmic reticulum resident molecule mediating hepatic lipid homeostatis. PLoS One, vol. 8, No. 6, e67234, Jun. 24, 2013, printed as pp. 1/19-19/19.*

Abelson, John N., "Combinatorial Chemistry," Methods in Enzymology, vol. 267, Academic Press, 5 pages—Title Page, Copyright Page and Table of Contents only (1996).

Accili, D. et al., "A Mutation in the Extracellular Domain of the Insulin Receptor Impairs the Ability of Insulin to Stimulate Receptor Autophosphorylation," The Journal of Biological Chemistry, vol. 266, No. 1, pp. 434-439 (Jan. 5, 1991).

Accili, Domenico, "The Struggle for Mastery in Insulin Action: From Triumvirate to Republic," Perspectives in Diabetes, vol. 53, pp. 1633-1642 (Jul. 2004).

Alemany, R. et al., "Blood clearance rates of adenovirus type 5 in mice," Journal of General Virology, vol. 81, pp. 2605-2609 (2000).

Allen, J. B. et al., "Finding prospective partners in the library: the two-hybrid system and phage display find a match," Trends Biochem Sci., vol. 20, No. 12, pp. 511-516 (Dec. 1995).

Altaras, N. E. et al., "Production and Formulation of Adenovirus Vectors," Adv. Biochem. Eng. Biotechnol., vol. 99, pp. 193-260 (2005).

Anderson, R. C. et al., "Analytical Techniques in Combinatorial Chemistry: MAS CH Correlation in Solvent-Swollen Resin," J. Org. Chem., vol. 60, pp. 2650-2651 (1995).

Anderson, W. French, "Human Gene Therapy," Science, Therapeutic horizons, Supplement to vol. 392, No. 6679, pp. 25-30, 8 pages (Apr. 30, 1998).

Ausubel, F. M. et al., "Current Protocols in Molecular Biology," vol. 1, John Wiley & Sons, Inc., New York, 10 pages—Title page, Copyright page and Table of Contents only (1987, 1988, 1989).

Back, S. H. and Kaufman, R. J., "Endoplasmic reticulum stress and type 2 diabetes," Annu. Rev. Biochem., vol. 81, pp. 767-793, 32 pages (2012).

Barbas III, C. F. et al., "Phage Display: A Laboratory Manual," Cold Spring Harbor Laboratory Press, New York, 5 pages—Title page, Copyright page and Table of Contents only (2001).

Barringer, K. J. et al., "Blunt-end and single-strand ligations by *Escherichia coli* ligase: influence on an in vitro amplification scheme," Gene, vol. 89, pp. 117-122 (1990).

Bartel, P. L. and Fields, S., "The Yeast Two-Hybrid System," Oxford University Press, New York, 5 pages—Title page, Copyright page and Table of Contents only (1997).

Bass, Brenda L., "The short answer," Nature, vol. 411, pp. 428-429 (May 24, 2001).

Bays, Harold E., "Current and Investigational Antiobesity Agents and Obesity Therapeutic Treatment Targets," Obesity Research, vol. 12, No. 8, pp. 1197-1211 (Aug. 8, 2004).

Berger, S. L. and Kimmel, A. R., "Guide to Molecular Cloning Techniques," Methods in Enzymology, vol. 152, 8 pages—Title page, Copyright page and Table of Contents only (1987).

Bevis, B. J. and Glick, B. S., "Rapidly maturing variants of the Discosoma red fluorescent protein (DsRed)," Nature Biotechnology, vol. 20, pp. 83-87 (Jan. 2002).

Biddinger, S. B. et al., "Hepatic insulin resistance is sufficient to produce dyslipidemia and susceptibility to atherosclerosis," Cell Metab., vol. 7, pp. 125-134, 21 pages (Feb. 2008).

Bligh, E.G. and Dyer, W. J., "A rapid method of total lipid extraction and purification," Canadian Journal of Biochemistry and Physiology, vol. 37, No. 8, pp. 911-917 (Aug. 1959).

Bodanszky, Miklos, "Principles of Peptide Synthesis," Second Revised Edition, Springer Laboratory, Springer Verlag, 7 pages—Title Page, Copyright Page and Table of Contents only (1993).

Boggon, T. J. et al, "Implication of Tubby Proteins as Transcription Factors by Structure-Based Functional Analysis," Science, vol. 286, No. 5447, pp. 2119-2125, 10 pages (Dec. 10, 1999).

Borck, G. et al., "Loss-of-function mutations of ILDR1 cause autosomal-recessive hearing impairment DFNB42," The American Journal of Human Genetics, vol. 88, pp. 127-137 (Feb. 11, 2011).

Brower, Vicki, "Naked DNA Vaccines Come of Age" Nature Biotechnology, vol. 16, pp. 1304-1305 (Dec. 1998).

Brummel, C. L. et al., "A Mass Spectrometric Solution to the Address Problem of Combinatorial Libraries," Science, vol. 264, pp. 399-402 (Apr. 15, 1994).

Bruning, J. C. et al, "A Muscle-Specific Insulin Receptor Knockout Exhibits Features of the Metabolic Syndrome of NIDDm without Altering Glucose Tolerance," Molecular Cell, vol. 2, pp. 559-569 (Nov. 1998).

Bugianesi, E. et al., "Insulin resistance in nonalcoholic fatty liver disease," Current Pharmaceutical Design, vol. 16, No. 17, pp. 1941-1951 (Jun. 2010).

Burg, J. L. et al., "Single Molecule Detection of RNA Reporter Probes by Amplification with QB Replicase," Molecular and Cellular Probes, vol. 10, pp. 257-271 (1996).

Buteau, J. et al., "Transcription Factor FOX01 Mediates Glucagon-Like Peptide-1 Effects on Pancreatic B-Cell Mass," Diabetes, vol. 55, pp. 1190-1196 (May 2006).

Cantley, J. L. et al., "CGI-58 knockdown sequesters diacylglycerols in lipid droplets/ER-preventing diacylglycerol-mediated hepatic insulin resistance," Proc. Natl. Acad. Sci. USA, vol. 110, No. 5, pp. 1869-1874 (Jan. 29, 2013).

(56) References Cited

OTHER PUBLICATIONS

Cao, J. et al., "Saturated fatty acid induction of endoplasmic reticulum stress and apoptosis in human liver cells via the PERK/ATF4/CHOP signaling pathway," Mol. Cell Biochem., vol. 364, pp. 115-129 (2012).
Chan, W. C. and White, P. D., "Fmoc Solid Phase Peptide Synthesis: A Practical Approach," A Practical Approach Series, Oxford University Press, 9 pages—Title Page, Copyright Page and Table of Contents only (Mar. 2000).
Chen, L. et al., "Herbicide resistance from a divided EPSPS protein: the split Synechocystis DnaE intein as an in vivo affinity domain," Gene, vol. 263, No. 1-2, pp. 39-48 (2001).
Chen, S.-H. et al., "Gene Therapy for Brain Tumors: Regression of Experimental Gliomas by Adenovirus-mediated gene transfer in vivo," Proc. Natl. Acad. Sci. USA, vol. 91, pp. 3054-3057 (Apr. 1994).
Choi, S. H. and Ginsberg, H. N., "Increased very low density lipoprotein secretion, hepatic steatosis, and insulin resistance," Trends Endocrinol. Metab., vol. 22, No. 9, pp. 353-363, 23 pages (Sep. 2011).
Chu, Y.-H. et al., "Free Solution Identification of Candidate Peptides from Combinatorial Libraries by Affinity Capillary Electrophoresis/Mass Spectrometry," J. Am. Chem. Soc., vol. 117, pp. 5419-5420 (1995).
Chung, W. K. et al., "Genetic modifiers of Leprfa associated with variability in insulin production and susceptibility to NIDDM," Genomics, vol. 41, pp. 332-344 (1997).
Cid-Arregui, A. and Garcia-Carranca, A., "Viral Vectors: Basic Science and Gene Therapy," Eaton Publishing Co., 6 pages—Title Page, Copyright Page and Table of Contents only (2000).
Cinti, S. et al., "Lack of insulin receptors affects the formation of white adipose tissue in mice. A morphometric and ultrastructural analysis," Diabetologia, vol. 41, pp. 171-177 (Feb. 1998).
Clark, William R., "The Experimental Foundations of Modern Immunology," 3rd Edition, John Wiley & Sons, 11 pages—Title Page, Copyright Page and Table of Contents only (1980, 1983, 1986).
Clee S. M. and Attie, A. D., "The genetic landscape of type 2 diabetes in mice," Endocr. Rev., vol. 28, No. 1, pp. 48-83 (2007).
Clee, S. M. et al., "Positional cloning of Sorcs1, a type 2 diabetes quantitative trait locus," Nature Genetics, vol. 38, No. 6, pp. 688-693 (Jun. 2006).
Cohen, B. A. et al., "An Artificial Cell Cycle Inhibitor Isolated From a Combinatorial Library," Proc. Natl. Acad. Sci. USA, vol. 95, pp. 14272-14277 (Nov. 1998).
Colas, P. et al., "Genetic Selection of peptide Aptamers that Recognize and Inhibit Cyclindependent Kinase 2," Nature, vol. 380, pp. 548-550 (Apr. 11, 1996).
Coloma, M. J. et al., "Novel vectors for the expression of antibody molecules using variable regions generated by polymerase chain reaction," J. Immunol. Methods, vol. 152, No. 1, pp. 89-104 (Jul. 1992).
Conn, P. Michael, "Green Fluorescent Protein," Methods in Enzymology, vol. 302, Academic Press, Inc., 6 pages—Title Page, Copyright Page and Table of Contents only (1999).
Cooper, C. A. et al., "GlycoSuiteDB: a new curated relational database of glycoprotein glycan structures and their biological sources," Nucleic Acids Res., vol. 29, No. 1, pp. 332-335 (2001).
Cormack, B. P. et al., "FACS-optimized mutants of the green fluorescent protein (GFP)," Gene, vol. 173, pp. 33-38 (1996).
Cowie, C. et al., "Prevalence of Diabetes and Impaired Fasting Glucose in Adults in the U.S. Population," Diabetes Care, vol. 29, No. 6, pp. 1263-1268 (Jun. 2006).
Cox, N. J. et al, "Mapping Diabetes-Susceptibility Genes Lessons Learned from Search for DNA Marker for Maturity-Onset Diabetes of the Young," Diabetes, vol. 41, No. 4, pp. 401-407, 9 pages (Apr. 1992).
Creighton, Thomas E., "Proteins: Structure and Molecular Principles," W. H. Freeman and Company, 6 pages—Title Page, Copyright Page and Table of Contents only (1983).
Cunningham, B. C. and Wells, J. A., "High-Resolution Epitope Mapping of hGh-Receptor Interactions by Alanine-Scanning Mutagenesis," Science, vol. 244, No. 4908, pp. 1081-1085 (Jun. 2, 1989).
Dallas, A. and Vlassov, A. V., "RNAi: A novel antisense technology and its therapeutic potential," Med. Sci. Monit., vol. 12, No. 4, pp. RA67-RA74 (2006).
Das, S. K. and Elbein, S. C., "The search for type 2 diabetes susceptibility Loci: the chromosome 1q story," Curr. Diab. Rep., vol. 7, pp. 154-164 (2007).
de Meijer, V. E. et al., "Dietary fat intake promotes the development of hepatic steatosis independently from excess caloric consumption in a murine model," Metabolism, vol. 59, No. 8, pp. 1092-1105, 23 pages (Aug. 2010).
Delgado, C. et al., "The Uses and Properties of PEG-Linked Proteins," Crit. Rev. Ther. Drug Carrier Syst., vol. 9, No. 3-4, pp. 249-304 (1992).
Dell, Anne, "Preparation and Desorption Mass Spectrometry of Permethyl and Peracetyl Derivatives of Oligosaccharides," Methods in Enzymology, vol. 193, pp. 647-660 (1990).
DeSantis, G. and Jones, J. B., "Chemical Modification of Enzymes for Enhanced Functionality," Curr. Opin. Biotechnol., vol. 10, No. 4, pp. 324-330 (1999).
Dokmanovic-Chouinard, M. et al., "Positional cloning of "Lisch-Like", a candidate modifier of susceptibility to type 2 diabetes in mice," PLoS Genet, vol. 4, No. 7, e1000137, pp. 1-19 (Jul. 2008).
Drees, Becky L., "Progress and Variations in Two-hybrid and Three-Hybrid technologies," Curr. Opin. Chem. Biol., vol. 3, No. 1, pp. 64-70 (1999).
Dzau, V. J. et al., "Gene Therapy for Cardiovascular Disease," Trends in Biotechnology, vol. 11, pp. 205-210 (May 1993).
Efrat, S. et al., "Beta-cell lines derived from transgenic mice expressing a hybrid insulin gene-oncogene," Proc. Natl. Acad. Sci. USA, vol. 85, pp. 9037-9041 (Dec. 1988).
Egner, B. J. et al., "Solid Phase Chemistry: Direct Monitoring by Matrix Assisted Laser Desorption/Ionization Time of Flight Mass Spectrometry. A Tool for Combinatorial Chemistry," J. Org. Chem., vol. 60, No. 9, pp. 2652-2653 (1995).
Elbashir, S. M. et al., "Duplexes of 21-nucleotide RNAs mediate RNA interference in cultured mammalian cells," Nature, vol. 411, pp. 494-498 (May 24, 2001).
Elbein, S. C. et al., "A Genome-Wide Search for Type 2 Diabetes Susceptibility Genes in utah Caucasians," Diabetes, vol. 48, pp. 1175-1182 (May 1999).
Eliyahu, H. et al., "Polymers for DNA Delivery," Molecules, vol. 10, No. 1, pp. 34-64 (Jan. 31, 2005).
Erbay, E. et al., "Reducing endoplasmic reticulum stress through a macrophage lipid chaperone alleviates atherosclerosis," Nat. Med., vol. 15, No. 12, pp. 1383-1391, 25 pages (Dec. 2009).
Eto, K. et al., "Genetic manipulations of fatty acid metabolism in beta-cells are associated with dysregulated insulin secretion," Diabetes, vol. 51, Suppl. 3, pp. S414-S420 (Dec. 2002).
Fabbrizio, E. et al., "Inhibition of mammalian cell proliferation by genetically selected peptide aptamers that functionally antagonize E2F activity," Oncogene, vol. 18, pp. 4357-4363 (Mar. 1999).
Fagone, P. and Jackowski, S., "Membrane phospholipid synthesis and endoplasmic reticulum function," J. Lipid Res., vol. 50, Suppl., pp. S311-S316, 11 pages (Apr. 2009).
Fashena, S. J. et al., "The continued evolution of two-hybrid screening approaches in yeast: how to outwit different preys with different baits," Gene, vol. 250, No. 1-2, pp. 1-14 (2000).
Fields, S. and Sternglanz, R., "The two-hybrid system: an assay for protein-protein interactions," Trends Genet., vol. 10, No. 8, pp. 286-292 (Aug. 1994).
Fitch, W. L. et al., "High Resolution H NMR in Solid-Phase Organic Synthesis," J. Org. Chem., vol. 59, pp. 7955-7956 (1994).
Flint, J. et al., "Strategies for mapping and cloning quantitative trait genes in rodents," Nat. Rev. Genet., vol. 6, pp. 271-286 (Apr. 2005).
Frankel, A. E., "Current Topics in Microbiology and Immunology," Clinical Applications of Immunotoxins, Springer-Verlag, 7 pages—Title Page, Copyright Page and Table of Contents only (1998).

(56) References Cited

OTHER PUBLICATIONS

Freeman, H. C. et al., "Deletion of nicotinamide nucleotide transhydrogenase: a new quantitive trait locus accounting for glucose intolerance in C57BL/6J mice," Diabetes, vol. 55, pp. 2153-2156 (Jul. 2006).
Freeman, H. et al., "Nicotinamide nucleotide transhydrogenase: a key role in insulin secretion," Cell Metab., vol. 3, pp. 35-45 (Jan. 2006).
Freshney, R. I., "Animal Cell Culture," IRL Press, 10 pages—Title Page, Copyright Page and Table of Contents only (1986).
Friedmann, Theodore, "Progress Toward Human Gene Therapy," Science, vol. 244, pp. 1275-1281 (Jun. 16, 1989).
Fu, S. et al., "Aberrant lipid metabolism disrupts calcium homeostasis causing liver endoplasmic reticulum stress in obesity," Nature, vol. 473, pp. 528-531, 10 pages (May 26, 2011).
Gait, M. J., "Oligonucleotide Synthesis," IRL Press, 12 pages—Title Page, Copyright Page and Table of Contents only (1984).
Garcia-Ocana, A. et al., "Hepatocyte growth factor overexpression in the islet of transgenic mice increases beta cell proliferation, enhances islet mass, and induces mild hypoglycemia," J. Biol. Chem., vol. 275, pp. 1226-1232 (Jan. 14, 2000).
Gelding, S. V. et al, "Increased secretion of 32,33 split proinsulin after intravenous glucose in glucose-tolerant first-degree relatives of patients with non-insulin dependent diabetes of European, but not Asian, origin," Clin. Endocrinol., vol. 42, pp. 255-264 (1995).
Gennaro, Alfonso R., "Remington: The Science and Practice of Pharmacy," 20th Edition, Lippincott Williams & Wilkins, 4 pages—Title Page, Copyright Page and Table of Contents only (2000).
Gentile, C. L. et al., "Fatty acids regulate CREBh via transcriptional mechanisms that are dependent on proteasome activity and insulin," Mol. Cell Biochem., vol. 344, No. 1-2, pp. 99-107, 16 pages (Nov. 2010).
Gietz, R. D. and Sugino, A., "New yeast *Escherichia coli* shuttle vectors constructed with in vitro mutagenized yeast genes lacking six base pair restriction sites," Gene, vol. 74, pp. 527-534 (1988).
Glover, D. M., "DNA Cloning—A Practical Approach," vols. I and II, IRL Press, 15 pages—Title Pages, Copyright Pages and Table of Contents only for vol. I and II (Jul. 1985).
Goodarzi, M. O. et al., "SORCS1: a novel human type 2 diabetes susceptibility gene suggested by the mouse," Diabetes, vol. 56, pp. 1922-1929 (Jul. 2007).
Guatelli, J. C. et al., "Isothermal in vitro amplification of nucleic acids by a multienzyme reaction modeled after retroviral replication," Proc. Natl. Acad. Sci. USA, vol. 87, pp. 1874-1878 (Mar. 1990).
Gupta, R. et al., "O-GLYCBASE version 4.0: a revised database of O-glycosylated proteins," Nucleic Acids Research, vol. 27, No. 1, pp. 370-372 (1999).
Guttieri, M. C. et al., "Cassette vectors for conversion of Fab fragments into full-length human IgG1 monoclonal antibodies by expression in stably transformed insect cells," Hybrid Hybridomics, vol. 22, No. 3, pp. 135-145 (Jun. 2003).
Hall, Walter A., "Immunotoxin Methods and Protocols," Methods in Molecular Biology, vol. 166, Humana Press, 4 pages—Title Page, Copyright Page and Table of Contents only (2001).
Halldorsdottir, S. et al., "Reproducibility and accuracy of body composition assessments in mice by dual energy x-ray absorptiometry and time domain nuclear magnetic resonance," Int. J. Body Compos. Res., vol. 7, No. 4, pp. 147-154, 21 pages (2009).
Hames, B. D. & Higgins, S. J., "Transcription and Translation: a practical approach," IRL Press, Oxford—Washington, DC, 13 pages—Title page, Copyright page and Table of Contents only (1984).
Hames, B. D. and Higgins, S. J., "Nucleic Acid Hybridisation," IRL Press, 8 pages—Title Page, Copyright Page and Table of Contents only (1985).
Han, S. et al., "Macrophage insulin receptor deficiency increases ER stress-induced apoptosis and necrotic core formation in advanced atherosclerotic lesions," Cell Metab., vol. 3, pp. 257-266 (Apr. 2006).
Hanley, A. J. G. et al., "Prediction of Type 2 Diabetes Using Simple Measures of Insulin Resistance: Combined Results From the San Antonio Heart Study, the Mexico City Diabetes Study, and the Insulin Resistance Atherosclerosis Study," Diabetes, vol. 52, pp. 463-469 (Feb. 2003).
Hanson, R. L. et al., "An Autosomal Genomic Scan for Loci Linked to Type II Diabetes Mellitus and Body-Mass Index in Pima Indians," J. Hum. Genet., vol. 63, pp. 1130-1138 (1998).
Harding, H. P. et al., "Diabetes mellitus and exocrine pancreatic dysfunction in perk-/- mice reveals a role for translational control in secretory cell survival," Mol. Cell, vol. 7, pp. 1153-1163 (Jun. 2001).
Hauge, H. et al., "Characterization of a novel immunoglobulin-like domain containing receptor," Biochem. Biophys. Res. Commun., vol. 323, pp. 970-978 (2004).
Heikal, A. A. et al., "Molecular Spectroscopy and dynamics of intrinsically fluorescent proteins: Coral red (dsRed) and yellow (Citrine)," Proc. Natl. Acad. Sci. USA, vol. 97, No. 22, pp. 11996-12001 (Oct. 24, 2000).
Heim, R. and Tsien, R. Y., "Engineering green fluorescent protein for improved brightness, longer wavelengths and fluorescence resonance energy transfer," Curr. Biol., vol. 6, pp. 178-182 (1996).
Henschen-Edman, Agnes H., "Fibrinogen non inherited heterogeneity and its relationship to function in health and disease," Ann. N.Y. Acad. Sci., vol. 936, pp. 580-593, 23 pages (Jun. 2001).
Hermeking, H. and Benzinger, A., "14-3-3 proteins in cell cycle regulation," Semin. Cancer Biol., vol. 16, pp. 183-192 (2006).
Herweijer, H. and Wolff, J. A., "Gene Therapy progress and prospects: Hydrodynamic gene delivery," Gene Ther., vol. 14, No. 2, pp. 99-107, 11 pages (Jan. 2007).
Hetz, Claudio, "The unfolded protein response: controlling cell fate decisions under ER stress and beyond," Nat. Rev. Mol. Cell Biol., vol. 13, No. 2, pp. 89-102, 18 pages (Feb. 2012).
Higashi, T. et al., "Analysis of the 'angulin' proteins LSR, ILDR1 and ILDR2—tricellulin recruitment, epithelial barrier function and implication in deafness pathogenesis," J. Cell Sci., vol. 126, pp. 966-977, 13 pages (2013).
Hingorani, S. R. et al., "Preinvasive and invasive ductal pancreatic cancer and its early detection in the mouse," Cancer Cell, vol. 4, pp. 437-450 (Dec. 2003).
Horton, J. D. et al., "SREBPs: activators of the complete program of cholesterol and fatty acid synthesis in the liver," J. Clin. Invest., vol. 109, pp. 1125-1131 (May 2002).
Hotamisligil, Gokhan S., "Endoplasmic reticulum stress and the inflammatory basis of metabolic disease," Cell, vol. 140, No. 6, pp. 900-917, 31 pages (Mar. 19, 2010).
Hsueh, W.-C. et al., "Genome-Wide and Fine-Mapping Linkage Studies of Type 2 Diabetes and Glucose Traits in the Old Order Amish," Diabetes, vol. 52, pp. 550-557 (Feb. 2003).
Innis, M. A. et al., "PCR Protocols: A Guide to Methods and Applications," Academic Press, N.Y., 16 pages—Title Page, Copyright Page and Table of Contents only (1990).
Innis, M. A. et al., "PCR Strategies," Academic Press, Inc., N.Y., 13 pages—Title Page, Copyright Page and Table of Contents only (1995).
Isaka, Y. and Imai, E., "Electroporation-mediated gene therapy," Expert Opin. Drug Deliv., vol. 4, No. 5, pp. 561-571 (Sep. 2007).
Ishibashi, S. et al., "Hypercholesterolemia in low density lipoprotein receptor knockout mice and its reversal by adenovirus-mediated gene delivery," J. Clin. Invest., vol. 92, pp. 883-893 (1993).
Ito, T. et al., "A comprehensive two-hybrid analysis to explore the yeast protein interactome," Proc. Natl. Acad. Sci. USA, vol. 98, pp. 4569-4574 (Apr. 10, 2001).
Jager, L. and Ehrhardt, A., "Emerging Adenoviral Vectors for Stable Correction of Genetic Disorders," Curr. Gene Ther., vol. 7, No. 4, pp. 272-283 (Aug. 2007).
Jensen, Thomas G., "Cutaneous gene therapy," Ann. Med., vol. 39, No. 2, pp. 108-115 (2007).
Jin, L. et al., "High Resolution Functional Analysis of Antibody-Antigen Interactions," J. Mol. Biol., vol. 226, No. 3, pp. 851-865 (1992).

(56) References Cited

OTHER PUBLICATIONS

Jones, John, "Amino Acid and Peptide Synthesis," Oxford University Press, 3 pages—Title Page, Copyright Page and Table of Contents only (1992).
Jones, P., "Vectors: Cloning Applications: Essential Techniques" Essential Techniques Series, John Wiley & Sons Ltd., 8 pages—Title Page, Copyright Page and Table of Contents only (1998).
Joober, R. et al., "Provisional mapping of quantitative trait loci modulating the acoustic startle response and prepulse inhibition of acoustic startle," Neuropsychopharmacology, vol. 27, pp. 765-781 (2002).
Kalota, A. et al., "Progress in the Development of Nucleic Acid Therapeutics," Handb. Exp. Pharmacol., vol. 173, pp. 173-196 (2006).
Kammoun, H. L. et al., "GRP78 expression inhibits insulin and ER stress-induced SREBP-1c activation and reduces hepatic steatosis in mice," J. Clin. Invest., vol. 119, No. 5, pp. 1201-1215 (May 2009).
Kamper, N. et al., "A novel BAT3 sequence generated by alternative RNA splicing of exon 11B displays cell type-specific expression and impacts on subcellular localization," PLoS One, vol. 7, No. 4, e35972, pp. 1-11 (Apr. 2012).
Kay, B. K. et al., "Phage Display of Peptides and Proteins: A Laboratory Manual," Academic Press, Inc., 10 pages—Title Page, Copyright Page and Table of Contents only (1996).
Khwaja, A. et al., "Prenylation inhibitors in renal disease," Lancet, vol. 355, pp. 741-744 (2000).
Kido, Y. et al., "Tissue-specific insulin resistance in mice with mutations in the insulin receptor, IRS-1, and IRS-2," J. Clin. Invest., vol. 105, pp. 199-205 (Jan. 2000).
Kikuchi, Y. et al., "Cutaneous gene delivery," J. Dermatol. Sci., vol. 50, No. 2, pp. 87-98 (May 2008).
Kim, J. J. et al., "Mitogenic and Metabolic Effects of Type I IGF Receptor Overexpression in Insulin Receptor-Deficient Hepatocytes," Endocrinology, vol. 142, pp. 3354-3360, 15 pages (Aug. 2001).
Kitamura, T. et al., "The forkhead transcription factor Foxo1 links insulin signaling to Pdx1 regulation of pancreatic B cell growth," J. Clin. Invest., vol. 110, No. 12, pp. 1839-1847 (Dec. 2002).
Kitamura, Y. I. et al., "Fox01 protects against pancreatic β cell Failure through NeuroD and MafA induction," Cell Metab., vol. 2, pp. 153-163 (Sep. 2005).
Klein, Jan, "Immunology: The Science of Self-Nonself Discrimination," John Wiley, New York, N.Y., 22 pages—Title Page, Copyright Page, Table of Contents and Index only (1982).
Klonoff, D. C. and Greenway, F., "Drugs in the Popeline for the Obesity Market," J. Diabetes Sci. Technol., vol. 2, No. 5, pp. 913-918 (Sep. 2008).
Knowler, W. C. et al, "Determinants of Diabetes Mellitus in the Pima Indians," Diabetes Care, vol. 16, Suppl. 1, pp. 216-227 (Jan. 1993).
Kole, H. K. et al., "Protein-Tyrosine Phosphatase Inhibition by a Peptide Containing the Phosphotyrosyl Mimetic, L-O-Malonyltyrosine," Biochem. Biophys. Res. Com., vol. 209, No. 3, pp. 817-822 (Apr. 26, 1995).
Kolonin, M. G. and Finley, Jr., R. L., "Targeting cyclin-dependent kinases in *Drosophila* with Peptide aptamers," Proc. Natl. Acad. Sci. USA, vol. 95, pp. 14266-14271 (Nov. 1998).
Kotronen, A. and Yki-Jarvinen, H., "Fatty liver: a novel component of the metabolic syndrome," Arterioscler. Thromb. Vasc. Biol., vol. 28, pp. 27-38 (2008).
Kreegipuu, A. et al., "PhosphoBase, a database of phosphorylation sites: release 2.0.," Nucleic Acids Res., vol. 27, No. 1, pp. 237-239 (1999).
Kricka, L. J. et al., "Comparison of 5-Hydroxy-2, 3-Dihydrophthalazine-1, 4-Dione and Luminol as Co-substrates for Detection of Horseradish peroxidase in Enhanced Chemiluminescent Reactions," J. Immmunoassay, vol. 17, No. 1, pp. 67-83 (1996).
Krishna, R. G. and Wold F., "Post-translational Modifications of Proteins," Methods in Protein Sequence Analysis, pp. 167-172, 8 pages (1993).
Kwoh, D. Y. et al., "Transcription-based amplification system and detection of amplified human immunodeficiency virus type 1 with a bead-based sandwich hybridization format," Proc. Natl. Acad. Sci. USA, vol. 86, pp. 1173-1177 (Feb. 1989).
Lai, E. et al., "Endoplasmic reticulum stress: signaling the unfolded protein response," Physiology, vol. 22, pp. 193-201 (2007).
Lam, K. S. et al., "The One-Bead-One-Compound Combinatorial Library Method," Chem. Rev., vol. 97, pp. 411-448 (1997).
Landegren, U. et al., "A Ligase-Mediated Gene Detection Technique," Science, vol. 241, pp. 1077-1080 (Aug. 26, 1988).
Lapidot, M. and Pilpel, Y., "Genome-wide natural antisense transcription: coupling its regulation to its different regulatory mechanisms," EMBO Rep., vol. 7, pp. 1216-1222 (2006).
Lattuada, G. et al., "Why does NAFLD predict type 2 diabetes?," Curr. Diab. Rep., vol. 11, No. 3, pp. 167-172 (Jun. 2011).
Lee, A.-H. et al., "Regulation of hepatic lipogenesis by the transcription factor XBP1," Science, vol. 320, No. 5882, pp. 1492-1496, 11 pages (Jun. 13, 2008).
Lee, J. S. et al., "Pharmacologic ER stress induces non-alcoholic steatohepatitis in an animal model," Toxicol. Lett., vol. 211, No. 1, pp. 29-38, 20 pages (May 20, 2012).
Lee, J. S. et al., "Pharmacological ER stress promotes hepatic lipogenesis and lipid droplet formation," Am. J. Transl. Res., vol. 4, No. 1, pp. 102-113 (2012).
Lee, M. W. et al., "Regulation of hepatic gluconeogenesis by an ER-bound transcription factor, CREBH," Cell Metab., vol. 11, pp. 331-339 (Apr. 7, 2010).
Legare, M. E. et al., "A major effect QTL determined by multiple genes in epileptic EL mice," Genome Res., vol. 10, pp. 42-48 (2000).
Lerner, Richard A., "Tapping the immunological repertoire to produce antibodies of predetermined specificity," Nature, vol. 299, pp. 592-596 (1982).
Levy, J. C. et al., "Correct homeostasis model assessment (HOMA) evaluation uses the computer program," Diabetes Care, vol. 21, No. 12, pp. 2191-2192 (Dec. 1998).
Li, X. et al., "Deletions of the Aequorea victoria Green Fluorescent Protein Define the Minimal Domain Required for Fluorescence," J. Biol. Chem., vol. 272, pp. 28545-28549 (Nov. 7, 1997).
Li, Y. et al., "Enrichment of endoplasmic reticulum with cholesterol inhibits sarcoplasmic-endoplasmic reticulum calcium ATPase-2b activity in parallel with increased order of membrane lipids: implications for depletion of endoplasmic reticulum calcium stores and apoptosis in cholesterol-loaded macrophages," J. Biol. Chem., vol. 279, No. 35, pp. 37030-37039 (Aug. 27, 2004).
Linnik, K. M. and Herscovitz, H., "Multiple molecular chaperones interact with apolipoprotein B during its maturation: The network of endoplasmic reticulum-resident chaperones (ERp72, GRP94, calreticulin, and BiP) interacts with apolipoprotein b regardless of its lipidation state," J. Biol. Chem., vol. 273, pp. 21368-21373 (Aug. 14, 1998).
Liu, D. R. and Schultz, P. G., "Progress toward the evolution of an organism with an expanded genetic code," Proc. Natl. Acad. Sci. USA, vol. 96, No. 9, pp. 4780-4785 (Apr. 1999).
Liu, S. M. et al., "Partial duplication in the Lepr(db-Pas) mutation is a result of unequal crossing over," Mamm. Genome, vol. 9, pp. 780-781 (1998).
Look, G. C. et al., "Methods for Combinatorial Organic Synthesis: The Use of Fast 13C NMR Analysis for Gel Phase Reaction Monitoring," J. Org. Chem., vol. 59, pp. 7588-7590 (1994).
Luban, J. and Goff, S. P., "The yeast two hybrid system for studying protein-protein interactions," Curr. Opin. Biotechnol., vol. 6, No. 1, pp. 59-64 (1995).
Lundberg, C. et al., "Applications of Lentiviral Vectors for Biology and Gene Therapy of Neurological Disorders," Curr. Gene Ther., vol. 8, No. 6, pp. 461-473 (2008).
Lundqvist, H. et al., "Influence of Different Luminols on the Characteristics of the Chemiluminescence Reaction in Human Neutrophils," J. Biolumin. Chemilumin., vol. 10, No. 6, pp. 353-359 (1995).

(56) References Cited

OTHER PUBLICATIONS

Lutzelberger, M. and Kjems, J., "Strategies to Identify Potential Therapeutic Target Sites in RNA," Handb. Exp. Pharmacol., vol. 173, pp. 243-259, 10 pages(2006).
Manjunath, N. et al., "Lentiviral delivery of short hairpin RNAs," Adv. Drug Deliv. Rev., vol. 61, No. 9, pp. 732-745, 29 pages (Jul. 25, 2009).
Maris, M. et al., "Deletion of C/EBP homologous protein (Chop) in C57Bl/6 mice dissociates obesity from insulin resistance," Diabetologia, vol. 55, pp. 1167-1178 (2012).
Masuda, S. et al., "LSR defines cell corners for tricellular tight junction formation in epithelial cells," J. Cell Sci., vol. 124, pp. 548-555 (2011).
Matsumoto, M. et al., "Dual role of transcription factor Fox01 in controlling hepatic insulin sensitivity and lipid metabolism," J. Clin. Invest., vol. 116, No. 9, pp. 2464-2472 (Sep. 2006).
McCaffrey, A. et al., "RNA Interference in adult mice," Nature, vol. 418, pp. 38-39 (2002).
McKeon, C. et al., "A Conserved Region in the First Intron of the Insulin Receptor Gene Binds Nuclear Proteins during Adipocyte Differentiation," Biochem. Biophys. Res. Commun., vol. 240, pp. 701-706 (1997).
McKeon, C. et al., "Structural and Functional Analysis of the Insulin Receptor Promoter," Mol. Endocrinol., vol. 4, pp. 647-656 (1990).
McLean, G. R. et al., "Human and murine immunoglobulin expression vector cassettes," Mol. Immunol., vol. 37, No. 14, pp. 837-845 (Oct. 2000).
McManus, M. T. et al., "Gene silencing using micro-RNA designed hairpins," RNA, vol. 8, pp. 842-850 (2002).
Meek, S. E. et al., "Comprehensive proteomic analysis of interphase and mitotic 14-3-3-binding proteins," J. Biol. Chem., vol. 279, pp. 32046-32054 (Jul. 30, 2004).
Meigs, J. B. et al., "A Genome-Wide Scan for Loci Linked to Plasma Levels of Glucose and HbA(1c) in a Community-Based Sample of Caucasian Pedigrees," Diabetes, vol. 51, pp. 833-840 (Mar. 2002).
Mendelsohn, A. R. and Brent, R., "Applications of interaction traps/two-hybrid systems to biotechnology research," Curr. Opin. Biotechnol., vol. 5, No. 5, pp. 482-486 (1994).
Mesli, S. et al., "Distribution of the lipolysis stimulated receptor in adult and embryonic murine tissues and lethality of LSR -/- embryos at 12.5 to 14.5 days of gestation," Eur. J. Biochem., vol. 271, pp. 3103-3114 (2004).
Metzger, J. W. et al., "Ion-spray Mass Spectrometry and High-Performance Liquid Chromatography—Mass spectrometry of Synthetic Peptide Libraries," Angew. Chem. Int. Ed. Engl., vol. 32, pp. 894-896 (1993).
Miller, A. Dusty, "Human gene therapy comes of age," Nature, vol. 357, pp. 455-460 (1992).
Minehira, K. et al., "Blocking VLDL secretion causes hepatic steatosis but does not affect peripheral lipid stores or insulin sensitivity in mice," J. Lipid Res., vol. 49, No. 9, pp. 2038-2044, 14 pages (Sep. 2008).
Mitsos, L. M. et al., "Genetic control of susceptibility to infection with *Mycobacterium tuberculosis* in mice," Genes Immun., vol. 1, pp. 467-477 (2000).
Miyawaki, A. et al., "Fluorescent indicators for Ca(2+) based on green fluorescent proteins and calmodulin," Nature, vol. 388, pp. 882-887 (1997).
Nagata, Y. and Zilversmit, D. B., "Blockade of intestinal lipoprotein clearance in rabbits injected with Triton WR 1339-ethyl oleate," J. Lipid Res., vol. 28, pp. 684-692 (1987).
Nakae, J. et al., "Differential regulation of gene expression by insulin and IGF-1 receptors correlates with phosphorylation of a single amino acid residue in the forkhead transcription factor FKHR," Embo. J., vol. 19, No. 5, pp. 989-996 (2000).
Nakae, J. et al., "Regulation of insulin action and pancreatic B-cell function by mutated alleles of the gene encoding forkhead transcription factor Foxo1," Nat. Genet., vol. 32, pp. 245-253 (Oct. 2002).
Nakae, J. et al., "The forkhead transcription factor Foxo1 (Fkhr) confers insulin sensitivity onto glucose-6-phosphatase expression," J. Clin. Invest., vol. 108, No. 9, pp. 1359-1367 (Nov. 2001).
Nefzi, A. et al., "The Current Status of Heterocyclic Combinatorial Libraries," Chem. Rev., vol. 97, pp. 449-472 (1997).
Norderhaug, L. et al., "Versatile vectors for transient and stable expression of recombinant antibody molecules in mammalian cells," J. Immunol. Methods, vol. 204, No. 1, pp. 77-87 (1997).
Norman, T. et al., "Genetic Selection of Peptide Inhibitors of Biological Pathways," Science, vol. 285, pp. 591-595 (1999).
Ohlmeyer, M. H. J. et al., "Complex Synthetic Chemical Libraries Indexed with Molecular Tags," Proc. Natl. Acad. Sci. USA, vol. 90, pp. 10922-10926 (Dec. 1993).
Okamoto, H. et al., "Restoration of liver insulin signaling in Insr knockout mice fails to normalize hepatic insulin action," J. Clin. Invest., vol. 115, No. 5, pp. 1314-1322 (May 2005).
Okamoto, H. et al., "Role of the forkhead protein FoxO1 in β cell compensation to insulin resistance," J. Clin. Invest., vol. 116, pp. 775-782 (2006).
Okamoto, H. et al., "Transgenic rescue of insulin receptor-deficient mice," J. Clin. Invest., vol. 114, No. 2, pp. 214-223 (Jul. 2004).
Ong, K. T. et al., "ATGL is a major hepatic lipase that regulates TAG turnover and fatty acid signaling and partitioning," Hepatology, vol. 53, No. 1, pp. 116-126, 17 pages (Jan. 2011).
Onuma, H. et al., "Identification of the insulin-regulated interaction of phosphodiesterase 3B with 14-3-3 beta protein," Diabetes, vol. 51, pp. 3362-3367 (Dec. 2002).
Ota, T. et al., "Inhibition of apolipoprotein B100 secretion by lipid-induced hepatic endoplasmic reticulum stress in rodents," J. Clin. Invest., vol. 118, No. 1, pp. 316-332 (Jan. 2008).
Ozcan, U. et al., "Endoplasmic reticulum stress links obesity, insulin action, and type 2 diabetes," Science, vol. 306, pp. 457-461 (2004).
Ozcan, L. and Tabas, I., "Role of endoplasmic reticulum stress in metabolic disease and other disorders," Annu. Rev. Med., vol. 63, pp. 317-328, 13 pages (2012).
Ozcan, L. et al., "Endoplasmic reticulum stress plays a central role in development of leptin resistance," Cell Metab., vol. 9, pp. 35-51 (Jan. 7, 2009).
Paddison, P. J. et al., "Short hairpin RNAs (shRNAs) induce sequence-specific silencing in mammalian cells," Genes Dev., vol. 16, pp. 948-958 (2002).
Palm, G. J. and Wlodawer, A., "Spectral Variants of Green Fluorescent Protein," Methods Enzymol., vol. 302, pp. 378-394 (1999).
Papatheodorou, P. et al., "Identification of the cellular receptor of Clostridium spiroforme toxin," Infect. Immun., vol. 80, No. 4, pp. 1418-1423 (Apr. 2012).
Park, B.-C. et al., "Differential Signaling of Insulin and IGF-1 Receptors to Glycogen Synthesis in Murine Hepatocytes," Biochemistry, vol. 38, pp. 7517-7523 (1999).
Park, S. W. et al., "Sarco(endo)plasmic reticulum Ca2+-ATPase 2b is a major regulator of endoplasmic reticulum stress and glucose homeostasis in obesity," Proc. Natl. Acad. Sci. USA, vol. 107, No. 45, pp. 19320-19325 (Nov. 9, 2010).
Perbal, Bernard, "A Practical Guide to Molecular Cloning," John Wiley & Sons, New York, 11 pages—Title page, Copyright page and Table of Contents only (1984).
Permutt, M. A. et al., "Genetic epidemiology of diabetes," J. Clin. Invest., vol. 115, No. 6, pp. 1431-1439 (Jun. 2005).
Pier, G. B. et al., "Immunology, Infection and Immunity," 1st Ed. American Society for Microbiology Press, Washington D.C., Book Review, Immunology and Cell Biology, vol. 82, pp. 651-652, 1 page (2004).
Pimenta, W. et al., "Pancreatic Beta-cell Dysfunction as the Primary Genetic Lesion in NIDDM," Jama, vol. 273, No. 23, pp. 1855-1861 (Jun. 21, 1995).
Postic, C. and Magnuson, M. A., "DNA Excision in Liver by an Albumin-Cre Transgene Occurs Progressively with Age," Genesis, vol. 26, pp. 149-150 (2000).
Pozuelo Rubio, M. et al., "14-3-3-affinity purification of over 200 human phosphoproteins reveals new links to regulation of cellular metabolism, proliferation and trafficking," Biochem. J., vol. 379, pp. 395-408 (2004).

(56) References Cited

OTHER PUBLICATIONS

Prendergast, G. C. and Oliff, A., "Farnesyltransferase inhibitors: antineoplastic properties, mechanisms of action, and clinical prospects," Cancer Biol., vol. 10, pp. 443-452 (2000).
Preston, M. J. et al., "Production and characterization of a set of mouse-human chimeric immunoglobulin G (IgG) subclass and IgA monoclonal antibodies with identical variable regions specific for Pseudomonas aeruginosa serogroup O6 lipopolysaccharide," Infect. Immun., vol. 66, No. 9, pp. 4137-4142 (Sep. 1998).
Rattan, S. I. S. et al., "Protein Synthesis, Posttranslational, Modifications, and Aging," Ann. N.Y. Acad. Sci., vol. 663, pp. 48-62 (1992).
Rickwood, D. and Hames, B. D., "Vectors: Essential Data," Essential Data Series, John Wiley & Sons Ltd., 7 pages—Copyright Page and Table of Contents only (1995).
Roitt, Ivan M., "Essential Immunology," 7th Edition, Blackwell Scientific Publications, Oxford, 6 pages—Cover Page, Copyright Page and Table of Contents only (1971, 1974, 1977, 1980, 1984, 1988, 1991).
Ron, D. and Walter, P., "Signal integration in the endoplasmic reticulum unfolded protein response," Nat. Rev. Mol. Cell Biol., vol. 8, No. 7, pp. 519-529 (Jul. 2007).
Rother, K. I. et al., "Evidence that IRS-2 Phosphorylation is Required for Insulin Action in Hepatocytes," J. Biol. Chem., vol. 273, pp. 17491-17497 (1998).
Rutkowski, D. T. et al., "UPR pathways combine to prevent hepatic steatosis caused by ER stress-mediated suppression of transcriptional master regulators," Dev. Cell, vol. 15, No. 6, pp. 829-840, 21 pages (Dec. 2008).
Saltiel, Alan R., "New perspectives into the molecular pathogenesis and treatment of type 2 diabetes," Cell, vol. 104, pp. 517-529 (Feb. 23, 2001).
Sambrook, J. and Russell, D. W., "Molecular Cloning: A Laboratory Manual," 3rd Edition, Cold Spring Harbor Laboratory, vol. 1, 21 pages—Title Page, Copyright Page and Table of Contents only (2001).
Santagata, S. et al., "G-Protein Signaling Through Tubby Proteins," Science, vol. 292, pp. 2041-2050 (Jun. 15, 2001).
Scaglia, L. et al., "Apoptosis Participates in the Remodeling of the Endocrine Pancreas in the Neonatal Rat," Endocrinology, vol. 138, pp. 1736-1741 (1997).
Schoner, B. E. et al., "Translation of a synthetic two-cistron mRNA in *Escherichia coli*," Proc. Natl. Acad. Sci. USA, vol. 83, pp. 8506-8510, 12 pages (Nov. 1986).
Scott, M. D. and Murad, K. L., "Cellular Camouflage: Fooling the Immune System with Polymers," Curr. Pharm. Des., vol. 4, No. 6, pp. 423-438 (1998).
Seifter, S. and Englard, S., "Analysis for Protein Modifications and Nonprotein Cofactors," Meth. Enzymol., vol. 182, pp. 626-646 (1990).
Shinnick, T. M. et al., "Synthetic Peptide Immunogens as Vaccines," Annu. Rev. Microbiol., vol. 37, pp. 425-446 (1983).
Singer, O. and Verma, I. M., "Applications of Lentiviral Vectors for shRNA Delivery and Transgenesis," Curr. Gene Ther., vol. 8, No. 6, pp. 483-488, 12 pages (Dec. 2008).
Smith, J. H. et al., "Detection of *Mycobacterium tuberculosis* Directly from Sputum by Using a Prototype Automated Q-Beta Replicase Assay," J. Clin. Microbiol., vol. 35, pp. 1477-1483 (Jun. 1997).
Sooknanan, R. and Malek, L. T., "NASBA: A detection and amplification system uniquely suited for RNA," Biotechnology, vol. 13, pp. 563-564 (Jun. 1995).
Stenger, C. et al., "Up-regulation of hepatic lipolysis stimulated lipoprotein receptor by leptin: a potential lever for controlling lipid clearance during the postprandial phase," FASEB J., vol. 24, pp. 4218-4228 (2010).
Stevanovic, S. et al., "Natural and Synthetic Peptide Pools: Characterization by Sequencing and Electrospray Mass Spectrometry," Bioorg. Med. Chem. Lett., vol. 3, No. 3, pp. 431-436 (1993).
Strnad, P. et al., "Intermediate filament cytoskeleton of the liver in health and disease," Histochem. Cell Biol., vol. 129, pp. 735-749 (2008).
Stutzmann, G. E. and Mattson, M. P., "Endoplasmic reticulum Ca(2+) handling in excitable cells in health and disease," Pharmacol. Rev., vol. 63, pp. 700-727 (2011).
Sutcliffe, J. G. et al., "Antibodies that react with predetermined sites on proteins," Science, vol. 219, No. 4585, pp. 660-666, 12 pages (Feb. 11, 1983).
Thorpe, G. H. G. and Kricka, L. J., "Enhanced Chemiluminescent Reactions Catalyzed by Horseradish Peroxidase," Methods Enzymol., vol. 133, pp. 331-353 (1986).
Tijssen, P., "Laboratory Techniques in Biochemistry and Molecular Biology: Hybridization With Nucleic Acid Probes: Hybridization with nucleic acid probes: Part II: Probe labeling and hybridization techniques," vol. 24, Elsevier, N.Y., 7 pages—Title Page, Copyright Page and Table of Contents Only (1993).
Todd, John A., "From genome to aetiology in a multifactorial disease, type 1 diabetes," Bioessays, vol. 21, pp. 164-174 (1999).
Topcu, Z. et al., "The Yeast Two-Hybrid System and Its Pharmaceutical Significance," Pharm. Res., vol. 17, No. 9, pp. 1049-1055 (2000).
Trak-Smayra, V. et al., "Pathology of the liver in obese and diabetic ob/ob and db/db mice fed a standard or high-calorie diet," Int. J. Exp. Pathol., vol. 92, pp. 413-421 (2011).
Uetz, P. et al., "A comprehensive analysis of protein-protein interactions in *Saccharomyces cerevisiae*," Nature, vol. 403, pp. 623-627 (2000).
van der Sanden, M. H. et al., "Inhibition of phosphatidylcholine synthesis induces expression of the endoplasmic reticulum stress and apoptosis-related protein CCAAT/enhancer-binding protein-homologous protein (CHOP/GADD153)," Biochem. J., vol. 369, pp. 643-650 (2003).
Ventura, A. et al., "Restoration of p53 function leads to tumour regression in vivo," Nature, vol. 445, pp. 661-665 (Feb. 8, 2007).
Verma, Inder M., "Gene Therapy," Scientific American, pp. 68-84 (Nov. 1990).
Vionnet, N. et al., "Genomewide Search for Type 2 Diabetes—Susceptibility Genes in French Whites: Evidence for a Novel Susceptibility Locus for Early Onset Diabetes on Chromosome 3q27-qter and Independent Replication of a Type 2-Diabetes Locus on Chromosome 1q21-q24," Am. J. Hum. Genet., vol. 67, pp. 1470-1480 (2000).
Waehler, R. et al., "Engineering targeted viral vectors for gene therapy," Nat. Rev. Genet., vol. 8, No. 8, pp. 573-587 (Aug. 2007).
Walls, M. A. et al., "Vectors for the expression of PCR-amplified immunoglobulin variable domains with human constant regions," Nucleic Acids Res., vol. 21, No. 12, pp. 2921-2929 (Jun. 25, 1993).
Wang, L. et al., "Expanding the Genetic Code of *Escherichia coli*," Science, vol. 292, No. 5516, pp. 498-500 (2001).
Wang, S. and Kaufman, R. J., "The impact of the unfolded protein response on human disease," J. Cell Biol., vol. 197, No. 7, pp. 857-867 (2012).
Weiss, G. A. et al., "Rapid mapping of protein functional epitopes by combinatorial alanine scanning," Proc. Natl. Acad. Sci. USA, vol. 97, No. 16, pp. 8950-8954 (2000).
Welch, C. L. et al., "Localization of atherosclerosis susceptibility loci to chromosomes 4 and 6 using the Ldlr knockout mouse model," Proc. Natl. Acad. Sci. USA, vol. 98, No. 14, pp. 7946-7951 (Jul. 3, 2001).
Wiltshire, S. et al., "A Genomewide Scan for Loci Predisposing to Type 2 Diabetes in a UK Population (The Diabetes UK Warren 2 Repository): Analysis of 573 Pedigrees Provides Independent Replication of a Susceptibility Locus on Chromosome 1q," Am. J. Hum. Genet., vol. 69, pp. 553-569 (2001).
Woodward, J., "Immobilised Cells and Enzymes," IRL Press, 7 pages—Title Page, Copyright Page and Table of Contents only (1985).
Worgall, S. et al., "Innate immune mechanisms dominate elimination of adenoviral vectors following in vivo administration," Hum. Gene Ther., vol. 8, No. 1, pp. 37-44, 12 pages (Jan. 1, 1997).

(56) References Cited

OTHER PUBLICATIONS

Wu, D. Y. et al., "The Ligation Amplification Reaction (LAR)—Amplification of Specific DNA Sequences Using Sequential Rounds of Template Dependent Ligation," Genomics, vol. 4, pp. 560-569 (1989).
Wu, J. W. et al., "Deficiency of liver adipose triglyceride lipase in mice causes progressive hepatic steatosis," Hepatology, vol. 54, No. 1, pp. 122-132 (2011).
Xiang, K. et al., "Genome-wide search for type 2 diabetes/impaired glucose homeostasis susceptibility genes in the Chinese: significant linkage to chromosome 6q21-q23 and chromosome 1q21-q24," Diabetes, vol. 53, pp. 228-234 (Jan. 2004).
Xu, C. et al., "Endoplasmic reticulum stress: cell life and death decisions," J. Clin. Invest., vol. 115, No. 10, pp. 2656-2664 (Oct. 2005).
Xu, C. W. et al., "Cells that register logical relationships among proteins," Proc. Natl. Acad. Sci. USA, vol. 94, pp. 12473-12478 (Nov. 11, 1997).
Xuan, S. et al., "Defective insulin secretion in pancreatic B cells lacking type 1 IGF receptor," J. Clin. Invest., vol. 110, No. 7, pp. 1011-1019 (Oct. 2002).
Yamamoto, K. et al., "Induction of liver steatosis and lipid droplet formation in ATF6alpha-knockout mice burdened with pharmacological endoplasmic reticulum stress," Mol. Biol. Cell, vol. 21, pp. 2975-2986 (Sep. 1, 2010).
Yang, M. et al., "Protein-peptide interactions analyzed with the yeast two-hybrid system," Nuc. Acids Res., vol. 23, No. 7, pp. 1152-1156 (1995).
Yang, T.-T. et al., "Improved Fluorescence and Dual Color Detection with Enhanced Blue and Green Variants of the Green Fluorescent Protein," J. Biol. Chem., vol. 273, pp. 8212-8216 (1998).
Yen, F. T. et al., "Identification of a Lipolysis-Stimulated Receptor That Is Distinct from the LDL Receptor and the LDL Receptor-Related Protein," Biochemistry, vol. 33, pp. 1172-1180 (1994).
Yen, F. T. et al., "Molecular Cloning of a Lipolysis-stimulated Remnant Receptor Expressed in the Liver," J. Biol. Chem., vol. 274, pp. 13390-13398 (May 7, 1999).
York, B. et al., "Sensitivity to dietary obesity linked to a locus on chromosome 15 in a CAST/Ei x C57BL/6J F2 intercross," Mamm. Genome, vol. 7, pp. 677-681 (1996).
Yoshida, H. et al., "A time-dependent phase shift in the mammalian unfolded protein response," Dev. Cell, vol. 4, pp. 265-271 (Feb. 2003).
Youngquist, R. S. et al., "Matrix-assisted Laser Desorption Ionization for Rapid Determination of the Sequences of Biologically Active Peptides Isolated from Support-bound Combinatorial Peptide Libraries," Rapid Commun. Mass Spect., vol. 8, pp. 77-81 (1994).
Yu, J.-Y. et al., "RNA interference by expression of short-interfering RNAs and hairpin RNAs in mammalian cells," Proc. Natl. Acad. Sci. USA, vol. 99, No. 9, pp. 6047-6052 (Apr. 30, 2002).
Yu, R. and Hinkle, P. M., "Effect of cell type on the subcellular localization of the thyrotropin-releasing hormone receptor," Mol. Pharmacol., vol. 51, pp. 785-793 (1997).
Zagaria, A. et al., "A new recurrent chromosomal translocation t(3;11)(q13;q14) in myelodysplastic syndromes associated with overexpression of the ILDR1 gene," Leuk. Res., vol. 36, No. 7, pp. 852-856 (Jul. 2012).
Zhang, C. et al., "ER-tethered transcription factor CREBH regulates hepatic lipogenesis, fatty acid oxidation, and lipolysis upon metabolic stress," Hepatology, vol. 55, No. 4, pp. 1070-1082, 24 pages (Apr. 2012).
Zhang, K. and Kaufmann, R. J., "From endoplasmic reticulum stress to the inflammatory response," Nature, vol. 454, pp. 455-462, 21 pages (Jul. 24, 2008).
Zhang, K. et al., "The unfolded protein response transducer IRE1alpha prevents ER stress-induced hepatic steatosis," EMBO J., vol. 30, pp. 1357-1375 (2011).
Zhu, L. and Hannon, G. L., "Yeast Hybrid Technologies," Eaton Publishing, 4 pages—Title Page, Copyright Page and Table of Contents only (2000).
Dong, J., et al., "Gene therapy for unresectable hepatocelluar carcinoma using recombinant human adenovirus type 5," Med. Oncol., vol. 31, No. 95, pp. 1-8 (2014).
Ginn, S. L., et al., "Gene therapy clinical trials worldwide to 2012—an update," The Journal of Gene Medicine, vol. 15, pp. 65-77 (2013).
Guan, Y. S., et al., "Successful management of postoperative recurrence of hepatocellular carcinoma with p53 gene therapy combining thranscatheter arterial chemoembolization," World J. Gastroenterol., vol. 11, No. 24, pp. 3803-3805 (2005).
Herzog, R. W., et al., "Two Decades of Clinical Gene Therapy—Success Is Finally Mounting," Discov. Med., vol. 9, No. 45, pp. 105-111, 8 pages (Feb. 2010).
Kozarsky, Karen, "Delivery Systems for Gene Therapy: Unit 13:10—Gene Delivery to the Liver," Current Protocols in Human Genetics, vol. 13, Suppl. 22, pp. 13.10.1-13.10.7 (1999).
Yang, Z. X., et al., "Clinical study of recombinant adenovirus-p53 combined with fractionated stereotactic radiotherapy for hepatocellular carcinoma," J. Cancer Res. Clin. Oncol., vol. 136, pp. 625-630 (2010).
Das and Kar, "Non-alcoholic steatohepatitis," J. Assoc. Physicians India, vol. 53, pp. 195-199 (2005).
Moore, "Conference on 'Over- and undernutrition: challenges and approaches' Symposium 1: Overnutrition: consequences and solutions Non-alcoholic fatty liver disease: the hepatic consequence of obesity and the metabolic syndrome," Proceedings of the Nutrition Society, 69, 211-220 (2010).
Tuyama and Chang, "Non-alcoholic fatty liver disease," J. Diabetes 4(3), 266-280 (2012).

* cited by examiner

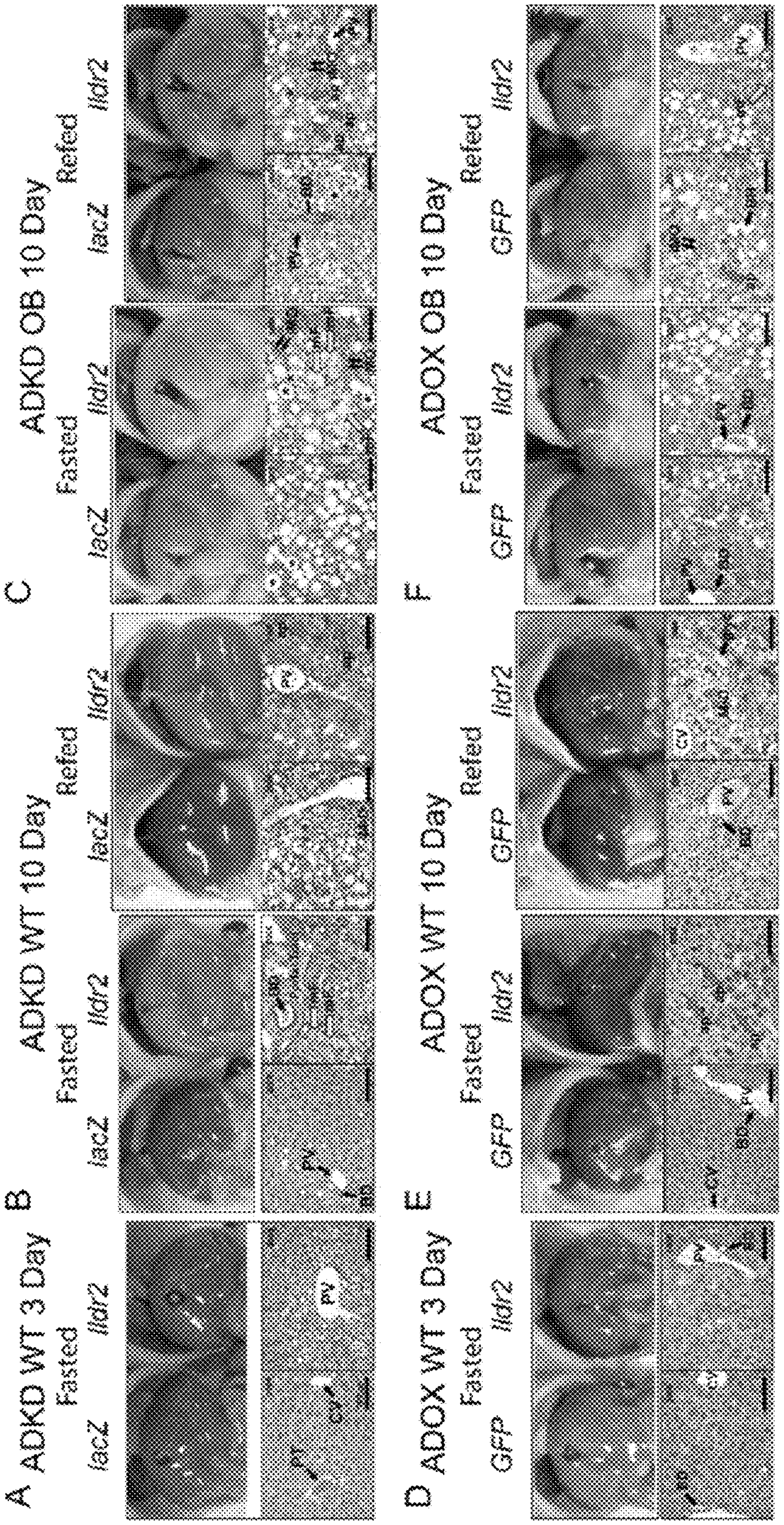
FIGS. 3A-F

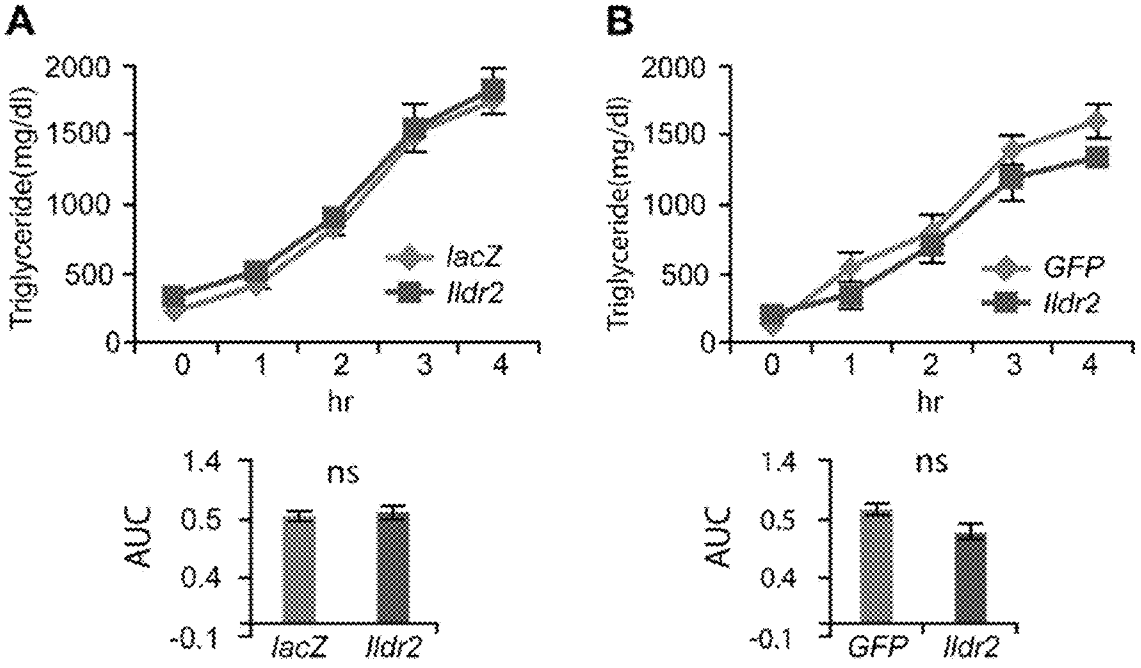
*FIGS. 4A-B*

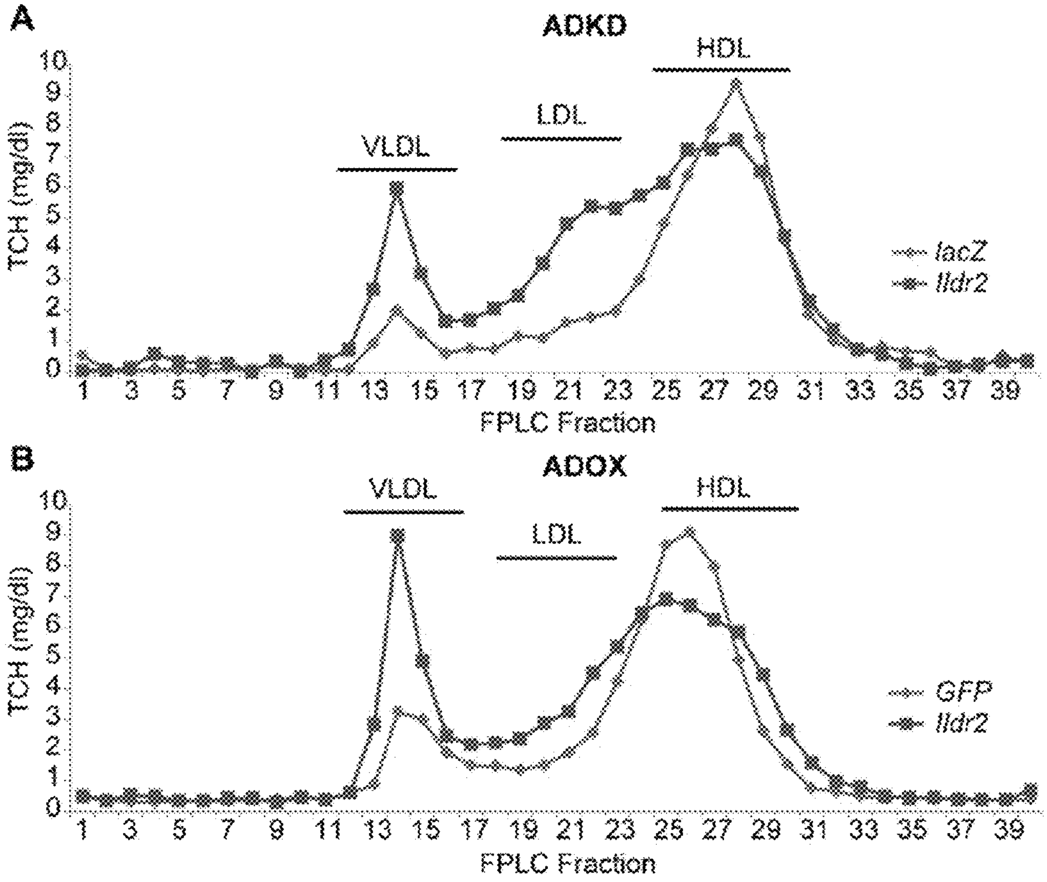
FIGS. 5A-B

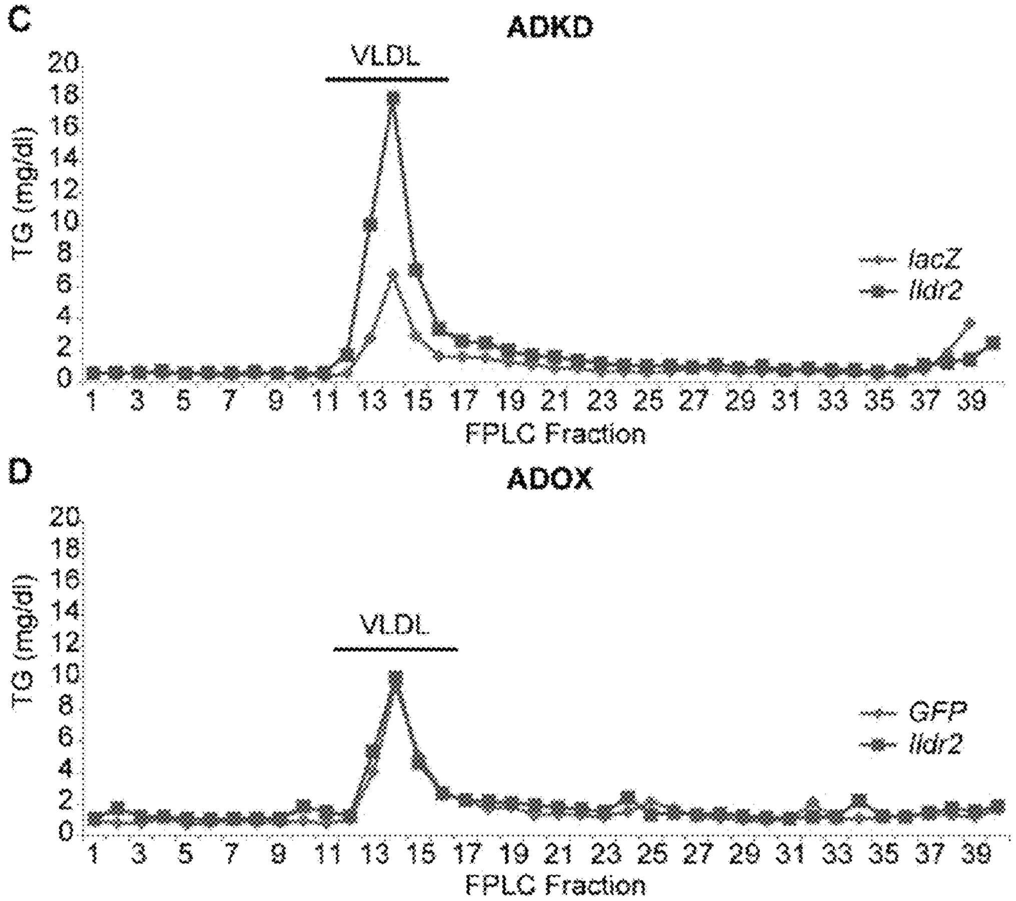
*FIGS. 5C-D*

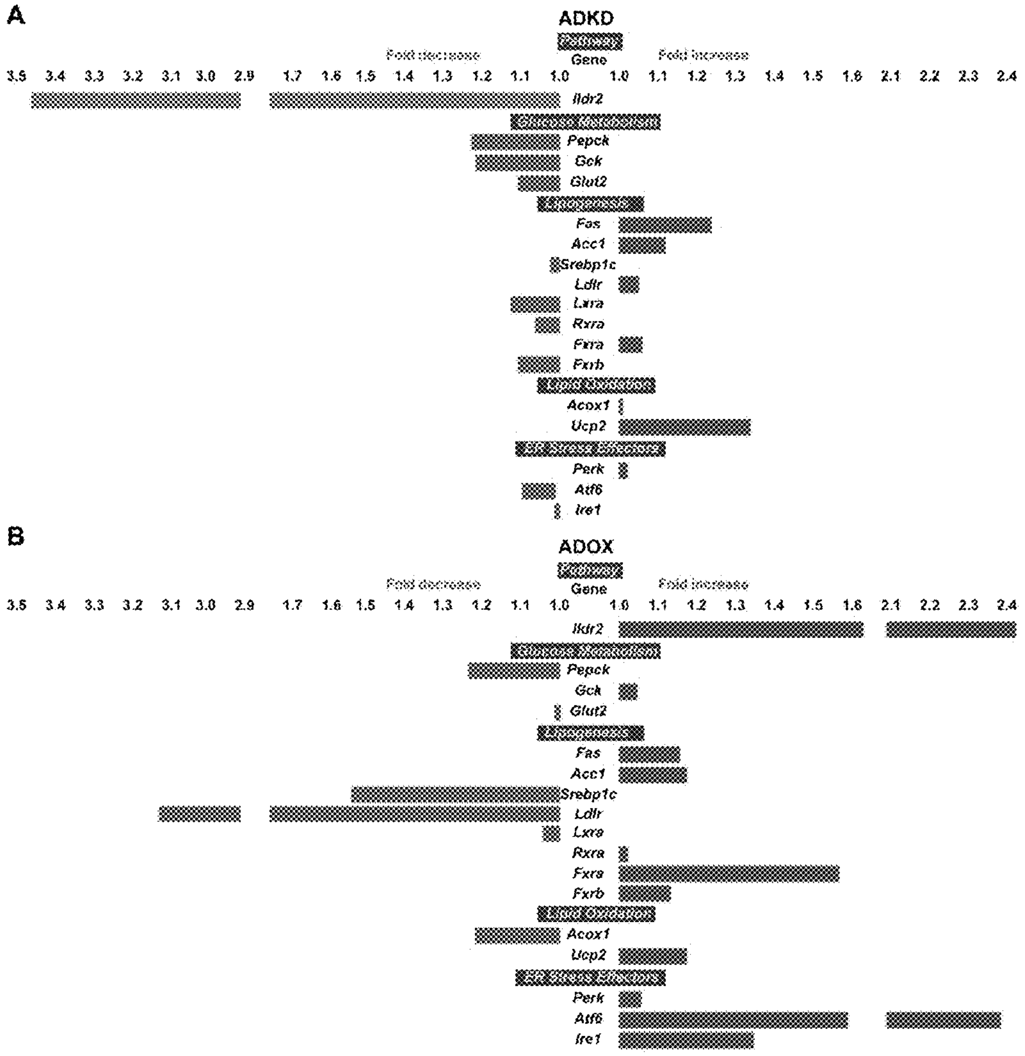
FIGS. 7A-B

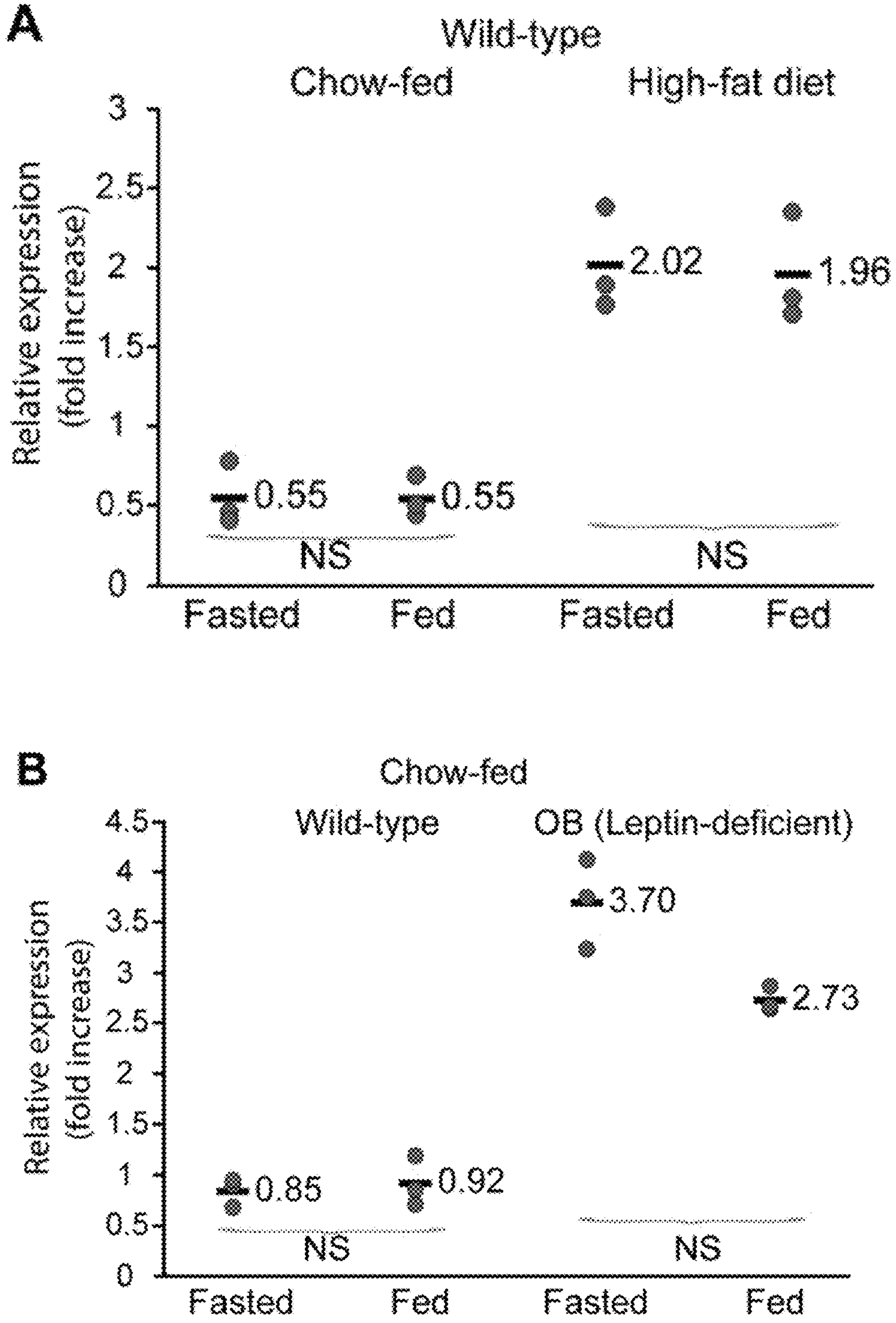
FIGS. 8A-B

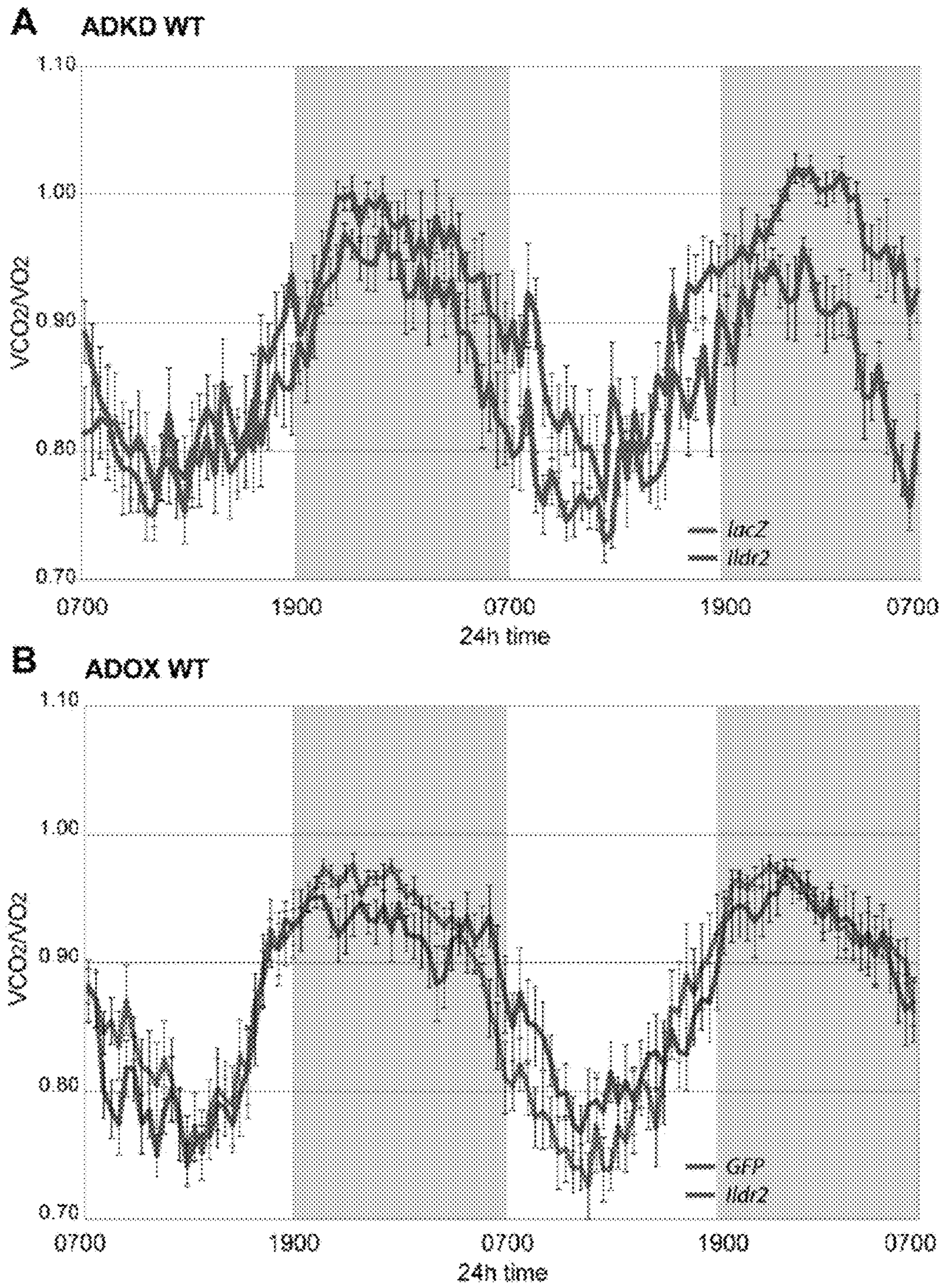
FIGS. 9A-B

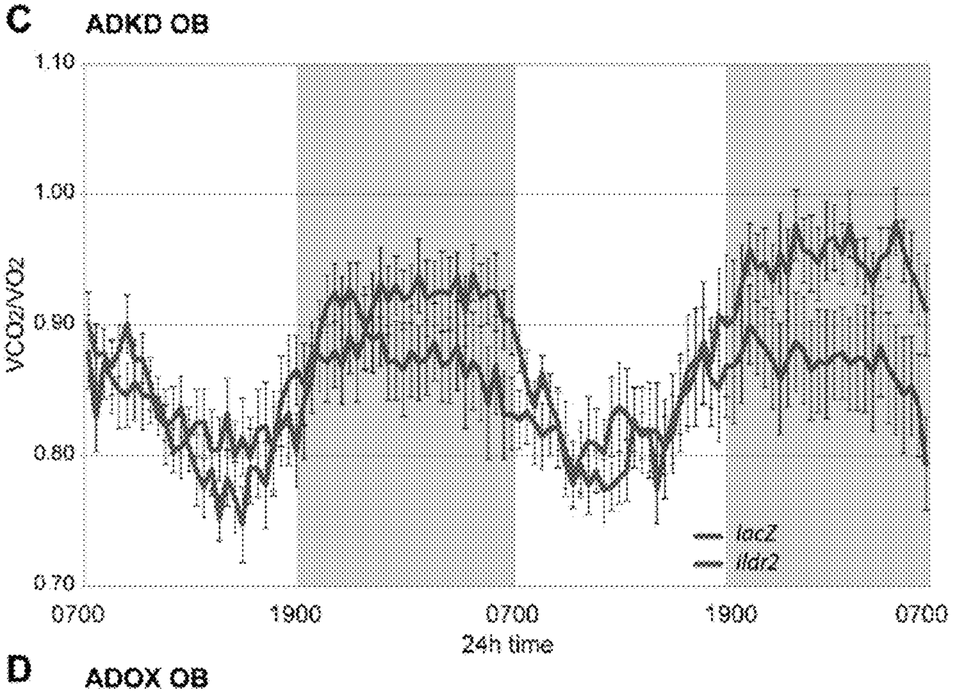
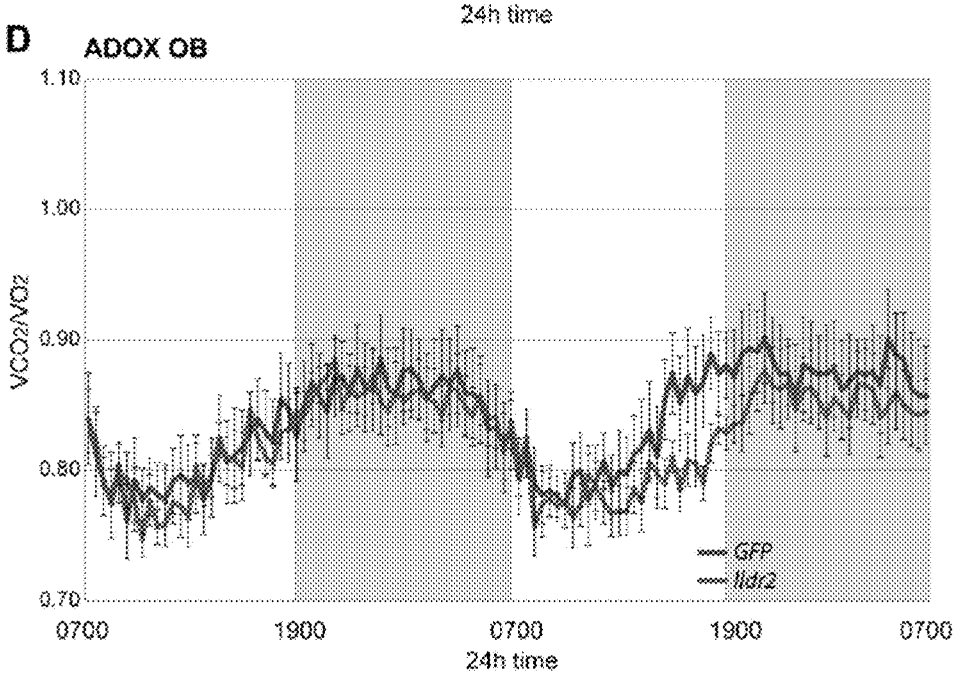
FIGS. 9C-D

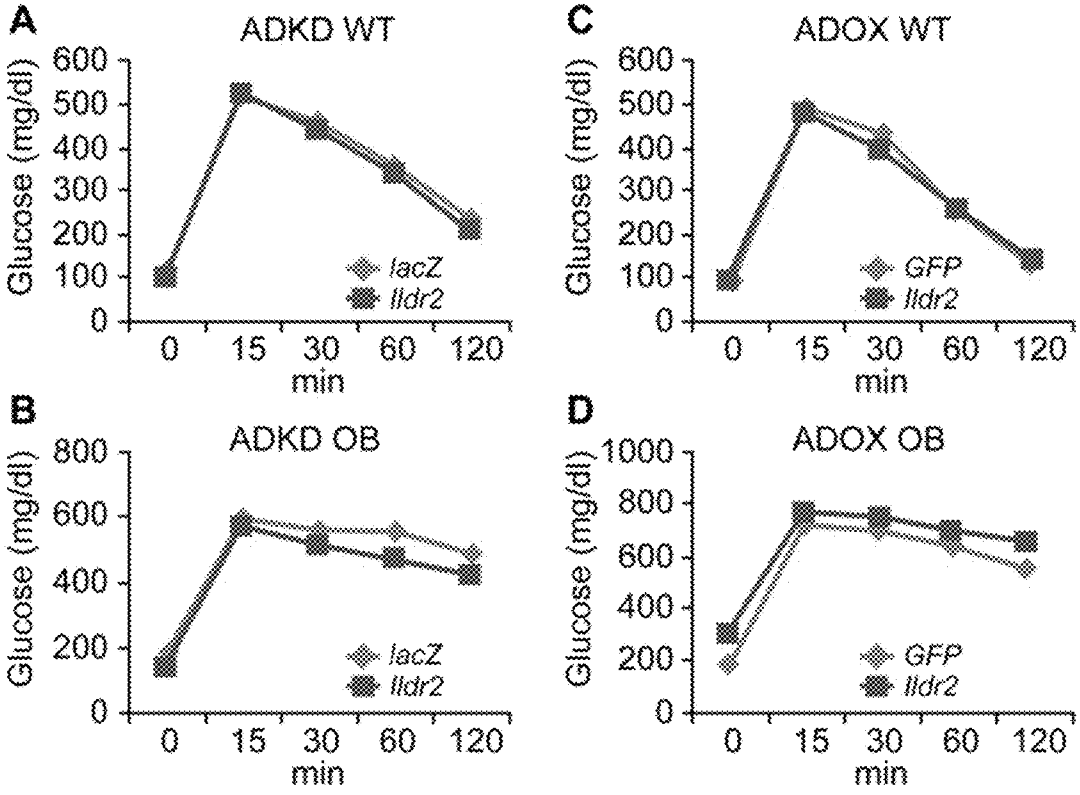
FIGS. 10A-D

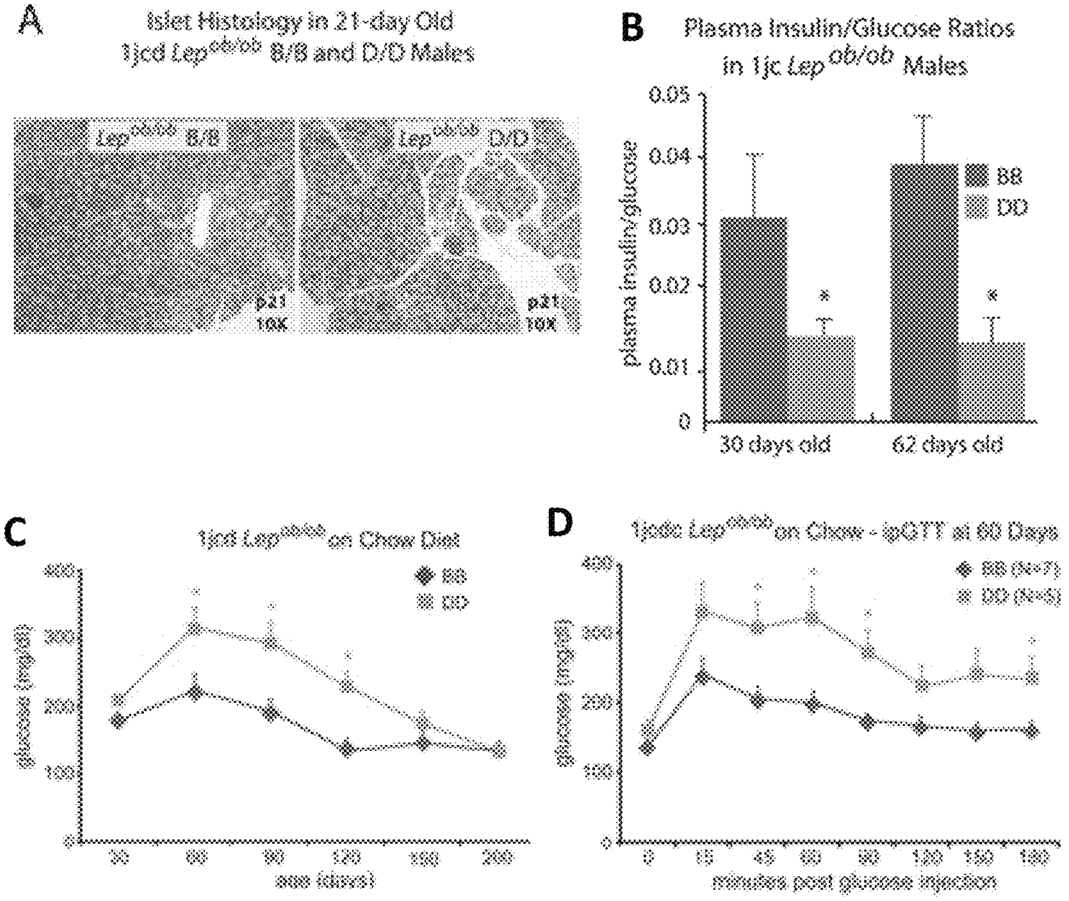
FIGS. 15A-D

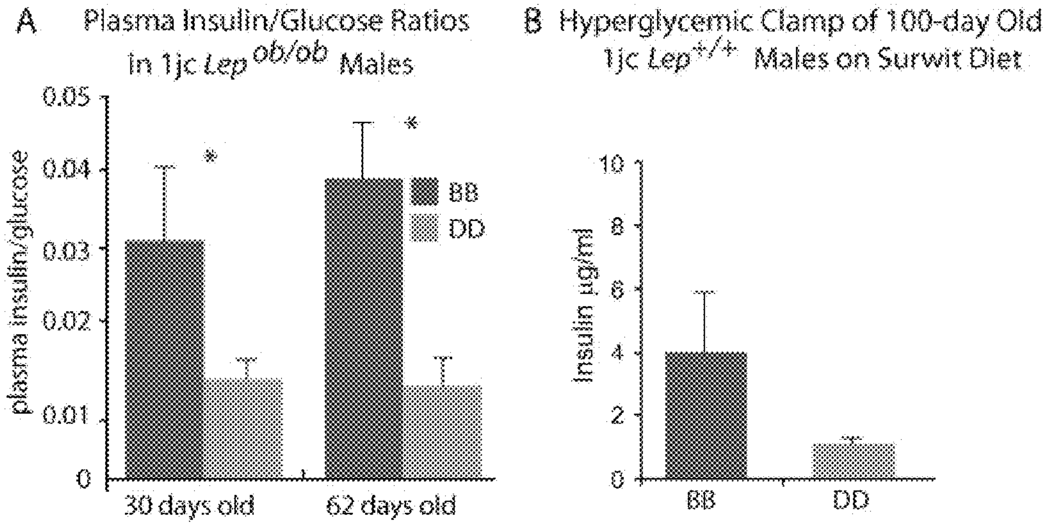
FIGS. 16A-B

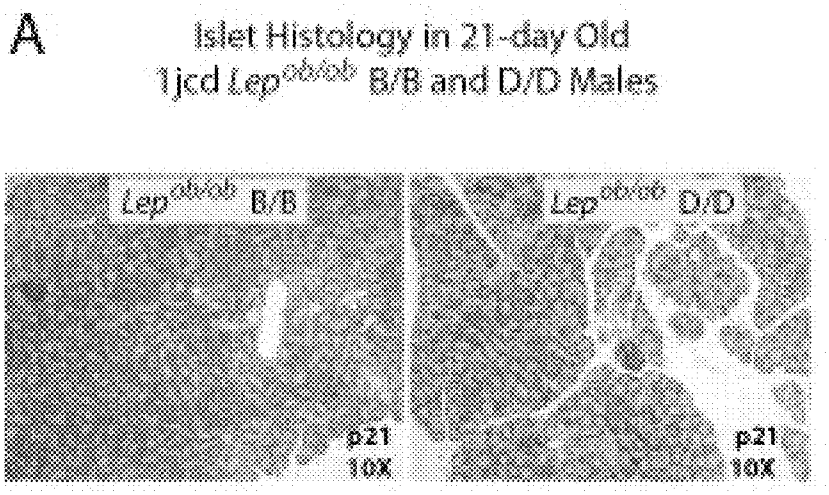
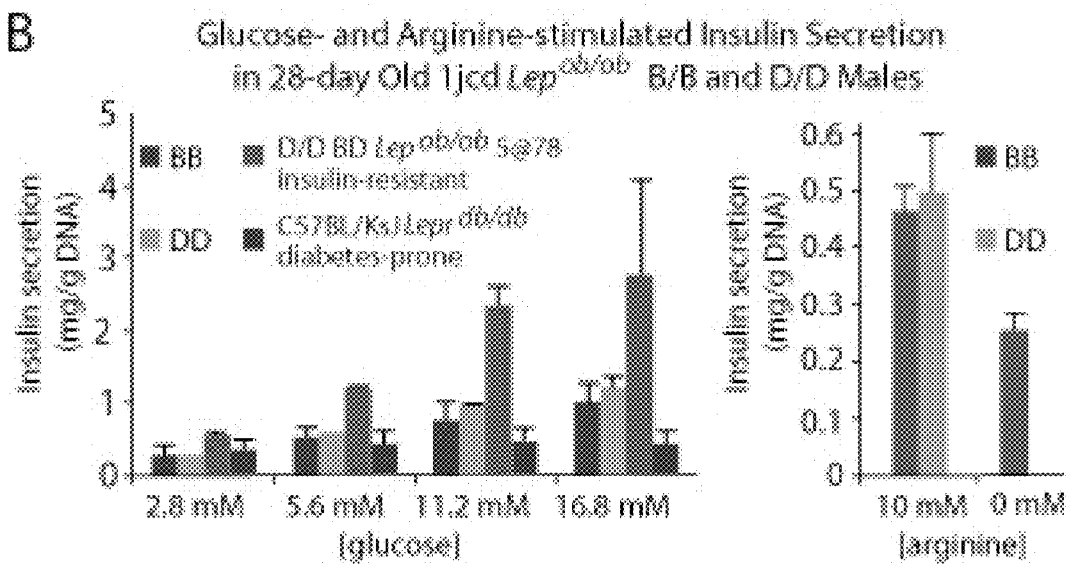
*FIGS. 17A-B*

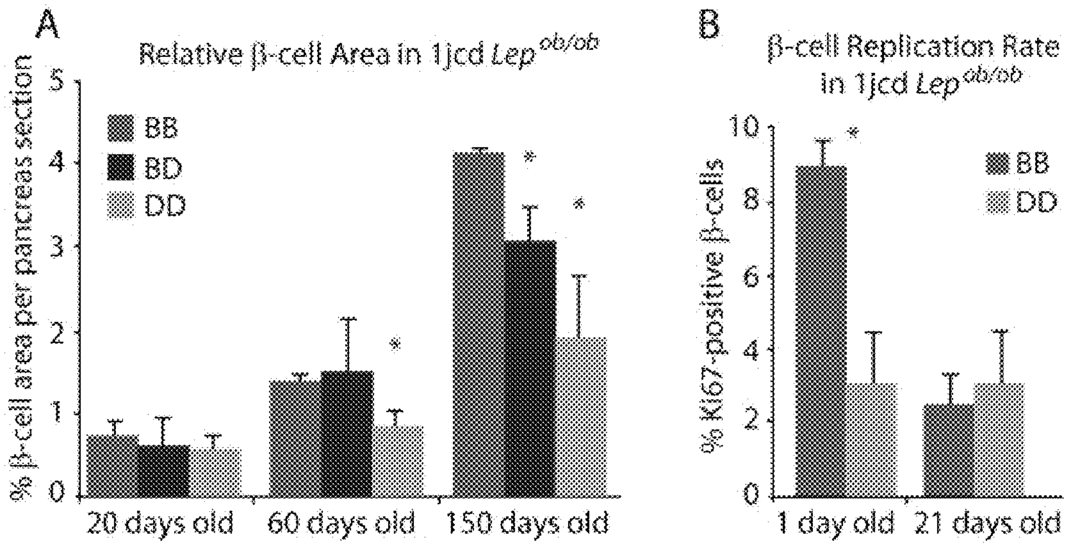
FIGS. 18A-B

(SEQ ID NO:1)

| Primary hepatocytes – LDL Uptake | Mean Fluorescence 4° C | Mean Fluorescence 37° C |
| --- | --- | --- |
| WT (N = 3) | 112± 85 | 313± 31.5 |
| W87* (N=3) | 58.7± 10.99 | 193± 20.2 |
| P-value | .0425 | .0423 |

*FIGS. 25A-B*

Knockdown

LacZi ILDR2i up
down

| | Fasted | | | Refed | | |
|---|---|---|---|---|---|---|
| | LacZi | ILDR2i | P value | LacZi | ILDR2i | P value |
| Glucose (mg/dL) | 81±7 | 86±3 | 0.619 | 187±8 | 183±8 | 0.069 |
| Insulin (μg/L) | 0.26±0.10 | 0.25±0.02 | 0.903 | 4.91±0.75 | 5.99±1.68 | 0.576 |

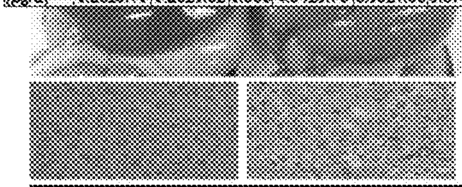

| | Fasted | | | Refed | | |
|---|---|---|---|---|---|---|
| | LacZi | ILDR2i | P value | LacZi | ILDR2i | P value |
| Plasma TG (mg/dL) | 114.2±19.0 | 138.0±17.0 | 0.362 | 203.8±22.9 | 243.0±27.0 | 0.275 |
| Plasma TC (mg/dL) | 131.7±4.0 | 264.0±24.8 | 0.003 | 135.5±8.8 | 313.3±32.4 | 0.001 |
| Hepatic TG (mg/g Liver) | 46.4±2.9 | 88.6±6.5 | 0.001 | 18.9±2.8 | 76.9±7.0 | 0.000 |
| Hepatic TC (mg/g Liver) | 9.8±0.6 | 18.0±1.7 | 0.005 | 7.6±0.4 | 14.8±1.4 | 0.003 |

Overexpression

GFP ILDR2

| | Fasted | | | Refed | | |
|---|---|---|---|---|---|---|
| | GFP | ILDR2 | P value | GFP | ILDR2 | P value |
| Glucose (mg/dL) | 105±4 | 92±4 | 0.066 | 211±4 | 155±3 | 0.001 |
| Insulin (μg/L) | 0.34±0.09 | 0.34±0.07 | 0.988 | 5.87±0.09 | 4.95±0.07 | 0.580 |

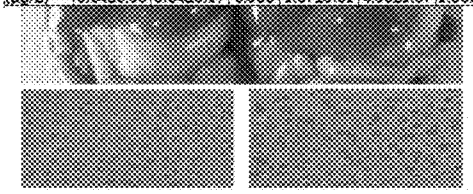

| | Fasted | | | Refed | | |
|---|---|---|---|---|---|---|
| | GFP | ILDR2 | P value | GFP | ILDR2 | P value |
| Plasma TG (mg/dL) | 67.6±2.5 | 98±9.6 | 0.005 | 192.8±23.0 | 246.1±22.4 | 0.117 |
| Plasma TC (mg/dL) | 114.6±6.9 | 133.8±11.6 | 0.563 | 135.7±2.3 | 145.7±1.2 | 0.005 |
| Hepatic TG (mg/g Liver) | 64.9±6.9 | 33.0±4.7 | 0.004 | 31.3±5.5 | 20.0±5.6 | 0.191 |
| Hepatic TC (mg/g Liver) | 11.4±0.8 | 7.4±0.8 | 0.005 | 6.8±0.7 | 5.4±0.9 | 0.272 |

*FIG. 28*

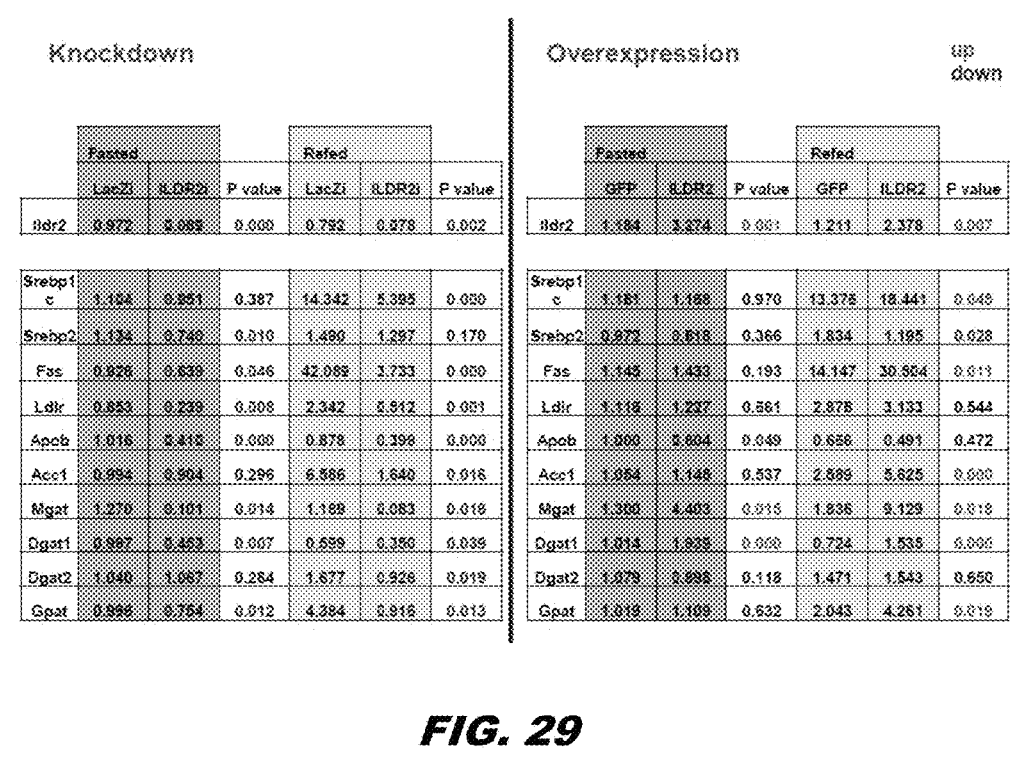

Knockdown

| | Fasted | | | Refed | | |
|---|---|---|---|---|---|---|
| | LacZi | ILDR2i | P value | LacZi | ILDR2i | P value |
| Ildr2 | 0.972 | 0.089 | 0.000 | 0.792 | 0.078 | 0.002 |
| Srebp1c | 1.124 | 0.851 | 0.387 | 14.342 | 5.395 | 0.000 |
| Srebp2 | 1.134 | 0.740 | 0.010 | 1.480 | 1.297 | 0.170 |
| Fas | 0.828 | 0.639 | 0.046 | 42.089 | 3.733 | 0.000 |
| Ldlr | 0.853 | 0.239 | 0.008 | 2.342 | 0.812 | 0.001 |
| Apob | 1.016 | 0.418 | 0.000 | 0.878 | 0.398 | 0.000 |
| Acc1 | 0.994 | 0.904 | 0.296 | 6.586 | 1.640 | 0.016 |
| Mgat | 1.270 | 0.101 | 0.014 | 1.188 | 0.083 | 0.019 |
| Dgat1 | 0.987 | 0.453 | 0.007 | 0.599 | 0.350 | 0.039 |
| Dgat2 | 1.040 | 1.067 | 0.284 | 1.677 | 0.928 | 0.019 |
| Gpat | 0.896 | 0.754 | 0.012 | 4.384 | 0.916 | 0.013 |

Overexpression up
down

| | Fasted | | | Refed | | |
|---|---|---|---|---|---|---|
| | GFP | ILDR2 | P value | GFP | ILDR2 | P value |
| Ildr2 | 1.184 | 3.274 | 0.001 | 1.211 | 2.378 | 0.007 |
| Srebp1c | 1.181 | 1.188 | 0.970 | 13.378 | 18.441 | 0.049 |
| Srebp2 | 0.972 | 0.818 | 0.366 | 1.834 | 1.185 | 0.028 |
| Fas | 1.145 | 1.433 | 0.193 | 14.147 | 30.504 | 0.011 |
| Ldlr | 1.118 | 1.237 | 0.561 | 2.878 | 3.133 | 0.544 |
| Apob | 1.000 | 0.604 | 0.049 | 0.658 | 0.491 | 0.472 |
| Acc1 | 1.054 | 1.148 | 0.537 | 2.889 | 5.825 | 0.000 |
| Mgat | 1.300 | 4.403 | 0.015 | 1.836 | 9.129 | 0.018 |
| Dgat1 | 1.014 | 1.928 | 0.000 | 0.724 | 1.538 | 0.000 |
| Dgat2 | 1.079 | 0.898 | 0.118 | 1.471 | 1.543 | 0.650 |
| Gpat | 1.019 | 1.109 | 0.632 | 2.043 | 4.261 | 0.019 |

FIG. 29

Knockdown up
down

| | LacZi Fasted | | | ILDR2i Refed | | |
|---|---|---|---|---|---|---|
| | LacZi | ILDR2i | P value | LacZi | ILDR2i | P value |
| Glucose (mg/dL) | 175±29 | 116±20 | 0.215 | 379±79 | 214±28 | 0.232 |
| Insulin (μg/L) | 18.1±10.1 | 27.2±19.5 | 0.707 | 77.8±33.1 | 103.6±5.3 | 0.576 |

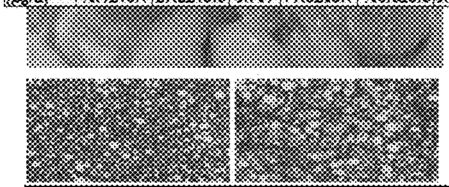

| | Fasted | | | Refed | | |
|---|---|---|---|---|---|---|
| | LacZi | ILDR2i | P value | LacZi | ILDR2i | P value |
| Plasma TG (mg/dL) | 97.8±36.0 | 133.6±16.1 | 0.365 | 121.0±24.5 | 195.4±24.2 | 0.135 |
| Plasma TC (mg/dL) | 110.3±2.6 | 104.0±2.5 | 0.173 | 112.6±9.7 | 133.7±8.5 | 0.231 |
| Hepatic TG (mg/g Liver) | 77.5±4.0 | 113.7±6.8 | 0.037 | 77.0±1.0 | 118.0±7.3 | 0.041 |
| Hepatic TC (mg/g Liver) | 10.6±1.5 | 18.5±3.4 | 0.188 | 8.9±0.7 | 16.9±3.6 | 0.203 |

Overexpression

| | GFP Fasted | | | ILDR2 Refed | | |
|---|---|---|---|---|---|---|
| | GFP | ILDR2 | P value | GFP | ILDR2 | P value |
| Glucose (mg/dL) | 161±10 | 174±24 | 0.420 | 224±29 | 263±30 | 0.349 |
| Insulin (μg/L) | 13.6±4.4 | 24.5±2.5 | 0.168 | 73.9±19.1 | 89.3±4.0 | 0.489 |

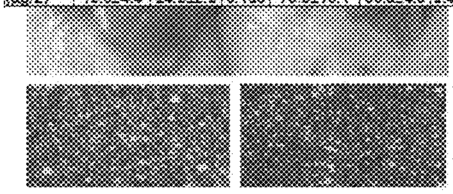

| | Fasted | | | Refed | | |
|---|---|---|---|---|---|---|
| | GFP | ILDR2 | P value | GFP | ILDR2 | P value |
| Plasma TG (mg/dL) | 94.3±27.2 | 129.8±43.4 | 0.538 | 137.6±18.3 | 135.4±11.7 | 0.925 |
| Plasma TC (mg/dL) | 134.0±3.5 | 129.0±3.8 | 0.383 | 143.1±4.8 | 130.9±2.6 | 0.086 |
| Hepatic TG (mg/g Liver) | 49.6±9.7 | 27.1±3.0 | 0.016 | 56.4±4.4 | 32.3±4.0 | 0.007 |
| Hepatic TC (mg/g Liver) | 7.7±0.6 | 5.6±0.3 | 0.036 | 6.4±0.2 | 5.1±0.29 | 0.015 |

*FIG. 32*

Relative gene expression from qRT-PCR data in ***ob/ob* mice** up
down

Knockdown

| | Fasted | | | Refed | | |
|---|---|---|---|---|---|---|
| | Lac2i | ILDR2i | P value | Lac2i | ILDR2i | P value |
| Ildr2 | 0.991 | 0.064 | 0.002 | 0.640 | 0.069 | 0.047 |

| | | | | | | |
|---|---|---|---|---|---|---|
| Srebp1c | 1.056 | 0.120 | 0.000 | 1.890 | 0.112 | 0.036 |
| Srebp2 | 0.951 | 0.488 | 0.000 | 1.009 | 0.326 | 0.028 |
| Fas | 0.986 | 0.140 | 0.019 | 1.481 | 0.188 | 0.000 |
| Ldlr | 1.025 | 0.119 | 0.006 | 0.867 | 0.107 | 0.008 |
| Apob | 1.053 | 0.141 | 0.000 | 1.003 | 0.153 | 0.030 |
| Acc1 | 0.991 | 0.171 | 0.010 | 1.616 | 0.183 | 0.033 |
| Mgat | 0.976 | 0.058 | 0.000 | 0.843 | 0.045 | 0.011 |
| Dgat1 | 1.047 | 0.295 | 0.007 | 0.895 | 0.275 | 0.051 |
| Dgat2 | 0.989 | 0.239 | 0.000 | 1.145 | 0.239 | 0.047 |
| Gpat | 1.014 | 0.134 | 0.004 | 0.531 | 0.114 | 0.003 |

Overexpression

| | Fasted | | | Refed | | |
|---|---|---|---|---|---|---|
| | GFP | ILDR2 | P value | GFP | ILDR2 | P value |
| Ildr2 | 1.016 | 2.056 | 0.000 | 0.652 | 2.308 | 0.000 |

| | | | | | | |
|---|---|---|---|---|---|---|
| Srebp1c | 0.993 | 1.503 | 0.038 | 1.875 | 4.581 | 0.000 |
| Srebp2 | 0.993 | 1.382 | 0.005 | 1.035 | 1.591 | 0.053 |
| Fas | 0.972 | 1.398 | 0.097 | 3.100 | 8.062 | 0.004 |
| Ldlr | 0.923 | 2.478 | 0.010 | 1.086 | 3.024 | 0.038 |
| Apob | 0.974 | 1.398 | 0.009 | 0.878 | 1.232 | 0.011 |
| Acc1 | 1.037 | 1.137 | 0.534 | 2.180 | 3.298 | 0.033 |
| Mgat | 1.047 | 1.963 | 0.004 | 0.794 | 1.862 | 0.028 |
| Dgat1 | 1.051 | 1.411 | 0.014 | 0.831 | 1.444 | 0.081 |
| Dgat2 | 0.974 | 1.768 | 0.018 | 1.077 | 1.768 | 0.013 |
| Gpat | 0.995 | 1.633 | 0.004 | 0.911 | 1.727 | 0.032 |

Mouse ILDR2 α-intracellular domain antigen (amino acid #298-401)
YRIQADKERDSMKVLYYVEKELAQFDPARRMRGRYNNTISELSSLHDDDSNFRQSY[redacted]
SGDLESNPDYWSGVMGGNSGTNRGPALEYNKEDRESFR (SEQ ID NO: 2)

FIG. 41A

Mouse ILDR2 α-extracellular domain antigen (amino acid #22-186)
QVTVPDKKKVAMLFQPTVLRCHFSTSSHQPAVVQWKFKSYCQDRMGESLGMSSPRAQ
ALSKRNLEWDPYLDCLDSRRTVRVVASKQGSTVTLGDFYRGREITIVHDADLQIGKLM
WGDSGLYYCIITTPDDLEGKNEDSVELLVLGRTGLLADLLPSFAVEIMPE (SEQ ID NO: 3)

FIG. 41B

Human ILDR2 Intracellular Domain Corresponding to amino acid 298-401 of Mouse ILDR2

YRIQADKERDSMKVLYYVEKELAQFDPARRMRGRYNNTISELSSLHEEDSNFRQSFHQ
MRSKQFPVSGDLESNPDYWSGVMGGSSGASRGPSAMEYNKEDRESFR (SEQ ID NO: 4)

FIG. 41C

Human ILDR2 Extracellular Domain Corresponding to amino acid #22-186 of Mouse ILDR2
QVTVPDKKKVAMLFQPTVLRCHFSTSSHQPAVVQWKFKSYCQDRMGESLGMSSTRAQ
SLSKRNLEWDPYLDCLDSRRTVRVVASKQGSTVTLGDFYRGREITIVHDADLQIGKLM
WGDSGLYYCIITTPDDLEGKNEDSVELLVLGRTGLLADLLPSFAVEIMPE (SEQ ID NO: 5)

FIG. 41D

Mouse ILDR2 β-intracellular domain antigen (amino acid # 354-363)
HQMRNKQFPM
(SEQ ID NO: 6)

FIG. 41E

Mouse ILDR2 β-extracellular domain antigen (amino acid #124-136)
IVHDADLQIGKLM (SEQ ID NO: 7)

FIG. 41F

Human ILDR2 Intracellular Peptide Corresponding to amino acid # 354-363 of Mouse ILDR2
HQMRSKQFPV
(SEQ ID NO: 8)

FIG. 41G

Human ILDR2 Extracellular Peptide Corresponding to amino acid #124-136 of Mouse ILDR2
IVHDADLQIGKLM (SEQ ID NO: 9)

FIG. 41H

*ILDR2* gene: DBA 5'UTR, transcript and 3'UTR (SEQ ID NO:10)

gtgggcatagcccatggaaatgtacgctgcaaatggagaatgtataggtgtagtctccctctccctcTccctccTcctcccc
.....cctccccctcTccctcccattctctctctccctctctctctct..gctcattttctgttaaaaaggccacatacgtt
ttaacagaaaaaagatttttgcctaaagggtttctcccctatggatcctaatttggttggggcctcttggttcgttgaacca
gatgcaccagccagggcacaacaa........aaacaaacaaacaaacaaacaccaTacaggtctaagccccaggagaagtt
atgccaagtccttgtagcctttctgtccctgacacccagtacaggtgcaaggaaacatcgagtcccagcctgcttggtggct
caagtagagcttgagtcgcagcccccgccacatggtccgccctctggggtggacttcgctgctaggTtctgacctcccagcc
ccgggagacggcacgtgaccgagaaactttggcgggcggtgttggcgcgggcggcggcgcggcgatcgagctcccccgcgcg
gcgagctctgctgcggggaggcgctcgccggtgccgcgcagcctgtgcgtgcgggaacggcccccgcagcccaatcggactc
tagagccagcggcagcgcgcctctcgcaggcggcggcgtccagcgcccggggccgggctgcgcggccagccccgagggctgc
ggcgccagggacgcgcggggcccgcgctccgccgccgccgccgcctgctgctgcgaggtcatccggatcttatcgtgccagc
tgatgcccgcttttcccactctggatctggatgggaagttggggaagATGGATAGGGTCGTGTTGGGTGGACTGCTGTCTT
CTGGTTAACAGCCATGGTTGAAGGCCTTCAGGTCACAGTGCCTGACAAGAAGAAGGTGGCCATGCTCTTCCAGCCCACTGTG
CTTCGATGCCACTTTTCCACGTCCTCCCATCAGCCTGCGGTGGTTCAGTGGAAGTTCAAATCCTACTGCCAGGATCGCATGG
GAGAATCCTTGGGCATGTCTTCTCCCCGAGCCCAAGCACTCAGCAAGAGGAACCTGGAATGGGACCCCTACTTGGATTGTTT
AGACAGCAGAAGGACCGTCCGAGTGGTAGCTTCCAAACAGGGCTCGACGGTTACCCTGGGAGATTTCTACAGGGGCAGAGAG
ATCACAATAGTTCACGATGCAGATCTTCAAATTGGAAAACTCATGTGGGAGACAGCGGACTCTACTACTGTATCATCACCA
CTCCGGATGACCTGGAAGGCAAAAACGAAGACTCAGTGGAACTGCTGGTGTTGGGCAGGACAGGGCTGCTTGCTGATCTCTT
GCCCAGTTTTGCTGTGGAGATTATGCCAGAGTGGGTGTTTGTCGGCCTGGTGATCCTGGGGATTTTCCTCTTCTTCGTGCTG
GTGGGGATCTGCTGGTGCCAATGCTGCCCTCACAGTTGCTGCTGCTATGTCCGCTGCCCATGCTGCCCAGATTCCTGCTGCT
GCCCTCAGGCCTTGTATGAAGCAGGGAAAGCAGCCAAGGCCGGGTACCCTCCCTCTGTCTCCGGTGTCCCCGGCCCCTACTC
CATCCCCTCTGTCCCTTTGGGAGGAGCCCCCTCTTCTGGCATGCTGATGGACAAGCCGCATCCACCTCCCCTGGCACCAAGT
GATTCCACTGGAGGAAGCCACAGTGTTCGAAAAGGTTACCGGATCCAGGCTGACAAAGAGAGAGACTCCATGAAGGTCCTGT
ACTATGTCGAGAAGGAGCTGGCTCAGTTTGATCCAGCCAGGAGGATGAGAGGCAGATATAACAACACCATCTCGGAACTCAG
CTCCCTGCATGATGATGACAGCAATTTCCGCCAGTCTTACCACCAGATGCGGAATAAGCAGTTCCCTATGTCTGGAGACCTG
GAAAGCAATCCCGACTACTGGTCAGGTGTCATGGGAGGCAACAGTGGGACCAACAGGGGGCCAGCCTTGGAGTATAACAAAG
AGGACCGTGAGAGCTTCAGGCACAGCCAGCAGCGCTCCAAATCCCAGATGCTGTCGCGCAAGAACTTTGCCACGGCGCTGCC
GGCCGTGTCGATGGACGAGCTGGCAGCCTTCGCAGACTCGTACGGCCAGCGGTCGCGGCGCGCCAATGGCAACAGCCACGAG
GCGCGGCGGGGAGCCGCTTCGAGCGCTCGGAGTCGCGGGCCCACGGTGCCTTCTACCAGGACGGCTCGCTGGATGAGTACT
ACGGGCGCGGACGCAGTCGCGAGCCCCCCGCAGACGGGGAGCGCGGCTGGACCTACAGCCCCCGCACCCGCACGCCGCCGGCC
GCCGGAGGATGCGCCCTCTGCCCGCGCCTGGTCAGCCGGACCCCGGGCACCGCGCCCAACTACGATCACTCGTACCTGAGCAGC
GTGCTGGAGCGCCAGGCGCGGCCGGAGACCAGCAGCCCGCGGGGCAGCCTGGAGACGCCGTCCAAGCTGGGCGCCCAGCTGG
GCCCGCGCAGCGCATCCTACTACGCCTGGTCGCCGCCAGCCACATACAAGGCTGGGGCCAGCGAGGGCGAAGACGAGGACGA
CGCGGCCGGATGAGGACGCGCTGCCACCCTACAGCGAGCTGGAGCTGAGCCGCGGAGAGCTGAGCCGGGGCCCGTCCTACCGT
GGGCGTGACCTGTCCTTCCACAGCAACTCGGAGAAGAGGAGGAAAAAGGAGCCCGTCAAGAAACCCGGTGACTTTCCAACCA
GGATGTCCCTTGTAGTCTGAtacttataagacacctctctggatgactggaaatcagatgcagactatggagacaagaccca
aatctgagagccggcaagcctaggatcttctctggccagcaGccaccttggaagctttgctgatctctgctttggcaaggga
tcctcctttaagaaggctgatttcaaatcttagtgcccaActatctcgagcaacttaccaagaaaacgctctgtgagaacat
atcacgtaataaccgaccaagtttatcttacacTcccacccccCacccccCatttccttagcagaaacaagactctgcgtcc
agttctgaagctggaagctttgaacccctgatctctagaaattacctatgcctgcagtatgtttttctaTgagtgctGttct
gtgcttagacagaggaatttactactacagttagaagaccgtctgctcacaagagagataaatggtaaaatgtaccttgtat
ccccttgcttccagtcactggtcaatgagtcttgttatgctaaaatcagaaggcctttagtgagcgtactggccgtgacctc
ctgggcaatcacagaaatggcttcaatttgctgctctgactcacaattctaagtggctgggacaaacagaggagagcatttt
gaaaaaccatcttaagtggtctttctttttccattcagaggacacaaactgcttttcatctttctgtcAaacagagtgacaa
tcctaaggttctccctgcccagcccacacCggtccctctcttTcctccctctcctggtcttttcagggctggtgcctctgag
ggtgttccactccatgcttcagtgtgaatagcttgtcatcaggtgcctttgacagatgcttcaaacaaacatttgagagaga
agaaaagcagaagtcggtgatacaaaatgaacaggaaatgaCatgtaggctcattatattttgaatgtgggttgtttcccca
caaacacactcagatttgtttttgttttttatttttggatttgtacttcacttaagaattatttctaccatcctgattc

FIG. 42 tgcagctgttgggcaccagggaatgtggtgtccacatcttttggcctcactggcccaccactattgatgctttgggg
aaaagaaggacagcacttcctcttcctgccattgcaaaaaaaaaaaaatgattttgcctgaatcccTaattgaact
tttgtaggtaaactgcaaaagtggcccacaaactcttcccctctcatgttcctgtgaagggatttgtcctcttgctgc
cacaggccctgccaaatgcacctcagctatcctacatgatgagagaagagcctggtcaccaccgtcattatctgtgc
ccatcttatcaactttaagcagacttggaagaacatctagccacgaccaacaaaagaactgcctagctgagccgagc
ccaaactggagattcccgcttgagaggagacattcagcattcctgtgttcGtttaCcatCgacgataaacctcccAt
cagaatatttgtctctggtcggttactcacccaaccttgggtgtcacacaaccttcactttgttagcagacttttc
aatctgcattattgtggtgagacacgtgactggatgaagtgactggagcaaggggatgcttgctatcccctaatcca
gtggtggtctacttctacttattgatctacatgtagtctctgattcactggtcagtatttccatggccaCgtgactg
gaattccagagtccattctgttagcatccattatacttcatgagatttccagaaaaggtcctctgtgagtggtgtaa
gagctgctgggttagggtgggtgttggggggtggaatcattacttggaggagaactggcctgcTaaaggacttcacg
gttgctttggcctgccctagatggatcaggaggatacttcagcccaatgctggcacttccaagggctggaagacaaa
agccataaccctGgtgctgagttttaggtttgCtagtgtccctggcctcagaacacctaggtctgatctgtctgttt
gggctctaaatcaatatggcaaaaacatcatttcttagtcaccagcttttgatttcaacttgctcaggcacttttga
agaatattggatagccgcagtagctattgttatactgagcactgtgtcaggcttcttagcaccaaagagccccatag
cacaggctacagagaccaaatatattgctttatagagccaggggcgtgtatgagcttggggaaagctgagggaGcga
tgaAtgaaagaaaaaagttaaaattggaaacataaggttctaaagacaacaagtctataggctgacaaattaaaaaa
aaAAtttcaatgtagagaagataacaggctttcaatataacggggaaagtggggcacagattgttctttataggggc
atgagtcacgtgggcttccagaccttcagtacagaggaaattcagttgcttctgggtccgtggataggagatgatct
gaatggacaaggctaagctggccgtccttgatgccctTgacatttctttacacacccctttgtttcttctccaaata
ctgtgtcctgCacaggaagtgcctatgcgtattagttcctttcctgtttttctagggcataagcaaagtgtaagagg
tgatctccatccactgatcccctacaatttaagaaggaagataagtcatgcccaagaaaggatgagtatattttatg
catatgataagaaatagtgctatggataaattataataaacccagagatttaaagtttttctttaaaaacaaaaacct
taaatgggaatattttgatatttaagtgttgtgtgtttgtccatccatTccattttaggacatgctcagtgatctg
caaagccaggctgtagaagtctgagctgaaaggaggtgaaggagaagaAagagggatgagtggcctcaggcaggagg
gaagagagtagaggcccgcttacaggagcttctgtctctgCctgtgactcacagctgagtcagggacaagctggagg
agggagtatggaagcaggtggcaggagaggtcccctggtgctcagagctcttctctaggctatgtatagactcatta
ggagactcaggactgtattcagttcttccatccaagcaagcccaggggagcttgggatttagtcctcctgccacttg
tatctacagcttggggtgcagtagTacctcacatgggttgggAacctcacctcccttctcatgatcctcactctgca
tgtggtgtaggggtgggcaccccagggtgagagggggctggcgctacatataaaaatctggttagatccgaagcagt
ctttgagaggagtggagtaactaacagacaccgctttggctcatctgctctccatccatttctaaatagatggataa
gccatcatccacatttatggagtcacaaaccagtcagatctttagattcccaatctataggcctttcctgctggatc
tgtgtttttgcaaaattgcctagtcataagaattacttgcctagggactggagagagatggcttaacagtcaaaaac
actgctttagccgaggacccgagtttggttcccagcactctactaatgctcacagctgtctgtaacttcaattccag
ggacccactgatctcatagagcatctgggagcactaaactcacatggtacgcatatataccatcaaaaaactctcag
gcacacaaaataaaaataaatacattgttaaaaactgaaaaagaaaggggctggagagatggctctgtgattacgtg
tgctggctactcttccagaggacccacattcatttttcagcacatggagactcccagcaccagttcagacacacaca
cacacacacacacacacacacacacacacACACACACACACACACgaaggcaaaatacacacctaacaaagaaataa
agcatttaaaaatacttggtaaaacaattacttgcctggggggactgggatgtggctcagttggtagagcActtgatt
agcatgcacaaagccctggttcaatccctagcacaataaactaggggtagtggcacatgcctgtgatcccaacatct
gggagagtttcaagttcaaggtcatccttggctacatagtgagttcaaggtcaccctgggctgtatgatactctgcc
ttaaagaaccaaacactgaaaataacaatgaaaaaacacaaggattactgactgccactgtcacaaatgctgttgCa
ctgtaccttggagaatggatgggtggatctggagtaaggatttgtattctgaacatatcctttttagaatgccttgtg
gtagatgcatttgggtggtgctatactggatcatacctctggtgcacccctatctgctggccaggaatattgtttgt
gctgtggattatttcattccaatatcactgtgaggtccctctaacttccttaggtctggcactggtgtggcatccag
cagtcccagctatgacactggagaatggctcaccagagtcaggctgaaaggaaacatttaaagggaggggcttggag
gacctccccccgggagActtcttgacatgttccaactcccagaatagtgatatgttgtgacaggctgagatcagaca
acaggaattacagacaatttcttattcccttaccatcctgaataaacttagctcatgaatagaaaaaaaaaaa.g
ccatcagagaaaatggcaaacgtaaatcattttaaagggtaaaaattaaaagctttgctaa...cataactttcat
gctaggaccaaaagtgggtggagaaaaaaatagtaaaatatatattacctattccaaaactgatttaattgcagcca
gaatcttatggaagtttagaagtgatgtatagagtacaggaatcacccatggaaattctaaggtcttagaaagcaaa

FIG. 42 cont.

aggttccctaccaggacctaccTcctagtcacttgggattacctgtgaagctcaaaggccctagtggcatcaaaggt
gagtaagaagaagccgagatgctttaagcaacagcgtgaggttggcatcaacggggcacatttgttcttcacagcaa
gcccagtgttttcccatcttacccaatgtggagctgggtctgaaagtgtgccaagtgatcacctattgccaaatagc
ttttagtctttagatggccttctgactgtccaggtcctaagcctacagtaatcacgggcccagcctctagtgtgttc
tcttcccaagcagAtggatagtggagagagccctgactcaatattcactcacacatcattggtgaggagaagctagg
aaggcaggcatttgccacttcatctatccacaggaggttccttgaagtctgccctgagaaggaggtgtctttgctgg
ggaggatcttcaGcatcagcatcaagctgtgaggggaaaggctttgacaaaagggttgccactttctgaattcttct
caaagaggaatttctaagccaagctacagattcatccaggctcagaattccatggctgtgggcaggagctgtcatct
tcactatattttgagatacattttttttt.aggtagaactcgaggtccagatctagaggggataaggGAgatgagaa
ggataaagttgtggcagttgagctaaaagtcatgttcgagtttttttggtgggtctgactggacaggggaaaatgtgg
tccgactCctttatctaaaagGttgggaaagatacccatagcttctctcttgccatgtttattaacaaagatgtta
gacactactccatgagaaatTtccttgtgaaaataaaaaccatgccatcaaaagagtcgggtgcaaagaCgcctact
tcatgagaatcacctgcccagttgtttttgtgccttgtctgtgacatcaaaactgaaacaTttatatcactgtcact
catggttttAttttcctgtgtcatacatacaaCgtgcatttgattgtaatgatttaaagtaaataaagcatttcatc
tacttttgtt

FIG. 42 – Cont.

*ILDR2* Anti-sense Transcript: DBA & B6 Variant Positions
(SEQ ID NO:11)

gactagCaaatgttgtctttaataatattttcaaagtctcagttaaaagatttagaaaacaagtggatcagttacat
tacaaataggttccctagatttaaAtaaaaggaaattcaatatatttctaagtttttaaaaaataatcAaaatttct
gttatttttctagctacatcataactcCggtcctagttcataagtacttctgcacaaagctTggaagtgagaaatct
gtgaccAcatctttcttacatttttaggcaggggccagagttcaagctacagcccagtggacacaaaggctaagtc
caccttccaaacTtctggcct......tcacaaccacaaacacctgcaatcctttgGtagggagggaaacaggtcta
cccaggccttaagtaggtctggtgagccttgggcagggcattacacagcaggagcAtggtctaaaaggtaagtgaac
tgaaaccaaggtatatgtccttcaccttgactttgagccatttggagagcagaatgggcctcttctaaagcacgggg
ttcatactggctctaaagacccc.ttttgggaccgggccagcagtagagaacatgctattagtagtggcttttt..
Ccccccttcctctcttggcccaacatagcctaaatcattgaagttcaccgcagtgattatataggacagagaaaaaca
tttgaacaagggagatAGATGCACGAGGAGGCCAGCTGCAGACAGCCTGAGTTccgggaagcctgccttaggtagaa
caaagacaattgtctccctattccaagaacagcatgtaggaagcctccctctctgtaagcaagttgggtttgagCtg
gagccaattcctgctgagtaacacaaataccacctgtgaGcatctacagctcacactggtcaggaccaAggctccca
ggcagaagattctggaatatgcgatcTCagcccttagcagcactcccttccaaCcatttagaaaaccatggtgcctg
cttttgttcctgcagATAACAACACCATCTCGGAACTCAGCTCCCTGCATGATGATGACAGCAATTTCCGCCAGTCT
TACCACCAGATGCGGAATAAGCAGTTCCCTATGTCTGGACACCTGGAAAGCAATCCCGACTACTGGTCAGGTGTCAT
GGGAGGCAACAGTGGACCAACAGGGGGCCAGCCTTGGAGTATAACAAAGAGGACCGTGAGAGCTTCAGGCACAG
gtgacggccatgagtgggaagggaccactgtgtatctgttcttctgtttctatagactatggaatatctcttacata
tattacacccttgtgatactgtgtgtgagaagtaaccagttaagcctttttgaaatgagtgtcttgggCcccgtaat
gagacactctc..catatgttttatcctagaacctttaaagaacccactatcttcaccaccctgatcatttgtcata
agaatgatAatcatgccaccatctcttgtaattaatccttatacttctaaaGagcagctactgtttatgttcctatt
ttaaggccaggaaatagaaagttccagatgctaaggaacttgcccagggtgataagtccaagcaacatttaataatc
tgtgtgacagctTgattcctgaatggcatgcTtgTactcattatctgtccttggaggacagtaggtac........
.ccccatttcctttaccTactgcagaggtctcaggcctcttgacttaataggcaacttggtccctgccccAgagaga
gatacaatcctttctatTttaCcGattattcctggtctcctgggaccagagctgtgtgttgctgtttgctgtggttg
tgagggtgggtgaagtaaaacatgtggctgtcacccaggggtctcaacacgataacaagctgatctgtgtgtttcag
cactacacagatcacaaggtattttcagatacacaaccattctggtcttccacacaaactcaggagagagccaggat
tgctctggctgaactcgcagcacGaaaggtgccaaagttgattTatcctgctgggctgaggggtaagatacacctgg
gcccctgaaactccaggggcgcgctgcaaggtttccatgcaGtaaccagtgaccatctgcccgcagCCAGCAGCGCT
CCAAATCCGAGATGCTGTCGCGGAAGAACTTTGCCACGGCCGTGCCGGCCGTGTCGATGGACGAGCTGGCAGCCTTC
GCAGACTCGTACGGCCAGCGGTCGCGGCGCCCAATGGCAACAGCCACGAGGCGCGGCGGGAGCCGCTTCGAGCG
CTCGGAGTCGCGGCCCACGGTGCCTTCTACCAGGACGGCTCGCTGGATGAGTACTACGGCGCGGACGCAGTCGCG
AGCCCCCGGGACACGGGGAGCGCGGCTGGACCTACAGCCCCGCACCCGCACGCCCGCCGGCCGCCGCAGGATGCGCCT
CTGCCGCGCCTGGTGAGCCGGACCCCGGGCACCGCGCCCAAGTACGATCACTCGTACCTGAGCAGCGTGCTGGAGCG
CCAGGCGCGGCCGGAGAGCAGCAGCCGCGGGGGCAGCCTGGAGACGCCGTCCAAGCTGGGCGCGCAGCTGGGCCCGC
GCAGCGCATCCTACTACGCCTGGTCGCCGCCAGCCACATACAAGGCTGGGGCCAGCGAGGGCGAAGACGAGGACGAC
GCGGCGGATGAGGACGCGCTGCCACCCTACAGCGAGCTGGAGCTGAGCCGCGGAGAGCTGAGCCGGGGCCCGTCCTA
CCGTGGGCGTGACCTGTCCTTCCACAGCAACTCGGAGAAGAGGAGGAAAAAGGAGCCCCGTCAAGAAACCCgtgaggA
ctcacccccatGtctctggagctgggtccgggaat

*FIG. 43*

*ILDR2* Anti-sense Transcript: DBA (SEQ ID NO:12) vs. B6 Genomic Sequence (SEQ ID NO:13)

```
                                                     cu_29
000000001 gactagcaaatgttgtctttaataatattttcaaagtctcagttaaaaga 000000050
>>>>>>>>> |||||| ||||||||||||||||||||||||||||||||||||||||||| >>>>>>>>>
168143416 gactagtaaatgttgtctttaataatattttcaaagtctcagttaaaaga 168143465

000000051 tttagaaaacaagtggatcagttacattacaaataggttccctagattta 000000100
>>>>>>>>> |||||||||||||||||||||||||||||||||||||||||||||||||| >>>>>>>>>
168143466 tttagaaaacaagtggatcagttacattacaaataggttccctagattta 168143515
       cu_30                                           cu_31
000000101 aataaaaggaaattcaatatatttctaagtttttaaaaaataatcaaaat 000000150
>>>>>>>>> | ||||||||||||||||||||||||||||||||||||||||||| |||| >>>>>>>>>
168143516 agtaaaaggaaattcaatatatttctaagtttttaaaaaataatcgaaat 168143565
                                          cu_32
000000151 ttctgttatttttctagctacatcataactccggtcctagttcataagta 000000200
>>>>>>>>> ||||||||||||||||||||||||||||||| |||||||||||||||||| >>>>>>>>>
168143566 ttctgttatttttctagctacatcataactctggtcctagttcataagta 168143615
                     cu_33                    cu_34
000000201 cttctgcacaaagcttggaagtgagaaatctgtgaccacatctttcttac 000000250
>>>>>>>>> ||||||||||||||| ||||||||||||||||||||| |||||||||||| >>>>>>>>>
168143616 cttctgcacaaagctaggaagtgagaaatctgtgaccgcatctttcttac 168143665

000000251 atttttaggcaggggccagagttcaagctacagcccagtggacacaaag 000000300
>>>>>>>>> |||||||||||||||||||||||||||||||||||||||||||||||||| >>>>>>>>>
168143666 atttttaggcaggggccagagttcaagctacagcccagtggacacaaag 168143715
                                cu_35  cu_36
000000301 gctaagtccaccttccaaacttctggcct......tcacaaccacaaaca 000000344
>>>>>>>>> |||||||||||||||||||| ||||||||      ||||||||||||||| >>>>>>>>>
168143716 gctaagtccaccttccaaacgtctggcctagccactcacaaccacaaaca 168143765
                     cu_37
000000345 cctgcaatcctttggtagggagggaaacaggtctacccaggccttaagta 000000394
>>>>>>>>> |||||||||||||| ||||||||||||||||||||||||||||||||||| >>>>>>>>>
168143766 cctgcaatcctttgatagggagggaaacaggtctacccaggccttaagta 168143815
                                                cu_38
000000395 ggtctggtgagccttgggcagggcattacacagcaggagcatggtctaaa 000000444
>>>>>>>>> |||||||||||||||||||||||||||||||||||||||| ||||||||| >>>>>>>>>
168143816 ggtctggtgagccttgggcagggcattacacagcaggagcgtggtctaaa 168143865

000000445 aggtaagtgaactgaaaccaaggtatatgtccttcaccttgactttgagc 000000494
>>>>>>>>> |||||||||||||||||||||||||||||||||||||||||||||||||| >>>>>>>>>
168143866 aggtaagtgaactgaaaccaaggtatatgtccttcaccttgactttgagc 168143915

000000495 catttggagagcagaatgggcctcttctaaagcacggggttcatactggc 000000544
>>>>>>>>> |||||||||||||||||||||||||||||||||||||||||||||||||| >>>>>>>>>
168143916 catttggagagcagaatgggcctcttctaaagcacggggttcatactggc 168143965
                     cu_39
000000545 tctaaagacccc.ttttgggaccgggccagcagtagagaacatgctatta 000000593
>>>>>>>>> |||||||||||| ||||||||||||||||||||||||||||||||||||| >>>>>>>>>
168143966 tctaaagacccccttttgggaccgggccagcagtagagaacatgctatta 168144015
```

*FIG. 44*

```
                   cu_40                                    cu_41
000000594 gtagtggcttttttt..ccccccttcctctcttggcccaacatagcctaaat 000000608
>>>>>>>>> ||||||||||||||   ||||||||||||||||||||||||||||||| ||| >>>>>>>>>
168144016 gtagtggctttttttttccccttcctctcttggcccaacatagcctgaat 168144065

000000609 cattgaagttcaccgcagtgattatataggacagagaaaaacatttgaac 000000658
>>>>>>>>> |||||||||||||||||||||||||||||||||||||||||||||||||| >>>>>>>>>
168144033 cattgaagttcaccgcagtgattatataggacagagaaaaacatttgaac 168144115
                        cu_42
000000659 aagggagatagatgcacgaggaggccagctgcagacagcctgagtt 000000700
>>>>>>>>> |||||||||                                    >>>>>>>>>
168144116 aagggagat.....................................  168144124

000000738 ccgggaagcctgccttaggtagaacaaagacaattgtctccctattccaa 000000787
>>>>>>>>> |||||||||||||||||||||||||||||||||||||||||||||||||| >>>>>>>>>
168144125 ccgggaagcctgccttaggtagaacaaagacaattgtctccctattccaa 168144174
                                               cu_43
000000788 gaacagcatgtaggaagcctccctctctgtaagcaagttgggtttgagct 000000837
>>>>>>>>> |||||||||||||||||||||||||||||||||||||||||||||||| | >>>>>>>>>
168144175 gaacagcatgtaggaagcctccctctctgtaagcaagttgggtttgagat 168144224
                                           cu_44
000000838 ggagccaattcctgctgagtaacacaaataccacctgtgagcatctacag 000000887
>>>>>>>>> ||||||||||||||||||||||||||||||||||||||||| |||||||| >>>>>>>>>
168144225 ggagccaattcctgctgagtaacacaaataccacctgtgatcatctacag 168144274
                      cu_45
000000888 ctcacactggtcaggaccaaggctcccaggcagaagattctggaatatgc 000000937
>>>>>>>>> ||||||||||||||||||| |||||||||||||||||||||||||||||| >>>>>>>>>
168144275 ctcacactggtcaggaccatggctcccaggcagaagattctggaatatgc 168144324
   cu_46                 cu_47
000000938 gatctcagcccttagcagcactcccttccaaccatttagaaaaccatggt 000000987
>>>>>>>>> ||||  ||||||||||||||||||||||||| |||||||||||||||||| >>>>>>>>>
168144325 gatcatagcccttagcagcactcccttccaatcatttagaaaaccatggt 168144374

000000988 gcctgcttttgttcctgcagATAACAACACCATCTCGGAACTCAGCTCCC 000001037
>>>>>>>>> |||||||||||||||||||||||||||||||||||||||||||||||||| >>>>>>>>>
168144375 gcctgcttttgttcctgcagATAACAACACCATCTCGGAACTCAGCTCCC 168144424

000001038 TGCATGATGATGACAGCAATTTCCGCCAGTCTTACCACCAGATGCGGAAT 000001087
>>>>>>>>> |||||||||||||||||||||||||||||||||||||||||||||||||| >>>>>>>>>
168144425 TGCATGATGATGACAGCAATTTCCGCCAGTCTTACCACCAGATGCGGAAT 168144474
                                       cu_9
000001088 AAGCAGTTCCCTATGTCTGGAGACCTGGAAAGCAATCCCGACTACTGGTC 000001137
>>>>>>>>> ||||||||||||||||||||||||||||||||||||||| |||||||||| >>>>>>>>>
168144475 AAGCAGTTCCCTATGTCTGGAGACCTGGAAAGCAATCCTGACTACTGGTC 168144524

000001138 AGGTGTCATGGGAGGCAACAGTGGGACCAACAGGGGGCCAGCCTTGGAGT 000001187
>>>>>>>>> |||||||||||||||||||||||||||||||||||||||||||||||||| >>>>>>>>>
168144525 AGGTGTCATGGGAGGCAACAGTGGGACCAACAGGGGGCCAGCCTTGGAGT 168144574
```

*FIG. 44 cont.*

```
000001188 ATAACAAAGAGGACCGTGAGAGCTTCAGGCACAGgtgacggccatgagtg 000001237
>>>>>>>>> |||||||||||||||||||||||||||||||||||||||||||||||||| >>>>>>>>>
168144575 ATAACAAAGAGGACCGTGAGAGCTTCAGGCACAGgtgacggccatgagtg 168144624

000001238 ggaagggaccactgtgtatctgttcttctgtttctatagactatggaata 000001287
>>>>>>>>> |||||||||||||||||||||||||||||||||||||||||||||||||| >>>>>>>>>
168144625 ggaagggaccactgtgtatctgttcttctgtttctatagactatggaata 168144674

000001288 tctcttacatatattacacccttgtgatactgtgtgtgagaagtaaccag 000001337
>>>>>>>>> |||||||||||||||||||||||||||||||||||||||||||||||||| >>>>>>>>>
168144675 tctcttacatatattacacccttgtgatactgtgtgtgagaagtaaccag 168144724


                                     cu_48
000001338 ttaagccttttgaaatgagtgtcttgggccccgtaatgagacactctc. 000001386
>>>>>>>>> |||||||||||||||||||||||||||| ||||||||||||||||||||  >>>>>>>>>
168144725 ttaagccttttgaaatgagtgtcttgggtcccgtaatgagacactctct 168144774
      cu_49
000001387 .catatgtttatcctagaacctttaaagaacccactatcttcaccaccc 000001435
>>>>>>>>>  ||||||||||||||||||||||||||||||||||||||||||||||||| >>>>>>>>>
168144775 ccatatgtttatcctagaacctttaaagaacccactatcttcaccaccc 168144824
                               cu_50
000001436 tgatcatttgtcataagaatgataatcatgccaccatctcttgtaattaa 000001485
>>>>>>>>> ||||||||||||||||||||||| |||||||||||||||||||||||||| >>>>>>>>>
168144825 tgatcatttgtcataagaatgatgatcatgccaccatctcttgtaattaa 168144874
                      cu_51
000001486 tccttatacttctaaagagcagctactgtttatgttcctattttaaggcc 000001535
>>>>>>>>> |||||||||||||||| ||||||||||||||||||||||||||||||||| >>>>>>>>>
168144875 tccttatacttctaaaaagcagctactgtttatgttcctattttaaggcc 168144924

000001536 aggaaatagaaagttccagatgctaaggaacttgcccagggtgataagtc 000001585
>>>>>>>>> |||||||||||||||||||||||||||||||||||||||||||||||||| >>>>>>>>>
168144925 aggaaatagaaagttccagatgctaaggaacttgcccagggtgataagtc 168144974
                                      cu_52
000001586 caagcaacatttaataatctgtgtgacagcttgattcctgaatggcatgc 000001635
>>>>>>>>> ||||||||||||||||||||||||||||||| |||||||||||||||||| >>>>>>>>>
168144975 caagcaacatttaataatctgtgtgacagctcgattcctgaatggcatgc 168145024
     cu_53 cu_54                         cu_55
000001636 ttgtactcattatctgtccttggaggacagtaggtac.......... 000001672
>>>>>>>>>  || |||||||||||||||||||||||||||||||||           >>>>>>>>>
168145025 ctgcactcattatctgtccttggaggacagtaggtacctaccccccc 168145071
                      cu_56
000001673 ccccatttcctttacctactgcagaggtctcaggcctcttgacttaatag 000001722
>>>>>>>>> |||||||||||||||| ||||||||||||||||||||||||||||||||| >>>>>>>>>
168145072 ccccatttcctttacccactgcagaggtctcaggcctcttgacttaatag 168145121
                            cu_57          cu_58 cu_59 cu_60
000001723 gcaacttggtccctgccccagagagagatacaatcctttctatttaccg 000001772
>>>>>>>>> ||||||||||||||||||| ||||||||||||||||||||||| ||| |  >>>>>>>>>
168145122 gcaacttggtccctgccccggagagagatacaatcctttctatgttaaca 168145171
```

*FIG. 44 cont.*

```
000001773 attattcctggtctcctgggaccagagctgtgtgttgctgtttgctgtgg 000001822
>>>>>>>>> |||||||||||||||||||||||||||||||||||||||||||||||||| >>>>>>>>>
168145172 attattcctggtctcctgggaccagagctgtgtgttgctgtttgctgtgg 168145221

000001823 ttgtgagggtgggtgaagtaaaacatgtggctgtcacccaggggtctcaa 000001872
>>>>>>>>> |||||||||||||||||||||||||||||||||||||||||||||||||| >>>>>>>>>
168145222 ttgtgagggtgggtgaagtaaaacatgtggctgtcacccaggggtctcaa 168145271

000001873 cacgataacaagctgatctgtgtgtttcagcactacacagatcacaaggt 000001922
>>>>>>>>> |||||||||||||||||||||||||||||||||||||||||||||||||| >>>>>>>>>
168145272 cacgataacaagctgatctgtgtgtttcagcactacacagatcacaaggt 168145321

000001923 attttcagatacacaaccattctggtcttccacacaaactcaggagagag 000001972
>>>>>>>>> |||||||||||||||||||||||||||||||||||||||||||||||||| >>>>>>>>>
168145322 attttcagatacacaaccattctggtcttccacacaaactcaggagagag 168145371
                                    cu_61
000001973 ccaggattgctctggctgaactcgcagcacgaaaggtgccaaagttgatt 000002022
>>>>>>>>> |||||||||||||||||||||||||||||| ||||||||||||||||||| >>>>>>>>>
168145372 ccaggattgctctggctgaactcgcagcacaaaaggtgccaaagttgatt 168145421

     cu_62
000002023 tatcctgctgggctgaggggtaagatacacctgggcccctgaaactccag 000002072
>>>>>>>>>  ||||||||||||||||||||||||||||||||||||||||||||||||| >>>>>>>>>
168145422 catcctgctgggctgaggggtaagatacacctgggcccctgaaactccag 168145471
                                 cu_63
000002073 gggcgcgctgcaaggtttccatgcagtaaccagtgaccatctgcccgcag 000002122
>>>>>>>>> ||||||||||||||||||||||||| |||||||||||||||||||||||| >>>>>>>>>
168145472 gggcgcgctgcaaggtttccatgcaataaccagtgaccatctgcccgcag 168145521
                     cu_10
000002123 CCAGCAGCGCTCCAAATCCGAGATGCTGTCGCGGAAGAACTTTGCCACGG 000002172
>>>>>>>>> |||||||||||||||||| ||||||||||||||||||||||||||||||| >>>>>>>>>
168145522 CCAGCAGCGCTCCAAATCTGAGATGCTGTCGCGGAAGAACTTTGCCACGG 168145571

000002173 GCGTGCCGGCCGTGTCGATGGACGAGCTGGCAGCCTTCGCAGACTCGTAC 000002222
>>>>>>>>> |||||||||||||||||||||||||||||||||||||||||||||||||| >>>>>>>>>
168145572 GCGTGCCGGCCGTGTCGATGGACGAGCTGGCAGCCTTCGCAGACTCGTAC 168145621

000002223 GGCCAGCGGTCGCGGCGCGCCAATGGCAACAGCCACGAGGCGCGGGCGGG 000002272
>>>>>>>>> |||||||||||||||||||||||||||||||||||||||||||||||||| >>>>>>>>>
168145622 GGCCAGCGGTCGCGGCGCGCCAATGGCAACAGCCACGAGGCGCGGGCGGG 168145671

000002273 GAGCCGCTTCGAGCGCTCGGAGTCGCGGGCCCACGGTGCCTTCTACCAGG 000002322
>>>>>>>>> |||||||||||||||||||||||||||||||||||||||||||||||||| >>>>>>>>>
168145672 GAGCCGCTTCGAGCGCTCGGAGTCGCGGGCCCACGGTGCCTTCTACCAGG 168145721
                                              rs32778376
000002323 ACGGCTCGCTGGATGAGTACTACGGGCGCGGACGCAGTCGCGAGCCCCCG 000002372
>>>>>>>>> |||||||||||||||||||||||||||||||||||||||||||||| ||| >>>>>>>>>
168145722 ACGGCTCGCTGGATGAGTACTACGGGCGCGGACGCAGTCGCGAGCCGCCG 168145771
```

*FIG. 44 cont.*

```
               rs31867924
000002373 GGAGACGGGGAGCGCGGCTGGACCTACAGCCCCGCACCCGCACGCCGCCG 000002422
>>>>>>>>> |||||||||||||| ||||||||||||||||||||||||||||||||||| >>>>>>>>>
168145772 GGAGACGGGGAGCGTGGCTGGACCTACAGCCCCGCACCCGCACGCCGCCG 168145821
          rs30498849
000002423 GCCGCCGGAGGATGCGCCTCTGCCGCGCCTGGTGAGCCGGACCCCGGGCA 000002472
>>>>>>>>> |||||| ||||||||||||||||||||||||||||||||||||||||||| >>>>>>>>>
168145822 GCCGCCAGAGGATGCGCCTCTGCCGCGCCTGGTGAGCCGGACCCCGGGCA 168145871

000002473 CCGCGCCCAAGTACGATCACTCGTACCTGAGCAGCGTGCTGGAGCGCCAG 000002522
>>>>>>>>> |||||||||||||||||||||||||||||||||||||||||||||||||| >>>>>>>>>
168145872 CCGCGCCCAAGTACGATCACTCGTACCTGAGCAGCGTGCTGGAGCGCCAG 168145921

000002523 GCGCGGCCGGAGAGCAGCAGCCGCGGGGGCAGCCTGGAGACGCCGTCCAA 000002572
>>>>>>>>> |||||||||||||||||||||||||||||||||||||||||||||||||| >>>>>>>>>
168145922 GCGCGGCCGGAGAGCAGCAGCCGCGGGGGCAGCCTGGAGACGCCGTCCAA 168145971

000002573 GCTGGGCGCGCAGCTGGGCCCGCGCAGCGCATCCTACTACGCCTGGTCGC 000002622
>>>>>>>>> |||||||||||||||||||||||||||||||||||||||||||||||||| >>>>>>>>>
168145972 GCTGGGCGCGCAGCTGGGCCCGCGCAGCGCATCCTACTACGCCTGGTCGC 168146021
        rs32723583     rs32602488
000002623 CGCCAGCCACATACAAGGCTGGGGCCAGCGAGGGCGAAGACGAGGACGAC 000002672
>>>>>>>>> ||||| |||||||||| ||||||||||||||||||||||||||||||||| >>>>>>>>>
168146022 CGCCAACCACATACAAAGCTGGGGCCAGCGAGGGCGAAGACGAGGACGAC 168146071

000002673 GCGGCGGATGAGGACGCGCTGCCACCCTACAGCGAGCTGGAGCTGAGCCG 000002722
>>>>>>>>> |||||||||||||||||||||||||||||||||||||||||||||||||| >>>>>>>>>
168146072 GCGGCGGATGAGGACGCGCTGCCACCCTACAGCGAGCTGGAGCTGAGCCG 168146121

000002723 CGGAGAGCTGAGCCGGGGCCCGTCCTACCGTGGGCGTGACCTGTCCTTCC 000002772
>>>>>>>>> |||||||||||||||||||||||||||||||||||||||||||||||||| >>>>>>>>>
168146122 CGGAGAGCTGAGCCGGGGCCCGTCCTACCGTGGGCGTGACCTGTCCTTCC 168146171
                                          cu_11
000002773 ACAGCAACTCGGAGAAGAGGAGGAAAAAGGAGCCCGTCAAGAAACCCgtg 000002822
>>>>>>>>> |||||||||||||||||||||||||||||||||||| ||||||||||||| >>>>>>>>>
168146172 ACAGCAACTCGGAGAAGAGGAGGAAAAAGGAGCCCGCCAAGAAACCCgtg 168146221
          cu_64   cu_65
000002823 aggactcacccccatgtctctggagctgggtccgggaat 000002861
>>>>>>>>> ||| ||||||||||| |||||||||||||||||||||||| >>>>>>>>>
168146222 agggctcacccccatctctctggagctgggtccgggaat 168146260
```

*FIG. 44 – cont.*

EXON 10

| | | |
|---|---|---|
| Mm_*Lisch-like* | -----[illegible] | 646 |
| Hs_clorf32 | -----[illegible] | 639 |
| Dr_*Lisch-like* | [illegible] | 590 |
| Mm_*LSR* | -----[illegible] | 594 |

FIG. 45 – Cont.

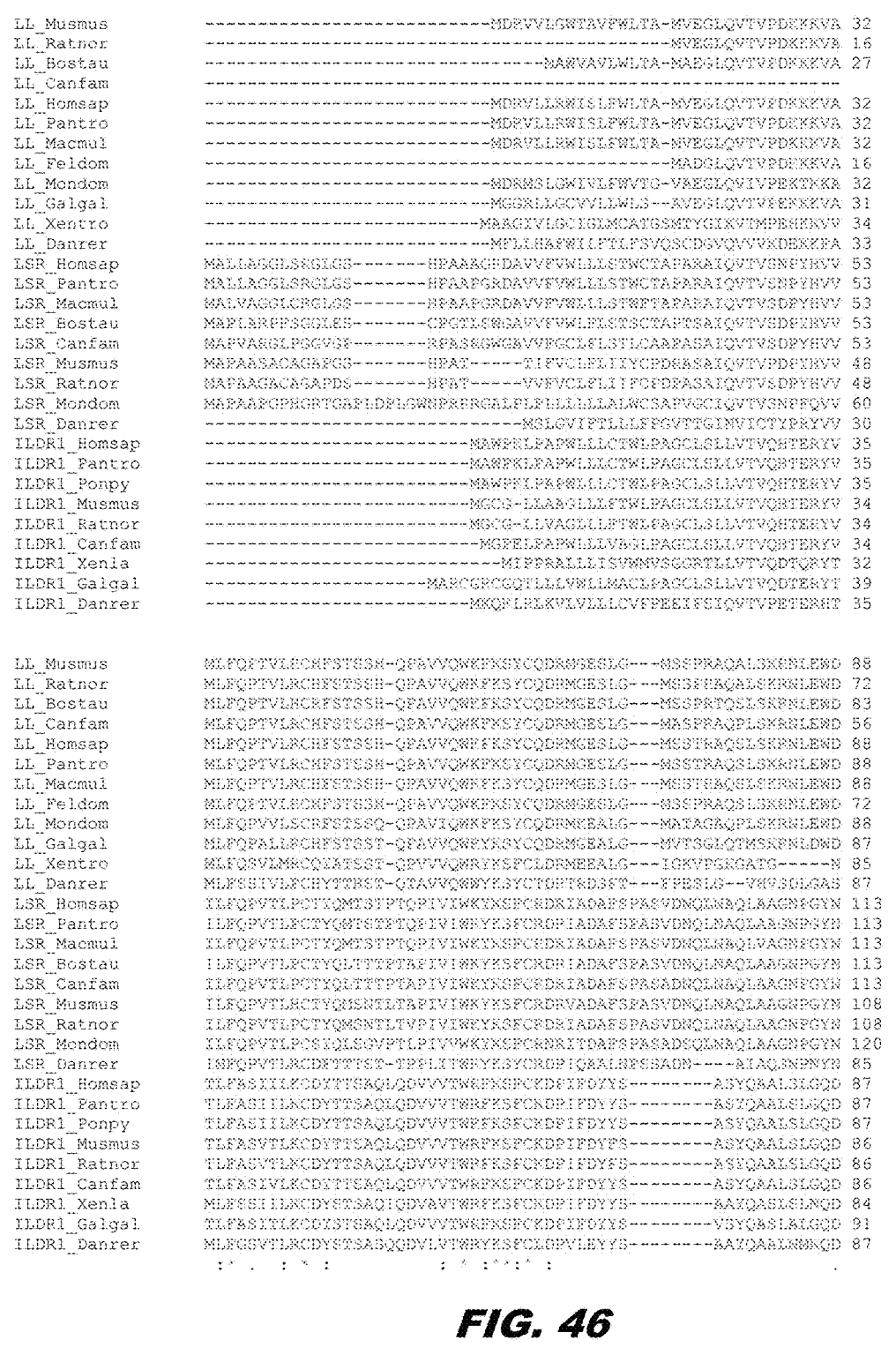

```
LL_Musmus       ----------------------------MDRVVLGWTAVFWLTA-MVEGLQVTVPDKKKVA 32
LL_Ratnor       --------------------------------------------MVEGLQVTVPDKKKVA 16
LL_Bostau       ---------------------------------MAWVAVLWLTA-MAEGLQVTVPDKKKVA 27
LL_Canfam       ------------------------------------------------------------
LL_Homsap       ----------------------------MDRVLLRWISLFWLTA-MVEGLQVTVPDKKKVA 32
LL_Pantro       ----------------------------MDRVLLRWISLFWLTA-MVEGLQVTVPDKKKVA 32
LL_Macmul       ----------------------------MDRVLLRWISLFWLTA-MVEGLQVTVPDKKKVA 32
LL_Feldom       --------------------------------------------MADGLQVTVPDKKKVA 16
LL_Mondom       ----------------------------MDKMSLGWIVLFWVTG-VAEGLQVIVPEKTKKA 32
LL_Galgal       ----------------------------MGGRLLGCVVLLWLS--AVEGLQVTVPEKKKVA 31
LL_Xentro       --------------------------MAAGIVLGCIGLMCATGSMTYGIKVTMPEHKKVV 34
LL_Danrer       ---------------------------MFLLHAFWILFTLFSVQSCDGVQVVVKDEKKFA 33
LSR_Homsap      MALLAGGLSRGLGS-------HPAAAGRDAVVFVWLLLSTWCTAPARAIQVTVSNPYHVV 53
LSR_Pantro      MALLAGGLSRGLGS-------HPAAPGRDAVVFVWLLLSTWCTAPARAIQVTVSNPYHVV 53
LSR_Macmul      MALVAGGLCRGLGS-------HPAAPGRDAVVFVWLLLSTWFTAPARAIQVTVSDPYHVV 53
LSR_Bostau      MAPLARPPSGGLES-------CPGTLSRGAVVFVWLPLSTSCTAPTSAIQVTVSDPYHVV 53
LSR_Canfam      MAPVARGLPGGVGP-------RPASRGWGAVVFGCLFLSTLCAAPASAIQVTVSDPYHVV 53
LSR_Musmus      MAPAASACAGAPGS-------HPAT-----TIFVCLFLIIYCPDRASAIQVTVPDPYHVV 48
LSR_Ratnor      MAPAAGACAGAPDS-------HPAT-----VVFVCLFLIIFCPDPASAIQVTVSDPYHVV 48
LSR_Mondom      MAPAAPGPHGRTGAPLDPLGWNPRRRGALPLPLLLLLLALWCSAPVGCIQVTVSNPPQVV 60
LSR_Danrer      ------------------------------MSLGVIPTLLLFPGVTTGINVICTYPRYVV 30
ILDR1_Homsap    -------------------------MAWPKLPAPWLLLCTWLPAGCLSLLVTVQHTERYV 35
ILDR1_Pantro    -------------------------MAWPKLPAPWLLLCTWLPAGCLSLLVTVQHTERYV 35
ILDR1_Ponpy     -------------------------MAWPKLPAPWLLLCTWLPAGCLSLLVTVQHTERYV 35
ILDR1_Musmus    -------------------------MGCG-LLAAGLLLFTWLPAGCLSLLVTVQHTERYV 34
ILDR1_Ratnor    -------------------------MGCG-LLVAGLLLFTWLPAGCLSLLVTVQHTERYV 34
ILDR1_Canfam    --------------------------MGPELPAPWLLLVAGLPAGCLSLLVTVQHTERYV 34
ILDR1_Xenla     ----------------------------MIPPRALLLISVWMVSGGRTLLVTVQDTQRYT 32
ILDR1_Galgal    ---------------------MARCGRCGQTLLLVWLLMACLPAGCLSLLVTVQDTERYT 39
ILDR1_Danrer    -------------------------MKQPLRLKVLVLLLCVFPEEIFSIQVTVPETERHT 35


LL_Musmus       MLFQPTVLRCHFSTSSH-QPAVVQWKFKSYCQDRMGESLG---MSSPRAQALSKRNLEWD 88
LL_Ratnor       MLFQPTVLRCHFSTSSH-QPAVVQWKFKSYCQDRMGESLG---MSSPHAQALSKRNLEWD 72
LL_Bostau       MLFQPTVLHCRFSTSSH-QPAVVQWKFKSYCQDRMGESLG---MSSPRTQSLSKRNLEWD 83
LL_Canfam       MLFQPTVLRCHFSTSSH-QPAVVQWKFKSYCQDRMGESLG---MASPRAQPLSKRNLEWD 56
LL_Homsap       MLFQPTVLRCHFSTSSH-QPAVVQWKFKSYCQDRMGESLG---MSSTRAQSLSKRNLEWD 88
LL_Pantro       MLFQPTVLRCHFSTSSH-QPAVVQWKFKSYCQDRMGESLG---MSSTRAQSLSKRNLEWD 88
LL_Macmul       MLFQPTVLRCHFSTSSH-QPAVVQWKFKSYCQDRMGESLG---MSSTRAQSLSKRNLEWD 88
LL_Feldom       MLFQPTVLRCHFSTSSH-QPAVVQWKFKSYCQDRMGESLG---MSSPRAQSLSKRNLEWD 72
LL_Mondom       MLFQPVVLSCRFSTSSQ-QPAVIQWKFKSYCQDRMKEALG---MATAGAQPLSKRNLEWD 88
LL_Galgal       MLFQPALLRCHFSTSST-QPAVVQWKYKSYCQDRMGEALG---MVTSGLQTMSKRNLDWD 87
LL_Xentro       MLFQSVLMRCQIATSST-QPVVVQWRYKSFCLDRMEEALG---IGKVPGKGATG-----N 85
LL_Danrer       MLFSSIVLRCHYTTHST-QTAVVQWWYKSYCTDRTRDSFT---FPESLG--VHVSDLGAS 87
LSR_Homsap      ILFQPVTLPCTYQMTSTPTQPIVIWKYKSFCRDRIADAFSPASVDNQLNAQLAAGNPGYN 113
LSR_Pantro      ILFQPVTLPCTYQMTSTPTQPIVIWKYKSFCRDRIADAFSPASVDNQLNAQLAAGNPGYN 113
LSR_Macmul      ILFQPVTLPCTYQMTSTPTQPIVIWKYKSFCRDRIADAFSPASVDNQLNAQLVAGNPGYN 113
LSR_Bostau      ILFQPVTLPCTYQLTTTPTAPIVIWKYKSFCRDRIADAFSPASVDNQLNAQLAAGNPGYN 113
LSR_Canfam      ILFQPVTLPCTYQLTTTPTAPIVIWKYKSFCRDRIADAFSPASADNQLNAQLAAGNPGYN 113
LSR_Musmus      ILFQPVTLHCTYQMSNTLTAPIVIWKYKSFCRDRVADAFSPASVDNQLNAQLAAGNPGYN 108
LSR_Ratnor      ILFQPVTLPCTYQMSNTLTVPIVIWKYKSFCRDRIADAFSPASVDNQLNAQLAAGNPGYN 108
LSR_Mondom      ILFQPVTLPCSIQLSGVPTLPIVVWKYKSFCRNRITDAFSPASADSQLNAQLAAGNPGYN 120
LSR_Danrer      IMFQPVTLRCDFTTTST-TPPLITWKYKSYCRDPIQAALNPSSADN----AIAQSNPNYN 85
ILDR1_Homsap    TLFASIILKCDYTTSAQLQDVVVTWRFKSFCKDPIFDYYS--------ASYQAALSLGQD 87
ILDR1_Pantro    TLFASIILKCDYTTSAQLQDVVVTWRFKSFCKDPIFDYYS--------ASYQAALSLGQD 87
ILDR1_Ponpy     TLFASIILKCDYTTSAQLQDVVVTWRFKSFCKDPIFDYYS--------ASYQAALSLGQD 87
ILDR1_Musmus    TLFASVTLKCDYTTSAQLQDVVVTWRFKSFCKDPIFDYFS--------ASYQAALSLGQD 86
ILDR1_Ratnor    TLFASVTLKCDYTTSAQLQDVVVTWRFKSFCKDPIFDYFS--------ASYQAALSLGQD 86
ILDR1_Canfam    TLFASIVLKCDYTTSAQLQDVVVTWRFKSFCKDPIFDYYS--------ASYQAALSLGQD 86
ILDR1_Xenla     MLFSSIILKCDYSTSAQIQDVAVTWRFKSFCKDPIFDYYS--------AAYQASLSLNQD 84
ILDR1_Galgal    TLFASITLKCDYSTSAQLQDVVVTWRFKSFCKDPIFDYYS--------VSYQASLALGQD 91
ILDR1_Danrer    MLFGSVTLRCDYSTSASQQDVLVTWRYKSFCLDPVLEYYS--------AAYQAALNMNQD 87
                :* .   : * :          : * :**:* :                          .
```

FIG. 46

```
LL_Musmus       PYLDCLDSPRTVRVVASKQG-STVTLGDFYRGREITIVHDADLQIGRLMWGDSGLYYCII 147
LL_Ratnor       PYLDCLDSRRTVRVVASKQG-STVTLGDFYRGREITIVHDADLQIGKLMWGDSGLYYCII 131
LL_Bostau       PYLDCLDSRRTVKVVASKQG-STVTLGDFYRGREITIVHDADLQISKLMWGDSGLYYCII 142
LL_Canfam       PYLDCLDSPRTVRVVASKQG-STVTLGDFYRGREITIVHDADLQIGRLMWGDSGLYYCII 115
LL_Homsap       PYLDCLDSRRTVRVVASKQG-STVTLGDFYRGREITIVHDADLQIGKLMWGDSGLYYCII 147
LL_Pantro       PYLDCLDSRRTVKVVASKQG-STVTLGDFYRGREITIVHDADLQIGKLMWGDSGLYYCII 147
LL_Macmul       PYLDCLDSPRTVRVVASKQG-STVTLGDFYRGREITIVHDADLQIGRLMWGDSGLYYCII 147
LL_Feldom       PYLDCLDSRRTVRVVASKQG-STVTLGDFYRGREITIVHDADLQIGKLMWGDSGLYYCII 131
LL_Mondom       PYLDCVDSRRTVKVVASKQG-AVVTLGEFYRGPDITPGEGAELRIGKVMWGDSGLYYCIV 147
LL_Galgal       PYLDCVDSPRTVPVVASKQG-SAVTIGDFYKERDVSIVHDADLQIGRLMWGDSGLYYCII 146
LL_Xentro       QYLDCADGSRTVRTVASKQG-STVTLGDFYRGRDITIVNDADLQFGNMQWGDSGLYYCLV 144
LL_Danrer       SHPDCSDNSRTVKIVASGQG-ASMTLAEHYRGRDISIINNADLHISQLQWGDSGVYFCKV 146
LSR_Homsap      PYVECQDSVRTVRVVATKQG-NAVTLGDYYQGRRITITGNADLTFDQTAWGDSGVYYCSV 172
LSR_Pantro      PYVECQDSVRTVRVVATKQG-NAVTLGDYYQGRRITITGNADLTFDQTAWGDSGVYYCSV 172
LSR_Macmul      PYVECQDSVRTIKVVATKQG-NAVTLGDYYQGRRITITGNADLTFDETAWGDSGVYYCSV 172
LSR_Bostau      PYVECQDSARTVRVVATKQG-NAVTLGDYYQGRRITITG--------------------- 151
LSR_Canfam      PYVECQDSMRTVRVVATKQG-NAVTLGDYYQGRRITITGNADLTFDQTGWGDSGVYYCSV 172
LSR_Musmus      PYVECQDSVRTVKVVATKQG-NAVTLGDYYQGRRITITGNADLTFEQTAWGDSGVYYCSV 167
LSR_Ratnor      PYVECQDSVRTVRVVATKQG-NAVTLGDYYQGRRITITGNADLTFEQTAWGDSGVYYCSV 167
LSR_Mondom      PYVECQDSVRTVRVVATKQG-NAVTLGDFYQGRRITITGNADLTFDQTAWGDSGVYYCSV 179
LSR_Danrer      PNIECADSARTVKIVASKQ--TAVTLGKEYQGRQISITNNADLSIVQTAWGDSGVYVCSA 143
ILDR1_Homsap    PSNDCNDNQREVRIVAQRRGQNEPVLGVDYRQRKITIQNRADLVINEVMWWDHGVYYCTI 147
ILDR1_Pantro    PSNDCNDNQREVRIVAQRRGQNEPVLGVDYRQRKITIQNRADLVINEVMWWDHGVYYCTI 147
ILDR1_Ponpy     PSNDCNDNQREVKIVAQRRGQNEPVLGVDYRQRKITIQNRADLVINEVMWWDHGVYYCTI 147
ILDR1_Musmus    PSNDCSDNQREVRIVAQRRGQSEPVLGVDYRQRKITIQNRADLVINEVMWWDHGVYYCTI 146
ILDR1_Ratnor    PSNDCSDNQREVRIVAQRRGQSEPVLGVDYRQRKITIQNRADLVINEVMWWDHGVYYCTI 146
ILDR1_Canfam    PSNDCNDSQREVKIVAQRRGQNEPVLGVDYRQRKITIQNRADLVINEVMWWDHGVYYCTI 146
ILDR1_Xenla     PANDCNDNQREVRIVIQKRGQNEPVLGVDYRQRKITIQNKADLVISEVMWWDHGVYFCSV 144
ILDR1_Galgal    PSDDCNDVQRKVRIVIQRYGQNEPVLGVDYRQRKITIQNRADLVISEVMWWDHGVYYCTV 151
ILDR1_Danrer    PANDCRDSKRTVKIVIQKRGINEPVLGTEYRQRKISIKNSADLSMNEIMWWDNGMYFCSI 147
                  :*  *   * :* *          .:.   *: : :::

LL_Musmus       TTPDDLEGKNEDSVELLVLGRTGLLADLLPSFAVEIMPEWVFVGLVILGIFLFFVLVGIC 207
LL_Ratnor       TTPDDLEGKNEESVELLVLGRTGLLADLLPSFAVEIMPEWVFVGLVILGIFLFFVLVGIC 191
LL_Bostau       TTPDDLEGKNEDSVEVLVLGRTGLLADLLPSFAVEIMPEWVFVGLVILGVFLFFVLVGIC 202
LL_Canfam       TTPDDLEGKNEDLAELLVLGRTGLLADLLPSFAVEIMPEWVFVGLVILGVFLFFVLVGIC 175
LL_Homsap       TTPDDLEGKNEDSVELLVLGRTGLLADLLPSFAVEIMPEWVFVGLVLLGVFLFFVLVGIC 207
LL_Pantro       TTPDDLEGKNEDSVELLVLGRTGLLADLLPSFAVEIMPEWVFVGLVLLGVFLFFVLVGIC 207
LL_Macmul       TTPDDLEGKNEDSVELLVLGRTGLLADLLPSFAVEIMPEWVFVGLVLLGVFLFFVLVGIC 207
LL_Feldom       TTPDDLEGKNEDSAELLVL--------------------EWVFVGLVILGIFLFFVLVGIC 172
LL_Mondom       TTPDDVEGKNEDSVELLVLGRTGWLAALLPSFAVKIMSEWVFVGLVILGVFLFFLLVGIC 207
LL_Galgal       ITPDDVEGKSEESVELLVLGRTGLLADLLPSFAVEIMPEWVFVGLVILGAFLFFLLVGIC 206
LL_Xentro       VTSDDLEGKNEDPVEILVLGQNG--ADQLVGAAADIRPEWAFVCLVILGTFLFFVMVGIC 202
LL_Danrer       IISDDLEGKNEGQVELLVQGRTGVLDDILPEFDLEIMPEWAFVGVVVVGSILFLLLVGIC 206
LSR_Homsap      VSAQDLQGNNEAYAELIVLGRTSGVAELLPGFQAGPIEDWLFVVVVCLAAFLIFLLLGIC 232
LSR_Pantro      VSAQDLQGNNEAYAELIVLGRTSGVAELLPGFQAGPMEDWLFVVVVCLAAFLIFLLLGIC 232
LSR_Macmul      VSAQDLEGNNEAYAELIVLGRTSGVAELLPGFQAGPMEDWLFVVVVCLAAFLVFLLLGIC 232
LSR_Bostau      --------------------SRTSGVAELLPGFQAGPMEDWLFVVVVCLAAFLVFLLLGIC 192
LSR_Canfam      VSAQDLQGNNEAYAELIVLGRTSGVAELLPGFQAGPMEDWLFVVVVCLAVFLVFLLLGIC 232
LSR_Musmus      VSAQDLDGNNEAYAELIVLGRTSEAPELLPGFRAGPLEDWLFVVVVCLASLLFFLLLGIC 227
LSR_Ratnor      VSAQDLDGNNEAYAELIVLGRTSEAPELLPGFRAGPLEDWLFVVVVCLASLLFLLLGIC 227
LSR_Mondom      ISAQDLQGNNEAYAELIVLGRTSGVAELLPDFQIGPMEDWLFVVVVGLAAFLVFLLLGIC 239
LSR_Danrer      ASAQDLSGNGECYTELIVLGRKSNTTDLLPGIDLLIMEDWLLVVLVVLGFLLLLLLIGIC 203
ILDR1_Homsap    EAPGDTSGDPDKEVKLIVLH--------------------WLTVIFIILGALLLLLLIGVC 188
ILDR1_Pantro    EAPGDTSGDPDKEVKLIVLH--------------------WLTVIFIILGALLLLLLIGVC 188
ILDR1_Ponpy     EAPGDTSGDPDKEVKLIVLH--------------------WLTVIFIILGALLLLLLIGVC 188
ILDR1_Musmus    EAPGDTSGDPDKEVKLIVLH--------------------WLTVIFIILGALLLLLLIGVC 187
ILDR1_Ratnor    EAPGDTSGDPDKEVKLIVLH--------------------WLTVIFIILGALLLLLLIGVC 187
ILDR1_Canfam    EAPGDTSGDPDKEVKLIVLH--------------------WLTVIFIILGALLLLLLIGVC 187
ILDR1_Xenla     EAQGDTSGDPDKEVKLVVLH--------------------WLTVLFIILGALFLFLLIGIC 185
ILDR1_Galgal    EAPGDTSGDPDKEVKLIVLH--------------------WLTVLLIILGGLLLLLLIGIC 192
ILDR1_Danrer    DAPGDVVGDSDKEIRLIVYN--------------------WLTVLLIILGALLLIILFGVC 188
                                                        *   * .: :. ::.:::.*:*
```

FIG. 46 – Cont.

```
LL_Musmus       WCQCCPHSCCCYVRCPCCPDSCCCPQALYEAGKAAKAGY----PPSVSG----------- 252
LL_Ratnor       WCQCCPHSCCCYVRCPCCPDSCCCPQALYEAGKAANAGY----PPSVSG----------- 236
LL_Bostau       WCQCCPHSCCCYIRCPCCPDSCCCPQALYEAGKAAKAGY----PPSVSG----------- 247
LL_Canfam       WCQCCPHSCCCYIRCPCCPDSCCCPQALYEAGKAAKAGY----PPSVSG----------- 220
LL_Homsap       WCQCCPHSCCCYVRCPCCPDSCCCPQALYEAGKAAKAGY----PPSVSG----------- 252
LL_Pantro       WCQCCPHSCCCYVRCPCCPDSCCCPQALYEAGKAAKAGY----PPSVSG----------- 252
LL_Macmul       WCQCCPHSCCCYVRCPCCPESCCCPQALYEAGKAAKAGY----PPSVSG----------- 252
LL_Feldom       WCQCCPHSCCCYIRCPCCPDSCCCPQALYEAGKAAKAGY----PPSVSG----------- 217
LL_Mondom       WCQCCPHSCCCYVRCPCCPDSCCCPKALYEAGKAAKSGY----PPSVSS----------- 252
LL_Galgal       WCQCCPHSCCCYVRCPCCPESCCCPPALYVAGKAAKAGY----PPVVSS----------- 251
LL_Xentro       WCQCCPHNCCCYVRCPCCPETCCCPKALYEAGKAAKVGY----PPTVPT----------- 247
LL_Danrer       WCQCCPHSCCCYVRCCCCPDTCCCPKHLYEAGKMAKSGQ----PPQIT------------ 250
LSR_Homsap      WCQCCPHTCCCYVRCPCCPDKCCCPEALYAAGKAATSGV----PSIYAP-----STYAHL 283
LSR_Pantro      WCQCCPHTCCCYVRCPCCPDKCCCPEALYAAGKAATSGV----PSIYAP-----STYAHL 283
LSR_Macmul      WCQCCPHTCCCYVRCPCCPDKCCCPEALYAAGKAATSGV----PSIYAP-----STYAHL 283
LSR_Bostau      WCQCCPHTCCCYVR---------------YAAGKAATSGV----PSIYAP-----STYAHL 229
LSR_Canfam      WCQCCPHTCCCYVRCPCCPEKCCCPEALYAAGKAATSGV----PSIYAP-----STYAHL 283
LSR_Musmus      WCQCCPHTCCCYVRCPCCPDKCCCPEALYAAGKAATSGV----PSIYAP-----SIYTHL 278
LSR_Ratnor      WCQCCPHTCCCYVRCPCCPDKCCCPEALYAAGKAATSGV----PSIYAP-----SIYTHL 278
LSR_Mondom      WCQCCPHTCCCYVRCPCCPEKCCCPEALYAAGKAATSGV----PSIYAPSVFAPSTYAHL 295
LSR_Danrer      WCQCCPHTCCCYVRCPCCPEPCCCPPALYEAGKMVKSGI----PSQYAATAYAQSMYGQP 259
ILDR1_Homsap    WCQCCPQYCCCYIRCPCCPAHCCCPEEALARHRYMKQAQ-ALGPQ--------------- 232
ILDR1_Pantro    WCQCCPQYCCCYIRCPCCPAHCCCPEEALARHRYMKQAQ-ALGPQ--------------- 232
ILDR1_Ponpy     WCQCCPQYCCCYIRCPCCPAHCCCPEEALARHRYMKQAQ-ALGPQ--------------- 232
ILDR1_Musmus    WCQCCPQYCCCYIRCPCCPTRCCCPEEALARHRYMKQVQ-ALGPQ--------------- 231
ILDR1_Ratnor    WCQCCPQYCCCYIRCPCCPTHCCCPEEALARHRYMKQVQ-ALGPQ--------------- 231
ILDR1_Canfam    WCQCCPQYCCCYIRCPCCPARCCCPEEALARHRYMKQAQ-ALGPQ--------------- 231
ILDR1_Xenla     WCQCCPHCCCCYVRCPCCPTRCCCPEEALARHNYMNQME-SMTPW--------------- 229
ILDR1_Galgal    WCQCCPQHCCCHIRCVCCPTRCCCNEKVLEPHEFMKRAQ-AFAPW--------------- 236
ILDR1_Danrer    CCQCCPQNCCCYVRCPCCPRTCCCPEKAVMRHKMMREAQKAMVPW--------------- 233
                 ****: ***::*            .            *

LL_Musmus       ----VPGPYSIPSVPLG-----------------GAPSSGMLMDKPHPPPLAPSDSTGGSH 292
LL_Ratnor       ----VPGPYSIPSVPLG-----------------GAPSSGMLTDKPHPPPLAPSDSTGGSH 276
LL_Bostau       ----VPGPYSIPSVPLG-----------------GAPSSGMLMDKPHPPPLAPSDSTGGSH 287
LL_Canfam       ----VPGPYSIPSVPLG-----------------GAPSSGMLMDKPHPPPLAPSDSTGGSH 260
LL_Homsap       ----VPGPYSIPSVPLG-----------------GAPSSGMLMDKPHPPPLAPSDSTGGSH 292
LL_Pantro       ----VPGPYSIPSVPLG-----------------GAPSSGMLMDKPHPPPLAPSDSTGGSH 292
LL_Macmul       ----VPGPYSIPSVPLG-----------------GAPSSGMLMDKPHPPPLAPSDSTGGSH 292
LL_Feldom       ----VPGPYSIPSVPLG-----------------GAPSSGMLMDKPHPPPLAPSDSTGGSH 257
LL_Mondom       ----VPGPYYIPSVPVG-----------------GVSSSAMLMDKPHPPPLASSDSIGGSQ 292
LL_Galgal       ----IPGPYYIPSVPVA-----------------GVPSPAVLMDKSHPPPLAPSDTGGGNQ 291
LL_Xentro       ----ACPPYYISTIPVS-----------------QVP-ACEVMDKPHVPPLVQSDSLPGQN 286
LL_Danrer       ----MYQPYYVPGVPVVP----------------VVPPAASSIIEPKLPTVPPSVENNIAG 291
LSR_Homsap      SP-AKTPPPP-AMIPM-----GPAYNGYPGGYPGDVDRSSSAGGQGSYVPLLRDTDSSVA 336
LSR_Pantro      SP-AKTPPPP-AMIPM-----GPAYNGYPGGYPGDVDRSSSAGGQGSYVPLLRDTDSSVA 336
LSR_Macmul      SP-AKTPPLP-TVIPM-----GPAYNGYPGGYPGDLDRSSSAGGQGSYVPLLRDTDSSVA 336
LSR_Bostau      SP-AKTPPPP-AMIPM-----GPLYN----GYSGDFDRNS-------------------- 258
LSR_Canfam      SP-AKTPPPP-AMIPM-----GPLYN----GYPGDFDRNSSVGGHSSQVPLLRDTDSSVT 332
LSR_Musmus      SP-AKTPPPPPAMIPM-----PPPY-----GYPGDFDRTSSVGGHSSQVPLLREVDGSVS 327
LSR_Ratnor      SP-AKTPPPPPAMIPM-----GPPY-----GYPGDFDRHSSVGGHSSQVPLLRDVDGSVS 327
LSR_Mondom      SP-AKAPSPP-PMIPL-----GPVYN---------DFDRQSSVGGHSSQVPLLRDTDSVRN 340
LSR_Danrer      AYGVGAAMPGIPMMPMQMGVGGPPSN----GYGPDYDGASSIG-QSSQVPLLQEHD---A 311
ILDR1_Homsap    ---MMGKPLYWG-----------------------ADPSSQVSSYPMHPLLQRDLSLPSS 266
ILDR1_Pantro    ---MMEKPLYWG-----------------------ADRSSQVSSYPMHPLLQRDLSLRSS 266
ILDR1_Ponpy     ---MMEKPLYWG-----------------------ADPSSQVSSYPMHPLLQRDLSLRSS 266
ILDR1_Musmus    ---MMEKPLYWG-----------------------ADRSSQVSSYAMNPLLQRDLSLQSS 265
ILDR1_Ratnor    ---MMEKPLYWG-----------------------ADPSSQVSSYAMNPLLQRDLSLRSS 265
ILDR1_Canfam    ---MMEKPLYWG-----------------------ADRSSQVSSYPMNPLLQRDLSLRSS 265
ILDR1_Xenla     ---MLDPPYYAG-----------------------ADRNSQHSSYQLNPLLQRDLSLQSS 263
ILDR1_Galgal    ---MLPNMFYGG-----------------------ADRNSQLSSYQLNPLLQQDVSLQNS 270
ILDR1_Danrer    ---PHGQPIYAP-----------------------IASNASQANPLLYSGGFSEHSSKHN 267
```

*FIG. 46 – Cont.*

```
LL_Musmus           -SVRKGYRIQAD-------------------KERDSMKVLYYVEKELAQFDPARR--MRG 330
LL_Ratnor           -SVRKGYRIQAD-------------------KERDSMKVLYYVEKELAQFDPARR--MRG 314
LL_Bostau           -SVRKGYRIQAD-------------------KERDSMKVLYYVEKELAQFDPARR--MPS 325
LL_Canfam           -SVRKGYRIQAD-------------------KERDSMKVLYYVEKELAQFDPARR--MRG 298
LL_Homsap           -SVRKGYRIQAD-------------------KERDSMKVLYYVEKELAQFDPARR--MRG 330
LL_Pantro           -SVRKGYRIQAD-------------------KERDSMKVLYYVEKELAQFDPARR--MRG 330
LL_Macmul           -SVRKGYRIQTD-------------------KERDSMKVLYYVEKELAQFDPARR--MRG 330
LL_Feldom           -SVRKGYRIQAD-------------------KERDSMKVLYYVEKELAQFDPARR--MRG 295
LL_Mondom           -SVRKGYRIQAD-------------------KERDSMKVLYYVEKELAQFDPARR--MRE 330
LL_Galgal           MAVRKGYRIQTD-------------------KDRDSMKVLYYVEKELAQFDPARR--MRE 330
LL_Xentro           -AVRKGYRIQAD-------------------KERDSMKVLYYVEKELAQFDPARR--MRE 324
LL_Danrer           --MRSGYRLQAS-------------------QGQDAMKVVYYLEEDLAQFHPTKG--ASR 328
LSR_Homsap          SEVRSGYRIQAS-------------------QQDDSMRVLYYMEKELANFDPSRPGPPSG 377
LSR_Pantro          SEVRSGYRIQAS-------------------QQDDSMRVLYYMEKELANFDPSRPGPPNG 377
LSR_Macmul          SEVRSGYRIQAS-------------------QQDDSMRVLYYMEKELANFDPSRPGPPNG 377
LSR_Bostau          SEIRSGYRIQAN-------------------QQDDSMRVLYYMEKELANFDPSRPGPPNG 299
LSR_Canfam          SEVRSGYRIQAS-------------------QQDDSMRVLYYMEKELANFDPSRPGAPNG 373
LSR_Musmus          SEVRSGYRIQAN-------------------QQDDSMRVLYYMEKELANFDPSRPGPPNG 368
LSR_Ratnor          SEVRSGYRIQAN-------------------QQDDSMRVLYYMEKELANFDPSRPGPPNG 368
LSR_Mondom          SEVRSGYRIQAN-------------------QQDDSMRVLYYMEKELANFDPSRPGLPNG 381
LSR_Danrer          GGNRSGYRVQAD-------------------QDSNPTRVLYYMEREVANLDPSRPGIAP- 351
ILDR1_Homsap        LPQMPMTQTTN--------------------QPPIANGVLEYLEKELPNLNLAQPLP--P 304
ILDR1_Pantro        LPQMPMTQTTN--------------------QPPIANGVLEYLEKELRNLNLAQPLP--P 304
ILDR1_Ponpy         LPQMPMTQTTN--------------------HPPIANGVLEYLEKELRNLNLAQPLP--P 304
ILDR1_Musmus        LPQMPMTQMAA--------------------HPPVANGVLEYLEKELPNLNPAQPLP--A 303
ILDR1_Ratnor        LPQMPMTQMAA--------------------HPPVANGVLEYLEKELRNLNPAQPLP--P 303
ILDR1_Canfam        LPQMPMTQTAAA-------------------HPPVTNGVLEYLEKELRNLNPAQPLP--P 304
ILDR1_Xenla         LP-MPAPMSPS----------------------PPNNKVLDFLETEIKNLNTAQPLMSAP 300
ILDR1_Galgal        LPLVQPQARLS-----------------------PNKGVLDYLESEIQNLNESQPRP--P 305
ILDR1_Danrer        LPMAPMAIFPPQPVPQFVPSHGYHANGSMNGNVKANNQMLDFLENQVQGMDNAVFML--Q 325
                                                          :: ::* ::  :. :

LL_Musmus           KYNNTISELSSLHDDDSNFRQSYHQMRNKQFPMSGDLESNPDYWSGVMGGNSGTNRGP-A 389
LL_Ratnor           RYNNTISELSSLHDDDSNFRQSYHQMRNKQFPMSGDVESNPDYWSGVMGGNSGTNRGP-A 373
LL_Bostau           RYNNTISELSSLHEEDSSLRQSYHQMRNKQFPVSGDLESNPDYWSGVMGGSSGASRGPSA 385
LL_Canfam           KYNNTISELSSLHEEDSNFRQAYHQMRSKQFPVSGDLESNPDYWSGVMGGSSGASRGPSA 358
LL_Homsap           RYNNTISELSSLHEEDSNFRQSFHQMRSKQFPVSGDLESNPDYWSGVMGGSSGASRGPSA 390
LL_Pantro           RYNNTISELSSLHEEDSNFRQSFHQMRSKQFPVSGDLESNPDYWSGVMGGSSGASRGPSA 390
LL_Macmul           KYNNTISELSSLHEEDSNFRQSFRQMRSKQFPVSGDLESNPDYWSGVMGGSSGASRGPSA 390
LL_Feldom           --------------------------RCEHLLVLCDLR--------VMR----------- 310
LL_Mondom           KYNNTISELSSLHEDNGNFCQSYRQMRRKPLPSLGNIESDTDYWTGVMGNSGGSGHGPSS 390
LL_Galgal           RYNNTVSELSSLHEDDLNFRQPYRQARRKPLPPAEDLDGDAEYWAGVMGGGS-TSRSQAI 389
LL_Xentro           RYSHTISELSSLHEDNTHFNHSYRQVRRKPLPPSCNADGDAEYWSGVVG-----SARPAT 379
LL_Danrer           PSADNLSELSSLHDGDVDFRQTYPQVQRKALPPIIDHLDEPRLRTASIG------HGLPP 382
LSR_Homsap          RVERAMSEVTSLHED---DWRSR-PSRGPALTPIRDEEWGGHSPRSPRG----------- 422
LSR_Pantro          RVERAMSEVTSLHED---DWRSR-PSRGPALTPIRDEEWGGHSPRSPRG----------- 422
LSR_Macmul          RVER-------------------------------------------------------- 381
LSR_Bostau          RVERAMSEVTSLHED---DWRSR-PSRGPALTPIRDEEWGHHSPRSSRR----------- 344
LSR_Canfam          RVERAMSEVTSLHED---DWRSR-PSRGPALTPIRDEEWDRHSPRSPRR----------- 418
LSR_Musmus          RVERAMSEVTSLHED---DWRSR-PSRAPALTPIRDEEWNRRSPRSPRT----------- 413
LSR_Ratnor          RVERAMSEVTSLHED---DWRSR-PSRAPALTPIRDEEWNRHSPQSPRT----------- 413
LSR_Mondom          RVERAMSEVTSLHED---DWRAR-PHRGPALTPIQDEDLDYHS-RSPGG----------- 425
LSR_Danrer          --VDGMSEVSSLHDGP--ESSNEGRARPPQLTTVYDDVDENMSTLSSVS----------- 396
ILDR1_Homsap        DLKGPPGHP--CSMLSSLG-SEVVERPIIHLPPLIPDLSSSRRTSDSLH----------- 350
ILDR1_Pantro        DLKGRPGHP--CSMLSSLG-SEVVERRIIHLPPLIRDLSSSRRTSDSLH----------- 350
ILDR1_Ponpy         DLRARPGHP--CSMLSSLG-SEVVERRPIHLPPLIRDLSSSRRTSDSLH----------- 350
ILDR1_Musmus        DLPAKSGHP--CSMLSSLGSAEVVERPVIHLPPLIPDPESSR-TSNPSH----------- 349
ILDR1_Ratnor        DLRTKSGHP--CSMLSSLGSAEVVEPRVIHLPPLIRDPLPSR-TSNSSH----------- 349
ILDR1_Canfam        DLRTISGQA--CSMLSSLG-SEVVERRIIHLPPLIPDLPPSWRTSSSSR----------- 350
ILDR1_Xenla         HYGGASHRPSMLSSLSEVG-VREVDRRVIQLPPLVERIVSSHRSSNSSH----------- 348
ILDR1_Galgal        SNQPQAVQP---SLLSSLG-SDIMQPGTNGLPPPTGHVSSSHGSSSSSR----------- 350
ILDR1_Danrer        PQHHYTGVP----LQNHQPQYAAQQPHYASPPPQSIPQAVTPPAPPPSM----------- 370
```

*FIG. 46 – Cont.*

```
LL_Musmus      LEYNKEDRESFRHSQQRSKSEMLSRKNFATGVPAVSMDELAAFADSYGQRSRRANGNSHE 449
LL_Ratnor      LEYNKEDPESFRHSQPRSKSEMLSRKNFATGVPAVSMDELAAFADSYGQRSPRANGNSHE 433
LL_Bostau      MEYNKEDRESFPHSQQRSKSEMLSRKNFATGVPAVSMDELAAFADSYGFHSRPADGNKQD 445
LL_Canfam      MEYNKEDRESFRYP-------NLSENNFAAGVPAVSMDELAAFADSYGARSRRADGDSHE 411
LL_Homsap      MEYNKEDRESFPHSQPRSNSEMLSRKNFATGVPAVSMDELAAFADSYGQHPRPADGNSHE 450
LL_Pantro      MEYNKEDRESFRHSQPRSKSEMLSRKNFATGVPAVSMDELAAFADSYGQRPRRADGNSHE 450
LL_Macmul      MEYNKEDRESFRHR-------ILN--------------------------------ISHL 411
LL_Feldom      -EFNA------------------------------------------------------- 314
LL_Mondom      SNYNKEDPDSFRHSQQPCKSEMLSKKNFAMGMPAVSMDELAAFADSYSQRSHRGEGNSQE 450
LL_Galgal      SDYRDE-RDSFPHSQQRSKSEMLSRKSFSVGVPAVSMDELAAFAESYSQHAKPAD--SQE 446
LL_Xentro      YSKFREDRESFRSSLQRPTSEVLEPKSFPMTIQAVSTDELAAFTDSYKQRPRRAD--SRG 437
LL_Danrer      SHYQSDHSLDEHDNPWNCRSEHLPRKAFDSRGRTVSLDELEEFAMSYGPHGRRRG----D 438
LSR_Homsap     ------WDQEPAPEQAG-------GGWRAPRPPARSVDALDDLTP----PSTAESGSRSP 465
LSR_Pantro     ------WDQEPAKEQAG-------GGWRARRPRARSVDALDDLTP----PSTAESGSRSP 465
LSR_Macmul     ------------------------------------------------------------
LSR_Bostau     ------WEQEAPMERPG-------NSRGAGPPRARSVDALDDPTR----PGSAESGERSP 387
LSR_Canfam     ------WEQEPPTEHPG-------SGWGAARPRAHSVDALDDLTR----PSSAESGRRSP 461
LSR_Musmus     ------WEQEPLQEQPR-------GGWGSGRPPARSVDALDDINR----PGSTESGRSSP 456
LSR_Ratnor     ------WEQEPLQEQPR-------GGWGSGRPRARSVDALDDINR----PGSTESGRSSP 456
LSR_Mondom     ------WGRERPHDRYGERPHDPYGDWGAGRPPARSVDALDDLAP----PSSVESGRTSP 475
LSR_Danrer     ------QHMRPDEPRRG----------ADSRGRARSMENLDDISRGYRDRDDYPPARPDG 440
ILDR1_Homsap   ---------QQWLTPIP------SRPWDLREGRSRHHYPDFHQELQDRGPKSWALERRELD 396
ILDR1_Pantro   ---------QQWLTPIP------SRPWDLREGRSHHHYPDFHQELQDRGPKSWALERRELD 396
ILDR1_Ponpy    ---------QQWLTPIP------SRPWDLREGRRQHHYPDFHQELQDRGPKSWALERRELD 396
ILDR1_Musmus   ---------QQRLNAVS------SRHCDLSERPPQRHHSDFLPELQDQGMRPWAPGRGELD 395
ILDR1_Ratnor   ---------QQPLNPVP------SRPPDPSEGRRQRNHSDFLRELQDRGMRPWAPGRGELD 395
ILDR1_Canfam   ---------QQWPAPGA------PGPWGVS-------SDVHPELQGHEPK--HLRP---- 382
ILDR1_Xenla    ---------QEPNMGSW-------DPLDGERDRRRNRQLDDSLSNETNWRAQERQHSDHSSG 394
ILDR1_Galgal   ---------PQRTTRSLRTWGEDTAENPREDRRWPLPSSEDGRSSYSHEPHDRQREDRPPR 402
ILDR1_Danrer   ---------LSALDEMG---VQGVEHRVIQLPPILGRPNQSSRPTNDQRPRQSSQSSGSSN 419

LL_Musmus      ARAGSRFERRSESRAHGAFYQDGSLDE-YYG-RGRS-REPPGDGERGWTYSPAPAPRRPPE 506
LL_Ratnor      ARAGSRFERRSESRAHGAFYQDGSLDE-YYG-RGRS-REPPGDGERGWTYSPAPARRRPPD 490
LL_Bostau      LRGGSRFERRSEARAHGGLYQDGSLEE-YYGPRSRS-PEPLTDADRGWSYS--PPRRRPPD 501
LL_Canfam      ARGGGRFERPEARALGGFFQDGSPEG-YYG-RSRS-REPLGDAGRAWAFS--PPPRRP-D 465
LL_Homsap      ARGGSRFERSESPAHSGFYQDDSLEE-YYGQRSRS-REPLTDADRGWAFS--PARRPPAE 506
LL_Pantro      ARGGSRFERSESRAHSGFYQDDSLEE-YYGQRSRS-REPLTDADRGWAFS--PAPRRPAE 506
LL_Macmul      SRQSTLVITCVE---------DDSLEE-YYGQRSRS-REPLTDADRGWAFS--PARPRPTE 459
LL_Feldom      ------------------------------------------------------------
LL_Mondom      PRGGSRFERRSESRAHSGLYHDSSLEE-YYSKRSRS-REPLTDSDRGWSYS--PPRPRANE 506
LL_Galgal      TPRFERSESRSGRGGGLTHQDSSMEE-YYTKRSPGNEEPLTDSDRGWSYS--PPRREAKE 503
LL_Xentro      PGSAPRFERSETRGRS-LYQDSSSDE-YYGKRNRG-KELFSDGERGWSFS--PSRIRAAE 492
LL_Danrer      IRGPQRDFEMAPPTRDHPTSYPNGPR-YLREDDDS-----DWHRPGSPPS--PPKRRDTA 490
LSR_Homsap     TSNGGR-SRAYMPPRS-RSPDDLYDQ--DDSRDFPRSRDPHY-DDFRSPERPPADPRSHH 520
LSR_Pantro     TSSGGRRSRAYMPPRS-RSRDDLYDQ--DDSRDFPRSRDPHY-DDLRSRERPPADPRSQH 521
LSR_Macmul     ------------------------------------------------------------
LSR_Bostau     PS-SGPRGRAYAPPRS-RSRDDLYDQDQDDSRHFPHSRDPHY-DDFRSRDQPHGDPRARY 444
LSR_Canfam     PS-RGRPGQAYGPPRS-RSRDDLYDQ--DGPREPPHPRDPHY-DDFRPRDRPHADPPSRN 516
LSR_Musmus     PS-SGRRGRAYAPPRS-RSPDDLYDP--DDPRDLPHSPDPHYYDDLRSRD-PRADPRSR- 510
LSR_Ratnor     PS-SGRPGRAYAPPRS-RSRDDLYDP--DDPRDLPHSRDPHYYDDIRSRD-PRADPRSR- 510
LSR_Mondom     SE--PSRSKAYAPLRS-RSRDDLYSR-----------SGDPHY-EDFRSPGRALDD----- 516
LSR_Danrer     GPRGGERGSDDEWSSSGRSYDPVDDR---PRRDYSPDNRPRRGDSYHSAGFQGRRTRSRD 497
ILDR1_Homsap   PSWSGRHRSSRLNGSPIHWSDRDSLS-----DVPSSSEAPWRPSHPPFRSRCQERPRRPS 451
ILDR1_Pantro   PSWSGRHRSSRLNGSPIHWSDRDSLS-----DVPSSSEARWRPSHPLFRSRCQERPRRPS 451
ILDR1_Ponpy    PSWSGRHRSSRLNGSPIHWSDRDSLS-----DVPSSIEARWQPSHPPFRSRCQERPRRPS 451
ILDR1_Musmus   PHWSGRHHRSPPSESSMPWSDWDSLS-----ECPSSSEAPWP-------------PRRPE 437
ILDR1_Ratnor   PHWSGRHHRSRPSESSMPWSDWDSLS-----ECPSSSEAPWP-------------SRRPE 437
ILDR1_Canfam   ----GRHPCSPPHGSHAPWSDRDSLG-----DGPSSWEALGLG---------------RG 418
ILDR1_Xenla    HRRDPPNNERPHRDVSRPRRYGDSYS-----DESANNDPRGRSNPHSDRARPTERRRSPE 449
ILDR1_Galgal   QRTGGYDGRSQYSRRDVSPTRQTEPG-----KSSSSSCSPYSEEAKEPSSHHRGRRQQPA 457
ILDR1_Danrer   RNGVHRDPASSRRGNQRSYSDESDWD-----DRRGGRSSSGRRG--------ESNRSRPR 466
```

FIG. 46 – Cont.

```
LL_Musmus       DAPLPRLVSRTPGTAPKYDHSYLSSVLERQARPESSSRGGSLETPSKLGAQLGPKSA-SY 565
LL_Ratnor       DAALPRLVSKTPGTAPKYDHSYLSSVLERQARPESNSRGGSLETPSKLGAQLGPRSA-SY 549
LL_Bostau       DAHLPPLVSRTPGTTPKYDHSFRGSGLERQVRPEGASRGGSLETPSKLSSQLGPLSA-SY 560
LL_Canfam       DAPLPRLVSRTPGTAPKYEHAPRAGGLERQARPEGASRGGSLETPSKLSAQLGPKSA-SY 524
LL_Homsap       DAHLPRLVSRTPGTAPKYDHSYLGSARERQARPEGASRGGSLETPSKRSAQLGPRSA-SY 565
LL_Pantro       DAHLPRLVSRTPGTAPKYDHSYLGSARERQARPEGASRGGSLETPSKRSAQLGPRSA-SY 565
LL_Macmul       DAHLPRLVSRTPGTAPKYDHSYLGSARERQPRPEGASRGGSLETPSKRSAQLGPKSA-SY 518
LL_Feldom       ------------------------------------------------------------
LL_Mondom       DKHLPPLVSRTPGVGQKYDHPYLSSVLERKSRGEGSSGGGSLETPSKRSSQPIQRSG-SY 565
LL_Galgal       EKHLPRLVSRTPGGSQKYDHSYLSSVLERKSRSYDES-GDPCETPSKLSSQPSQKGGGTY 562
LL_Xentro       DKHLPKRITR---MGQSYDDAYLSRVLERRSP----GLEDTTVTPSKLS----------- 534
LL_Danrer       DSE--PYVSP----QKSYDDTYLNSLLEPKARGHGERGGRVDDDSDTPSKGSSKKSSDCY 544
LSR_Homsap      HRTRDPRDNGSRSGDLPYDGRLLEEAVRKKGSEERRRPHKEEEEEAY------------- 567
LSR_Pantro      HRTRDPRDNGSRSGDLPYDGRLLQEAVRKKGSEERRRPHKEEEEEAY------------- 568
LSR_Macmul      ------------------------------------------------------------
LSR_Bostau      QRSRDPRDDGSRSPDPPYDGRLLEEALRKKGPAEPR-PYREEEEEEA------------- 490
LSR_Canfam      HRSRDSPEDGSRSGDPQYDGRLLEEALRKKGPAERRPAYREEEEEEA------------- 563
LSR_Musmus      QRSHDPRDAGFRSRDPQYDGRLLEEALKKKGAGERRRVYPEEEEEEEE------------ 558
LSR_Ratnor      QRSRDPRDAGFRSPDPQYDGRLLEEALKKKGSGEPRRVYREEEEEEE------------- 557
LSR_Mondom      -SRRDPHENHPRSRDPEYDGRFLEEVMRKKGVGERRRPYREEEEEPY------------- 562
LSR_Danrer      DLMDLVRDPGRGGRD-EYDDSFLREAMEKKKLGEQQRGRGKERLDSESDRSDRYRGH--- 553
ILDR1_Homsap    PRE-----STQRHGRPRPHPSYSPPLPSGLSSWSSEEDKE---RQPQSWRAHR------- 496
ILDR1_Pantro    PRE-----STQRDGRRRRHRSYSPPLPSGLSSWSSEEDKE---RQPQSWRAHR------- 496
ILDR1_Ponpy     PRE-----STQRHGRPRRHRSYSPPLPSGLSSWSSEEDKE---RQPQSWGAHR------- 496
ILDR1_Musmus    PRE-----GAQRREKPR-HRSYSPPLPSGPSSWSSEEEKE---SLPRNWGAQRPHHH--- 485
ILDR1_Ratnor    PRE-----GSQRHGRRR-HRSYSPPLPSGPSSWSSEEEKE---SLPPNWGAQRRHHR--- 485
ILDR1_Canfam    PRG-----DAQRP-RRPRHRSYSPPSPSGLSSWSSEEEGEEGDERPRGRGTPYSS----- 467
ILDR1_Xenla     PGDQGRRGSPDRYSRSQRHRRSYSP-PHRRDSWSSEDETR---NNQRGRGRPE------- 498
ILDR1_Galgal    VRR--EYQQHTRNSNNSRHRRHSYSPPSRPGSWSSSEEQIP--LPATNPRRHR------- 506
ILDR1_Danrer    VPSKAELLEELERATNNGNRSYSSP---HRGSWSSDEEDS----YRNGR----------- 508

LL_Musmus       YAWSPPTTYKAGA-----SEGEDEDD--AADEDALPPYSELELSRGELSRGPSYRGRDLS 618
LL_Ratnor       YAWSPPATYKAGA-----SEGEDEDD--AADEDALPPYSELELSRGELSRGPSYKGRDLS 602
LL_Bostau       YAWSPPATYEAGA-----PPDDEED----TPDDTLPPYSELELSRG-----PSYRGRDLP 606
LL_Canfam       YAWSPPATYKAAA-----PQDDDDDDDDSADDALPPYSERELSRG-----PSYRGRDLP 574
LL_Homsap       YAWSPPGTYKAGS-----SQDDQED----ASDDALPPYSELELTRG-----PSYRGRDLP 611
LL_Pantro       YAWSPPGTYKAGS-----SQDDQED----ASDDALPPYSELELTRG-----PSYRGRDLP 611
LL_Macmul       YAWSPPGTYKAGS-----SQDDQED----ASDDALPPYSELELTRG-----PSYRGRDLP 564
LL_Feldom       ------------------------------------------------------------
LL_Mondom       YAWSPPSTYKAGSGQQPSPQAGEED----EMEDALPPYSELELTRG-----PSYRGRESL 616
LL_Galgal       YAWSPPSTYKSDTSQQQQTPPPEQE----EGEDTLPPYSERELSRG-----PSYRAPEQA 613
LL_Xentro       ----------------------------------LRQNSSRSYGRS-----PTPCVNDFE 555
LL_Danrer       QSRSPSNRPEEEDRLPPYSEREGERFRTEEPTGPEEYRIADPANRP----PSYTRPPHGL 600
LSR_Homsap      ----------------------------------------------------YPPAPPPY 575
LSR_Pantro      ----------------------------------------------------YPPAPPPY 576
LSR_Macmul      ------------------------------------------------------------
LSR_Bostau      ---------------------------------------------------YYPPAPPPY 499
LSR_Canfam      ---------------------------------------------------YYPPAPPPY 572
LSR_Musmus      --------------------------------------------------GHYPPAPPPY 568
LSR_Ratnor      --------------------------------------------------GQYPPAPPPY 567
LSR_Mondom      ----------------------------------------------------YPPAPPPY 570
LSR_Danrer      ----------------------------HSGPPPLPLVPASGNPDRRGNHSNPPPPPPPY 585
ILDR1_Homsap    --------------------------------------RGSHSPHWPEEKPPSYRSLDIT 518
ILDR1_Pantro    --------------------------------------RGSHPPHNPEEIPPSYKSLDII 518
ILDR1_Ponpy     --------------------------------------RRSHSPHWPEEKPPSYRSLDVT 518
ILDR1_Musmus    -----------------------------------R-PRRSQSPNWPEEKPPSYRSLDVT 509
ILDR1_Ratnor    -----------------------------------RSRRRSQSPNWLEERPPSYKSLDVT 510
ILDR1_Canfam    --------------------------------------QATTWATWAEEKPPSYRSLDVL 489
ILDR1_Xenla     -----------------------------------------RSYEWPEEKPPSYKSLEIC 517
ILDR1_Galgal    -----------------------------------------RSREWPEDKPPSYKSLEII 525
ILDR1_Danrer    -----------------------------------------RSQGKLSENPPAYSSIDIL 527
```

FIG. 46 – Cont.

```
LL_Musmus       FHSNSEKRRKKEPAKKPGDFPTRMSLVV 646
LL_Ratnor       FHSNSEKRRKKEPAKKTGDFPTRMSLVV 630
LL_Bostau       YHSNSEKKRKKETPAKKTDFPTRMSLVV 634
LL_Canfam       YHSNSEKKRKKE---------------- 586
LL_Homsap       YHSNSEKKRKKEPAKKTNDFPTRMSLVV 639
LL_Pantro       YHSNSEKRRKKEPAKKTNDFPTRMSLVV 639
LL_Macmul       YHSNSEKRRKKEPAKKTNDFPTRMSLVV 592
LL_Feldom       ----------------------------
LL_Mondom       YHSNSEKKRKKDSLKKTNDFPTRMSLVV 644
LL_Galgal       YLNASDKKRKKDP-KKTNDFPTRMSLVV 640
LL_Xentro       ILTAN---------------PSGTFLSV 568
LL_Danrer       SQTLQERKEDRDKPRKLTTHLSRDSLIV 628
LSR_Homsap      SETDS--QASRERRLEKNLALSRESLVV 601
LSR_Pantro      SETDS--QASKERRLFK----------- 591
LSR_Macmul      ----------------------------
LSR_Bostau      SETDS--QASRERRLKKNLALSRESLVV 525
LSR_Canfam      SETDS--QASREKRLEKNLALSRESLIV 598
LSR_Musmus      SETDS--QASRERRMKENLALSRESLVV 594
LSR_Ratnor      SETDS--QASRERRLKENLALSRESLVV 593
LSR_Mondom      TETDS--QASRERKLEKNLALSRESLVV 596
LSR_Danrer      TEDTDSLPSSKESNLEKNGAVSRESLVV 613
ILDR1_Homsap    PGKNSRKKGSVERRSEKDSSHSGRSVVI 546
ILDR1_Pantro    GGKNNKKKGSVERRSEKDSSHSGRSVVI 546
ILDR1_Ponpy     PGKNSRKEGSVERRSEKDSSHSGRSVVI 546
ILDR1_Musmus    PGKNNRKKGNVERRLERESSHSGRSVVI 537
ILDR1_Ratnor    PGKNNMKKGNVERRLERESSHSGRSVVI 538
ILDR1_Canfam    PGRKGERGGSVERRSERDSSHSGRSVVI 517
ILDR1_Xenla     AGKAPTQRPGAVRQSDRASSRSGRSMVI 545
ILDR1_Galgal    PDRDSKHREGAGPRS------------- 540
ILDR1_Danrer    PG-HSKRGEQLSDKS----SRSGTSVVI 550
```

FIG. 46 – Cont.

Human ILDR2 Antisense RNA

DB504869 is unspliced anti-sense transcript corresponding to
chr1:165156756-165157239

AGTAGGAGGCGCTGCGCGGGCCGAGCTGCGCGCTCCGCTTGGATGGCGTCTCCAGGCTGCCACCGCGGCTGGCGCCCT
CGGGCCGCGCCTGGCGCTCCCGCGCGCTGCCCAGGTACGAGTGGTCGTATTTGGGTGCGGTGCCTGGCGTGCGGCTCA
CCAGCCGCGGCAGGTGTGCGTCCTCGGCGGGTCTGCGGCGCGCGGGGCTGAAGGCCCAGCCGCGGTCAGCATCGGTCA
GGGGCTCGCGGCTGCGGCTGCGCTGACCGTAGTACTCCTCCAAGGAGTCGTCCTGGTAGAAGCCGCTGTGCGCCCGCG
ACTCCGAGCGCTCGAAGCGGCTCCCGCCCCGCGCCTCGTGACTGTTGCCGTCTGCCCGGCGGGGCCGCTGGCCGTAGG
AGTCAGCGAAGGCCGCCAGCTCGTCCATGGAAACGGCCGGCACCCCCGTGGCGAAGTTCTTCCGCGACAGCATCTCCG
ACTTGGAGCGCGGCTG(SEQ ID NO: 48)

FIG. 47A

DA322725 is a spliced anti-sense transcript of Human ILDR2 corresponding to chr1:165156961 – 165228581.

Underlined nucleotides in transcript correspond to genomic sequences from chr1:165156191-165157293.

Italicized nucleotides in transcript correspond to genomic sequences from chr1:165163328 – 165163468

Lower case sequences correspond to chr1:165228547-165228581

GAAGGCCCAGCCGCGGTCAGCATCGGTCAGGGGCTCGCGGCTGCGGCTGCGCTGACCGTAGTACT
CCTCCAAGGAGTCGTCCTGGTAGAAGCCGCTGTGCGCCCGCGACTCCGAGCGCTCGAAGCGGCAT
CCCGCCCCGCGCCTCGTGACTGTTGCCGTCTGCCCGGCGGGGCCGCTGGCCGTAGGAGTCAGCGA
AGGCCGCCAGCTCGTCCATGGAAACGGCCGGCACCCCCGTGGCGAAGTTCTTCCGCGACAGCATC
TCCGACTTGGAGCGCGGCTGGCTGCGGGCAGAGAAGGAGGGGGTCAGACGGCCGGTCCCTCCCTG
GAGCTCCAG*CTCCACTTAGTGCTCATCTTCTCAGCGCTTTTGCGTTCCATTGGAGGAGCATATTC*
*ACACTAAAAAAAGACCACTTTCTAGATTGAGGACATGCGTCACTCTAGCATCTGAGGATCCCACC*
*TTCACTTTGTGAGAGCACAG*ctctccttggaggcatttttatttttgaacatt (SEQ ID NO: 49)

FIG. 47B

DA565656 is spliced anti-sense transcript extending from chr1:165156982-165225636.

Underlined nucleotides in transcript correspond to genomic sequences from chr1: 165156982-165157293.

Italicized nucleotides in transcript correspond to genomic sequences from chr1:165163328 – 165163468

Lower case sequences correspond to 165225162 – 165225345

Upper case sequences correspond to 165225598-165225636

ATCGGTCAGGGGCTCGCGGCTGCGGCTGCGCTGACCGTAGTACTCCTCCAAGGAGTCGTCCTGGTAGAAGCCGCTGTG
CGCCCGCGACTCCGAGCGCTCGAAGCGGCTCCCGCCCCGCGCCTCGTGACTGTTGCCGTCTGCCCGGCGGGGCCGCTG
GCCTGTAGGAGTCAGCGAAGGCCGCCAGCTCGTCCATGGAAACGGCCGGCACCCCCGTGGCGAAGTTCTTCCGCGACA
GCATCTCCGACTTGGAGCGCGGCTGGCTGCGGGCAGAGAAGGAGGGGGTCAGACGGCCGGTCCCTCCCTGGAGCTCCA
G*CTCCACTTAGTGCTCATCTTCTCAGCGCTTTTGCGTTCCATTGGAGGAGCATATTCACACTAAAAAAAGACCACTTT*
*CTAGATTGAGGACATGCGTCACTCTAGCATCTGAGGATCCCACCTTCACTTTGTGAGAGCACAG*gagaagatccccga
actacggcgacgaggcctgcctgtggctcgcgttgctgatgccatcccttactgctccgcagactgggcgCTTCTGAG
GGAGGAAGAAAAGGAGAAATACGCAGAAATG (SEQ ID NO: 50)

FIG. 47C

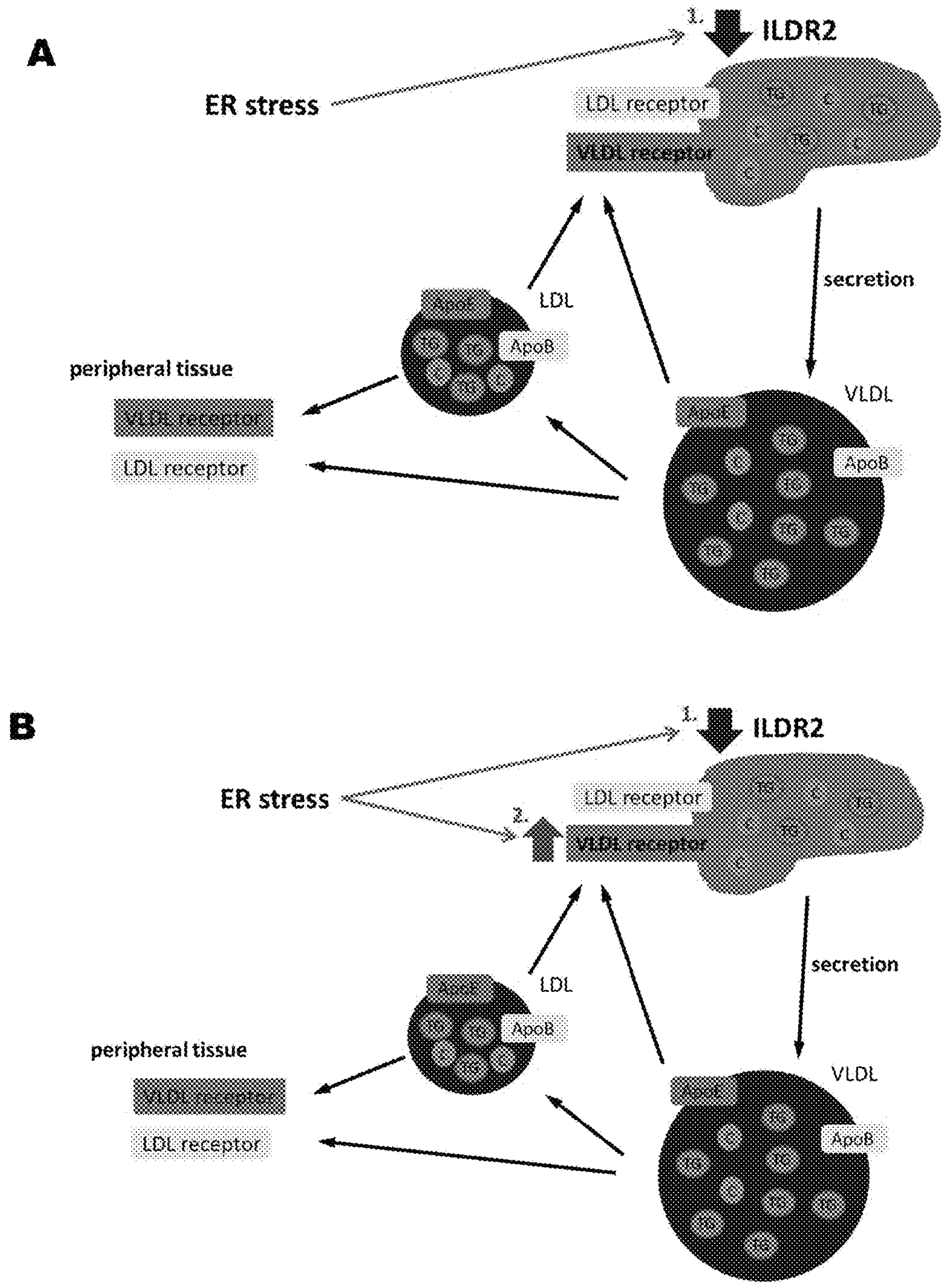
FIGS. 49A-B

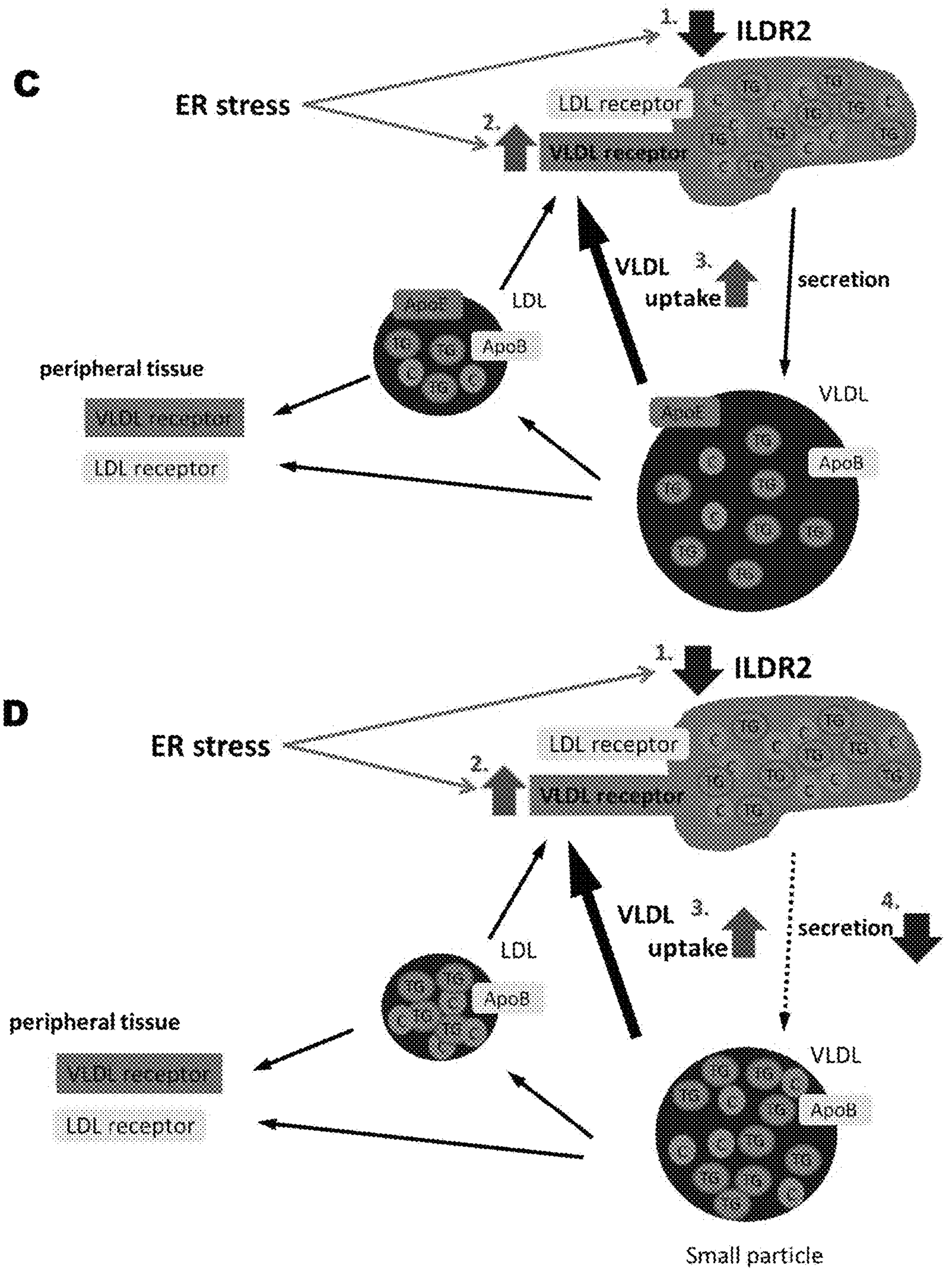
*FIGS. 49C-D*

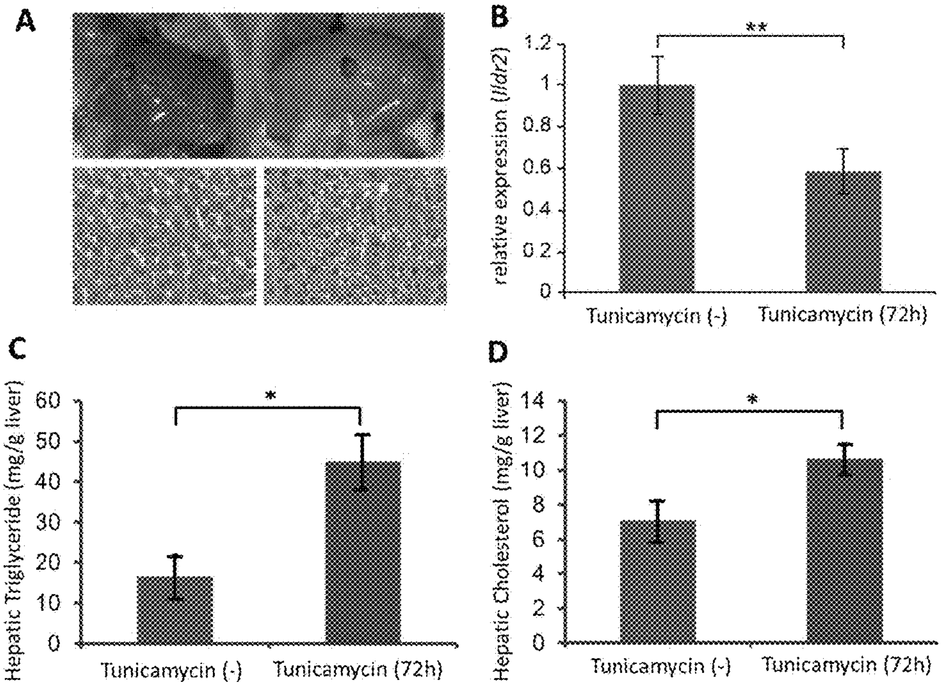
*FIGS. 60A-D*

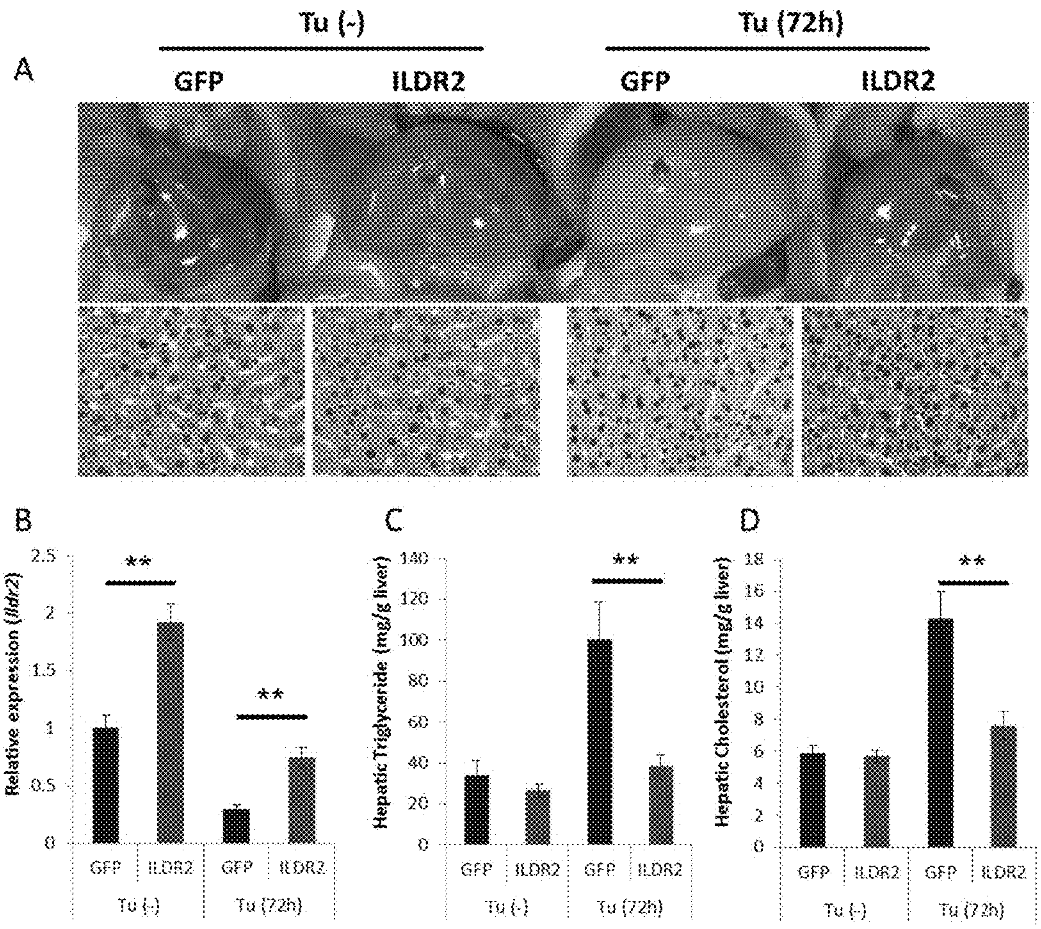
*FIGS. 61A-D*

SEQUENCE LISTING

```
<160> NUMBER OF SEQ ID NOS: 152

<210> SEQ ID NO 1
<211> LENGTH: 88
<212> TYPE: PRT
<213> ORGANISM: Mus musculus

<400> SEQUENCE: 1

Met Asp Arg Val Val Leu Gly Trp Thr Ala Val Phe Trp Leu Thr Ala
1               5                   10                  15

Met Val Glu Gly Leu Gln Val Thr Val Pro Asp Lys Lys Lys Val Ala
            20                  25                  30

Met Leu Phe Gln Pro Thr Val Leu Arg Cys His Phe Ser Thr Ser Ser
        35                  40                  45

His Gln Pro Ala Val Val Gln Trp Lys Phe Lys Ser Tyr Cys Gln Asp
    50                  55                  60

Arg Met Gly Glu Ser Leu Gly Met Ser Ser Pro Arg Ala Gln Ala Leu
65                  70                  75                  80

Ser Lys Arg Asn Leu Glu Trp Asp
                85


<210> SEQ ID NO 2
<211> LENGTH: 104
<212> TYPE: PRT
<213> ORGANISM: Mus musculus

<400> SEQUENCE: 2

Tyr Arg Ile Gln Ala Asp Lys Glu Arg Asp Ser Met Lys Val Leu Tyr
1               5                   10                  15

Tyr Val Glu Lys Glu Leu Ala Gln Phe Asp Pro Ala Arg Arg Met Arg
            20                  25                  30

Gly Arg Tyr Asn Asn Thr Ile Ser Glu Leu Ser Ser Leu His Asp Asp
        35                  40                  45

Asp Ser Asn Phe Arg Gln Ser Tyr His Gln Met Arg Asn Lys Gln Phe
    50                  55                  60

Pro Met Ser Gly Asp Leu Glu Ser Asn Pro Asp Tyr Trp Ser Gly Val
65                  70                  75                  80

Met Gly Gly Asn Ser Gly Thr Asn Arg Gly Pro Ala Leu Glu Tyr Asn
                85                  90                  95

Lys Glu Asp Arg Glu Ser Phe Arg
            100


<210> SEQ ID NO 3
<211> LENGTH: 165
<212> TYPE: PRT
<213> ORGANISM: Mus musculus

<400> SEQUENCE: 3

Gln Val Thr Val Pro Asp Lys Lys Lys Val Ala Met Leu Phe Gln Pro
1               5                   10                  15

Thr Val Leu Arg Cys His Phe Ser Thr Ser Ser His Gln Pro Ala Val
            20                  25                  30

Val Gln Trp Lys Phe Lys Ser Tyr Cys Gln Asp Arg Met Gly Glu Ser
        35                  40                  45

Leu Gly Met Ser Ser Pro Arg Ala Gln Ala Leu Ser Lys Arg Asn Leu
    50                  55                  60

Glu Trp Asp Pro Tyr Leu Asp Cys Leu Asp Ser Arg Arg Thr Val Arg
65                  70                  75                  80
```

```
Val Val Ala Ser Lys Gln Gly Ser Thr Val Thr Leu Gly Asp Phe Tyr
                85                  90                  95

Arg Gly Arg Glu Ile Thr Ile Val His Asp Ala Asp Leu Gln Ile Gly
            100                 105                 110

Lys Leu Met Trp Gly Asp Ser Gly Leu Tyr Tyr Cys Ile Ile Thr Thr
        115                 120                 125

Pro Asp Asp Leu Glu Gly Lys Asn Glu Asp Ser Val Glu Leu Leu Val
    130                 135                 140

Leu Gly Arg Thr Gly Leu Leu Ala Asp Leu Leu Pro Ser Phe Ala Val
145                 150                 155                 160

Glu Ile Met Pro Glu
                165


<210> SEQ ID NO 4
<211> LENGTH: 105
<212> TYPE: PRT
<213> ORGANISM: Homo sapiens

<400> SEQUENCE: 4

Tyr Arg Ile Gln Ala Asp Lys Glu Arg Asp Ser Met Lys Val Leu Tyr
1               5                   10                  15

Tyr Val Glu Lys Glu Leu Ala Gln Phe Asp Pro Ala Arg Arg Met Arg
            20                  25                  30

Gly Arg Tyr Asn Asn Thr Ile Ser Glu Leu Ser Ser Leu His Glu Glu
        35                  40                  45

Asp Ser Asn Phe Arg Gln Ser Phe His Gln Met Arg Ser Lys Gln Phe
    50                  55                  60

Pro Val Ser Gly Asp Leu Glu Ser Asn Pro Asp Tyr Trp Ser Gly Val
65                  70                  75                  80

Met Gly Gly Ser Ser Gly Ala Ser Arg Gly Pro Ser Ala Met Glu Tyr
                85                  90                  95

Asn Lys Glu Asp Arg Glu Ser Phe Arg
            100                 105


<210> SEQ ID NO 5
<211> LENGTH: 165
<212> TYPE: PRT
<213> ORGANISM: Homo sapiens

<400> SEQUENCE: 5

Gln Val Thr Val Pro Asp Lys Lys Lys Val Ala Met Leu Phe Gln Pro
1               5                   10                  15

Thr Val Leu Arg Cys His Phe Ser Thr Ser Ser His Gln Pro Ala Val
            20                  25                  30

Val Gln Trp Lys Phe Lys Ser Tyr Cys Gln Asp Arg Met Gly Glu Ser
        35                  40                  45

Leu Gly Met Ser Ser Thr Arg Ala Gln Ser Leu Ser Lys Arg Asn Leu
    50                  55                  60

Glu Trp Asp Pro Tyr Leu Asp Cys Leu Asp Ser Arg Arg Thr Val Arg
65                  70                  75                  80

Val Val Ala Ser Lys Gln Gly Ser Thr Val Thr Leu Gly Asp Phe Tyr
                85                  90                  95

Arg Gly Arg Glu Ile Thr Ile Val His Asp Ala Asp Leu Gln Ile Gly
            100                 105                 110

Lys Leu Met Trp Gly Asp Ser Gly Leu Tyr Tyr Cys Ile Ile Thr Thr
        115                 120                 125
```

```
Pro Asp Asp Leu Glu Gly Lys Asn Glu Asp Ser Val Glu Leu Leu Val
    130                 135                 140

Leu Gly Arg Thr Gly Leu Leu Ala Asp Leu Leu Pro Ser Phe Ala Val
145                 150                 155                 160

Glu Ile Met Pro Glu
                165


<210> SEQ ID NO 6
<211> LENGTH: 10
<212> TYPE: PRT
<213> ORGANISM: Mus musculus

<400> SEQUENCE: 6

His Gln Met Arg Asn Lys Gln Phe Pro Met
1               5                   10


<210> SEQ ID NO 7
<211> LENGTH: 13
<212> TYPE: PRT
<213> ORGANISM: Mus musculus

<400> SEQUENCE: 7

Ile Val His Asp Ala Asp Leu Gln Ile Gly Lys Leu Met
1               5                   10


<210> SEQ ID NO 8
<211> LENGTH: 10
<212> TYPE: PRT
<213> ORGANISM: Homo sapiens

<400> SEQUENCE: 8

His Gln Met Arg Ser Lys Gln Phe Pro Val
1               5                   10


<210> SEQ ID NO 9
<211> LENGTH: 13
<212> TYPE: PRT
<213> ORGANISM: Homo sapiens

<400> SEQUENCE: 9

Ile Val His Asp Ala Asp Leu Gln Ile Gly Lys Leu Met
1               5                   10


<210> SEQ ID NO 10
<211> LENGTH: 8845
<212> TYPE: DNA
<213> ORGANISM: Mus musculus

<400> SEQUENCE: 10

gtgggcatag cccatggaaa tgtacgctgc aaatggagaa tgtataggtg tagtctccct      60

ctccctctcc ctcctcctcc cccctccccc tctccctccc attctctctc tccctctctc     120

tctctgctca ttttctgtta aaaaggccac atacgtttta acagaaaaaa gatttttgcc     180

taaagggttt ctcccctatg gatcctaatt tggttggggc ctcttggttc gttgaaccag     240

atgcaccagc cagggcacaa caaaaacaaa caaacaaaca aacaccatac aggtctaagc     300

cccaggagaa gttatgccaa gtccttgtag cctttctgtc cctgacaccc agtacaggtg     360

caaggaaaca tcgagtccca gcctgcttgg tggctcaagt agagcttgag tcgcagcccc     420

cgccacatgg tccgccctct ggggtggact tcgctgctag gttctgacct cccagccccg     480

ggagacggca cgtgaccgag aaactttggc gggcggtgtt ggcgcgggcg gcggcgcggc     540
```

-continued gatcgagctc ccccgcgcgg cgagctctgc tgcggggagg cgctcgccgg tgccgcgcag 600
cctgtgcgtg cgggaacggc cccgcagcc caatcggact ctagagccag cggcagcgcg 660
cctctcgcag gcggcggcgt ccagcgcccg gggccgggct gcgcggccag ccccgagggc 720
tgcggcgcca gggacgcgcg gggcccgcgc tccgccgccg ccgccgcctg ctgctgcgag 780
gtcatccgga tcttatcgtg ccagctgatg cccgcttttc ccactctgga tctggatggg 840
aagttgggga agatggatag ggtcgtgttg gggtggactg ctgtcttctg gttaacagcc 900
atggttgaag gccttcaggt cacagtgcct gacaagaaga aggtggccat gctcttccag 960
cccactgtgc ttcgatgcca cttttccacg tcctcccatc agcctgcggt ggttcagtgg 1020
aagttcaaat cctactgcca ggatcgcatg ggagaatcct tgggcatgtc ttctccccga 1080
gcccaagcac tcagcaagag gaacctggaa tgggacccct acttggattg tttagacagc 1140
agaaggaccg tccgagtggt agcttccaaa cagggctcga cggttaccct gggagatttc 1200
tacaggggca gagagatcac aatagttcac gatgcagatc ttcaaattgg aaaactcatg 1260
tggggagaca gcggactcta ctactgtatc atcaccaccc cggatgacct ggaaggcaaa 1320
aacgaagact cagtggaact gctggtgttg ggcaggacag ggctgcttgc tgatctcttg 1380
cccagttttg ctgtggagat tatgccagag tgggtgtttg tcggcctggt gatcctgggg 1440
attttcctct tcttcgtgct ggtggggatc tgctggtgcc aatgctgccc tcacagttgc 1500
tgctgctatg tccgctgccc atgctgccca gattcctgct gctgccctca ggccttgtat 1560
gaagcaggga aagcagccaa ggccgggtac cctccctctg tctccggtgt ccccggcccc 1620
tactccatcc cctctgtccc tttgggagga gccccctctt ctggcatgct gatggacaag 1680
ccgcatccac ctcccctggc accaagtgat tccactggag gaagccacag tgttcgaaaa 1740
ggttaccgga tccaggctga caaagagaga gactccatga aggtcctgta ctatgtcgag 1800
aaggagctgg ctcagtttga tccagccagg aggatgagag gcagatataa caacaccatc 1860
tcggaactca gctccctgca tgatgatgac agcaatttcc gccagtctta ccaccagatg 1920
cggaataagc agttccctat gtctggagac ctggaaagca atcccgacta ctggtcaggt 1980
gtcatgggag gcaacagtgg gaccaacagg gggccagcct tggagtataa caaagaggac 2040
cgtgagagct tcaggcacag ccagcagcgc tccaaatccg agatgctgtc gcggaagaac 2100
tttgccacgg gcgtgccggc cgtgtcgatg gacgagctgg cagccttcgc agactcgtac 2160
ggccagcggt cgcggcgcgc caatggcaac agccacgagg cgcgggcggg gagccgcttc 2220
gagcgctcgg agtcgcgggc ccacggtgcc ttctaccagg acggctcgct ggatgagtac 2280
tacgggcgcg gacgcagtcg cgagcccccg ggagacgggg agcgcggctg gacctacagc 2340
cccgcacccg cacgccgccg gccgccggag gatgcgcctc tgccgcgcct ggtgagccgg 2400
accccgggca ccgcgcccaa gtacgatcac tcgtacctga gcagcgtgct ggagcgccag 2460
gcgcggccgg agagcagcag ccgcgggggc agcctggaga cgccgtccaa gctgggcgcg 2520
cagctgggcc cgcgcagcgc atcctactac gcctggtcgc cgccagccac atacaaggct 2580
ggggccagcg agggcgaaga cgaggacgac gcggcggatg aggacgcgct gccaccctac 2640
agcgagctgg agctgagccg cggagagctg agccggggcc cgtcctaccg tgggcgtgac 2700
ctgtccttcc acagcaactc ggagaagagg aggaaaaagg agcccgtcaa gaaacccggt 2760
gactttccaa ccaggatgtc ccttgtagtc tgatacttat aagacacctc tctggatgac 2820
tggaaatcag atgcagacta tggagacaag acccaaatct gagagccggc aagcctagga 2880

-continued

```
tcttctctgg ccagcagcca ccttggaagc tttgctgatc tctgctttgg caagggatcc   2940
tcctttaaga aggctgattt caaatcttag tgcccaacta tctcgagcaa cttaccaaga   3000
aaacgctctg tgagaacata tcacgtaata accgaccaag tttatcttac actcccaccc   3060
cccacccccc atttccttag cagaaacaag actctgcgtc cagttctgaa gctggaagct   3120
ttgaacccct gatctctaga aattacctat gcctgcagta tgtttttcta tgagtgctgt   3180
tctgtgctta gacagaggaa tttactacta cagttagaag accgtctgct cacaagagag   3240
ataaatggta aaatgtacct tgtatcccct tgcttccagt cactggtcaa tgagtcttgt   3300
tatgctaaaa tcagaaggcc tttagtgagc gtactggccg tgacctcctg ggcaatcaca   3360
gaaatggctt caatttgctg ctctgactca caattctaag tggctgggac aaacagagga   3420
gagcattttg aaaaaccatc ttaagtggtc tttctttttc cattcagagg acacaaactg   3480
cttttcatct ttctgtcaaa cagagtgaca atcctaaggt tctccctgcc cagcccacac   3540
cggtccctct ctttcctccc tctcctggtc ttttcagggc tggtgcctct gagggtgttc   3600
cactccatgc ttcagtgtga atagcttgtc atcaggtgcc tttgacagat gcttcaaaca   3660
aacatttgag agagaagaaa agcagaagtc ggtgatacaa aatgaacagg aaatgacatg   3720
taggctcatt atattttgaa tgtgggttgt ttccccacaa acacactcag atttgttttt   3780
gtttttattt ttggatttgt acttcactta agaattattt ctaccatcct gattctgcag   3840
ctgttgggca ccagggaatg tggtgtccac atcttttggc ctcactggcc caccactatt   3900
gatgctttgg ggaaaagaag gacagcactt cctcttcctg ccattgcaaa aaaaaaaaaa   3960
tgatttttgc ctgaatccct aattgaactt ttgtaggtaa actgcaaaag tggccacaaa   4020
ctcttcccct ctcatgttcc tgtgaaggga tttgtcctct tgctgccaca ggccctgcca   4080
aatgcacctc agctatccta catgatgaga gaagagcctg gtcaccaccg tcattatctg   4140
tgcccatctt atcaacttta agcagacttg gaagaacatc tagccacgac caacaaaaga   4200
actgcctagc tgagccgagc ccaaactgga gattcccgct tgagaggaga cattcagcat   4260
tcctgtgttc gtttaccatc gacgataaac ctcccatcag aatatttgtc tctggtcggt   4320
tactcaccca accttgggtg tcacacaacc ttcacttttg ttagcagact tttcaatctg   4380
cattattgtg gtgagacacg tgactggatg aagtgactgg agcaagggga tgcttgctat   4440
cccctaatcc agtggtggtc tacttctact tattgatcta catgtagtct ctgattcact   4500
ggtcagtatt tccatggcca cgtgactgga attccagagt ccattctgtt agcatccatt   4560
atacttcatg agatttccag aaaaggtcct ctgtgagtgg tgtaagagct gctgggttag   4620
ggtgggtgtt ggggggtgga atcattactt ggaggagaac tggcctgcta aaggacttca   4680
cggttgcttt ggcctgccct agatggatca ggaggatact tcagcccaat gctggcactt   4740
ccaagggctg gaagacaaaa gccataaccc tggtgctgag ttttaggttt gctagtgtcc   4800
ctggcctcag aacacctagg tctgatctgt ctgtttgggc tctaaatcaa tatggcaaaa   4860
acatcatttc ttagtcacca gcttttgatt tcaacttgct caggcacttt tgaagaatat   4920
tggatagccg cagtagctat tgttatactg agcactgtgt caggcttctt agcaccaaag   4980
agccccatag cacaggctac agagaccaaa tatattgctt tatagagcca ggggcgtgta   5040
tgagcttggg gaaagctgag ggagcgatga atgaaagaaa aaagttaaaa ttggaaacat   5100
aaggttctaa agacaacaag tctataggct gacaaattaa aaaaaaaatt tcaatgtaga   5160
gaagataaca ggctttcaat ataacggggg aaagtggggc acagattgtt ctttataggg   5220
catgagtcac gtgggcttcc agaccttcag tacagaggaa attcagttgc ttctgggtcc   5280
```

-continued gtggatagga gatgatctga atggacaagg ctaagctggc cgtccttgat gcccttgaca 5340
tttctttaca cacccctttg tttcttctcc aaatactgtg tcctgcacag gaagtgccta 5400
tgcgtattag ttcctttcct gtttttctag ggcataagca aagtgtaaga ggtgatctcc 5460
atccactgat cccctacaat ttaagaagga agataagtca tgcccaagaa aggatgagta 5520
tattttatgc atatgataag aaatagtgct atggataaat tataataaac ccagagattt 5580
aaagttttct ttaaaaacaa aaaccttaaa tgggaatatt ttgatattta agtgttgtgt 5640
gtttgtccat ccattccatt tttaggacat gctcagtgat ctgcaaagcc aggctgtaga 5700
agtctgagct gaaaggaggt gaaggagaag aaagagggat gagtggcctc agggaggagg 5760
gaagagagta gaggcccgct tacaggagct tctgtctctg cctgtgactc acagctgagt 5820
cagggacaag ctggaggagg gagtatggaa gcaggtggca ggagaggtcc cctggtgctc 5880
agagctcttc tctaggctat gtatagactc attaggagac tcaggactgt attcagttct 5940
tccatccaag caagcccagg ggagcttggg atttagtcct cctggcactt gtatctacag 6000
cttggggtgc agtagtacct cacatgggtt gggaacctca cctcccttct catgatcctc 6060
actctgcatg tggtgtaggg gtgggcaccc cagggtgaga gggggctggc gctacatata 6120
aaaatctggt tagatccgaa gcagtctttg agaggagtgg agtaactaac agacaccgct 6180
ttggctcatc tgctctccat ccatttctaa atagatggat aagccatcat ccacatttat 6240
ggagtcacaa accagtcaga tctttagatt cccaatctat aggcctttcc tgctggatct 6300
gtgtttttgc aaaattgcct agtcataaga attacttgcc tagggactgg agagagatgg 6360
cttaacagtc aaaaacactg ctttagccga ggacccgagt ttggttccca gcactctact 6420
aatgctcaca gctgtctgta acttcaattc cagggaccca ctgatctcat agagcatctg 6480
ggagcactaa actcacatgg tacgcatata taccatcaaa aaactctcag gcacacaaaa 6540
taaaaataaa tacattgtta aaaactgaaa aagaaagggg ctggagagat ggctctgtga 6600
ttacgtgtgc tggctactct tccagaggac ccacattcat ttttcagcac atggagactc 6660
ccagcaccag ttcagacaca cacacacaca cacacacaca cacacacaca cacacacaca 6720
cacacacacg aaggcaaaat acacacctaa caaagaaata aagcatttaa aaatacttgg 6780
taaaacaatt acttgcctgg gggactggga tgtggctcag ttggtagagc acttgattag 6840
catgcacaaa gccctggttc aatccctagc acaataaact aggggtagtg gcacatgcct 6900
gtgatcccaa catctgggag agtttcaagt tcaaggtcat ccttggctac atagtgagtt 6960
caaggtcacc ctgggctgta tgatactctg ccttaaagaa ccaaacactg aaaataacaa 7020
tgaaaaaaca caaggattac tgactgccac tgtcacaaat gctgttgcac tgtaccttgg 7080
agaatggatg ggtggatctg gagtaaggat ttgtattctg aacatatcct tttagaatgc 7140
cttgtggtag atgcatttgg gtggtgctat actggatcat acctctggtg cacccctatc 7200
tgctggccag gaatattgtt tgtgctgtgg attatttcat tccaatatca ctgtgaggtc 7260
cctctaactt ccttaggtct ggcactggtg tggcatccag cagtcccagc tatgacactg 7320
gagaatggct caccagagtc aggctgaaag gaaacattta aagggagggg gttggaggac 7380
ctccccccgg gagacttctt gacatgttcc aactcccaga atagtgatat gttgtgacag 7440
gctgagatca gacaacagga attacagaca attttcttat tcccttacca tcctgaataa 7500
aacttagctc atgaatagaa aaaaaaaaag ccatcagaga aaatggcaaa cgtaaatcat 7560
ttttaaaggg taaaaattaa aagctttgct aacataactt tcatgctagg accaaaagtg 7620

```
ggtggagaaa aaaatagtaa aatatatatt acctattcca aaactgattt aattgcagcc   7680

agaatcttat ggaagtttag aagtgatgta tagagtacag gaatcaccca tggaaattct   7740

aaggtcttag aaagcaaaag gttccctacc aggacctacc tcctagtcac ttgggattac   7800

ctgtgaagct caaaggccct agtggcatca aaggtgagta agaagaagcc gagatgcttt   7860

aagcaacagc gtgaggttgg catcaacggg gcacatttgt tcttcacagc aagcccagtg   7920

ttttcccatc ttacccaatg tggagctggg tctgaaagtg tgccaagtga tcacctattg   7980

ccaaatagct tttagtcttt agatggcctt ctgactgtcc aggtcctaag cctacagtaa   8040

tcacgggccc agcctctagt gtgttctctt cccaagcaga tggatagtgg agagagccct   8100

gactcaatat tcactcacac atcattggtg aggagaagct aggaaggcag gcatttgcca   8160

cttcatctat ccacaggagg ttccttgaag tctgccctga gaaggaggtg tctttgctgg   8220

ggaggatctt cagcatcagc atcaagctgt gaggggaaag gctttgacaa aagggttgcc   8280

actttctgaa ttcttctcaa agaggaattt ctaagccaag ctacagattc atccaggctc   8340

agaattccat ggctgtgggc aggagctgtc atcttcacta tattttgaga tacatttttt   8400

ttaggtagaa ctcgaggtcc agatctagag gggataaggg gagatgagaa ggataaagtt   8460

gtggcagttg agctaaaagt catgttcgag ttttttggtg ggtctgactg gacaggggaa   8520

aatgtggtcc gactcctttt atctaaaagg ttgggaaaga tacccatagc ttctctcttg   8580

ccatgtttat taacaaagat gttagacact actccatgag aaatttcctt gtgaaaataa   8640

aaaccatgcc atcaaaagag tcgggtgcaa agacgcctac ttcatgagaa tcacctgccc   8700

agttgttttt gtgccttgtc tgtgacatca aaactgaaac atttatatca ctgtcactca   8760

tggttttatt ttcctgtgtc atacatacaa cgtgcatttg attgtaatga tttaaagtaa   8820

ataaagcatt tcatctactt ttgtt                                          8845
```

<210> SEQ ID NO 11
<211> LENGTH: 2861
<212> TYPE: DNA
<213> ORGANISM: Mus musculus

<400> SEQUENCE: 11

```
gactagcaaa tgttgtcttt aataatattt tcaaagtctc agttaaaaga tttagaaaac     60

aagtggatca gttacattac aaataggttc cctagattta aataaaagga aattcaatat    120

atttctaagt ttttaaaaaa taatcaaaat ttctgttatt tttctagcta catcataact    180

ccggtcctag ttcataagta cttctgcaca aagcttggaa gtgagaaatc tgtgaccaca    240

tctttcttac attttttagg caggggccag agttcaagct acagcccagt ggacacaaag    300

gctaagtcca ccttccaaac ttctggcctt cacaaccaca aacacctgca atcctttggt    360

agggagggaa acaggtctac ccaggcctta agtaggtctg gtgagccttg ggcagggcat    420

tacacagcag gagcatggtc taaaaggtaa gtgaactgaa accaaggtat atgtccttca    480

ccttgacttt gagccatttg gagagcagaa tgggcctctt ctaaagcacg gggttcatac    540

tggctctaaa gaccccttttt gggaccgggc cagcagtaga gaacatgcta ttagtagtgg   600

ctttttttccc ccttcctctc ttggcccaac atagcctaaa tcattgaagt tcaccgcagt   660

gattatatag gacagagaaa aacatttgaa caagggagat agatgcacga ggaggccagc    720

tgcagacagc ctgagttccg ggaagcctgc cttaggtaga acaaagacaa ttgtctccct    780

attccaagaa cagcatgtag gaagcctccc tctctgtaag caagttgggt ttgagctgga    840

gccaattcct gctgagtaac acaaatacca cctgtgagca tctacagctc acactggtca    900
```

-continued

```
ggaccaaggc tcccaggcag aagattctgg aatatgcgat ctcagccctt agcagcactc    960

ccttccaacc atttagaaaa ccatggtgcc tgcttttgtt cctgcagata acaacaccat   1020

ctcggaactc agctccctgc atgatgatga cagcaatttc cgccagtctt accaccagat   1080

gcggaataag cagttcccta tgtctggaga cctggaaagc aatcccgact actggtcagg   1140

tgtcatggga ggcaacagtg ggaccaacag gggccagcc ttggagtata acaaagagga   1200

ccgtgagagc ttcaggcaca ggtgacggcc atgagtggga agggaccact gtgtatctgt   1260

tcttctgttt ctatagacta tggaatatct cttacatata ttacaccctt gtgatactgt   1320

gtgtgagaag taaccagtta agccttttttg aaatgagtgt cttgggcccc gtaatgagac   1380

actctccata tgttttatcc tagaaccttt aaagaaccca ctatcttcac caccctgatc   1440

atttgtcata agaatgataa tcatgccacc atctcttgta attaatcctt atacttctaa   1500

agagcagcta ctgtttatgt tcctatttta aggccaggaa atagaaagtt ccagatgcta   1560

aggaacttgc ccagggtgat aagtccaagc aacatttaat aatctgtgtg acagcttgat   1620

tcctgaatgg catgcttgta ctcattatct gtccttggag gacagtaggt acccccattt   1680

cctttaccta ctgcagaggt ctcaggcctc ttgacttaat aggcaacttg gtccctgccc   1740

cagagagaga tacaatcctt tctattttac cgattattcc tggtctcctg ggaccagagc   1800

tgtgtgttgc tgtttgctgt ggttgtgagg gtgggtgaag taaaacatgt ggctgtcacc   1860

caggggtctc aacacgataa caagctgatc tgtgtgtttc agcactacac agatcacaag   1920

gtattttcag atacacaacc attctggtct tccacacaaa ctcaggagag agccaggatt   1980

gctctggctg aactcgcagc acgaaaggtg ccaaagttga tttatcctgc tgggctgagg   2040

ggtaagatac acctgggccc ctgaaactcc aggggcgcgc tgcaaggttt ccatgcagta   2100

accagtgacc atctgcccgc agccagcagc gctccaaatc cgagatgctg tcgcggaaga   2160

actttgccac gggcgtgccg gccgtgtcga tggacgagct ggcagccttc gcagactcgt   2220

acggccagcg gtcgcggcgc gccaatggca acagccacga ggcgcgggcg gggagccgct   2280

tcgagcgctc ggagtcgcgg gcccacggtg ccttctacca ggacggctcg ctggatgagt   2340

actacgggcg cggacgcagt cgcgagcccc cgggagacgg ggagcgcggc tggacctaca   2400

gccccgcacc cgcacgccgc cggccgccgg aggatgcgcc tctgccgcgc ctggtgagcc   2460

ggaccccggg caccgcgccc aagtacgatc actcgtacct gagcagcgtg ctggagcgcc   2520

aggcgcggcc ggagagcagc agccgcgggg gcagcctgga gacgccgtcc aagctgggcg   2580

cgcagctggg cccgcgcagc gcatcctact acgcctggtc gccgccagcc acatacaagg   2640

ctggggccag cgagggcgaa gacgaggacg acgcggcgga tgaggacgcg ctgccaccct   2700

acagcgagct ggagctgagc cgcggagagc tgagccgggg cccgtcctac cgtgggcgtg   2760

acctgtcctt ccacagcaac tcggagaaga ggaggaaaaa ggagcccgtc aagaaacccg   2820

tgaggactca cccccatgtc tctggagctg ggtccgggaa t                       2861
```

<210> SEQ ID NO 12
<211> LENGTH: 2861
<212> TYPE: DNA
<213> ORGANISM: Mus musculus

<400> SEQUENCE: 12

```
gactagcaaa tgttgtcttt aataatattt tcaaagtctc agttaaaaga tttagaaaac     60

aagtggatca gttacattac aaataggttc cctagattta aataaaagga aattcaatat    120
```

-continued

```
atttctaagt ttttaaaaaa taatcaaaat ttctgttatt tttctagcta catcataact    180
ccggtcctag ttcataagta cttctgcaca aagcttggaa gtgagaaatc tgtgaccaca    240
tctttcttac attttttagg caggggccag agttcaagct acagcccagt ggacacaaag    300
gctaagtcca ccttccaaac ttctggcctt cacaaccaca aacacctgca atcctttggt    360
agggagggaa acaggtctac ccaggcctta agtaggtctg gtgagccttg ggcagggcat    420
tacacagcag gagcatggtc taaaaggtaa gtgaactgaa accaaggtat atgtccttca    480
ccttgacttt gagccatttg gagagcagaa tgggcctctt ctaaagcacg gggttcatac    540
tggctctaaa gaccccttt gggaccgggc cagcagtaga gaacatgcta ttagtagtgg     600
ctttttccc ccttcctctc ttggcccaac atagcctaaa tcattgaagt tcaccgcagt     660
gattatatag gacagagaaa aacatttgaa caagggagat agatgcacga ggaggccagc    720
tgcagacagc ctgagttccg ggaagcctgc cttaggtaga acaaagacaa ttgtctccct    780
attccaagaa cagcatgtag gaagcctccc tctctgtaag caagttgggt ttgagctgga    840
gccaattcct gctgagtaac acaaatacca cctgtgagca tctacagctc acactggtca    900
ggaccaaggc tcccaggcag aagattctgg aatatgcgat ctcagccctt agcagcactc    960
ccttccaacc atttagaaaa ccatggtgcc tgcttttgtt cctgcagata acaacaccat   1020
ctcggaactc agctccctgc atgatgatga cagcaatttc cgccagtctt accaccagat   1080
gcggaataag cagttcccta tgtctggaga cctggaaagc aatcccgact actggtcagg   1140
tgtcatggga ggcaacagtg ggaccaacag gggccagcc ttggagtata acaaagagga    1200
ccgtgagagc ttcaggcaca ggtgacggcc atgagtggga agggaccact gtgtatctgt   1260
tcttctgttt ctatagacta tggaatatct cttacatata ttacaccctt gtgatactgt   1320
gtgtgagaag taaccagtta agccttttg aaatgagtgt cttgggcccc gtaatgagac    1380
actctccata tgttttatcc tagaaccttt aaagaaccca ctatcttcac caccctgatc   1440
atttgtcata agaatgataa tcatgccacc atctcttgta attaatcctt atacttctaa   1500
agagcagcta ctgtttatgt tcctatttta aggccaggaa atagaaagtt ccagatgcta   1560
aggaacttgc ccagggtgat aagtccaagc aacatttaat aatctgtgtg acagcttgat   1620
tcctgaatgg catgcttgta ctcattatct gtccttggag gacagtaggt acccccattt   1680
cctttaccta ctgcagaggt ctcaggcctc ttgacttaat aggcaacttg gtccctgccc   1740
cagagagaga tacaatcctt tctattttac cgattattcc tggtctcctg ggaccagagc   1800
tgtgtgttgc tgtttgctgt ggttgtgagg gtgggtgaag taaaacatgt ggctgtcacc   1860
caggggtctc aacacgataa caagctgatc tgtgtgtttc agcactacac agatcacaag   1920
gtattttcag atacacaacc attctggtct tccacacaaa ctcaggagag agccaggatt   1980
gctctggctg aactcgcagc acgaaaggtg ccaaagttga tttatcctgc tgggctgagg   2040
ggtaagatac acctgggccc ctgaaactcc aggggcgcgc tgcaaggttt ccatgcagta   2100
accagtgacc atctgcccgc agccagcagc gctccaaatc cgagatgctg tcgcggaaga   2160
actttgccac gggcgtgccg gccgtgtcga tggacgagct ggcagccttc gcagactcgt   2220
acggccagcg gtcgcggcgc gccaatggca acagccacga ggcgcgggcg gggagccgct   2280
tcgagcgctc ggagtcgcgg gcccacggtg ccttctacca ggacggctcg ctggatgagt   2340
actacgggcg cggacgcagt cgcgagcccc cgggagacgg ggagcgcggc tggacctaca   2400
gccccgcacc cgcacgccgc cggccgccgg aggatgcgcc tctgccgcgc ctggtgagcc   2460
ggaccccggg caccgcgccc aagtacgatc actcgtacct gagcagcgtg ctggagcgcc   2520
```

-continued aggcgcggcc ggagagcagc agccgcgggg gcagcctgga gacgccgtcc aagctgggcg 2580
cgcagctggg cccgcgcagc gcatcctact acgcctggtc gccgccagcc acatacaagg 2640
ctggggccag cgagggcgaa gacgaggacg acgcggcgga tgaggacgcg ctgccaccct 2700
acagcgagct ggagctgagc cgcggagagc tgagccgggg cccgtcctac cgtgggcgtg 2760
acctgtcctt ccacagcaac tcggagaaga ggaggaaaaa ggagcccgtc aagaaacccg 2820
tgaggactca cccccatgtc tctggagctg ggtccgggaa t 2861

<210> SEQ ID NO 13
<211> LENGTH: 2845
<212> TYPE: DNA
<213> ORGANISM: Mus musculus

<400> SEQUENCE: 13
gactagtaaa tgttgtcttt aataatattt tcaaagtctc agttaaaaga tttagaaaac 60
aagtggatca gttacattac aaataggttc cctagattta agtaaaagga aattcaatat 120
atttctaagt ttttaaaaaa taatcgaaat ttctgttatt tttctagcta catcataact 180
ctggtcctag ttcataagta cttctgcaca aagctaggaa gtgagaaatc tgtgaccgca 240
tctttcttac attttttagg caggggccag agttcaagct acagcccagt ggacacaaag 300
gctaagtcca ccttccaaac gtctggccta gccactcaca accacaaaca cctgcaatcc 360
tttgataggg agggaaacag gtctacccag gccttaagta ggtctggtga gccttgggca 420
gggcattaca cagcaggagc gtggtctaaa aggtaagtga actgaaacca aggtatatgt 480
ccttcacctt gactttgagc catttggaga gcagaatggg cctcttctaa agcacggggt 540
tcatactggc tctaaagacc cccttttggg accgggccag cagtagagaa catgctatta 600
gtagtggctt tttttttccc cttcctctct tggcccaaca tagcctgaat cattgaagtt 660
caccgcagtg attatatagg acagagaaaa acatttgaac aagggagatc cgggaagcct 720
gccttaggta gaacaaagac aattgtctcc ctattccaag aacagcatgt aggaagcctc 780
cctctctgta agcaagttgg gtttgagatg gagccaattc ctgctgagta acacaaatac 840
cacctgtgat catctacagc tcacactggt caggaccatg gctcccaggc agaagattct 900
ggaatatgcg atcatagccc ttagcagcac tcccttccaa tcatttagaa aaccatggtg 960
cctgcttttg ttcctgcaga taacaacacc atctcggaac tcagctccct gcatgatgat 1020
gacagcaatt tccgccagtc ttaccaccag atgcggaata agcagttccc tatgtctgga 1080
gacctggaaa gcaatcctga ctactggtca ggtgtcatgg gaggcaacag tgggaccaac 1140
agggggccag ccttggagta taacaaagag gaccgtgaga gcttcaggca caggtgacgg 1200
ccatgagtgg gaagggacca ctgtgtatct gttcttctgt ttctatagac tatggaatat 1260
ctcttacata tattacaccc ttgtgatact gtgtgtgaga agtaaccagt taagcctttt 1320
tgaaatgagt gtcttgggtc ccgtaatgag acactctctc catatgtttt atcctagaac 1380
ctttaaagaa cccactatct tcaccaccct gatcatttgt cataagaatg atgatcatgc 1440
caccatctct tgtaattaat ccttatactt ctaaaaagca gctactgttt atgttcctat 1500
tttaaggcca ggaaatagaa agttccagat gctaaggaac ttgcccaggg tgataagtcc 1560
aagcaacatt taataatctg tgtgacagct cgattcctga atggcatgcc tgcactcatt 1620
atctgtcctt ggaggacagt aggtacctac cccccccccc atttccttta cccactgcag 1680
aggtctcagg cctcttgact taataggcaa cttggtccct gccccggaga gagatacaat 1740

```
cctttctatg ttaacaatta ttcctggtct cctgggacca gagctgtgtg ttgctgtttg   1800

ctgtggttgt gagggtgggt gaagtaaaac atgtggctgt cacccagggg tctcaacacg   1860

ataacaagct gatctgtgtg tttcagcact acacagatca caaggtattt tcagatacac   1920

aaccattctg gtcttccaca caaactcagg agagagccag gattgctctg gctgaactcg   1980

cagcacaaaa ggtgccaaag ttgattcatc ctgctgggct gaggggtaag atacacctgg   2040

gcccctgaaa ctccaggggc gcgctgcaag gtttccatgc aataaccagt gaccatctgc   2100

ccgcagccag cagcgctcca aatctgagat gctgtcgcgg aagaactttg ccacgggcgt   2160

gccggccgtg tcgatggacg agctggcagc cttcgcagac tcgtacggcc agcggtcgcg   2220

gcgcgccaat ggcaacagcc acgaggcgcg ggcggggagc cgcttcgagc gctcggagtc   2280

gcgggcccac ggtgccttct accaggacgg ctcgctggat gagtactacg ggcgcggacg   2340

cagtcgcgag ccgccgggag acggggagcg tggctggacc tacagccccg cacccgcacg   2400

ccgccggccg ccagaggatg cgcctctgcc gcgcctggtg agccggaccc cgggcaccgc   2460

gcccaagtac gatcactcgt acctgagcag cgtgctggag cgccaggcgc ggccggagag   2520

cagcagccgc gggggcagcc tggagacgcc gtccaagctg ggcgcgcagc tgggcccgcg   2580

cagcgcatcc tactacgcct ggtcgccgcc aaccacatac aaagctgggg ccagcgaggg   2640

cgaagacgag gacgacgcgg cggatgagga cgcgctgcca ccctacagcg agctggagct   2700

gagccgcgga gagctgagcc ggggcccgtc ctaccgtggg cgtgacctgt ccttccacag   2760

caactcggag aagaggagga aaaaggagcc cgccaagaaa cccgtgaggg ctcaccccca   2820

tctctctgga gctgggtccg ggaat                                         2845
```

<210> SEQ ID NO 14
<211> LENGTH: 646
<212> TYPE: PRT
<213> ORGANISM: Mus musculus

<400> SEQUENCE: 14

```
Met Asp Arg Val Val Leu Gly Trp Thr Ala Val Phe Trp Leu Thr Ala
1               5                   10                  15

Met Val Glu Gly Leu Gln Val Thr Val Pro Asp Lys Lys Lys Val Ala
            20                  25                  30

Met Leu Phe Gln Pro Thr Val Leu Arg Cys His Phe Ser Thr Ser Ser
        35                  40                  45

His Gln Pro Ala Val Val Gln Trp Lys Phe Lys Ser Tyr Cys Gln Asp
    50                  55                  60

Arg Met Gly Glu Ser Leu Gly Met Ser Ser Pro Arg Ala Gln Ala Leu
65                  70                  75                  80

Ser Lys Arg Asn Leu Glu Trp Asp Pro Tyr Leu Asp Cys Leu Asp Ser
                85                  90                  95

Arg Arg Thr Val Arg Val Val Ala Ser Lys Gln Gly Ser Thr Val Thr
            100                 105                 110

Leu Gly Asp Phe Tyr Arg Gly Arg Glu Ile Thr Ile Val His Asp Ala
        115                 120                 125

Asp Leu Gln Ile Gly Lys Leu Met Trp Gly Asp Ser Gly Leu Tyr Tyr
    130                 135                 140

Cys Ile Ile Thr Thr Pro Asp Asp Leu Glu Gly Lys Asn Glu Asp Ser
145                 150                 155                 160

Val Glu Leu Leu Val Leu Gly Arg Thr Gly Leu Leu Ala Asp Leu Leu
                165                 170                 175
```

-continued

```
Pro Ser Phe Ala Val Glu Ile Met Pro Glu Trp Val Phe Val Gly Leu
            180                 185                 190

Val Ile Leu Gly Ile Phe Leu Phe Phe Val Leu Val Gly Ile Cys Trp
        195                 200                 205

Cys Gln Cys Cys Pro His Ser Cys Cys Cys Tyr Val Arg Cys Pro Cys
    210                 215                 220

Cys Pro Asp Ser Cys Cys Cys Pro Gln Ala Leu Tyr Glu Ala Gly Lys
225                 230                 235                 240

Ala Ala Lys Ala Gly Tyr Pro Pro Ser Val Ser Gly Val Pro Gly Pro
                245                 250                 255

Tyr Ser Ile Pro Ser Val Pro Leu Gly Gly Ala Pro Ser Ser Gly Met
            260                 265                 270

Leu Met Asp Lys Pro His Pro Pro Pro Leu Ala Pro Ser Asp Ser Thr
        275                 280                 285

Gly Gly Ser His Ser Val Arg Lys Gly Tyr Arg Ile Gln Ala Asp Lys
    290                 295                 300

Glu Arg Asp Ser Met Lys Val Leu Tyr Tyr Val Glu Lys Glu Leu Ala
305                 310                 315                 320

Gln Phe Asp Pro Ala Arg Arg Met Arg Gly Arg Tyr Asn Asn Thr Ile
                325                 330                 335

Ser Glu Leu Ser Ser Leu His Asp Asp Asp Ser Asn Phe Arg Gln Ser
            340                 345                 350

Tyr His Gln Met Arg Asn Lys Gln Phe Pro Met Ser Gly Asp Leu Glu
        355                 360                 365

Ser Asn Pro Asp Tyr Trp Ser Gly Val Met Gly Gly Asn Ser Gly Thr
    370                 375                 380

Asn Arg Gly Pro Ala Leu Glu Tyr Asn Lys Glu Asp Arg Glu Ser Phe
385                 390                 395                 400

Arg His Ser Gln Gln Arg Ser Lys Ser Glu Met Leu Ser Arg Lys Asn
                405                 410                 415

Phe Ala Thr Gly Val Pro Ala Val Ser Met Asp Glu Leu Ala Ala Phe
            420                 425                 430

Ala Asp Ser Tyr Gly Gln Arg Ser Arg Arg Ala Asn Gly Asn Ser His
        435                 440                 445

Glu Ala Arg Ala Gly Ser Arg Phe Glu Arg Ser Glu Ser Arg Ala His
    450                 455                 460

Gly Ala Phe Tyr Gln Asp Gly Ser Leu Asp Glu Tyr Tyr Gly Arg Gly
465                 470                 475                 480

Arg Ser Arg Glu Pro Pro Gly Asp Gly Glu Arg Gly Trp Thr Tyr Ser
                485                 490                 495

Pro Ala Pro Ala Arg Arg Arg Pro Pro Glu Asp Ala Pro Leu Pro Arg
            500                 505                 510

Leu Val Ser Arg Thr Pro Gly Thr Ala Pro Lys Tyr Asp His Ser Tyr
        515                 520                 525

Leu Ser Ser Val Leu Glu Arg Gln Ala Arg Pro Glu Ser Ser Ser Arg
    530                 535                 540

Gly Gly Ser Leu Glu Thr Pro Ser Lys Leu Gly Ala Gln Leu Gly Pro
545                 550                 555                 560

Arg Ser Ala Ser Tyr Tyr Ala Trp Ser Pro Pro Thr Thr Tyr Lys Ala
                565                 570                 575

Gly Ala Ser Glu Gly Glu Asp Glu Asp Asp Ala Ala Asp Glu Asp Ala
            580                 585                 590

Leu Pro Pro Tyr Ser Glu Leu Glu Leu Ser Arg Gly Glu Leu Ser Arg
```

-continued

```
        595                 600                 605

Gly Pro Ser Tyr Arg Gly Arg Asp Leu Ser Phe His Ser Asn Ser Glu
    610                 615                 620

Lys Arg Arg Lys Lys Glu Pro Ala Lys Lys Pro Gly Asp Phe Pro Thr
625                 630                 635                 640

Arg Met Ser Leu Val Val
                645


<210> SEQ ID NO 15
<211> LENGTH: 639
<212> TYPE: PRT
<213> ORGANISM: Homo sapiens

<400> SEQUENCE: 15

Met Asp Arg Val Leu Leu Arg Trp Ile Ser Leu Phe Trp Leu Thr Ala
1               5                   10                  15

Met Val Glu Gly Leu Gln Val Thr Val Pro Asp Lys Lys Lys Val Ala
            20                  25                  30

Met Leu Phe Gln Pro Thr Val Leu Arg Cys His Phe Ser Thr Ser Ser
        35                  40                  45

His Gln Pro Ala Val Val Gln Trp Lys Phe Lys Ser Tyr Cys Gln Asp
    50                  55                  60

Arg Met Gly Glu Ser Leu Gly Met Ser Ser Thr Arg Ala Gln Ser Leu
65                  70                  75                  80

Ser Lys Arg Asn Leu Glu Trp Asp Pro Tyr Leu Asp Cys Leu Asp Ser
                85                  90                  95

Arg Arg Thr Val Arg Val Val Ala Ser Lys Gln Gly Ser Thr Val Thr
            100                 105                 110

Leu Gly Asp Phe Tyr Arg Gly Arg Glu Ile Thr Ile Val His Asp Ala
        115                 120                 125

Asp Leu Gln Ile Gly Lys Leu Met Trp Gly Asp Ser Gly Leu Tyr Tyr
    130                 135                 140

Cys Ile Ile Thr Thr Pro Asp Asp Leu Glu Gly Lys Asn Glu Asp Ser
145                 150                 155                 160

Val Glu Leu Leu Val Leu Gly Arg Thr Gly Leu Leu Ala Asp Leu Leu
                165                 170                 175

Pro Ser Phe Ala Val Glu Ile Met Pro Glu Trp Val Phe Val Gly Leu
            180                 185                 190

Val Leu Leu Gly Val Phe Leu Phe Phe Val Leu Val Gly Ile Cys Trp
        195                 200                 205

Cys Gln Cys Cys Pro His Ser Cys Cys Cys Tyr Val Arg Cys Pro Cys
    210                 215                 220

Cys Pro Asp Ser Cys Cys Cys Pro Gln Ala Leu Tyr Glu Ala Gly Lys
225                 230                 235                 240

Ala Ala Lys Ala Gly Tyr Pro Pro Ser Val Ser Gly Val Pro Gly Pro
                245                 250                 255

Tyr Ser Ile Pro Ser Val Pro Leu Gly Gly Ala Pro Ser Ser Gly Met
            260                 265                 270

Leu Met Asp Lys Pro His Pro Pro Pro Leu Ala Pro Ser Asp Ser Thr
        275                 280                 285

Gly Gly Ser His Ser Val Arg Lys Gly Tyr Arg Ile Gln Ala Asp Lys
    290                 295                 300

Glu Arg Asp Ser Met Lys Val Leu Tyr Tyr Val Glu Lys Glu Leu Ala
305                 310                 315                 320
```

-continued

```
Gln Phe Asp Pro Ala Arg Arg Met Arg Gly Arg Tyr Asn Asn Thr Ile
                325                 330                 335

Ser Glu Leu Ser Ser Leu His Glu Glu Asp Ser Asn Phe Arg Gln Ser
            340                 345                 350

Phe His Gln Met Arg Ser Lys Gln Phe Pro Val Ser Gly Asp Leu Glu
        355                 360                 365

Ser Asn Pro Asp Tyr Trp Ser Gly Val Met Gly Gly Ser Ser Gly Ala
    370                 375                 380

Ser Arg Gly Pro Ser Ala Met Glu Tyr Asn Lys Glu Asp Arg Glu Ser
385                 390                 395                 400

Phe Arg His Ser Gln Pro Arg Ser Lys Ser Glu Met Leu Ser Arg Lys
                405                 410                 415

Asn Phe Ala Thr Gly Val Pro Ala Val Ser Met Asp Glu Leu Ala Ala
            420                 425                 430

Phe Ala Asp Ser Tyr Gly Gln Arg Pro Arg Arg Ala Asp Gly Asn Ser
        435                 440                 445

His Glu Ala Arg Gly Gly Ser Arg Phe Glu Arg Ser Glu Ser Arg Ala
    450                 455                 460

His Ser Gly Phe Tyr Gln Asp Asp Ser Leu Glu Glu Tyr Tyr Gly Gln
465                 470                 475                 480

Arg Ser Arg Ser Arg Glu Pro Leu Thr Asp Ala Asp Arg Gly Trp Ala
                485                 490                 495

Phe Ser Pro Ala Arg Arg Arg Pro Ala Glu Asp Ala His Leu Pro Arg
            500                 505                 510

Leu Val Ser Arg Thr Pro Gly Thr Ala Pro Lys Tyr Asp His Ser Tyr
        515                 520                 525

Leu Gly Ser Ala Arg Glu Arg Gln Ala Arg Pro Glu Gly Ala Ser Arg
    530                 535                 540

Gly Gly Ser Leu Glu Thr Pro Ser Lys Arg Ser Ala Gln Leu Gly Pro
545                 550                 555                 560

Arg Ser Ala Ser Tyr Tyr Ala Trp Ser Pro Pro Gly Thr Tyr Lys Ala
                565                 570                 575

Gly Ser Ser Gln Asp Asp Gln Glu Asp Ala Ser Asp Asp Ala Leu Pro
            580                 585                 590

Pro Tyr Ser Glu Leu Glu Leu Thr Arg Gly Pro Ser Tyr Arg Gly Arg
        595                 600                 605

Asp Leu Pro Tyr His Ser Asn Ser Glu Lys Lys Arg Lys Lys Glu Pro
    610                 615                 620

Ala Lys Lys Thr Asn Asp Phe Pro Thr Arg Met Ser Leu Val Val
625                 630                 635


<210> SEQ ID NO 16
<211> LENGTH: 590
<212> TYPE: PRT
<213> ORGANISM: Danio rerio

<400> SEQUENCE: 16

Met Phe Leu Leu His Ala Phe Trp Ile Leu Phe Thr Leu Phe Ser Leu
1               5                   10                  15

Gln Ser Cys Asp Gly Val Gln Val Val Val Lys Asp Glu Lys Lys Phe
            20                  25                  30

Ala Met Leu Phe Ser Ser Ile Val Leu Pro Cys His Tyr Thr Thr His
        35                  40                  45

Ser Thr Gln Thr Ala Val Val Gln Trp Trp Tyr Lys Ser Tyr Cys Thr
    50                  55                  60
```

-continued

```
Asp Arg Thr Arg Asp Ser Phe Thr Phe Pro Glu Ser Leu Gly Val His
65                  70                  75                  80

Val Ser Asp Leu Gly Ala Ser Ser His Arg Asp Cys Ser Asp Asn Ser
                85                  90                  95

Arg Thr Val Arg Ile Val Ala Ser Gly Gln Gly Ala Ser Met Thr Leu
            100                 105                 110

Ala Glu His Tyr Lys Gly Arg Asp Ile Ser Ile Ile Asn Lys Ala Asp
        115                 120                 125

Leu His Ile Gly Gln Leu Gln Trp Gly Asp Ser Gly Val Tyr Phe Cys
    130                 135                 140

Lys Val Ile Ile Ser Asp Asp Leu Glu Gly Lys Asn Glu Gly Gln Val
145                 150                 155                 160

Glu Leu Leu Val Gln Gly Arg Thr Gly Val Leu Asp Asp Ile Leu Pro
                165                 170                 175

Glu Phe Asp Leu Glu Ile Met Pro Glu Trp Ala Phe Val Gly Val Val
            180                 185                 190

Val Val Gly Ser Ile Leu Phe Leu Leu Leu Val Gly Ile Cys Trp Cys
        195                 200                 205

Gln Cys Cys Pro His Ser Cys Cys Cys Tyr Val Arg Cys Cys Cys Cys
    210                 215                 220

Pro Asp Thr Cys Cys Cys Pro Lys His Leu Tyr Glu Ala Gly Lys Met
225                 230                 235                 240

Ala Lys Ser Gly Gln Pro Pro Gln Ile Thr Met Tyr Gln Pro Tyr Tyr
                245                 250                 255

Val Pro Gly Val Pro Val Val Pro Val Val Pro Pro Ala Ala Ser Ser
            260                 265                 270

Ile Ile Glu Pro Lys Leu Pro Thr Val Pro Pro Ser Val Glu Asn Asn
        275                 280                 285

Ile Ala Gly Thr Ala Asp Asn Leu Ser Glu Leu Ser Ser Leu His Asp
    290                 295                 300

Gly Asp Val Asp Phe Arg Gln Thr Tyr Arg Gln Val Gln Arg Lys Ala
305                 310                 315                 320

Leu Pro Pro Ile Ile Asp His Leu Asp Glu Pro Arg Leu Arg Thr Ala
                325                 330                 335

Ser Ile Gly His Gly Leu Arg Pro Ser His Tyr Gln Ser Asp His Ser
            340                 345                 350

Leu Asp Glu His Asp Asn Arg Trp Asn Cys Arg Ser Glu His Leu Pro
        355                 360                 365

Arg Lys Ala Phe Asp Ser Arg Gly Arg Thr Val Ser Leu Asp Glu Leu
    370                 375                 380

Glu Glu Phe Ala Met Ser Tyr Gly Pro His Gly Arg Arg Arg Gly Asp
385                 390                 395                 400

Ile Arg Gly Pro Gln Arg Asp Phe Glu Met Ala Pro Arg Thr Arg Asp
                405                 410                 415

His Pro Thr Ser Tyr Arg Asn Gly Pro Arg Tyr Leu Arg Glu Asp Asp
            420                 425                 430

Asp Ser Asp Trp His Arg Arg Gly Ser Pro Pro Ser Pro Pro Lys Arg
        435                 440                 445

Arg Asp Thr Ala Asp Ser Glu Arg Tyr Val Ser Arg Gln Arg Ser Tyr
    450                 455                 460

Asp Asp Thr Tyr Leu Asn Ser Leu Leu Glu Arg Lys Ala Arg Gly His
465                 470                 475                 480
```

-continued

```
Gly Glu Arg Gly Gly Arg Val Asp Asp Asp Ser Asp Thr Pro Ser Lys
                485                 490                 495

Gly Ser Ser Lys Lys Ser Ser Asp Cys Tyr Gln Ser Arg Ser Pro Ser
            500                 505                 510

Asn Arg Pro Glu Glu Glu Asp Pro Leu Pro Pro Tyr Ser Glu Arg Glu
        515                 520                 525

Gly Glu Arg Phe Arg Thr Glu Glu Pro Thr Gly Arg Glu Arg Tyr Arg
    530                 535                 540

Thr Ala Asp Pro Ala Met Arg Pro Phe Ser Tyr Thr Arg Pro Pro His
545                 550                 555                 560

Gly Leu Ser Gln Thr Leu Gln Glu Arg Arg Glu Asp Arg Asp Lys Pro
                565                 570                 575

Arg Lys Leu Thr Thr His Leu Ser Arg Asp Ser Leu Ile Val
            580                 585                 590


<210> SEQ ID NO 17
<211> LENGTH: 573
<212> TYPE: PRT
<213> ORGANISM: Mus musculus

<400> SEQUENCE: 17

Met Ala Pro Ala Ala Ser Ala Cys Ala Gly Ala Pro Gly Ser His Pro
1               5                   10                  15

Ala Thr Thr Ile Phe Val Cys Leu Phe Leu Ile Ile Tyr Cys Pro Asp
            20                  25                  30

Arg Ala Ser Ala Ile Gln Val Thr Val Pro Asp Pro Tyr His Val Val
        35                  40                  45

Ile Leu Phe Gln Pro Val Thr Leu His Cys Thr Tyr Gln Met Ser Asn
    50                  55                  60

Thr Leu Thr Ala Pro Ile Val Ile Trp Lys Tyr Lys Ser Phe Cys Arg
65                  70                  75                  80

Asp Arg Val Ala Asp Ala Phe Ser Pro Ala Ser Val Asp Asn Gln Leu
                85                  90                  95

Asn Ala Gln Leu Ala Ala Gly Asn Pro Gly Tyr Asn Pro Tyr Val Glu
            100                 105                 110

Cys Gln Asp Ser Val Arg Thr Val Arg Val Val Ala Thr Lys Gln Gly
        115                 120                 125

Asn Ala Val Thr Leu Gly Asp Tyr Tyr Gln Gly Arg Arg Ile Thr Ile
    130                 135                 140

Thr Gly Asn Ala Asp Leu Thr Phe Glu Gln Thr Ala Trp Gly Asp Ser
145                 150                 155                 160

Gly Val Tyr Tyr Cys Ser Val Val Ser Ala Gln Asp Leu Asp Gly Asn
                165                 170                 175

Asn Glu Ala Tyr Ala Glu Leu Ile Val Leu Gly Arg Thr Ser Glu Ala
            180                 185                 190

Pro Glu Leu Leu Pro Gly Phe Arg Ala Gly Pro Leu Glu Asp Trp Leu
        195                 200                 205

Phe Val Val Val Val Cys Leu Ala Ser Leu Leu Phe Phe Leu Leu Leu
    210                 215                 220

Gly Ile Cys Trp Cys Gln Cys Cys Pro His Thr Cys Cys Cys Tyr Val
225                 230                 235                 240

Arg Cys Pro Cys Cys Pro Asp Lys Cys Cys Cys Pro Glu Ala Leu Tyr
                245                 250                 255

Ala Ala Gly Lys Ala Ala Thr Ser Gly Val Pro Ser Ile Tyr Ala Pro
            260                 265                 270
```

```
Ser Ile Tyr Thr His Leu Ser Pro Ala Lys Thr Pro Pro Pro Pro Pro
        275                 280                 285

Ala Met Ile Pro Met Arg Pro Pro Tyr Gly Tyr Pro Gly Asp Phe Asp
    290                 295                 300

Arg Thr Ser Ser Val Arg Ser Gly Tyr Arg Ile Gln Ala Asn Gln Gln
305                 310                 315                 320

Asp Asp Ser Met Arg Val Leu Tyr Tyr Met Glu Lys Glu Leu Ala Asn
                325                 330                 335

Phe Asp Pro Ser Arg Pro Gly Pro Pro Asn Gly Arg Val Glu Arg Ala
            340                 345                 350

Met Ser Glu Val Thr Ser Leu His Glu Asp Asp Trp Arg Ser Arg Pro
        355                 360                 365

Ser Arg Ala Pro Ala Leu Thr Pro Ile Arg Asp Glu Glu Trp Asn Arg
    370                 375                 380

His Ser Pro Arg Ser Pro Arg Thr Trp Glu Gln Glu Pro Leu Gln Glu
385                 390                 395                 400

Gln Pro Arg Gly Gly Trp Gly Ser Gly Arg Pro Arg Ala Arg Ser Val
                405                 410                 415

Asp Ala Leu Asp Asp Ile Asn Arg Pro Gly Ser Thr Glu Ser Gly Arg
            420                 425                 430

Ser Ser Pro Pro Ser Ser Gly Arg Arg Gly Arg Ala Tyr Ala Pro Pro
        435                 440                 445

Arg Ser Arg Ser Arg Asp Asp Leu Tyr Asp Pro Asp Asp Pro Arg Asp
    450                 455                 460

Leu Pro His Ser Arg Asp Pro His Tyr Tyr Asp Asp Leu Arg Ser Arg
465                 470                 475                 480

Asp Pro Arg Ala Asp Pro Arg Ser Arg Gln Arg Ser His Asp Pro Arg
                485                 490                 495

Asp Ala Gly Phe Arg Ser Arg Asp Pro Gln Tyr Asp Gly Arg Leu Leu
            500                 505                 510

Glu Glu Ala Leu Lys Lys Lys Gly Ala Gly Glu Arg Arg Arg Val Tyr
        515                 520                 525

Arg Glu Glu Glu Glu Glu Glu Glu Glu Gly His Tyr Pro Pro Ala Pro
    530                 535                 540

Pro Pro Tyr Ser Glu Thr Asp Ser Gln Ala Ser Arg Glu Arg Arg Met
545                 550                 555                 560

Lys Lys Asn Leu Ala Leu Ser Arg Glu Ser Leu Val Val
                565                 570


<210> SEQ ID NO 18
<211> LENGTH: 646
<212> TYPE: PRT
<213> ORGANISM: Mus musculus

<400> SEQUENCE: 18

Met Asp Arg Val Val Leu Gly Trp Thr Ala Val Phe Trp Leu Thr Ala
1               5                   10                  15

Met Val Glu Gly Leu Gln Val Thr Val Pro Asp Lys Lys Lys Val Ala
            20                  25                  30

Met Leu Phe Gln Pro Thr Val Leu Arg Cys His Phe Ser Thr Ser Ser
        35                  40                  45

His Gln Pro Ala Val Val Gln Trp Lys Phe Lys Ser Tyr Cys Gln Asp
    50                  55                  60

Arg Met Gly Glu Ser Leu Gly Met Ser Ser Pro Arg Ala Gln Ala Leu
```

-continued

```
65                  70                  75                  80

Ser Lys Arg Asn Leu Glu Trp Asp Pro Tyr Leu Asp Cys Leu Asp Ser
                85                  90                  95

Arg Arg Thr Val Arg Val Val Ala Ser Lys Gln Gly Ser Thr Val Thr
            100                 105                 110

Leu Gly Asp Phe Tyr Arg Gly Arg Glu Ile Thr Ile Val His Asp Ala
        115                 120                 125

Asp Leu Gln Ile Gly Lys Leu Met Trp Gly Asp Ser Gly Leu Tyr Tyr
    130                 135                 140

Cys Ile Ile Thr Thr Pro Asp Asp Leu Glu Gly Lys Asn Glu Asp Ser
145                 150                 155                 160

Val Glu Leu Leu Val Leu Gly Arg Thr Gly Leu Leu Ala Asp Leu Leu
                165                 170                 175

Pro Ser Phe Ala Val Glu Ile Met Pro Glu Trp Val Phe Val Gly Leu
            180                 185                 190

Val Ile Leu Gly Ile Phe Leu Phe Phe Val Leu Val Gly Ile Cys Trp
        195                 200                 205

Cys Gln Cys Cys Pro His Ser Cys Cys Cys Tyr Val Arg Cys Pro Cys
    210                 215                 220

Cys Pro Asp Ser Cys Cys Cys Pro Gln Ala Leu Tyr Glu Ala Gly Lys
225                 230                 235                 240

Ala Ala Lys Ala Gly Tyr Pro Pro Ser Val Ser Gly Val Pro Gly Pro
                245                 250                 255

Tyr Ser Ile Pro Ser Val Pro Leu Gly Gly Ala Pro Ser Ser Gly Met
            260                 265                 270

Leu Met Asp Lys Pro His Pro Pro Pro Leu Ala Pro Ser Asp Ser Thr
        275                 280                 285

Gly Gly Ser His Ser Val Arg Lys Gly Tyr Arg Ile Gln Ala Asp Lys
    290                 295                 300

Glu Arg Asp Ser Met Lys Val Leu Tyr Tyr Val Glu Lys Glu Leu Ala
305                 310                 315                 320

Gln Phe Asp Pro Ala Arg Arg Met Arg Gly Arg Tyr Asn Asn Thr Ile
                325                 330                 335

Ser Glu Leu Ser Ser Leu His Asp Asp Asp Ser Asn Phe Arg Gln Ser
            340                 345                 350

Tyr His Gln Met Arg Asn Lys Gln Phe Pro Met Ser Gly Asp Leu Glu
        355                 360                 365

Ser Asn Pro Asp Tyr Trp Ser Gly Val Met Gly Gly Asn Ser Gly Thr
    370                 375                 380

Asn Arg Gly Pro Ala Leu Glu Tyr Asn Lys Glu Asp Arg Glu Ser Phe
385                 390                 395                 400

Arg His Ser Gln Gln Arg Ser Lys Ser Glu Met Leu Ser Arg Lys Asn
                405                 410                 415

Phe Ala Thr Gly Val Pro Ala Val Ser Met Asp Glu Leu Ala Ala Phe
            420                 425                 430

Ala Asp Ser Tyr Gly Gln Arg Ser Arg Arg Ala Asn Gly Asn Ser His
        435                 440                 445

Glu Ala Arg Ala Gly Ser Arg Phe Glu Arg Ser Glu Ser Arg Ala His
    450                 455                 460

Gly Ala Phe Tyr Gln Asp Gly Ser Leu Asp Glu Tyr Tyr Gly Arg Gly
465                 470                 475                 480

Arg Ser Arg Glu Pro Pro Gly Asp Gly Glu Arg Gly Trp Thr Tyr Ser
                485                 490                 495
```

```
Pro Ala Pro Ala Arg Arg Arg Pro Pro Glu Asp Ala Pro Leu Pro Arg
            500                 505                 510

Leu Val Ser Arg Thr Pro Gly Thr Ala Pro Lys Tyr Asp His Ser Tyr
        515                 520                 525

Leu Ser Ser Val Leu Glu Arg Gln Ala Arg Pro Glu Ser Ser Ser Arg
    530                 535                 540

Gly Gly Ser Leu Glu Thr Pro Ser Lys Leu Gly Ala Gln Leu Gly Pro
545                 550                 555                 560

Arg Ser Ala Ser Tyr Tyr Ala Trp Ser Pro Pro Thr Thr Tyr Lys Ala
                565                 570                 575

Gly Ala Ser Glu Gly Glu Asp Glu Asp Asp Ala Ala Asp Glu Asp Ala
            580                 585                 590

Leu Pro Pro Tyr Ser Glu Leu Glu Leu Ser Arg Gly Glu Leu Ser Arg
        595                 600                 605

Gly Pro Ser Tyr Arg Gly Arg Asp Leu Ser Phe His Ser Asn Ser Glu
    610                 615                 620

Lys Arg Arg Lys Lys Glu Pro Ala Lys Lys Pro Gly Asp Phe Pro Thr
625                 630                 635                 640

Arg Met Ser Leu Val Val
                645
```

<210> SEQ ID NO 19
<211> LENGTH: 630
<212> TYPE: PRT
<213> ORGANISM: Rattus norvegicus

<400> SEQUENCE: 19

```
Met Val Glu Gly Leu Gln Val Thr Val Pro Asp Lys Lys Lys Val Ala
1               5                   10                  15

Met Leu Phe Gln Pro Thr Val Leu Arg Cys His Phe Ser Thr Ser Ser
            20                  25                  30

His Gln Pro Ala Val Val Gln Trp Lys Phe Lys Ser Tyr Cys Gln Asp
        35                  40                  45

Arg Met Gly Glu Ser Leu Gly Met Ser Ser Pro Arg Ala Gln Ala Leu
    50                  55                  60

Ser Lys Arg Asn Leu Glu Trp Asp Pro Tyr Leu Asp Cys Leu Asp Ser
65                  70                  75                  80

Arg Arg Thr Val Arg Val Val Ala Ser Lys Gln Gly Ser Thr Val Thr
                85                  90                  95

Leu Gly Asp Phe Tyr Arg Gly Arg Glu Ile Thr Ile Val His Asp Ala
            100                 105                 110

Asp Leu Gln Ile Gly Lys Leu Met Trp Gly Asp Ser Gly Leu Tyr Tyr
        115                 120                 125

Cys Ile Ile Thr Thr Pro Asp Asp Leu Glu Gly Lys Asn Glu Glu Ser
    130                 135                 140

Val Glu Leu Leu Val Leu Gly Arg Thr Gly Leu Leu Ala Asp Leu Leu
145                 150                 155                 160

Pro Ser Phe Ala Val Glu Ile Met Pro Glu Trp Val Phe Val Gly Leu
                165                 170                 175

Val Ile Leu Gly Ile Phe Leu Phe Phe Val Leu Val Gly Ile Cys Trp
            180                 185                 190

Cys Gln Cys Cys Pro His Ser Cys Cys Cys Tyr Val Arg Cys Pro Cys
        195                 200                 205

Cys Pro Asp Ser Cys Cys Cys Pro Gln Ala Leu Tyr Glu Ala Gly Lys
```

-continued

```
    210                 215                 220

Ala Ala Lys Ala Gly Tyr Pro Pro Ser Val Ser Gly Val Pro Gly Pro
225                 230                 235                 240

Tyr Ser Ile Pro Ser Val Pro Leu Gly Gly Ala Pro Ser Ser Gly Met
                245                 250                 255

Leu Thr Asp Lys Pro His Pro Pro Pro Leu Ala Pro Ser Asp Ser Thr
            260                 265                 270

Gly Gly Ser His Ser Val Arg Lys Gly Tyr Arg Ile Gln Ala Asp Lys
        275                 280                 285

Glu Arg Asp Ser Met Lys Val Leu Tyr Tyr Val Glu Lys Glu Leu Ala
    290                 295                 300

Gln Phe Asp Pro Ala Arg Arg Met Arg Gly Arg Tyr Asn Asn Thr Ile
305                 310                 315                 320

Ser Glu Leu Ser Ser Leu His Asp Asp Asp Ser Asn Phe Arg Gln Ser
                325                 330                 335

Tyr His Gln Met Arg Asn Lys Gln Phe Pro Met Ser Gly Asp Val Glu
            340                 345                 350

Ser Asn Pro Asp Tyr Trp Ser Gly Val Met Gly Gly Asn Ser Gly Thr
        355                 360                 365

Asn Arg Gly Pro Ala Leu Glu Tyr Asn Lys Glu Asp Arg Glu Ser Phe
    370                 375                 380

Arg His Ser Gln Pro Arg Ser Lys Ser Glu Met Leu Ser Arg Lys Asn
385                 390                 395                 400

Phe Ala Thr Gly Val Pro Ala Val Ser Met Asp Glu Leu Ala Ala Phe
                405                 410                 415

Ala Asp Ser Tyr Gly Gln Arg Ser Arg Arg Ala Asn Gly Asn Ser His
            420                 425                 430

Glu Ala Arg Ala Gly Ser Arg Phe Glu Arg Ser Glu Ser Arg Ala His
        435                 440                 445

Gly Ala Phe Tyr Gln Asp Gly Ser Leu Asp Glu Tyr Tyr Gly Arg Gly
    450                 455                 460

Arg Ser Arg Glu Pro Pro Gly Asp Gly Glu Arg Gly Trp Thr Tyr Ser
465                 470                 475                 480

Pro Ala Pro Ala Arg Arg Arg Pro Pro Asp Asp Ala Ala Leu Pro Arg
                485                 490                 495

Leu Val Ser Arg Thr Pro Gly Thr Ala Pro Lys Tyr Asp His Ser Tyr
            500                 505                 510

Leu Ser Ser Val Leu Glu Arg Gln Ala Arg Pro Glu Ser Asn Ser Arg
        515                 520                 525

Gly Gly Ser Leu Glu Thr Pro Ser Lys Leu Gly Ala Gln Leu Gly Pro
    530                 535                 540

Arg Ser Ala Ser Tyr Tyr Ala Trp Ser Pro Pro Ala Thr Tyr Lys Ala
545                 550                 555                 560

Gly Ala Ser Glu Gly Glu Asp Glu Asp Asp Ala Ala Asp Glu Asp Ala
                565                 570                 575

Leu Pro Pro Tyr Ser Glu Leu Glu Leu Ser Arg Gly Glu Leu Ser Arg
            580                 585                 590

Gly Pro Ser Tyr Arg Gly Arg Asp Leu Ser Phe His Ser Asn Ser Glu
        595                 600                 605

Lys Arg Arg Lys Lys Glu Pro Ala Lys Lys Thr Gly Asp Phe Pro Thr
    610                 615                 620

Arg Met Ser Leu Val Val
625                 630
```

<210> SEQ ID NO 20
<211> LENGTH: 634
<212> TYPE: PRT
<213> ORGANISM: Bos taurus

<400> SEQUENCE: 20

```
Met Ala Trp Val Ala Val Leu Trp Leu Thr Ala Met Ala Glu Gly Leu
1               5                   10                  15

Gln Val Thr Val Pro Asp Lys Lys Lys Val Ala Met Leu Phe Gln Pro
            20                  25                  30

Thr Val Leu His Cys Arg Phe Ser Thr Ser Ser His Gln Pro Ala Val
        35                  40                  45

Val Gln Trp Lys Phe Lys Ser Tyr Cys Gln Asp Arg Met Gly Glu Ser
    50                  55                  60

Leu Gly Met Ser Ser Pro Arg Thr Gln Ser Leu Ser Lys Arg Asn Leu
65                  70                  75                  80

Glu Trp Asp Pro Tyr Leu Asp Cys Leu Asp Ser Arg Arg Thr Val Arg
                85                  90                  95

Val Val Ala Ser Lys Gln Gly Ser Thr Val Thr Leu Gly Asp Phe Tyr
            100                 105                 110

Arg Gly Arg Glu Ile Thr Ile Val His Asp Ala Asp Leu Gln Ile Gly
        115                 120                 125

Lys Leu Met Trp Gly Asp Ser Gly Leu Tyr Tyr Cys Ile Ile Thr Thr
    130                 135                 140

Pro Asp Asp Leu Glu Gly Lys Asn Glu Asp Ser Val Glu Val Leu Val
145                 150                 155                 160

Leu Gly Arg Thr Gly Leu Leu Ala Asp Leu Leu Pro Ser Phe Ala Val
                165                 170                 175

Glu Ile Met Pro Glu Trp Val Phe Val Gly Leu Val Ile Leu Gly Val
            180                 185                 190

Phe Leu Phe Phe Val Leu Val Gly Ile Cys Trp Cys Gln Cys Cys Pro
        195                 200                 205

His Ser Cys Cys Cys Tyr Ile Arg Cys Pro Cys Cys Pro Asp Ser Cys
    210                 215                 220

Cys Cys Pro Gln Ala Leu Tyr Glu Ala Gly Lys Ala Ala Lys Ala Gly
225                 230                 235                 240

Tyr Pro Pro Ser Val Ser Gly Val Pro Gly Pro Tyr Ser Ile Pro Ser
                245                 250                 255

Val Pro Leu Gly Gly Ala Pro Ser Ser Gly Met Leu Met Asp Lys Pro
            260                 265                 270

His Pro Pro Pro Leu Ala Pro Ser Asp Ser Thr Gly Gly Ser His Ser
        275                 280                 285

Val Arg Lys Gly Tyr Arg Ile Gln Ala Asp Lys Glu Arg Asp Ser Met
    290                 295                 300

Lys Val Leu Tyr Tyr Val Glu Lys Glu Leu Ala Gln Phe Asp Pro Ala
305                 310                 315                 320

Arg Arg Met Arg Ser Arg Tyr Asn Asn Thr Ile Ser Glu Leu Ser Ser
                325                 330                 335

Leu His Glu Glu Asp Ser Ser Leu Arg Gln Ser Tyr His Gln Met Arg
            340                 345                 350

Asn Lys Gln Phe Pro Val Ser Gly Asp Leu Glu Ser Asn Pro Asp Tyr
        355                 360                 365

Trp Ser Gly Val Met Gly Gly Ser Ser Gly Ala Ser Arg Gly Pro Ser
```

370 375 380

Ala Met Glu Tyr Asn Lys Glu Asp Arg Glu Ser Phe Arg His Ser Gln
385 390 395 400

Gln Arg Ser Lys Ser Glu Met Leu Ser Arg Lys Asn Phe Ala Thr Gly
405 410 415

Val Pro Ala Val Ser Met Asp Glu Leu Ala Ala Phe Ala Asp Ser Tyr
420 425 430

Gly Pro Arg Ser Arg Arg Ala Asp Gly Asn Lys Gln Asp Leu Arg Gly
435 440 445

Gly Ser Arg Phe Glu Arg Ser Glu Ala Arg Ala His Gly Gly Leu Tyr
450 455 460

Gln Asp Gly Ser Leu Glu Glu Tyr Tyr Gly Pro Arg Ser Arg Ser Arg
465 470 475 480

Glu Pro Leu Thr Asp Ala Asp Arg Gly Trp Ser Tyr Ser Pro Pro Arg
485 490 495

Arg Arg Pro Pro Asp Asp Ala His Leu Pro Arg Leu Val Ser Arg Thr
500 505 510

Pro Gly Thr Thr Pro Lys Tyr Asp His Ser Phe Arg Gly Ser Gly Leu
515 520 525

Glu Arg Gln Val Arg Pro Glu Gly Ala Ser Arg Gly Gly Ser Leu Glu
530 535 540

Thr Pro Ser Lys Leu Ser Ser Gln Leu Gly Pro Leu Ser Ala Ser Tyr
545 550 555 560

Tyr Ala Trp Ser Pro Pro Ala Thr Tyr Glu Ala Gly Ala Pro Pro Asp
565 570 575

Asp Glu Glu Asp Thr Pro Asp Asp Thr Leu Pro Pro Tyr Ser Glu Leu
580 585 590

Glu Leu Ser Arg Gly Pro Ser Tyr Arg Gly Arg Asp Leu Pro Tyr His
595 600 605

Ser Asn Ser Glu Lys Lys Arg Lys Lys Glu Thr Pro Ala Lys Lys Thr
610 615 620

Asp Phe Pro Thr Arg Met Ser Leu Val Val
625 630

<210> SEQ ID NO 21
<211> LENGTH: 586
<212> TYPE: PRT
<213> ORGANISM: Canis familiaris

<400> SEQUENCE: 21

Met Leu Phe Gln Pro Thr Val Leu Arg Cys His Phe Ser Thr Ser Ser
1 5 10 15

His Gln Pro Ala Val Val Gln Trp Lys Phe Lys Ser Tyr Cys Gln Asp
20 25 30

Arg Met Gly Glu Ser Leu Gly Met Ala Ser Pro Arg Ala Gln Pro Leu
35 40 45

Ser Lys Arg Asn Leu Glu Trp Asp Pro Tyr Leu Asp Cys Leu Asp Ser
50 55 60

Arg Arg Thr Val Arg Val Val Ala Ser Lys Gln Gly Ser Thr Val Thr
65 70 75 80

Leu Gly Asp Phe Tyr Arg Gly Arg Glu Ile Thr Ile Val His Asp Ala
85 90 95

Asp Leu Gln Ile Gly Lys Leu Met Trp Gly Asp Ser Gly Leu Tyr Tyr
100 105 110

-continued

```
Cys Ile Ile Thr Thr Pro Asp Asp Leu Glu Gly Lys Asn Glu Asp Leu
        115                 120                 125

Ala Glu Leu Leu Val Leu Gly Arg Thr Gly Leu Leu Ala Asp Leu Leu
    130                 135                 140

Pro Ser Phe Ala Val Glu Ile Met Pro Glu Trp Val Phe Val Gly Leu
145                 150                 155                 160

Val Ile Leu Gly Val Phe Leu Phe Phe Val Leu Val Gly Ile Cys Trp
                165                 170                 175

Cys Gln Cys Cys Pro His Ser Cys Cys Cys Tyr Ile Arg Cys Pro Cys
            180                 185                 190

Cys Pro Asp Ser Cys Cys Cys Pro Gln Ala Leu Tyr Glu Ala Gly Lys
        195                 200                 205

Ala Ala Lys Ala Gly Tyr Pro Pro Ser Val Ser Gly Val Pro Gly Pro
    210                 215                 220

Tyr Ser Ile Pro Ser Val Pro Leu Gly Gly Ala Pro Ser Ser Gly Met
225                 230                 235                 240

Leu Met Asp Lys Pro His Pro Pro Pro Leu Ala Pro Ser Asp Ser Thr
                245                 250                 255

Gly Gly Ser His Ser Val Arg Lys Gly Tyr Arg Ile Gln Ala Asp Lys
            260                 265                 270

Glu Arg Asp Ser Met Lys Val Leu Tyr Tyr Val Glu Lys Glu Leu Ala
        275                 280                 285

Gln Phe Asp Pro Ala Arg Arg Met Arg Gly Arg Tyr Asn Asn Thr Ile
    290                 295                 300

Ser Glu Leu Ser Ser Leu His Glu Glu Asp Ser Asn Phe Arg Gln Ala
305                 310                 315                 320

Tyr His Gln Met Arg Ser Lys Gln Phe Pro Val Ser Gly Asp Leu Glu
                325                 330                 335

Ser Asn Pro Asp Tyr Trp Ser Gly Val Met Gly Gly Ser Ser Gly Ala
            340                 345                 350

Ser Arg Gly Pro Ser Ala Met Glu Tyr Asn Lys Glu Asp Arg Glu Ser
        355                 360                 365

Phe Arg Tyr Arg Met Leu Ser Arg Lys Asn Phe Ala Ala Gly Val Pro
    370                 375                 380

Ala Val Ser Met Asp Glu Leu Ala Ala Phe Ala Asp Ser Tyr Gly Ala
385                 390                 395                 400

Arg Ser Arg Arg Ala Asp Gly Asp Ser His Glu Ala Arg Gly Gly Gly
                405                 410                 415

Arg Phe Glu Arg Pro Glu Ala Arg Ala Leu Gly Gly Phe Phe Gln Asp
            420                 425                 430

Gly Ser Pro Glu Gly Tyr Tyr Gly Arg Ser Arg Ser Arg Glu Pro Leu
        435                 440                 445

Gly Asp Ala Gly Arg Ala Trp Ala Pro Ser Pro Pro Arg Arg Arg Pro
    450                 455                 460

Asp Asp Ala Pro Leu Pro Arg Leu Val Ser Arg Thr Pro Gly Thr Ala
465                 470                 475                 480

Pro Lys Tyr Glu His Ala Pro Arg Ala Gly Gly Leu Glu Arg Gln Ala
                485                 490                 495

Arg Pro Glu Gly Ala Ser Arg Gly Gly Ser Leu Glu Thr Pro Ser Arg
            500                 505                 510

Leu Ser Ala Gln Leu Gly Arg Arg Ser Ala Ser Tyr Tyr Ala Trp Ser
        515                 520                 525

Pro Pro Ala Thr Tyr Lys Ala Ala Ala Pro Gln Asp Asp Asp Asp Asp
```

```
    530                 535                 540

Asp Asp Asp Asp Ser Ala Asp Asp Ala Leu Pro Pro Tyr Ser Glu Arg
545                 550                 555                 560

Glu Leu Ser Arg Gly Pro Ser Tyr Arg Gly Arg Asp Leu Pro Tyr His
                565                 570                 575

Ser Asn Ser Glu Lys Lys Arg Lys Lys Glu
            580                 585


<210> SEQ ID NO 22
<211> LENGTH: 639
<212> TYPE: PRT
<213> ORGANISM: Homo sapiens

<400> SEQUENCE: 22

Met Asp Arg Val Leu Leu Arg Trp Ile Ser Leu Phe Trp Leu Thr Ala
1               5                   10                  15

Met Val Glu Gly Leu Gln Val Thr Val Pro Asp Lys Lys Lys Val Ala
            20                  25                  30

Met Leu Phe Gln Pro Thr Val Leu Arg Cys His Phe Ser Thr Ser Ser
        35                  40                  45

His Gln Pro Ala Val Val Gln Trp Lys Phe Lys Ser Tyr Cys Gln Asp
    50                  55                  60

Arg Met Gly Glu Ser Leu Gly Met Ser Ser Thr Arg Ala Gln Ser Leu
65                  70                  75                  80

Ser Lys Arg Asn Leu Glu Trp Asp Pro Tyr Leu Asp Cys Leu Asp Ser
                85                  90                  95

Arg Arg Thr Val Arg Val Val Ala Ser Lys Gln Gly Ser Thr Val Thr
            100                 105                 110

Leu Gly Asp Phe Tyr Arg Gly Arg Glu Ile Thr Ile Val His Asp Ala
        115                 120                 125

Asp Leu Gln Ile Gly Lys Leu Met Trp Gly Asp Ser Gly Leu Tyr Tyr
    130                 135                 140

Cys Ile Ile Thr Thr Pro Asp Asp Leu Glu Gly Lys Asn Glu Asp Ser
145                 150                 155                 160

Val Glu Leu Leu Val Leu Gly Arg Thr Gly Leu Leu Ala Asp Leu Leu
                165                 170                 175

Pro Ser Phe Ala Val Glu Ile Met Pro Glu Trp Val Phe Val Gly Leu
            180                 185                 190

Val Leu Leu Gly Val Phe Leu Phe Phe Val Leu Val Gly Ile Cys Trp
        195                 200                 205

Cys Gln Cys Cys Pro His Ser Cys Cys Cys Tyr Val Arg Cys Pro Cys
    210                 215                 220

Cys Pro Asp Ser Cys Cys Cys Pro Gln Ala Leu Tyr Glu Ala Gly Lys
225                 230                 235                 240

Ala Ala Lys Ala Gly Tyr Pro Pro Ser Val Ser Gly Val Pro Gly Pro
                245                 250                 255

Tyr Ser Ile Pro Ser Val Pro Leu Gly Gly Ala Pro Ser Ser Gly Met
            260                 265                 270

Leu Met Asp Lys Pro His Pro Pro Pro Leu Ala Pro Ser Asp Ser Thr
        275                 280                 285

Gly Gly Ser His Ser Val Arg Lys Gly Tyr Arg Ile Gln Ala Asp Lys
    290                 295                 300

Glu Arg Asp Ser Met Lys Val Leu Tyr Tyr Val Glu Lys Glu Leu Ala
305                 310                 315                 320
```

-continued

```
Gln Phe Asp Pro Ala Arg Arg Met Arg Gly Arg Tyr Asn Asn Thr Ile
                325                 330                 335

Ser Glu Leu Ser Ser Leu His Glu Glu Asp Ser Asn Phe Arg Gln Ser
            340                 345                 350

Phe His Gln Met Arg Ser Lys Gln Phe Pro Val Ser Gly Asp Leu Glu
        355                 360                 365

Ser Asn Pro Asp Tyr Trp Ser Gly Val Met Gly Gly Ser Ser Gly Ala
    370                 375                 380

Ser Arg Gly Pro Ser Ala Met Glu Tyr Asn Lys Glu Asp Arg Glu Ser
385                 390                 395                 400

Phe Arg His Ser Gln Pro Arg Ser Lys Ser Glu Met Leu Ser Arg Lys
                405                 410                 415

Asn Phe Ala Thr Gly Val Pro Ala Val Ser Met Asp Glu Leu Ala Ala
            420                 425                 430

Phe Ala Asp Ser Tyr Gly Gln Arg Pro Arg Arg Ala Asp Gly Asn Ser
        435                 440                 445

His Glu Ala Arg Gly Gly Ser Arg Phe Glu Arg Ser Glu Ser Arg Ala
    450                 455                 460

His Ser Gly Phe Tyr Gln Asp Asp Ser Leu Glu Glu Tyr Tyr Gly Gln
465                 470                 475                 480

Arg Ser Arg Ser Arg Glu Pro Leu Thr Asp Ala Asp Arg Gly Trp Ala
                485                 490                 495

Phe Ser Pro Ala Arg Arg Arg Pro Ala Glu Asp Ala His Leu Pro Arg
            500                 505                 510

Leu Val Ser Arg Thr Pro Gly Thr Ala Pro Lys Tyr Asp His Ser Tyr
        515                 520                 525

Leu Gly Ser Ala Arg Glu Arg Gln Ala Arg Pro Glu Gly Ala Ser Arg
    530                 535                 540

Gly Gly Ser Leu Glu Thr Pro Ser Lys Arg Ser Ala Gln Leu Gly Pro
545                 550                 555                 560

Arg Ser Ala Ser Tyr Tyr Ala Trp Ser Pro Pro Gly Thr Tyr Lys Ala
                565                 570                 575

Gly Ser Ser Gln Asp Asp Gln Glu Asp Ala Ser Asp Asp Ala Leu Pro
            580                 585                 590

Pro Tyr Ser Glu Leu Glu Leu Thr Arg Gly Pro Ser Tyr Arg Gly Arg
        595                 600                 605

Asp Leu Pro Tyr His Ser Asn Ser Glu Lys Lys Arg Lys Lys Glu Pro
    610                 615                 620

Ala Lys Lys Thr Asn Asp Phe Pro Thr Arg Met Ser Leu Val Val
625                 630                 635


<210> SEQ ID NO 23
<211> LENGTH: 639
<212> TYPE: PRT
<213> ORGANISM: Pan troglodytes

<400> SEQUENCE: 23

Met Asp Arg Val Leu Leu Arg Trp Ile Ser Leu Phe Trp Leu Thr Ala
1               5                   10                  15

Met Val Glu Gly Leu Gln Val Thr Val Pro Asp Lys Lys Lys Val Ala
            20                  25                  30

Met Leu Phe Gln Pro Thr Val Leu Arg Cys His Phe Ser Thr Ser Ser
        35                  40                  45

His Gln Pro Ala Val Val Gln Trp Lys Phe Lys Ser Tyr Cys Gln Asp
    50                  55                  60
```

-continued

```
Arg Met Gly Glu Ser Leu Gly Met Ser Ser Thr Arg Ala Gln Ser Leu
65                  70                  75                  80

Ser Lys Arg Asn Leu Glu Trp Asp Pro Tyr Leu Asp Cys Leu Asp Ser
                85                  90                  95

Arg Arg Thr Val Arg Val Val Ala Ser Lys Gln Gly Ser Thr Val Thr
            100                 105                 110

Leu Gly Asp Phe Tyr Arg Gly Arg Glu Ile Thr Ile Val His Asp Ala
        115                 120                 125

Asp Leu Gln Ile Gly Lys Leu Met Trp Gly Asp Ser Gly Leu Tyr Tyr
    130                 135                 140

Cys Ile Ile Thr Thr Pro Asp Asp Leu Glu Gly Lys Asn Glu Asp Ser
145                 150                 155                 160

Val Glu Leu Leu Val Leu Gly Arg Thr Gly Leu Leu Ala Asp Leu Leu
                165                 170                 175

Pro Ser Phe Ala Val Glu Ile Met Pro Glu Trp Val Phe Val Gly Leu
            180                 185                 190

Val Leu Leu Gly Val Phe Leu Phe Phe Val Leu Val Gly Ile Cys Trp
        195                 200                 205

Cys Gln Cys Cys Pro His Ser Cys Cys Cys Tyr Val Arg Cys Pro Cys
    210                 215                 220

Cys Pro Asp Ser Cys Cys Cys Pro Gln Ala Leu Tyr Glu Ala Gly Lys
225                 230                 235                 240

Ala Ala Lys Ala Gly Tyr Pro Pro Ser Val Ser Gly Val Pro Gly Pro
                245                 250                 255

Tyr Ser Ile Pro Ser Val Pro Leu Gly Gly Ala Pro Ser Ser Gly Met
            260                 265                 270

Leu Met Asp Lys Pro His Pro Pro Pro Leu Ala Pro Ser Asp Ser Thr
        275                 280                 285

Gly Gly Ser His Ser Val Arg Lys Gly Tyr Arg Ile Gln Ala Asp Lys
    290                 295                 300

Glu Arg Asp Ser Met Lys Val Leu Tyr Tyr Val Glu Lys Glu Leu Ala
305                 310                 315                 320

Gln Phe Asp Pro Ala Arg Arg Met Arg Gly Arg Tyr Asn Asn Thr Ile
                325                 330                 335

Ser Glu Leu Ser Ser Leu His Glu Glu Asp Ser Asn Phe Arg Gln Ser
            340                 345                 350

Phe His Gln Met Arg Ser Lys Gln Phe Pro Val Ser Gly Asp Leu Glu
        355                 360                 365

Ser Asn Pro Asp Tyr Trp Ser Gly Val Met Gly Gly Ser Ser Gly Ala
    370                 375                 380

Ser Arg Gly Pro Ser Ala Met Glu Tyr Asn Lys Glu Asp Arg Glu Ser
385                 390                 395                 400

Phe Arg His Ser Gln Pro Arg Ser Lys Ser Glu Met Leu Ser Arg Lys
                405                 410                 415

Asn Phe Ala Thr Gly Val Pro Ala Val Ser Met Asp Glu Leu Ala Ala
            420                 425                 430

Phe Ala Asp Ser Tyr Gly Gln Arg Pro Arg Arg Ala Asp Gly Asn Ser
        435                 440                 445

His Glu Ala Arg Gly Gly Ser Arg Phe Glu Arg Ser Glu Ser Arg Ala
    450                 455                 460

His Ser Gly Phe Tyr Gln Asp Asp Ser Leu Glu Glu Tyr Tyr Gly Gln
465                 470                 475                 480
```

```
Arg Ser Arg Ser Arg Glu Pro Leu Thr Asp Ala Asp Arg Gly Trp Ala
                485                 490                 495

Phe Ser Pro Ala Arg Arg Arg Pro Ala Glu Asp Ala His Leu Pro Arg
            500                 505                 510

Leu Val Ser Arg Thr Pro Gly Thr Ala Pro Lys Tyr Asp His Ser Tyr
        515                 520                 525

Leu Gly Ser Ala Arg Glu Arg Gln Ala Arg Pro Glu Gly Ala Ser Arg
    530                 535                 540

Gly Gly Ser Leu Glu Thr Pro Ser Lys Arg Ser Ala Gln Leu Gly Pro
545                 550                 555                 560

Arg Ser Ala Ser Tyr Tyr Ala Trp Ser Pro Pro Gly Thr Tyr Lys Ala
                565                 570                 575

Gly Ser Ser Gln Asp Asp Gln Glu Asp Ala Ser Asp Asp Ala Leu Pro
            580                 585                 590

Pro Tyr Ser Glu Leu Glu Leu Thr Arg Gly Pro Ser Tyr Arg Gly Arg
        595                 600                 605

Asp Leu Pro Tyr His Ser Asn Ser Glu Lys Lys Arg Lys Lys Glu Pro
    610                 615                 620

Ala Lys Lys Thr Asn Asp Phe Pro Thr Arg Met Ser Leu Val Val
625                 630                 635
```

<210> SEQ ID NO 24
<211> LENGTH: 592
<212> TYPE: PRT
<213> ORGANISM: Macaca mulatta

<400> SEQUENCE: 24

```
Met Asp Arg Val Leu Leu Arg Trp Ile Ser Leu Phe Trp Leu Thr Ala
1               5                   10                  15

Met Val Glu Gly Leu Gln Val Thr Val Pro Asp Lys Lys Lys Val Ala
            20                  25                  30

Met Leu Phe Gln Pro Thr Val Leu Arg Cys His Phe Ser Thr Ser Ser
        35                  40                  45

His Gln Pro Ala Val Val Gln Trp Lys Phe Lys Ser Tyr Cys Gln Asp
    50                  55                  60

Arg Met Gly Glu Ser Leu Gly Met Ser Ser Thr Arg Ala Gln Ser Leu
65                  70                  75                  80

Ser Lys Arg Asn Leu Glu Trp Asp Pro Tyr Leu Asp Cys Leu Asp Ser
                85                  90                  95

Arg Arg Thr Val Arg Val Val Ala Ser Lys Gln Gly Ser Thr Val Thr
            100                 105                 110

Leu Gly Asp Phe Tyr Arg Gly Arg Glu Ile Thr Ile Val His Asp Ala
        115                 120                 125

Asp Leu Gln Ile Gly Lys Leu Met Trp Gly Asp Ser Gly Leu Tyr Tyr
    130                 135                 140

Cys Ile Ile Thr Thr Pro Asp Asp Leu Glu Gly Lys Asn Glu Asp Ser
145                 150                 155                 160

Val Glu Leu Leu Val Leu Gly Arg Thr Gly Leu Leu Ala Asp Leu Leu
                165                 170                 175

Pro Ser Phe Ala Val Glu Ile Met Pro Glu Trp Val Phe Val Gly Leu
            180                 185                 190

Val Leu Leu Gly Val Phe Leu Phe Phe Val Leu Val Gly Ile Cys Trp
        195                 200                 205

Cys Gln Cys Cys Pro His Ser Cys Cys Cys Tyr Val Arg Cys Pro Cys
    210                 215                 220
```

```
Cys Pro Glu Ser Cys Cys Cys Pro Gln Ala Leu Tyr Glu Ala Gly Lys
225                 230                 235                 240

Ala Ala Lys Ala Gly Tyr Pro Pro Ser Val Ser Gly Val Pro Gly Pro
                245                 250                 255

Tyr Ser Ile Pro Ser Val Pro Leu Gly Gly Ala Pro Ser Ser Gly Met
            260                 265                 270

Leu Met Asp Lys Pro His Pro Pro Pro Leu Ala Pro Ser Asp Ser Thr
        275                 280                 285

Gly Gly Ser His Ser Val Arg Lys Gly Tyr Arg Ile Gln Thr Asp Lys
    290                 295                 300

Glu Arg Asp Ser Met Lys Val Leu Tyr Tyr Val Glu Lys Glu Leu Ala
305                 310                 315                 320

Gln Phe Asp Pro Ala Arg Arg Met Arg Gly Arg Tyr Asn Asn Thr Ile
                325                 330                 335

Ser Glu Leu Ser Ser Leu His Glu Glu Asp Ser Asn Phe Arg Gln Ser
            340                 345                 350

Phe Arg Gln Met Arg Ser Lys Gln Phe Pro Val Ser Gly Asp Leu Glu
        355                 360                 365

Ser Asn Pro Asp Tyr Trp Ser Gly Val Met Gly Gly Ser Ser Gly Ala
    370                 375                 380

Ser Arg Gly Pro Ser Ala Met Glu Tyr Asn Lys Glu Asp Arg Glu Ser
385                 390                 395                 400

Phe Arg His Arg Ile Leu Asn Ile Ser His Leu Ser Arg Gln Gly Thr
                405                 410                 415

Leu Val Ile Thr Cys Val Glu Asp Asp Ser Leu Glu Glu Tyr Tyr Gly
            420                 425                 430

Gln Arg Ser Arg Ser Arg Glu Pro Leu Thr Asp Ala Asp Arg Gly Trp
        435                 440                 445

Ala Phe Ser Pro Ala Arg Arg Arg Pro Thr Glu Asp Ala His Leu Pro
    450                 455                 460

Arg Leu Val Ser Arg Thr Pro Gly Thr Ala Pro Lys Tyr Asp His Ser
465                 470                 475                 480

Tyr Leu Gly Gly Ala Arg Glu Arg Gln Pro Arg Pro Glu Gly Ala Ser
                485                 490                 495

Arg Gly Gly Ser Leu Glu Thr Pro Ser Lys Arg Ser Ala Gln Leu Gly
            500                 505                 510

Pro Arg Ser Ala Ser Tyr Tyr Ala Trp Ser Pro Pro Gly Thr Tyr Lys
        515                 520                 525

Ala Gly Ser Ser Gln Asp Asp Gln Glu Asp Ala Ser Asp Asp Ala Leu
    530                 535                 540

Pro Pro Tyr Ser Glu Leu Glu Leu Thr Arg Gly Pro Ser Tyr Arg Gly
545                 550                 555                 560

Arg Asp Leu Pro Tyr His Ser Asn Ser Glu Lys Arg Arg Lys Lys Glu
                565                 570                 575

Pro Ala Lys Lys Thr Asn Asp Phe Pro Thr Arg Met Ser Leu Val Val
            580                 585                 590


<210> SEQ ID NO 25
<211> LENGTH: 314
<212> TYPE: PRT
<213> ORGANISM: Felis sp.

<400> SEQUENCE: 25

Met Ala Asp Gly Leu Gln Val Thr Val Pro Asp Lys Lys Lys Val Ala
```

-continued

```
1               5                   10                  15

Met Leu Phe Gln Pro Thr Val Leu Arg Cys His Phe Ser Thr Ser Ser
            20                  25                  30

His Gln Pro Ala Val Val Gln Trp Lys Phe Lys Ser Tyr Cys Gln Asp
        35                  40                  45

Arg Met Gly Glu Ser Leu Gly Met Ser Ser Pro Arg Ala Gln Ser Leu
    50                  55                  60

Ser Lys Arg Asn Leu Glu Trp Asp Pro Tyr Leu Asp Cys Leu Asp Ser
65                  70                  75                  80

Arg Arg Thr Val Arg Val Val Ala Ser Lys Gln Gly Ser Thr Val Thr
                85                  90                  95

Leu Gly Asp Phe Tyr Arg Gly Arg Glu Ile Thr Ile Val His Asp Ala
            100                 105                 110

Asp Leu Gln Ile Gly Lys Leu Met Trp Gly Asp Ser Gly Leu Tyr Tyr
        115                 120                 125

Cys Ile Ile Thr Thr Pro Asp Asp Leu Glu Gly Lys Asn Glu Asp Ser
    130                 135                 140

Ala Glu Leu Leu Val Leu Glu Trp Val Phe Val Gly Leu Val Ile Leu
145                 150                 155                 160

Gly Ile Phe Leu Phe Phe Val Leu Val Gly Ile Cys Trp Cys Gln Cys
                165                 170                 175

Cys Pro His Ser Cys Cys Cys Tyr Ile Arg Cys Pro Cys Cys Pro Asp
            180                 185                 190

Ser Cys Cys Cys Pro Gln Ala Leu Tyr Glu Ala Gly Lys Ala Ala Lys
        195                 200                 205

Ala Gly Tyr Pro Pro Ser Val Ser Gly Val Pro Gly Pro Tyr Ser Ile
    210                 215                 220

Pro Ser Val Pro Leu Gly Gly Ala Pro Ser Ser Gly Met Leu Met Asp
225                 230                 235                 240

Lys Pro His Pro Pro Pro Leu Ala Pro Ser Asp Ser Thr Gly Gly Ser
                245                 250                 255

His Ser Val Arg Lys Gly Tyr Arg Ile Gln Ala Asp Lys Glu Arg Asp
            260                 265                 270

Ser Met Lys Val Leu Tyr Tyr Val Glu Lys Glu Leu Ala Gln Phe Asp
        275                 280                 285

Pro Ala Arg Arg Met Arg Gly Arg Cys Glu His Leu Leu Val Leu Cys
    290                 295                 300

Asp Leu Arg Val Met Arg Glu Phe Asn Ala
305                 310


<210> SEQ ID NO 26
<211> LENGTH: 644
<212> TYPE: PRT
<213> ORGANISM: Monodelphis domestica

<400> SEQUENCE: 26

Met Asp Arg Met Ser Leu Gly Trp Ile Val Leu Phe Trp Val Thr Gly
1               5                   10                  15

Val Ala Glu Gly Leu Gln Val Ile Val Pro Glu Lys Thr Lys Lys Ala
            20                  25                  30

Met Leu Phe Gln Pro Val Val Leu Ser Cys Arg Phe Ser Thr Ser Ser
        35                  40                  45

Gln Gln Pro Ala Val Ile Gln Trp Lys Phe Lys Ser Tyr Cys Gln Asp
    50                  55                  60
```

-continued

```
Arg Met Lys Glu Ala Leu Gly Met Ala Thr Ala Gly Ala Gln Pro Leu
65                  70                  75                  80

Ser Lys Arg Asn Leu Glu Trp Asp Pro Tyr Leu Asp Cys Val Asp Ser
                85                  90                  95

Arg Arg Thr Val Arg Val Val Ala Ser Lys Gln Gly Ala Val Val Thr
            100                 105                 110

Leu Gly Glu Phe Tyr Arg Gly Arg Asp Ile Thr Phe Gly Glu Gly Ala
        115                 120                 125

Glu Leu Lys Ile Gly Lys Val Met Trp Gly Asp Ser Gly Leu Tyr Tyr
    130                 135                 140

Cys Ile Val Thr Thr Pro Asp Asp Val Glu Gly Lys Asn Glu Asp Ser
145                 150                 155                 160

Val Glu Leu Leu Val Leu Gly Arg Thr Gly Trp Leu Ala Ala Leu Leu
                165                 170                 175

Pro Ser Phe Ala Val Lys Ile Met Ser Glu Trp Val Phe Val Gly Leu
            180                 185                 190

Val Ile Leu Gly Val Phe Leu Phe Phe Leu Leu Val Gly Ile Cys Trp
        195                 200                 205

Cys Gln Cys Cys Pro His Ser Cys Cys Cys Tyr Val Arg Cys Pro Cys
    210                 215                 220

Cys Pro Asp Ser Cys Cys Cys Pro Arg Ala Leu Tyr Glu Ala Gly Lys
225                 230                 235                 240

Ala Ala Lys Ser Gly Tyr Pro Pro Ser Val Ser Ser Val Pro Gly Pro
                245                 250                 255

Tyr Tyr Ile Pro Ser Val Pro Val Gly Gly Val Ser Ser Ser Ala Met
            260                 265                 270

Leu Met Asp Lys Pro His Pro Pro Leu Ala Ser Ser Asp Ser Ile
        275                 280                 285

Gly Gly Ser Gln Ser Val Arg Lys Gly Tyr Arg Ile Gln Ala Asp Lys
    290                 295                 300

Glu Arg Asp Ser Met Lys Val Leu Tyr Tyr Val Glu Lys Glu Leu Ala
305                 310                 315                 320

Gln Phe Asp Pro Ala Arg Arg Met Arg Glu Arg Tyr Asn Asn Thr Ile
                325                 330                 335

Ser Glu Leu Ser Ser Leu His Glu Asp Asn Gly Asn Phe Cys Gln Ser
            340                 345                 350

Tyr Arg Gln Met Arg Arg Lys Pro Leu Pro Ser Leu Gly Asn Ile Glu
        355                 360                 365

Ser Asp Thr Asp Tyr Trp Thr Gly Val Met Gly Asn Ser Gly Gly Ser
    370                 375                 380

Gly His Gly Pro Ser Ser Ser Asn Tyr Asn Lys Glu Asp Arg Asp Ser
385                 390                 395                 400

Phe Arg His Ser Gln Gln Arg Cys Lys Ser Glu Met Leu Ser Arg Lys
                405                 410                 415

Asn Phe Ala Met Gly Met Pro Ala Val Ser Met Asp Glu Leu Ala Ala
            420                 425                 430

Phe Ala Asp Ser Tyr Ser Gln Arg Ser His Arg Gly Glu Gly Asn Ser
        435                 440                 445

Gln Glu Pro Arg Gly Gly Ser Arg Phe Glu Arg Ser Glu Ser Arg Ala
    450                 455                 460

His Gly Gly Leu Tyr His Asp Gly Ser Leu Glu Glu Tyr Tyr Ser Lys
465                 470                 475                 480

Arg Ser Arg Ser Arg Glu Pro Leu Thr Asp Ser Asp Arg Gly Trp Ser
```

```
                485                 490                 495

Tyr Ser Pro Pro Arg Arg Arg Ala Asn Glu Asp Lys His Leu Pro Arg
            500                 505                 510

Leu Val Ser Arg Thr Pro Gly Val Gly Gln Lys Tyr Asp His Pro Tyr
        515                 520                 525

Leu Ser Ser Val Leu Glu Arg Lys Ser Arg Gly Glu Gly Ser Ser Gly
    530                 535                 540

Gly Gly Ser Leu Glu Thr Pro Ser Lys Arg Ser Ser Gln Pro Ile Gln
545                 550                 555                 560

Arg Ser Gly Ser Tyr Tyr Ala Trp Ser Pro Pro Ser Thr Tyr Lys Ala
                565                 570                 575

Gly Ser Gly Gln Gln Pro Ser Pro Gln Ala Gly Glu Glu Asp Glu Met
            580                 585                 590

Glu Asp Ala Leu Pro Pro Tyr Ser Glu Leu Glu Leu Thr Arg Gly Pro
        595                 600                 605

Ser Tyr Arg Gly Arg Glu Ser Leu Tyr His Ser Asn Ser Glu Lys Lys
    610                 615                 620

Arg Lys Lys Asp Ser Leu Lys Lys Thr Asn Asp Phe Pro Thr Arg Met
625                 630                 635                 640

Ser Leu Val Val


<210> SEQ ID NO 27
<211> LENGTH: 640
<212> TYPE: PRT
<213> ORGANISM: Gallus gallus

<400> SEQUENCE: 27

Met Gly Gly Arg Leu Leu Gly Cys Val Val Leu Leu Trp Leu Ser Ala
1               5                   10                  15

Val Glu Gly Leu Gln Val Thr Val Pro Glu Lys Lys Lys Val Ala Met
            20                  25                  30

Leu Phe Gln Pro Ala Leu Leu Arg Cys His Phe Ser Thr Ser Ser Thr
        35                  40                  45

Gln Pro Ala Val Val Gln Trp Arg Tyr Lys Ser Tyr Cys Gln Asp Arg
    50                  55                  60

Met Gly Glu Ala Leu Gly Met Val Thr Ser Gly Leu Gln Thr Met Ser
65                  70                  75                  80

Lys Arg Asn Leu Asp Trp Asp Pro Tyr Leu Asp Cys Val Asp Ser Arg
                85                  90                  95

Arg Thr Val Arg Val Val Ala Ser Lys Gln Gly Ser Ala Val Thr Ile
            100                 105                 110

Gly Asp Phe Tyr Lys Glu Arg Asp Val Ser Ile Val His Asp Ala Asp
        115                 120                 125

Leu Gln Ile Gly Lys Leu Met Trp Gly Asp Ser Gly Leu Tyr Tyr Cys
    130                 135                 140

Ile Ile Ile Thr Pro Asp Asp Val Glu Gly Lys Ser Glu Glu Ser Val
145                 150                 155                 160

Glu Leu Leu Val Leu Gly Arg Thr Gly Leu Leu Ala Asp Leu Leu Pro
                165                 170                 175

Ser Phe Ala Val Glu Ile Met Pro Glu Trp Val Phe Val Gly Leu Val
            180                 185                 190

Ile Leu Gly Ala Phe Leu Phe Phe Leu Leu Val Gly Ile Cys Trp Cys
        195                 200                 205

Gln Cys Cys Pro His Ser Cys Cys Cys Tyr Val Arg Cys Pro Cys Cys
```

```
    210                 215                 220

Pro Glu Ser Cys Cys Cys Pro Arg Ala Leu Tyr Val Ala Gly Lys Ala
225                 230                 235                 240

Ala Lys Ala Gly Tyr Pro Pro Val Val Ser Ser Ile Pro Gly Pro Tyr
                245                 250                 255

Tyr Ile Pro Ser Val Pro Val Ala Gly Val Pro Ser Pro Ala Val Leu
            260                 265                 270

Met Asp Lys Ser His Pro Pro Pro Leu Ala Pro Ser Asp Thr Gly Gly
        275                 280                 285

Gly Asn Gln Asn Ala Val Arg Lys Gly Tyr Arg Ile Gln Thr Asp Lys
    290                 295                 300

Asp Arg Asp Ser Met Lys Val Leu Tyr Tyr Val Glu Lys Glu Leu Ala
305                 310                 315                 320

Gln Phe Asp Pro Ala Arg Arg Met Arg Glu Arg Tyr Asn Asn Thr Val
                325                 330                 335

Ser Glu Leu Ser Ser Leu His Glu Asp Asp Leu Asn Phe Arg Gln Pro
            340                 345                 350

Tyr Arg Gln Ala Arg Arg Lys Pro Leu Pro Pro Ala Glu Asp Leu Asp
        355                 360                 365

Gly Asp Ala Glu Tyr Trp Ala Gly Val Met Gly Gly Gly Ser Thr Ser
    370                 375                 380

Arg Ser Gln Ala Ile Ser Asp Tyr Arg Asp Glu Arg Asp Ser Phe Arg
385                 390                 395                 400

His Ser Gln Gln Arg Ser Lys Ser Glu Met Leu Ser Arg Lys Ser Phe
                405                 410                 415

Ser Val Gly Val Pro Ala Val Ser Met Asp Glu Leu Ala Ala Phe Ala
            420                 425                 430

Glu Ser Tyr Ser Gln Arg Ala Arg Arg Ala Asp Ser Gln Glu Thr Arg
        435                 440                 445

Arg Phe Glu Arg Ser Glu Ser Arg Ser Gly Arg Gly Gly Gly Leu Thr
    450                 455                 460

His Gln Asp Ser Ser Met Glu Glu Tyr Tyr Thr Lys Arg Ser Arg Gly
465                 470                 475                 480

Asn Arg Glu Pro Leu Thr Asp Ser Asp Arg Gly Trp Ser Tyr Ser Pro
                485                 490                 495

Pro Arg Arg Arg Ala His Glu Glu Lys His Leu Pro Arg Leu Val Ser
            500                 505                 510

Arg Thr Pro Gly Gly Ser Gln Lys Tyr Asp His Ser Tyr Leu Ser Ser
        515                 520                 525

Val Leu Glu Arg Lys Ser Arg Ser Tyr Asp Glu Ser Gly Asp Pro Cys
    530                 535                 540

Glu Thr Pro Ser Lys Leu Ser Ser Gln Pro Ser Gln Arg Gly Gly Gly
545                 550                 555                 560

Thr Tyr Tyr Ala Trp Ser Pro Pro Ser Thr Tyr Lys Ser Asp Thr Ser
                565                 570                 575

Gln Gln Gln Gln Thr Pro Pro Pro Glu Gln Glu Glu Gly Glu Asp Thr
            580                 585                 590

Leu Pro Pro Tyr Ser Glu Arg Glu Leu Ser Arg Gly Pro Ser Tyr Arg
        595                 600                 605

Ala Arg Glu Gln Ala Tyr Leu Asn Ala Ser Asp Lys Lys Arg Lys Lys
    610                 615                 620

Asp Pro Lys Lys Thr Asn Asp Phe Pro Thr Arg Met Ser Leu Val Val
625                 630                 635                 640
```

<210> SEQ ID NO 28
<211> LENGTH: 568
<212> TYPE: PRT
<213> ORGANISM: Xenopus tropicalis

<400> SEQUENCE: 28

```
Met Ala Ala Gly Ile Val Leu Gly Cys Ile Gly Leu Met Cys Ala Thr
1               5                   10                  15

Gly Ser Met Thr Tyr Gly Ile Lys Val Thr Met Pro Glu His Lys Lys
            20                  25                  30

Val Val Met Leu Phe Gln Ser Val Leu Met Arg Cys Gln Tyr Ala Thr
        35                  40                  45

Ser Ser Thr Gln Pro Val Val Val Gln Trp Arg Tyr Lys Ser Phe Cys
    50                  55                  60

Leu Asp Arg Met Glu Glu Ala Leu Gly Ile Gly Lys Val Pro Gly Lys
65                  70                  75                  80

Gly Ala Thr Gly Asn Gln Tyr Leu Asp Cys Ala Asp Gly Ser Arg Thr
                85                  90                  95

Val Arg Thr Val Ala Ser Lys Gln Gly Ser Thr Val Thr Leu Gly Asp
            100                 105                 110

Phe Tyr Lys Gly Lys Asp Ile Thr Ile Val Asn Asp Ala Asp Leu Gln
        115                 120                 125

Phe Gly Asn Met Gln Trp Gly Asp Ser Gly Leu Tyr Tyr Cys Leu Val
    130                 135                 140

Val Thr Ser Asp Asp Leu Glu Gly Lys Asn Glu Asp Arg Val Glu Ile
145                 150                 155                 160

Leu Val Leu Gly Gln Asn Gly Ala Asp Gln Leu Val Gly Ala Ala Ala
                165                 170                 175

Asp Ile Arg Pro Glu Trp Ala Phe Val Cys Leu Val Ile Leu Gly Thr
            180                 185                 190

Phe Leu Phe Phe Val Met Val Gly Ile Cys Trp Cys Gln Cys Cys Pro
        195                 200                 205

His Asn Cys Cys Cys Tyr Val Arg Cys Pro Cys Cys Pro Glu Thr Cys
    210                 215                 220

Cys Cys Pro Arg Ala Leu Tyr Glu Ala Gly Lys Ala Ala Lys Val Gly
225                 230                 235                 240

Tyr Pro Pro Thr Val Pro Thr Ala Cys Pro Pro Tyr Tyr Ile Ser Thr
                245                 250                 255

Ile Pro Val Ser Gln Val Pro Ala Cys Arg Val Met Asp Lys Pro His
            260                 265                 270

Val Pro Pro Leu Val Gln Ser Asp Ser Leu Pro Gly Gln Asn Ala Val
        275                 280                 285

Arg Lys Gly Tyr Arg Ile Gln Ala Asp Lys Glu Arg Asp Ser Met Lys
    290                 295                 300

Val Leu Tyr Tyr Val Glu Lys Glu Leu Ala Gln Phe Asp Pro Ala Arg
305                 310                 315                 320

Arg Met Arg Glu Arg Tyr Ser His Thr Ile Ser Glu Leu Ser Ser Leu
                325                 330                 335

His Glu Asp Asn Thr His Phe Asn His Ser Tyr Arg Gln Val Arg Arg
            340                 345                 350

Lys Pro Leu Pro Pro Ser Cys Asn Ala Asp Gly Asp Ala Glu Tyr Trp
        355                 360                 365

Ser Gly Val Val Gly Ser Ala Arg Pro Ala Thr Tyr Ser Lys Phe Arg
```

-continued

```
    370                 375                 380

Glu Asp Arg Glu Ser Phe Arg Ser Ser Leu Gln Arg Pro Thr Ser Glu
385                 390                 395                 400

Val Leu Glu Arg Lys Ser Phe Pro Met Thr Ile Gln Ala Val Ser Thr
                405                 410                 415

Asp Glu Leu Ala Ala Phe Thr Asp Ser Tyr Lys Gln Arg Pro Arg Arg
            420                 425                 430

Ala Asp Ser Arg Gly Pro Gly Ser Ala Pro Arg Phe Glu Arg Ser Glu
        435                 440                 445

Thr Arg Gly Arg Ser Leu Tyr Gln Asp Ser Ser Ser Asp Glu Tyr Tyr
    450                 455                 460

Gly Lys Arg Asn His Gly Arg Glu Leu Phe Ser Asp Gly Glu Arg Gly
465                 470                 475                 480

Trp Ser Phe Ser Pro Ser Arg Ile Arg Ala Ala Glu Asp Lys His Leu
                485                 490                 495

Pro Lys Arg Ile Thr Arg Met Gly Gln Ser Tyr Asp Asp Ala Tyr Leu
            500                 505                 510

Ser Arg Val Leu Glu Arg Lys Ser Arg Gly Leu Glu Asp Thr Thr Val
        515                 520                 525

Thr Pro Ser Lys Leu Ser Leu Arg Gln Asn Ser Ser Arg Ser Tyr Gly
    530                 535                 540

Arg Ser Pro Thr Phe Cys Val Asn Asp Phe Glu Ile Leu Thr Ala Asn
545                 550                 555                 560

Pro Ser Gly Thr Phe Leu Ser Val
                565


<210> SEQ ID NO 29
<211> LENGTH: 628
<212> TYPE: PRT
<213> ORGANISM: Danio rerio

<400> SEQUENCE: 29

Met Phe Leu Leu His Ala Phe Trp Ile Leu Phe Thr Leu Phe Ser Val
1               5                   10                  15

Gln Ser Cys Asp Gly Val Gln Val Val Val Lys Asp Glu Lys Lys Phe
            20                  25                  30

Ala Met Leu Phe Ser Ser Ile Val Leu Pro Cys His Tyr Thr Thr His
        35                  40                  45

Ser Thr Gln Thr Ala Val Val Gln Trp Trp Tyr Lys Ser Tyr Cys Thr
    50                  55                  60

Asp Arg Thr Arg Asp Ser Phe Thr Phe Pro Glu Ser Leu Gly Val His
65                  70                  75                  80

Val Ser Asp Leu Gly Ala Ser Ser His Arg Asp Cys Ser Asp Asn Ser
                85                  90                  95

Arg Thr Val Arg Ile Val Ala Ser Gly Gln Gly Ala Ser Met Thr Leu
            100                 105                 110

Ala Glu His Tyr Lys Gly Arg Asp Ile Ser Ile Ile Asn Lys Ala Asp
        115                 120                 125

Leu His Ile Gly Gln Leu Gln Trp Gly Asp Ser Gly Val Tyr Phe Cys
    130                 135                 140

Lys Val Ile Ile Ser Asp Asp Leu Glu Gly Lys Asn Glu Gly Gln Val
145                 150                 155                 160

Glu Leu Leu Val Gln Gly Arg Thr Gly Val Leu Asp Asp Ile Leu Pro
                165                 170                 175
```

```
Glu Phe Asp Leu Glu Ile Met Pro Glu Trp Ala Phe Val Gly Val Val
            180                 185                 190

Val Val Gly Ser Ile Leu Phe Leu Leu Leu Val Gly Ile Cys Trp Cys
        195                 200                 205

Gln Cys Cys Pro His Ser Cys Cys Cys Tyr Val Arg Cys Cys Cys Cys
    210                 215                 220

Pro Asp Thr Cys Cys Cys Pro Lys His Leu Tyr Glu Ala Gly Lys Met
225                 230                 235                 240

Ala Lys Ser Gly Gln Pro Pro Gln Ile Thr Met Tyr Gln Pro Tyr Tyr
                245                 250                 255

Val Pro Gly Val Pro Val Val Pro Val Val Pro Pro Ala Ala Ser Ser
            260                 265                 270

Ile Ile Glu Pro Lys Leu Pro Thr Val Pro Pro Ser Val Glu Asn Asn
        275                 280                 285

Ile Ala Gly Met Arg Ser Gly Tyr Arg Leu Gln Ala Ser Gln Gly Gln
    290                 295                 300

Asp Ala Met Lys Val Val Tyr Tyr Leu Glu Arg Asp Leu Ala Gln Phe
305                 310                 315                 320

His Pro Thr Lys Gly Ala Ser His Pro Ser Ala Asp Asn Leu Ser Glu
                325                 330                 335

Leu Ser Ser Leu His Asp Gly Asp Val Asp Phe Arg Gln Thr Tyr Arg
            340                 345                 350

Gln Val Gln Arg Lys Ala Leu Pro Pro Ile Ile Asp His Leu Asp Glu
        355                 360                 365

Pro Arg Leu Arg Thr Ala Ser Ile Gly His Gly Leu Arg Pro Ser His
    370                 375                 380

Tyr Gln Ser Asp His Ser Leu Asp Glu His Asp Asn Arg Trp Asn Cys
385                 390                 395                 400

Arg Ser Glu His Leu Pro Arg Lys Ala Phe Asp Ser Arg Gly Arg Thr
                405                 410                 415

Val Ser Leu Asp Glu Leu Glu Glu Phe Ala Met Ser Tyr Gly Pro His
            420                 425                 430

Gly Arg Arg Arg Gly Asp Ile Arg Gly Pro Gln Arg Asp Phe Glu Met
        435                 440                 445

Ala Pro Arg Thr Arg Asp His Pro Thr Ser Tyr Arg Asn Gly Pro Arg
    450                 455                 460

Tyr Leu Arg Glu Asp Asp Asp Ser Asp Trp His Arg Arg Gly Ser Pro
465                 470                 475                 480

Pro Ser Pro Pro Lys Arg Arg Asp Thr Ala Asp Ser Glu Arg Tyr Val
                485                 490                 495

Ser Arg Gln Arg Ser Tyr Asp Asp Thr Tyr Leu Asn Ser Leu Leu Glu
            500                 505                 510

Arg Lys Ala Arg Gly His Gly Glu Arg Gly Gly Arg Val Asp Asp Asp
        515                 520                 525

Ser Asp Thr Pro Ser Lys Gly Ser Ser Lys Lys Ser Ser Asp Cys Tyr
    530                 535                 540

Gln Ser Arg Ser Pro Ser Asn Arg Pro Glu Glu Glu Asp Pro Leu Pro
545                 550                 555                 560

Pro Tyr Ser Glu Arg Glu Gly Glu Arg Phe Arg Thr Glu Glu Pro Thr
                565                 570                 575

Gly Arg Glu Arg Tyr Arg Thr Ala Asp Pro Ala Met Arg Pro Phe Ser
            580                 585                 590

Tyr Thr Arg Pro Pro His Gly Leu Ser Gln Thr Leu Gln Glu Arg Arg
```

```
        595                 600                 605

Glu Asp Arg Asp Lys Pro Arg Lys Leu Thr Thr His Leu Ser Arg Asp
    610                 615                 620

Ser Leu Ile Val
625


<210> SEQ ID NO 30
<211> LENGTH: 601
<212> TYPE: PRT
<213> ORGANISM: Homo sapiens

<400> SEQUENCE: 30

Met Ala Leu Leu Ala Gly Gly Leu Ser Arg Gly Leu Gly Ser His Pro
1               5                   10                  15

Ala Ala Ala Gly Arg Asp Ala Val Val Phe Val Trp Leu Leu Leu Ser
            20                  25                  30

Thr Trp Cys Thr Ala Pro Ala Arg Ala Ile Gln Val Thr Val Ser Asn
        35                  40                  45

Pro Tyr His Val Val Ile Leu Phe Gln Pro Val Thr Leu Pro Cys Thr
    50                  55                  60

Tyr Gln Met Thr Ser Thr Pro Thr Gln Pro Ile Val Ile Trp Lys Tyr
65                  70                  75                  80

Lys Ser Phe Cys Arg Asp Arg Ile Ala Asp Ala Phe Ser Pro Ala Ser
                85                  90                  95

Val Asp Asn Gln Leu Asn Ala Gln Leu Ala Ala Gly Asn Pro Gly Tyr
            100                 105                 110

Asn Pro Tyr Val Glu Cys Gln Asp Ser Val Arg Thr Val Arg Val Val
        115                 120                 125

Ala Thr Lys Gln Gly Asn Ala Val Thr Leu Gly Asp Tyr Tyr Gln Gly
    130                 135                 140

Arg Arg Ile Thr Ile Thr Gly Asn Ala Asp Leu Thr Phe Asp Gln Thr
145                 150                 155                 160

Ala Trp Gly Asp Ser Gly Val Tyr Tyr Cys Ser Val Val Ser Ala Gln
                165                 170                 175

Asp Leu Gln Gly Asn Asn Glu Ala Tyr Ala Glu Leu Ile Val Leu Gly
            180                 185                 190

Arg Thr Ser Gly Val Ala Glu Leu Leu Pro Gly Phe Gln Ala Gly Pro
        195                 200                 205

Ile Glu Asp Trp Leu Phe Val Val Val Val Cys Leu Ala Ala Phe Leu
    210                 215                 220

Ile Phe Leu Leu Leu Gly Ile Cys Trp Cys Gln Cys Cys Pro His Thr
225                 230                 235                 240

Cys Cys Cys Tyr Val Arg Cys Pro Cys Cys Pro Asp Lys Cys Cys Cys
                245                 250                 255

Pro Glu Ala Leu Tyr Ala Ala Gly Lys Ala Ala Thr Ser Gly Val Pro
            260                 265                 270

Ser Ile Tyr Ala Pro Ser Thr Tyr Ala His Leu Ser Pro Ala Lys Thr
        275                 280                 285

Pro Pro Pro Pro Ala Met Ile Pro Met Gly Pro Ala Tyr Asn Gly Tyr
    290                 295                 300

Pro Gly Gly Tyr Pro Gly Asp Val Asp Arg Ser Ser Ser Ala Gly Gly
305                 310                 315                 320

Gln Gly Ser Tyr Val Pro Leu Leu Arg Asp Thr Asp Ser Ser Val Ala
                325                 330                 335
```

-continued

```
Ser Glu Val Arg Ser Gly Tyr Arg Ile Gln Ala Ser Gln Gln Asp Asp
            340                 345                 350

Ser Met Arg Val Leu Tyr Tyr Met Glu Lys Glu Leu Ala Asn Phe Asp
        355                 360                 365

Pro Ser Arg Pro Gly Pro Pro Ser Gly Arg Val Glu Arg Ala Met Ser
    370                 375                 380

Glu Val Thr Ser Leu His Glu Asp Asp Trp Arg Ser Arg Pro Ser Arg
385                 390                 395                 400

Gly Pro Ala Leu Thr Pro Ile Arg Asp Glu Glu Trp Gly Gly His Ser
                405                 410                 415

Pro Arg Ser Pro Arg Gly Trp Asp Gln Glu Pro Ala Arg Glu Gln Ala
            420                 425                 430

Gly Gly Gly Trp Arg Ala Arg Arg Pro Arg Ala Arg Ser Val Asp Ala
        435                 440                 445

Leu Asp Asp Leu Thr Pro Pro Ser Thr Ala Glu Ser Gly Ser Arg Ser
    450                 455                 460

Pro Thr Ser Asn Gly Gly Arg Ser Arg Ala Tyr Met Pro Pro Arg Ser
465                 470                 475                 480

Arg Ser Arg Asp Asp Leu Tyr Asp Gln Asp Asp Ser Arg Asp Phe Pro
                485                 490                 495

Arg Ser Arg Asp Pro His Tyr Asp Asp Phe Arg Ser Arg Glu Arg Pro
            500                 505                 510

Pro Ala Asp Pro Arg Ser His His His Arg Thr Arg Asp Pro Arg Asp
        515                 520                 525

Asn Gly Ser Arg Ser Gly Asp Leu Pro Tyr Asp Gly Arg Leu Leu Glu
    530                 535                 540

Glu Ala Val Arg Lys Lys Gly Ser Glu Glu Arg Arg Arg Pro His Lys
545                 550                 555                 560

Glu Glu Glu Glu Glu Ala Tyr Tyr Pro Pro Ala Pro Pro Pro Tyr Ser
                565                 570                 575

Glu Thr Asp Ser Gln Ala Ser Arg Glu Arg Arg Leu Lys Lys Asn Leu
            580                 585                 590

Ala Leu Ser Arg Glu Ser Leu Val Val
        595                 600


<210> SEQ ID NO 31
<211> LENGTH: 591
<212> TYPE: PRT
<213> ORGANISM: Pan troglodytes

<400> SEQUENCE: 31

Met Ala Leu Leu Ala Gly Gly Leu Ser Arg Gly Leu Gly Ser His Pro
1               5                   10                  15

Ala Ala Pro Gly Arg Asp Ala Val Val Phe Val Trp Leu Leu Leu Ser
            20                  25                  30

Thr Trp Cys Thr Ala Pro Ala Arg Ala Ile Gln Val Thr Val Ser Asn
        35                  40                  45

Pro Tyr His Val Val Ile Leu Phe Gln Pro Val Thr Leu Pro Cys Thr
    50                  55                  60

Tyr Gln Met Thr Ser Thr Pro Thr Gln Pro Ile Val Ile Trp Lys Tyr
65                  70                  75                  80

Lys Ser Phe Cys Arg Asp Arg Ile Ala Asp Ala Phe Ser Pro Ala Ser
                85                  90                  95

Val Asp Asn Gln Leu Asn Ala Gln Leu Ala Ala Gly Asn Pro Gly Tyr
            100                 105                 110
```

-continued

```
Asn Pro Tyr Val Glu Cys Gln Asp Ser Val Arg Thr Val Arg Val Val
        115                 120                 125

Ala Thr Lys Gln Gly Asn Ala Val Thr Leu Gly Asp Tyr Tyr Gln Gly
    130                 135                 140

Arg Arg Ile Thr Ile Thr Gly Asn Ala Asp Leu Thr Phe Asp Gln Thr
145                 150                 155                 160

Ala Trp Gly Asp Ser Gly Val Tyr Tyr Cys Ser Val Val Ser Ala Gln
                165                 170                 175

Asp Leu Gln Gly Asn Asn Glu Ala Tyr Ala Glu Leu Ile Val Leu Gly
            180                 185                 190

Arg Thr Ser Gly Val Ala Glu Leu Leu Pro Gly Phe Gln Ala Gly Pro
        195                 200                 205

Met Glu Asp Trp Leu Phe Val Val Val Val Cys Leu Ala Ala Phe Leu
    210                 215                 220

Ile Phe Leu Leu Leu Gly Ile Cys Trp Cys Gln Cys Cys Pro His Thr
225                 230                 235                 240

Cys Cys Cys Tyr Val Arg Cys Pro Cys Cys Pro Asp Lys Cys Cys Cys
                245                 250                 255

Pro Glu Ala Leu Tyr Ala Ala Gly Lys Ala Ala Thr Ser Gly Val Pro
            260                 265                 270

Ser Ile Tyr Ala Pro Ser Thr Tyr Ala His Leu Ser Pro Ala Lys Thr
        275                 280                 285

Pro Pro Pro Pro Ala Met Ile Pro Met Gly Pro Ala Tyr Asn Gly Tyr
    290                 295                 300

Pro Gly Gly Tyr Pro Gly Asp Val Asp Arg Ser Ser Ser Ala Gly Gly
305                 310                 315                 320

Gln Gly Ser Tyr Val Pro Leu Leu Arg Asp Thr Asp Ser Ser Val Ala
                325                 330                 335

Ser Glu Val Arg Ser Gly Tyr Arg Ile Gln Ala Ser Gln Gln Asp Asp
            340                 345                 350

Ser Met Arg Val Leu Tyr Tyr Met Glu Lys Glu Leu Ala Asn Phe Asp
        355                 360                 365

Pro Ser Arg Pro Gly Pro Pro Asn Gly Arg Val Glu Arg Ala Met Ser
    370                 375                 380

Glu Val Thr Ser Leu His Glu Asp Asp Trp Arg Ser Arg Pro Ser Arg
385                 390                 395                 400

Gly Pro Ala Leu Thr Pro Ile Arg Asp Glu Glu Trp Gly Gly His Ser
                405                 410                 415

Pro Arg Ser Pro Arg Gly Trp Asp Gln Glu Pro Ala Arg Glu Gln Ala
            420                 425                 430

Gly Gly Gly Trp Arg Ala Arg Arg Pro Arg Ala Arg Ser Val Asp Ala
        435                 440                 445

Leu Asp Asp Leu Thr Pro Pro Ser Thr Ala Glu Ser Gly Ser Arg Ser
    450                 455                 460

Pro Thr Ser Ser Gly Gly Arg Arg Ser Arg Ala Tyr Met Pro Pro Arg
465                 470                 475                 480

Ser Arg Ser Arg Asp Asp Leu Tyr Asp Gln Asp Asp Ser Arg Asp Phe
                485                 490                 495

Pro Arg Ser Arg Asp Pro His Tyr Asp Asp Leu Arg Ser Arg Glu Arg
            500                 505                 510

Pro Pro Ala Asp Pro Arg Ser Gln His His Arg Thr Arg Asp Pro Arg
        515                 520                 525
```

```
Asp Asn Gly Ser Arg Ser Gly Asp Leu Pro Tyr Asp Gly Arg Leu Leu
    530                 535                 540

Gln Glu Ala Val Arg Lys Lys Gly Ser Glu Glu Arg Arg Arg Pro His
545                 550                 555                 560

Lys Glu Glu Glu Glu Glu Ala Tyr Tyr Pro Pro Ala Pro Pro Pro Tyr
                565                 570                 575

Ser Glu Thr Asp Ser Gln Ala Ser Arg Glu Arg Arg Leu Lys Lys
            580                 585                 590


<210> SEQ ID NO 32
<211> LENGTH: 381
<212> TYPE: PRT
<213> ORGANISM: Macaca mulatta

<400> SEQUENCE: 32

Met Ala Leu Val Ala Gly Gly Leu Cys Arg Gly Leu Gly Ser His Pro
1               5                   10                  15

Ala Ala Pro Gly Arg Asp Ala Val Val Phe Val Trp Leu Leu Leu Ser
            20                  25                  30

Thr Trp Phe Thr Ala Pro Ala Arg Ala Ile Gln Val Thr Val Ser Asp
        35                  40                  45

Pro Tyr His Val Val Ile Leu Phe Gln Pro Val Thr Leu Pro Cys Thr
    50                  55                  60

Tyr Gln Met Thr Ser Thr Pro Thr Gln Pro Ile Val Ile Trp Lys Tyr
65                  70                  75                  80

Lys Ser Phe Cys Arg Asp Arg Ile Ala Asp Ala Phe Ser Pro Ala Ser
                85                  90                  95

Val Asp Asn Gln Leu Asn Ala Gln Leu Val Ala Gly Asn Pro Gly Tyr
            100                 105                 110

Asn Pro Tyr Val Glu Cys Gln Asp Ser Val Arg Thr Ile Arg Val Val
        115                 120                 125

Ala Thr Lys Gln Gly Asn Ala Val Thr Leu Gly Asp Tyr Tyr Gln Gly
    130                 135                 140

Arg Arg Ile Thr Ile Thr Gly Asn Ala Asp Leu Thr Phe Asp Glu Thr
145                 150                 155                 160

Ala Trp Gly Asp Ser Gly Val Tyr Tyr Cys Ser Val Val Ser Ala Gln
                165                 170                 175

Asp Leu Glu Gly Asn Asn Glu Ala Tyr Ala Glu Leu Ile Val Leu Gly
            180                 185                 190

Arg Thr Ser Gly Val Ala Glu Leu Leu Pro Gly Phe Gln Ala Gly Pro
        195                 200                 205

Met Glu Asp Trp Leu Phe Val Val Val Val Cys Leu Ala Ala Phe Leu
    210                 215                 220

Val Phe Leu Leu Leu Gly Ile Cys Trp Cys Gln Cys Cys Pro His Thr
225                 230                 235                 240

Cys Cys Cys Tyr Val Arg Cys Pro Cys Cys Pro Asp Lys Cys Cys Cys
                245                 250                 255

Pro Glu Ala Leu Tyr Ala Ala Gly Lys Ala Ala Thr Ser Gly Val Pro
            260                 265                 270

Ser Ile Tyr Ala Pro Ser Thr Tyr Ala His Leu Ser Pro Ala Lys Thr
        275                 280                 285

Pro Pro Leu Pro Thr Val Ile Pro Met Gly Pro Ala Tyr Asn Gly Tyr
    290                 295                 300

Pro Gly Gly Tyr Pro Gly Asp Leu Asp Arg Ser Ser Ser Ala Gly Gly
305                 310                 315                 320
```

```
Gln Gly Ser Tyr Val Pro Leu Leu Arg Asp Thr Asp Ser Ser Val Ala
                325                 330                 335

Ser Glu Val Arg Ser Gly Tyr Arg Ile Gln Ala Ser Gln Gln Asp Asp
            340                 345                 350

Ser Met Arg Val Leu Tyr Tyr Met Glu Lys Glu Leu Ala Asn Phe Asp
        355                 360                 365

Pro Ser Arg Pro Gly Pro Pro Asn Gly Arg Val Glu Arg
    370                 375                 380


<210> SEQ ID NO 33
<211> LENGTH: 525
<212> TYPE: PRT
<213> ORGANISM: Bos taurus

<400> SEQUENCE: 33

Met Ala Pro Leu Ala Arg Pro Phe Ser Gly Gly Leu Glu Ser Cys Pro
1               5                   10                  15

Gly Thr Leu Ser Trp Gly Ala Val Val Phe Val Trp Leu Phe Leu Ser
            20                  25                  30

Thr Ser Cys Thr Ala Pro Thr Ser Ala Ile Gln Val Thr Val Ser Asp
        35                  40                  45

Pro Tyr His Val Val Ile Leu Phe Gln Pro Val Thr Leu Pro Cys Thr
    50                  55                  60

Tyr Gln Leu Thr Thr Thr Pro Thr Ala Pro Ile Val Ile Trp Lys Tyr
65                  70                  75                  80

Lys Ser Phe Cys Arg Asp Arg Ile Ala Asp Ala Phe Ser Pro Ala Ser
                85                  90                  95

Val Asp Asn Gln Leu Asn Ala Gln Leu Ala Ala Gly Asn Pro Gly Tyr
            100                 105                 110

Asn Pro Tyr Val Glu Cys Gln Asp Ser Ala Arg Thr Val Arg Val Val
        115                 120                 125

Ala Thr Lys Gln Gly Asn Ala Val Thr Leu Gly Asp Tyr Tyr Gln Gly
    130                 135                 140

Arg Arg Ile Thr Ile Thr Gly Ser Arg Thr Ser Gly Val Ala Glu Leu
145                 150                 155                 160

Leu Pro Gly Phe Gln Ala Gly Pro Met Glu Asp Trp Leu Phe Val Val
                165                 170                 175

Val Val Cys Leu Ala Ala Phe Leu Val Phe Leu Leu Leu Gly Ile Cys
            180                 185                 190

Trp Cys Gln Cys Cys Pro His Thr Cys Cys Cys Tyr Val Arg Tyr Ala
        195                 200                 205

Ala Gly Lys Ala Ala Thr Ser Gly Val Pro Ser Ile Tyr Ala Pro Ser
    210                 215                 220

Thr Tyr Ala His Leu Ser Pro Ala Lys Thr Pro Pro Pro Pro Ala Met
225                 230                 235                 240

Ile Pro Met Gly Pro Leu Tyr Asn Gly Tyr Ser Gly Asp Phe Asp Arg
                245                 250                 255

Asn Ser Ser Glu Ile Arg Ser Gly Tyr Arg Ile Gln Ala Asn Gln Gln
            260                 265                 270

Asp Asp Ser Met Arg Val Leu Tyr Tyr Met Glu Lys Glu Leu Ala Asn
        275                 280                 285

Phe Asp Pro Ser Arg Pro Gly Pro Pro Asn Gly Arg Val Glu Arg Ala
    290                 295                 300

Met Ser Glu Val Thr Ser Leu His Glu Asp Asp Trp Arg Ser Arg Pro
```

305 310 315 320

Ser Arg Gly Pro Ala Leu Thr Pro Ile Arg Asp Glu Glu Trp Gly His
325 330 335

His Ser Pro Arg Ser Ser Arg Arg Trp Glu Gln Glu Ala Pro Met Glu
340 345 350

Arg Pro Gly Asn Ser Arg Gly Ala Gly Arg Pro Arg Ala Arg Ser Val
355 360 365

Asp Ala Leu Asp Asp Phe Thr Arg Pro Gly Ser Ala Glu Ser Gly Arg
370 375 380

Arg Ser Pro Pro Ser Ser Gly Arg Arg Gly Arg Ala Tyr Ala Pro Pro
385 390 395 400

Arg Ser Arg Ser Arg Asp Asp Leu Tyr Asp Gln Asp Gln Asp Asp Ser
405 410 415

Arg His Phe Pro His Ser Arg Asp Pro His Tyr Asp Asp Phe Arg Ser
420 425 430

Arg Asp Gln Pro His Gly Asp Pro Arg Ala Arg Tyr Gln Arg Ser Arg
435 440 445

Asp Pro Arg Asp Asp Gly Ser Arg Ser Arg Asp Pro Pro Tyr Asp Gly
450 455 460

Arg Leu Leu Glu Glu Ala Leu Arg Lys Lys Gly Pro Ala Glu Arg Arg
465 470 475 480

Pro Tyr Arg Glu Glu Glu Glu Glu Glu Ala Tyr Tyr Pro Pro Ala Pro
485 490 495

Pro Pro Tyr Ser Glu Thr Asp Ser Gln Ala Ser Arg Glu Arg Arg Leu
500 505 510

Lys Lys Asn Leu Ala Leu Ser Arg Glu Ser Leu Val Val
515 520 525

<210> SEQ ID NO 34
<211> LENGTH: 598
<212> TYPE: PRT
<213> ORGANISM: Canis familiaris

<400> SEQUENCE: 34

Met Ala Pro Val Ala Arg Gly Leu Pro Gly Gly Val Gly Pro Arg Pro
1 5 10 15

Ala Ser Arg Gly Trp Gly Ala Val Val Phe Gly Cys Leu Phe Leu Ser
20 25 30

Thr Leu Cys Ala Ala Pro Ala Ser Ala Ile Gln Val Thr Val Ser Asp
35 40 45

Pro Tyr His Val Val Ile Leu Phe Gln Pro Val Thr Leu Pro Cys Thr
50 55 60

Tyr Gln Leu Thr Thr Thr Pro Thr Ala Pro Ile Val Ile Trp Lys Tyr
65 70 75 80

Lys Ser Phe Cys Arg Asp Arg Ile Ala Asp Ala Phe Ser Pro Ala Ser
85 90 95

Ala Asp Asn Gln Leu Asn Ala Gln Leu Ala Ala Gly Asn Pro Gly Tyr
100 105 110

Asn Pro Tyr Val Glu Cys Gln Asp Ser Met Arg Thr Val Arg Val Val
115 120 125

Ala Thr Lys Gln Gly Asn Ala Val Thr Leu Gly Asp Tyr Tyr Gln Gly
130 135 140

Arg Arg Ile Thr Ile Thr Gly Asn Ala Asp Leu Thr Phe Asp Gln Thr
145 150 155 160

```
Gly Trp Gly Asp Ser Gly Val Tyr Tyr Cys Ser Val Val Ser Ala Gln
                165                 170                 175

Asp Leu Gln Gly Asn Asn Glu Ala Tyr Ala Glu Leu Ile Val Leu Gly
            180                 185                 190

Arg Thr Ser Gly Val Ala Glu Leu Leu Pro Gly Phe Gln Ala Gly Pro
        195                 200                 205

Met Glu Asp Trp Leu Phe Val Val Val Val Cys Leu Ala Val Phe Leu
    210                 215                 220

Val Phe Leu Leu Leu Gly Ile Cys Trp Cys Gln Cys Cys Pro His Thr
225                 230                 235                 240

Cys Cys Cys Tyr Val Arg Cys Pro Cys Cys Pro Glu Lys Cys Cys Cys
                245                 250                 255

Pro Glu Ala Leu Tyr Ala Ala Gly Lys Ala Ala Thr Ser Gly Val Pro
            260                 265                 270

Ser Ile Tyr Ala Pro Ser Thr Tyr Ala His Leu Ser Pro Ala Lys Thr
        275                 280                 285

Pro Pro Pro Pro Ala Met Ile Pro Met Gly Pro Leu Tyr Asn Gly Tyr
    290                 295                 300

Pro Gly Asp Phe Asp Arg Asn Ser Ser Val Gly Gly His Ser Ser Gln
305                 310                 315                 320

Val Pro Leu Leu Arg Asp Thr Asp Ser Ser Val Thr Ser Glu Val Arg
                325                 330                 335

Ser Gly Tyr Arg Ile Gln Ala Ser Gln Gln Asp Asp Ser Met Arg Val
            340                 345                 350

Leu Tyr Tyr Met Glu Lys Glu Leu Ala Asn Phe Asp Pro Ser Arg Pro
        355                 360                 365

Gly Ala Pro Asn Gly Arg Val Glu Arg Ala Met Ser Glu Val Thr Ser
    370                 375                 380

Leu His Glu Asp Asp Trp Arg Ser Arg Pro Ser Arg Gly Pro Ala Leu
385                 390                 395                 400

Thr Pro Ile Arg Asp Glu Glu Trp Asp Arg His Ser Pro Arg Ser Pro
                405                 410                 415

Arg Arg Trp Glu Gln Glu Pro Pro Thr Glu Arg Pro Gly Ser Gly Trp
            420                 425                 430

Gly Ala Ala Arg Pro Arg Ala Arg Ser Val Asp Ala Leu Asp Asp Leu
        435                 440                 445

Thr Arg Pro Ser Ser Ala Glu Ser Gly Arg Arg Ser Pro Pro Ser Arg
    450                 455                 460

Gly Arg Arg Gly Gln Ala Tyr Gly Arg Pro Arg Ser Arg Ser Arg Asp
465                 470                 475                 480

Asp Leu Tyr Asp Gln Asp Gly Pro Arg Glu Phe Pro His Pro Arg Asp
                485                 490                 495

Pro His Tyr Asp Asp Phe Arg Pro Arg Asp Arg Pro His Ala Asp Pro
            500                 505                 510

Arg Ser Arg Asn His Arg Ser Arg Asp Ser Arg Glu Asp Gly Ser Arg
        515                 520                 525

Ser Gly Asp Pro Gln Tyr Asp Gly Arg Leu Leu Glu Glu Ala Leu Arg
    530                 535                 540

Lys Lys Gly Pro Ala Glu Arg Arg Arg Ala Tyr Arg Glu Glu Glu Glu
545                 550                 555                 560

Glu Glu Ala Tyr Tyr Pro Pro Ala Pro Pro Pro Tyr Ser Glu Thr Asp
                565                 570                 575

Ser Gln Ala Ser Arg Glu Arg Arg Leu Lys Lys Asn Leu Ala Leu Ser
```

```
            580                 585                 590

Arg Glu Ser Leu Ile Val
        595


<210> SEQ ID NO 35
<211> LENGTH: 594
<212> TYPE: PRT
<213> ORGANISM: Mus musculus

<400> SEQUENCE: 35

Met Ala Pro Ala Ala Ser Ala Cys Ala Gly Ala Pro Gly Ser His Pro
1               5                   10                  15

Ala Thr Thr Ile Phe Val Cys Leu Phe Leu Ile Ile Tyr Cys Pro Asp
            20                  25                  30

Arg Ala Ser Ala Ile Gln Val Thr Val Pro Asp Pro Tyr His Val Val
        35                  40                  45

Ile Leu Phe Gln Pro Val Thr Leu His Cys Thr Tyr Gln Met Ser Asn
    50                  55                  60

Thr Leu Thr Ala Pro Ile Val Ile Trp Lys Tyr Lys Ser Phe Cys Arg
65                  70                  75                  80

Asp Arg Val Ala Asp Ala Phe Ser Pro Ala Ser Val Asp Asn Gln Leu
                85                  90                  95

Asn Ala Gln Leu Ala Ala Gly Asn Pro Gly Tyr Asn Pro Tyr Val Glu
            100                 105                 110

Cys Gln Asp Ser Val Arg Thr Val Arg Val Val Ala Thr Lys Gln Gly
        115                 120                 125

Asn Ala Val Thr Leu Gly Asp Tyr Tyr Gln Gly Arg Arg Ile Thr Ile
    130                 135                 140

Thr Gly Asn Ala Asp Leu Thr Phe Glu Gln Thr Ala Trp Gly Asp Ser
145                 150                 155                 160

Gly Val Tyr Tyr Cys Ser Val Val Ser Ala Gln Asp Leu Asp Gly Asn
                165                 170                 175

Asn Glu Ala Tyr Ala Glu Leu Ile Val Leu Gly Arg Thr Ser Glu Ala
            180                 185                 190

Pro Glu Leu Leu Pro Gly Phe Arg Ala Gly Pro Leu Glu Asp Trp Leu
        195                 200                 205

Phe Val Val Val Val Cys Leu Ala Ser Leu Leu Phe Phe Leu Leu Leu
    210                 215                 220

Gly Ile Cys Trp Cys Gln Cys Cys Pro His Thr Cys Cys Cys Tyr Val
225                 230                 235                 240

Arg Cys Pro Cys Cys Pro Asp Lys Cys Cys Cys Pro Glu Ala Leu Tyr
                245                 250                 255

Ala Ala Gly Lys Ala Ala Thr Ser Gly Val Pro Ser Ile Tyr Ala Pro
            260                 265                 270

Ser Ile Tyr Thr His Leu Ser Pro Ala Lys Thr Pro Pro Pro Pro Pro
        275                 280                 285

Ala Met Ile Pro Met Arg Pro Pro Tyr Gly Tyr Pro Gly Asp Phe Asp
    290                 295                 300

Arg Thr Ser Ser Val Gly Gly His Ser Ser Gln Val Pro Leu Leu Arg
305                 310                 315                 320

Glu Val Asp Gly Ser Val Ser Ser Glu Val Arg Ser Gly Tyr Arg Ile
                325                 330                 335

Gln Ala Asn Gln Gln Asp Asp Ser Met Arg Val Leu Tyr Tyr Met Glu
            340                 345                 350
```

```
Lys Glu Leu Ala Asn Phe Asp Pro Ser Arg Pro Gly Pro Pro Asn Gly
        355                 360                 365

Arg Val Glu Arg Ala Met Ser Glu Val Thr Ser Leu His Glu Asp Asp
    370                 375                 380

Trp Arg Ser Arg Pro Ser Arg Ala Pro Ala Leu Thr Pro Ile Arg Asp
385                 390                 395                 400

Glu Glu Trp Asn Arg His Ser Pro Arg Ser Pro Arg Thr Trp Glu Gln
                405                 410                 415

Glu Pro Leu Gln Glu Gln Pro Arg Gly Gly Trp Gly Ser Gly Arg Pro
            420                 425                 430

Arg Ala Arg Ser Val Asp Ala Leu Asp Asp Ile Asn Arg Pro Gly Ser
        435                 440                 445

Thr Glu Ser Gly Arg Ser Ser Pro Pro Ser Ser Gly Arg Arg Gly Arg
    450                 455                 460

Ala Tyr Ala Pro Pro Arg Ser Arg Ser Arg Asp Asp Leu Tyr Asp Pro
465                 470                 475                 480

Asp Asp Pro Arg Asp Leu Pro His Ser Arg Asp Pro His Tyr Tyr Asp
                485                 490                 495

Asp Leu Arg Ser Arg Asp Pro Arg Ala Asp Pro Arg Ser Arg Gln Arg
            500                 505                 510

Ser His Asp Pro Arg Asp Ala Gly Phe Arg Ser Arg Asp Pro Gln Tyr
        515                 520                 525

Asp Gly Arg Leu Leu Glu Glu Ala Leu Lys Lys Lys Gly Ala Gly Glu
    530                 535                 540

Arg Arg Arg Val Tyr Arg Glu Glu Glu Glu Glu Glu Glu Glu Gly His
545                 550                 555                 560

Tyr Pro Pro Ala Pro Pro Pro Tyr Ser Glu Thr Asp Ser Gln Ala Ser
                565                 570                 575

Arg Glu Arg Arg Met Lys Lys Asn Leu Ala Leu Ser Arg Glu Ser Leu
            580                 585                 590

Val Val


<210> SEQ ID NO 36
<211> LENGTH: 593
<212> TYPE: PRT
<213> ORGANISM: Rattus norvegicus

<400> SEQUENCE: 36

Met Ala Pro Ala Ala Gly Ala Cys Ala Gly Ala Pro Asp Ser His Pro
1               5                   10                  15

Ala Thr Val Val Phe Val Cys Leu Phe Leu Ile Ile Phe Cys Pro Asp
            20                  25                  30

Pro Ala Ser Ala Ile Gln Val Thr Val Ser Asp Pro Tyr His Val Val
        35                  40                  45

Ile Leu Phe Gln Pro Val Thr Leu Pro Cys Thr Tyr Gln Met Ser Asn
    50                  55                  60

Thr Leu Thr Val Pro Ile Val Ile Trp Lys Tyr Lys Ser Phe Cys Arg
65                  70                  75                  80

Asp Arg Ile Ala Asp Ala Phe Ser Pro Ala Ser Val Asp Asn Gln Leu
                85                  90                  95

Asn Ala Gln Leu Ala Ala Gly Asn Pro Gly Tyr Asn Pro Tyr Val Glu
            100                 105                 110

Cys Gln Asp Ser Val Arg Thr Val Arg Val Val Ala Thr Lys Gln Gly
        115                 120                 125
```

```
Asn Ala Val Thr Leu Gly Asp Tyr Tyr Gln Gly Arg Arg Ile Thr Ile
    130                 135                 140

Thr Gly Asn Ala Asp Leu Thr Phe Glu Gln Thr Ala Trp Gly Asp Ser
145                 150                 155                 160

Gly Val Tyr Tyr Cys Ser Val Val Ser Ala Gln Asp Leu Asp Gly Asn
                165                 170                 175

Asn Glu Ala Tyr Ala Glu Leu Ile Val Leu Gly Arg Thr Ser Glu Ala
            180                 185                 190

Pro Glu Leu Leu Pro Gly Phe Arg Ala Gly Pro Leu Glu Asp Trp Leu
        195                 200                 205

Phe Val Val Val Val Cys Leu Ala Ser Leu Leu Leu Phe Leu Leu Leu
    210                 215                 220

Gly Ile Cys Trp Cys Gln Cys Cys Pro His Thr Cys Cys Cys Tyr Val
225                 230                 235                 240

Arg Cys Pro Cys Cys Pro Asp Lys Cys Cys Cys Pro Glu Ala Leu Tyr
                245                 250                 255

Ala Ala Gly Lys Ala Ala Thr Ser Gly Val Pro Ser Ile Tyr Ala Pro
            260                 265                 270

Ser Ile Tyr Thr His Leu Ser Pro Ala Lys Thr Pro Pro Pro Pro Pro
        275                 280                 285

Ala Met Ile Pro Met Gly Pro Pro Tyr Gly Tyr Pro Gly Asp Phe Asp
    290                 295                 300

Arg His Ser Ser Val Gly Gly His Ser Ser Gln Val Pro Leu Leu Arg
305                 310                 315                 320

Asp Val Asp Gly Ser Val Ser Ser Glu Val Arg Ser Gly Tyr Arg Ile
                325                 330                 335

Gln Ala Asn Gln Gln Asp Asp Ser Met Arg Val Leu Tyr Tyr Met Glu
            340                 345                 350

Lys Glu Leu Ala Asn Phe Asp Pro Ser Arg Pro Gly Pro Pro Asn Gly
        355                 360                 365

Arg Val Glu Arg Ala Met Ser Glu Val Thr Ser Leu His Glu Asp Asp
    370                 375                 380

Trp Arg Ser Arg Pro Ser Arg Ala Pro Ala Leu Thr Pro Ile Arg Asp
385                 390                 395                 400

Glu Glu Trp Asn Arg His Ser Pro Gln Ser Pro Arg Thr Trp Glu Gln
                405                 410                 415

Glu Pro Leu Gln Glu Gln Pro Arg Gly Gly Trp Gly Ser Gly Arg Pro
            420                 425                 430

Arg Ala Arg Ser Val Asp Ala Leu Asp Asp Ile Asn Arg Pro Gly Ser
        435                 440                 445

Thr Glu Ser Gly Arg Ser Ser Pro Pro Ser Ser Gly Arg Arg Gly Arg
    450                 455                 460

Ala Tyr Ala Pro Pro Arg Ser Arg Ser Arg Asp Asp Leu Tyr Asp Pro
465                 470                 475                 480

Asp Asp Pro Arg Asp Leu Pro His Ser Arg Asp Pro His Tyr Tyr Asp
                485                 490                 495

Asp Ile Arg Ser Arg Asp Pro Arg Ala Asp Pro Arg Ser Arg Gln Arg
            500                 505                 510

Ser Arg Asp Pro Arg Asp Ala Gly Phe Arg Ser Arg Asp Pro Gln Tyr
        515                 520                 525

Asp Gly Arg Leu Leu Glu Glu Ala Leu Lys Lys Lys Gly Ser Gly Glu
    530                 535                 540

Arg Arg Arg Val Tyr Arg Glu Glu Glu Glu Glu Glu Glu Gly Gln Tyr
```

545 550 555 560

Pro Pro Ala Pro Pro Pro Tyr Ser Glu Thr Asp Ser Gln Ala Ser Arg
565 570 575

Glu Arg Arg Leu Lys Lys Asn Leu Ala Leu Ser Arg Glu Ser Leu Val
580 585 590

Val

<210> SEQ ID NO 37
<211> LENGTH: 596
<212> TYPE: PRT
<213> ORGANISM: Monodelphis domestica

<400> SEQUENCE: 37

Met Ala Pro Ala Ala Pro Gly Pro His Gly Arg Thr Gly Ala Pro Leu
1 5 10 15

Asp Pro Leu Gly Trp Asn Pro Arg Arg Arg Gly Ala Leu Pro Leu Pro
20 25 30

Leu Leu Leu Leu Leu Leu Ala Leu Trp Cys Ser Ala Pro Val Gly Cys
35 40 45

Ile Gln Val Thr Val Ser Asn Pro Phe Gln Val Val Ile Leu Phe Gln
50 55 60

Pro Val Thr Leu Pro Cys Ser Tyr Gln Leu Ser Gly Val Pro Thr Leu
65 70 75 80

Pro Ile Val Val Trp Lys Tyr Lys Ser Phe Cys Arg Asn Arg Ile Thr
85 90 95

Asp Ala Phe Ser Pro Ala Ser Ala Asp Ser Gln Leu Asn Ala Gln Leu
100 105 110

Ala Ala Gly Asn Pro Gly Tyr Asn Pro Tyr Val Glu Cys Gln Asp Ser
115 120 125

Val Arg Thr Val Arg Val Val Ala Thr Lys Gln Gly Asn Ala Val Thr
130 135 140

Leu Gly Asp Phe Tyr Gln Gly Arg Arg Ile Thr Ile Thr Gly Asn Ala
145 150 155 160

Asp Leu Thr Phe Asp Gln Thr Ala Trp Gly Asp Ser Gly Val Tyr Tyr
165 170 175

Cys Ser Val Ile Ser Ala Gln Asp Leu Gln Gly Asn Asn Glu Ala Tyr
180 185 190

Ala Glu Leu Ile Val Leu Gly Arg Thr Ser Gly Val Ala Glu Leu Leu
195 200 205

Pro Asp Phe Gln Ile Gly Pro Met Glu Asp Trp Leu Phe Val Val Val
210 215 220

Val Gly Leu Ala Ala Phe Leu Val Phe Leu Leu Leu Gly Ile Cys Trp
225 230 235 240

Cys Gln Cys Cys Pro His Thr Cys Cys Cys Tyr Val Arg Cys Pro Cys
245 250 255

Cys Pro Glu Lys Cys Cys Cys Pro Glu Ala Leu Tyr Ala Ala Gly Lys
260 265 270

Ala Ala Thr Ser Gly Val Pro Ser Ile Tyr Ala Pro Ser Val Phe Ala
275 280 285

Pro Ser Thr Tyr Ala His Leu Ser Pro Ala Lys Ala Pro Ser Pro Pro
290 295 300

Pro Met Ile Pro Leu Gly Pro Val Tyr Asn Asp Phe Asp Arg Gln Ser
305 310 315 320

Ser Val Gly Gly His Ser Ser Gln Val Pro Leu Leu Arg Asp Thr Asp

```
                325                 330                 335

Ser Val Arg Asn Ser Glu Val Arg Ser Gly Tyr Arg Ile Gln Ala Asn
            340                 345                 350

Gln Gln Asp Asp Ser Met Lys Val Leu Tyr Tyr Met Glu Lys Glu Leu
        355                 360                 365

Ala Asn Phe Asp Pro Ser Arg Pro Gly Leu Pro Asn Gly Arg Val Glu
    370                 375                 380

Arg Ala Met Ser Glu Val Thr Ser Leu His Glu Asp Asp Trp Arg Ala
385                 390                 395                 400

Arg Pro His Arg Gly Pro Ala Leu Thr Pro Ile Gln Asp Glu Asp Leu
                405                 410                 415

Asp Tyr His Ser Arg Ser Pro Gly Gly Trp Gly Arg Glu Arg Pro His
            420                 425                 430

Asp Arg Tyr Gly Glu Arg Pro His Asp Pro Tyr Gly Asp Trp Gly Ala
        435                 440                 445

Gly Arg Pro Arg Ala Arg Ser Val Asp Ala Leu Asp Asp Leu Ala Arg
    450                 455                 460

Pro Ser Ser Val Glu Ser Gly Arg Thr Ser Pro Ser Glu Arg Ser Arg
465                 470                 475                 480

Ser Lys Ala Tyr Ala Pro Leu Arg Ser Arg Ser Arg Asp Asp Leu Tyr
                485                 490                 495

Ser Arg Ser Gly Asp Pro His Tyr Glu Asp Phe Arg Ser Arg Gly Arg
            500                 505                 510

Ala Leu Asp Asp Ser Arg Arg Asp Pro His Glu Asn His Arg Arg Ser
        515                 520                 525

Arg Asp Pro Glu Tyr Asp Gly Arg Phe Leu Glu Glu Val Met Arg Lys
    530                 535                 540

Lys Gly Val Gly Glu Arg Arg Arg Pro Tyr Arg Glu Glu Glu Glu Glu
545                 550                 555                 560

Pro Tyr Tyr Pro Pro Ala Pro Pro Pro Tyr Thr Glu Thr Asp Ser Gln
                565                 570                 575

Ala Ser Arg Glu Arg Lys Leu Arg Lys Asn Leu Ala Leu Ser Arg Glu
            580                 585                 590

Ser Leu Val Val
        595


<210> SEQ ID NO 38
<211> LENGTH: 613
<212> TYPE: PRT
<213> ORGANISM: Danio rerio

<400> SEQUENCE: 38

Met Ser Leu Gly Val Ile Phe Thr Leu Leu Leu Phe Pro Gly Val Thr
1               5                   10                  15

Thr Gly Ile Asn Val Ile Cys Thr Tyr Pro Arg Tyr Val Val Ile Met
            20                  25                  30

Phe Gln Pro Val Thr Leu Arg Cys Asp Phe Thr Thr Thr Ser Thr Thr
        35                  40                  45

Pro Pro Leu Ile Thr Trp Lys Tyr Lys Ser Tyr Cys Arg Asp Pro Ile
    50                  55                  60

Gln Ala Ala Leu Asn Pro Ser Ser Ala Asp Asn Ala Ile Ala Gln Ser
65                  70                  75                  80

Asn Pro Asn Tyr Asn Pro Asn Ile Glu Cys Ala Asp Ser Ala Arg Thr
                85                  90                  95
```

```
Val Arg Ile Val Ala Ser Lys Gln Thr Ala Val Thr Leu Gly Lys Glu
            100                 105                 110

Tyr Gln Gly Arg Gln Ile Ser Ile Thr Asn Asn Ala Asp Leu Ser Ile
        115                 120                 125

Val Gln Thr Ala Trp Gly Asp Ser Gly Val Tyr Val Cys Ser Ala Ala
    130                 135                 140

Ser Ala Gln Asp Leu Ser Gly Asn Gly Glu Cys Tyr Thr Glu Leu Ile
145                 150                 155                 160

Val Leu Gly Arg Lys Ser Asn Thr Thr Asp Leu Leu Pro Gly Ile Asp
                165                 170                 175

Leu Leu Ile Met Glu Asp Trp Leu Leu Val Val Leu Val Val Leu Gly
            180                 185                 190

Phe Leu Leu Leu Leu Leu Leu Ile Gly Ile Cys Trp Cys Gln Cys Cys
        195                 200                 205

Pro His Thr Cys Cys Cys Tyr Val Arg Cys Pro Cys Cys Pro Glu Arg
    210                 215                 220

Cys Cys Cys Pro Arg Ala Leu Tyr Glu Ala Gly Lys Met Val Lys Ser
225                 230                 235                 240

Gly Ile Pro Ser Gln Tyr Ala Ala Thr Ala Tyr Ala Gln Ser Met Tyr
                245                 250                 255

Gly Gln Pro Ala Tyr Gly Val Gly Ala Ala Met Pro Gly Ile Pro Met
            260                 265                 270

Met Pro Met Gln Met Gly Val Gly Gly Pro Pro Ser Asn Gly Tyr Gly
        275                 280                 285

Arg Asp Tyr Asp Gly Ala Ser Ser Ile Gly Gln Gly Ser Gln Val Pro
    290                 295                 300

Leu Leu Gln Glu His Asp Ala Gly Gly Asn Arg Ser Gly Tyr Arg Val
305                 310                 315                 320

Gln Ala Asp Gln Asp Gly Asn Pro Thr Arg Val Leu Tyr Tyr Met Glu
                325                 330                 335

Arg Glu Val Ala Asn Leu Asp Pro Ser Arg Pro Gly Ile Ala Pro Val
            340                 345                 350

Asp Gly Met Ser Glu Val Ser Ser Leu His Asp Gly Pro Glu Ser Arg
        355                 360                 365

Asn Arg Gly Arg Ala Arg Pro Pro Gln Leu Thr Thr Val Tyr Asp Asp
    370                 375                 380

Val Asp Glu Asn Met Ser Thr Ile Ser Ser Val Ser Gln His Met Arg
385                 390                 395                 400

Arg Asp Glu Pro Arg Arg Gly Ala Asp Ser Arg Gly Arg Ala Arg Ser
                405                 410                 415

Met Glu Asn Leu Asp Asp Ile Ser Arg Gly Tyr Arg Asp Arg Asp Asp
            420                 425                 430

Tyr Pro Pro Ala Arg Arg Asp Gly Gly Pro Arg Gly Gly Arg Arg Gly
        435                 440                 445

Ser Asp Asp Glu Trp Ser Ser Ser Gly Arg Gly Tyr Asp Pro Val Asp
    450                 455                 460

Asp Arg Arg Arg Arg Asp Tyr Ser Pro Asp Asn Arg Pro Arg Arg Gly
465                 470                 475                 480

Asp Ser Phe Arg Gly Ala Gly Phe Gln Gly Arg Arg Thr Arg Ser Arg
                485                 490                 495

Asp Asp Leu Met Asp Leu Val Arg Asp Pro Gly Arg Gly Gly Arg Asp
            500                 505                 510

Glu Tyr Asp Asp Ser Phe Leu Arg Glu Ala Met Glu Lys Lys Lys Leu
```

```
        515                 520                 525

Gly Glu Gln Gln Arg Gly Arg Ser Arg Glu Arg Leu Asp Ser Glu Ser
    530                 535                 540

Asp Arg Ser Asp Arg Tyr Arg Gly His His Ser Gly Pro Pro Pro Leu
545                 550                 555                 560

Pro Leu Val Pro Ala Ser Gly Asn Pro Asp Arg Arg Gly Asn His Ser
                565                 570                 575

Asn Phe Pro Pro Pro Pro Pro Pro Tyr Thr Glu Asp Thr Asp Ser Leu
            580                 585                 590

Pro Ser Ser Lys Lys Ser Asn Leu Lys Lys Asn Gly Ala Val Ser Arg
        595                 600                 605

Glu Ser Leu Val Val
    610


<210> SEQ ID NO 39
<211> LENGTH: 546
<212> TYPE: PRT
<213> ORGANISM: Homo sapiens

<400> SEQUENCE: 39

Met Ala Trp Pro Lys Leu Pro Ala Pro Trp Leu Leu Leu Cys Thr Trp
1               5                   10                  15

Leu Pro Ala Gly Cys Leu Ser Leu Leu Val Thr Val Gln His Thr Glu
            20                  25                  30

Arg Tyr Val Thr Leu Phe Ala Ser Ile Ile Leu Lys Cys Asp Tyr Thr
        35                  40                  45

Thr Ser Ala Gln Leu Gln Asp Val Val Val Thr Trp Arg Phe Lys Ser
    50                  55                  60

Phe Cys Lys Asp Pro Ile Phe Asp Tyr Tyr Ser Ala Ser Tyr Gln Ala
65                  70                  75                  80

Ala Leu Ser Leu Gly Gln Asp Pro Ser Asn Asp Cys Asn Asp Asn Gln
                85                  90                  95

Arg Glu Val Arg Ile Val Ala Gln Arg Arg Gly Gln Asn Glu Pro Val
            100                 105                 110

Leu Gly Val Asp Tyr Arg Gln Arg Lys Ile Thr Ile Gln Asn Arg Ala
        115                 120                 125

Asp Leu Val Ile Asn Glu Val Met Trp Trp Asp His Gly Val Tyr Tyr
    130                 135                 140

Cys Thr Ile Glu Ala Pro Gly Asp Thr Ser Gly Asp Pro Asp Lys Glu
145                 150                 155                 160

Val Lys Leu Ile Val Leu His Trp Leu Thr Val Ile Phe Ile Ile Leu
                165                 170                 175

Gly Ala Leu Leu Leu Leu Leu Leu Ile Gly Val Cys Trp Cys Gln Cys
            180                 185                 190

Cys Pro Gln Tyr Cys Cys Cys Tyr Ile Arg Cys Pro Cys Cys Pro Ala
        195                 200                 205

His Cys Cys Cys Pro Glu Glu Ala Leu Ala Arg His Arg Tyr Met Lys
    210                 215                 220

Gln Ala Gln Ala Leu Gly Pro Gln Met Met Gly Lys Pro Leu Tyr Trp
225                 230                 235                 240

Gly Ala Asp Arg Ser Ser Gln Val Ser Ser Tyr Pro Met His Pro Leu
                245                 250                 255

Leu Gln Arg Asp Leu Ser Leu Pro Ser Ser Leu Pro Gln Met Pro Met
            260                 265                 270
```

```
Thr Gln Thr Thr Asn Gln Pro Pro Ile Ala Asn Gly Val Leu Glu Tyr
        275                 280                 285

Leu Glu Lys Glu Leu Arg Asn Leu Asn Leu Ala Gln Pro Leu Pro Pro
    290                 295                 300

Asp Leu Lys Gly Arg Phe Gly His Pro Cys Ser Met Leu Ser Ser Leu
305                 310                 315                 320

Gly Ser Glu Val Val Glu Arg Arg Ile Ile His Leu Pro Pro Leu Ile
                325                 330                 335

Arg Asp Leu Ser Ser Ser Arg Arg Thr Ser Asp Ser Leu His Gln Gln
            340                 345                 350

Trp Leu Thr Pro Ile Pro Ser Arg Pro Trp Asp Leu Arg Glu Gly Arg
        355                 360                 365

Ser His His His Tyr Pro Asp Phe His Gln Glu Leu Gln Asp Arg Gly
    370                 375                 380

Pro Lys Ser Trp Ala Leu Glu Arg Arg Glu Leu Asp Pro Ser Trp Ser
385                 390                 395                 400

Gly Arg His Arg Ser Ser Arg Leu Asn Gly Ser Pro Ile His Trp Ser
                405                 410                 415

Asp Arg Asp Ser Leu Ser Asp Val Pro Ser Ser Ser Glu Ala Arg Trp
            420                 425                 430

Arg Pro Ser His Pro Pro Phe Arg Ser Arg Cys Gln Glu Arg Pro Arg
        435                 440                 445

Arg Pro Ser Pro Arg Glu Ser Thr Gln Arg His Gly Arg Arg Arg Arg
    450                 455                 460

His Arg Ser Tyr Ser Pro Pro Leu Pro Ser Gly Leu Ser Ser Trp Ser
465                 470                 475                 480

Ser Glu Glu Asp Lys Glu Arg Gln Pro Gln Ser Trp Arg Ala His Arg
                485                 490                 495

Arg Gly Ser His Ser Pro His Trp Pro Glu Glu Lys Pro Pro Ser Tyr
            500                 505                 510

Arg Ser Leu Asp Ile Thr Pro Gly Lys Asn Ser Arg Lys Lys Gly Ser
        515                 520                 525

Val Glu Arg Arg Ser Glu Lys Asp Ser Ser His Ser Gly Arg Ser Val
    530                 535                 540

Val Ile
545


<210> SEQ ID NO 40
<211> LENGTH: 546
<212> TYPE: PRT
<213> ORGANISM: Pan troglodytes

<400> SEQUENCE: 40

Met Ala Trp Pro Lys Leu Pro Ala Pro Trp Leu Leu Leu Cys Thr Trp
1               5                   10                  15

Leu Pro Ala Gly Cys Leu Ser Leu Leu Val Thr Val Gln His Thr Glu
            20                  25                  30

Arg Tyr Val Thr Leu Phe Ala Ser Ile Ile Leu Lys Cys Asp Tyr Thr
        35                  40                  45

Thr Ser Ala Gln Leu Gln Asp Val Val Val Thr Trp Arg Phe Lys Ser
    50                  55                  60

Phe Cys Lys Asp Pro Ile Phe Asp Tyr Tyr Ser Ala Ser Tyr Gln Ala
65                  70                  75                  80

Ala Leu Ser Leu Gly Gln Asp Pro Ser Asn Asp Cys Asn Asp Asn Gln
                85                  90                  95
```

-continued

```
Arg Glu Val Arg Ile Val Ala Gln Arg Arg Gly Gln Asn Glu Pro Val
            100                 105                 110

Leu Gly Val Asp Tyr Arg Gln Arg Lys Ile Thr Ile Gln Asn Arg Ala
        115                 120                 125

Asp Leu Val Ile Asn Glu Val Met Trp Trp Asp His Gly Val Tyr Tyr
    130                 135                 140

Cys Thr Ile Glu Ala Pro Gly Asp Thr Ser Gly Asp Pro Asp Lys Glu
145                 150                 155                 160

Val Lys Leu Ile Val Leu His Trp Leu Thr Val Ile Phe Ile Ile Leu
                165                 170                 175

Gly Ala Leu Leu Leu Leu Leu Leu Ile Gly Val Cys Trp Cys Gln Cys
            180                 185                 190

Cys Pro Gln Tyr Cys Cys Cys Tyr Ile Arg Cys Pro Cys Cys Pro Ala
        195                 200                 205

His Cys Cys Cys Pro Glu Glu Ala Leu Ala Arg His Arg Tyr Met Lys
    210                 215                 220

Gln Ala Gln Ala Leu Gly Pro Gln Met Met Glu Lys Pro Leu Tyr Trp
225                 230                 235                 240

Gly Ala Asp Arg Ser Ser Gln Val Ser Ser Tyr Pro Met His Pro Leu
                245                 250                 255

Leu Gln Arg Asp Leu Ser Leu Arg Ser Ser Leu Pro Gln Met Pro Met
            260                 265                 270

Thr Gln Thr Thr Asn Gln Pro Pro Ile Ala Asn Gly Val Leu Glu Tyr
        275                 280                 285

Leu Glu Lys Glu Leu Arg Asn Leu Asn Leu Ala Gln Pro Leu Pro Pro
    290                 295                 300

Asp Leu Lys Gly Arg Phe Gly His Pro Cys Ser Met Leu Ser Ser Leu
305                 310                 315                 320

Gly Ser Glu Val Val Glu Arg Arg Ile Ile His Leu Pro Pro Leu Ile
                325                 330                 335

Arg Asp Leu Ser Ser Ser Arg Arg Thr Ser Asp Ser Leu His Gln Gln
            340                 345                 350

Trp Leu Thr Pro Ile Pro Ser Arg Pro Trp Asp Leu Arg Glu Gly Arg
        355                 360                 365

Ser His His His Tyr Pro Asp Phe His Gln Glu Leu Gln Asp Arg Gly
    370                 375                 380

Pro Lys Ser Trp Ala Leu Glu Arg Arg Glu Leu Asp Pro Ser Trp Ser
385                 390                 395                 400

Gly Arg His Arg Ser Ser Arg Leu Asn Gly Ser Pro Ile His Trp Ser
                405                 410                 415

Asp Arg Asp Ser Leu Ser Asp Val Pro Ser Ser Ser Glu Ala Arg Trp
            420                 425                 430

Arg Pro Ser His Pro Leu Phe Arg Ser Arg Cys Gln Glu Arg Pro Arg
        435                 440                 445

Arg Pro Ser Pro Arg Glu Ser Thr Gln Arg Asp Gly Arg Arg Arg Arg
    450                 455                 460

His Arg Ser Tyr Ser Pro Pro Leu Pro Ser Gly Leu Ser Ser Trp Ser
465                 470                 475                 480

Ser Glu Glu Asp Lys Glu Arg Gln Pro Gln Ser Trp Arg Ala His Arg
                485                 490                 495

Arg Gly Ser His Pro Pro His Trp Pro Glu Glu Ile Pro Pro Ser Tyr
            500                 505                 510
```

Arg Ser Leu Asp Ile Ile Gly Gly Lys Asn Asn Lys Lys Lys Gly Ser
        515                 520                 525

Val Glu Arg Arg Ser Glu Lys Asp Ser Ser His Ser Gly Arg Ser Val
    530                 535                 540

Val Ile
545

<210> SEQ ID NO 41
<211> LENGTH: 546
<212> TYPE: PRT
<213> ORGANISM: Pongo pygmaeus

<400> SEQUENCE: 41

Met Ala Trp Pro Lys Leu Pro Ala Pro Trp Leu Leu Leu Cys Thr Trp
1               5                   10                  15

Leu Pro Ala Gly Cys Leu Ser Leu Leu Val Thr Val Gln His Thr Glu
            20                  25                  30

Arg Tyr Val Thr Leu Phe Ala Ser Ile Ile Leu Lys Cys Asp Tyr Thr
        35                  40                  45

Thr Ser Ala Gln Leu Gln Asp Val Val Val Thr Trp Arg Phe Lys Ser
    50                  55                  60

Phe Cys Lys Asp Pro Ile Phe Asp Tyr Tyr Ser Ala Ser Tyr Gln Ala
65                  70                  75                  80

Ala Leu Ser Leu Gly Gln Asp Pro Ser Asn Asp Cys Asn Asp Asn Gln
                85                  90                  95

Arg Glu Val Arg Ile Val Ala Gln Arg Arg Gly Gln Asn Glu Pro Val
            100                 105                 110

Leu Gly Val Asp Tyr Arg Gln Arg Lys Ile Thr Ile Gln Asn Arg Ala
        115                 120                 125

Asp Leu Val Ile Asn Glu Val Met Trp Trp Asp His Gly Val Tyr Tyr
    130                 135                 140

Cys Thr Ile Glu Ala Pro Gly Asp Thr Ser Gly Asp Pro Asp Lys Glu
145                 150                 155                 160

Val Lys Leu Ile Val Leu His Trp Leu Thr Val Ile Phe Ile Ile Leu
                165                 170                 175

Gly Ala Leu Leu Leu Leu Leu Leu Ile Gly Val Cys Trp Cys Gln Cys
            180                 185                 190

Cys Pro Gln Tyr Cys Cys Cys Tyr Ile Arg Cys Pro Cys Cys Pro Ala
        195                 200                 205

Arg Cys Cys Cys Pro Glu Glu Ala Leu Ala Arg His Arg Tyr Met Lys
    210                 215                 220

Gln Ala Gln Ala Leu Gly Pro Gln Met Met Glu Lys Pro Leu Tyr Trp
225                 230                 235                 240

Gly Ala Asp Arg Ser Ser Gln Val Ser Ser Tyr Pro Met His Pro Leu
                245                 250                 255

Leu Gln Arg Asp Leu Ser Leu Arg Ser Ser Leu Pro Gln Met Pro Met
            260                 265                 270

Thr Gln Thr Thr Asn His Pro Pro Ile Ala Asn Gly Val Leu Glu Tyr
        275                 280                 285

Leu Glu Lys Glu Leu Arg Asn Leu Asn Leu Ala Gln Pro Leu Pro Pro
    290                 295                 300

Asp Leu Lys Ala Arg Phe Gly His Pro Cys Ser Met Leu Ser Ser Leu
305                 310                 315                 320

Gly Ser Glu Val Val Glu Arg Arg Phe Ile His Leu Pro Pro Leu Ile
                325                 330                 335

```
Arg Asp Leu Ser Ser Ser Arg Arg Thr Ser Asp Ser Leu His Gln Gln
            340                 345                 350

Trp Leu Thr Pro Ile Pro Ser Arg Pro Trp Asp Leu Arg Glu Gly Arg
        355                 360                 365

Arg Gln His His Tyr Pro Asp Phe His Gln Glu Leu Gln Asp Arg Gly
    370                 375                 380

Pro Lys Ser Trp Ala Leu Glu Arg Arg Glu Leu Asp Pro Ser Trp Ser
385                 390                 395                 400

Gly Arg His Arg Ser Ser Arg Leu Asn Gly Ser Pro Ile His Trp Ser
                405                 410                 415

Asp Arg Asp Ser Leu Ser Asp Val Pro Ser Ser Ile Glu Ala Arg Trp
            420                 425                 430

Gln Pro Ser His Pro Pro Phe Arg Ser Arg Cys Gln Glu Arg Pro Arg
        435                 440                 445

Arg Pro Ser Pro Arg Glu Ser Thr Gln Arg His Gly Arg Arg Arg Arg
    450                 455                 460

His Arg Ser Tyr Ser Pro Pro Leu Pro Ser Gly Leu Ser Ser Trp Ser
465                 470                 475                 480

Ser Glu Glu Asp Lys Glu Arg Gln Pro Gln Ser Trp Gly Ala His Arg
                485                 490                 495

Arg Arg Ser His Ser Pro His Trp Pro Glu Glu Lys Pro Pro Ser Tyr
            500                 505                 510

Arg Ser Leu Asp Val Thr Pro Gly Lys Asn Ser Arg Lys Lys Gly Ser
        515                 520                 525

Val Glu Arg Arg Ser Glu Lys Asp Ser Ser His Ser Gly Arg Ser Val
    530                 535                 540

Val Ile
545


<210> SEQ ID NO 42
<211> LENGTH: 537
<212> TYPE: PRT
<213> ORGANISM: Mus musculus

<400> SEQUENCE: 42

Met Gly Cys Gly Leu Leu Ala Ala Gly Leu Leu Leu Phe Thr Trp Leu
1               5                   10                  15

Pro Ala Gly Cys Leu Ser Leu Leu Val Thr Val Gln His Thr Glu Arg
            20                  25                  30

Tyr Val Thr Leu Phe Ala Ser Val Thr Leu Lys Cys Asp Tyr Thr Thr
        35                  40                  45

Ser Ala Gln Leu Gln Asp Val Val Val Thr Trp Arg Phe Lys Ser Phe
    50                  55                  60

Cys Lys Asp Pro Ile Phe Asp Tyr Phe Ser Ala Ser Tyr Gln Ala Ala
65                  70                  75                  80

Leu Ser Leu Gly Gln Asp Pro Ser Asn Asp Cys Ser Asp Asn Gln Arg
                85                  90                  95

Glu Val Arg Ile Val Ala Gln Arg Arg Gly Gln Ser Glu Pro Val Leu
            100                 105                 110

Gly Val Asp Tyr Arg Gln Arg Lys Ile Thr Ile Gln Asn Arg Ala Asp
        115                 120                 125

Leu Val Ile Asn Glu Val Met Trp Trp Asp His Gly Val Tyr Tyr Cys
    130                 135                 140

Thr Ile Glu Ala Pro Gly Asp Thr Ser Gly Asp Pro Asp Lys Glu Val
```

-continued

```
145                 150                 155                 160

Lys Leu Ile Val Leu His Trp Leu Thr Val Ile Phe Ile Ile Leu Gly
                165                 170                 175

Ala Leu Leu Leu Leu Leu Leu Ile Gly Val Cys Trp Cys Gln Cys Cys
            180                 185                 190

Pro Gln Tyr Cys Cys Cys Tyr Ile Arg Cys Pro Cys Cys Pro Thr Arg
        195                 200                 205

Cys Cys Cys Pro Glu Glu Ala Leu Ala Arg His Arg Tyr Met Lys Gln
    210                 215                 220

Val Gln Ala Leu Gly Pro Gln Met Met Glu Lys Pro Leu Tyr Trp Gly
225                 230                 235                 240

Ala Asp Arg Ser Ser Gln Val Ser Ser Tyr Ala Met Asn Pro Leu Leu
                245                 250                 255

Gln Arg Asp Leu Ser Leu Gln Ser Ser Leu Pro Gln Met Pro Met Thr
            260                 265                 270

Gln Met Ala Ala His Pro Pro Val Ala Asn Gly Val Leu Glu Tyr Leu
        275                 280                 285

Glu Lys Glu Leu Arg Asn Leu Asn Pro Ala Gln Pro Leu Pro Ala Asp
    290                 295                 300

Leu Arg Ala Lys Ser Gly His Pro Cys Ser Met Leu Ser Ser Leu Gly
305                 310                 315                 320

Ser Ala Glu Val Val Glu Arg Arg Val Ile His Leu Pro Pro Leu Ile
                325                 330                 335

Arg Asp Pro Pro Ser Ser Arg Thr Ser Asn Pro Ser His Gln Gln Arg
            340                 345                 350

Leu Asn Ala Val Ser Ser Arg His Cys Asp Leu Ser Glu Arg Pro Arg
        355                 360                 365

Gln Arg His His Ser Asp Phe Leu Arg Glu Leu Gln Asp Gln Gly Met
    370                 375                 380

Arg Pro Trp Ala Pro Gly Arg Gly Glu Leu Asp Pro His Trp Ser Gly
385                 390                 395                 400

Arg His His Arg Ser Arg Pro Ser Glu Ser Ser Met Pro Trp Ser Asp
                405                 410                 415

Trp Asp Ser Leu Ser Glu Cys Pro Ser Ser Ser Glu Ala Pro Trp Pro
            420                 425                 430

Pro Arg Arg Pro Glu Pro Arg Glu Gly Ala Gln Arg Arg Glu Arg Arg
        435                 440                 445

Arg His Arg Ser Tyr Ser Pro Pro Leu Pro Ser Gly Pro Ser Ser Trp
    450                 455                 460

Ser Ser Glu Glu Glu Lys Glu Ser Leu Pro Arg Asn Trp Gly Ala Gln
465                 470                 475                 480

Arg Arg His His His Arg Arg Arg Arg Ser Gln Ser Pro Asn Trp Pro
                485                 490                 495

Glu Glu Lys Pro Pro Ser Tyr Arg Ser Leu Asp Val Thr Pro Gly Lys
            500                 505                 510

Asn Asn Arg Lys Lys Gly Asn Val Glu Arg Arg Leu Glu Arg Glu Ser
        515                 520                 525

Ser His Ser Gly Arg Ser Val Val Ile
    530                 535
```

<210> SEQ ID NO 43
<211> LENGTH: 538
<212> TYPE: PRT
<213> ORGANISM: Rattus norvegicus

<400> SEQUENCE: 43

Met Gly Cys Gly Leu Leu Val Ala Gly Leu Leu Leu Phe Thr Trp Leu
1               5                   10                  15

Pro Ala Gly Cys Leu Ser Leu Leu Val Thr Val Gln His Thr Glu Arg
            20                  25                  30

Tyr Val Thr Leu Phe Ala Ser Val Thr Leu Lys Cys Asp Tyr Thr Thr
        35                  40                  45

Ser Ala Gln Leu Gln Asp Val Val Val Thr Trp Arg Phe Lys Ser Phe
    50                  55                  60

Cys Lys Asp Pro Ile Phe Asp Tyr Phe Ser Ala Ser Tyr Gln Ala Ala
65                  70                  75                  80

Leu Ser Leu Gly Gln Asp Pro Ser Asn Asp Cys Ser Asp Asn Gln Arg
                85                  90                  95

Glu Val Arg Ile Val Ala Gln Arg Arg Gly Gln Ser Glu Pro Val Leu
            100                 105                 110

Gly Val Asp Tyr Arg Gln Arg Lys Ile Thr Ile Gln Asn Arg Ala Asp
        115                 120                 125

Leu Val Ile Asn Glu Val Met Trp Trp Asp His Gly Val Tyr Tyr Cys
    130                 135                 140

Thr Ile Glu Ala Pro Gly Asp Thr Ser Gly Asp Pro Asp Lys Glu Val
145                 150                 155                 160

Lys Leu Ile Val Leu His Trp Leu Thr Val Ile Phe Ile Ile Leu Gly
                165                 170                 175

Ala Leu Leu Leu Leu Leu Leu Ile Gly Val Cys Trp Cys Gln Cys Cys
            180                 185                 190

Pro Gln Tyr Cys Cys Cys Tyr Ile Arg Cys Pro Cys Cys Pro Thr His
        195                 200                 205

Cys Cys Cys Pro Glu Glu Ala Leu Ala Arg His Arg Tyr Met Lys Gln
    210                 215                 220

Val Gln Ala Leu Gly Pro Gln Met Met Glu Lys Pro Leu Tyr Trp Gly
225                 230                 235                 240

Ala Asp Arg Ser Ser Gln Val Ser Ser Tyr Ala Met Asn Pro Leu Leu
                245                 250                 255

Gln Arg Asp Leu Ser Leu Arg Ser Ser Leu Pro Gln Met Pro Met Thr
            260                 265                 270

Gln Met Ala Ala His Pro Pro Val Ala Asn Gly Val Leu Glu Tyr Leu
        275                 280                 285

Glu Lys Glu Leu Arg Asn Leu Asn Pro Ala Gln Pro Leu Pro Pro Asp
    290                 295                 300

Leu Arg Thr Lys Ser Gly His Pro Cys Ser Met Leu Ser Ser Leu Gly
305                 310                 315                 320

Ser Ala Glu Val Val Glu Arg Arg Val Ile His Leu Pro Pro Leu Ile
                325                 330                 335

Arg Asp Pro Leu Pro Ser Arg Thr Ser Asn Ser Ser His Gln Gln Arg
            340                 345                 350

Leu Asn Pro Val Pro Ser Arg Pro Arg Asp Pro Ser Glu Gly Arg Arg
        355                 360                 365

Gln Arg Asn His Ser Asp Phe Leu Arg Glu Leu Gln Asp Arg Gly Met
    370                 375                 380

Arg Pro Trp Ala Pro Gly Arg Gly Glu Leu Asp Pro His Trp Ser Gly
385                 390                 395                 400

Arg His His Arg Ser Arg Pro Ser Glu Ser Ser Met Pro Trp Ser Asp

```
                405                 410                 415

Trp Asp Ser Leu Ser Glu Cys Pro Ser Ser Ser Glu Ala Pro Trp Pro
            420                 425                 430

Ser Arg Arg Pro Glu Pro Arg Glu Gly Ser Gln Arg His Gly Arg Arg
        435                 440                 445

Arg His Arg Ser Tyr Ser Pro Pro Leu Pro Ser Gly Pro Ser Ser Trp
    450                 455                 460

Ser Ser Glu Glu Glu Lys Glu Ser Leu Pro Arg Asn Trp Gly Ala Gln
465                 470                 475                 480

Arg Arg His His Arg Arg Ser Arg Arg Arg Ser Gln Ser Pro Asn Trp
                485                 490                 495

Leu Glu Glu Lys Pro Pro Ser Tyr Arg Ser Leu Asp Val Thr Pro Gly
            500                 505                 510

Lys Asn Asn Met Lys Lys Gly Asn Val Glu Arg Arg Leu Glu Arg Glu
        515                 520                 525

Ser Ser His Ser Gly Arg Ser Val Val Ile
    530                 535


<210> SEQ ID NO 44
<211> LENGTH: 517
<212> TYPE: PRT
<213> ORGANISM: Canis familiaris

<400> SEQUENCE: 44

Met Gly Pro Glu Leu Pro Ala Pro Trp Leu Leu Leu Val Ala Gly Leu
1               5                   10                  15

Pro Ala Gly Cys Leu Ser Leu Leu Val Thr Val Gln His Thr Glu Arg
            20                  25                  30

Tyr Val Thr Leu Phe Ala Ser Ile Val Leu Lys Cys Asp Tyr Thr Thr
        35                  40                  45

Ser Ala Gln Leu Gln Asp Val Val Val Thr Trp Arg Phe Lys Ser Phe
    50                  55                  60

Cys Lys Asp Pro Ile Phe Asp Tyr Tyr Ser Ala Ser Tyr Gln Ala Ala
65                  70                  75                  80

Leu Ser Leu Gly Gln Asp Pro Ser Asn Asp Cys Asn Asp Ser Gln Arg
                85                  90                  95

Glu Val Arg Ile Val Ala Gln Arg Arg Gly Gln Asn Glu Pro Val Leu
            100                 105                 110

Gly Val Asp Tyr Arg Gln Arg Lys Ile Thr Ile Gln Asn Arg Ala Asp
        115                 120                 125

Leu Val Ile Asn Glu Val Met Trp Trp Asp His Gly Val Tyr Tyr Cys
    130                 135                 140

Thr Ile Glu Ala Pro Gly Asp Thr Ser Gly Asp Pro Asp Lys Glu Val
145                 150                 155                 160

Lys Leu Ile Val Leu His Trp Leu Thr Val Ile Phe Ile Ile Leu Gly
                165                 170                 175

Ala Leu Leu Leu Leu Leu Leu Ile Gly Val Cys Trp Cys Gln Cys Cys
            180                 185                 190

Pro Gln Tyr Cys Cys Cys Tyr Ile Arg Cys Pro Cys Cys Pro Ala Arg
        195                 200                 205

Cys Cys Cys Pro Glu Glu Ala Leu Ala Arg His Arg Tyr Met Lys Gln
    210                 215                 220

Ala Gln Ala Leu Gly Pro Gln Met Met Glu Lys Pro Leu Tyr Trp Gly
225                 230                 235                 240
```

```
Ala Asp Arg Ser Ser Gln Val Ser Ser Tyr Pro Met Asn Pro Leu Leu
                245                 250                 255

Gln Arg Asp Leu Ser Leu Arg Ser Ser Leu Pro Gln Met Pro Met Thr
            260                 265                 270

Gln Thr Ala Ala Ala His Pro Pro Val Thr Asn Gly Val Leu Glu Tyr
        275                 280                 285

Leu Glu Lys Glu Leu Arg Asn Leu Asn Pro Ala Gln Pro Leu Pro Pro
    290                 295                 300

Asp Leu Lys Thr Ile Ser Gly Gln Ala Cys Ser Met Leu Ser Ser Leu
305                 310                 315                 320

Gly Ser Glu Val Val Glu Arg Arg Ile Ile His Leu Pro Pro Leu Ile
                325                 330                 335

Arg Asp Leu Pro Pro Ser Trp Arg Thr Ser Ser Ser Ser Arg Gln Gln
            340                 345                 350

Trp Pro Ala Pro Gly Ala Pro Gly Pro Trp Gly Val Ser Ser Asp Val
        355                 360                 365

His Arg Glu Leu Gln Gly Arg Glu Pro Lys Arg Leu Arg Arg Gly Arg
    370                 375                 380

His Pro Cys Ser Arg Pro His Gly Ser His Ala Pro Trp Ser Asp Arg
385                 390                 395                 400

Asp Ser Leu Gly Asp Gly Pro Ser Ser Trp Glu Ala Leu Gly Leu Gly
                405                 410                 415

Arg Gly Pro Arg Gly Asp Ala Gln Arg Pro Arg Arg Arg Arg His Arg
            420                 425                 430

Ser Tyr Ser Pro Pro Ser Pro Ser Gly Leu Ser Ser Trp Ser Ser Glu
        435                 440                 445

Glu Glu Gly Glu Glu Gly Asp Arg Arg Pro Arg Gly Arg Gly Thr Pro
    450                 455                 460

Tyr Ser Ser Gln Ala Thr Thr Trp Ala Thr Trp Ala Glu Glu Lys Pro
465                 470                 475                 480

Pro Ser Tyr Arg Ser Leu Asp Val Leu Pro Gly Arg Lys Gly Arg Arg
                485                 490                 495

Gly Gly Ser Val Glu Arg Arg Ser Glu Arg Asp Ser Ser His Ser Gly
            500                 505                 510

Arg Ser Val Val Ile
        515


<210> SEQ ID NO 45
<211> LENGTH: 545
<212> TYPE: PRT
<213> ORGANISM: Xenopus laevis

<400> SEQUENCE: 45

Met Ile Pro Pro Arg Ala Leu Leu Leu Ile Ser Val Trp Met Val Ser
1               5                   10                  15

Gly Gly Arg Thr Leu Leu Val Thr Val Gln Asp Thr Gln Arg Tyr Thr
            20                  25                  30

Met Leu Phe Ser Ser Ile Ile Leu Lys Cys Asp Tyr Ser Thr Ser Ala
        35                  40                  45

Gln Ile Gln Asp Val Ala Val Thr Trp Arg Phe Lys Ser Phe Cys Lys
    50                  55                  60

Asp Pro Ile Phe Asp Tyr Tyr Ser Ala Ala Tyr Gln Ala Ser Leu Ser
65                  70                  75                  80

Leu Asn Gln Asp Pro Ala Asn Asp Cys Asn Asp Asn Gln Arg Glu Val
                85                  90                  95
```

-continued

```
Arg Ile Val Ile Gln Lys Arg Gly Gln Asn Glu Pro Val Leu Gly Val
            100                 105                 110

Asp Tyr Arg Gln Arg Lys Ile Thr Ile Gln Asn Lys Ala Asp Leu Val
        115                 120                 125

Ile Ser Glu Val Met Trp Trp Asp His Gly Val Tyr Phe Cys Ser Val
    130                 135                 140

Glu Ala Gln Gly Asp Thr Ser Gly Asp Pro Asp Lys Glu Val Lys Leu
145                 150                 155                 160

Val Val Leu His Trp Leu Thr Val Leu Phe Ile Ile Leu Gly Ala Leu
                165                 170                 175

Phe Leu Phe Leu Leu Ile Gly Ile Cys Trp Cys Gln Cys Cys Pro His
            180                 185                 190

Cys Cys Cys Cys Tyr Val Arg Cys Pro Cys Cys Pro Thr Arg Cys Cys
        195                 200                 205

Cys Pro Glu Glu Ala Leu Ala Arg His Asn Tyr Met Lys Gln Met Glu
    210                 215                 220

Ser Met Thr Pro Trp Met Leu Asp Arg Pro Tyr Tyr Ala Gly Ala Asp
225                 230                 235                 240

Arg Asn Ser Gln His Ser Ser Tyr Gln Leu Asn Pro Leu Leu Gln Arg
                245                 250                 255

Asp Leu Ser Leu Gln Ser Ser Leu Pro Met Pro Ala Pro Met Ser Phe
            260                 265                 270

Ser Pro Pro Asn Asn Lys Val Leu Asp Phe Leu Glu Thr Glu Ile Lys
        275                 280                 285

Asn Leu Asn Thr Ala Gln Pro Leu Met Ser Ala Pro His Tyr Gly Gly
    290                 295                 300

Ala Ser His His Pro Ser Met Leu Ser Ser Leu Ser Glu Val Gly Val
305                 310                 315                 320

Arg Glu Val Asp Arg Arg Val Ile Gln Leu Pro Pro Leu Val Glu His
                325                 330                 335

Ile Val Ser Ser His Arg Ser Ser Asn Ser Ser His Gln Arg Arg Asn
            340                 345                 350

Met Gly Ser Trp Asp Pro Leu Asp Gly Glu Arg Asp Arg Arg Arg Asn
        355                 360                 365

Arg Gln Leu Asp Asp Ser Leu Ser Asn Glu Thr Asn Trp Arg Ala Gln
    370                 375                 380

Glu Arg Gln His Ser Asp Arg Ser Ser Gly His Arg Arg Asp Pro Pro
385                 390                 395                 400

Asn Asn Arg Arg Pro Arg Arg Asp Val Ser Pro Pro Arg Arg Tyr Gly
                405                 410                 415

Asp Ser Tyr Ser Asp Glu Ser Ala Asn Asn Asp Pro Arg Gly Arg Ser
            420                 425                 430

Asn Pro His Ser Asp Arg Ala Arg Pro Thr Glu Arg Arg Arg Ser Pro
        435                 440                 445

Glu Arg Gly Asp Gln Gly Arg Arg Gly Ser Pro Asp Arg Tyr Ser Arg
    450                 455                 460

Ser Gln Arg His Arg Arg Ser Tyr Ser Pro Pro His Arg Arg Asp Ser
465                 470                 475                 480

Trp Ser Ser Glu Asp Glu Thr Arg Asn Asn Gln Arg Gly Arg Gly Arg
                485                 490                 495

Arg Glu Arg Ser Tyr Glu Trp Pro Glu Glu Lys Pro Pro Ser Tyr Lys
            500                 505                 510
```

Ser Leu Glu Ile Cys Ala Gly Lys Ala Pro Thr Gln Arg Pro Gly Ala
515 520 525

Val Arg Gln Ser Asp Arg Ala Ser Ser Arg Ser Gly Arg Ser Met Val
530 535 540

Ile
545

<210> SEQ ID NO 46
<211> LENGTH: 540
<212> TYPE: PRT
<213> ORGANISM: Gallus gallus

<400> SEQUENCE: 46

Met Ala Arg Cys Gly Arg Cys Gly Gln Thr Leu Leu Leu Val Trp Leu
1 5 10 15

Leu Met Ala Cys Leu Pro Ala Gly Cys Leu Ser Leu Leu Val Thr Val
20 25 30

Gln Asp Thr Glu Arg Tyr Thr Thr Leu Phe Ala Ser Ile Thr Leu Lys
35 40 45

Cys Asp Tyr Ser Thr Ser Ala Gln Leu Gln Asp Val Val Val Thr Trp
50 55 60

Arg Phe Lys Ser Phe Cys Lys Asp Pro Ile Phe Asp Tyr Tyr Ser Val
65 70 75 80

Ser Tyr Gln Ala Ser Leu Ala Leu Gly Gln Asp Pro Ser Asp Asp Cys
85 90 95

Asn Asp Val Gln Arg Lys Val Arg Ile Val Ile Gln Lys Tyr Gly Gln
100 105 110

Asn Glu Pro Val Leu Gly Val Asp Tyr Arg Gln Arg Lys Ile Thr Ile
115 120 125

Gln Asn Arg Ala Asp Leu Val Ile Ser Glu Val Met Trp Trp Asp His
130 135 140

Gly Val Tyr Tyr Cys Thr Val Glu Ala Pro Gly Asp Thr Ser Gly Asp
145 150 155 160

Pro Asp Lys Glu Val Lys Leu Ile Val Leu His Trp Leu Thr Val Leu
165 170 175

Leu Ile Ile Leu Gly Gly Leu Leu Leu Leu Leu Leu Ile Gly Ile Cys
180 185 190

Trp Cys Gln Cys Cys Pro Gln His Cys Cys Cys His Ile Arg Cys Val
195 200 205

Cys Cys Pro Thr Arg Cys Cys Cys Asn Glu Lys Val Leu Glu Arg His
210 215 220

Arg Phe Met Lys Arg Ala Gln Ala Phe Ala Pro Trp Met Leu Pro Asn
225 230 235 240

Met Phe Tyr Gly Gly Ala Asp Arg Asn Ser Gln Leu Ser Ser Tyr Gln
245 250 255

Leu Asn Pro Leu Leu Gln Gln Asp Val Ser Leu Gln Asn Ser Leu Pro
260 265 270

Leu Val Gln Pro Gln Ala Arg Leu Ser Pro Asn Lys Gly Val Leu Asp
275 280 285

Tyr Leu Glu Ser Glu Ile Gln Asn Leu Asn Pro Ser Gln Pro Arg Pro
290 295 300

Pro Ser Asn Gln Arg Gln Ala Val Gln Pro Ser Leu Leu Ser Ser Leu
305 310 315 320

Gly Ser Asp Ile Met Gln Arg Gly Thr Asn Gly Leu Pro Pro Phe Thr
325 330 335

```
Gly His Val Ser Ser Ser His Gly Ser Ser Ser Ser Ser Arg Pro Gln
            340                 345                 350

Arg Thr Thr Arg Ser Leu Arg Thr Trp Gly Glu Asp Thr Ala Glu Asn
        355                 360                 365

Arg Arg Glu Asp Arg Arg Trp Pro Leu Pro Ser Ser Glu Asp Ser Arg
    370                 375                 380

Ser Ser Tyr Ser Arg Glu Pro Arg Asp Arg Gln Arg Glu Asp His Pro
385                 390                 395                 400

Pro Arg Gln Arg Thr Gly Gly Tyr Asp Gly Arg Ser Gln Tyr Ser Arg
                405                 410                 415

Arg Asp Val Ser Pro Thr Arg Gln Thr Glu Arg Gly Lys Ser Ser Ser
            420                 425                 430

Ser Ser Cys Ser Phe Tyr Ser Glu Glu Ala Lys Glu Arg Ser Ser His
        435                 440                 445

His Arg Gly Arg Arg Gln Gln Pro Ala Val Arg Arg Glu Tyr Gln Gln
    450                 455                 460

His Thr Arg Asn Ser Asn Asn Ser Arg His Arg Arg His Ser Tyr Ser
465                 470                 475                 480

Pro Pro Ser Arg Arg Gly Ser Trp Ser Ser Ser Glu Glu Gln Ile Arg
                485                 490                 495

Leu Pro Ala Thr Asn Arg Arg Arg His Asn Arg Ser Arg Glu Trp Pro
            500                 505                 510

Glu Asp Lys Pro Pro Ser Tyr Arg Ser Leu Glu Ile Ile Pro Asp Arg
        515                 520                 525

Asp Ser Lys His Arg Glu Gly Ala Gly Pro Arg Ser
    530                 535                 540


<210> SEQ ID NO 47
<211> LENGTH: 550
<212> TYPE: PRT
<213> ORGANISM: Danio rerio

<400> SEQUENCE: 47

Met Lys Gln Lys Leu Arg Leu Lys Val Leu Val Leu Leu Leu Cys Val
1               5                   10                  15

Phe Pro Glu Glu Ile Phe Ser Ile Gln Val Thr Val Pro Glu Thr Glu
            20                  25                  30

Arg His Thr Met Leu Phe Gly Ser Val Thr Leu Arg Cys Asp Tyr Ser
        35                  40                  45

Thr Ser Ala Ser Gln Gln Asp Val Leu Val Thr Trp Arg Tyr Lys Ser
    50                  55                  60

Phe Cys Leu Asp Pro Val Leu Glu Tyr Tyr Ser Ala Ala Tyr Gln Ala
65                  70                  75                  80

Ala Leu Asn Met Lys Gln Asp Pro Ala Asn Asp Cys Pro Asp Ser Lys
                85                  90                  95

Arg Thr Val Arg Ile Val Ile Gln Lys Arg Gly Ile Asn Glu Pro Val
            100                 105                 110

Leu Gly Thr Glu Tyr Arg Gln Arg Lys Ile Ser Ile Lys Asn Ser Ala
        115                 120                 125

Asp Leu Ser Met Asn Glu Ile Met Trp Trp Asp Asn Gly Met Tyr Phe
    130                 135                 140

Cys Ser Ile Asp Ala Pro Gly Asp Val Val Gly Asp Ser Asp Lys Glu
145                 150                 155                 160

Ile Arg Leu Ile Val Tyr Asn Trp Leu Thr Val Leu Leu Ile Ile Leu
```

-continued

```
                165                 170                 175

Gly Ala Leu Leu Leu Ile Ile Leu Phe Gly Val Cys Cys Cys Gln Cys
            180                 185                 190

Cys Pro Gln Asn Cys Cys Cys Tyr Val Arg Cys Pro Cys Cys Pro Arg
        195                 200                 205

Thr Cys Cys Cys Pro Glu Lys Ala Val Met Arg His Lys Met Met Arg
    210                 215                 220

Glu Ala Gln Lys Ala Met Val Pro Trp Phe His Gly Gln Pro Ile Tyr
225                 230                 235                 240

Ala Pro Ile Ala Ser Asn Ala Ser Gln Ala Asn Pro Leu Leu Tyr Ser
                245                 250                 255

Gly Ser Phe Ser Glu His Ser Ser Lys His Asn Leu Pro Met Ala Pro
            260                 265                 270

Met Ala Ile Pro Pro Pro Gln Pro Val Pro Gln Phe Val Pro Ser His
        275                 280                 285

Gly Tyr His Ala Asn Gly Ser Met Asn Gly Asn Val Arg Ala Asn Asn
    290                 295                 300

Gln Met Leu Asp Phe Leu Glu Asn Gln Val Gln Gly Met Asp Met Ala
305                 310                 315                 320

Val Pro Met Leu Gln Pro Gln His His Tyr Thr Gly Val Pro Leu Gln
                325                 330                 335

Asn His Gln Pro Gln Tyr Ala Ala Gln Gln Pro His Tyr Ala Ser Pro
            340                 345                 350

Pro Pro Gln Ser Ile Pro Gln Ala Val Thr Phe Pro Ala Arg Pro Pro
        355                 360                 365

Ser Met Leu Ser Ala Leu Asp Glu Met Gly Val Gln Gly Val Glu Arg
    370                 375                 380

Arg Val Ile Gln Leu Pro Pro Ile Leu Gly Arg Pro Lys Gln Ser Ser
385                 390                 395                 400

Arg Arg Thr Asn Asp Gln Arg Pro Arg Gln Ser Ser Gln Ser Ser Gly
                405                 410                 415

Ser Ser Asn Arg Asn Gly Val His Arg Asp Pro Ala Ser Ser Arg Arg
            420                 425                 430

Gly Asn Gln Arg Ser Tyr Ser Asp Glu Ser Asp Trp Asp Asp Arg Arg
        435                 440                 445

Gly Gly Arg Ser Ser Ser Gly Arg Arg Gly Glu Ser Asn Arg Ser Arg
    450                 455                 460

Pro Arg Val Arg Ser Lys Ala Glu Leu Leu Glu Glu Leu Glu His Ala
465                 470                 475                 480

Thr Asn Asn Gly Asn Arg Ser Tyr Ser Ser Pro His Arg Gly Ser Trp
                485                 490                 495

Ser Ser Asp Glu Glu Asp Ser Tyr Arg Lys Gly Arg Arg Ser Gln Gly
            500                 505                 510

Lys Leu Ser Glu Asn Pro Pro Ala Tyr Ser Ser Ile Asp Ile Leu Pro
        515                 520                 525

Gly His Ser Arg Arg Gly Glu Gln Leu Ser Asp Lys Ser Ser Arg Ser
    530                 535                 540

Gly Thr Ser Val Val Ile
545                 550
```

<210> SEQ ID NO 48
<211> LENGTH: 484
<212> TYPE: DNA
<213> ORGANISM: Homo sapiens

<400> SEQUENCE: 48
agtaggaggc gctgcgcggg ccgagctgcg cgctccgctt ggatggcgtc tccaggctgc 60
caccgcggct ggcgccctcg ggccgcgcct ggcgctcccg cgcgctgccc aggtacgagt 120
ggtcgtattt gggtgcggtg cctggcgtgc ggctcaccag ccgcggcagg tgtgcgtcct 180
cggcgggtct gcggcgcgcg gggctgaagg cccagccgcg gtcagcatcg gtcaggggct 240
cgcggctgcg gctgcgctga ccgtagtact cctccaagga gtcgtcctgg tagaagccgc 300
tgtgcgcccg cgactccgag cgctcgaagc ggctcccgcc ccgcgcctcg tgactgttgc 360
cgtctgcccg gcggggccgc tggccgtagg agtcagcgaa ggccgccagc tcgtccatgg 420
aaacggccgg cacccccgtg gcgaagttct tccgcgacag catctccgac ttggagcgcg 480
gctg 484

<210> SEQ ID NO 49
<211> LENGTH: 510
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 49
gaaggcccag ccgcggtcag catcggtcag gggctcgcgg ctgcggctgc gctgaccgta 60
gtactcctcc aaggagtcgt cctggtagaa gccgctgtgc gcccgcgact ccgagcgctc 120
gaagcggcat cccgccccgc gcctcgtgac tgttgccgtc tgcccggcgg ggccgctggc 180
cgtaggagtc agcgaaggcc gccagctcgt ccatggaaac ggccggcacc cccgtggcga 240
agttcttccg cgacagcatc tccgacttgg agcgcggctg gctgcgggca gagaaggagg 300
gggtcagacg gccggtccct ccctggagct ccagctccac ttagtgctca tcttctcagc 360
gcttttgcgt tccattggag gagcatattc acactaaaaa aagaccactt tctagattga 420
ggacatgcgt cactctagca tctgaggatc ccaccttcac tttgtgagag cacagctctc 480
cttggaggca ttttttattt tttgaacatt 510

<210> SEQ ID NO 50
<211> LENGTH: 577
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 50
atcggtcagg ggctcgcggc tgcggctgcg ctgaccgtag tactcctcca aggagtcgtc 60
ctggtagaag ccgctgtgcg cccgcgactc cgagcgctcg aagcggctcc cgccccgcgc 120
ctcgtgactg ttgccgtctg cccggcgggg ccgctggcct gtaggagtca gcgaaggccg 180
ccagctcgtc catggaaacg gccggcaccc ccgtggcgaa gttcttccgc gacagcatct 240
ccgacttgga gcgcggctgg ctgcgggcag agaaggaggg ggtcagacgg ccggtccctc 300
cctggagctc cagctccact tagtgctcat cttctcagcg cttttgcgtt ccattggagg 360
agcatattca cactaaaaaa agaccacttt ctagattgag gacatgcgtc actctagcat 420
ctgaggatcc caccttcact ttgtgagagc acaggagaag atccccgaac tacggcgacg 480
aggcctgcct gtggctcgcg ttgctgatgc catcccttac tgctccgcag actgggcgct 540
tctgagggag gaagaaaagg agaaatacgc agaaatg 577

<210> SEQ ID NO 51
<211> LENGTH: 19
<212> TYPE: PRT
<213> ORGANISM: Mus musculus

<400> SEQUENCE: 51

Cys Leu Phe Leu Ile Ile Tyr Cys Pro Asp Arg Ala Ser Ala Ile Gln
1 5 10 15

Val Thr Val

<210> SEQ ID NO 52
<211> LENGTH: 19
<212> TYPE: PRT
<213> ORGANISM: Mus musculus

<400> SEQUENCE: 52

Gly Trp Thr Ala Val Phe Trp Leu Thr Ala Met Val Glu Gly Leu Gln
1 5 10 15

Val Thr Val

<210> SEQ ID NO 53
<211> LENGTH: 10
<212> TYPE: PRT
<213> ORGANISM: Mus musculus

<400> SEQUENCE: 53

Leu Glu Asp Trp Leu Phe Val Val Val Val
1 5 10

<210> SEQ ID NO 54
<211> LENGTH: 10
<212> TYPE: PRT
<213> ORGANISM: Mus musculus

<400> SEQUENCE: 54

Met Pro Glu Trp Val Phe Val Gly Leu Val
1 5 10

<210> SEQ ID NO 55
<211> LENGTH: 36
<212> TYPE: PRT
<213> ORGANISM: Mus musculus

<400> SEQUENCE: 55

Cys Leu Ala Ser Leu Leu Phe Phe Leu Leu Leu Gly Ile Cys Trp Cys
1 5 10 15

Gln Cys Cys Pro His Thr Cys Cys Cys Tyr Val Arg Cys Pro Cys Cys
20 25 30

Pro Asp Lys Cys
35

<210> SEQ ID NO 56
<211> LENGTH: 36
<212> TYPE: PRT
<213> ORGANISM: Mus musculus

<400> SEQUENCE: 56

Ile Leu Gly Ile Phe Leu Phe Phe Val Leu Val Gly Ile Cys Trp Cys
1 5 10 15

Gln Cys Cys Pro His Ser Cys Cys Cys Tyr Val Arg Cys Pro Cys Cys

```
            20                  25                  30

Pro Asp Ser Cys
        35


<210> SEQ ID NO 57
<211> LENGTH: 15
<212> TYPE: PRT
<213> ORGANISM: Mus musculus

<400> SEQUENCE: 57

Glu Arg Arg Arg Val Tyr Arg Glu Glu Glu Glu Glu Glu Glu Glu
1               5                   10                  15


<210> SEQ ID NO 58
<211> LENGTH: 47
<212> TYPE: PRT
<213> ORGANISM: Mus musculus

<400> SEQUENCE: 58

Glu Ser Ser Ser Arg Gly Gly Ser Leu Glu Thr Pro Ser Lys Leu Gly
1               5                   10                  15

Ala Gln Leu Gly Pro Arg Ser Ala Ser Tyr Tyr Ala Trp Ser Pro Pro
            20                  25                  30

Thr Thr Tyr Lys Ala Gly Ala Ser Glu Gly Glu Asp Glu Asp Asp
        35                  40                  45


<210> SEQ ID NO 59
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59

caccatggat agggtcgtgt tggg                                              24


<210> SEQ ID NO 60
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60

tcagactaca agggacatcc tggttggaaa gtcacc                                 36


<210> SEQ ID NO 61
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61

tcattgtcct gcattggctg a                                                 21


<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
```

primer

<400> SEQUENCE: 62
caacagcggg taggacagca 20

<210> SEQ ID NO 63
<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 63
acagggctcg acggttac 18

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 64
acacccactc caacaccagc 20

<210> SEQ ID NO 65
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 65
tcaccatcac aggaaatgct gac 23

<210> SEQ ID NO 66
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 66
gcttctgagg tcctgccaag g 21

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 67
tgtcatccgc aagctgaaga 20

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 68
ttcgatcctg gccacatctc 20

<210> SEQ ID NO 69
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 69
tccctgtaag gcacgaagac at 22

<210> SEQ ID NO 70
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 70
attgccacca catccatctc a 21

<210> SEQ ID NO 71
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 71
ggaaccttgg ctttcactgt ctt 23

<210> SEQ ID NO 72
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 72
ggaacaccca aaacatgtcg at 22

<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 73
ggctacgtcc gagtggattt t 21

<210> SEQ ID NO 74
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 74
aacatcattc ggtcttgaag gaa 23

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 75
ctggttctgt ttcccgttgt 20

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 76
ggtgaatgtt cctgggtgag 20

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 77
cctcagcctt cttccatgag 20

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 78
actggggcat cgtagttgag 20

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 79
tccagctggt gaagacacac 20

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 80
gatgcctcca gacatcaggt 20

<210> SEQ ID NO 81
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 81
atcctggaac gagaacacga tct 23

<210> SEQ ID NO 82
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 82
agagacgtgt cactcctgga ctt 23

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 83
gggcacagac cgtggtagtt 20

<210> SEQ ID NO 84
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 84
caggatcagc tgggatactg agt 23

<210> SEQ ID NO 85
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 85
ttccactatg gagttcatgc ttgt 24

<210> SEQ ID NO 86
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 86
tccggcagtt aagatcacac cta 23

<210> SEQ ID NO 87
<211> LENGTH: 15
<212> TYPE: DNA
<213> ORGANISM: Artificial Sequence
<220> FEATURE:
<223> OTHER INFORMATION: Description of Artificial Sequence: Synthetic primer

<400> SEQUENCE: 87
cggcgcggaa gctgt 15

<210> SEQ ID NO 88
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 88
tgcaatccat ggctccgt 18

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 89
ctgcagcctc aagtgcaaag 20

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 90
cagtgtgcca ttggctgtct 20

<210> SEQ ID NO 91
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 91
tggaggatga gaaccggct 19

<210> SEQ ID NO 92
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 92
gcactgaaaa tggcttcgtt ta 22

<210> SEQ ID NO 93
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 93
tcacccccgg gatcaag 17

<210> SEQ ID NO 94
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 94
tccaaggaca cagagggctt t 21

<210> SEQ ID NO 95
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 95
cctcagggta ccactacgga gt 22

<210> SEQ ID NO 96
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 96
gccgaatagt tcgccgaa 18

<210> SEQ ID NO 97
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 97
cctgggcatg attgcaaag 19

<210> SEQ ID NO 98
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 98
ggacgccact cacgatgtt 19

<210> SEQ ID NO 99
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 99
cgatccagac ttccaacatg ag 22

<210> SEQ ID NO 100
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 100
ccatggtggc actcttctta aca 23

<210> SEQ ID NO 101
<211> LENGTH: 27
<212> TYPE: DNA
<213> ORGANISM: Artificial Sequence
<220> FEATURE:
<223> OTHER INFORMATION: Description of Artificial Sequence: Synthetic
primer

<400> SEQUENCE: 101
tgcttttgat agaaccagac ctacagt 27

<210> SEQ ID NO 102
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 102
cttggtgctc cactagcagc tt 22

<210> SEQ ID NO 103
<211> LENGTH: 26
<212> TYPE: DNA
<213> ORGANISM: Artificial Sequence
<220> FEATURE:
<223> OTHER INFORMATION: Description of Artificial Sequence: Synthetic
primer

<400> SEQUENCE: 103
gacctcatca aagatactct cctgaa 26

<210> SEQ ID NO 104
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 104
atctcgtctt gaccacatca acag 24

-continued

<210> SEQ ID NO 105
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 105
ggcaaacatg gggctgaac 19

<210> SEQ ID NO 106
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 106
gcttgtctgc tgcttgacag at 22

<210> SEQ ID NO 107
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 107
tgggctccga atcctcttag a 21

<210> SEQ ID NO 108
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 108
tggtcctcaa ataagatcct tgg 23

<210> SEQ ID NO 109
<211> LENGTH: 26
<212> TYPE: DNA
<213> ORGANISM: Artificial Sequence
<220> FEATURE:
<223> OTHER INFORMATION: Description of Artificial Sequence: Synthetic
primer

<400> SEQUENCE: 109
gggcttagaa aatccaattc agatta 26

<210> SEQ ID NO 110
<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 110
cgtccggcac aaatcctg 18

<210> SEQ ID NO 111

<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 111
ccttggtttc atctagcctc a 21

<210> SEQ ID NO 112
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 112
atccagggag gggatgat 18

<210> SEQ ID NO 113
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 113
ggacgaggtg gtgtcagag 19

<210> SEQ ID NO 114
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 114
gacagctctt cgctttggac 20

<210> SEQ ID NO 115
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 115
tgaaacaccc cttcttctgg 20

<210> SEQ ID NO 116
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 116 cctcctttc tattcggtca ctt 23

<210> SEQ ID NO 117
<211> LENGTH: 18

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117

atgatggctt ggccagtg                                                  18


<210> SEQ ID NO 118
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118

ccattttctc caacatccaa tc                                             22


<210> SEQ ID NO 119
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119

tgacgaggtt ccagaggtg                                                 19


<210> SEQ ID NO 120
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120

tgcagaggtg cacatagtct g                                              21


<210> SEQ ID NO 121
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121

tccctgcctt tcaccttg                                                  18


<210> SEQ ID NO 122
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122

gccctggctc ctctgtca                                                  18


<210> SEQ ID NO 123
<211> LENGTH: 20
<212> TYPE: DNA
```

<213> ORGANISM: Artificial Sequence
<220> FEATURE:
<223> OTHER INFORMATION: Description of Artificial Sequence: Synthetic primer

<400> SEQUENCE: 123
ctgaggcgta tttgggaaag 20

<210> SEQ ID NO 124
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 124
tcatgacatt cagtccagca a 21

<210> SEQ ID NO 125
<211> LENGTH: 41
<212> TYPE: DNA
<213> ORGANISM: Artificial Sequence
<220> FEATURE:
<223> OTHER INFORMATION: Description of Artificial Sequence: Synthetic primer

<400> SEQUENCE: 125
atttacaagc ttcaggtcac agtgcctgac aagaagaagg t 41

<210> SEQ ID NO 126
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 126
catgcagaat tctcagacta caagggacat cctg 34

<210> SEQ ID NO 127
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 127
atcttgctag cggtaatgga tagggtcgtg ttgg 34

<210> SEQ ID NO 128
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 128
catgcagaat tcggactaca agggacatcc tg 32

<210> SEQ ID NO 129
<211> LENGTH: 8127
<212> TYPE: DNA
<213> ORGANISM: Homo sapiens

<400> SEQUENCE: 129

```
gttccagcca tttcccactt tcctcactcc gtaattcggc tgggaagttg gggaagatgg     60
atagggtctt gctgaggtgg atttctctct tctggctaac agccatggtc gaaggccttc    120
aggtcacagt gcccgacaag aagaaggtgg ccatgctctt ccagcccact gtgcttcgct    180
gccacttctc aacatcctcc catcagcctg cagttgtgca gtggaagttc aagtcctact    240
gccaggatcg catgggagaa tccttgggca tgtcctctac ccgggcccaa tctctcagca    300
agagaaacct ggaatgggac ccctacttgg attgtttgga cagcaggagg actgttcgag    360
tagtagcttc aaaacagggc tcgactgtca ccctgggaga tttctacagg ggcagagaga    420
tcacgattgt tcatgatgca gatcttcaaa ttggaaagct tatgtgggga gacagcggac    480
tctattactg tattatcacc accccagatg acctggaggg gaaaaatgag gactcagtgg    540
aactgctggt gttgggcagg acagggctgc ttgctgatct cttgcccagt tttgctgtgg    600
agattatgcc agagtgggtg tttgttggcc tggtgctcct gggcgtcttc ctcttcttcg    660
tcctggtggg gatctgctgg tgccagtgct gccctcacag ctgctgctgc tatgtccgct    720
gcccatgctg cccagattcc tgctgctgcc ctcaagcctt gtatgaagca gggaaagcag    780
caaaggccgg gtaccctccc tctgtctccg gtgtccccgg cccttactcc atcccctctg    840
tccctttggg aggagccccc tcatctggca tgctgatgga caagccgcat ccacctccct    900
tggcaccaag tgactccact ggaggaagcc acagtgttcg caaaggttac cggatccagg    960
ctgacaaaga gagagactcc atgaaggtcc tgtactatgt tgagaaggag ctggctcagt   1020
ttgatccagc cagaaggatg agaggcagat ataacaacac catctcagaa ctcagctccc   1080
tacatgagga ggacagcaat ttccgccagt ctttccatca gatgagaagc aagcagttcc   1140
ctgtgtctgg ggacttggag agcaatcctg actattggtc aggtgtcatg ggaggcagca   1200
gtggggcaag ccgcgggccc tcagccatgg agtataacaa agaggatcga gagagcttca   1260
ggcacagcca gccgcgctcc aagtcggaga tgctgtcgcg gaagaacttc gccacggggg   1320
tgccggccgt ttccatggac gagctggcgg ccttcgctga ctcctacggc cagcggcccc   1380
gccgggcaga cggcaacagt cacgaggcgc ggggcgggag ccgcttcgag cgctcggagt   1440
cgcgggcgca cagcggcttc taccaggacg actccttgga ggagtactac ggtcagcgca   1500
gccgcagccg cgagcccctg accgatgctg accgcggctg ggccttcagc cccgcgcgcc   1560
gcagacccgc cgaggacgcg cacctgccgc ggctggtgag ccgcacgcca ggcaccgcac   1620
ccaaatacga ccactcgtac ctgggcagcg cgcgggagcg ccaggcgcgg cccgagggcg   1680
ccagccgcgg tggcagcctg gagacgccat ccaagcggag cgcgcagctc ggcccgcgca   1740
gcgcctccta ctacgcttgg tcgccgcccg gcacctacaa ggccggctcg tcgcaggacg   1800
accaggagga cgcgtccgac gacgcgctgc cgccctacag cgagctggag ctgacccgcg   1860
gcccgtccta ccgcggccgc gacctgccct accacagcaa ctcggagaag aagaggaaaa   1920
aggagcccgc caagaaaacc aatgactttc caaccaggat gtcccttgtg gtctgatgtt   1980
gtcaacattt ctctggataa tgagaaatca gacatggact acggggacaa gacacaaatc   2040
taagaaccag caggcccagg accttctctg gccatcacct tggaagattt gctgatctct   2100
gctttggcaa gggatggcag gcagccttta agggaggctg atttcaaacc tctgtgccca   2160
tctaactagt ttgagaagct taccaagaaa gcaagaatgt gtgagaacat tcctacatac   2220
agagtttctc aactatagcg tttatcctgc ccagcctcct cccttaacag aaccaggact   2280
```

-continued

```
ccatttgcaa ttctgaaaga gagttagctc tggactgcta aactccagaa attgcctatg   2340
cctacaatat gcttttctat acctcctgtg ctatacttag agacagaaga atttattact   2400
actattagaa ggccttcttc tgacaaggga agatagcttc aagtcaaaat ataccttta    2460
tccccatcac tttacagtca ctagtcaatg actgttgtta cactaaaatc aaaaggcctt   2520
tggtgagctc agtgacagtg acctctggga caatcacaga aatgacttca ctgctgttct   2580
gaatgacaat tcttaagtgg ctaggacaaa gcaaaagcga gtataccttt ttgaaaagct   2640
gtctaagtgg tatttccttt tccattctga gaacgtaaac tgctttttcc ttttctgctg   2700
cacatgtcaa tatcggagtc ttagacatta agggctcttc tcttcctccc ctctcctgga   2760
cttcccacag gttggtgcca cacacacagc cctgcctccc tctgcactct gattagattg   2820
tcattgaatg ccttgtgata aatgcttaaa atatacacat gaaagagaag agggaggaaa   2880
gaggagaaag cagtaatgca tatagaaaag aatgagaagg aatttaaaag ggaaataaca   2940
tcatctcatt atattttgaa tgtggaccat ttcacccaca aacttcactc agtcttttcc   3000
ggttttgtgc ttcacttgcc gttaattgtt tctgccatcc cagttctgcc attctaggac   3060
atgggggatg tggaacatac agcatttggc ctgactagac tgccactatg gctgctttca   3120
agagattaga gatactgctt tctcaggaag gagtacttcc tattcccacc cttgcctaaa   3180
tgatagattt tgcctaaatc ccaaagctag atctctggat tttatcgttt gtgtagatag   3240
caaaaatggc cacgaactct ttccttctca tcaagaggtg ccatcttttt tccaacccct   3300
tgaatctgga gttggctatg tgatttgatt tagccagtag cccaacaaat gtgacacaag   3360
cagagacttg aaaagttctt gtgcatgggg cttgtcctct tttgctgctc ttgggaacct   3420
tgcaactacc atcaggtgaa caagcctgga ctatcctgct gcatgacaaa agaaaagggc   3480
ccagttaccc ttgtcaccct atctgacagc ccgtcaactt ccagctgatg cagacatggg   3540
tgagtccagg tgataccaat agaagaactg cctagctgaa cccagcccaa atttctgatt   3600
cctactcgag gcgtgagaag ttggtgcatt ctttatgttc atttctcttt aagaacaaac   3660
ctgactcgtt cttgtctgaa tgttcatccc tgaacctctt aatccatcca aacttgtgtt   3720
tctcatagcc tccactattg ttgacaaatt tttatcaaag cttttcaccc tgcactcttg   3780
tggagtggag gataatgctt gactttgcta tcccttaatc cagcagtggt ttcttccctg   3840
tctatggatc cgtggacaac ctctgaagat ctcttcttta ccatcctttt ggtcttctcc   3900
agagccaccc tactggggct agaccctatt ctcaaagtac cattcctcta gtatccattt   3960
gtacttcatg acatttccaa aaaaagtcct atgtttgcaa tgaaataaga aagtggctgg   4020
gtgagggtcg gagggatgag ctggtatgtg tcattgcttg gagaattgac ctaccaaagg   4080
acttccgtgt tgctttggcc agtcccagag aaatcaggag aacagttgaa cccagtgctg   4140
gcacttccaa gggctggaag acacaagcca taaccctggt gctgagtttt agacttgctg   4200
gtgtccctgg cctctgaaag cctaggtcta gcctgtctgt ttggacccca gttcagatgg   4260
aaaagatgat aaaaaacatt tcttagtcac cagctttgga tttcaacttg ctcaggcaat   4320
tttggagaat attgggtagc tgtggtagct attatcgctt tatactgagc actgtgtcag   4380
gcttttcacc accaaagagc ctcatagcac cagctgcaga gaccaaaaat aatgtttttt   4440
taaagctacg gacgtatgat tttggtgaag gttgagggta gcaatgggaa agaaagaatt   4500
attaaaattg gaaacctgca attccaaaga caacaaaact acagatagac tgaaaagtac   4560
aaagaagata gcaggctact gaattaacct tgggagttgg gaccaggttg tcctttgtag   4620
aactggataa atcattcaga cttccaggct ttcagtagag agaaaaagca gttgtttctg   4680
```

```
ggtatatgga caggagttaa ggctgagttg acaagtcaaa acttcttgtc ctcagcaccc   4740
ctgactttcc tctatgtgtc cttttgtttc ttctcctttg aatagtgtgt cctgcacagg   4800
aaatggttat atttgttagc ttctttccta ggtcttattg gagtacaaag taaatcttgt   4860
gtaagacata atctctgtcc actaggaccc cgtaatttaa taggggaaat aagacatgct   4920
caagaaagga gattttatac atagagtatg aaatagtgct atggataaat tataataaaa   4980
ccagagattt agttttttta aaaaatgaga atactttgat attaaagtgt tgtatgtgtt   5040
tgtccatcat cttatttaaa catagacttg gtgatctgaa aagccaatac tcaaaagtct   5100
gaactgaaaa gaggtgaatt aggatcggga aagggtgagc agcaggggtc ccagggggat   5160
gatgcataag ctgctgtgct tgcctgtgag tcactactga gtcaggaaca cgctggagga   5220
gggagtgtgg atgcaggtgg cagggaggtg tcccctggta gatgagctgc ttctctaggc   5280
catgcatgga ttcattagga agttggagac aatggccatg gacctggtgc atggcagcta   5340
ttccatccaa gcacgttcac aggggagctc agcgtggctg ctcctggggc tcagttctgc   5400
ggctgtgagt gctgctgccc atattcacca acacagggca ggcctcacgg agatgctagg   5460
cctcacatcc cccttctcat gatcctcact gtgcacttga cataggatta ggcatactgg   5520
agatgagaaa aggctgccac ccaaacccaa ggcacctgac cacatctgta aatatttctg   5580
aatagtccac aaaatttcac ataggtagtc tgattagatc ttgcctttga gagaagctga   5640
agtcacagat actgttgtaa tttaccaccg cccctcaccc aatttttttt aataggtgaa   5700
gaaaccatca ctgccattaa tgaagtcaca aacctattag gtctttagac tcccaacctc   5760
tggatctttt ctgctgatta gtgtttccca aaattgccta accacaagaa ttaacttgat   5820
agctgctgtt aaaaaggtat tgttggaccc tgttttggag attgattggg tgggtctaga   5880
gccagaattc atatttttaa tatgcattcc aggagactcc tgtgatcaga tgcatttgga   5940
aatcattgca ctaagtcata cctctgggta ctccaaacag ctagtcctga ggcttccttg   6000
ggccttagaa tttttcttc aaatgtcctg gtgaggtccc tctcaatcct ttggggctgg   6060
ctgtggtgag tcactcagaa gtctggctgt gacctggatg ggctcaccag agtacgctag   6120
tggtagtggg aaaacaggca gagagaaagg agtgtcagga gcactcccag ggaggctgtt   6180
gtagatattt ccattcccag aacagtgatc tattgtgaca gtctcagaac agacaacaag   6240
aattacaggt aattttctca ttctcttgat atatttttag caaaacttaa atcatgaata   6300
gaaggaaaag atgccattgg ggaaatagaa aaactcaatc attttataaa gcatacaaat   6360
cataaggatg actggccaat agcactccca ctttggtctt acctaaagtt gggtggacaa   6420
gaataataaa agtcctcatt ttatatcctt ccaaaatcag atttaaatgc tgccagcatc   6480
ttaatggaag tctgaaattg attgatagga tgtagaaatc caaattcact aaaatagggg   6540
gccagctaca taaagtccta gaaggaaaaa gtgcctcgct tttttctgcc attatcctac   6600
cccctagtca tctggggaat tgatctatga agcttgaaga aggggcattt aacatcagag   6660
tggtgcaagg gcagtgttga gatgctttaa gcagcagcct gagctttagc actatttgaa   6720
ggggagaagg ttaatactaa taatatttgt gttattttta tgatatatta ctgtttacag   6780
aacactttca tttgatccca acatcaactg ctgtgataga ggcagggcag atgttgtggt   6840
ctcattacat agaatgtaaa actgaggttg aaaaatacta agtgacttgt ctgtagtcaa   6900
atggttttta aaattataaa gccaggcctt ctgactgtct tgtctggtgt cctttccaat   6960
tccttaaata ctcatgggac tggaatctgg gtattccaga ttccagtttc tcttcacagc   7020
```

```
cagacatctg gtgagaagag ccgtagactt gatgcttgtt catatgtcat ggatgtggcg   7080

aagccatgaa gacagatact gttgctgctt catccaacta agcaccattc attcctcaaa   7140

tgctaatcta agagggagtt gtagcttcac tcaaggagag tttcgttttc tttttctttc   7200

ttttttttt ttttgagaca gggtcttgct ctgtggccca tggtgcagtg cagtgcagtg   7260

gtgctatcag ctcactgcag tctcaaactc ctagctcaag caatcctcct ccctcagcct   7320

cccaagtagg taggactaca gatatatgcc accacgtcca gcaaattttg tttgtttgta   7380

gagatggggt cttgctatat ttcccaggct tgtctcaaac tcctggcctc aagtgatcct   7440

cccaccttgg ctgcctaaag tgctggtatt acagacatga gccactgaac ccagctgaga   7500

gcctcacttt catcacctgt gctgtgaggg gtaatatatg cttcaggttt tctggagaat   7560

ccttcttgca gagaagtttc tgaatgaaac gacagattca tctggattca gaactccagg   7620

cagaagctgc ttaacagcaa aaatctggca tcttcactac attttaagat tttaggtaga   7680

actaagaggg atcagatata gaggaataag gaatgtgaga aggaaaaaga tatagtagtt   7740

tagctaaatt tttcttagag tttcttggtg gggctggcca tgaagtaact agtctgactc   7800

atttcttctg ggaaggctaa aagagacaca gatagcttct cttttacctt ggctttaagg   7860

aaaagccatt ttattaacaa aagtattaga cacgactgca taagaaattt gctgtgtgag   7920

aataaagaac aagggagtag gagggtggga cagagaaggg tgagaagttg gcttcgtgag   7980

ggccacctgt cagttgtctt tgtgccttgt gacatcaaaa ctgaaatgtt tgtattactg   8040

ttgtccatga cttttttttt ctgtgtcaga catacaaatt gaatttggtt gtaatgtttt   8100

aaacgtaata aagaattctt acctaca                                       8127
```

<210> SEQ ID NO 130
<211> LENGTH: 1116
<212> TYPE: PRT
<213> ORGANISM: Homo sapiens

<400> SEQUENCE: 130

```
Met Glu Arg Ala Ile Ser Pro Gly Leu Leu Val Arg Ala Leu Leu Leu
1               5                   10                  15

Leu Leu Leu Leu Leu Gly Leu Ala Ala Arg Thr Val Ala Ala Gly Arg
            20                  25                  30

Ala Arg Gly Leu Pro Ala Pro Thr Ala Glu Ala Ala Phe Gly Leu Gly
        35                  40                  45

Ala Ala Ala Ala Pro Thr Ser Ala Thr Arg Val Pro Ala Ala Gly Ala
    50                  55                  60

Val Ala Ala Ala Glu Val Thr Val Glu Asp Ala Glu Ala Leu Pro Ala
65                  70                  75                  80

Ala Ala Gly Glu Gln Glu Pro Arg Gly Pro Glu Pro Asp Asp Glu Thr
                85                  90                  95

Glu Leu Arg Pro Arg Gly Arg Ser Leu Val Ile Ile Ser Thr Leu Asp
            100                 105                 110

Gly Arg Ile Ala Ala Leu Asp Pro Glu Asn His Gly Lys Lys Gln Trp
        115                 120                 125

Asp Leu Asp Val Gly Ser Gly Ser Leu Val Ser Ser Ser Leu Ser Lys
    130                 135                 140

Pro Glu Val Phe Gly Asn Lys Met Ile Ile Pro Ser Leu Asp Gly Ala
145                 150                 155                 160

Leu Phe Gln Trp Asp Gln Asp Arg Glu Ser Met Glu Thr Val Pro Phe
                165                 170                 175
```

```
Thr Val Glu Ser Leu Leu Glu Ser Ser Tyr Lys Phe Gly Asp Asp Val
            180                 185                 190

Val Leu Val Gly Gly Lys Ser Leu Thr Thr Tyr Gly Leu Ser Ala Tyr
        195                 200                 205

Ser Gly Lys Val Arg Tyr Ile Cys Ser Ala Leu Gly Cys Arg Gln Trp
    210                 215                 220

Asp Ser Asp Glu Met Glu Gln Glu Glu Asp Ile Leu Leu Leu Gln Arg
225                 230                 235                 240

Thr Gln Lys Thr Val Arg Ala Val Gly Pro Arg Ser Gly Asn Glu Lys
                245                 250                 255

Trp Asn Phe Ser Val Gly His Phe Glu Leu Arg Tyr Ile Pro Asp Met
            260                 265                 270

Glu Thr Arg Ala Gly Phe Ile Glu Ser Thr Phe Lys Pro Asn Glu Asn
        275                 280                 285

Thr Glu Glu Ser Lys Ile Ile Ser Asp Val Glu Glu Gln Glu Ala Ala
    290                 295                 300

Ile Met Asp Ile Val Ile Lys Val Ser Val Ala Asp Trp Lys Val Met
305                 310                 315                 320

Ala Phe Ser Lys Lys Gly Gly His Leu Glu Trp Glu Tyr Gln Phe Cys
                325                 330                 335

Thr Pro Ile Ala Ser Ala Trp Leu Leu Lys Asp Gly Lys Val Ile Pro
            340                 345                 350

Ile Ser Leu Phe Asp Asp Thr Ser Tyr Thr Ser Asn Asp Asp Val Leu
        355                 360                 365

Glu Asp Glu Glu Asp Ile Val Glu Ala Ala Arg Gly Ala Thr Glu Asn
    370                 375                 380

Ser Val Tyr Leu Gly Met Tyr Arg Gly Gln Leu Tyr Leu Gln Ser Ser
385                 390                 395                 400

Val Arg Ile Ser Glu Lys Phe Pro Ser Ser Pro Lys Ala Leu Glu Ser
                405                 410                 415

Val Thr Asn Glu Asn Ala Ile Ile Pro Leu Pro Thr Ile Lys Trp Lys
            420                 425                 430

Pro Leu Ile His Ser Pro Ser Arg Thr Pro Val Leu Val Gly Ser Asp
        435                 440                 445

Glu Phe Asp Lys Cys Leu Ser Asn Asp Lys Phe Ser His Glu Glu Tyr
    450                 455                 460

Ser Asn Gly Ala Leu Ser Ile Leu Gln Tyr Pro Tyr Asp Asn Gly Tyr
465                 470                 475                 480

Tyr Leu Pro Tyr Tyr Lys Arg Glu Arg Asn Lys Arg Ser Thr Gln Ile
                485                 490                 495

Thr Val Arg Phe Leu Asp Asn Pro His Tyr Asn Lys Asn Ile Arg Lys
            500                 505                 510

Lys Asp Pro Val Leu Leu Leu His Trp Trp Lys Glu Ile Val Ala Thr
        515                 520                 525

Ile Leu Phe Cys Ile Ile Ala Thr Thr Phe Ile Val Arg Arg Leu Phe
    530                 535                 540

His Pro His Pro His Arg Gln Arg Lys Glu Ser Glu Thr Gln Cys Gln
545                 550                 555                 560

Thr Glu Asn Lys Tyr Asp Ser Val Ser Gly Glu Ala Asn Asp Ser Ser
                565                 570                 575

Trp Asn Asp Ile Lys Asn Ser Gly Tyr Ile Ser Arg Tyr Leu Thr Asp
            580                 585                 590

Phe Glu Pro Ile Gln Cys Leu Gly Arg Gly Gly Phe Gly Val Val Phe
```

```
        595                 600                 605

Glu Ala Lys Asn Lys Val Asp Asp Cys Asn Tyr Ala Ile Lys Arg Ile
    610                 615                 620

Arg Leu Pro Asn Arg Glu Leu Ala Arg Glu Lys Val Met Arg Glu Val
625                 630                 635                 640

Lys Ala Leu Ala Lys Leu Glu His Pro Gly Ile Val Arg Tyr Phe Asn
                645                 650                 655

Ala Trp Leu Glu Ala Pro Pro Glu Lys Trp Gln Glu Lys Met Asp Glu
            660                 665                 670

Ile Trp Leu Lys Asp Glu Ser Thr Asp Trp Pro Leu Ser Ser Pro Ser
        675                 680                 685

Pro Met Asp Ala Pro Ser Val Lys Ile Arg Arg Met Asp Pro Phe Ala
    690                 695                 700

Thr Lys Glu His Ile Glu Ile Ile Ala Pro Ser Pro Gln Arg Ser Arg
705                 710                 715                 720

Ser Phe Ser Val Gly Ile Ser Cys Asp Gln Thr Ser Ser Ser Glu Ser
                725                 730                 735

Gln Phe Ser Pro Leu Glu Phe Ser Gly Met Asp His Glu Asp Ile Ser
            740                 745                 750

Glu Ser Val Asp Ala Ala Tyr Asn Leu Gln Asp Ser Cys Leu Thr Asp
        755                 760                 765

Cys Asp Val Glu Asp Gly Thr Met Asp Gly Asn Asp Glu Gly His Ser
    770                 775                 780

Phe Glu Leu Cys Pro Ser Glu Ala Ser Pro Tyr Val Arg Ser Arg Glu
785                 790                 795                 800

Arg Thr Ser Ser Ser Ile Val Phe Glu Asp Ser Gly Cys Asp Asn Ala
                805                 810                 815

Ser Ser Lys Glu Glu Pro Lys Thr Asn Arg Leu His Ile Gly Asn His
            820                 825                 830

Cys Ala Asn Lys Leu Thr Ala Phe Lys Pro Thr Ser Ser Lys Ser Ser
        835                 840                 845

Ser Glu Ala Thr Leu Ser Ile Ser Pro Pro Arg Pro Thr Thr Leu Ser
    850                 855                 860

Leu Asp Leu Thr Lys Asn Thr Thr Glu Lys Leu Gln Pro Ser Ser Pro
865                 870                 875                 880

Lys Val Tyr Leu Tyr Ile Gln Met Gln Leu Cys Arg Lys Glu Asn Leu
                885                 890                 895

Lys Asp Trp Met Asn Gly Arg Cys Thr Ile Glu Glu Arg Glu Arg Ser
            900                 905                 910

Val Cys Leu His Ile Phe Leu Gln Ile Ala Glu Ala Val Glu Phe Leu
        915                 920                 925

His Ser Lys Gly Leu Met His Arg Asp Leu Lys Pro Ser Asn Ile Phe
    930                 935                 940

Phe Thr Met Asp Asp Val Val Lys Val Gly Asp Phe Gly Leu Val Thr
945                 950                 955                 960

Ala Met Asp Gln Asp Glu Glu Glu Gln Thr Val Leu Thr Pro Met Pro
                965                 970                 975

Ala Tyr Ala Arg His Thr Gly Gln Val Gly Thr Lys Leu Tyr Met Ser
            980                 985                 990

Pro Glu Gln Ile His Gly Asn Ser  Tyr Ser His Lys Val  Asp Ile Phe
        995                 1000                1005

Ser Leu  Gly Leu Ile Leu Phe  Glu Leu Leu Tyr Pro  Phe Ser Thr
    1010                1015                1020
```

```
Gln Met  Glu Arg Val Arg Thr  Leu Thr Asp Val Arg  Asn Leu Lys
    1025                 1030                 1035

Phe Pro  Pro Leu Phe Thr Gln  Lys Tyr Pro Cys Glu  Tyr Val Met
    1040                 1045                 1050

Val Gln  Asp Met Leu Ser Pro  Ser Pro Met Glu Arg  Pro Glu Ala
    1055                 1060                 1065

Ile Asn  Ile Ile Glu Asn Ala  Val Phe Glu Asp Leu  Asp Phe Pro
    1070                 1075                 1080

Gly Lys  Thr Val Leu Arg Gln  Arg Ser Arg Ser Leu  Ser Ser Ser
    1085                 1090                 1095

Gly Thr  Lys His Ser Arg Gln  Ser Asn Asn Ser His  Ser Pro Leu
    1100                 1105                 1110

Pro Ser  Asn
    1115


<210> SEQ ID NO 131
<211> LENGTH: 4665
<212> TYPE: DNA
<213> ORGANISM: Homo sapiens

<400> SEQUENCE: 131

ggaaagtcca ccttccccaa caaggccagc ctgggaacat ggagtggcag cggccgcagc     60

caatgagaga gcaaacgcgc ggaaagtttg ctcaatgggc gatgtccgag ataggctgtc    120

actcaggtgg cagcggcaga ggccgggctg agacgtggcc aggggaacac ggctggctgt    180

ccaggccgtc ggggcggcag tagggtccct agcacgtcct tgccttcttg ggagctccaa    240

gcggcgggag aggcaggcgt cagtggctgc gcctccatgc ctgcgcgcgg ggcgggacgc    300

tgatggagcg cgccatcagc ccggggctgc tggtacgggc gctgctgctg ctgctgctgc    360

tgctggggct cgcggcaagg acggtggccg cggggcgcgc ccgtggcctc ccagcgccga    420

cggcggaggc ggcgttcggc ctcggggcgg ccgctgctcc cacctcagcg acgcgagtac    480

cggcggcggg cgccgtggct gcggccgagg tgactgtgga ggacgctgag gcgctgccgg    540

cagccgcggg agagcaggag cctcggggtc cggaaccaga cgatgagaca gagttgcgac    600

cgcgcggcag gtcattagta attatcagca ctttagatgg gagaattgct gccttggatc    660

ctgaaaatca tggtaaaaag cagtgggatt tggatgtggg atccggttcc ttggtgtcat    720

ccagccttag caaaccagag gtatttggga ataagatgat cattccttcc ctggatggag    780

ccctcttcca gtgggaccaa gaccgtgaaa gcatggaaac agttcctttc acagttgaat    840

cacttcttga atcttcttat aaatttggag atgatgttgt tttggttgga ggaaaatctc    900

tgactacata tggactcagt gcatatagtg gaaaggtgag gtatatctgt tcagctctgg    960

gttgtcgcca atgggatagt gacgaaatgg aacaagagga agacatcctg cttctacagc   1020

gtacccaaaa aactgttaga gctgtcggac ctcgcagtgg caatgagaag tggaatttca   1080

gtgttggcca ctttgaactt cggtatattc cagacatgga aacgagagcc ggatttattg   1140

aaagcacctt taagcccaat gagaacacag aagagtctaa aattatttca gatgtggaag   1200

aacaggaagc tgccataatg gacatagtga taaaggtttc ggttgctgac tggaaagtta   1260

tggcattcag taagaaggga ggacatctgg aatgggagta ccagttttgt actccaattg   1320

catctgcctg gttacttaag gatgggaaag tcattcccat cagtcttttt gatgatacaa   1380

gttatacatc taatgatgat gttttagaag atgaagaaga cattgtagaa gctgccagag   1440

gagccacaga aaacagtgtt tacttgggaa tgtatagagg ccagctgtat ctgcagtcat   1500
```

```
cagtcagaat ttcagaaaag tttccttcaa gtcccaaggc tttggaatct gtcactaatg   1560
aaaacgcaat tattccttta ccaacaatca aatggaaacc cttaattcat tctccttcca   1620
gaactcctgt cttggtagga tctgatgaat ttgacaaatg tctcagtaat gataagtttt   1680
ctcatgaaga atatagtaat ggtgcacttt caatcttgca gtatccatat gataatggtt   1740
attatctacc atactacaag agggagagga acaaacgaag cacacagatt acagtcagat   1800
tcctcgacaa cccacattac aacaagaata tccgcaaaaa ggatcctgtt cttcttttac   1860
actggtggaa agaaatagtt gcaacgattt tgttttgtat catagcaaca acgtttattg   1920
tgcgcaggct tttccatcct catcctcaca ggcaaaggaa ggagtctgaa actcagtgtc   1980
aaactgaaaa taaatatgat tctgtaagtg gtgaagccaa tgacagtagc tggaatgaca   2040
taaaaaactc tggatatata tcacgatatc taactgattt tgagccaatt caatgcctgg   2100
gacgtggtgg ctttggagtt gtttttgaag ctaaaaacaa agtagatgac tgcaattatg   2160
ctatcaagag gatccgtctc cccaataggg aattggctcg ggaaaaggta atgcgagaag   2220
ttaaagcctt agccaagctt gaacacccgg gcattgttag atatttcaat gcctggctcg   2280
aagcaccacc agagaagtgg caagaaaaga tggatgaaat ttggctgaaa gatgaaagca   2340
cagactggcc actcagctct cctagcccaa tggatgcacc atcagttaaa atacgcagaa   2400
tggatccttt cgctacaaaa gaacatattg aaatcatagc tccttcacca caaagaagca   2460
ggtctttttc agtagggatt tcctgtgacc agacaagttc atctgagagc cagttctcac   2520
cactggaatt ctcaggaatg gaccatgagg acatcagtga gtcagtggat gcagcataca   2580
acctccagga cagttgcctt acagactgtg atgtggaaga tgggactatg gatggcaatg   2640
atgaggggca ctcctttgaa ctttgtcctt ctgaagcttc tccttatgta aggtcaaggg   2700
agagaacctc ctcttcaata gtatttgaag attctggctg tgataatgct tccagtaaag   2760
aagagccgaa aactaatcga ttgcatattg gcaaccattg tgctaataaa ctaactgctt   2820
tcaagcccac cagtagcaaa tcttcttctg aagctacatt gtctatttct cctccaagac   2880
caaccacttt aagtttagat ctcactaaaa acaccacaga aaaactccag cccagttcac   2940
caaaggtgta tctttacatt caaatgcagc tgtgcagaaa agaaaacctc aaagactgga   3000
tgaatggacg atgtaccata gaggagagag agaggagcgt gtgtctgcac atcttcctgc   3060
agatcgcaga ggcagtggag tttcttcaca gtaaaggact gatgcacagg gacctcaagc   3120
catccaacat attctttaca atggatgatg tggtcaaggt tggagacttt gggttagtga   3180
ctgcaatgga ccaggatgag gaagagcaga cggttctgac ccccatgcca gcttatgcca   3240
gacacacagg acaagtaggg accaaactgt atatgagccc agagcagatt catggaaaca   3300
gctattctca taaagtggac atcttttctt taggcctgat tctatttgaa ttgctgtatc   3360
cattcagcac tcagatggag agagtcagga ccttaactga tgtaagaaat ctcaaatttc   3420
caccattatt tactcagaaa tatccttgtg agtacgtgat ggttcaagac atgctctctc   3480
catcccccat ggaacgacct gaagctataa acatcattga aaatgctgta tttgaggact   3540
tggactttcc aggaaaaaca gtgctcagac agaggtctcg ctccttgagt tcatcgggaa   3600
caaaacattc aagacagtcc aacaactccc atagcccttt gccaagcaat tagccttaag   3660
ttgtgctagc aaccctaata ggtgatgcag ataatagcct acttcttaga atatgcctgt   3720
ccaaaattgc agacttgaaa agtttgttct tcgctcaatt tttttgtgga ctactttttt   3780
tatatcaaat ttaagctgga tttgggggca taacctaatt tgagccaact cctgagtttt   3840
```

```
gctatactta aggaaagggc tatctttgtt ctttgttagt ctcttgaaac tggctgctgg   3900

ccaagcttta tagccctcac catttgccta aggaggtagc agcaatccct aatatatata   3960

tatagtgaga actaaaatgg atatattttt ataatgcaga agaaggaaag tccccctgtg   4020

tggtaactgt attgttctag aaatatgctt tctagagata tgatgatttt gaaactgatt   4080

tctagaaaaa gctgactcca tttttgtccc tggcgggtaa attaggaatc tgcactattt   4140

tggaggacaa gtagcacaaa ctgtataacg gtttatgtcc gtagttttat agtcctattt   4200

gtagcattca atagctttat tccttagatg gttctagggt gggtttacag ctttttgtac   4260

ttttacctcc aataaaggga aaatgaagct ttttatgtaa attggttgaa aggtctagtt   4320

ttgggaggaa aaaagccgta gtaagaaatg gatcatatat attacaacta acttcttcaa   4380

ctatggactt tttaagccta atgaaatctt aagtgtctta tatgtaatcc tgtaggttgg   4440

tacttccccc aaactgatta taggtaacag tttaatcatc tcacttgcta acatgttttt   4500

atttttcact gtaaatatgt ttatgtttta tttataaaaa ttctgaaatc aatccatttg   4560

ggttggtggt gtacagaaca cacttaagtg tgttaacttg tgacttcttt caagtctaaa   4620

tgatttaata aaactttttt taaattaaaa aaaaaaaaaa aaaaa                   4665
```

<210> SEQ ID NO 132
<211> LENGTH: 977
<212> TYPE: PRT
<213> ORGANISM: Homo sapiens

<400> SEQUENCE: 132

```
Met Pro Ala Arg Arg Leu Leu Leu Leu Leu Thr Leu Leu Leu Pro Gly
1               5                   10                  15

Leu Gly Ile Phe Gly Ser Thr Ser Thr Val Thr Leu Pro Glu Thr Leu
            20                  25                  30

Leu Phe Val Ser Thr Leu Asp Gly Ser Leu His Ala Val Ser Lys Arg
        35                  40                  45

Thr Gly Ser Ile Lys Trp Thr Leu Lys Glu Asp Pro Val Leu Gln Val
    50                  55                  60

Pro Thr His Val Glu Glu Pro Ala Phe Leu Pro Asp Pro Asn Asp Gly
65                  70                  75                  80

Ser Leu Tyr Thr Leu Gly Ser Lys Asn Asn Glu Gly Leu Thr Lys Leu
                85                  90                  95

Pro Phe Thr Ile Pro Glu Leu Val Gln Ala Ser Pro Cys Arg Ser Ser
            100                 105                 110

Asp Gly Ile Leu Tyr Met Gly Lys Lys Gln Asp Ile Trp Tyr Val Ile
        115                 120                 125

Asp Leu Leu Thr Gly Glu Lys Gln Gln Thr Leu Ser Ser Ala Phe Ala
    130                 135                 140

Asp Ser Leu Cys Pro Ser Thr Ser Leu Leu Tyr Leu Gly Arg Thr Glu
145                 150                 155                 160

Tyr Thr Ile Thr Met Tyr Asp Thr Lys Thr Arg Glu Leu Arg Trp Asn
                165                 170                 175

Ala Thr Tyr Phe Asp Tyr Ala Ala Ser Leu Pro Glu Asp Asp Val Asp
            180                 185                 190

Tyr Lys Met Ser His Phe Val Ser Asn Gly Asp Gly Leu Val Val Thr
        195                 200                 205

Val Asp Ser Glu Ser Gly Asp Val Leu Trp Ile Gln Asn Tyr Ala Ser
    210                 215                 220

Pro Val Val Ala Phe Tyr Val Trp Gln Arg Glu Gly Leu Arg Lys Val
```

-continued

```
225                 230                 235                 240

Met His Ile Asn Val Ala Val Glu Thr Leu Arg Tyr Leu Thr Phe Met
                245                 250                 255

Ser Gly Glu Val Gly Arg Ile Thr Lys Trp Lys Tyr Pro Phe Pro Lys
            260                 265                 270

Glu Thr Glu Ala Lys Ser Lys Leu Thr Pro Thr Leu Tyr Val Gly Lys
        275                 280                 285

Tyr Ser Thr Ser Leu Tyr Ala Ser Pro Ser Met Val His Glu Gly Val
    290                 295                 300

Ala Val Val Pro Arg Gly Ser Thr Leu Pro Leu Leu Glu Gly Pro Gln
305                 310                 315                 320

Thr Asp Gly Val Thr Ile Gly Asp Lys Gly Glu Cys Val Ile Thr Pro
                325                 330                 335

Ser Thr Asp Val Lys Phe Asp Pro Gly Leu Lys Ser Lys Asn Lys Leu
            340                 345                 350

Asn Tyr Leu Arg Asn Tyr Trp Leu Leu Ile Gly His His Glu Thr Pro
        355                 360                 365

Leu Ser Ala Ser Thr Lys Met Leu Glu Arg Phe Pro Asn Asn Leu Pro
    370                 375                 380

Lys His Arg Glu Asn Val Ile Pro Ala Asp Ser Glu Lys Lys Ser Phe
385                 390                 395                 400

Glu Glu Val Ile Asn Leu Val Asp Gln Thr Ser Glu Asn Ala Pro Thr
                405                 410                 415

Thr Val Ser Arg Asp Val Glu Glu Lys Pro Ala His Ala Pro Ala Arg
            420                 425                 430

Pro Glu Ala Pro Val Asp Ser Met Leu Lys Asp Met Ala Thr Ile Ile
        435                 440                 445

Leu Ser Thr Phe Leu Leu Ile Gly Trp Val Ala Phe Ile Ile Thr Tyr
    450                 455                 460

Pro Leu Ser Met His Gln Gln Gln Gln Leu Gln His Gln Gln Phe Gln
465                 470                 475                 480

Lys Glu Leu Glu Lys Ile Gln Leu Leu Gln Gln Gln Gln Gln Leu
                485                 490                 495

Pro Phe His Pro Pro Gly Asp Thr Ala Gln Asp Gly Glu Leu Leu Asp
            500                 505                 510

Thr Ser Gly Pro Tyr Ser Glu Ser Ser Gly Thr Ser Ser Pro Ser Thr
        515                 520                 525

Ser Pro Arg Ala Ser Asn His Ser Leu Cys Ser Gly Ser Ser Ala Ser
    530                 535                 540

Lys Ala Gly Ser Ser Pro Ser Leu Glu Gln Asp Asp Gly Asp Glu Glu
545                 550                 555                 560

Thr Ser Val Val Ile Val Gly Lys Ile Ser Phe Cys Pro Lys Asp Val
                565                 570                 575

Leu Gly His Gly Ala Glu Gly Thr Ile Val Tyr Arg Gly Met Phe Asp
            580                 585                 590

Asn Arg Asp Val Ala Val Lys Arg Ile Leu Pro Glu Cys Phe Ser Phe
        595                 600                 605

Ala Asp Arg Glu Val Gln Leu Leu Arg Glu Ser Asp Glu His Pro Asn
    610                 615                 620

Val Ile Arg Tyr Phe Cys Thr Glu Lys Asp Arg Gln Phe Gln Tyr Ile
625                 630                 635                 640

Ala Ile Glu Leu Cys Ala Ala Thr Leu Gln Glu Tyr Val Glu Gln Lys
                645                 650                 655
```

```
Asp Phe Ala His Leu Gly Leu Glu Pro Ile Thr Leu Leu Gln Gln Thr
            660                 665                 670

Thr Ser Gly Leu Ala His Leu His Ser Leu Asn Ile Val His Arg Asp
        675                 680                 685

Leu Lys Pro His Asn Ile Leu Ile Ser Met Pro Asn Ala His Gly Lys
    690                 695                 700

Ile Lys Ala Met Ile Ser Asp Phe Gly Leu Cys Lys Lys Leu Ala Val
705                 710                 715                 720

Gly Arg His Ser Phe Ser Arg Arg Ser Gly Val Pro Gly Thr Glu Gly
                725                 730                 735

Trp Ile Ala Pro Glu Met Leu Ser Glu Asp Cys Lys Glu Asn Pro Thr
            740                 745                 750

Tyr Thr Val Asp Ile Phe Ser Ala Gly Cys Val Phe Tyr Tyr Val Ile
        755                 760                 765

Ser Glu Gly Ser His Pro Phe Gly Lys Ser Leu Gln Arg Gln Ala Asn
    770                 775                 780

Ile Leu Leu Gly Ala Cys Ser Leu Asp Cys Leu His Pro Glu Lys His
785                 790                 795                 800

Glu Asp Val Ile Ala Arg Glu Leu Ile Glu Lys Met Ile Ala Met Asp
                805                 810                 815

Pro Gln Lys Arg Pro Ser Ala Lys His Val Leu Lys His Pro Phe Phe
            820                 825                 830

Trp Ser Leu Glu Lys Gln Leu Gln Phe Phe Gln Asp Val Ser Asp Arg
        835                 840                 845

Ile Glu Lys Glu Ser Leu Asp Gly Pro Ile Val Lys Gln Leu Glu Arg
    850                 855                 860

Gly Gly Arg Ala Val Val Lys Met Asp Trp Arg Glu Asn Ile Thr Val
865                 870                 875                 880

Pro Leu Gln Thr Asp Leu Arg Lys Phe Arg Thr Tyr Lys Gly Gly Ser
                885                 890                 895

Val Arg Asp Leu Leu Arg Ala Met Arg Asn Lys Lys His His Tyr Arg
            900                 905                 910

Glu Leu Pro Ala Glu Val Arg Glu Thr Leu Gly Ser Leu Pro Asp Asp
        915                 920                 925

Phe Val Cys Tyr Phe Thr Ser Arg Phe Pro His Leu Leu Ala His Thr
    930                 935                 940

Tyr Arg Ala Met Glu Leu Cys Ser His Glu Arg Leu Phe Gln Pro Tyr
945                 950                 955                 960

Tyr Phe His Glu Pro Pro Glu Pro Gln Pro Pro Val Thr Pro Asp Ala
                965                 970                 975

Leu
```

<210> SEQ ID NO 133
<211> LENGTH: 4005
<212> TYPE: DNA
<213> ORGANISM: Homo sapiens

<400> SEQUENCE: 133

```
tgcctagtca gttctgcgtc cgctgaggct cggtcaccgc ctcgctgtcg tcgcggcgcc      60

cccgccccgt cctctgtccg taccgccccc ggagccaggg ccgagtcctc gccatgccgg     120

cccggcggct gctgctgctg ctgacgctgc tgctgcccgg cctcgggatt tttggaagta     180

ccagcacagt gacgcttcct gaaaccttgt tgtttgtgtc aacgctggat ggaagtttgc     240
```

-continued

```
atgctgtcag caagaggaca ggctcaatca aatggacttt aaaagaagat ccagtcctgc    300
aggtcccaac acatgtggaa gagcctgcct ttctcccaga tcctaatgat ggcagcctgt    360
atacgcttgg aagcaagaat aatgaaggcc tgacgaaact tccttttacc atcccagaat    420
tggtgcaggc atccccatgc cgaagttcag atggaatcct ctacatgggt aaaaagcagg    480
acatctggta tgttattgac ctcctgaccg gagagaagca gcagactttg tcatcggcct    540
ttgcagatag tctctgccca tcaacctctc ttctgtatct tgggcgaaca gaatacacca    600
tcaccatgta cgacaccaaa acccgagagc tccggtggaa tgccacctac tttgactatg    660
cggcctcact gcctgaggac gacgtggact acaagatgtc ccactttgtg tccaatggtg    720
atgggctggt ggtgactgtg gacagtgaat ctggggacgt cctgtggatc caaaactacg    780
cctcccctgt ggtggccttt tatgtctggc agcgggaggg tctgaggaag gtgatgcaca    840
tcaatgtcgc tgtggagacc ctgcgctatc tgaccttcat gtctggggag gtggggcgca    900
tcacaaagtg gaagtacccg ttccccaagg agacagaggc caagagcaag ctgacgccca    960
ctctgtatgt tgggaaatac tctaccagcc tctatgcctc tccctcaatg gtacacgagg   1020
gggttgctgt cgtgccccgc ggcagcacac ttcctttgct ggaagggccc cagactgatg   1080
gcgtcaccat tggggacaag ggggagtgtg tgatcacgcc cagcacggac gtcaagtttg   1140
atcccggact caaaagcaag aacaagctca actacttgag gaattactgg cttctgatag   1200
gacaccatga aaccccactg tctgcgtcta ccaagatgct ggagagattt cccaacaatc   1260
tacccaaaca tcgggaaaat gtgattcctg ctgattcaga gaaaaagagc tttgaggaag   1320
ttatcaacct ggttgaccag acttcagaaa acgcacctac caccgtgtct cgggatgtgg   1380
aggagaagcc cgcccatgcc cctgcccggc ccgaggcccc cgtggactcc atgcttaagg   1440
acatggctac catcatcctg agcaccttcc tgctgattgg ctgggtggcc ttcatcatca   1500
cctatcccct gagcatgcat cagcagcagc agctccagca ccagcagttc cagaaggaac   1560
tggagaagat ccagctcctg cagcagcagc agcagcagct gcccttccac ccacctggag   1620
acacggctca ggacggcgag ctcctggaca cgtctggccc gtactcagag agctcgggca   1680
ccagcagccc cagcacgtcc cccagggcct ccaaccactc gctctgctcc ggcagctctg   1740
cctccaaggc tggcagcagc ccctccctgg aacaagacga tggagatgag gaaaccagcg   1800
tggtgatagt tgggaaaatt tccttctgtc ccaaggatgt cctgggccat ggagctgagg   1860
gcacaattgt gtaccggggc atgtttgaca accgcgacgt ggccgtgaag aggatcctcc   1920
ccgagtgttt tagcttcgca gaccgtgagg tccagctgtt gcgagaatcg gatgagcacc   1980
cgaacgtgat ccgctacttc tgcacggaga aggaccggca attccagtac attgccatcg   2040
agctgtgtgc agccaccctg caagagtatg tggagcagaa ggactttgcg catctcggcc   2100
tggagcccat caccttgctg cagcagacca cctcgggcct ggcccacctc cactccctca   2160
acatcgttca cagagaccta aagccacaca acatcctcat atccatgccc aatgcacacg   2220
gcaagatcaa ggccatgatc tccgactttg gcctctgcaa gaagctggca gtgggcagac   2280
acagtttcag ccgccgatct ggggtgcctg gcacagaagg ctggatcgct ccagagatgc   2340
tgagcgaaga ctgtaaggag aaccctacct acacggtgga catcttttct gcaggctgcg   2400
tcttttacta cgtaatctct gagggcagcc accccttttgg caagtccctg cagcggcagg   2460
ccaacatcct cctgggtgcc tgcagccttg actgcttgca cccagagaag cacgaagacg   2520
tcattgcacg tgaattgata gagaagatga ttgcgatgga tcctcagaaa cgcccctcag   2580
cgaagcatgt gctcaaacac ccgttcttct ggagcctaga gaagcagctc cagttcttcc   2640
```

```
aggacgtgag cgacagaata gaaaaggaat ccctggatgg cccgatcgtg aagcagttag   2700

agagaggcgg gagagccgtg gtgaagatgg actggcggga gaacatcact gtccccctcc   2760

agacagacct gcgtaaattc aggacctata aaggtggttc tgtcagagat ctcctccgag   2820

ccatgagaaa taagaagcac cactaccggg agctgcctgc agaggtgcgg gagacgctgg   2880

ggtccctccc cgacgacttc gtgtgctact tcacatctcg cttcccccac ctcctcgcac   2940

acacctaccg ggccatggag ctgtgcagcc acgagagact cttccagccc tactacttcc   3000

acgagccccc agagccccag cccccagtga ctccagacgc cctctgagcg agggcggccc   3060

ctctgttctg gtggccccag ctgtgactga gggcctggtc accacaatta gagcttgatg   3120

cctcccggct ttgcagggag accaggcttc ccaaaccaag tgccttgagc tgcctgctct   3180

gcagcccaca gaggacagtg ctgaccccag gaagtgggag aagtggcccc tcgtgaccta   3240

cagggaactg ggaagatgct ggccccaaaa gccttacggt catgatgtct gcaaaggagg   3300

gcctcagaga cagcgcgagt agcacccccca gccatctact ggataaactt gcttcagact   3360

ttttaaattc ctgcttaatg tcagtctaca ggcctttcag gaagggagag gagggaatcg   3420

tacattttgc ttgcgtgctg ggacagctag gctgagatgc accaagtaca gccttcactg   3480

gagaccggaa ttgagaggtg ggggatgctg aggaggggga ggacggagtt cagagggtgt   3540

cgtcctgcag tgtgagattt ctcattgatc acagatgtgc ccagagtagc ccaggtcact   3600

gttaactagt gtttctgcag aggcagcagg agccatgagc atgaggtgtg gcattaggga   3660

ctggtcagct atgcatgctg gcaggtgggg ttgtgtctgc aggtctcaga aatgaagagg   3720

ctgctctgtt ctggaggcag ccgtggccca gtgccagtgg ccagaacagt ggcctttggt   3780

gggtgtgtcc cgggccatct cggggtggtg ctcaggagcg cctggggcaa gaggtaaaga   3840

gttccctggc cttcaaggag agcagcgaag acccagacag gggccagcct tcaggaccag   3900

agggaggccg ccgaatggga ccctcctggt caccaggaga aagccctggg ccagcgagta   3960

ggcagtcaaa ctccttcgtc cccaaggccg gtggaacaag aggct                   4005
```

<210> SEQ ID NO 134
<211> LENGTH: 670
<212> TYPE: PRT
<213> ORGANISM: Homo sapiens

<400> SEQUENCE: 134

```
Met Gly Glu Pro Ala Gly Val Ala Gly Thr Met Glu Ser Pro Phe Ser
1               5                   10                  15

Pro Gly Leu Phe His Arg Leu Asp Glu Asp Trp Asp Ser Ala Leu Phe
            20                  25                  30

Ala Glu Leu Gly Tyr Phe Thr Asp Thr Asp Glu Leu Gln Leu Glu Ala
        35                  40                  45

Ala Asn Glu Thr Tyr Glu Asn Asn Phe Asp Asn Leu Asp Phe Asp Leu
    50                  55                  60

Asp Leu Met Pro Trp Glu Ser Asp Ile Trp Asp Ile Asn Asn Gln Ile
65                  70                  75                  80

Cys Thr Val Lys Asp Ile Lys Ala Glu Pro Gln Pro Leu Ser Pro Ala
                85                  90                  95

Ser Ser Ser Tyr Ser Val Ser Ser Pro Arg Ser Val Asp Ser Tyr Ser
            100                 105                 110

Ser Thr Gln His Val Pro Glu Glu Leu Asp Leu Ser Ser Ser Ser Gln
        115                 120                 125
```

```
Met Ser Pro Leu Ser Leu Tyr Gly Glu Asn Ser Asn Ser Leu Ser Ser
    130                 135                 140

Ala Glu Pro Leu Lys Glu Asp Lys Pro Val Thr Gly Pro Arg Asn Lys
145                 150                 155                 160

Thr Glu Asn Gly Leu Thr Pro Lys Lys Lys Ile Gln Val Asn Ser Lys
                165                 170                 175

Pro Ser Ile Gln Pro Lys Pro Leu Leu Leu Pro Ala Ala Pro Lys Thr
            180                 185                 190

Gln Thr Asn Ser Ser Val Pro Ala Lys Thr Ile Ile Ile Gln Thr Val
        195                 200                 205

Pro Thr Leu Met Pro Leu Ala Lys Gln Gln Pro Ile Ile Ser Leu Gln
    210                 215                 220

Pro Ala Pro Thr Lys Gly Gln Thr Val Leu Leu Ser Gln Pro Thr Val
225                 230                 235                 240

Val Gln Leu Gln Ala Pro Gly Val Leu Pro Ser Ala Gln Pro Val Leu
                245                 250                 255

Ala Val Ala Gly Gly Val Thr Gln Leu Pro Asn His Val Val Asn Val
            260                 265                 270

Val Pro Ala Pro Ser Ala Asn Ser Pro Val Asn Gly Lys Leu Ser Val
        275                 280                 285

Thr Lys Pro Val Leu Gln Ser Thr Met Arg Asn Val Gly Ser Asp Ile
    290                 295                 300

Ala Val Leu Arg Arg Gln Gln Arg Met Ile Lys Asn Arg Glu Ser Ala
305                 310                 315                 320

Cys Gln Ser Arg Lys Lys Lys Lys Glu Tyr Met Leu Gly Leu Glu Ala
                325                 330                 335

Arg Leu Lys Ala Ala Leu Ser Glu Asn Glu Gln Leu Lys Lys Glu Asn
            340                 345                 350

Gly Thr Leu Lys Arg Gln Leu Asp Glu Val Val Ser Glu Asn Gln Arg
        355                 360                 365

Leu Lys Val Pro Ser Pro Lys Arg Arg Val Val Cys Val Met Ile Val
    370                 375                 380

Leu Ala Phe Ile Ile Leu Asn Tyr Gly Pro Met Ser Met Leu Glu Gln
385                 390                 395                 400

Asp Ser Arg Arg Met Asn Pro Ser Val Ser Pro Ala Asn Gln Arg Arg
                405                 410                 415

His Leu Leu Gly Phe Ser Ala Lys Glu Ala Gln Asp Thr Ser Asp Gly
            420                 425                 430

Ile Ile Gln Lys Asn Ser Tyr Arg Tyr Asp His Ser Val Ser Asn Asp
        435                 440                 445

Lys Ala Leu Met Val Leu Thr Glu Glu Pro Leu Leu Tyr Ile Pro Pro
    450                 455                 460

Pro Pro Cys Gln Pro Leu Ile Asn Thr Thr Glu Ser Leu Arg Leu Asn
465                 470                 475                 480

His Glu Leu Arg Gly Trp Val His Arg His Glu Val Glu Arg Thr Lys
                485                 490                 495

Ser Arg Arg Met Thr Asn Asn Gln Gln Lys Thr Arg Ile Leu Gln Gly
            500                 505                 510

Ala Leu Glu Gln Gly Ser Asn Ser Gln Leu Met Ala Val Gln Tyr Thr
        515                 520                 525

Glu Thr Thr Ser Ser Ile Ser Arg Asn Ser Gly Ser Glu Leu Gln Val
    530                 535                 540

Tyr Tyr Ala Ser Pro Arg Ser Tyr Gln Asp Phe Phe Glu Ala Ile Arg
```

```
545                 550                 555                 560

Arg Arg Gly Asp Thr Phe Tyr Val Val Ser Phe Arg Arg Asp His Leu
                565                 570                 575

Leu Leu Pro Ala Thr Thr His Asn Lys Thr Thr Arg Pro Lys Met Ser
            580                 585                 590

Ile Val Leu Pro Ala Ile Asn Ile Asn Glu Asn Val Ile Asn Gly Gln
        595                 600                 605

Asp Tyr Glu Val Met Met Gln Ile Asp Cys Gln Val Met Asp Thr Arg
    610                 615                 620

Ile Leu His Ile Lys Ser Ser Ser Val Pro Pro Tyr Leu Arg Asp Gln
625                 630                 635                 640

Gln Arg Asn Gln Thr Asn Thr Phe Phe Gly Ser Pro Pro Ala Ala Thr
                645                 650                 655

Glu Ala Thr His Val Val Ser Thr Ile Pro Glu Ser Leu Gln
            660                 665                 670


<210> SEQ ID NO 135
<211> LENGTH: 7563
<212> TYPE: DNA
<213> ORGANISM: Homo sapiens

<400> SEQUENCE: 135

aaaagtagtt tgtctttact aggccaccgt ctcgtcagcg ttacggagta ttttgtccgc     60

ctgccgccgc cgtcccagat attaatcacg gagttccagg gagaaggaac ttgtgaaatg    120

ggggagccgg ctggggttgc cggcaccatg gagtcacctt ttagcccggg actctttcac    180

aggctggatg aagattggga ttctgctctc tttgctgaac tcggttattt cacagacact    240

gatgagctgc aattggaagc agcaaatgag acgtatgaaa acaattttga taatcttgat    300

tttgatttgg atttgatgcc ttgggagtca gacatttggg acatcaacaa ccaaatctgt    360

acagttaaag atattaaggc agaacctcag ccactttctc cagcctcctc aagttattca    420

gtctcgtctc ctcggtcagt ggactcttat tcttcaactc agcatgttcc tgaggagttg    480

gatttgtctt ctagttctca gatgtctccc ctttccttat atggtgaaaa ctctaatagt    540

ctctcttcag cggagccact gaaggaagat aagcctgtca ctggtcctag gaacaagact    600

gaaaatggac tgactccaaa gaaaaaaatt caggtgaatt caaaaccttc aattcagccc    660

aagcctttat tgcttccagc agcacccaag actcaaacaa actccagtgt tccagcaaaa    720

accatcatta ttcagacagt accaacgctt atgccattgg caaagcagca accaattatc    780

agtttacaac ctgcacccac taaaggccag acggttttgc tgtctcagcc tactgtggta    840

caacttcaag cacctggagt tctgccctct gctcagccag tccttgctgt tgctggggga    900

gtcacacagc tccctaatca cgtggtgaat gtggtaccag ccccttcagc gaatagccca    960

gtgaatggaa aactttccgt gactaaacct gtcctacaaa gtaccatgag aaatgtcggt   1020

tcagatattg ctgtgctaag gagacagcaa cgtatgataa aaaatcgaga atccgcttgt   1080

cagtctcgca agaagaagaa agaatatatg ctagggttag aggcgagatt aaaggctgcc   1140

ctctcagaaa acgagcaact gaagaaagaa aatggaacac tgaagcggca gctggatgaa   1200

gttgtgtcag agaaccagag gcttaaagtc cctagtccaa agcgaagagt tgtctgtgtg   1260

atgatagtat tggcatttat aatactgaac tatggaccta tgagcatgtt ggaacaggat   1320

tccaggagaa tgaaccctag tgtgagccct gcaaatcaaa ggaggcacct tctaggattt   1380

tctgctaaag aggcacagga cacatcagat ggtattatcc agaaaaacag ctacagatat   1440
```

```
gatcattctg tttcaaatga caaagccctg atggtgctaa ctgaagaacc attgctttac   1500
attcctccac ctccttgtca gcccctaatt aacacaacag agtctctcag gttaaatcat   1560
gaacttcgag gatgggttca tagacatgaa gtagaaagga ccaagtcaag aagaatgaca   1620
aataatcaac agaaaacccg tattcttcag ggtgctctgg aacagggctc aaattctcag   1680
ctgatggctg ttcaatacac agaaaccact agtagtatca gcaggaactc agggagtgag   1740
ctacaagtgt attatgcttc acccagaagt tatcaagact tttttgaagc catccgcaga   1800
aggggagaca cattttatgt tgtgtcattt cgaagggatc acctgctgtt accagctacc   1860
acccataaca agaccacaag accaaaaatg tcaattgtgt taccagcaat aaacataaat   1920
gagaatgtga tcaatgggca ggactacgaa gtgatgatgc agattgactg tcaggtgatg   1980
gacaccagga tcctccatat caaaagttcg tcagttcctc cttacctccg agatcagcag   2040
aggaatcaaa ccaacacctt ctttggctcc cctcccgcag ccacagaggc aacccacgtt   2100
gtcagcacca tccctgagtc attacaatag caccctgcag ctatgctgga aaactgagcg   2160
tgggaccctg ccagactgaa gagcaggtga gcaaaatgct gctttctgcc ttggtggcag   2220
gcagagaact gtctcgtact agaattcaag gaggaaagaa gaagaaataa aagaagctgc   2280
tccatttttc atcatctacc catctatttg gaaagcactg gaattcagat gcaagagaac   2340
aatgtttctt cagtggcaaa tgtagccctg catcctccag tgttacctgg tgtagatttt   2400
tttttctgta cctttctaaa cctctcttcc ctctgtgatg gttttgtgtt taaacagtca   2460
tcttctttta aataatatcc acctctcctt tttgccattt cacttattga ttcataaagt   2520
gaattttatt taaagctatg ccacacatgc atgttcaaat ggtttccact gattcgattt   2580
ttcattcatt taatgcaaac ccattctgga tattgtgctt atttgagaaa acacatttca   2640
aaaccagaaa agccaaaaac actccaaaaa caagcaaaac aatttggagc tttagataaa   2700
aggaaaaact cccagttggt aaagtttatc tttacttagg atttgtggct cacacctaaa   2760
caaagggggt cagggagtgg gtacaaattt gagaaaatag aagggtaagg gaagggccag   2820
tggtggggtt tggagagagg agatagctcc attaatacac atgtttaaaa gatggaaagt   2880
tcacgcctgt aatcccagca ctttgggagg ccgaggcggg tggatcacga ggtcaggaga   2940
tcaagaccat cccggctaaa acggtgaaac cccgtctcta ctaaaaatac aaaaaattag   3000
ccgggcgtag tgacgggcgc ctgtagtccc agctacttgg gaggctgagg caggagaatg   3060
gcgtgaaccc gggaggcgga gcttgcagtg agccgagatc ccgccactgc actccagcct   3120
gggcgacaga gcgagactcc gtctcaaaaa aaaaaaaaaa aaaaaaaaaa gatggaaagt   3180
tcgatgtgac tgcagtatga gattaaagcc acaactattg tttattttgg ggactctagg   3240
ccaccaagta ttagcacaca tacttatgtt ttctctacta atctggtcca ggtcctcatg   3300
gaccacagga caaagctttc attttcattc attcttctat tgaaattata ccaaattcag   3360
ctgaggaata tggaagtaac tttagactta aacaagacaa aagttttttc actgaagaat   3420
tgacaagtat ttgctcctta aaacaacgca gattagtgaa cgtggattcc tgctgaggga   3480
gtgcatccca taatatggca ataattttca gtttctccaa cgaaaagata gtgaaggaat   3540
taaatctttt gtcctcccat ggttaaaaaa aaaaaaaaag ctgtgttcat ttttactgta   3600
ctatgcctct tttttcacca tagtagacaa ttatgtttca tttgatgaat tcatagaact   3660
ggatctcata cagcgatgtc ctctctaatg ttctaccttt cagtttctaa agtgagtctt   3720
cctccctctc ctacaaaact tttcaatttt ttgatgtaac tcatctacaa atactgtttc   3780
ttaccccagt tgacttgcct ttgtcagatt tcttcttgtt ccacactata gcaatcaatt   3840
```

```
tctcttcttc cttacaagaa agggaacgag aaattgtagc aacctctcaa ggattatatg   3900
cagctagtta gttttctgcc tgtgaaatta ggtctggctc ctaaataatt ttaaagaacc   3960
atcagcactt ctaactctct ggacaggtgc ctctttgtcc aagctagtta aatgctttcc   4020
aaggaaatca gttcaacttt tgtgagcggg gaaaagcagg gctttattgt tgtgttacct   4080
gggagtctgg agtttgaaaa gtgctaatta accttcctct ttttccacat tacaaacctt   4140
tttaagcagc gcagcactcc ccttagattt ggctatcctg ggtgattttc agacaagaac   4200
cattttctct ggggaccatt cttctgctgg gtgccaagga atataaggca aatgcccaga   4260
agaccttcag gtgactgggc agtcttatca tgggatattt cttctggccc tgccccttcc   4320
cattctgtaa tgtgaattag ccacaccaga ggctgtgacc atggctagta gacagtggca   4380
acatagtcat ccccaagatg ctaatcttct gctggaactg tcatacgtta tcatggtcaa   4440
tgtaaacctg gtttgtgtgg ggtgattata aatagagttt ccctcctctc tgtgacagaa   4500
tcacaggaga aggacccatc tcgtggcctt cttgttctta gcgcttcact tttacttcat   4560
ccctcgattc ccagcttttt ctatcatcat tttgccaact cctcagatgc aagactttgg   4620
ttatgtcata ctcaccaacg ttagtccctc tcttccaggt gaaaaggtgg gtagcggttg   4680
ggagggagtc tccactgaag agcaggaagg tggtagcagg gccggcagct ctgccacaga   4740
gctaggggtg cctgtaaggt gccgcctaga gcagcctggg agctttgcct tcttttgtct   4800
ctcactagcc cttctactct ttgtcattgc ctgttcttga gtggatcttt gaaatgaggg   4860
gacaggattc tcctaagggt agagtttcag gaaatgagtg aaaggcaatt gacaaatgca   4920
aagaagtagt cactttttaa attgctggca aagctataat taatccctag gcacaattgt   4980
agtttttatt ttaatgtttg tatgcacaag gccctttagg aaatgagaag ttgccatgcc   5040
agattaattt tttttttttt ttttggtggg attgcctttt gggggttgca gccagaaatt   5100
gtgggtaatg tgtgtatttt tttatttatt aaattttaaa caggattgtg caagcttatg   5160
agacaattag ataaactcat ggaggaggca ggtcctcctg ttattagatg attttgtgct   5220
cttggggctg acaataatac actcttggga agtgatggta gagactgatg ggaatagtct   5280
ttctgcctgg ttgcaagtcc caaattttta agggttaatg gaagtaagtg gatgtttcct   5340
catgttaact actgaatcag atgttaggag cttgtccctt tggggttgac ttatgcccag   5400
cagtacaggg acacagcttc attagagtgt tagtgtaaac taactccaaa gttaggagtt   5460
aatgtgaaag gatcatcctt gaaacaaatc tgctgtttgc catgcttgta gtacagaaac   5520
ttcacatgga gttttgggtg ggatttgtgt tttcacaagt aaaaaatccc tcacgattat   5580
aaaactcaga gcatcatcta attttttttt ttaatgacta caagttccag cacaaaactg   5640
gcatttcttt gccatttctt gccagtaaga agttgacacg gaggtatttg aaagcaatgt   5700
tatgtgagtc attcttaagt gttccaagta agtttagaaa cagaaaagga acttgggatt   5760
caaattgatt tttcaaatca tttttaaaga gacatcatcc tgactaaatc ttagcctgaa   5820
ccttcctccc ctgtgtgtat tccccggtag tcaccgcagc gagatgctgg tgagactgcc   5880
gtggtggcat ttagcatcgt taaaactgga aaactctcaa gctctttgcc actttcctac   5940
tatttttga ttcttgccat tttaccaagc ttaggttgtg aaacttgaca gaaatgtatt    6000
acaggaaaaa cttataattg tatttgactt tctaacacat tgcaaagttt caaagtgact   6060
ttcactttca acaacatatt agaagtaacc acttttgctt tcacagcctg aagagttaga   6120
gcctgatctg atgccccctt tcactctgaa gtcatgggaa attttccagc catgaaagcc   6180
```

-continued

```
ctctttccac tgcatactga tgggctgact cagcttcctt cagccgactg agatcttttc   6240

atactattgg ctatttcata ccaattaacc tcttaaataa gattgtgaat tgccaaaatt   6300

gatagacact tattaccacc tgtggactcc atattcctta ccacaaatgt tattttcatc   6360

agtcctgagt cattttaact tacagaaatt aggattgttg ctgctaatat gaataccaat   6420

tataactttt agaaacaaga ataaagccta aaagagaatg aaatataaga aatgttcgtt   6480

cccaccccta ataacatttg gaagtgaata ttcccatttt cttccaccca cagggattgg   6540

gattgatttt taatttccta ggaaacaata ctagactacc caaaaagatg ttgccagaat   6600

ccaaaaggaa ctatgctcgt aaaagaaatg cagttttctc ctacctaaaa aaaagaaagt   6660

aaagtgtgtt ctgttcttat ctttttaatg actaagcttt aaacagttta ttttgggtaa   6720

gactagaact ttcggccatt tgttctaata tgtgtgttat tagatgcaat agaatttatg   6780

aaaagaagaa tgacaaaggt atctgattag aaaatttgat cttacgcatg aatccatgtc   6840

atggccagcc actgtcacat agtgggtgcc attctcaaca tattggtttg ctaactttaa   6900

gcattaggga tttagcacac taaaatactt ttaattatat taggtttggt aactaaggag   6960

taaataaatc ataatttatc atttgccaag gccaacaaac aacactattg tgctgtttgc   7020

tctcaatgaa gttgaataaa ccaggaggct tggcatatcc cctttatgtt aatcccagct   7080

agagattagt aggttgactt tcacagcaat tgtatattga tccattttaa ctcatccttg   7140

ccataatttc caggccagtc accaggacag aggagatgat ggggaaacag agctttagat   7200

gaaaactact atgcactact agccttagag gcactggttt cctgttacca ctttggcaag   7260

tatggatggt ctaagtccag tagggcttca tccatggagc cattagaact gagggggggag  7320

tgttagagat gccatttcac caggatcttt ttgctcaggt tgtacccatg ccaattgaag   7380

aacgtgttaa agatgaggag gagagatgta ccattctctc ccttaataat gatgttggtt   7440

tgcaaaacct aaagaaataa taacaacaga ctatttcata ctttcaagca agtctttata   7500

ctacctgtta tttctctaaa attcaaataa agaattttta aacttaaaaa aaaaaaaaaa   7560

aaa                                                                 7563
```

```
<210> SEQ ID NO 136
<211> LENGTH: 261
<212> TYPE: PRT
<213> ORGANISM: Homo sapiens

<400> SEQUENCE: 136

Met Val Val Val Ala Ala Ala Pro Asn Pro Ala Asp Gly Thr Pro Lys
1               5                   10                  15

Val Leu Leu Leu Ser Gly Gln Pro Ala Ser Ala Ala Gly Ala Pro Ala
            20                  25                  30

Gly Gln Ala Leu Pro Leu Met Val Pro Ala Gln Arg Gly Ala Ser Pro
        35                  40                  45

Glu Ala Ala Ser Gly Gly Leu Pro Gln Ala Arg Lys Arg Gln Arg Leu
    50                  55                  60

Thr His Leu Ser Pro Glu Glu Lys Ala Leu Arg Arg Lys Leu Lys Asn
65                  70                  75                  80

Arg Val Ala Ala Gln Thr Ala Arg Asp Arg Lys Lys Ala Arg Met Ser
                85                  90                  95

Glu Leu Glu Gln Gln Val Val Asp Leu Glu Glu Glu Asn Gln Lys Leu
            100                 105                 110

Leu Leu Glu Asn Gln Leu Leu Arg Glu Lys Thr His Gly Leu Val Val
        115                 120                 125
```

```
Glu Asn Gln Glu Leu Arg Gln Arg Leu Gly Met Asp Ala Leu Val Ala
    130                 135                 140

Glu Glu Glu Ala Glu Ala Lys Gly Asn Glu Val Arg Pro Val Ala Gly
145                 150                 155                 160

Ser Ala Glu Ser Ala Ala Leu Arg Leu Arg Ala Pro Leu Gln Gln Val
                165                 170                 175

Gln Ala Gln Leu Ser Pro Leu Gln Asn Ile Ser Pro Trp Ile Leu Ala
            180                 185                 190

Val Leu Thr Leu Gln Ile Gln Ser Leu Ile Ser Cys Trp Ala Phe Trp
        195                 200                 205

Thr Thr Trp Thr Gln Ser Cys Ser Ser Asn Ala Leu Pro Gln Ser Leu
    210                 215                 220

Pro Ala Trp Arg Ser Ser Gln Arg Ser Thr Gln Lys Asp Pro Val Pro
225                 230                 235                 240

Tyr Gln Pro Pro Phe Leu Cys Gln Trp Gly Arg His Gln Pro Ser Trp
                245                 250                 255

Lys Pro Leu Met Asn
            260


<210> SEQ ID NO 137
<211> LENGTH: 1820
<212> TYPE: DNA
<213> ORGANISM: Homo sapiens

<400> SEQUENCE: 137

ggcgctgggc ggctgcggcg cgcggtgcgc ggtgcgtagt ctggagctat ggtggtggtg     60

gcagccgcgc cgaacccggc cgacgggacc cctaaagttc tgcttctgtc ggggcagccc    120

gcctccgccg ccggagcccc ggccggccag gccctgccgc tcatggtgcc agcccagaga    180

ggggccagcc cggaggcagc gagcgggggg ctgccccagg cgcgcaagcg acagcgcctc    240

acgcacctga gccccgagga gaaggcgctg aggaggaaac tgaaaaacag agtagcagct    300

cagactgcca gagatcgaaa gaaggctcga atgagtgagc tggaacagca agtggtagat    360

ttagaagaag agaaccaaaa acttttgcta gaaaatcagc ttttacgaga gaaaactcat    420

ggccttgtag ttgagaacca ggagttaaga cagcgcttgg ggatggatgc cctggttgct    480

gaagaggagg cggaagccaa ggggaatgaa gtgaggccag tggccgggtc tgctgagtcc    540

gcagcactca gactacgtgc acctctgcag caggtgcagg cccagttgtc accccctccag    600

aacatctccc catggattct ggcggtattg actcttcaga ttcagagtct gatatcctgt    660

tgggcattct ggacaacttg gacccagtca tgttcttcaa atgcccttcc ccagagcctg    720

ccagcctgga ggagctccca gaggtctacc cagaaggacc cagttcctta ccagcctccc    780

tttctctgtc agtggggacg tcatcagcca agctggaagc cattaatgaa ctaattcgtt    840

ttgaccacat atataccaag cccctagtct tagagatacc ctctgagaca gagagccaag    900

ctaatgtggt agtgaaaatc gaggaagcac ctctcagccc ctcagagaat gatcaccctg    960

aattcattgt ctcagtgaag gaagaacctg tagaagatga cctcgttccg gagctgggta   1020

tctcaaatct gctttcatcc agccactgcc caaagccatc ttcctgccta ctggatgctt   1080

acagtgactg tggatacggg ggttcccttt ccccattcag tgacatgtcc tctctgcttg   1140

gtgtaaacca ttcttgggag gacacttttg ccaatgaact ctttccccag ctgattagtg   1200

tctaaggaat gatccaatac tgttgccctt ttccttgact attacactgc ctggaggata   1260

gcagagaagc ctgtctgtac ttcattcaaa aagccaaaat agagagtata cagtcctaga   1320
```

```
gaattcctct atttgttcag atctcataga tgacccccag gtattgtctt ttgacatcca   1380

gcagtccaag gtattgagac atattactgg aagtaagaaa tattactata attgagaact   1440

acagctttta agattgtact tttatcttaa aagggtggta gttttcccta aaatacttat   1500

tatgtaaggg tcattagaca aatgtcttga agtagacatg gaatttatga atggttcttt   1560

atcatttctc ttccccttt ttggcatcct ggcttgcctc cagttttagg tcctttagtt   1620

tgcttctgta agcaacggga acacctgctg agggggctct ttccctcatg tatacttcaa   1680

gtaagatcaa gaatcttttg tgaaattata gaaatttact atgtaaatgc ttgatggaat   1740

tttttcctgc tagtgtagct tctgaaaggt gctttctcca tttatttaaa actacccatg   1800

caattaaaag gtacaatgca                                              1820
```

```
<210> SEQ ID NO 138
<211> LENGTH: 376
<212> TYPE: PRT
<213> ORGANISM: Homo sapiens

<400> SEQUENCE: 138

Met Val Val Val Ala Ala Ala Pro Asn Pro Ala Asp Gly Thr Pro Lys
1               5                   10                  15

Val Leu Leu Leu Ser Gly Gln Pro Ala Ser Ala Ala Gly Ala Pro Ala
            20                  25                  30

Gly Gln Ala Leu Pro Leu Met Val Pro Ala Gln Arg Gly Ala Ser Pro
        35                  40                  45

Glu Ala Ala Ser Gly Gly Leu Pro Gln Ala Arg Lys Arg Gln Arg Leu
    50                  55                  60

Thr His Leu Ser Pro Glu Glu Lys Ala Leu Arg Arg Lys Leu Lys Asn
65                  70                  75                  80

Arg Val Ala Ala Gln Thr Ala Arg Asp Arg Lys Lys Ala Arg Met Ser
                85                  90                  95

Glu Leu Glu Gln Gln Val Val Asp Leu Glu Glu Glu Asn Gln Lys Leu
            100                 105                 110

Leu Leu Glu Asn Gln Leu Leu Arg Glu Lys Thr His Gly Leu Val Val
        115                 120                 125

Glu Asn Gln Glu Leu Arg Gln Arg Leu Gly Met Asp Ala Leu Val Ala
    130                 135                 140

Glu Glu Glu Ala Glu Ala Lys Gly Asn Glu Val Arg Pro Val Ala Gly
145                 150                 155                 160

Ser Ala Glu Ser Ala Ala Gly Ala Gly Pro Val Val Thr Pro Pro Glu
                165                 170                 175

His Leu Pro Met Asp Ser Gly Gly Ile Asp Ser Ser Asp Ser Glu Ser
            180                 185                 190

Asp Ile Leu Leu Gly Ile Leu Asp Asn Leu Asp Pro Val Met Phe Phe
        195                 200                 205

Lys Cys Pro Ser Pro Glu Pro Ala Ser Leu Glu Glu Leu Pro Glu Val
    210                 215                 220

Tyr Pro Glu Gly Pro Ser Ser Leu Pro Ala Ser Leu Ser Leu Ser Val
225                 230                 235                 240

Gly Thr Ser Ser Ala Lys Leu Glu Ala Ile Asn Glu Leu Ile Arg Phe
                245                 250                 255

Asp His Ile Tyr Thr Lys Pro Leu Val Leu Glu Ile Pro Ser Glu Thr
            260                 265                 270

Glu Ser Gln Ala Asn Val Val Val Lys Ile Glu Glu Ala Pro Leu Ser
```

-continued

```
        275                 280                 285

Pro Ser Glu Asn Asp His Pro Glu Phe Ile Val Ser Val Lys Glu Glu
    290                 295                 300

Pro Val Glu Asp Asp Leu Val Pro Glu Leu Gly Ile Ser Asn Leu Leu
305                 310                 315                 320

Ser Ser Ser His Cys Pro Lys Pro Ser Ser Cys Leu Leu Asp Ala Tyr
                325                 330                 335

Ser Asp Cys Gly Tyr Gly Gly Ser Leu Ser Pro Phe Ser Asp Met Ser
            340                 345                 350

Ser Leu Leu Gly Val Asn His Ser Trp Glu Asp Thr Phe Ala Asn Glu
        355                 360                 365

Leu Phe Pro Gln Leu Ile Ser Val
    370                 375


<210> SEQ ID NO 139
<211> LENGTH: 1810
<212> TYPE: DNA
<213> ORGANISM: Homo sapiens

<400> SEQUENCE: 139

ggcgctgggc ggctgcggcg cgcggtgcgc ggtgcgtagt ctggagctat ggtggtggtg     60

gcagccgcgc cgaacccggc cgacgggacc cctaaagttc tgcttctgtc ggggcagccc    120

gcctccgccg ccggagcccc ggccggccag gccctgccgc tcatggtgcc agcccagaga    180

ggggccagcc cggaggcagc gagcgggggg ctgccccagg cgcgcaagcg acagcgcctc    240

acgcacctga gccccgagga gaaggcgctg aggaggaaac tgaaaaacag agtagcagct    300

cagactgcca gagatcgaaa gaaggctcga atgagtgagc tggaacagca agtggtagat    360

ttagaagaag agaaccaaaa acttttgcta gaaaatcagc ttttacgaga gaaaactcat    420

ggccttgtag ttgagaacca ggagttaaga cagcgcttgg ggatggatgc cctggttgct    480

gaagaggagg cggaagccaa ggggaatgaa gtgaggccag tggccgggtc tgctgagtcc    540

gcagcaggtg caggcccagt tgtcacccct ccagaacatc tccccatgga ttctggcggt    600

attgactctt cagattcaga gtctgatatc ctgttgggca ttctggacaa cttggaccca    660

gtcatgttct tcaaatgccc ttccccagag cctgccagcc tggaggagct cccagaggtc    720

tacccagaag gacccagttc cttaccagcc tccctttctc tgtcagtggg gacgtcatca    780

gccaagctgg aagccattaa tgaactaatt cgttttgacc acatatatac caagccccta    840

gtcttagaga taccctctga gacagagagc caagctaatg tggtagtgaa aatcgaggaa    900

gcacctctca gcccctcaga gaatgatcac cctgaattca ttgtctcagt gaaggaagaa    960

cctgtagaag atgacctcgt tccggagctg ggtatctcaa atctgctttc atccagccac   1020

tgcccaaagc catcttcctg cctactggat gcttacagtg actgtggata cggggggttcc  1080

ctttccccat tcagtgacat gtcctctctg cttggtgtaa accattcttg ggaggacact   1140

tttgccaatg aactctttcc ccagctgatt agtgtctaag gaatgatcca atactgttgc   1200

ccttttcctt gactattaca ctgcctggag gatagcagag aagcctgtct gtacttcatt   1260

caaaaagcca aaatagagag tatacagtcc tagagaattc ctctatttgt tcagatctca   1320

tagatgaccc ccaggtattg tcttttgaca tccagcagtc caaggtattg agacatatta   1380

ctggaagtaa gaaatattac tataattgag aactacagct tttaagattg tacttttatc   1440

ttaaaagggt ggtagttttc cctaaaatac ttattatgta agggtcatta gacaaatgtc   1500

ttgaagtaga catggaattt atgaatggtt ctttatcatt tctcttcccc ctttttggca   1560
```

```
tcctggcttg cctccagttt taggtccttt agtttgcttc tgtaagcaac gggaacacct   1620

gctgaggggg ctctttccct catgtatact tcaagtaaga tcaagaatct tttgtgaaat   1680

tatagaaatt tactatgtaa atgcttgatg gaattttttc ctgctagtgt agcttctgaa   1740

aggtgctttc tccatttatt taaaactacc catgcaatta aaaggtacaa tgcaaaaaaa   1800

aaaaaaaaaa                                                          1810
```

<210> SEQ ID NO 140
<211> LENGTH: 4
<212> TYPE: PRT
<213> ORGANISM: Unknown
<220> FEATURE:
<223> OTHER INFORMATION: Description of Unknown:
"KDEL" motif peptide

<400> SEQUENCE: 140

Lys Asp Glu Leu
1

<210> SEQ ID NO 141
<211> LENGTH: 4
<212> TYPE: PRT
<213> ORGANISM: Mus musculus

<400> SEQUENCE: 141

Asn Pro Gly Tyr
1

<210> SEQ ID NO 142
<211> LENGTH: 4
<212> TYPE: PRT
<213> ORGANISM: Mus musculus

<400> SEQUENCE: 142

Asn Pro Asp Tyr
1

<210> SEQ ID NO 143
<211> LENGTH: 4
<212> TYPE: PRT
<213> ORGANISM: Mus musculus

<400> SEQUENCE: 143

Arg Ser Arg Ser
1

<210> SEQ ID NO 144
<211> LENGTH: 6
<212> TYPE: PRT
<213> ORGANISM: Mus musculus

<400> SEQUENCE: 144

```
Arg Ser Arg Ala Ser Tyr
1               5
```

<210> SEQ ID NO 145
<211> LENGTH: 6
<212> TYPE: PRT
<213> ORGANISM: Mus musculus

<400> SEQUENCE: 145

```
Arg Ala Gly Ser Arg Phe
1               5
```

<210> SEQ ID NO 146
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 146

His His His His His His
1               5

<210> SEQ ID NO 147
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
caccgttcaa atcctactgc cagacgtgtg ctgtccgtct ggcagtagga tttgaac        57

<210> SEQ ID NO 148
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Phe Lys Ser Tyr Cys Gln
1               5

<210> SEQ ID NO 149
<211> LENGTH: 7
<212> TYPE: PRT
<213> ORGANISM: Mus musculus

<400> SEQUENCE: 149

Lys Tyr Leu Tyr Tyr Val Glu
1               5

<210> SEQ ID NO 150
<211> LENGTH: 7
<212> TYPE: PRT
<213> ORGANISM: Mus musculus

<400> SEQUENCE: 150

Lys Val Leu Tyr Tyr Val Glu
1               5

<210> SEQ ID NO 151
<211> LENGTH: 88
<212> TYPE: PRT
<213> ORGANISM: Mus musculus
<220> FEATURE:
<221> NAME/KEY: MOD_RES
<222> LOCATION: (37)..(37)
<223> OTHER INFORMATION: Pro or Arg
<220> FEATURE:
<221> NAME/KEY: MOD_RES
<222> LOCATION: (49)..(49)
<223> OTHER INFORMATION: His or Leu
<220> FEATURE:
<221> NAME/KEY: MOD_RES

```
<222> LOCATION: (63)..(63)
<223> OTHER INFORMATION: Gln or Leu
<220> FEATURE:
<221> NAME/KEY: MOD_RES
<222> LOCATION: (64)..(64)
<223> OTHER INFORMATION: Asp or Val
<220> FEATURE:
<221> NAME/KEY: MOD_RES
<222> LOCATION: (87)..(88)
<223> OTHER INFORMATION: This region may encompass "Trp Asp" or is not
      present

<400> SEQUENCE: 151

Met Asp Arg Val Val Leu Gly Trp Thr Ala Val Phe Trp Leu Thr Ala
1               5                   10                  15

Met Val Glu Gly Leu Gln Val Thr Val Pro Asp Lys Lys Lys Val Ala
            20                  25                  30

Met Leu Phe Gln Xaa Thr Val Leu Arg Cys His Phe Ser Thr Ser Ser
        35                  40                  45

Xaa Gln Pro Ala Val Val Gln Trp Lys Phe Lys Ser Tyr Cys Xaa Xaa
    50                  55                  60

Arg Met Gly Glu Ser Leu Gly Met Ser Ser Pro Arg Ala Gln Ala Leu
65                  70                  75                  80

Ser Lys Arg Asn Leu Glu Trp Asp
                85


<210> SEQ ID NO 152
<211> LENGTH: 41
<212> TYPE: DNA
<213> ORGANISM: Homo sapiens

<400> SEQUENCE: 152

gggggccagc acgtgaccga gaaactttgg cagtcgcggc a                           41
```

METHODS OF TREATING METABOLIC DISEASE

This application claims priority to U.S. Provisional Patent Application No. 61/919,367, filed on Dec. 20, 2013, the contents of which is hereby incorporated by reference in its entirety.

GOVERNMENT INTERESTS

This invention was made with government support under N.I.H. Grant Number DK66518-08. As such the United States government has certain rights in this invention.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

Throughout this application, various publications are referenced. The disclosures of these publications in their entireties are hereby incorporated by reference into this application in order to more fully describe the state of the art as known to those skilled therein as of the date of the invention described and claimed herein.

SEQUENCE LISTING

The instant application contains a Sequence Listing which has been submitted electronically in ASCII format and is hereby incorporated by reference in its entirety. Said ASCII copy, created on Mar. 17, 2015, is named 19240.1030US2_SL.txt and is 288,360 bytes in size.

BACKGROUND

Metabolic risk factors can lead to heart disease, diabetes and stroke. Metabolic syndrome is becoming more common due to a rise in obesity rates in adults.

Type 2 diabetes (T2DM) afflicts 246 million people worldwide, including 21 million in the United States. Another 54 million Americans have pre-diabetes. If the incidence of T2DM continues to increase at the present rate, one in three Americans, and one in two minorities born in 2000 will develop diabetes in their lifetime (Cowie C, MMWR 52: 833-837, 2003). In addition to the human cost, direct medical costs associated with diabetes in the United States currently exceed $132 billion a year and consume ~10% of health care costs in industrialized nations (Saltiel A R Cell 104: 517-529, 2001). Diabetes is the leading cause of both end stage renal disease and blindness (in people aged 20-74 years), and its association with cardiovascular disease increases mortality rates two-fold.

Although intensive genetic analyses of human populations have confirmed contributory roles for some specific genes, these cannot account—even in the aggregate—for powerful genetic predisposition T2DM. The link between obesity and diabetes is the result of obesity-related insulin resistance stress on the insulin-producing cells of the pancreas. Genetic differences and differences in numbers of insulin producing beta cells can cause differential susceptibility among individuals to T2DM. Therefore, there is a need to identify relevant genes associated with susceptibility to diabetes. This invention addresses this need and provides treatment strategies for manipulating beta cells and treating T2DM.

SUMMARY OF THE INVENTION

In one aspect, the invention provides a method of treating a metabolic disease in a subject, the method comprising administering to the subject a therapeutically effective amount of an agent which increases expression of Ildr2 mRNA or ILDR2 protein.

In one embodiment, the metabolic disease is a fatty liver disease, dyslipidemia, metabolic syndrome, a cardiovascular disease, obesity, a leptin disorder, or any combination thereof. In one embodiment, the fatty liver disease is hepatic steatosis, non-alcoholic steatohepatitis, non-alcoholic fatty liver disease, elevated liver cholesterol level, elevated liver triglyceride level, elevated liver fatty acid level, elevated liver LDL-cholesterol level, elevated liver VLDL cholesterol level, or elevated liver non-HDL cholesterol level, or any combination thereof. In one embodiment, the dyslipidemia is hyperlipidemia, mixed dyslipidemia, hypercholesterolemia, polygenic hypercholesterolemia, hypertriglyceridemia, hyperfattyacidemia, elevated ApoB, elevated cholesterol, elevated LDL-cholesterol, elevated VLDL-cholesterol, or elevated non-HDL cholesterol, or any combination thereof. In one embodiment, the cardiovascular disease is coronary heart disease, acute coronary syndrome, early onset coronary heart disease, or atherosclerosis, or any combination thereof. In one embodiment, the leptin disorder is hyperleptinemia, or tissue leptin resistance, or any combination thereof. In one embodiment, the treatment improves cardiovascular outcome. In one embodiment, the treatment results in slowed progression and/or amelioration of the metabolic disease. In one embodiment, the expression of Ildr2 mRNA or ILDR2 protein is increased in liver tissue. In one embodiment, the expression of Ildr2 mRNA or ILDR2 protein is increased in hepatocytes. In one embodiment, the agent is a nucleic acid which comprises a nucleic acid sequence encoding an ILDR2 protein, an ILDR2 polypeptide, an ILDR2 isoform, or an ILDR2 functional fragment. In one embodiment, the nucleic acid is administered to the subject by an adenovirus or a adeno-associated virus. In one embodiment, the agent is an ILDR2 protein, an ILDR2 polypeptide, an ILDR2 isoform, or an ILDR2 functional fragment. In one embodiment, the agent is a peptide having SEQ ID NO: 2-9. In one embodiment, the agent is an inhibitor of PERK, IRE1a, active ATF6, or spliced XBP1. In one embodiment, the inhibitor of PERK, IRE1a, active ATF6, or spliced XBP1 is a RNAi. In one embodiment, the agent is an ER stress inhibitor. In one embodiment, the subject is administered an additional therapy. In one embodiment, the additional therapy is a lipid lowering therapy. In one embodiment, the lipid lowering therapy is a therapeutic lifestyle change, a HMG-CoA reductase inhibitor, niacin, a fibrate, a cholesterol absorption inhibitor, a MTP inhibitor, or any combination thereof. In one embodiment, the subject has type II diabetes or insulin resistance. In one embodiment, the expression of ILDR2 protein in a subject is measured using an antibody. In one embodiment, the antibody specifically binds to a peptide having SEQ ID NOs: 2-9, or an ILDR2 protein, an ILDR2 polypeptide, an ILDR2 isoform, or any fragment thereof. In one embodiment, the subject has a reduced level of expression of Ildr2 mRNA or ILDR2 protein compared to the level of expression of Ildr2 mRNA or ILDR2 protein in a subject without a metabolic disease. In one embodiment, the level of expression is determined before administrating to the subject the therapeutically effective amount of an agent which increases expression of Ildr2 mRNA or ILDR2 protein. In one embodiment, the expression of ILDR2 protein in a subject is measured using an antibody. In one embodiment, the antibody specifically binds to a peptide having SEQ ID NOs: 2-9, or an ILDR2 protein, an ILDR2 polypeptide, an ILDR2 isoform, or any fragment thereof.

In another aspect, the invention provides a method of decreasing lipid levels in a subject, the method comprising administering to the subject a therapeutically effective amount of an agent which increases expression of Ildr2 mRNA or ILDR2 protein.

In one embodiment, the lipid level is a cholesterol level, triglyceride level, ApoB level, LDL-cholesterol level, VLDL-cholesterol level, small LDL-particle level, small VLDL-particle level, non-HDL-cholesterol level, phospholipid level, or fatty acid level, or any combination thereof. In one embodiment, the level is the concentration in blood plasma. In one embodiment, the level is the concentration in liver. In one embodiment, the lipid level is decreased relative to a lipid level in the subject before administrating the therapeutically effective amount of an agent which increases expression of Ildr2 mRNA or ILDR2 protein. In one embodiment, the expression of Ildr2 mRNA or ILDR2 protein is increased in liver tissue. In one embodiment, the expression of Ildr2 mRNA or ILDR2 protein is increased in hepatocytes. In one embodiment, the agent is a nucleic acid which comprises a nucleic acid sequence encoding an ILDR2 protein, an ILDR2 polypeptide, an ILDR2 isoform, or an ILDR2 functional fragment. In one embodiment, the nucleic acid is administered to the subject by an adenovirus or a adeno-associated virus. In one embodiment, the agent is an ILDR2 protein, an ILDR2 polypeptide, an ILDR2 isoform, or an ILDR2 functional fragment. In one embodiment, the agent is a peptide having SEQ ID NO: 2-9. In one embodiment, the agent is an inhibitor of PERK, IRE1a, active ATF6, or spliced XBP1. In one embodiment, the inhibitor of PERK, IRE1a, active ATF6, or spliced XBP1 is a RNAi. In one embodiment, the agent is an ER stress inhibitor. In one embodiment, the subject is administered an additional therapy. In one embodiment, the additional therapy is a lipid lowering therapy. In one embodiment, the lipid lowering therapy is a therapeutic lifestyle change, a HMG-CoA reductase inhibitor, niacin, a fibrate, a cholesterol absorption inhibitor, a MTP inhibitor, or any combination thereof. In one embodiment, the subject has type II diabetes or insulin resistance. In one embodiment, the expression of ILDR2 protein in a subject is measured using an antibody. In one embodiment, the antibody specifically binds to a peptide having SEQ ID NOs: 2-9, or an ILDR2 protein, an ILDR2 polypeptide, an ILDR2 isoform, or any fragment thereof. In one embodiment, the subject has a reduced level of expression of Ildr2 mRNA or ILDR2 protein compared to the level of expression of Ildr2 mRNA or ILDR2 protein in a subject without a metabolic disease. In one embodiment, the level of expression is determined before administrating to the subject the therapeutically effective amount of an agent which increases expression of Ildr2 mRNA or ILDR2 protein. In one embodiment, the expression of ILDR2 protein in a subject is measured using an antibody. In one embodiment, the antibody specifically binds to a peptide having SEQ ID NOs: 2-9, or an ILDR2 protein, an ILDR2 polypeptide, an ILDR2 isoform, or any fragment thereof.

In another aspect, the invention provides a method of increasing expression of Ildr2 mRNA or ILDR2 protein in a hepatocyte, the method comprising contacting the cell with an agent which increases expression of the Ildr2 mRNA or ILDR2 protein.

In one embodiment, the agent is a nucleic acid which comprises a nucleic acid sequence encoding an ILDR2 protein, an ILDR2 polypeptide, an ILDR2 isoform, or an ILDR2 functional fragment. In one embodiment, the nucleic acid is administered to the subject by an adenovirus or a adeno-associated virus. In one embodiment, the agent is an ILDR2 protein, an ILDR2 polypeptide, an ILDR2 isoform, or an ILDR2 functional fragment. In one embodiment, the agent is a peptide having SEQ ID NO: 2-9. In one embodiment, the agent is an inhibitor of PERK, IRE1a, active ATF6, or spliced XBP1. In one embodiment, the inhibitor of PERK, IRE1a, active ATF6, or spliced XBP1 is a RNAi. In one embodiment, the agent is an ER stress inhibitor. In one embodiment, the subject is administered an additional therapy. In one embodiment, the additional therapy is a lipid lowering therapy. In one embodiment, the lipid lowering therapy is a therapeutic lifestyle change, a HMG-CoA reductase inhibitor, niacin, a fibrate, a cholesterol absorption inhibitor, a MTP inhibitor, or any combination thereof. In one embodiment, the subject has type II diabetes or insulin resistance. In one embodiment, the expression of ILDR2 protein in a subject is measured using an antibody. In one embodiment, the antibody specifically binds to a peptide having SEQ ID NOs: 2-9, or an ILDR2 protein, an ILDR2 polypeptide, an ILDR2 isoform, or any fragment thereof. In one embodiment, the subject has a reduced level of expression of Ildr2 mRNA or ILDR2 protein compared to the level of expression of Ildr2 mRNA or ILDR2 protein in a subject without a metabolic disease. In one embodiment, the level of expression is determined before administrating to the subject the therapeutically effective amount of an agent which increases expression of Ildr2 mRNA or ILDR2 protein. In one embodiment, the expression of ILDR2 protein in a subject is measured using an antibody. In one embodiment, the antibody specifically binds to a peptide having SEQ ID NOs: 2-9, or an ILDR2 protein, an ILDR2 polypeptide, an ILDR2 isoform, or any fragment thereof.

In another aspect, the invention provide a method of treating fatty liver disease in a subject, the method comprising administering to the subject a therapeutically effective amount of an agent which increases expression of Ildr2 mRNA or ILDR2 protein. In one embodiment, the agent is a nucleic acid which comprises a nucleic acid sequence encoding an ILDR2 protein, an ILDR2 polypeptide, an ILDR2 isoform, or an ILDR2 functional fragment. In one embodiment, the nucleic acid is administered to the subject by an adenovirus or a adeno-associated virus. In one embodiment, the agent is an ILDR2 protein, an ILDR2 polypeptide, an ILDR2 isoform, or an ILDR2 functional fragment. In one embodiment, the agent is a peptide having SEQ ID NO: 2-9. In one embodiment, the agent is an inhibitor of PERK, IRE1a, active ATF6, or spliced XBP1. In one embodiment, the inhibitor of PERK, IRE1a, active ATF6, or spliced XBP1 is a RNAi. In one embodiment, the agent is an ER stress inhibitor.

In another aspect, the invention provides a method of decreasing liver fat deposits in a subject, the method comprising administering to the subject a therapeutically effective amount of an agent which increases expression of Ildr2 mRNA or ILDR2 protein. In one embodiment, the agent is a nucleic acid which comprises a nucleic acid sequence encoding an ILDR2 protein, an ILDR2 polypeptide, an ILDR2 isoform, or an ILDR2 functional fragment. In one embodiment, the nucleic acid is administered to the subject by an adenovirus or a adeno-associated virus. In one embodiment, the agent is an ILDR2 protein, an ILDR2 polypeptide, an ILDR2 isoform, or an ILDR2 functional fragment. In one embodiment, the agent is a peptide having SEQ ID NO: 2-9. In one embodiment, the agent is an inhibitor of PERK, IRE1a, active ATF6, or spliced XBP1. In one embodiment, the inhibitor of PERK, IRE1a, active ATF6, or spliced XBP1 is a RNAi. In one embodiment, the agent is an ER stress inhibitor.

In another aspect, the invention provides a method of modifying liver lipid metabolism in a subject, the method comprising administering to the subject a therapeutically effective amount of an agent which increases expression of Ildr2 mRNA or ILDR2 protein.

In another aspect, the invention provides a method of modifying liver lipid metabolism in a subject, the method comprising administering to the subject a therapeutically effective amount of an agent which decreases expression of Ildr2 mRNA or ILDR2 protein.

In another aspect, the invention provides a method of modifying ER stress responses in a subject, the method comprising administering to the subject a therapeutically effective amount of an agent which increases expression of Ildr2 mRNA or ILDR2 protein.

In another aspect, the invention provides a method of modifying ER stress responses in a subject, the method comprising administering to the subject a therapeutically effective amount of an agent which decreases expression of Ildr2 mRNA or ILDR2 protein.

BRIEF DESCRIPTION OF THE FIGURES

This patent or application file contains at least one drawing executed in color. Copies of this patent or patent application publication with color drawing(s) will be provided by the Office upon request and payment of the necessary fee.

(FIG. 2A) GT1-7 cells. ILDR2-isoform 2-YFP merges with DsRed-ER probe to produce a yellow signal over the ER, but does not merge with the red DsRed-PM probe. (FIG. 2B) Hepa1c1c7 cells. The green ILDR2-isoform 4-YFP probe merges with the red DsRed-ER probe to produce an orange signal over the ER; expression levels of labeled proteins are less uniform than in GT1-7 cells. The red DsRed-PM and green ILDR2-YFP signals do not merge in the PM. (FIG. 2C) Hepa1c1c7 cells. N-terminal fusion of ILDR2-isoform 1 with 3×FLAG epitope co-transduced with DsRed-probes to ER. Tag geometry does not interfere with subcellular localization.

FIGS. 3A-F shows liver morphology and histology in ADKD and ADOX WT and OB mice. Chow-fed, 10-week-old B6 males were sacrificed after 24-hr fast (Fasted) or following a 24-hr fast and 12-hr refeeding (Refed). Liver morphology is shown in the upper panels and hematoxylin and eosin staining of representative sections is shown in the lower panels at 200× magnification (scale is 100 mm). Asterisk (*) identifies large droplet, macrovesicular lipid vacuoles, particularly evident in Ob sections; large open arrows (M-D) denote intra-hepatocellular Mallory-Denk-like eosinophilic material; open yellow arrows (mF) denote small droplet, microvesicular fat within hepatocytes; short double black arrows (iMO) indicate mononuclear inflammatory cells, consistent with lymphocytes; large blue arrows (ap) indicate apoptotic hepatocytes; (glyc) identifies a "clear"-appearing hepatocyte with increased glycogen content (e.g., ADOX WT 10d Refed); Portal Tract (or PT) is above the hatched line in ADKD WT 10d Fasted); (CV) is Central Vein; (PV) is Portal Vein; (BD) is Bile Duct. (FIG. 3A) Wild-type mice, 3 days p.t. with adenovirus knockdown vectors expressing RNAi for lacZ or Ildr2 (FIG. 3B) Wild-type mice, 10 days p.t. with adenovirus knockdown vectors expressing RNAi for lacZ or Ildr2 (FIG. 3C) ob/ob mice, 10 days p.t. with adenovirus knockdown vectors expressing RNAi for lacZ or Ildr2 (FIG. 3D) Wild-type mice, 3 days p.t. with adenovirus vector over-expressing GFP or Ildr2; there is no significant steatosis or inflammation (FIG. 3E) Wild-type mice, 10 days p.t. with adenovirus vector over-expressing GFP or Ildr2 (FIG. 3F) ob/ob mice, 10 days p.t. with adenovirus vector over-expressing GFP or Ildr2. As described in the text, increased apoptosis without inflammation is consistent with a primary role for ILDR2 in ER stress responses.

FIGS. 4A-B shows TG secretion analysis in ADKD and ADOX WT mice. Chow-fed, 10-week-old B6 (WT) males were intravenously injected with ADKD or ADOX vectors expressing RNAi for lacZ or Ildr2. At 7 days p.t., following a 16 hr fast, mice were intravenously injected with 15% Triton WR1339 at a dose of 500 mg/kg. Plasma (from 100 ul of blood) was collected hourly for 4 hr and TG measured. (FIG. 4A) Wild-type mice, 7 days p.t. with adenovirus knockdown vector expressing RNAi for lacZ or Ildr2; (FIG. 4B) Wild-type mice, 7 days post-transduction with adenovirus vector over-expressing GFP or Ildr2. AUC: area under the curve. Insignificant differences by AUC analysis show that hepatic lipoprotein secretion is unaffected by Triton WR1339 administration in ADKD and ADOX mice.

FIGS. 5A-D shows FPLC analysis of plasma lipoprotein fractions in ADKD and ADOX WT mice. At 7 days p.t. with either ADKD or ADOX vectors, plasma from 6 wild-type mice was collected, pooled and TCH and TG profiles were analyzed by FPLC using Sepharose 6 Fast Flow columns. HDL, high-density lipoprotein; LDL, low-density lipoprotein; VLDL, very low-density lipoprotein. (FIG. 5A) TCH profile in wild-type mice, 7 days p.t. with adenovirus knockdown vector expressing RNAi for lacZ or Ildr2; (FIG. 5B) TCH profile in wild-type mice, 7 days p.t. with adenovirus vector over-expressing GFP or Ildr2; (FIG. 5C) TG profile in wild-type mice, 7 days after adenovirus knockdown vector expressing RNAi for lacZ or Ildr2; (FIG. 5D) TG profile in wild-type mice, 7 days p.t. with adenovirus vector over-expressing GFP or Ildr2. These experiments show an increase in plasma TG (as VLDL) in ADKD mice but not in ADOX mice. TCH shifts in ADKD mice from HDL to LDL and VLDL, while in ADOX mice the decrease in HDL is accompanied by an increase in VLDL only.

(FIG. 6A) Expression in wild-type mice, 3 days p.t. with adenovirus knockdown vector expressing RNAi for lacZ or Ildr2; (FIG. 6B) Expression in wild-type mice, 10 days p.t. with adenovirus knockdown vector expressing RNAi for lacZ or Ildr2; (FIG. 6C) Expression in wild-type mice, 10 days p.t. with adenovirus vector over-expressing GFP or Ildr2; (FIG. 6D) Expression in wild-type mice, 3 days p.t. with adenovirus knockdown vector expressing RNAi for lacZ or Ildr2: (FIG. 6E) Expression in ob/ob mice, 10 days p.t. with adenovirus knockdown vector expressing RNAi for lacZ or Ildr2; (FIG. 6**F) Expression in ob/ob mice, 10 days p.t. with adenovirus vector over-expressing GFP or Ildr2. Changes in transcriptional profiles appear to be secondary to changes in lipid content.

FIGS. 7A-B shows relative expression of selected genes in ADKD and ADOX primary hepatocytes. To identify short-term effects of changes in Ildr2 expression, hepatocytes from five 10-week-old B6 mice were extracted, pooled and plated into individual wells and exposed, in triplicate, for 24 hr to ADOX or ADKD viral vectors. RNA was extracted, transcribed into cDNA, and expression was determined by qPCR. (FIG. 7A) Expression in hepatocytes transduced with adenovirus knockdown vector expressing RNAi for lacZ or Ildr2; (FIG. 7B) Expression in hepatocytes transduced with adenovirus vector over-expressing GFP or Ildr2. These results recapitulate those seen the in vivo studies.

FIGS. 8A-B shows expression of Ildr2 in liver is increased by adiposity through high-fat diet or leptin deficiency. Expression of Ildr2 was determined by qPCR, normalized to 36B4 in mice sacrificed after either fasting for 24 hr or after fasting for 24 hr and followed by a 12-hr refeeding period. (FIG. 8A) Wild type B6 mice at 6 weeks of age were fed ad libitum either chow or a high fat diet (60% of kcal from fat) for 3 additional months. (FIG. 8B) Chow-fed wild type B6 and leptin-deficient OB mice (B6.Cg-Lepob/J) were purchased at 9 weeks and sacrificed at 10 weeks of age. Wild-type mice fed a high fat diet and genetically obese mice showed a similar (3.6 to 3.7-fold) increase in Ildr2 liver expression compared to age-matched wild-type mice (p value, 0.01) regardless of feeding status.

FIGS. 9A-D shows Respiratory Exchange Ratio (RER) in ADKD and ADOX WT and OB mice. Mice were chow-fed, 10-week-old B6 (WT) or B6.V-Lepob/J (OB) males, at 4 to 5 days p.t. with adenovirus knockdown vectors expressing RNAi for lacZ or Ildr2 or with adenovirus vectors over-expressing GFP or Ildr2. Data shown are mean 6 SEM (8 mice per group) and run in a TSE systems indirect calorimeter for 48 hr. (FIG. 9A) WT ADKD; (FIG. 9B) OB ADKD; (FIG. 9C) WT ADOX; (FIG. 9D) OB ADOX. ADKD mice show decreased RER at night, whereas ADOX mice show no differences, day or night. AUC calculations are shown in Table 9.

FIGS. 10A-D shows ipGTT in WT and OB mice 7 days p.t. At 7 days p.t. with adenovirus knockdown vectors expressing RNAi for lacZ or Ildr2 (left) or with adenovirus vectors over-expressing GFP or Ildr2 (right), the 10-week-old chow-fed male B6 mice that were used in the 10 day experiments were injected intraperitoneally after 12 hr fast with 2 g/kg glucose. The mice used in this experiment are the same mice that on which indirect calorimetry was conducted on day 5 p.t. (FIG. 10A) WT ADKD; (FIG. 10B) OB ADKD; (FIG. 10C) WT ADOX; (FIG. 10D) OB ADOX. In both ADKD and ADOX animals, IPGTT was unaffected.

FIGS. 15A-D show the phenotypes of those obese B6.DBA congenic mice were reduced β-cell mass (FIG. 15A), reduced plasma insulin/glucose ratio (FIG. 15B), reduced glucose tolerance (FIG. 15C), and persistent mild hypoinsulinemic hyperglycemia (FIG. 15D).

FIGS. 16A-B show plasma insulin/glucose ratios and hyperglycemic clamps in age-grouped 1jc congenic males. FIG. 16A: Fasting plasma insulin/glucose ratios in 30- and 62-day old 1jc Lepob/ob B/B and D/D male mice, chow-fed since weaning Asterisk (*) indicates significant difference between B/B and D/D animals; p-value <0.05 for 2-tailed t-test. FIG. 16B: Hyperglycemic clamping in 100-day old 1jc males on Surwit Diet for 18 weeks. 1jc DD male mice fed a Surwit diet for 18 wks were clamped at a blood glucose concentration of 250 mg/dl for 1 hr and serum insulin concentrations measured at 1 hr. Asterisk (*) indicates p-value <0.05 for 2-tailed t-test.

FIGS. 17A-B show the relationship between islet histology and insulin secretion. FIG. 17A: Islet histology in 21-day old ljcd Lepob/ob B/B and D/D male mice. 4 μm pancreatic sections from 21-day old ljcd Lepob/ob B/B and D/D male mice were insulin-stained with anti-guinea pig IgG and visualized by light microscopy at 10× magnification. In D/D animals, islets were smaller and less numerous. By histomorphometry, the proportion of small islets (250-2000 μm2) in 21-day old Lepob/ob males was greater in D/D (1jc and ljcd) mice (73%) than in B/B (60%); whereas the proportion of large islets (10,000-50,000 μm2) was lower (9% in D/D and 14% in B/B). FIG. 17B: In vitro glucose-stimulated insulin secretion in pancreatic islets in 28-day old 1jc Lepob/ob B/B and D/D males. Each congenic genotype group consisted of 3 male animals. Negative control consisted of 3 4-week old diabetes-prone Leprdb/db KsJ male animals that are hypo-responsive to glucose stimulation; positive control was 3 4-week old insulin-resistant animals segregating for a diabetes-susceptibility QTL on Chr5@78cM, characterized by hyperglycemia and hyperinsulinemia. B/B and D/D show dose response, but no B/B vs. D/D difference at any concentration of glucose. Response to 10 mM arginine in the same animals confirms that the β-cells of the B/B and D/D congenics are comparable with regard to insulin release to a non-glucose stimulus. The 0 mM arginine control in B/B is shown to establish baseline insulin levels.

FIGS. 18A-B show B-cell mass and replication rates in ljcd $Lep^{ob/ob}$ males. FIG. 18A: Relative β-cell area in 20-, 60, and 150-day old Lepob/ob males segregating for B and D ljcd congenic intervals. In 60 and 150-day old males segregating for the D/D sub-congenic interval, relative β-cell mass was approximately half that of B/B littermates; B/D animals were intermediate at 150 days. N=10 for each of the 3 groups of animals. Mean+/−SEM. The asterisk (*) indicates that p<0.05 for D/D vs. B/B at 60 days, and D/D and B/D vs B/B at 150 days. These findings are consistent with in vivo data showing onset of elevated blood glucose at rest and during ipGTT by 60 days. FIG. 18B: β-cell replication rates (Ki67) in 1- and 21-day old Lepob/ob B/B and D/D ljcd males. To estimate the proportion of dividing cells, the number of Ki67-positive β-cells was normalized to the total number of insulin-positive cells. Replication of β-cells in 1-day old D/D males was ~⅓ that of B/B littermates (p=0.017). This difference, not present in 21-day old animals, was probably due to normally reduced β-cell replication by the time of weaning. Mean+/−SEM. The asterisk (*) indicates that p<0.05 for D/D vs. B/B in 1-day old animals.

FIG. 20A: Tissue-specific expression analysis of genes in the “variable” portion of the minimum congenic interval. Data for relative expression (B/B to D/D) for hypothalamus, islets, liver and EDL-muscle are displayed graphically and numerically below the graph. 21-day old DD and BB Lepob/ob 1jc congenic animals males were analyzed using Affymetrix #430A microarrays. FIG. 20B: Liver expression of ILDR2 in 1jc B/B and D/D males from 21-120 days. Samples from Lepob/ob 1jc males were analyzed by qPCR.

FIG. 21A: Developmental expression of zebra fish ILDR2 (Lisch-like) and Lsr-like orthologs. ILDR2 RNA was hybridized in situ to whole-mount zebra fish embryos at 48 hours post-fertilization (hpf), dorsal view with anterior towards the top; and 72 hpf, lateral view with anterior towards the top, ventral towards the right and yolk removed. Lsr-like RNA was hybridized at 48 hpf and 34 hpf. Ildr2 (Lisch-like) panels show ventral views of embryos with yolks removed and anterior towards the top. Lsr-like panels show the same image captured in the focal plane of the anterior (ap) and posterior (pp) pancreatic buds, respectively. i, intestine; ph, pharynx; pn, pronephric ducts; 1, liver; ap, anterior pancreatic bud; pp, posterior pancreatic bud; p, pancreas (after anterior and posterior bud fusion); b, brain; o, otic vesicle. FIG. 21B: Morpholino knockdown of ILDR2 (Lisch-like) and Lsr-like orthologs at 48 hpf. Two dimensional ventral views (anterior towards top) of confocal stacks of 48 hpf embryos, uninjected or injected with 15 ng morpholino: control, Lsr-like sp1, and ILDR2 (Lisch-like) ATG. Gut-GFP transgene expression (green); insulin immunolabelling (red).

FIG. 23A: Fat mass measured at 3 and 6 months; body weight and lean mass measured at 6 months. FIG. 23B: BG, blood glucose, measured in W87* and WT males following 24 hr fast and postprandially 12 hrs after fast. (*=p<0.05; T test; n=10 WT and 11 W87*).

FIG. 25A: Isolated primary heptocytes were extracted from 2 month old wild type B6 mice. The hepatocytes were either not transfected, transfected with scrambled siRNA, siRNA targeting Ldlr (a positive control showing the assay was working), or siRNA targeting Ildr2. The cells were incubated for 2 hours in the presence of DiI-LDL. The red indicates the LDL that is taken up by the cell (nuclei are stained with Dapi-blue). FIG. 25B: Primary hepatocytes were isolated from both wildtype and W87* age matched male mice. Cells were incubated at 4° C. and 37° C. in the presence of bodipy-labled LDL to determine binding and internalization of LDL, respectively. The cells were then analyzed by facs and an average of X thousand cells per mouse per condition were measured for fluorescence intensity. The W87* isolated primary hepatocytes showed decreases in both binding and internalization of LDL compared to the wildtype mice.

FIG. 28 shows the phenotype after Ildr2 knockdown or overexpression for 10 days in 10 week-old WT mice. 24 hrs fasted or 12 hrs refed. Adenovirus were made by invitrogen's adenovirus expression system using pAd/CMV-V5 DEST vector for OE and BLOCK-iT Adenoviral RNAi Expression System for KD. 10 days after Ildr2 knockdown or overexpression by adenovirus infection, the fasting-refeeding experiment was performed. P value's color indicate that values are significantly increased in red and significantly decreased in blue. ILDR2 knockdown liver were enlarged and had increased lipid droplet. Plasma TG and TC were increased in knockdown mice. Hepatic TG and TC were also increased. Regarding overexpression mice, ILDR2 liver were enlarged compared to control, but HE stain liver sections were not different. Plasma TG and TC levels were increased but hepatic TG and TC were markedly decreased. This results suggested that Ildr2 is involved in positively regulate lipid metabolism.

FIG. 29 shows relative gene expression in the liver from qRT-PCR data in WT mice. srebp1c and its target genes FAS and ACCC were decreased. TG synthesis genes were also decreased in knockdown mice. Regarding overexpression mice, these lipogenic genes expression were opposite to knockdown mice.

FIG. 32 shows the phenotype after Ildr2 knockdown or overexpression for 10 days in 10 week-old ob/ob mice. 24 hrs fasted or 12 hrs refed. To determine whether consistent with metabolic effects of wild-type mice, we infected ob/ob mice with knockdown and overexpression adenovirus. Knockdown liver were markedly enlarged and had increased lipid droplet compared to control. Both plasma fasted and refed TG levels were higher than control mice. Plasma TC levels were slightly higher in refed state. Consistent with WT knockdown mice, hepatic TG and TC were increased in knockdown mice. Regarding overexpression mice, overexpressing ILDR2 improve hepatic steatosis. Plasma TG and TC levels were no difference but hepatic TG and TC were markedly decreased. These results of hepatic lipids levels were totally consistent with both knockdown and overexpression WT mice.

FIG. 33 shows relative gene expression in the liver from qRT-PCR data in ob/ob mice. Regarding gene expression, consistent with knockdown WT mice, srebp1c and its target genes and TG synthesis genes were decreased in knockdown ob mice. In overexpression mice, these lipogenic genes expression were opposite to knockdown mice. Genes expression levels were also totally consistent with WT mice experiment.

FIGS. 41A-H shows the sequences of the mouse peptides used to make antibodies to the LL protein. FIG. 41A shows the amino acid sequence of the ILDR2 α-intracellular domain antigen (amino acid #298-401) (SEQ ID NO: 2). FIG. 41B shows the amino acid sequence of the ILDR2 α-extracellular domain antigen (amino acid #22-186) (SEQ ID NO: 3). FIG. 41C shows the amino acid sequence of the human (ILDR2) cytoplasmic domain corresponding to amino acid 298-401 of Mouse ILDR2 (SEQ ID NO: 4). FIG. 41D shows the amino acid sequence of the human (ILDR2) intracellular domain corresponding to amino acid 22-186 of Mouse ILDR2 (SEQ ID NO: 5). FIG. 41E shows the ILDR2 α-intracellular domain antigen (amino acid #354-363) for the anti-intracellular-ILDR2 antibodies of the invention (SEQ ID NO: 6). FIG. 41F shows the ILDR2 α-extracellular domain antigen (amino acid #124-136) for the anti-extracellular-ILDR2 antibodies of the invention (SEQ ID NO: 7). FIG. 41G shows the amino acid sequence of the human (ILDR2) cytoplasmic domain corresponding to amino acid 354-363 of Mouse ILDR2 (SEQ ID NO: 8). FIG. 41H shows the amino acid sequence of the human (ILDR2) extracellular domain corresponding to amino acid 124-136 of Mouse ILDR2 (SEQ ID NO: 9).

FIG. 42 shows the DBA mouse ILDR2 gene 5'UTR, transcript and 3'UTR (SEQ ID NO:10). Shown are the DBA sequence of the 5'UTR, coding exons and 3'UTR of the mouse Ildr2 gene. The positions corresponding to B6 variants are shown in uppercase and highlighted clear. The 5'UTR is underlined, and each exon is alternately highlighted in gray; the 3'UTR is underlined.

FIG. 43 shows variant positions in the mouse ILDR2 anti-sense Transcript in DBA and B6 mice (SEQ ID NO: 11). Shown is the genomic DBA sequence corresponding to the anti-sense transcript, 5330438103RiK. The sequences of the intron preceding exon 8 are underlined. Exon 8 is highlighted gray. The intron between exons 8 and 9 is italicized. Exon 9 is highlighted gray and underlined. The intronic sequences telomeric to exon 9 and underlying the anti-sense transcript are shown in bold.

FIG. 44 shows SNP variants and positions in the mouse ILDR2 anti-sense Transcript in DBA (SEQ ID NO: 12) and B6 mice (SEQ ID NO: 13). Shown is a display generated by a BLAT analysis of the anti-sense transcript of the Ildr2 gene in mouse strain DBA/2J on the reference c57BL/6j genomic sequence. Exons 8 and 9 are underlined.

FIG. 46 shows an alignment of comparative amino acid sequences for ILDR2 (LL) and related proteins. LL_Musmus (SEQ ID NO: 18); LL_Ratnor (SEQ ID NO: 19); LL_Bostau (SEQ ID NO: 20); LL_Canfam (SEQ ID NO: 21); LL_Homsap (SEQ ID NO: 22); LL_Pantro (SEQ ID NO: 23); LL_Macmul (SEQ ID NO: 24); LL_Feldom (SEQ ID NO: 25); LL_Mondom (SEQ ID NO: 26); LL_Galgal (SEQ ID NO: 27); LL_Xentro (SEQ ID NO:28); LL_Danrer (SEQ ID NO: 29); LSR_Homsap (SEQ ID NO: 30); LSR_Pantro (SEQ ID NO: 31); LSR_Macmul (SEQ ID NO: 32); LSR_Bostau (SEQ ID NO: 33); LSR_Canfam (SEQ ID NO: 34); LSR_Musmus (SEQ ID NO: 35); LSR_Ratnor (SEQ ID NO: 36); LSR_Mondom (SEQ ID NO: 37); LSR_Danrer (SEQ ID NO: 38); ILDR1_Homsap (SEQ ID NO: 39); ILDR1_Pantro (SEQ ID NO: 40); ILDR1_Ponpy (SEQ ID NO: 41); ILDR1_Musmus (SEQ ID NO: 42); ILDR1_Ratnor (SEQ ID NO: 43); ILDR1_Canfam (SEQ ID NO: 44); ILDR1_Xenla (SEQ ID NO: 45); ILDR1_Galgal (SEQ ID NO: 46); and ILDR1_Danrer (SEQ ID NO: 47).

FIGS. 47A-C shows spliced and unspliced sequences of the human ILDR2 (C1Orf32) Antisense RNA transcript. FIG. 47A shows the sequence of the unspliced human ILDR2 (C1Orf32) Antisense RNA transcript (SEQ ID NO: 48). FIG. 47B shows DA322725, a spliced anti-sense transcript of human ILDR2 (C1Orf32) corresponding to chr1:165156961-165228581 (SEQ ID NO: 49). FIG. 47C shows DA565656, a spliced anti-sense transcript of human ILDR2 (C1Orf32) corresponding to chr1:165156982-165225636 (SEQ ID NO 50).

FIGS. 49A-E show a schematic of the proposed effects of ER-stress on ILDR2 and downstream VLDL secretion and uptake in the liver. ER stress decreases ILDR2 (1)(FIG. 49A), causing increased VLDLR(2) (FIG. 49B). This causes increased uptake of VLDR particles in the liver (3) (FIG. 49C). Meanwhile, reduced ILDR2 also reduced VLDL secretion (4) (FIG. 49D) and suppress VLDL uptake (5) (FIG. 49E), possibly due to reduced incorporation of apoE into VLDL particles.

FIG. 55 shows an Ildr2 mRNA degradation assay, Actinomycin D was added in Hepa1c1c7 cells. Xbp1 was spliced by IRE1a in time dependent and spliced Xbp1 increased. Ildr2 mRNA transcription was decreased by IRE1a but not dominant negative K599A IRE1a.

FIG. 56A: Hepa1c1c7 cells were treated with various concentrations of tunicamycin, then harvested at 12 hrs. FIG. 56B: Hepa1c1c7 cells were treated with 10 mg/mL tunicamycin, then harvested at various time points

FIGS. 60A-D show the in vivo effects of tunicamycin on liver ILDR2 (lowering), and the protective effect of over-expressing ILDR2 in liver exposed to tunicamycin. Liver morphology and histology and Ildr2 expression in tunicamycin-treated mice is shown. Chow-fed, 10-week-old B6 males were administered tunicamycin for 72 h. FIG. 60A: Liver morphology at 72 hours post-injection in untreated and tunicamycin-treated samples. Lower panel: HE staining of representative sections. FIG. 60B: Ildr2 expression level determined by qPCR. FIG. 60C: Hepatic triglyceride increased from 16.4±5.4 to 45.0±6.7 mg/g liver (n=4). FIG. 60D. Hepatic Cholesterol increased from 7.1±1.2 to 10.6±0.9 mg/g liver. * indicates $p<0.05$; ** indicates $p<0.01$ (2 tailed t-test).

FIGS. 61A-D Liver phenotypes in tunicamycin-treated mice in which Ildr2 was overexpressed in liver. Chow-fed, 10-week-old B6 males overexpressing Ildr2 (GFP as control) in liver (3 days) were administered tunicamycin for 72 h. FIG. 61A: Liver gross morphology at 72 hours post-injection in untreated and tunicamycin-treated samples in hepatic ILDR2 overexpression mice. Lower panel: HE staining of representative sections. FIG. 61B: Ildr2 expression level determined by qPCR. FIGS. 61C and D: Measurements of hepatic triglyceride and cholesterol.

DETAILED DESCRIPTION

Figure 1:
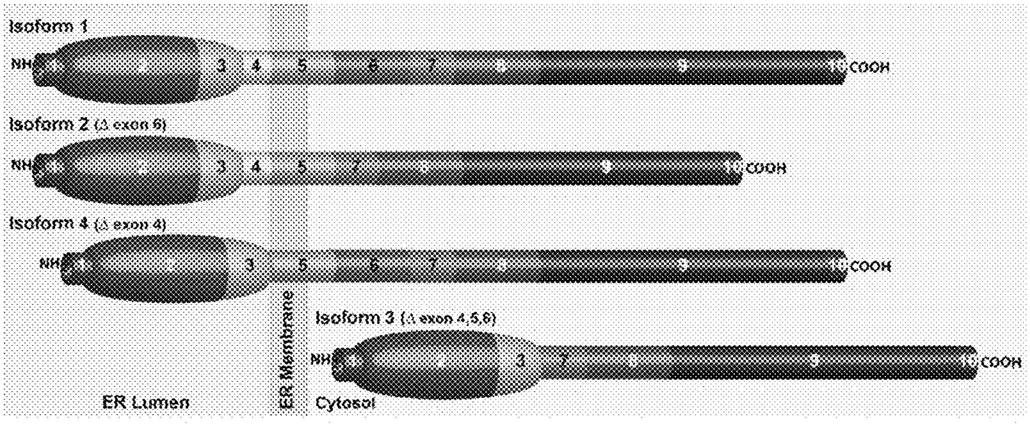
FIG. 1 shows the predicted structure of major ILDR2 isoforms. Isoform 1 (GENBANK: FJ024495.1) is full-length. There are 10 predicted exons. Exon 1 is an amino terminal signal peptide; exons 2 and 3 code for an IgV-like immunoglobulin domain; exon 4 is amino proximal to the trans-membrane domain of exon 5; exons 6-10 comprise a randomly-coiled, carboxy-terminal tail (simplified in this depiction as rod-like). Based on results shown in FIGS. 2A-C, exons 1-4 are lumenal and exons 6-10 are cytosolic. Isoform 2 (GENBANK: FJ024496.1) lacks cytosolic exon 6. Isoform 4 (GENBANK: FJ024498.1) lacks lumenal exon 4. Isoform 3 (GENBANK: FJ024497.1) lacks exons 4, 5, and 6 and, therefore has no transmembrane domain, and is depicted as entirely cytosolic.

The issued patents, applications, and other publications that are cited herein are hereby incorporated by reference to the same extent as if each was specifically and individually indicated to be incorporated by reference.

All patent applications, published patent applications, issued and granted patents, texts, and literature references cited in this specification are hereby incorporated herein by reference in their entirety to more fully describe the state of the art to which the present disclosed subject matter pertains.

As various changes can be made in the methods and compositions described herein without departing from the scope and spirit of the disclosed subject matter as described, it is intended that all subject matter contained in this application and claims, shown in the accompanying drawings, or defined in the appended claims be interpreted as illustrative, and not in a limiting sense.

DEFINITIONS

The singular forms “a,” “an,” and “the” include plural reference unless the context clearly dictates otherwise.

The term “about” is used herein to mean approximately, in the region of, roughly, or around. When the term “about” is used in conjunction with a numerical range, it modifies that range by extending the boundaries above and below the numerical values set forth. In general, the term “about” is used herein to modify a numerical value above and below the stated value by a variance of 20%.

As used herein the term “ILDR2” or “Ildr2” refers to immunoglobulin-like domain containing receptor 2. ILDR2 is also known as, “Lisch-like” (“D” or “LL”) and “C1ORF32”. “ILDR2” refers to all ILDR2 orthologs, including, but not limited to, those found in mice and humans.

As used herein the term “Ildr2 RNA” includes any RNA, for example but not limited to unprocessed RNA, any mRNA of any splice variant (isoform), which encodes a full length Ildr2 protein (ILDR2), any fragment, any protein isoform, or any Ildr2 protein variant thereof. The term Ildr2 RNA also includes an antisense RNA to any Ildr2 mRNA, including but not limited to an antisense RNA to a full length mRNA, any portion of the full length mRNA, or any splice variant.

As used herein the terms “ILDR2” and “Ildr2” which are used interchangeably, include a full length ILDR2 protein, any ILDR2 protein fragment, ILDR2 isoform, or ILDR2 protein variant thereof.

As used herein, a “ILDR2 molecule” refers to an ILDR2 protein, or a fragment thereof. A “ILDR2 molecule” can also refer to a nucleic acid (including, for example, Ildr2 RNA, genomic DNA, complementary DNA (cDNA), synthetic DNA, as well as any form of corresponding RNA) which encodes a polypeptide corresponding to an ILDR2 protein, or fragment thereof.

As used herein the term “variant” covers nucleotide or amino acid sequence variants which have about 95%, about 90%, about 85%, about 80%, about 85%, about 80%, about 75%, about 70%, or about 65% nucleotide identity, or about 95%, about 90%, about 85%, about 80%, about 85%, about 80%, about 75%, or about 70% amino acid identity, including but not limited to variants comprising conservative, or non-conservative substitutions, deletions, insertions, duplications, or any other modification. The term variant as used herein includes functional and non-functional variants, and variants with reduced or altered activity.

As used herein, the term “agent” include, but are not limited to, biological or chemical agents, such as peptides, peptidomimetics, amino acids, amino acid analogs, polynucleotides, polynucleotide analogs, nucleotides, nucleotide analogs, organic or inorganic compounds (i.e. including heteroorganic and organometallic compounds), and salts, esters, and other pharmaceutically acceptable forms of such compounds. Salts, esters, and other pharmaceutically acceptable forms of such compounds are also encompassed.

Type 2 Diabetes and ILDR2

The identification of susceptibility genes in humans is complicated by the polygenic nature of the phenotype (Cox et al, 1992, Diabetes 41:401-407). This is refected in convergent yet distinct metabolic processes producing identical phenotypes (phenocopies) in a background of gene/gene and gene/environment (e.g., obesity) interactions that characterize the disease. Clear genetic influences on the endophenotypes (intermediate phenotypes) of β cell mass/function and insulin resistance vary among ethnic groups (Pimenta et al, 1995, Jama 273:1855-1861; Gelding et al, 1995, Clin Endocrinol (Oxf) 42:255-264; Knowler et al, 1993, Care 16:216-227; Hanley et al, 2003, Diabetes 52:463-469). Although more than 20 genome scans in ethnic and racial groups have detected numerous diabetes-susceptibility intervals of modest statistical significance, many of these results have not been replicated in other populations. Despite some successes (e.g. PPARG, CAPN10, TCF7L2), the number of genes conveying diabetes can vary by race/environment (Permutt et al, 2005, J Clin Invest 115:1431-1439).

Like humans, mouse strains differ widely in susceptibility to diabetes when made obese. As described herein, the differential diabetes susceptibilities of the B6 and DBA strains segregating for the obesity mutation $Lep^{ob}$ (Clee S M, Attie A D (2007) The genetic landscape of type 2 diabetes in mice. Endocr Rev 28: 48-83) were used to identify a diabetes susceptibility QTL in B6×DBA progeny and then used congenic lines derived from the implicated interval to clone a candidate gene accounting for the QTL. Similar strategies have been used to identify QTLs (and responsible genes) for other complex phenotypes in mice (Flint J, Valdar W, Shifman S, Mott R (2005) Strategies for mapping and cloning quantitative trait genes in rodents. Nat Rev Genet 6: 271-286) such as type 1 diabetes (Todd J A (1999) From genome to aetiology in a multifactorial disease, type 1 diabetes. Bioessays 21: 164-174), diet-induced obesity (York B, Lei K, West D B (1996) Sensitivity to dietary obesity linked to a locus on chromosome 15 in a CAST/Ei× C57BL/6J F2 intercross. Mamm Genome 7: 677-681), tuberculosis susceptibility (Mitsos L M, Cardon L R, Fortin A, Ryan L, LaCourse R, et al. (2000) Genetic control of susceptibility to infection with *Mycobacterium tuberculosis* in mice. Genes Immun 1: 467-477), atherosclerosis (Welch C L, Bretschger S, Latib N, Bezouevski M, Guo Y, et al. (2001) Localization of atherosclerosis susceptibility loci to chromosomes 4 and 6 using the Ldlr knockout mouse model. Proc Natl Acad Sci USA 98: 7946-7951), epilepsy (Legare M E, Bartlett F S, 2nd, Frankel W N (2000) A major effect QTL determined by multiple genes in epileptic EL mice. Genome Res 10: 42-48), schizophrenia (Joober R, Zarate J M, Rouleau G A, Skamene E, Boksa P (2002) Provisional mapping of quantitative trait loci modulating the acoustic startle response and prepulse inhibition of acoustic startle. Neuropsychopharmacology 27: 765-781) and, also, T2DM (Clee S M, Yandell B S, Schueler K M, Rabaglia M E, Richards O C, et al. (2006) Positional cloning of Sorcs1, a type 2 diabetes quantitative trait locus. Nat Genet 38: 688-693; Goodarzi M O, Lehman D M, Taylor K D, Guo X, Cui J, et al. (2007) SORCS1: a novel human type 2 diabetes susceptibility gene suggested by the mouse. Diabetes 56: 1922-1929; Freeman H, Shimomura K, Horner E, Cox R D, Ashcroft F M (2006) Nicotinamide nucleotide transhydrogenase: a key role in insulin secretion. Cell Metab 3: 35-45; Freeman H C, Hugill A, Dear N T, Ashcroft F M, Cox R D (2006) Deletion of nicotinamide nucleotide transhydrogenase: a new quantitative trait locus accounting for glucose intolerance in C57BL/6J mice. Diabetes 55: 2153-2156).

In one aspect of this invention, these differential diabetes susceptibilities were exploited to map diabetes-susceptibility regions of the mouse genome using genetic crosses between a diabetes-susceptible (DBA) and a resistant strain (B6). In another aspect, the invention provides the identification of the genes responsible for the diabetes-related phenotypes of B6.DBA $Lep^{ob/ob}$ F2 and F3 mice segregating for a QTL in the distal portion of Chr1. As described in the Examples of section herein, molecular genetic methods were used to identify to immunoglobulin-like domain containing receptor 2 (Ildr2), as a gene that accounts for diabetes susceptibility conveyed by the DBA interval in the intercross, and in B6.DBA N12-15 congenic progeny. The gene affects the early development and replication of beta cells and a reduced beta cell mass resulting in a predisposition to diabetes. In certain aspects, the invention provides methods to increase Ildr2 activity to reverse these effects. The gene encodes multiple, tissue-specific transcripts in brain, liver and islets. The functional consequences of the hypomorphic DBA allele (diabetes-prone) in $Lep^{ob/ob}$ mice appear to be late embryonic to early postnatal reductions in β-cell mass due to diminished rates of β-cell replication, some "catch-up" of β-cell mass by 2-3 months, followed by mild glucose intolerance at >6 months of age. These phenotypes are recapitulated in mice with an ENU-induced null allele of Ildr2.

Ildr2 is a gene that produces multiple tissue-specific transcripts and is most highly expressed in brain, liver, and islets. Encoding a 10-exon 646 amino acid protein with significant homology to Lsr on Chr1qB1 and to Lldr1 on Chr16B3, Ildr2 spans 62.7 kb on Chr1qH2. The largest ILDR2 isoform is a predicted single-pass trans-membrane molecule with a signal sequence, an immunoglobulin-like extra-cellular domain and a serine/threonine rich intra-cellular domain that also contains a 14-3-3 binding domain and a terminal PDZ-binding motif.

The amounts of L1 transcripts are reduced 2-10 fold in these organs in mice segregating for DBA (v. B6) congenic intervals containing Ildr2. A recombination event between exons 8 and 9 of the 10 exon Ildr2 gene, has allowed characterization of the phenotypes of lines segregating for the complete DBA allele of Ildr2 versus B6. DBA lines containing only the distal portions (exons 9, 10 and 3'UTR) of the gene. The latter lines display phenotypes and organ-specific rates of Ildr2 expression comparable to the line containing the entire DBA allele of Ildr2, implicating 3' UTR-mediated effects on message stability as a potential primary mechanism for the DBA allele's affects on diabetes-related phenotypes. There is also a 2845 bp in-frame anti-sense transcript running centromeric from exon 9 of Ildr2. In one embodiment, this antisense sequence can be used to squelch message in DBA v. B6 alleles of Ildr2. In another embodiment, this antisense sequence can be used to protect message in DBA v. B6 alleles of Ildr2. (Lapidot and Pilpel 2006, EMBO Rep 7:1216-1222; Costa 2005, Gene 357:83-94.).

The amino acid sequence of Ildr2 is highly homologous to the so-called "Lipolysis-stimulated receptor" (Lsr) (Yen et al, 1999, J Biol Chem 274:13390-13398). "Knockdown" of embryonic Zebrafish (D. rerio) paralogs of Ildr2 and Lsr results in disruption of endodermal organization and the integrity of the single large pancreatic islet in these animals. The physiological role(s) of Lsr—an apparent plasma membrane receptor—are unclear. The molecule is expressed in different tissues, including brain and liver. Homozygosity for a null allele of Lsr is embryonic lethal at E12.5-15.5 and associated with hepatic hypoplasticity, whereas the heterozygotes appear normal (Mesli et al, 2004, Eur J Biochem 271:3103-3114). LSR binds to apoliproteins B/E in the presence of free fatty acids, and can assist in the clearance of triglyceride-rich lipoproteins (Yen et al, 1999, J Biol Chem 274:13390-13398; Yen et al, 1994, Biochemistry 33:1172-1180). While LSR and ILDR2 are structurally homologous and may have overlapping functions, they are distinct enough so that they may also have non-overlapping functions and that reagents designed to be specific to either protein would not be predicted to cross-react.

LSR protein domains are described in U.S. Pat. No. 7,291,709. The table 11 below and description that follows show the sequence of several LSR domains compared to the corresponding aligned sequence in mouse ILDR2. Start and end amino acid residues refer to SEQ ID NO:17 (mouse LSR) and SEQ ID NO:14 (mouse ILDR2).

TABLE 11

Sequence of several LSR domains compared to the corresponding aligned sequence in mouse ILDR2

| Domain in LSR | Amino acid sequence (LSR and ILDR2) |
|---|---|
| Potential fatty acid binding site | LSR 23-41:<br>CLFLIIYCPDRASAIQVTV ((SEQ ID NO: 51)<br>ILDR2 7-25:<br>GWTAVFWLTAMVEGLQVTV (SEQ ID NO: 52) |
| Transmembrane domain | LSR 204-213:<br>LEDWLFVVVV (SEQ ID NO: 53)<br>ILDR2 184-193:<br>MPEWVFVGLV (SEQ ID NO: 54) |
| Potential cytokine receptor site | LSR 214-249:<br>CLASLLFFLLLGICWCQCCPHTCCCYVRCPCCPDKC (SEQ ID NO: 55)<br>ILDR2 194-229:<br>ILGIFLFFVLVGICWCQCCPHSCCCYVRCPCCPDSC (SEQ ID NO: 56) |
| Potential lipoprotein ligand binding site | LSR 544-558:<br>ERR--------------------------------RVYREEEEEEEE (SEQ ID NO: 57)<br>ILDR2 540-586:<br>ESSSRGGSLETPSKLGAQLGPRSASYYAWSPPTTYKAGASEGEDEDD (SEQ ID NO: 58) |

There are other structural similarities between LSR and ILDR2. For example, the NPGY sequence (SEQ ID NO: 141) in LSR (104-107), referred to as a putative clathrin-binding sequence on LSR, is a phosphotyrosine binding ligand of the class NPXY, that is contained in β-amyloid precursor proteins. The sequence NPDY (SEQ ID NO: 142) is found between residues 370-373 in ILDR2. Additionally, the RSRS motif (SEQ ID NO: 143) is within a proline-rich domain in LSR (470-473); a similar motif RSRASY (SEQ ID NO: 144) (561-565 of ILDR2) was identified by Motif Scan as a putative 14-3-3 Mode 1 binding motif. The ILDR2 sequence RAGSRF (SEQ ID NO: 145) (451-456 of ILDR2) was identified by the ELM Server as a potential 14-3-3 ligand.

ILDR2 may participate in a variety of processes. Like LSR, ILDR2 may be involved in the transport of fatty acids and and/or cholesterol. ILDR2 is expressed in liver, islets and the hypothalamus, and, based upon developmental and physiological studies, has effects on beta cell development and, possibly, function. These effects could be conveyed directly on the beta cell, or could be secondary to changes in the liver and/or hypothalamus. The high specific expression of ILDR2 transcripts in the hypothalamus and the relatively high specific concentration of ILDR2 polypeptide in the hypothalamus are consistent with a role for ILDR2 in control of hepatic glucose homeostasis and/or beta cell function by autonomic efferents from the hypothalamus. These have not yet been directly tested.

Non-limiting examples include for islet cell ontogenesis, cellular lipid homeostasis, hepatic and muscle insulin responsiveness and islet β cell function and survival. Identification of such functions can be important for understanding aspects of the pathogenesis of T2DM. In certain aspects, the invention provides methods to characterize the molecular physiology of ILDR2 in mice.

The human ortholog of mouse ILDR2, is 90% identical to Ildr2 at the amino acid level, maps to a region of Chr1q23 that has been repeatedly implicated in T2DM in seven ethnically diverse populations including Caucasians (Northern Europeans in Utah) (Elbein et al, 1999, Diabetes 48:1175-1182), Amish Family Study (Hsueh et al, 2003, Diabetes 52:550-557, St. Jean 2000, American Journal of Human Genetics 67), United Kingdom Warren 2 study (Wiltshire et al, 2001 Am J Hum Genet 69:553-569), French families (Vionnet et al, 2000, Am J Hum Genet 67:1470-1480), and Framingham Offspring study (Meigs et al, 2002, Diabetes 51:833-840), Pima Indians (Hanson et al, 1998, J Hum Genet 63:1130-1138), and Chinese (Xiang, et al, 2004, Diabetes 53:228-234) with LOD scores as high as 4.3. There is evidence of association of alleles of Ildr2 with T2D in several of these populations. The mouse congenic interval examined as described herein is in the middle of, and physically ~10× smaller than, the 30 Mb human interval. Recent analysis of the broad interval ascertained in Utah identified two peaks, one of which, at D152762 (@163.6 Mb), is just 12 kb telomeric to the 5' end of the Ildr2 gene (Das S K, Elbein S C (2007) The search for type 2 diabetes susceptibility Loci: the chromosome 1q story. Curr Diab Rep 7: 154-164). The genes, and gene order, are generally conserved between mouse and human in the region syntenic to the congenic interval. The metabolic phenotypes documented in human subjects with T2DM linked to 1q23 resemble diabetic phenotypes observed in congenic mice segregating for the DBA interval in B6.DBA congenics examined here (McCarthy M, Shuldiner, A. R., Bogardus, C., Hanson, R. L., Elbein, S., (2004) Positional Cloning of a Type 2 Diabetes Susceptibility Gene on Chromosome 1q: A collaborative effort by the Chromosome 1q Diabetes Positional Cloning Consortium. 1-39), suggesting that the diabetes-susceptibility gene in congenic mice and human subjects may be the same gene, or among the genes, acting in the same genetic pathway(s). The syntenic interval in the GK rat also correlates with diabetes-susceptibility (Chung W K, Zheng M, Chua M, Kershaw E, Power-Kehoe L, et al. (1997) Genetic modifiers of Leprfa associated with variability in insulin production and susceptibility to NIDDM. Genomics 41: 332-344).

Data described herein identify two non-synonymous amino acid variants in ILDR2 of DD mice: T587A and A647V (both found in exon 9 in Ildr2). These positions correspond to Glycine-572 and Alanine-625 in human Ildr2, respectively. In certain aspects, the invention provides methods to determine whether these amino acid variants: (a) decrease protein stability and (b) change protein function in any way. To determine the effect of these amino acids changes, these mutation can be engineered in expression vectors for mammalian transfections, and functional characterization experiments as described herein can be carried out for the mutant Ildr2 variants. The T587A mutation abolishes a potential phosphorylation site. Methods for investigating the role of phosphorylation are well known to those skilled in the art.

Insight into the function(s) of the mouse Ildr2 protein may be gained from similarities in structure, expression, and cellular location with the human paralog and with genes encoding related trans-membrane receptors, Ildr1 (Hauge H, Patzke S, Delabie J, Aasheim H C (2004) Characterization of a novel immunoglobulin-like domain containing receptor. Biochem Biophys Res Commun 323: 970-978) and Lsr (Yen F T, Masson M, Clossais-Besnard N, Andre P, Grosset J M, et al. (1999) Molecular cloning of a lipolysis-stimulated remnant receptor expressed in the liver. J Biol Chem 274: 13390-13398). Splicing patterns of these genes generate isoforms, similar to those of Ildr2. Each gene's largest isoform includes an extra-cellular Ig-like domain, a single TMD, and a similar set of ICDs in related order. In one isoform of each protein, the TMD and cysteine-rich domains are absent. An evolutionary, regulatory relationship is suggested by the observation that the Ildr2-paralog and Ildr1 are adjacent in the zebra fish genome (Zv6 assembly, UCSC Genome Browser). All three genes are abundantly expressed in the brain, liver and pancreas (and islets, where studied), and all are predicted to have 14-3-3 interacting domains (thus far experimentally verified for the human LSR) (Garcia-Ocana A, Takane K K, Syed M A, Philbrick W M, Vasavada R C, et al. (2000) Hepatocyte growth factor overexpression in the islet of transgenic mice increases beta cell proliferation, enhances islet mass, and induces mild hypoglycemia. J Biol Chem 275: 1226-1232). Although 14-3-3 interacting domains may be present on as many as 0.6% of human proteins, their occurrence on all of these Lisch-related proteins is notable, since among known 14-3-3-interacting proteins is phoshodiesterase-3B, which is implicated in diabetes and pancreatic β-cell physiology (Onuma H, Osawa H, Yamada K, Ogura T, Tanabe F, et al. (2002) Identification of the insulin-regulated interaction of phosphodiesterase 3B with 14-3-3 beta protein. Diabetes 51: 3362-3367; Xiang K, Wang Y, Zheng T, Jia W, Li J, et al. (2004) Genome-wide search for type 2 diabetes/impaired glucose homeostasis susceptibility genes in the Chinese: significant linkage to chromosome 6q21-q23 and chromosome 1q21-q24. Diabetes 53: 228-234; Pozuelo Rubio M, Geraghty K M, Wong B H, Wood N T, Campbell D G, et al. (2004) 14-3-3-affinity purification of over 200 human phosphoproteins reveals new links to regulation of cellular metabolism, proliferation and trafficking Biochem J 379: 395-408), and others, such as the Cdc25 family members, important in regulating cell proliferation and survival (Meek S E, Lane W S, Piwnica-Worms H (2004) Comprehensive proteomic analysis of interphase and mitotic 14-3-3-binding proteins. J Biol Chem 279: 32046-32054; Hermeking H, Benzinger A (2006) 14-3-3 proteins in cell cycle regulation. Semin Cancer Biol 16: 183-192).

Screening Methods to Identify Agents which Modulate Expression of Ildr2 or ILDR2

In certain aspects the invention provides methods to identify agents which modulate expression of Ildr2 or ILDR2, the method comprising determining expression in the absence of a candidate agent, contacting a cell with a candidate agent, determining expression in the presence of the candidate agent, and comparing the expression determined in the presence and the absence of the candidate agent. In certain aspects, the invention provides a method for identifying an agent which modulates expression of an Ildr2 RNA comprising: (a) determining expression of an Ildr2 RNA in a cell, (b) contacting the cell with an agent; and (c) determining expression of the Ildr2 RNA in the presence of the agent, wherein a change in the expression of the Ildr2 RNA in the presence of the agent, compared to the expression of the Ildr2 RNA in the absence of the agent, is indicative of an agent which modulates the expression of the Ildr2 RNA. In certain embodiments, the method comprises: (a) contacting a cell with an agent; (b) determining expression of the Ildr2 RNA in the presence and the absence of the agent; and (c) comparing expression of the Ildr2 RNA in the presence and the absence of the agent, wherein a change in the expression of the Ildr2 RNA in the presence of the agent is indicative of an agent which modulates the level of expression of the RNA. In certain embodiments, the method measures expression of ILDR2 RNA. In certain embodiments, the assay is carried out in a cell which is comprised in an animal. In a non-limiting example the animal is a mouse. In other embodiments, the assay is carried out in a cell which is comprised in a tissue culture and/or a cell line derived from tissues of a mouse, or a human subject. In certain aspects, the cell is comprised in a diabetes-relevant tissue. In other aspects, the cell is derived from any tissue or source which allows to determine modulation of expression of Ildr2 or ILDR2. In non-limiting examples, the cell is a pancreatic cell, an insulin producing beta cell, or a hepatocyte, a hypothalamic or other brain cell, or any combination thereof.

In certain embodiments, the method is carried out in a cell which expresses endogenous Ildr2 or ILDR2. In other embodiments, the method is carried out in a cell comprising an expression vector or a construct comprising nucleic acid which encodes Ildr2 or ILDR2. The nucleic acid encoding Ildr2 or ILDR2 can be a nucleic acid, for example encoding any splice variant, isoform, or a fragment, a genomic DNA, or any portion of the genomic DNA. In certain aspects, the expression vector is introduced by transfection into an autologous cell type. In other aspects, the expression vector is introduced by transfection into a non-autologous cell type. Methods to create expression vectors and constructs are well known in the art. Non-limiting examples of various expression vectors, cells, tissues, and cell lines are described herein. In certain embodiments, the cell can comprise any other suitable nucleic acid or an expression vectors comprising a nucleic acid which encodes such suitable nucleic acid. In non-limiting examples, such suitable nucleic acid can be a nucleic acid which encodes a Ildr2- or ILDR2-interacting, and/or regulatory partner.

In certain embodiments, determining comprises quantitative determination of the level of expression. In other embodiments, determining comprises quantitative determination of the stability or turnover of Ildr2 or ILDR2. Methods for determining expression of a RNA or a protein, including quantitative and/or qualitative determinations, are described herein and well known in the art. In certain embodiments, the methods of the invention determine an increase in the expression. In other embodiments, the methods of the invention determine a decrease in the expression. The expression of a gene can be readily detected, e.g., by quantifying the protein and/or RNA encoded by the gene. Many methods standard in the art can be thus employed, including, but not limited to, immunoassays to detect and/or visualize protein expression, nonlimiting examples include western blot, immunoprecipitation followed by sodium dodecyl sulfate polyacrylamide gel electrophoresis (SDS-PAGE), immunocytochemistry, etc., and/or hybridization assays to detect gene expression by detecting and/or visualizing respectively RNA, including but not limited to mRNA encoding a gene (PCR, northern assays, dot blots, in situ hybridization, etc.). Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Non-limiting exemplary assays are described herein.

In certain embodiments, the methods of the invention can determine changes in the expression, associated with changes in the localization, processing, trafficking, post-translational modification, or any other cellular modification of Ildr2 or ILDR2. Determining expression of Ildr2 or ILDR2 can be carried out by any suitable method as described herein, or known in the art.

In certain embodiments, the step of contacting a cell with an agent is under conditions suitable for gene or protein expression. In certain embodiments, contacting step is in an aqueous solution comprising a buffer and a combination of salts. In certain embodiments, the aqueous solution approximates or mimics physiologic conditions.

In certain embodiments, once an agent has been identified to modulate expression, and optionally, the structure of the compound has been identified, the agent can be further tested for biological activity in additional assays and/or animal models for type 2 diabetes or metabolic disease. In addition, a lead compound can be used to design analogs, and other structurally similar compounds.

In certain embodiments, the invention provides screening of libraries of agents, including combinatorial libraries, to identify an agent which modulate the expression. Libraries screened using the methods of the present invention can comprise a variety of types of compounds. Non-limiting examples of libraries that can be screened in accordance with the methods of the invention include, but are not limited to, peptoids; random biooligomers; diversomers such as hydantoins, benzodiazepines and dipeptides; vinylogous polypeptides; nonpeptidal peptidomimetics; oligocarbamates; peptidyl phosphonates; peptide nucleic acid libraries; antibody libraries; carbohydrate libraries; and small molecule libraries, for example but not limited to small organic molecules. In certain embodiments, the compounds in the libraries screened are nucleic acid or peptide molecules. In a non-limiting example, peptide molecules can exist in a phage display library. In other embodiments, the types of compounds include, but are not limited to, peptide analogs including peptides comprising non-naturally occurring amino acids, e.g., D-amino acids, phosphorous analogs of amino acids, such as $\alpha$-amino phosphoric acids and $\alpha$-amino phosphoric acids, or amino acids having non-peptide linkages, nucleic acid analogs such as phosphorothioates and PNAs, hormones, antigens, synthetic or naturally occurring drugs, opiates, dopamine, serotonin, catecholamines, thrombin, acetylcholine, prostaglandins, organic molecules, pheromones, adenosine, sucrose, glucose, lactose and galactose. Libraries of polypeptides or proteins can also be used in the assays of the invention.

In certain embodiments, the combinatorial libraries are small organic molecule libraries including, but not limited to, benzodiazepines, isoprenoids, beta carbalines, thiazolidinones, metathiazanones, pyrrolidines, morpholino compounds, small inhibitory RNAs short hairpin RNAs, and benzodiazepines. In another embodiment, the combinatorial libraries comprise peptoids; random bio-oligomers; benzodiazepines; diversomers such as hydantoins, benzodiazepines and dipeptides, vinylogous polypeptides; nonpeptidal peptidomirnetics; oligocarbamates; peptidyl phosphonates; peptide nucleic acid libraries; antibody libraries; or carbohydrate libraries. Combinatorial libraries are themselves commercially available from different sources.

In a certain embodiments, the library is preselected so that the compounds of the library are more amenable for cellular uptake. For example, compounds are selected based on specific parameters such as, but not limited to, size, lipophilicity, hydrophilicity, and hydrogen bonding, which enhance the ability of compounds to enter into the cells. In other embodiments, the compounds are analyzed by three-dimensional or four-dimensional computer computation programs.

Methods to synthesize and screen combinatorial libraries are known in the art. In one embodiment, the combinatorial compound library can be synthesized in solution. In other embodiments the combinatorial libraries can be synthesized on solid support. For non-limiting examples of such methods see U.S. Pat. No. 5,866,341 to Spinella et al., U.S. Pat. No. 6,190,619 to Kilcoin et al., U.S. Pat. No. 6,194,612 to Boger et al.; Egner et al., 1995, J. Org. Chem. 60:2652; Anderson et al., 1995, J. Org. Chem. 60:2650; Fitch et al., 1994, J. Org. Chem. 59:7955; Look et al., 1994, J. Org. Chem. 49:7588; Metzger et al., 1993, Angew. Chem., Int. Ed. Engl. 32:894; Youngquist et al., 1994, Rapid Commun. Mass Spect. 8:77; Chu et al., 1995, J. Am. Chem. Soc. 117:5419; Brummel et al., 1994, Science 264:399; and Stevanovic et al., 1993, Bioorg. Med. Chem. Lett. 3:431; Lam et al., 1997, Chem. Rev. 97:41-448; Ohlmeyer et al., 1993, Proc. Natl. Acad. Sci. USA 90:10922-10926 a Nefzi et al., 1997, Chem. Rev. 97:449-472; and references cited therein, all of which are hereby incorporated by reference in their entirety.

Agents that modulate expression, as identified by the methods described herein can be selected and characterized by methods known in the art. For example, if the library comprises arrays or microarrays of agents, wherein each agent has an address or identifier, the agent can be deconvoluted, e.g., by cross-referencing the positive sample to original compound list that was applied to the individual test assays. If the library is a peptide or nucleic acid library, the sequence of the compound can be determined by direct sequencing of the peptide or nucleic acid. Such methods are well known to one of skill in the art. A number of physicochemical techniques can also be used for the de novo characterization of compounds that modulate expression as determined by the methods of the present invention. Examples of such techniques include, but are not limited to, mass spectrometry, NMR spectroscopy, X-ray crystallography and vibrational spectroscopy.

In certain aspects, the invention provides methods for identifying metabolic or environmental agents and/or stimuli (e.g., exposure to different concentrations of metabolites, nutrients, or the like, or of $CO_2$ and/or $O_2$, stress and different pHs,) that modulate untranslated region-dependent expression of a target gene utilizing the cell-based reporter gene assays described herein. In another embodiment, the environmental stimuli does not include a compound. In non-limiting examples, the metabolic agent is insulin, cAMP, glucose, free fatty acids, cholesterol or a combination thereof.

Antibodies to ILDR2

Using standard immunization protocols, polyclonal rabbit and guinea pig antibodies (Covance Research Products) were generated against the predicted extracellular domain (ECD) of mouse ILDR2 spanning residues 22-186, and intracellular domain (ICD) spanning residues 298-401. α-ICD and α-ECD rabbit antibodies detected the appropriate fusion proteins, showing only minor cross-reactivity. Another set of antibodies to smaller ECD and ICD epitopes (FIG. 41A and FIG. 41B) were generated to detect the localized expression pattern of Ildr2 in pancreatic β cells in non-diabetic mice, as well as an undetectable ILDR2 protein level in diabetic D/D mice—that show reduced β cell replication and reduced islet mass—indicates that Ildr2 can play a critical role in β cell development.

In one aspect, the invention provides antibody that binds to the peptide which is from the extracellular domain (ECD) of mouse ILDR2 spanning residues 22-186 (SEQ ID NO: 3), or a (poly)peptide which comprises the peptide of SEQ ID NO: 7. In another aspect of the invention provides antibody that binds to the peptide which is from the intracellular domain (ICD) of mouse ILDR2 spanning residues 298-401 (SEQ ID NO: 2), or a (poly)peptide which comprises the peptide of SEQ ID NO: 6. In another aspect of the invention provides antibody that binds to the peptide which is from the extracellular domain (ECD) of human ILDR2 spanning residues shown in SEQ ID NO: 5, or a (poly)peptide which comprises the peptide of SEQ ID NO: 9. In another aspect of the invention provides antibody that binds to the peptide which is from the intracellular domain (ICD) of human ILDR2 spanning residues shown in SEQ ID NO: 4, or a (poly)peptide which comprises the peptide of SEQ ID NO: 8. In one aspect, the invention provides antibody that binds to an epitope of the polypeptide of SEQ ID NO: 22.

In another aspect, the antibodies of the invention are isolated. The antibodies of the invention can be monoclonal or polyclonal. Methods for making polyclonal and monoclonal antibodies are well known in the art. Antibodies of the invention can be produced by methods known in the art in any suitable animal host such as but not limited to rabbit, goat, mouse, sheep. In one embodiment, the antibodies can be chimeric, i.e. a combination of sequences of more than one species. In another embodiment, the antibodies can be fully-human or humanized Abs. Humanized antibodies contain complementarity determining regions that are derived from non-human species immunoglobulin, while the rest of the antibody molecule is derived from human immunoglobulin. Fully-human or humanized antibodies avoid certain problems of antibodies that possess non-human regions which can trigger host immune response leading to rapid antibody clearance. In still another embodiment, antibodies of the invention can be produced by immunizing a non-human animal with an immunogenic composition comprising a polypeptide of the invention in the monomeric form. In other embodiments, dimeric or multimeric forms can be used. The immunogenic composition can also comprise other components that can increase the antigenicity of the inventive peptide. In one embodiment the non-human animal is a transgenic mouse model, for e.g., the HuMAb-Mouse™ or the Xenomouse®, which can produce human antibodies. Neutralizing antibodies against peptides of interest and the cells producing such antibodies can be identified and isolated by methods know in the art.

Making of monoclonal antibodies is well known in the art. In one embodiment, the monoclonal antibodies of the invention are made by harvesting spleen tissue from a rabbit which produces a polyclonal antibody. Harvested cells are fused with the immortalized myeloma cell line partner. After an initial period of growth of the fused cells, single antibody producing clones are isolated by cell purification, grown and analyzed separately using a binding assay (e.g., ELISA, or Western). Hybridomas can be selected based on the ability of their secreted antibody to bind to a peptide interest, including a polypeptide comprising SEQ ID NOs: 2-9. Variable regions can be cloned from the hybridomas by PCR and the sequence of the epitope binding region can be determined by sequencing methods known in the art.

The invention provides antibodies and antibody fragments of various isotypes. The recombined immunoglobulin (Ig) genes, for example the variable region genes, can be isolated from the deposited hybridomas, by methods known in the art, and cloned into an Ig recombination vector that codes for human Ig constant region genes of both heavy and light chains. The antibodies can be generated of any isotype such as IgG1, IgG2, IgG3, IgG4, IgD, IgE, IgM, IgA1, IgA2, or sIgA isotype. The invention provides isotypes found in non-human species as well such as but not limited to IgY in birds and sharks. Vectors encoding the constant regions of various isotypes are known and previously described. (See, for example, Preston et al. Production and characterization of a set of mouse-human chimeric immunoglobulin G (IgG) subclass and IgA monoclonal antibodies with identical variable regions specific for *P. aeruginosa* serogroup O6 lipopolysaccharide. Infect Immun. 1998 September; 66(9):4137-42; Coloma et al. Novel vectors for the expression of antibody molecules using variable regions generated by polymerase chain reaction. J Immunol Methods. 1992 Jul. 31; 152(1):89-104; Guttieri et al. Cassette vectors for conversion of Fab fragments into full-length human IgG1 monoclonal antibodies by expression in stably transformed insect cells. Hybrid Hybridomics. 2003 June; 22(3):135-45; McLean et al. Human and murine immunoglobulin expression vector cassettes. Mol Immunol. 2000 October; 37(14): 837-45; Walls et al. Vectors for the expression of PCR-amplified immunoglobulin variable domains with human constant regions. Nucleic Acids Res. 1993 Jun. 25; 21(12): 2921-9; Norderhaug et al. Versatile vectors for transient and stable expression of recombinant antibody molecules in mammalian cells. J Immunol Methods. 1997 Can 12; 204 (1):77-87.)

The antibodies of the invention bind to a polypeptide having the sequence of any of SEQ ID NOs: 2-9, comprised in a longer polypeptide, in a specific manner. In one embodiment, the antibodies, or antibody fragments of the invention bind specifically to a peptide of SEQ ID NO: 2, 3, 4, or 5. In one embodiment, the antibodies, or antibody fragments of the invention bind specifically to a peptide of SEQ ID NO: 6, 7, 8, or 9. For example, antibodies that bind specifically to a peptide that comprises a sequences shown in any of SEQ ID NOs: 2-9 will not bind to polypeptides which do not comprise the amino acid sequence of any of SEQ ID NO: 2-9 to the same extent and with the same affinity as they bind to a peptide that comprises a sequences shown in any of SEQ ID NOs: 2-9. In another embodiment, the antibody, or/and antibody fragments, of the invention can bind specifically to polypeptides which comprise any of SEQ ID NOs: 14-47, but this binding can occur with lesser affinity compared to the binding to a polypeptide that comprises a sequences shown in any of SEQ ID NOs: 2-9. Lesser affinity can include at least 10% less, 20% less, 30% less, 40% less, 50% less, 60% less, 70% less, 80% less, 90% less, or 95% less.

The present invention provides specific monoclonal antibodies, including but not limited to rabbit, mouse and human, which recognize a peptide of SEQ ID NO: 2, 3, 4, or 5, including a polypeptide comprising SEQ ID NO: 6, 7, 8, or 9. When used in vivo in humans, human monoclonal antibodies are far less likely to be immunogenic (as compared to antibodies from another species).

Variable region nucleic acids for the heavy and light chains of the antibodies can be cloned into an human Ig expression vector that contain any suitable constant region, for example (i.e., TCAE6) that contains the IgG1 (gamma 1) constant region coding sequences for the heavy chain and the lambda constant region for the light chains. (See, for example, Preston et al. Production and characterization of a set of mouse-human chimeric immunoglobulin G (IgG) subclass and IgA monoclonal antibodies with identical variable regions specific for *P. aeruginosa* serogroup O6 lipopolysaccharide. Infect Immun. 1998 September; 66(9):4137-42.) The variable regions can be placed in any vector that encodes constant region coding sequences. For example, human Ig heavy-chain constant-region expression vectors containing genomic clones of the human IgG2, IgG3, IgG4 and IgA heavy-chain constant-region genes and lacking variable-region genes have been described in Coloma, et al. 1992 J. Immunol. Methods 152:89-104.) These expression vectors can then be transfected into cells (e.g., CHO DG44 cells), the cells are grown in vitro, and IgG1 are subsequently harvested from the supernatant. Resultant antibodies can be generated to posses human variable regions and human IgG1 and lambda constant regions. In other embodiments, the Fc portions of the antibodies of the invention can be replaced so as to produce IgM.

In other embodiments, the antibody of the invention also includes an antibody fragment. It is well-known in the art, only a portion of an antibody molecule, the paratope, is involved in the binding of the antibody to its epitope (see, in general, Clark, W. R. (1986) The Experimental Foundations of Modern Immunology Wiley & Sons, Inc., New York; Roitt, I. (1991) Essential Immunology, 7th Ed., Blackwell Scientific Publications, Oxford; and Pier G B, Lyczak J B, Wetzler L M, (eds). Immunology, Infection and Immunity (2004) 1st Ed. American Society for Microbiology Press, Washington D.C.). The pFc' and Fc regions of the antibody, for example, are effectors of the complement cascade and can mediate binding to Fc receptors on phagocytic cells, but are not involved in antigen binding. An antibody from which the pFc' region has been enzymatically cleaved, or which has been produced without the pFc' region, e.g. an $F(ab')_2$ fragment, retains both of the antigen binding sites of an intact antibody. An isolated $F(ab')_2$ fragment is referred to as a bivalent monoclonal fragment because of its two antigen binding sites. Similarly, an antibody from which the Fc region has been enzymatically cleaved, or which has been produced without the Fc region, e.g. an Fab fragment, retains one of the antigen binding sites of an intact antibody molecule. Proceeding further, Fab fragments consist of a covalently bound antibody light chain and a portion of the antibody heavy chain denoted Fd (heavy chain variable region). The Fd fragments are the major determinant of antibody specificity (a single Fd fragment can be associated with up to ten different light chains without altering antibody specificity) and Fd fragments retain epitope-binding ability in isolation. An antibody fragment is a polypeptide which can be targeted to the nucleus. Methods to modify polypeptides for targeting to the nucleus are known in the art.

Additional methods of producing and using antibodies and antibody fragments comprising Fab, Fc, pFc', $F(ab')_2$ and Fv regions are well known in the art [Klein, Immunology (John Wiley, New York, N.Y., 1982); Clark, W. R. (1986) The Experimental Foundations of Modern Immunology (Wiley & Sons, Inc., New York); Roitt, I. (1991) Essential Immunology, 7th Ed., (Blackwell Scientific Publications, Oxford); and Pier G B, Lyczak J B, Wetzler L M, (eds). Immunology, Infection and Immunity (2004) 1st Ed. American Society for Microbiology Press, Washington D.C.].

Usually the CDR regions in humanized antibodies are substantially identical, and more usually, identical to the corresponding CDR regions of the donor antibody. However, in certain embodiments, it can be desirable to modify one or more CDR regions to modify the antigen binding specificity of the antibody and/or reduce the immunogenicity of the antibody. One or more residues of a CDR can be altered to modify binding to achieve a more favored on-rate of binding, a more favored off-rate of binding, or both, such that an idealized binding constant is achieved. Using this strategy, an antibody having high or ultra high binding affinity of can be achieved. Briefly, the donor CDR sequence is referred to as a base sequence from which one or more residues are then altered. Affinity maturation techniques can be used to alter the CDR region(s) followed by screening of the resultant binding molecules for the desired change in binding. The method can also be used to alter the donor CDR to be less immunogenic such that a potential chimeric antibody response is minimized or avoided. Accordingly, as CDR(s) are altered, changes in binding affinity as well as immunogenicity can be monitored and scored such that an antibody optimized for the best combined binding and low immunogenicity are achieved (see, e.g., U.S. Pat. No. 6,656,467 and U.S. Pat. Pub. Nos: US20020164326A1; US20040110226A1; US20060121042A1).

The antibodies of the invention can be used in a variety of applications including but not limited to (a) methods for diagnosing type 2 diabetes or metabolic disease in a subject, wherein the antibody is used to determine different expression of ILDR2 in a blood or other tissue sample from a subject compared to the expression of ILDR2 in a control sample, (b) methods for screening agents, including but not limited to small molecule drugs, biological agents, in order to identify and monitor agents which can modulate the expression, production, localization, and/or stability of ILDR2. Additionally, such antibodies could be used to affect the action or regulate the activity of the native peptide at surface of the cell, or to detect shed molecules in the circulation as a diagnostic.

In one aspect, the antibodies that specifically bind polypeptide of SEQ ID NO: 2-9 or a polypeptide which comprises the corresponding peptide, can be used in a screening method to evaluate agents designed to affect the levels of expression of ILDR2. Because the antibody can be used to quantitate protein levels and expression, protein localization, or protein modification of ILDR2. The effect, including the efficiency and/or potency, of the drug can be addressed by following its effect on the presence, or absence, or change, for example but not limited to change in levels of the ILDR2, which can be detected by the antibody of the invention.

The antibodies of the present invention, including fragments and derivatives thereof, can be labeled. It is, therefore, another aspect of the present invention to provide labeled antibodies that bind specifically to one or more of the polypeptides of the present invention, to one or more of the polypeptides encoded by the isolated nucleic acid molecules of the present invention, or the binding of which can be competitively inhibited by one or more of the polypeptides of the present invention or one or more of the polypeptides encoded by the isolated nucleic acid molecules of the present invention. The choice of label depends, in part, upon the desired use.

For example, when the antibodies of the present invention are used for immunohistochemical staining of tissue samples, the label can usefully be an enzyme that catalyzes production and local deposition of a detectable product. Enzymes useful as conjugates to antibodies to permit antibody detection are well known. Exemplary conjugataes are alkaline phosphatase, p-galactosidase, glucose oxidase, horseradish peroxidase (HRP), and urease. Exemplary substrates for production and deposition of visually detectable products are o-nitrophenyl-beta-D-galactopyranoside (ONPG); o-phenylenediamine dihydrochloride (OPD); p-nitrophenyl phosphate (NPP); p-nitrophenyl-beta-D-galactopryanoside (PNPG); 3',3'-diaminobenzidine (DAB); 3-amino-9-ethylcarbazole (AEC); 4-chloro-1-naphthol (CN); 5-bromo-4-chloro-3-indolyl-phosphate (BCIP); ABTS®; BluoGal; iodonitrotetrazolium (INT); nitroblue tetrazolium chloride (NBT); phenazine methosulfate (PMS); phenolphthalein monophosphate (PMP); tetramethyl benzidine (TMB); tetranitroblue tetrazolium (TNBT); X-Gal; X-Gluc; and X-Glucoside.

Other substrates can be used to produce luminescent products for local deposition. For example, in the presence of hydrogen peroxide ($H_2O_2$), horseradish peroxidase (HRP) can catalyze the oxidation of cyclic diacylhydrazides, such as luminol. Immediately following the oxidation, the luminol is in an excited state (intermediate reaction product), which decays to the ground state by emitting light. Strong enhancement of the light emission is produced by enhancers, such as phenolic compounds. Advantages include high sensitivity, high resolution, and rapid detection without radioactivity and requiring only small amounts of antibody. See, e.g., Thorpe et al., Methods Enzymol. 133: 331-53 (1986); Kricka et al., J. Immmunoassay 17(1): 67-83 (1996); and Lundqvist et al., J. Biolumin. Chemiluimin. 10(6): 353-9 (1995). Kits for such enhanced chemiluminescent detection (ECL) are available commercially. The antibodies can also be labeled using colloidal gold.

As another example, when the antibodies of the present invention are used, e.g., for flow cytometric detection, for scanning laser cytometric detection, or for fluorescent immunoassay, they can usefully be labeled with fluorophores. There are a wide variety of fluorophore labels that can usefully be attached to the antibodies of the present invention. For flow cytometric applications, both for extracellular detection and for intracellular detection, common useful fluorophores can be fluorescein isothiocyanate (FITC), allophycocyanin (APC), R-phycoerythrin (PE), peridinin chlorophyll protein (PerCP), Texas Red, Cy3, CyS, fluorescence resonance energy tandem fluorophores such as PerCP-Cy5.5, PE-CyS, PE-Cy5.5, PE-Cy7, PE-Texas Red, and APC-Cy7.

Other fluorophores include, inter alia, Alexa Fluor® 350, Alexa Fluor® 488, Alexa Fluor® 532, Alexa Fluor® 546, Alexa Fluor® 568, Alexa Fluor® 594, Alexa Fluor® 647 (monoclonal antibody labeling kits available from Molecular Probes, Inc., Eugene, Oreg., USA), BODIPY dyes, such as BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY TR, BODIPY 630/650, BODIPY 650/665, Cascade Blue, Cascade Yellow, Dansyl, lissamine rhodamine B, Marina Blue, Oregon Green 488, Oregon Green 514, Pacific Blue, rhodamine 6G, rhodamine green, rhodamine red, tetramethylrhodamine, Texas Red (available from Molecular Probes, Inc., Eugene, Oreg., USA), and Cy2, Cy3, Cy3.5, Cy5, Cy5.5, Cy7, all of which are also useful for fluorescently labeling the antibodies of the present invention. For secondary detection using labeled avidin, streptavidin, captavidin or neutravidin, the antibodies of the present invention can usefully be labeled with biotin.

When the antibodies of the present invention are used, e.g., for western blotting applications, they can usefully be labeled with radioisotopes, such as $^{33}P$, $^{32}P$, $^{35}S$, $^{3}H$, and $^{125}I$. As another example, when the antibodies of the present invention are used for radioimmunotherapy, the label can usefully be $^{228}Th$, $^{227}Ac$, $^{225}Ac$, $^{223}Ra$, $^{213}Bi$, $^{212}Pb$, $^{212}Bi$, $^{211}At$, $^{203}Pb$, $^{194}Os$, $^{188}Re$, $^{186}Re$, $^{153}Sm$, $^{149}Tb$, $^{131}I$, $^{125}I$, $^{111}In$, $^{105}Rh$, $^{99m}Tc$, $^{97}Ru$, $^{90}Y$, $^{90}Sr$, $^{88}Y$, $^{72}Se$, $^{67}Cu$, or $^{47}Sc$.

As another example, when the antibodies of the present invention are to be used for in vivo diagnostic use, they can be rendered detectable by conjugation to MRI contrast agents, such as gadolinium diethylenetriaminepentaacetic acid (DTPA), Lauffer et al., Radiology 207(2): 529-38 (1998), or by radioisotopic labeling.

The antibodies of the present invention, including fragments and derivatives thereof, can also be conjugated to toxins, in order to target the toxin's ablative action to cells that display and/or express the polypeptides of the present invention. The antibody in such immunotoxins is conjugated to *Pseudomonas* exotoxin A, diphtheria toxin, shiga toxin A, anthrax toxin lethal factor, or ricin. See Hall (ed.), Immunotoxin Methods and Protocols (Methods in Molecular Biology, vol. 166), Humana Press (2000); and Frankel et al. (eds.), Clinical Applications of Immunotoxins, Springer-Verlag (1998).

The antibodies of the present invention can usefully be attached to a substrate, and it is, therefore, another aspect of the invention to provide antibodies that bind specifically to one or more of the polypeptides of the present invention, to one or more of the polypeptides encoded by the isolated nucleic acid molecules of the present invention, or the binding of which can be competitively inhibited by one or more of the polypeptides of the present invention or one or more of the polypeptides encoded by the isolated nucleic acid molecules of the present invention, attached to a substrate. Substrates can be porous or nonporous, planar or nonplanar. For example, the antibodies of the present invention can usefully be conjugated to filtration media, such as NHS-activated Sepharose or CNBr-activated Sepharose for purposes of immunoaffinity chromatography. For example, the antibodies of the present invention can usefully be attached to paramagnetic microspheres by, for example, biotin-streptavidin interaction. The microsphere can then be used for isolation of one or more cells that express or display the polypeptides of the present invention. As another example, the antibodies of the present invention can be attached to the surface of a microtiter plate for ELISA.

As noted herein, the antibodies of the present invention can be produced in prokaryotic and eukaryotic cells. It is, therefore, another aspect of the present invention to provide cells that express the antibodies of the present invention, including hybridoma cells, Beta cells, plasma cells, and host cells recombinantly modified to express the antibodies of the present invention.

In yet a further aspect, the present invention provides aptamers evolved to bind specifically to one or more of the ILDR2 proteins of the present invention or to polypeptides encoded by the nucleic acids of the invention.

In sum, one of skill in the art, provided with the teachings of this invention, has available a variety of methods which can be used to alter the biological properties of the antibodies of this invention including methods which can increase or decrease the stability or half-life, immunogenicity, toxicity, affinity or yield of a given antibody molecule, or to alter it in any other way that can render it more suitable for a particular application.

Cellular Biology of ILDR2 (Ildr2)

Embodiments and aspects described herein refer specifically to Ildr2, however, any of the described assays, techniques, reagents, experiments and so forth are equally applicable to determining and characterizing function and cellular biology of other ILDR2 homologues and orthologues, including but not limited to the human orthologue Ildr2.

In certain aspects, the invention provides that ILDR2 promotes Beta cell growth, and can regulate peripheral metabolism through its effects on liver function. Both of these effects can be conveyed via the CNS/hypothalamus where ILDR2 is expressed. There are precedents for such effects on liver glucose metabolism and islet Beta cell function. ILDR2 function can be determined using assays of protein biosynthesis, processing, sub-cellular localization, signaling properties. Structure/function relationships are analyzed by way of gain- and loss-of-function experiments in appropriate cellular contexts.

In certain embodiments, the invention provides that highest levels of Ildr2 expression are found in liver, brain, Beta cell/islet, and skeletal muscle. The metabolic properties of these organs are distinct, and make it difficult to identify an overarching function of the ILDR2 protein. Ki67 labeling studies indicate that Beta cell proliferation is reduced in the early post-natal period in DD (hypomorphic) congenics, indicating function for Ildr2 in the regulation of 0 cell mass. Thus, ILDR2 modulates pancreatic Beta cell proliferation directly, or indirectly. ILDR2 cellular biological features can be determined by assays described herein and any other suitable method known in the art, in physiologically relevant cell types.

In certain aspects the invention provides antisera and antibodies against epitopes of predicted intra and extracellular domains that detect ILDR2 in immunoprecipitation, immunoblot and immunohistochemistry assays. These antibodies can be used to determine the cellular properties of the endogenous protein.

In other aspects the invention provides reagents to study the properties of Ildr2 in gain-of-function experiments. Non-limiting examples of such reagents are FLAG epitope-tagged mammalian expression vectors. An ILDR2-GFP fusion protein has been constructed and can be used to analyze sub-cellular localization. ILDR2- and/or C1ORF32-fusion proteins to any other fluorescent protein variant, or any other protein reporter, or protein tag can also be generated. Also provided are mammalian expression vectors with N-terminal and C-terminal epitope tags and adenoviruses encoding WT Ildr2. Ildr2 siRNA constructs have been tested and shown effective in HEK 293 cells. These probes can be engineered into adenoviral vectors for efficient gene knockdown in cultured cells and mice. siRNA-resistant rescue vectors can be generated in which synonymous nucleotide changes are introduced in the Ildr2 cDNA to render it resistant to siRNA-mediated degradation. These constructs can be used to validate the specificity of the Ildr2 siRNA. For most experiments described, mammalian expression vectors provide adequate expression levels, but to detect effects of ILDR2 on biological processes where high transfection and expression efficiency is needed, an adenovirus can be used.

Expression Vectors, Host Cells and Recombinant Methods of Producing Polypeptides Another aspect of the present invention provides vectors that comprise one or more of the isolated nucleic acid molecules of the present invention, and host cells in which such vectors have been introduced.

The vectors can be used, inter alia, for propagating the nucleic acid molecules of the present invention in host cells (cloning vectors), for shuttling the nucleic acid molecules of the present invention between host cells derived from disparate organisms (shuttle vectors), for inserting the nucleic acid molecules of the present invention into host cell chromosomes (insertion vectors), for expressing sense or antisense RNA transcripts of the nucleic acid molecules of the present invention in vitro or within a host cell, and for expressing polypeptides encoded by the nucleic acid molecules of the present invention, alone or as fusion proteins with heterologous polypeptides (expression vectors). Vectors are by now well known in the art, and are described, inter alia, in Jones et al. (eds.), Vectors: Cloning Applications: Essential Techniques (Essential Techniques Series), John Wiley & Son Ltd. (1998); Jones et al. (eds.), Vectors: Expression Systems: Essential Techniques (Essential Techniques Series), John Wiley & Son Ltd. (1998); Gacesa et al., Vectors: Essential Data, John Wiley & Sons Ltd. (1995); Cid-Arregui (eds.), Viral Vectors: Basic Science and Gene Therapy, Eaton Publishing Co. (2000); Sambrook (2001), supra; Ausubel (1999), supra. Furthermore, a variety of vectors are available commercially. Use of existing vectors and modifications thereof are well within the skill in the art.

Nucleic acid sequences can be expressed by operatively linking them to an expression control sequence in an appropriate expression vector and employing that expression vector to transform an appropriate unicellular host. Expression control sequences are sequences that control the transcription, post-transcriptional events and translation of nucleic acid sequences. Such operative linking of a nucleic sequence of this invention to an expression control sequence, of course, includes, if not already part of the nucleic acid sequence, the provision of a translation initiation codon, ATG or GTG, in the correct reading frame upstream of the nucleic acid sequence.

A wide variety of host/expression vector combinations can be employed in expressing the nucleic acid sequences of this invention. Useful expression vectors, for example, can consist of segments of chromosomal, non-chromosomal and synthetic nucleic acid sequences.

In one embodiment, prokaryotic cells can be used with an appropriate vector. Prokaryotic host cells are often used for cloning and expression. In one embodiment, prokaryotic host cells include *E. coli, Pseudomonas, Bacillus* and Streptonzyces. In another embodiment, bacterial host cells are used to express the nucleic acid molecules and polypeptides of the invention. Useful expression vectors for bacterial hosts include bacterial plasmids, such as those from *E. coli, Bacillus* or Streptoinyces, including pBluescript, pGEX-2T, pUC vectors, col E1, pCR1, pBR322, pMB9 and their derivatives, wider host range plasmids, such as RP4, phage DNAs, e.g., the numerous derivatives of phage lambda, e.g., NM989, λGT10 and λGT11, and other phages, e.g., M13 and filamentous single stranded phage DNA. Where *E. coli* is used as host, selectable markers are, analogously, chosen for selectivity in gram negative bacteria: e.g., typical markers confer resistance to antibiotics, such as ampicillin, tetracycline, chloramphenicol, kanamycin, streptomycin and zeocin; auxotrophic markers can also be used.

In other embodiments, eukaryotic host cells, such as yeast, insect, mammalian or plant cells, can be used. Yeast cells, can be useful for eukaryotic genetic studies, due to the ease of targeting genetic changes by homologous recombination and the ability to easily complement genetic defects using recombinantly expressed proteins. Yeast cells are useful for identifying interacting protein components, e.g. through use of a two-hybrid system. In one embodiment, yeast cells are useful for protein expression. Vectors of the present invention for use in yeast can contain an origin of replication suitable for use in yeast and a selectable marker that is functional in yeast. Yeast vectors include Yeast Integrating plasmids (e.g., YIp5) and Yeast Replicating plasmids (the YRp and YEp series plasmids), Yeast Centromere plasmids (the YCp series plasmids), Yeast Artificial Chromosomes (YACs) which are based on yeast linear plasmids, denoted YLp, pGPD-2, 2 μplasmids and derivatives thereof, and improved shuttle vectors such as those described in Gietz et al., Gene, 74: 527-34 (1988) (YIplac, YEplac and YCplac). Selectable markers in yeast vectors include a variety of auxotrophic markers, the most common of which are (in *Saccharomyces cerevisiae*) URA3, HIS3, LEU2, TRP1 and LYS2, which complement specific auxotrophic mutations, such as ura3-52, his3-D1, leu2-D1, trp1-D1 and lys2-201.

Insect cells can be chosen for high efficiency protein expression. Where the host cells are from *Spodoptera frugiperda*, e.g., Sf9 and Sf21 cell lines, and ExpresSF™ cells (Protein Sciences Corp., Meriden, Conn., USA), the vector replicative strategy can be based upon the baculovirus life cycle. Baculovirus transfer vectors can be used to replace the wild-type AcMNPV polyhedrin gene with a heterologous gene of interest. Sequences that flank the polyhedrin gene in the wild-type genome can be positioned 5' and 3' of the expression cassette on the transfer vectors. Following co-transfection with AcMNPV DNA, a homologous recombination event occurs between these sequences resulting in a recombinant virus carrying the gene of interest and the polyhedrin or p10 promoter. Selection can be based upon visual screening for lacZ fusion activity.

The host cells can also be mammalian cells, which can be useful for expression of proteins intended as pharmaceutical agents, and for screening of potential agonists and antagonists of a protein or a physiological pathway. Mammalian vectors intended for autonomous extrachromosomal replication can include a viral origin, such as the SV40 origin, the papillomavirus origin, or the EBV origin for long term episomal replication. Vectors intended for integration, and thus replication as part of the mammalian chromosome, can include an origin of replication functional in mammalian cells, such as the SV40 origin. Vectors based upon viruses, such as adenovirus, adeno-associated virus, vaccinia virus, and various mammalian retroviruses, can replicate according to the viral replicative strategy. Selectable markers for use in mammalian cells include, include but are not limited to, resistance to neomycin (G418), blasticidin, hygromycin and zeocin, and selection based upon the purine salvage pathway using HAT medium.

Expression in mammalian cells can be achieved using a variety of plasmids, including pSV2, pBC12BI, and p91023, as well as lytic virus vectors (e.g., vaccinia virus, adeno virus, and baculovirus), episomal virus vectors (e.g., bovine papillomavirus), and retroviral vectors (e.g., murine retroviruses). Useful vectors for insect cells include baculoviral vectors and pVL 941.

Plant cells can also be used for expression, with the vector replicon derived from a plant virus (e.g., cauliflower mosaic virus, CaMV; tobacco mosaic virus, TMV) and selectable markers chosen for suitability in plants.

It is known that codon usage of different host cells can be different. For example, a plant cell and a human cell can exhibit a difference in codon preference for encoding a particular amino acid. As a result, human mRNA can not be efficiently translated in a plant, bacteria or insect host cell. Therefore, another embodiment of this invention is directed to codon optimization. The codons of the nucleic acid molecules of the invention can be modified to resemble genes naturally contained within the host cell without altering the amino acid sequence encoded by the nucleic acid molecule.

Any of a wide variety of expression control sequences can be used in these vectors to express the nucleic acid molecules of this invention. Such useful expression control sequences include the expression control sequences associated with structural genes of the foregoing expression vectors. Expression control sequences that control transcription include, e.g., promoters, enhancers and transcription termination sites. Expression control sequences in eukaryotic cells that control post-transcriptional events include splice donor and acceptor sites and sequences that modify the half-life of the transcribed RNA, e.g., sequences that direct poly(A) addition or binding sites for RNA-binding proteins. Expression control sequences that control translation include ribosome binding sites, sequences which direct targeted expression of the polypeptide to or within cellular compartments, and sequences in the 5' and 3' untranslated regions that modify the rate or efficiency of translation.

Examples of useful expression control sequences for a prokaryote, e.g., *E. coli*, will include a promoter, often a phage promoter, such as phage lambda pL promoter, the trc promoter, a hybrid derived from the trp and lac promoters, the bacteriophage T7 promoter (in *E. coli* cells engineered to express the T7 polymerase), the TAC or TRC system, the major operator and promoter regions of phage lambda, the control regions of fd coat protein, and the araBAD operon. Prokaryotic expression vectors can further include transcription terminators, such as the aspA terminator, and elements that facilitate translation, such as a consensus ribosome binding site and translation termination codon, Schomer et al., Proc. Natl. Acad. Sci. USA 83: 8506-8510 (1986).

Expression control sequences for yeast cells can include a yeast promoter, such as the CYC1 promoter, the GAL1 promoter, the GAL10 promoter, ADH1 promoter, the promoters of the yeast α-mating system, or the GPD promoter, and can have elements that facilitate transcription termination, such as the transcription termination signals from the CYC1 or ADH1 gene.

Expression vectors useful for expressing proteins in mammalian cells will include a promoter active in mammalian cells. These promoters include, but are not limited to, those derived from mammalian viruses, such as the enhancer-promoter sequences from the immediate early gene of the human cytomegalovirus (CMV), the enhancer-promoter sequences from the Rous sarcoma virus long terminal repeat (RSV LTR), the enhancer-promoter from SV40 and the early and late promoters of adenovirus. Other expression control sequences include the promoter for 3-phosphoglycerate kinase or other glycolytic enzymes, the promoters of acid phosphatase. Other expression control sequences include those from the gene comprising the OSNA of interest. Often, expression is enhanced by incorporation of polyadenylation sites, such as the late SV40 polyadenylation site and the polyadenylation signal and transcription termination sequences from the bovine growth hormone (BGH) gene, and ribosome binding sites. Furthermore, vectors can include introns, such as intron II of rabbit β-globin gene and the SV40 splice elements.

Nucleic acid vectors also include a selectable or amplifiable marker gene and means for amplifying the copy number of the gene of interest. Such marker genes are well known in the art. Nucleic acid vectors can also comprise stabilizing sequences (e.g., ori- or ARS-like sequences and telomere-like sequences), or can alternatively be designed to favor directed or non-directed integration into the host cell genome. In one embodiment, nucleic acid sequences of this invention are inserted in frame into an expression vector that allows a high level expression of an RNA which encodes a protein comprising the encoded nucleic acid sequence of interest. Nucleic acid cloning and sequencing methods are well known to those of skill in the art and are described in an assortment of laboratory manuals, including Sambrook (1989), supra, Sambrook (2000), supra; and Ausubel (1992), supra, Ausubel (1999), supra. Product information from manufacturers of biological, chemical and immunological reagents also provide useful information.

Expression vectors can be constitutive or inducible. Inducible vectors include naturally inducible promoters, such as the trc promoter, which is regulated by the lac operon, and the pL promoter, which is regulated by tryptophan, the MMTV-LTR promoter, which is inducible by dexamethasone, or can contain synthetic promoters and/or additional elements that confer inducible control on adjacent promoters. Examples of inducible synthetic promoters are the hybrid Plac/ara-1 promoter and the PLtetO-1 promoter. The PLtetO-1 promoter takes advantage of the high expression levels from the PL promoter of phage lambda, but replaces the lambda repressor sites with two copies of operator 2 of the Tn10 tetracycline resistance operon, causing this promoter to be tightly repressed by the Tet repressor protein and induced in response to tetracycline (Tc) and Tc derivatives such as anhydrotetracycline. Vectors can also be inducible because they contain hormone response elements, such as the glucocorticoid response element (GRE) and the estrogen response element (ERE), which can confer hormone inducibility where vectors are used for expression in cells having the respective hormone receptors. To reduce background levels of expression, elements responsive to ecdysone, an insect hormone, can be used instead, with coexpression of the ecdysone receptor.

In one embodiment of the invention, expression vectors can be designed to fuse the expressed polypeptide to small protein tags that facilitate purification and/or visualization. Such tags include a polyhistidine tag that facilitates purification of the fusion protein by immobilized metal affinity chromatography, for example using NiNTA resin (Qiagen Inc., Valencia, Calif., USA) or TALON™ resin (cobalt immobilized affinity chromatography medium, Clontech Labs, Palo Alto, Calif., USA). The fusion protein can include a chitin-binding tag and self-excising intein, permitting chitin-based purification with self-removal of the fused tag (IMPACT™ system, New England Biolabs, Inc., Beverley, Mass., USA). Alternatively, the fusion protein can include a calmodulin-binding peptide tag, permitting purification by calmodulin affinity resin (Stratagene, La Jolla, Calif., USA), or a specifically excisable fragment of the biotin carboxylase carrier protein, permitting purification of in vivo biotinylated protein using an avidin resin and subsequent tag removal (Promega, Madison, Wis., USA). As another useful alternative, the polypeptides of the present invention can be expressed as a fusion to glutathione-S-transferase, the affinity and specificity of binding to glutathione permitting purification using glutathione affinity resins, such as Glutathione-Superflow Resin (Clontech Laboratories, Palo Alto, Calif., USA), with subsequent elution with free glutathione. Other tags include, for example, the Xpress epitope, detectable by anti-Xpress antibody (Invitrogen, Carlsbad, Calif., USA), a myc tag, detectable by anti-myc tag antibody, the V5 epitope, detectable by anti-V5 antibody (Invitrogen, Carlsbad, Calif., USA), FLAG® epitope, detectable by anti-FLAG® antibody (Stratagene, La Jolla, Calif., USA), and the HA epitope, detectable by anti-HA antibody.

For secretion of expressed polypeptides, vectors can include appropriate sequences that encode secretion signals, such as leader peptides. For example, the pSecTag2 vectors (Invitrogen, Carlsbad, Calif., USA) are 5.2 kb mammalian expression vectors that carry the secretion signal from the V-J2-C region of the mouse Ig kappa-chain for efficient secretion of recombinant proteins from a variety of mammalian cell lines.

Expression vectors can also be designed to fuse proteins encoded by the heterologous nucleic acid insert to polypeptides that are larger than purification and/or identification tags. Useful protein fusions include those that permit display of the encoded protein on the surface of a phage or cell, fusions to intrinsically fluorescent proteins, such as those that have a green fluorescent protein (GFP)-like chromophore, fusions to the IgG Fc region, and fusions for use in two hybrid systems.

Vectors for phage display fuse the encoded polypeptide to, e.g., the gene III protein (pIII) or gene VIII protein (pVIII) for display on the surface of filamentous phage, such as M13. See Barbas et al., Phage Display: A Laboratory Manual, Cold Spring Harbor Laboratory Press (2001); Kay et al. (eds.), Phage Display of Peptides and Proteins: A Laboratory Manual, Academic Press, Inc., (1996); Abelson et al. (eds.), Combinatorial Chemistry (Methods in Enzymology, Vol. 267) Academic Press (1996). Vectors for yeast display, e.g. the pYD1 yeast display vector (Invitrogen, Carlsbad, Calif., USA), use the α-agglutinin yeast adhesion receptor to display recombinant protein on the surface of *S. cerevisiae*. Vectors for mammalian display, e.g., the pDisplay™ vector (Invitrogen, Carlsbad, Calif., USA), target recombinant proteins using an N-terminal cell surface targeting signal and a C-terminal transmembrane anchoring domain of platelet derived growth factor receptor.

A wide variety of vectors now exist that fuse proteins encoded by heterologous nucleic acids to the chromophore of the substrate-independent, intrinsically fluorescent green fluorescent protein from Aequorea Victoria ("GFP") and its variants. The GFP-like chromophore can be selected from GFP-like chromophores found in naturally occurring proteins, such as A. Victoria GFP (GENBANK accession number AAA27721), *Renilla reniformis* GFP, FP583 (GENBANK accession no. AF168419) (DsRed), FP593 (AF272711), FP483 (AF168420), FP484 (AF168424), FP595 (AF246709), FP486 (AF168421), FP538 (AF168423), and FP506 (AF168422), and need include only so much of the native protein as is needed to retain the chromophore's intrinsic fluorescence. Methods for determining the minimal domain required for fluorescence are known in the art. See Li et al., J. Biol. Chem. 272: 28545-28549 (1997). Alternatively, the GFP-like chromophore can be selected from GFP-like chromophores modified from those found in nature. The methods for engineering such modified GFP-like chromophores and testing them for fluorescence activity, both alone and as part of protein fusions, are well known in the art. See Heim et al., Curr. Biol. 6: 178-182 (1996) and Palm et al., Methods Enzymol. 302: 378-394 (1999). A variety of such modified chromophores are now commercially available and can readily be used in the fusion proteins of the present invention. These include EGFP ("enhanced GFP"), EBFP ("enhanced blue fluorescent protein"), BFP2, EYFP ("enhanced yellow fluorescent protein"), ECFP ("enhanced cyan fluorescent protein") or Citrine. EGFP (see, e.g, Cormack et al., Gene 173: 33-38 (1996); U.S. Pat. Nos. 6,090,919 and 5,804,387, the disclosures of which are incorporated herein by reference in their entireties) is found on a variety of vectors, both plasmid and viral, which are available commercially (Clontech Labs, Palo Alto, Calif., USA); EBFP is optimized for expression in mammalian cells whereas BFP2, which retains the original jellyfish codons, can be expressed in bacteria (see, e.g, Heim et al., Curr. Biol. 6: 178-182 (1996) and Cormack et al., Gene 173: 33-38 (1996)). Vectors containing these blue-shifted variants are available from Clontech Labs (Palo Alto, Calif., USA). Vectors containing EYFP, ECFP (see, e.g., Heim et al., Curr. Biol. 6: 178-182 (1996); Miyawaki et al., Nature 388: 882-887 (1997)) and Citrine (see, e.g., Heikal et al., Proc. Natl. Acad. Sci. USA 97: 11996-12001 (2000)) are also available from Clontech Labs. The GFP-like chromophore can also be drawn from other modified GFPs, including those described in U.S. Pat. Nos. 6,124,128; 6,096,865; 6,090,919; 6,066,476; 6,054,321; 6,027,881; 5,968,750; 5,874,304; 5,804,387; 5,777,079; 5,741,668; and 5,625,048, the disclosures of which are incorporated herein by reference in their entireties. See also Conn (ed.), Green Fluorescent Protein (Methods in Enzymology, Vol. 302), Academic Press, Inc. (1999); Yang, et al., J Biol Chem, 273: 8212-6 (1998); Bevis et al., Nature Biotechnology, 20:83-7 (2002). The GFP-like chromophore of each of these GFP variants can usefully be included in the fusion proteins of the present invention.

Polypeptides, Including Fragments Mutant Proteins, Homologous Proteins, Allelic Variants, Analogs and Derivatives Another aspect of the invention relates to polypeptides encoded by the nucleic acid molecules described herein. In one embodiment, the polypeptide is an ILDR2 polypeptide. A polypeptide as defined herein can be produced recombinantly, as discussed supra, can be isolated from a cell that naturally expresses the protein, or can be chemically synthesized following the teachings of the specification and using methods well known to those having ordinary skill in the art. One skilled in the art understands that polypeptides (for example, ILDR2) can be obtained in several ways, which include but are not limited to, expressing a nucleotide sequence encoding the protein of interest, or fragment thereof, by genetic engineering methods.

In one embodiment, the nucleic acid is expressed in an expression cassette, for example, to achieve overexpression in a cell. The nucleic acids of the invention can be an RNA, cDNA, cDNA-like, or a DNA of interest in an expressible format, such as an expression cassette, which can be expressed from the natural promoter or an entirely heterologous promoter. The nucleic acid of interest can encode a protein, and may or may not include introns. Any recombinant expression system can be used, including, but not limited to, bacterial, mammalian, yeast, insect, or plant cell expression systems.

Polypeptides of the present invention can also comprise a part or fragment of a ILDR2. In one embodiment, the fragment is derived from a polypeptide having an amino acid sequence selected from the group consisting of SEQ ID NO: 2-9, or 14-47. Polypeptides of the present invention comprising a part or fragment of an entire ILDR2 protein can or can not be ILDR2 proteins. A polypeptide that is not an ILDR2 protein, whether it is a fragment, analog, mutant protein, homologous protein or derivative, is nevertheless useful, especially for immunizing animals to prepare anti-ILDR2 protein antibodies. In one embodiment, the part or fragment is an ILDR2 protein. Methods of determining whether a polypeptide of the present invention is a ILDR2 protein are described herein.

Polypeptides of the present invention comprising fragments of at least 8 contiguous amino acids, often at least 15 contiguous amino acids, are useful as immunogens for raising antibodies that recognize polypeptides of the present invention. See, e.g., Lerner, Nature 299: 592-596 (1982); Shinnick et al., Annu Rev. Microbiol. 37: 425-46 (1983); Sutcliffe et al., Science 219: 660-6 (1983). As further described in the references cited herein, 8-mers, conjugated to a carrier, such as a protein, prove immunogenic and are capable of eliciting antibody for the conjugated peptide; accordingly, fragments of at least 8 amino acids of the polypeptides of the present invention have utility as immunogens.

Polypeptides comprising fragments of at least 8, 9, 10 or 12 contiguous amino acids are also useful as competitive inhibitors of binding of the entire polypeptide, or a portion thereof, to antibodies (as in epitope mapping), and to natural binding partners, such as subunits in a multimeric complex or to receptors or ligands of the subject protein; this competitive inhibition permits identification and separation of molecules that bind specifically to the polypeptide of interest. See U.S. Pat. Nos. 5,539,084 and 5,783,674, incorporated herein by reference in their entireties.

The polypeptides of the present invention thus can be at least 6 amino acids in length, at least 8 amino acids in length, at least 9 amino acids in length, at least 10 amino acids in length, at least 12 amino acids in length, at least 15 amino acids in length, at least 20 amino acids in length, at least 25 amino acids in length, at least 30 amino acids in length, at least 35 amino acids in length, at least 50 amino acids in length, at least 75 amino acids in length, at least 100 amino acids in length, or at least 150 amino acids in length. Polypeptides of the present invention can also be larger and comprise a full-length ILDR2 protein and/or an epitope tag and/or a fusion protein.

One having ordinary skill in the art can produce fragments by truncating the nucleic acid molecule, encoding the polypeptide and then expressing it recombinantly. Alternatively, one can produce a fragment by chemically synthesizing a portion of the full-length polypeptide. One can also produce a fragment by enzymatically cleaving a recombinant polypeptide or an isolated naturally occurring polypeptide. Methods of producing polypeptide fragments are well known in the art. See, e.g., Sambrook (1989), supra; Sambrook (2001), supra; Ausubel (1992), supra; and Ausubel (1999), supra. In one embodiment, a polypeptide comprising only a fragment can be produced by chemical or enzymatic cleavage of a ILDR2 polypeptide.

Polypeptides of the present invention are also inclusive of mutants, fusion proteins, homologous proteins and allelic variants.

A mutant protein can have the same or different properties compared to a naturally occurring polypeptide and comprises at least one amino acid insertion, duplication, deletion, rearrangement or substitution compared to the amino acid sequence of a native polypeptide. Small deletions and insertions can often be found that do not alter the function of a protein. The mutant protein can be a polypeptide that comprises at least one amino acid insertion, duplication, deletion, rearrangement or substitution compared to the amino acid sequence of SEQ ID NO: 2-9, or 14-47. Accordingly, in one embodiment, the mutant protein is one that exhibits at least 60% sequence identity, at least 70%, or at least 80% sequence identity, at least 85% sequence identity, at least 90% sequence identity, at least 95% sequence identity, at least 97%, sequence identity at least 985, sequence identity at least 99% or sequence identity at least 99.5% to an ILDR2 protein.

A mutant protein can be produced by isolation from a naturally occurring mutant cell, tissue or organism. A mutant protein can be produced by isolation from a cell, tissue or organism that has been experimentally mutagenized. Alternatively, a mutant protein can be produced by chemical manipulation of a polypeptide, such as by altering the amino acid residue to another amino acid residue using synthetic or semi-synthetic chemical techniques. In one embodiment, a mutant protein is produced from a host cell comprising a mutated nucleic acid molecule compared to the naturally occurring nucleic acid molecule. For instance, one can produce a mutant protein of a polypeptide by introducing one or more mutations into a nucleic acid molecule of the invention and then expressing it recombinantly. These mutations can be targeted, in which encoded amino acids are altered, or can be untargeted, in which random encoded amino acids within the polypeptide are altered. Mutant proteins with random amino acid alterations can be screened for a biological activity or property. Multiple random mutations can be introduced into the gene by methods well known to the art, e.g., by error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis and site-specific mutagenesis. Methods of producing mutant proteins with targeted or random amino acid alterations are well known in the art. See, e.g., Sambrook (1989), supra; Sambrook (2001), supra; Ausubel (1992), supra; and Ausubel (1999), as well as U.S. Pat. No. 5,223,408, which is herein incorporated by reference in its entirety.

The invention also contemplates polypeptides that are homologous to a polypeptide of the invention. By homologous polypeptide it is means one that exhibits significant sequence identity to an ILDR2 protein. By significant sequence identity it is meant that the homologous polypeptide exhibits at least exhibits at least 60% sequence identity, at least 70%, or at least 80% sequence identity, at least 85% sequence identity, at least 90% sequence identity, at least 95% sequence identity, at least 97%, sequence identity at least 985, sequence identity at least 99% or sequence identity at least 99.5% to an ILDR2 protein. In one embodiment, the amino acid substitutions of the homologous polypeptide are conservative amino acid substitutions.

Homologous polypeptides of the present invention can be naturally occurring and derived from another species, especially one derived from another primate, such as chimpanzee, gorilla, rhesus macaque, or baboon, wherein the homologous polypeptide comprises an amino acid sequence that exhibits significant sequence identity to a polypepetide of the invention. The homologous polypeptide can also be a naturally occurring polypeptide from a human, when the ILDR2 protein is a member of a family of polypeptides. The homologous polypeptide can also be a naturally occurring polypeptide derived from a non-primate, mammalian species, including without limitation, domesticated species, e.g., dog, cat, mouse, rat, rabbit, guinea pig, hamster, cow, horse, goat or pig. The homologous polypeptide can also be a naturally occurring polypeptide derived from a non-mammalian species, such as birds or reptiles. The naturally occurring homologous protein can be isolated directly from humans or other species. Alternatively, the nucleic acid molecule encoding the naturally occurring homologous polypeptide can be isolated and used to express the homologous polypeptide recombinantly. The homologous polypeptide can also be one that is experimentally produced by random mutation of a nucleic acid molecule and subsequent expression of the nucleic acid molecule. Alternatively, the homologous polypeptide can be one that is experimentally produced by directed mutation of one or more codons to alter the encoded amino acid of an ILDR2 protein.

Relatedness of proteins can also be characterized using a second functional test, the ability of a first protein competitively to inhibit the binding of a second protein to an antibody. It is, therefore, another aspect of the present invention to provide isolated polpeptide not only identical in sequence to those described herein, but also to provide isolated polypeptide ("cross-reactive proteins") that can competitively inhibit the binding of antibodies to all or to a portion of various of the isolated polypeptides of the present invention. Such competitive inhibition can readily be determined using immunoassays well known in the art.

As discussed herein, single nucleotide polymorphisms (SNPs) occur frequently in eukaryotic genomes, and the sequence determined from one individual of a species can differ from other allelic forms present within the population. Thus, polypeptides of the present invention are also inclusive of those encoded by an allelic variant of a nucleic acid molecule encoding an ILDR2 protein.

Polypeptides of the present invention are also inclusive of derivative polypeptides encoded by a nucleic acid molecule according to the invention. Also inclusive are derivative polypeptides having an amino acid sequence selected from the group consisting of an ILDR2 protein or a polypeptide of SEQ ID NO: 2-9, or 14-47 and which has been acetylated, carboxylated, phosphorylated, glycosylated, ubiquitinated or other post-translational modifications. In another embodiment, the derivative has been labeled with, e.g., radioactive isotopes such as $^{125}I$, $^{32}P$, $^{35}S$, and $^{3}H$. In another embodiment, the derivative has been labeled with fluorophores, chemiluminescent agents, enzymes, and antiligands that can serve as specific binding pair members for a labeled ligand.

Polypeptide modifications are well known to those of skill and have been described in detail in the scientific literature. Several common modifications, such as glycosylation, lipid attachment, sulfation, gamma-carboxylation of glutamic acid residues, hydroxylation and ADP-ribosylation, for instance, are described in most basic texts, such as, for instance Creighton, Protein Structure and Molecular Properties, 2nd ed., W. H. Freeman and Company (1993). Many detailed reviews are available on this subject, such as, for example, those provided by Wold, in Johnson (ed.), Post-translational Covalent Modification of Proteins, pgs. 1-12, Academic Press (1983); Seifter et al., Meth. Enzymol. 182: 626-646 (1990) and Rattan et al., Ann. N.Y. Acad. Sci. 663: 48-62 (1992).

One can determine whether a polypeptide of the invention will be post-translationally modified by analyzing the sequence of the polypeptide to determine if there are peptide motifs indicative of sites for post-translational modification. There are a number of computer programs that permit prediction of post-translational modifications. See, e.g., expasy with the extension.org of the world wide web (accessed Nov. 11, 2002), which includes PSORT, for prediction of protein sorting signals and localization sites, SignalP, for prediction of signal peptide cleavage sites, MITOPROT and Predotar, for prediction of mitochondrial targeting sequences, NetOGlyc, for prediction of type O-glycosylation sites in mammalian proteins, big-PI Predictor and DGPI, for prediction of prenylation-anchor and cleavage sites, and NetPhos, for prediction of Ser, Thr and Tyr phosphorylation sites in eukaryotic proteins. Other computer programs, such as those included in GCG, also can be used to determine post-translational modification peptide motifs.

Examples of types of post-translational modifications include, but are not limited to: (Z)-dehydrobutyrine; 1-chondroitin sulfate-L-aspartic acid ester; 1'-glycosyl-L-tryptophan; 1'-phospho-L-histidine; 1-thioglycine; 2'-(S-L-cysteinyl)-L-histidine; 2'-[3-carboxamido (trimethylammonio) propyl]-L-histidine; 2'-alpha-mannosyl-L-tryptophan; 2-methyl-L-glutamine; 2-oxobutanoic acid; 2-pyrrolidone carboxylic acid; 3'-(1'-L-histidyl)-L-tyrosine; 3'-(8alpha-FAD)-L-histidine; 3'-(S-L-cysteinyl)-L-tyrosine; 3',3",5'-triiodo-L-thyronine; 3'-4'-phospho-L-tyrosine; 3-hydroxy-L-proline; 3'-methyl-L-histidine; 3-methyl-L-lanthionine; 3'-phospho-L-histidine; 4'-(L-tryptophan)-L-tryptophyl quinone; 42 N-cysteinyl-glycosylphosphatidylinositolethanolamine; 43-(T-L-histidyl)-L-tyrosine; 4-hydroxy-L-arginine; 4-hydroxy-L-lysine; 4-hydroxy-L-proline; 5'-(N6-L-lysine)-L-topaquinone; 5-hydroxy-L-lysine; 5-methyl-L-arginine; alpha-1-microglobulin-Ig alpha complex chromophore; bis-L-cysteinyl bis-L-histidino diiron disulfide; bis-L-cysteinyl-L-N3'-histidino-L-serinyl tetrairon' tetrasulfide; chondroitin sulfate D-glucuronyl-D-galactosyl-D-galactosyl-D-xylosyl-L-serine; //D-alanine; D-allo-isoleucine; D-asparagine; dehydroalanine; dehydrotyrosine; dermatan 4-sulfate D-glucuronyl-D-galactosyl-D-galactosyl-D-xylosyl-L-serine; D-glucuronyl-N-glycine; dipyrrolylmethanemethyl-L-cysteine; D-leucine; D-methionine; D-phenylalanine; D-serine; D-tryptophan; glycine amide; glycine oxazolecarboxylic acid; glycine thiazolecarboxylic acid; heme P450-bis-L-cysteine-L-tyrosine; heme-bis-L-cysteine; hemediol-L-aspartyl ester-L-glutamyl ester; hemediol-L-aspartyl ester-L-glutamyl ester-L-methionine sulfonium; heme-L-cysteine; heme-L-histidine; heparan sulfate D-glucuronyl-D-galactosyl-D-galactosyl-D-xylosyl-L-serine; heme P450-bis-L-cysteine-L-lysine; hexakis-L-cysteinyl hexairon hexasulfide; keratan sulfate D-glucuronyl-D-galactosyl-D-galactosyl-D-xylosyl-L-threonine; L oxoalanine-lactic acid; L phenyllactic acid; 1'-(8alpha-FAD)-L-histidine; L-2'.4',5'-topaquinone; L-3',4'-dihydroxyphenylalanine; L-3'.4'.5'-trihydroxyphenylalanine; L-4'-bromophenylalanine; L-6'-bromotryptophan; L-alanine amide; L-alanyl imidazolinone glycine; L-allysine; L-arginine amide; L-asparagine amide; L-aspartic 4-phosphoric anhydride; L-aspartic acid 1-amide; L-beta-methylthioaspartic acid; L-bromohistidine; L-citrulline; L-cysteine amide; L-cysteine glutathione disulfide; L-cysteine methyl disulfide; L-cysteine methyl ester; L-cysteine oxazolecarboxylic acid; L-cysteine oxazolinecarboxylic acid; L-cysteine persulfide; L-cysteine sulfenic acid; L-cysteine sulfinic acid; L-cysteine thiazolecarboxylic acid; L-cysteinyl homocitryl molybdenum-heptairon-nonasulfide; L-cysteinyl imidazolinone glycine; L-cysteinyl molybdopterin; L-cysteinyl molybdopterin guanine dinucleotide; L-cystine; L-erythro-beta-hydroxyasparagine; L-erythro-beta-hydroxyaspartic acid; L-gamma-carboxyglutarnic acid; L-glutamic acid 1-amide; L-glutamic acid 5-methyl ester; L-glutamine amide; L-glutamyl 5-glycerylphosphorylethanolarnine; L-histidine amide; L-isoglutamyl-polyglutamic acid; L-isoglutamyl-polyglycine; L-isoleucine amide; L-lanthionine; L-leucine amide; L-lysine amide; L-lysine thiazolecarboxylic acid; L-lysinoalanine; L-methionine amide; L-methionine sulfone; L-phenyalanine thiazolecarboxylic acid; L-phenylalanine amide; L-proline amide; L-selenocysteine; L-selenocysteinyl molybdopterin guanine dinucleotide; L-serine amide; L-serine thiazolecarboxylic acid; L-seryl imidazolinone glycine; L-T-bromophenylalanine; L-T-bromophenylalanine; L-threonine amide; L-thyroxine; L-tryptophan amide; L-tryptophyl quinone; L-tyrosine amide; L-valine amide; meso-lanthionine; N-(L-glutamyl)-L-tyrosine; N-(L-isoaspartyl)-glycine; N-(L-isoaspartyl)-L-cysteine; N,N,N-trimethyl-L-alanine; N,N-dimethyl-L-proline; N2-acetyl-L-lysine; N2-succinyl-L-tryptophan; N4-(ADP-ribosyl)-L-asparagine; N4-glycosyl-L-asparagine; N4-hydroxymethyl-L-asparagine; N4-methyl-L-asparagine; N5-methyl-L-glutamine; N6-1-carboxyethyl-L-lysine; N6-(4-amino hydroxybutyl)-L-lysine; N6-(L-isoglutamyl)-L-lysine; N6-(phospho-5'-adenosine)-L-lysine; N6-(phospho-5'-guanosine)-L-lysine; N6,N6,N6-trimethyl-L-lysine; N6,N6-dimethyl-L-lysine; N6-acetyl-L-lysine; N6-biotinyl-L-lysine; N6-carboxy-L-lysine; N6-formyl-L-lysine; N6-glycyl-L-lysine; N6-lipoyl-L-lysine; N6-methyl-L-lysine; N6-methyl-N6-poly(N-methyl-propylamine)-L-lysine; N6-mureinyl-L-lysine; N6-myristoyl-L-lysine; N6-palmitoyl-L-lysine; N6-pyridoxal phosphate-L-lysine; N6-pyruvic acid 2-iminyl-L-lysine; N6-retinal-L-lysine; N-acetylglycine; N-acetyl-L-glutamine; N-acetyl-L-alanine; N-acetyl-L-aspartic acid; N-acetyl-L-cysteine; N-acetyl-L-glutamic acid; N-acetyl-L-isoleucine; N-acetyl-L-methionine; N-acetyl-L-proline; N-acetyl-L-serine; N-acetyl-L-threonine; N-acetyl-L-tyrosine; N-acetyl-L-valine; N-alanyl-glycosylphosphatidylinositolethanolamine; N-asparaginyl-glycosylphosphatidylinositolethanolamine; N-aspartyl-glycosylphosphatidylinositolethanolamine; N-formylglycine; N-formyl-L-methionine; N-glycyl-glycosylphosphatidylinositolethanolamine; N-L-glutamyl-poly-L-glutamic acid; N-methylglycine; N-methyl-L-alanine; N-methyl-L-methionine; N-methyl-L-phenylalanine; N-myristoyl-glycine; N-palmitoyl-L-cysteine; N-pyruvic acid 2-iminyl-L-cysteine; N-pyruvic acid 2-iminyl-L-valine; N-seryl-glycosylphosphatidylinositolethanolamine; N-seryl-glycosyOSPhingolipidinositolethanolamine; O-(ADP-ribosyl)-L-serine; O-(phospho-5'-adenosine)-L-threonine; O-(phospho-5'-DNA)-L-serine; O-(phospho-5'-DNA)-L-threonine; 0-(phospho-5'rRNA)-L-serine; O-(phosphoribosyl dephospho-coenzyme A)-L-serine; O-(sn-1-glycerophosphoryl)-L-serine; O4'-(8alpha-FAD)-L-tyrosine; O4'-(phospho-5'-adenosine)-L-tyrosine; O4'-(phospho-5'-DNA)-L-tyrosine; O4'-(phospho-5'-RNA)-L-tyrosine; O4'-(phospho-5'-uridine)-L-tyrosine; O4-glycosyl-L-hydroxyproline; O4'-glycosyl-L-tyrosine; O4'-sulfo-L-tyrosine; O5-glycosyl-L-hydroxylysine; O-glycosyl-L-serine; O-glycosyl-L-threonine; omega-N-(ADP-ribosyl)-L-arginine; omega-N-omega-N'-dimethyl-L-arginine; omega-N-methyl-L-arginine; omega-N-omega-N-dimethyl-L-arginine; omega-N-phospho-L-arginine; O'octanoyl-L-serine; O-palmitoyl-L-serine; O-palmitoyl-L-threonine; O-phospho-L-serine; O-phospho-L-threonine; O-phosphopantetheine-L-serine; phycoerythrobilin-bis-L-cysteine; phycourobilin-bis-L-cysteine; pyrroloquinoline quinone; pyruvic acid; S hydroxycinnamyl-L-cysteine; S-(2-aminovinyl)methyl-D-cysteine; S-(2-aminovinyl)-D-cysteine; S-(6-FW-L-cysteine; S-(8alpha-FAD)-L-cysteine; S-(ADP-ribosyl)-L-cysteine; S-(L-isoglutamyl)-L-cysteine; S-12-hydroxyfamesyl-L-cysteine; S-acetyl-L-cysteine; S-diacylglycerol-L-cysteine; S-diphytanylglycerot diether-L-cysteine; S-famesyl-L-cysteine; S-geranylgeranyl-L-cysteine; S-glycosyl-L-cysteine; S-glycyl-L-cysteine; S-methyl-L-cysteine; S-nitrosyl-L-cysteine; S-palmitoyl-L-cysteine; S-phospho-L-cysteine; S-phycobiliviolin-L-cysteine; S-phycocyanobilin-L-cysteine; S-phycoerythrobilin-L-cysteine; S-phytochromobilin-L-cysteine; S-selenyl-L- cysteine; S-sulfo-L-cysteine; tetrakis-L-cysteinyl diiron disulfide; tetrakis-L-cysteinyl iron; tetrakis-L-cysteinyl tetrairon tetrasulfide; trans-2,3-cis 4-dihydroxy-L-proline; tris-L-cysteinyl triiron tetrasulfide; tris-L-cysteinyl triiron trisulfide; tris-L-cysteinyl-L-aspartato tetrairon tetrasulfide; tris-L-cysteinyl-L-cysteine persulfido-bis-L-glutamato-L-histidino tetrairon disulfide trioxide; tris-L-cysteinyl-L-N3'-histidino tetrairon tetrasulfide; tris-L-cysteinyl-L-NM'-histidino tetrairon tetrasulfide; and tris-L-cysteinyl-L-serinyl tetrairon tetrasulfide.

Additional examples of post translational modifications can be found in web sites such as the Delta Mass database based on Krishna, R. G. and F. Wold (1998). Posttranslational Modifications. Proteins—Analysis and Design. R. H. Angeletti. San Diego, Academic Press. 1: 121-206.; Methods in Enzymology, 193, J. A. McClosky (ed) (1990), pages 647-660; Methods in Protein Sequence Analysis edited by Kazutomo Imahori and Fumio Sakiyama, Plenum Press, (1993) "Post-translational modifications of proteins" R. G. Krishna and F. Wold pages 167-172; "GlycoSuiteDB: a new curated relational database of glycoprotein glycan structures and their biological sources" Cooper et al. Nucleic Acids Res. 29; 332-335 (2001) "O-GLYCBASE version 4.0: a revised database of O-glycosylated proteins" Gupta et al. Nucleic Acids Research, 27: 370-372 (1999); and "PhosphoBase, a database of phosphorylation sites: release 2.0.", Kreegipuu et al. Nucleic Acids Res 27(1):237-239 (1999) see also, WO 02/211 39A2, the disclosure of which is incorporated herein by reference in its entirety.

Disease states are often accompanied by alterations in the post-translational modifications of proteins. Thus, in another embodiment, the invention provides polypeptides from diseased cells or tissues that have altered post-translational modifications compared to the post-translational modifications of polypeptides from normal cells or tissues. A number of altered post-translational modifications are known. One common alteration is a change in phosphorylation state, wherein the polypeptide from the diseased cell or tissue is hyperphosphorylated or hypophosphorylated compared to the polypeptide from a normal tissue, or wherein the polypeptide is phosphorylated on different residues than the polypeptide from a normal cell. Another common alteration is a change in glycosylation state, wherein the polypeptide from the diseased cell or tissue has more or less glycosylation than the polypeptide from a normal tissue, and/or wherein the polypeptide from the diseased cell or tissue has a different type of glycosylation than the polypeptide from a non-diseased cell or tissue.

Another post-translational modification that can be altered in diseased cells is prenylation. Prenylation is the covalent attachment of a hydrophobic prenyl group (farnesyl or geranylgeranyl) to a polypeptide. Prenylation is required for localizing a protein to a cell membrane and is often required for polypeptide function. For instance, the Ras superfamily of GTPase signalling proteins must be prenylated for function in a cell. See, e.g., Prendergast et al., Semin. Cancer Biol. 10: 443-452 (2000) and Khwaja et al., Lancet 355: 741-744 (2000).

Other post-translation modifications that can be altered in diseased cells include, without limitation, polypeptide methylation, acetylation, arginylation or racemization of amino acid residues. In these cases, the polypeptide from the diseased cell can exhibit increased or decreased amounts of the post-translational modification compared to the corresponding polypeptides from non-diseased cells.

Other polypeptide alterations in diseased cells include abnormal polypeptide cleavage of proteins and aberrant protein-protein interactions. Abnormal polypeptide cleavage can be cleavage of a polypeptide in a diseased cell that does not usually occur in a normal cell, or a lack of cleavage in a diseased cell, wherein the polypeptide is cleaved in a normal cell. Aberrant protein-protein interactions can be covalent cross-linking or non-covalent binding between proteins that do not normally bind to each other. Alternatively, in a diseased cell, a protein can fail to bind to another protein to which it is bound in a non-diseased cell. Alterations in cleavage or in protein-protein interactions can be due to over- or underproduction of a polypeptide in a diseased cell compared to that in a normal cell, or can be due to alterations in post-translational modifications of one or more proteins in the diseased cell. See, e.g., Henschen-Edman, Ann. N.Y. Acad. Sci. 936: 580-593 (2001).

Alterations in polypeptide post-translational modifications, as well as changes in polypeptide cleavage and protein-protein interactions, can be determined by any method known in the art. For instance, alterations in phosphorylation can be determined by using anti-phosphoserine, anti-phosphothreonine or anti-phosphotyrosine antibodies or by amino acid analysis. Glycosylation alterations can be determined using antibodies specific for different sugar residues, by carbohydrate sequencing, or by alterations in the size of the glycoprotein, which can be determined by, e.g., SDS polyacrylamide gel electrophoresis (PAGE). Other alterations of post-translational modifications, such as prenylation, racemization, methylation, acetylation and arginylation, can be determined by chemical analysis, protein sequencing, amino acid analysis, or by using antibodies that bind a post-translational modification. Changes in protein-protein interactions and in polypeptide cleavage can be analyzed by any method known in the art including, without limitation, non-denaturing PAGE (for non-covalent protein-protein interactions), SDS PAGE (for covalent protein-protein interactions and protein cleavage), chemical cleavage, protein sequencing or immunoassays.

In another embodiment, the invention provides polypeptides that have been post-translationally modified. In one embodiment, polypeptides can be modified enzymatically or chemically, by addition or removal of a post-translational modification. For example, a polypeptide can be glycosylated or deglycosylated enzymatically. Similarly, polypeptides can be phosphorylated using a purified kinase, such as a MAP kinase (e.g, p38, ERK, or JNK) or a tyrosine kinase (e.g., Src or erbB2). A polypeptide can also be modified through synthetic chemistry. Alternatively, one can isolate the polypeptide of interest from a cell or tissue that expresses the polypeptide with the desired post-translational modification. In another embodiment, a nucleic acid molecule encoding the polypeptide of interest is introduced into a host cell that is capable of post-translationally modifying the encoded polypeptide in the desired fashion. If the polypeptide does not contain a motif for a desired post-translational modification, one can alter the post-translational modification by mutating the nucleic acid sequence of a nucleic acid molecule encoding the polypeptide so that it contains a site for the desired post-translational modification. Amino acid sequences that can be post-translationally modified are known in the art. See, e.g., the programs described herein on the Expasy website. The nucleic acid molecule can also be introduced into a host cell that is capable of post-translationally modifying the encoded polypeptide. Similarly, one can delete sites that are post-translationally modified by mutating the nucleic acid sequence so that the encoded polypeptide does not contain the post-translational modification motif, or by introducing the native nucleic acid molecule into a host cell that is not capable of post-translationally modifying the encoded polypeptide.

Polypeptides are not always entirely linear. For instance, polypeptides can be branched as a result of ubiquitination, and they can be circular, with or without branching, as a result of posttranslation events, including natural processing event and events brought about by human manipulation which do not occur naturally. Circular, branched and branched circular polypeptides can be synthesized by non-translation natural process and by entirely synthetic methods, as well. Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications can be present in polypeptides of the present invention, as well. For instance, the amino terminal residue of polypeptides made in *E. coli*, prior to proteolytic processing, almost invariably will be N-formylmethionine.

Useful post-synthetic (and post-translational) modifications include conjugation to detectable labels, such as fluorophores. A wide variety of amine-reactive and thiol-reactive fluorophore derivatives have been synthesized that react under nondenaturing conditions with N-terminal amino groups and epsilon amino groups of lysine residues, on the one hand, and with free thiol groups of cysteine residues, on the other.

Kits are available commercially that permit conjugation of proteins to a variety of amine-reactive or thiol-reactive fluorophores: Molecular Probes, Inc. (Eugene, Oreg., USA), e.g., offers kits for conjugating proteins to Alexa Fluor 350, Alexa Fluor 430, Fluorescein-EX, Alexa Fluor 488, Oregon Green 488, Alexa Fluor 532, Alexa Fluor 546, Alexa Fluor 546, Alexa Fluor 568, Alexa Fluor 594, and Texas Red-X A wide variety of other amine-reactive and thiol-reactive fluorophores are available commercially (Molecular Probes, Inc., Eugene, Oreg., USA), including Alexa Fluor® 350, Alexa Fluor® 488, Alexa Fluor® 532, Alexa Fluor® 546, Alexa Fluor® 568, Alexa Fluor® 594, Alexa Fluor® 647 (monoclonal antibody labeling kits available from Molecular Probes, Inc., Eugene, Oreg., USA), BODIPY dyes, such as BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY TR, BODIPY 630/650, BODIPY 650/665, Cascade Blue, Cascade Yellow, Dansyl, lissamine rhodamine B, Marina Blue, Oregon Green 488, Oregon Green 514, Pacific Blue, rhodamine 6G, rhodamine green, rhodamine red, tetramethylrhodamine, Texas Red (available from Molecular Probes, Inc., Eugene, Oreg., USA).

The polypeptides of the present invention can also be conjugated to fluorophores, other proteins, and other macromolecules, using bifunctional linking reagents. Common homobifunctional reagents include, e.g., APG, AEDP, BASED, BMB, BMDB, BMH, BMOE, BM[PEO]3, BM[PEO]4, BS3, BSOCOES, DFDNB, DMA, DMP, DMS, DPDPB, DSG, DSP (Lomant's Reagent), DSS, DST, DTBP, DTME, DTSSP, EGS, HBVS, Sulfo-BSOCOES, Sulfo-DST, Sulfo-EGS (available from Pierce, Rockford, Ill., USA); common heterobifunctional cross-linkers include ABH, AMAS, ANB-NOS, APDP, ASBA, BMPA, BMPH, BMPS, EDC, EMCA, EMCH, EMCS, KMUA, KMUH, GMBS, LC-SMCC, LC-SPDP, MBS, M2C2H, MPBH, MSA, NHS-ASA, PDPH, PMPI, SADP, SAED, SAND, SANPAH, SASD, SATP, SBAP, SFAD, SIA, SLAB, SMCC, SMPB, SMPH, SMPT, SPDP, Sulfo-EMCS, Sulfo-GMBS, Sulfo-HSAB, Sulfo-KMUS, Sulfo-LC-SPDP, Sulfo-MBS, Sulfo-NHS-LC-ASA, Sulfo-SADP, Sulfo-SANPAH, Sulfo-SIAB, Sulfo-SMCC, Sulfo-SMPB, Sulfo-LC-SMPT, SVSB, TFCS (available Pierce, Rockford, Ill., USA).

Polypeptides of the present invention, including full length polypeptides, fragments and fusion proteins, can be conjugated, using such cross-linking reagents, to fluorophores that are not amine- or thiol-reactive. Other labels that usefully can be conjugated to polypeptides of the present invention include radioactive labels, echosonographic contrast reagents, and MRI contrast agents.

Polypeptides of the present invention, including full length polypeptide, fragments and fusion proteins, can also usefully be conjugated using cross-linking agents to carrier proteins, such as KLH, bovine thyroglobulin, and even bovine serum albumin (BSA), to increase immunogenicity for raising anti-ILDR2 protein antibodies.

Polypeptides of the present invention, including full length polypeptide, fragments and fusion proteins, can also usefully be conjugated to polyethylene glycol (PEG); PEGylation increases the serum half life of proteins administered intravenously for replacement therapy. Delgado et al., Crit. Rev. Ther. Drug Carrier Syst. 9(3-4): 249-304 (1992); Scott et al., Curr. Pharm. Des. 4(6): 423-38 (1998); DeSantis et al., Curr. Opin. Biotechnol. 10(4): 324-30 (1999). PEG monomers can be attached to the protein directly or through a linker, with PEGylation using PEG monomers activated with tresyl chloride (2,2,2-trifluoroethanesulphonyl chloride) permitting direct attachment under mild conditions.

Polypeptides of the present invention are also inclusive of analogs of a polypeptide encoded by a nucleic acid molecule according to the invention. In one embodiment, this polypeptide is an ILDR2 protein. In another embodiment the analog polypeptide comprises one or more substitutions of non-natural amino acids or non-native inter-residue bonds compared to the naturally occurring polypeptide. In one embodiment, the analog is structurally similar to an ILDR2 protein, but one or more peptide linkages is replaced by a linkage selected from the group consisting of $—CH_2NH—$, $—CH_2S—$, $—CH_2—CH_2—$, —CH═CH-(cis and trans), $—COCH_2—$, $—CH(OH)CH_2—$ and $—CH_2SO—$. In another embodiment, the analog comprises substitution of one or more amino acids of a ILDR2 protein with a D-amino acid of the same type or other non-natural amino acid in order to generate more stable peptides. D-amino acids can readily be incorporated during chemical peptide synthesis: peptides assembled from D-amino acids are more resistant to proteolytic attack; incorporation of D-amino acids can also be used to confer specific three-dimensional conformations on the peptide. Other amino acid analogues that can be added during chemical synthesis include ornithine, norleucine, phosphorylated amino acids (for example, phosphoserine, phosphothreonine, phosphotyrosine), L-malonyltyrosine, a non-hydrolyzable analog of phosphotyrosine (see, e.g., Kole et al., Biocheem. Biophlys. Res. Com. 209: 817-821 (1995)), and various halogenated phenylalanine derivatives.

Non-natural amino acids can be incorporated during solid phase chemical synthesis or by recombinant techniques. Solid phase chemical synthesis of peptides is well established in the art. Procedures are described, inter alia, in Chan et al. (eds.), Fmoc Solid Phase Peptide Synthesis: A Practical Approach (Practical Approach Series), Oxford Univ. Press (March 2000); Jones, Amino Acid and Peptide Synthesis (Oxford Chemistry Primers, No 7), Oxford Univ. Press (1992); and Bodanszky, Principles of Peptide Synthesis (Springer Laboratory), Springer Verlag (1993).

Amino acid analogues having detectable labels are also usefully incorporated during synthesis to provide derivatives and analogs. Biotin, for example can be added using biotinoyl-(9-fluorenylmethoxycarbonyl)-L-lysine (FMOC biocytin) (Molecular Probes, Eugene, Oreg., USA). Biotin can also be added enzymatically by incorporation into a fusion protein of a *E. coli* BirA substrate peptide. The FMOC and tBOC derivatives of dabcyl-L-lysine (Molecular Probes, Inc., Eugene, Oreg., USA) can be used to incorporate the dabcyl chromophore at selected sites in the peptide sequence during synthesis. The aminonaphthalene derivative EDANS, the most common fluorophore for pairing with the dabcyl quencher in fluorescence resonance energy transfer (FRET) systems, can be introduced during automated synthesis of peptides by using EDANS-FMOC-L-glutamic acid or the corresponding tBOC derivative (both from Molecular Probes, Inc., Eugene, Oreg., USA). Tetramethylrhodamine fluorophores can be incorporated during automated FMOC synthesis of peptides using (FMOC)-TMR-L-lysine (Molecular Probes, Inc. Eugene, Oreg., USA).

Other useful amino acid analogues that can be incorporated during chemical synthesis include aspartic acid, glutamic acid, lysine, and tyrosine analogues having allyl side-chain protection (Applied Biosystems, Inc., Foster City, Calif., USA); the allyl side chain permits synthesis of cyclic, branched-chain, sulfonated, glycosylated, and phosphorylated peptides.

A large number of other FMOC-protected non-natural amino acid analogues capable of incorporation during chemical synthesis are available commercially, including, e.g., Fmoc-2-aminobicyclo[2.2.1]heptane-2-carboxylic acid, Fmoc-3-endo-aminobicyclo[2.2.1]heptane-2-endo-carboxylic acid, Fmoc-3-exo-aminobicyclo[2.2.1]heptane-2-exo-carboxylic acid, Fmoc-3-endo-amino-bicyclo[2.2.1]hept-5-ene-2-endo-carboxylic acid, Fmoc-3-exo-amino-bicyclo[2.2.1]hept-5-ene-2-exo-carboxylic acid, Fmoc-cis-2-amino-1-cyclohexanecarboxylic acid, Fmoc-trans-2-amino-1-cyclohexanecarboxylic acid, Fmoc-1-amino-1-cyclopentanecarboxylic acid, Fmoc-cis-2-amino-1-cyclopentanecarboxylic acid, Fmoc-1-amino-1-cyclopropanecarboxylic acid, Fmoc-D-2-amino-4-(ethylthio)butyric acid, Fmoc-L-2-amino-4-(ethylthio)butyric acid, Fmoc-L-buthionine, Fmoc-S-methyl-L-Cysteine, Fmoc-2-aminobenzoic acid (anthranillic acid), Fmoc-3-aminobenzoic acid, Fmoc-4-aminobenzoic acid, Fmoc-2-aminobenzophenone-2'-carboxylic acid, Fmoc-N-(4-aminobenzoyl)-β-alanine, Fmoc-2-amino4,5-dimethoxybenzoic acid, Fmoc-4-aminohippuric acid, Fmoc-2-amino-3-hydroxybenzoic acid, Fmoc-2-amino-5-hydroxybenzoic acid, Fmoc-3-amino4-hydroxybenzoic acid, Fmoc4-amino-3-hydroxybenzoic acid, Fmoc-4-amino-2-hydroxybenzoic acid, Fmoc-5-amino-2-hydroxybenzoic acid, Fmoc-2-amino-3-methoxybenzoic acid, Fmoc4-amino-3-methoxybenzoic acid, Fmoc-2-amino-3-methylbenzoic acid, Fmoc-2-amino-5-methylbenzoic acid, Fmoc-2-amino-6-methylbenzoic acid, Fmoc-3-amino-2-methylbenzoic acid, Fmoc-3-amino4-methylbenzoic acid, Fmoc-4-amino-3-methylbenzoic acid, Fmoc-3-amino-2-naphtoic acid, Fmoc-D,L-3-amino-3-phenylpropionic acid, Fmoc-L-Methyldopa, Fmoc-2-amino-4,6-dimethyl-3-pyridinecarboxylic acid, Fmoc-D,L-amino-2-thiophenacetic acid, Fmoc-4-(carboxymethyl)piperazine, Fmoc-4-carboxypiperazine, Fmoc-4-(carboxymethyl)homopiperazine, Fmoc-4-phenyl-4-piperidinecarboxylic acid, Fmoc-L-1,2,3,4-tetrahydronorharman-3-carboxylic acid, Fmoc-L-thiazolidine4-carboxylic acid, available from—The Peptide Laboratory (Richmond, Calif., USA).

Non-natural residues can also be added biosynthetically by engineering a suppressor tRNA by chemical aminoacylation with the desired unnatural amino acid. Conventional site-directed mutagenesis is used to introduce the chosen stop codon UAG at the site of interest in the protein gene. When the acylated suppressor tRNA and the mutant gene are combined in an in vitro transcription/translation system, the unnatural amino acid is incorporated in response to the UAG codon to give a protein containing that amino acid at the specified position. Liu et al., Proc. Natl Acad. Sci. USA 96(9): 4780-5 (1999); Wang et al., Science 292(5516): 498-500 (2001).

Fusion Proteins

Another aspect of the present invention relates to the fusion of a polypeptide of the present invention to heterologous polypeptides. In one embodiment, the polypeptide of the present invention is an ILDR2 protein or is a mutant protein, homologous polypeptide, analog or derivative thereof.

The fusion proteins of the present invention will include at least one fragment of a polypeptide of the present invention, which fragment is at least 6 amino acids in length, at least 8 amino acids in length, at least 9 amino acids in length, at least 10 amino acids in length, at least 12 amino acids in length, at least 15 amino acids in length, at least 20 amino acids in length, at least 25 amino acids in length, at least 30 amino acids in length, at least 35 amino acids in length, at least 50 amino acids in length, at least 75 amino acids in length, at least 100 amino acids in length, or at least 150 amino acids in length. Fusions proteins that include the entirety of a polypeptide of the present invention are also useful.

The heterologous polypeptide included within the fusion protein of the present invention is at least 6 amino acids in length, often at least 8 amino acids in length, and can be at least 15, 20, or 25 amino acids in length. Fusions that include larger polypeptides, such as the IgG Fc region, and even entire proteins (such as GFP chromophore-containing proteins) can be useful.

Heterologous polypeptides to be included in the fusion proteins of the present invention can usefully include those designed to facilitate purification and/or visualization of recombinantly-expressed proteins. See, e.g., Ausubel, Chapter 16, (1992), supra. Although purification tags can also be incorporated into fusions that are chemically synthesized, chemical synthesis can also provides sufficient purity. Such tags can retain their utility even when the protein is produced by chemical synthesis, and when so included render the fusion proteins of the present invention useful as directly detectable markers of the presence of a polypeptide of the invention.

Heterologous polypeptides to be included in the fusion proteins of the present invention can usefully include those that facilitate secretion of recombinantly expressed proteins into the periplasmic space or extracellular milieu for prokaryotic hosts or into the culture medium for eukaryotic cells through incorporation of secretion signals and/or leader sequences. For example, a $His^6$ tagged protein (SEQ ID NO: 146) can be purified on a Ni affinity column and a GST fusion protein can be purified on a glutathione affinity column. Similarly, a fusion protein comprising the Fc domain of IgG can be purified on a Protein A or Protein G column and a fusion protein comprising an epitope tag such as myc can be purified using an immunoaffinity column containing an anti-c-myc antibody. The epitope tag can be separated from the protein encoded by the essential gene by an enzymatic cleavage site that can be cleaved after purification. See also the discussion of nucleic acid molecules encoding fusion proteins that can be expressed on the surface of a cell.

Other useful fusion proteins of the present invention include those that permit use of the polypeptide of the present invention as bait in a yeast two-hybrid system. See Bartel et al. (eds.), The Yeast Two-Hybrid System, Oxford University Press (1997); Zhu et al., Yeast Hybrid Technologies, Eaton Publishing (2000); Fields et al., Trends Genet. 10(8): 286-92 (1994); Mendelsohn et al, Curr. Opin. Biotechnol. 5(5): 482-6 (1994) Luban et al., Curr. Opin. Biotechnol. 6(1): 59-64 (1995); Allen et al., Trends Biochem. Sci. 20(12): 511-6 (1995); Drees, Curr. Opin. Cliem. Biol. 3(1): 64-70 (1999); Topcu et al, Pharm. Res. 17(9): 1049-55 (2000); Fashena et al., Gene 250(1-2): 1-14 (2000); Colas et al., Nature 380, 548-550 (1996); Norman, T. et al., Science 285, 591-595 (1999); Fabbrizio et al., Oncogene 18, 4357-4363 (1999); Xu et al., Proc Natl Acad Sci USA. 94, 12473-12478 (1997); Yang, et al., Nuc. Acids Res. 23, 1152-1156 (1995); Kolonin et al., Proc Natl Acad Sci USA 95, 14266-14271 (1998); Cohen et al., Proc Natl Acad Sci USA 95, 14272-14277 (1998); Uetz, et al. Nature 403, 623-627(2000); Ito, et al., Proc Natl Acad Sci USA 98, 4569-4574 (2001). Such fusion can be made to *E. coli* LexA or yeast GAL4 DNA binding domains. Related bait plasmids are available that express the bait fused to a nuclear localization signal.

Other useful fusion proteins include those that permit display of the encoded polypeptide on the surface of a phage or cell, fusions to intrinsically fluorescent proteins, such as green fluorescent protein (GFP), and fusions to the IgG Fc region, as described herein.

The polypeptides of the present invention can also usefully be fused to protein toxins, such as *Pseudomonas* exotoxin A, diphtheria toxin, shiga toxin A, anthrax toxin lethal factor, ricin, in order to effect ablation of cells that bind or take up the proteins of the present invention.

Fusion partners include, inter alia, myc, hemagglutinin (HA), GST, immunoglobulins, p-galactosidase, biotin trpE, protein A, β-lactamase, α-amylase, maltose binding protein, alcohol dehydrogenase, polyhistidine (for example, six histidine (SEQ ID NO: 146) at the amino and/or carboxyl terminus of the polypeptide), lacZ, green fluorescent protein (GFP), yeast a mating factor, GALA transcription activation or DNA binding domain, luciferase, and serum proteins such as ovalbumin, albumin and the constant domain of IgG. See, e.g., Ausubel (1992), supra and Ausubel (1999), supra. Fusion proteins can also contain sites for specific enzymatic cleavage, such as a site that is recognized by enzymes such as Factor XIII, trypsin, pepsin, or any other enzyme known in the art. Fusion proteins can be made by recombinant nucleic acid methods or chemically synthesized using techniques well known in the art (e.g., a Merrifield synthesis), or produced by chemical cross-linking.

Another advantage of fusion proteins is that the epitope tag can be used to bind the fusion protein to a plate or column through an affinity linkage for screening binding proteins or other molecules that bind to the ILDR2 protein.

The polypeptides of the present invention can readily be used as specific immunogens to raise antibodies that specifically recognize polypeptides of the present invention including ILDR2 proteins and their allelic variants and homologues. The antibodies can be used to specifically to assay for the polypeptides of the present invention with the use of several techniques, for example ELISA, immunohistochemistry, laser scanning cytometry, flow cytometry, immunoprecipitation, immunoblotting and for detection of ILDR2 proteins or for use as specific agonists or antagonists of ILDR2 proteins.

One can determine whether polypeptides of the present invention including ILDR2 proteins, mutant proteins, homologous proteins or allelic variants or fusion proteins of the present invention are functional by methods known in the art. For instance, residues that are tolerant of change while retaining function can be identified by altering the polypeptide at known residues using methods known in the art, such as alanine scanning mutagenesis, Cunningham et al., Science 244(4908): 1081-5 (1989); transposon linker scanning mutagenesis, Chen et al., Gene 263(1-2): 39-48 (2001); combinations of homolog- and alanine-scanning mutagenesis, Jin et al., J. Mol. Biol. 226(3): 851-65 (1992); combinatorial alanine scanning, Weiss et al., Proc. Natl. Acad. Sci USA 97(16): 8950-4 (2000), followed by functional assay. Transposon linker scanning kits are available commercially (New England Biolabs, Beverly, Mass., USA, catalog. no. E7-1025; EZ::TN™ In-Frame Linker Insertion Kit, catalogue no. EZI04KN, (Epicentre Technologies Corporation, Madison, Wis., USA).

Purification of the polypeptides or fusion proteins of the present invention is well known and within the skill of one having ordinary skill in the art. See, e.g., Scopes, Protein Purification, 2d ed. (1987). Purification of recombinantly expressed polypeptides is described herein. Purification of chemically-synthesized peptides can readily be effected, e.g., by HPLC.

Accordingly, it is an aspect of the present invention to provide the isolated polypeptides or fusion proteins of the present invention in pure or substantially pure form in the presence of absence of a stabilizing agent. Stabilizing agents include both proteinaceous and non-proteinaceous material and are well known in the art. Stabilizing agents, such as albumin and polyethylene glycol (PEG) are known and are commercially available.

Although high levels of purity can be useful when the isolated polypeptide or fusion protein of the present invention are used as therapeutic agents, such as in vaccines and replacement therapy, the isolated polypeptides of the present invention are also useful at lower purity. For example, partially purified polypeptides of the present invention can be used as immununogens to raise antibodies in laboratory animals. The purified and substantially purified polypeptides of the present invention are in compositions that lack detectable ampholytes, acrylamide monomers, bis-acrylamide monomers, and polyacrylamide.

The polypeptides or fusion proteins of the present invention can usefully be attached to a substrate. The substrate can be porous or solid, planar or non-planar; the bond can be covalent or noncovalent. For example, the peptides of the invention can be stabilized by covalent linkage to albumin. See, U.S. Pat. No. 5,876,969, the contents of which are hereby incorporated in its entirety.

For example, the polypeptides or fusion proteins of the present invention can usefully be bound to a porous substrate or a membrane such as nitrocellulose, polyvinylidene fluoride (PVDF), or cationically derivatized, hydrophilic PVDF. When bound the polypeptides or fusion proteins of the present invention can be used to detect and quantify antibodies, e.g. in serum, that bind specifically to the immobilized polypeptide or fusion protein of the present invention.

As another example, the polypeptides or fusion proteins of the present invention can usefully be bound to a substantially nonporous substrate, such as plastic, to detect and quantify antibodies, e.g. in serum, that bind specifically to the immobilized protein of the present invention. Such plastics include polymethylacrylic, polyethylene, polypropylene, polyacrylate, polymethylmethacrylate, polyvinylchloride, polytetrafluoroethylene, polystyrene, polycarbonate, polyacetal, polysulfone, celluloseacetate, cellulosenitrate, nitrocellulose, or mixtures thereof; when the assay is performed in a standard microtiter dish, the plastic can be polystyrene.

The polypeptides and fusion proteins of the present invention can also be attached to a substrate suitable for use as a surface enhanced laser desorption ionization source; so attached, the polypeptide or fusion protein of the present invention is useful for binding and then detecting secondary proteins that bind with sufficient affinity or avidity to the surface-bound polypeptide or fusion protein to indicate biologic interaction there between. The polypeptides or fusion proteins of the present invention can also be attached to a substrate suitable for use in surface plasmon resonance detection; so attached, the polypeptide or fusion protein of the present invention is useful for binding and then detecting secondary proteins that bind with sufficient affinity or avidity to the surface-bound polypeptide or fusion protein to indicate biological interaction there between.

Purification of Recombinant Proteins

An ILDR2 protein can be purified from any human or non-human cell which expresses the polypeptide, including those which have been transfected with expression constructs that express an ILDR2. A purified ILDR2 protein can be separated from other compounds which normally associate with ILDR2 protein, in the cell, such as certain proteins, carbohydrates, or lipids, using methods practiced in the art. For protein recovery, isolation and/or purification, the cell culture medium or cell lysate is centrifuged to remove particulate cells and cell debris. The desired polypeptide molecule (for example, an ILDR2 protein) is isolated or purified away from contaminating soluble proteins and polypeptides by suitable purification techniques. Non-limiting purification methods for proteins include: size exclusion chromatography; affinity chromatography; ion exchange chromatography; ethanol precipitation; reverse phase HPLC; chromatography on a resin, such as silica, or cation exchange resin, e.g., DEAE; chromatofocusing; SDS-PAGE; ammonium sulfate precipitation; gel filtration using, e.g., Sephadex G-75, Sepharose; protein A sepharose chromatography for removal of immunoglobulin contaminants; and the like. Other additives, such as protease inhibitors (e.g., PMSF or proteinase K) can be used to inhibit proteolytic degradation during purification. Purification procedures that can select for carbohydrates can also be used, e.g., ion-exchange soft gel chromatography, or HPLC using cation- or anion-exchange resins, in which the more acidic fraction(s) is/are collected.

Alternative Transcripts

In another aspect, the present invention provides splice variants of genes and proteins encoded thereby. The identification of a splice variant which encodes an amino acid sequence with a region that can be targeted for the generation of reagents for use in detection and/or treatment of diabetes or metabolic disease. The amino acid sequence can lead to a unique protein structure, protein subcellular localization, biochemical processing or function of the splice variant. This information can be used to directly or indirectly facilitate the generation of additional or therapeutics or diagnostics. The nucleotide sequence in this splice variant can be used as a nucleic acid probe for the diagnosis and/or treatment of diabetes or metabolic disease.

Specifically, the newly identified sequences can enable the production of antibodies or compounds directed against the region for use as a therapeutic or diagnostic. Alternatively, the newly identified sequences can alter the biochemical or biological properties of the encoded protein in such a way as to enable the generation of improved or different therapeutics targeting this protein.

Tissues, Cells, Cell Lines: Protein Synthesis, Processing, Degradation

Ildr2 is expressed as several variably spliced isoforms with specificity by strain and organ. In certain aspects, the invention provides a full-length cDNA cloned in a mammalian expression vector, adding C-terminal and/or N-terminal tags—as noted—to facilitate detection following transfection. In certain embodiments, transient transfection assays can be carried out in β-TC3 insulinoma cells and SV40-transformed hepatocytes (Rother, 1998, J Biol Chem 273: 17491-17497) followed by immunoprecipitation with anti-HA antiserum and immunoblot with anti-Ildr2 antiserum. These cell lines have been chosen because they maintain at least some physiologic properties of β cells and hepatocytes. Moreover, they are well characterized, easy to maintain, and handle transfecting/transducing them with a variety of expression and viral vectors. These lines were successfully transfected with full length Ildr2 constructs. Using these lines, experiments can be performed in the presence and absence of cycloheximide to block protein synthesis and visualize on the blots the molecular weight of the expressed products, how rapidly they are degraded, and whether they differ in different cell types. Transient transfection assays can be used for this type of experiment because they are easier and prevent clonal artifact. Although transfection efficiency is irrelevant in this context, this technique can be optimized in these cell types. Using modified lipofection reagents, 30-40% efficiency can be achieved in SV40 hepatocytes. Using the Amaxa system, up to 80-90% of β-TC3 cells can be transfected.

In alternative embodiments of the methods of the present invention, different insulinoma cells, such as Ins1, MIN-6 or HIT can be transfected. In other embodiments, screening methods of the invention, or basic studies of (cell) biology of ILDR2 or C1ORF32 can be carried out in HEK293 or 3T3 cells. The former cells have the advantage of being easily transfectable but—HEK293 being a human kidney-derived cell line—Ildr2 processing can or can not reflect that in murine Ildr2 target tissues. To circumvent this problem, murine 3T3 cells, or any other suitable cell type can be used.

Sub-Cellular Localization

Ildr2 is predicted to encode a single membrane-spanning domain, with a large extracellular domain and a C-terminal intracellular domain. In GT1-7, a mouse hypothalamic neuronal cell line, Ildr2-isoform 2 localized solely to the ER membrane. In Hepa1c1c7, a mouse hepatoma cell line, Ildr2-isoform 4 localized solely to the ER membrane. Localization of ILDR2 can be addressed using the cell types described herein, and confocal microscopy. In certain embodiments, cycloheximide can be used to determine whether ILDR2 localization changes as a function of protein turnover. Time-lapse microscopy will be used to visualize protein fate in the presence of cycloheximide. The GFP or mYFP tag is located at the C-terminus or N-terminus of ILDR2. Thus, if ILDR2 is cleaved during its intracellular journey, this construct will only allow detection of the C-terminal domain. To circumvent this potential problem, immunocytochemistry will be performed with HA antiserum in cells transfected with Ildr2 constructs bearing a double tag N-terminal (HA) and C-terminal (FLAG-tag). In one embodiment, ILDR2 can be processed as a single peptide with a stable sub-cellular localization. In this case, the Ildr2-GFP or the Ildr2-mYFP construct and the double-tag construct will yield overlapping patterns of sub-cellular localization. In another embodiment, ILDR2 can be processed into different peptides, each with a distinct sub-cellular localization in a manner that may be similar to Tubby (Santagata et al, 2001, Science 292:2041-2050; Boggon et al, 1999, Science 286:2119-2125) and SREBP1C proteins, which are proteolytically cleaved to activate their transcriptional functions can be considered (Horton et al, 2002, J Clin Invest 109:1125-1131). In this case, the sub-cellular localization of the HA-tagged and FLAG-tagged constructs will differ, and only the FLAG-tagged construct will overlap with Ildr2-GFP or Ildr2-mYFP—appropriate cellular markers can be used to identify cellular compartments to which ILDR2 localizes; ILDR2 sub-cellular localization, as a single peptide, or as multiple processed products, changes in response to various cues—the effect of various hormonal and metabolic treatments on this process can be examined. In non-limiting examples, in Beta cells, the effects of glucose and cAMP can be determined, while in liver the effect of insulin and cAMP can be determined. In both cell types, the effects of FFA and lipoproteins can be determined. As a control for these experiments, Foxo-GFP, which undergoes rapid sub-cellular re-localization in response to these various agents, can be used. Actual experimental details (dose response, time course, etc) will be patterned according to prior experience in this area (Nakae et al, 2001, J Clin Invest 108:1359-1367; Nakae et al, 2000, Embo J 19:989-996).

Phosphorylation

Figure 12:
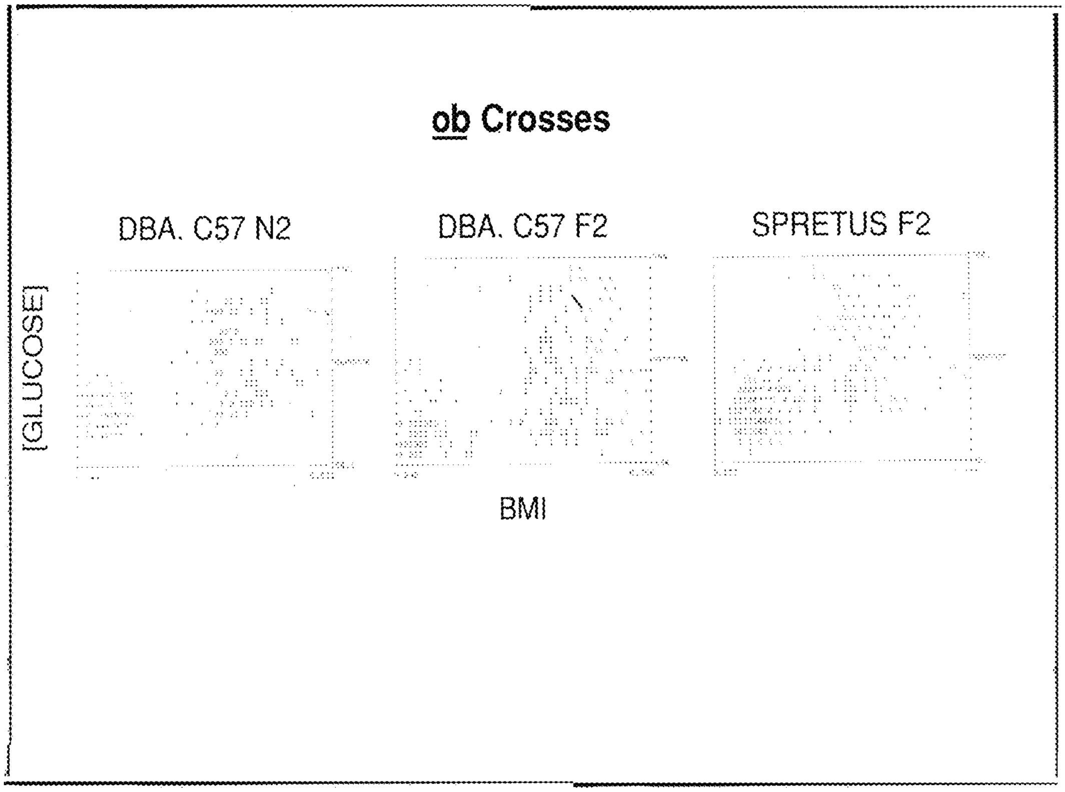
FIG. 12 shows BMI versus glucose for ob crosses.
Figure 13:
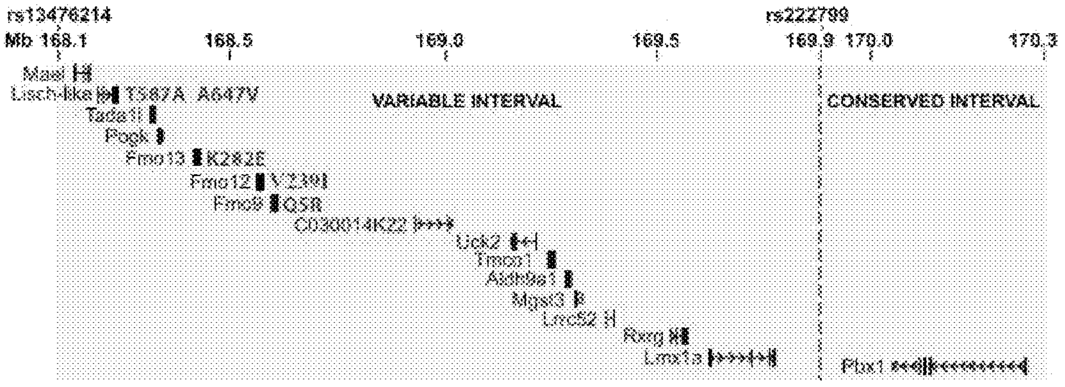
FIG. 13 shows genes in the minimal congenic interval on Chr1:168.1-170.3 Mb. Gray background corresponds to the minimal DBA "variable" interval from 168.1 Mb-169.9 Mb, between markers rs33860076 and rs30708865. Yellow background corresponds to the centromeric end of the DBA vs. B6 "conserved" interval (i.e. nominally invariant). Genes in blue are from RefSeq; genes in black are predicted and locally confirmed. The N-scan predicted gene chr1:1224.1 is designated here as "Lisch-like" (also known as ILDR2). Amino acid variants are shown in red to the right of the corresponding gene. Nucleotide substitutions were confirmed by bidirectional sequencing in both C57BL/6J and DBA/2J DNA.
Figure 14:
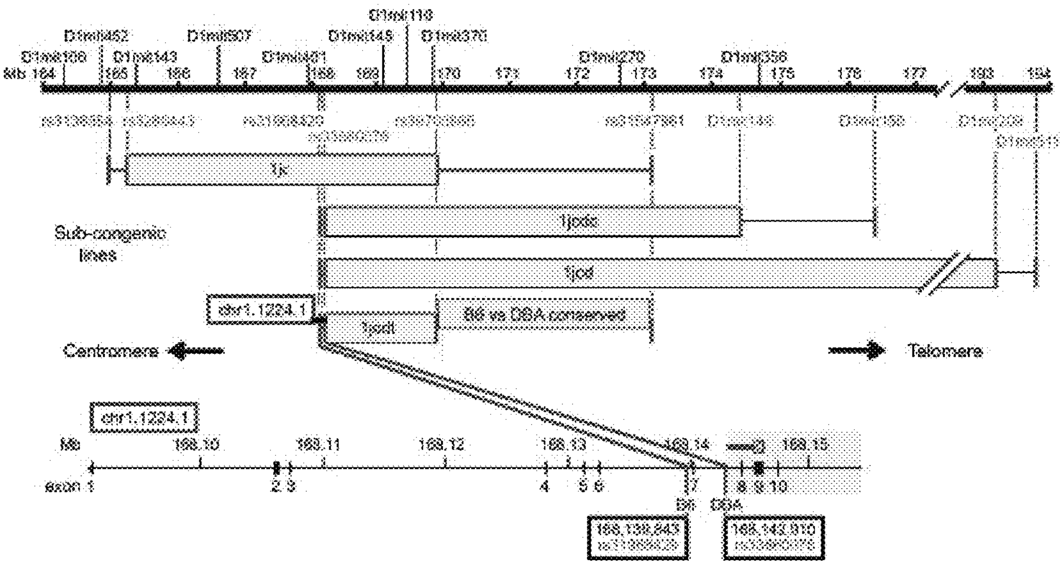
FIG. 14 shows shows sub-congenic lines (1jc, 1jcdc, 1jcd, 1jcdt) in the interval Chr1:164-194 Mb that display hypo-insulinemic hyperglycemia in association with histological evidence of a relative reduction in β-cell mass in the first 21-28 days of life due to reduced β-cell proliferation. An expanded view of the L1 gene (chr1.1224.1) is shown at bottom. Above the map scale, in black type, are microsatellite markers that were used to genotype B6 and DBA alleles to establish general boundaries of these congenic intervals. D1mit110 is the peak of the F2/F3 QTL linkage map (see Mapping T2D-related Phenotypes in B6×DBA F2/F3 Progeny). Below map scale, RefSNP (rs) and D-markers in red type identify DBA sequence limits of the respective congenic lines. Markers in blue type identify the closest, confirmed non-DBA (B6) sequence. Sequences in intervals between markers in red and blue type are DBA vs. B6 invariant. Gray bars are DBA-derived sequences. Yellow box corresponds to a 3.2 Mb interval, conserved between DBA and B6. The red box identifies the N-scan predicted gene, chr1.1224.1, subsequently identified as Lisch-like (L1) or ILDR2, extending centromerically from line 1jcdt. In the expanded view of L1, the B6 boundary (rs31968429) for lines 1jcdc, 1jcd, 1jcdt is 333 bp centromeric of exon 7; the DBA boundary, (rs33860076) is 2,700 bp telomeric of exon 7. 5330438I03Rik is an anti-sense transcript described in detail in the text. Marker positions are from the mouse genome annotation (NCBI Build 36, February 2006). Variants in ILDR2=T587A; A647V.
Figure 19:
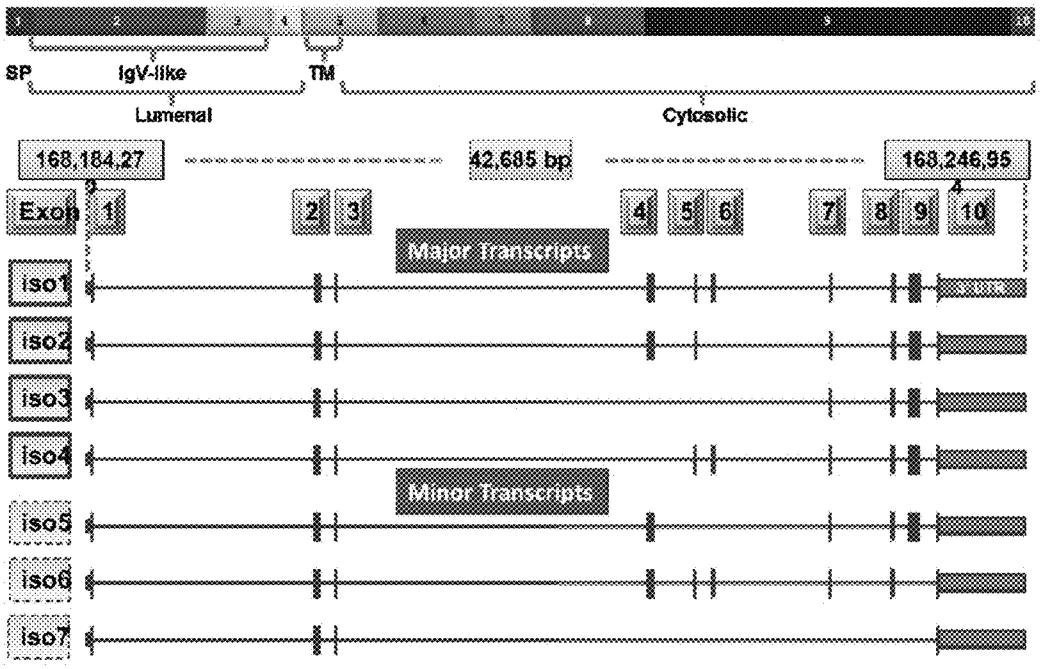
FIG. 19 shows the mouse ILDR2 gene map. Isoform 2 is absent exon 6; isoform 3 is absent exons 4, 5, 6; isoform 4 is absent exon 4.

Many proteins with metabolic functions are modified via phosphorylation by tyrosine and serine/threonine kinases. As indicated, the putative intracellular domain of ILDR2 contains several putative sites for Ser/Thr kinases. Using 32P-orthophosphate labeling of intact cells, it can be determined whether ILDR2 is phosphorylated in vivo and whether changes in the cell's metabolic status affect ILDR2 phosphorylation. The initial experiments will be carried out by in vivo labeling followed by immunoprecipitation and autoradiography. If required, phospho-peptide maps will be employed (Accili et al, 1991, J Biol Chem 266:434-439) and mass spectrometry to identify individual phosphorylation sites. If ILDR2 phosphorylation changes with the cell's hormonal/nutritional status, further experiments will be conducted to identify phosphorylation sites on ILDR2 and relevant kinases. There are a number of potential Ser/Thr phosphorylation sites in the intracellular domain of ILDR2 (FIG. 12). Of special interest are four PKA sites (at amino acid residue 307, 352, 399, 403), an Akt site at position 618, and a CDK site at position 550. Given that PKA and Akt are activated in response to glucagon and insulin signaling, respectively, it will be of interest to determine whether these agents affect ILDR2 phosphorylation. If so, these sites will be mutated to probe their involvement in ILDR2 phosphorylation and function. Similarly, it will be important to test ILDR2 phosphorylation as function of cell cycle progression, given preliminary data that in dd mice (with low ILDR2 levels) replication of Beta cells is decreased. If there are changes in ILDR2 phosphorylation as function of cell cycle progression, the CDK phosphorylation site can be mutated to determine whether ILDR2 function is affected. One of the two non-conservative nucleotide substitutions identified in DD mice abolishes a potential Ck1 site (T572A). Thus, the phosphorylation state of the WT vs T572A mutant ILDR2 will be compared to determine whether (a) the site is phosphorylated and (b) its mutation into a non-phosphorylatable amino acid changes localization, signaling or bioeffects of Ildr2. Candidate phosphorylation sites described herein will be replaced by non-phosphorylatable amino acids (alanine) to generate phosphorylation-deficient mutants, or by charged amino acids (aspartic or glutamic acid) to mimic the phosphorylated state and generate "constitutively phosphorylated" mutants Readout Assays of Ildr2 Gain-of-Function In certain aspects, the basic cell biology of Ildr2 can be characterized. In other aspects, transgenic and knockout mice can be generated and characterized by methods and techniques as described herein, and also known in the art.

In certain aspects, the invention provides that Ildr2 function is related to decrease in Beta cell mass, which is secondary to reduced proliferation. In other aspects, the invention provides that ILDR2 has a role to bind lipids—based upon close sequence homology to LSR (lipolysis-stimulated receptor). To further characterize these, β-TC3 cells (very low in endogenous Ildr2) will be transfected with WT (B6-derived) HA-Ildr2, and Beta cell proliferation will be measured. Gain of Ildr2 function can result in increased Beta cell proliferation. To carry out these experiments it can be necessary to achieve high transfection frequency to measure an effect in an unselected cell population. In non-limiting examples, transfection efficiency can be monitored using tagged constructs, or/and carrying out immunocytochemistry (for HA-tagged constructs) or fluorescence (for GFP-tagged constructs) with Ki67 or BrdU immunocytochemistry to co-localize transfected Ildr2 with in actively replicating cells. Ildr2-expressing cells will stain positive for Ki67 or BrdU enable measurement of replication rates using pulse-chase experiments. Because β-TC3 cells express very low levels of endogenous Ildr2, transfection of recombinant Ildr2 can result in a gain-of-function that may not be apparent in other Beta cell lines expressing higher levels of Ildr2 where pathways may active due to endogenous Ildr2. Tet-dependent β-TC3 clones exist in which addition of tetracycline to the medium results in rapid cell cycle arrest (Efrat et al, 1998, Proc Natl Acad Sci USA 85:9037-9041). Thus, if the replication rates of β-TC3 are unaffected by Ildr2 in regular culture conditions, the ability of Ildr2 over-expression to promote cell cycle progression in Tet-arrested β-TC3 cells can be studied.

To examine the mechanism of Ildr2-induced changes in cellular proliferation, markers of cell cycle progression, including Foxo1/3, p27kip, p21 and pRb will be analyzed (Okamoto et al, 2006, J Clin Invest 116:775-782; Buteau et al, 2006, Diabetes 55:1190-1196; Kitamura et al, 2005, Cell Metab 2:153-163; Kitamura et al, 2002, J Clin Invest 110:1839-1847). ILDR2 can also affect proliferation by reducing apoptosis. Rate of apoptosis can be determined in cultured β cells, and in vivo. In certain aspects, the invention provides that DD mice, have reduced Beta cell proliferation in the early post-natal stage. A physiologic remodeling of β-cell mass occurs in rodents at this stage (Scaglia et al, 1997, Endocrinology 138:1736-1741), due to a wave of apoptosis. ILDR2 can be involved in this process. Apoptosis markers such as Fas1, Caspase-3, −8, Bax and Bim will be examined.

In addition to cell replication, insulin secretion assays in response to glucose and other secretagogues, as well as mitochondrial function experiments to measure mitochondrial integrity will be performed (Buteau et al, 2006, Diabetes 55:1190-1196). Because insulin secretion and β cell proliferation are linked (Okamoto et al, 2006, J Clin Invest 116:775-782), ILDR2 can affect primarily secretion, which secondarily impairs β cell proliferation. The expression of markers of terminally differentiated Beta cells, such as MafA, a transcription factor expressed at low levels in Beta-TC3 cells, which makes them an ideal system to study MafA induction (Kitamura 2005) will be determined. Foxo1-3, Pdx1, Nkx2.2 and Hnf4 will be measured. ILDR2 can beneficially affect stimulus/secretion coupling in the β cell, and thus upregulate expression of relevant transcription factors.

Signaling Pathways Activated by ILDR2 and Protein/Protein Interactions

In certain aspects, the invention provides that ILDR2 function affects signaling pathways in insulinoma cells. Following Ildr2 over-expression activation of candidate pathways, including but not limited to PI 3-kinase/Akt, mTOR/S6k, AMPK/Acc, cAMP/PKA pathways will be measured (Buteau et al, 2006, Diabetes 55:1190-1196; Kitamura et al, 2005, Cell Metab 2:153-163). These assays can be carried out in an unselected population of cells after transient transfection. In other embodiments, similar experiments can be carried in cells transduced with Ildr2 adenovirus (Kitamura et al, 2005, Cell Metab 2:153-163).

Loss-of-Function Experiments

In other aspects, the invention provides methods to determine the effect of Ildr2 reduction or ablation on the aforementioned parameters and characteristics in islet cells. Because Beta-TC3 cells express low endogenous Ildr2 levels and are not suitable for this purpose, these experiments will be carried out in MIN-6 cells. To carry out these experiments, high-efficiency transfection with the Amaxa system, or siRNA adenovirus will be used (Matsumoto et al, 2006, J Clin Invest 116:2464-2472). As control, transfections of mutant siRNA or siRNA-resistant Ildr2 will be used. In certain aspects, the invention provides that gain of Ildr2 function increases cellular proliferation and loss of Ildr2 function decreases it. In certain embodiments, the invention provides methods to determine Ildr2 function in primary cultures of mouse islets transduced with adenoviral constructs (Kitamura et al, 2005, Cell Metab 2:153-163).

ILDR2 Functions in the Hepatocyte

In liver, the outcome of functional experiments is more complex. Proliferation of hepatocytes, while important in many pathophysiologic conditions, is not considered a predisposing factor in diabetes/insulin resistance. Thus, the actions of ILDR2 in hepatocytes must be deduced from other assays. The phenotypes of the ENU Ildr2-null mice (and a transgenic or conditional knockout mouse) will guide experimental approach to ILDR2 function in hepatocytes. In certain aspects, the invention provides methods to carry out gain-of-function experiments in hepatocytes to study Ildr2's cell biological properties: localization, processing, signaling properties. These experiments will employ SV40-transformed hepatocytes, a cell type that retains many of the properties of terminally differentiated hepatocytes (Rother et al, 1998, J Biol Chem 273:17491-17497; Kim et al, 2001, Endocrinology 142:3354-3360; Park et al, 1999, Biochemistry 38:7517-7523). Processing, turnover, localization and phosphorylation can be examined as described herein and by any other suitable method known in the art. Among the signaling pathways that can be studied following Ildr2 over-expression are: cAMP and insulin signaling, as well as adiponectin, lipids (FFA) and bile acids-activated signaling. Candidate effectors of ILDR2 signaling and/or, Srebp1c include PI 3-kinase, mTOR/S6 kinase, AMP kinase, Ppar induction. The biological responses that can be measured include glucose production, glycogen synthesis, TG content and synthesis, ApoB and LDL/VLDL secretion (Han et al, 2006, Cell Metab 3:257-266; Matsumoto et al, 2006, J Clin Invest 116:2464-2472). The liver, in which there are large differences in B6 v. DBA expression of Ildr2, affects Beta cells by a metabolic, e.g. lipoprotein, or endocrine pathway, hepatokine production, or by agents in these pathways. Liver-mediated effects on Beta cell development/function can be examined by co-culture of congenic line or knockout hepatocytes with suitable Beta cell line, expression arrays, and analysis of isolated liver proteins by 2-D gel and mass spectrometry.

Ildr2 Alternatively Spliced Isoforms

Ildr2 is expressed as several different transcripts. Notably, the abundance and assortment of transcripts varies from cell type to cell type, and by strain. Complete transcripts from 7 isoforms were isolated. However, isoforms 5,6,7 were only isolated in trace quantities from cDNA libraries. Isoform 1 contains the ten exons intact, while the others have missing or truncated exons. Complete transcripts for isoforms 1-4 were isolated and partial transcripts in trace quantities were isolated from pooled DBA cDNA libraries for isoforms 5-7.

Evaluating the full spectrum of the functions of these various isoforms can be carried out by methods as described herein and by any suitable methods know in the art (Liu et al, 1998, Mamm Genome 9:780-781; Chua et al, 1997, Genomics 45:264-270). One determination includes whether these spliced isoforms are translated. A protein isoform expression survey using western blot analysis will be carried out. If different molecular species are observed, tissue expression and mRNA variants will be monitored. Some of these isoforms have reduced stability, and that alternative message splicing provides a mechanism to indirectly regulate ILDR2 levels by altering its post-transcriptional or translational degradation. Certain isoforms are secreted and can be detected in the circulation, acting as a decoy receptor for a putative ILDR2 ligand. This will easily become apparent from western blot surveys of various tissues/cell types and incubation media in different conditions, as described herein. To address the issue of secreted isoforms, serum protein will also be included in the tissue survey. The turnover rates of the most prominent splice variants will be investigated using pulse-chase experiments with cycloheximide, and survey their intracellular localization by immunocytochemistry.

The putative transmembrane structure of ILDR2 shows that ILDR2 can be a cell surface receptor. This is supported by the presence of several Ig repeats in the putative extracellular domain, a defining feature of cell adhesion molecules and various cell surface receptors. Methods of identifying ligands for cell surface receptors are well known in the art and can be readily used to identify a ligand for ILDR2 or ILDR2 homologs.

Molecular Basis of Decreased Ildr2 Expression in DD Congenic Mice

In certain aspects, the invention provides that the DBA allele decreases Ildr2 expression levels through a cis-acting DNA element(s). The mechanism can be explained by: (a) reduced gene transcription; (b) decreased mRNA stability, and/or (c) increased protein degradation; these are not mutually exclusive. In other aspects, the invention provides that the DBA allele of Ildr2 results in reduced protein levels in hepatocytes, Beta cells and the brain. Understanding the relevant mechanism(s) will help to elucidate the molecular physiology of ILDR2.

The Ildr2 gene encodes large, alternatively spliced transcripts. Coding (exon 9) and non-coding (mainly 3' UTR) sequence changes can be evaluated in the DDA vs. BBA strains as candidate mutations causing alterations of mRNA levels. Because the extent of the decrease in mRNA levels is different from tissue to tissue (Table 4), tissue-specific factors can contribute to the process. Because the largest differences in mRNA levels were found in the liver, cis-acting variations in Ildr2 can be examined in this tissue. The results described herein show that the region downstream of exon 8 is implicated in conveying diabetes susceptibility. Because this is a region of sequence overlap within Ildr2 in the congenic lines described herein such analysis can be used to determine whether the 5'UTR is cis-acting region that can contribute variation to differences in gene expression among the congenic lines. For examples, regulatory DNA elements acting upstream of the transcription start site may interact with elements downstream of exon 8 to decrease mRNA transcription/stability. These experiments can determine whether the low levels of Ildr2 transcripts seen in liver are due to decreased transcription. mRNA stability and decay can be also analyzed.

Chances in Gene Transcription

The promoter regions of Ildr2 in DD and BB mice are extremely well conserved. Although, there are no nucleotide substitutions detected in the 10 kb upstream of the transcription start site, cis-acting elements controlling Ildr2 expression have not been mapped and may reside outside the sequenced regions. In one embodiment, in vivo run-on studies using livers of DD vs DB mice can be performed to determine if the two alleles are transcribed at different rates. Because the mRNA levels in liver differ >10-fold between the two strains (Table 4), one can detect a difference, if indeed mRNA transcription is responsible for the molecular phenotype. Methods known in the art can be used to address these questions (McKeon et al, 1997, Biochem Biophys Res Commun 240:701-706; McKeon et al, 1990, Mol Endocrinol 4:647-656). In another embodiment, primary hepatocytes from the two strains can be prepared and run-on experiments can be performed in this culture system, which is more amenable to hormonal/metabolic control (i.e., it can be determined if the process is critically dependent on various hormone/metabolic cues). Comparison of a strain that segregates for DBA alleles only in exons 8-10+3' UTR (e.g. 1jcdt) to one in which the entire Ildr2 gene is DBA (1jc) can allow apportioning effects via the 5' promoter region.

In Vivo Analysis of Ildr2 Function in Mice

In certain aspects, the invention provides that loss or reduction of Ildr2 function predisposes to diabetes in mice, of a susceptible genetic background by impairing β cell proliferation and hepatic metabolism. In other aspect, the invention provides that loss or reduction of ILDR2 function predisposes human subject to diabetes or metabolic disease.

In certain aspects, the invention provides that loss-of-function conveyed by the DBA allele of Ildr2 is the cause of diabetes susceptibility in DD mice. Thus, conference of diabetes susceptibility can be achieved by introducing loss of Ildr2 function in diabetes-susceptible strains.

ENU mutagenesis provides a powerful tool to introduce mutations in the mouse genome. In certain embodiments, the invention provides an ENU-mutagenized mouse (C3HeB/FeJ) segregating for a W87* (stop) mutation in Ildr2. The ENU amber mutation in exon 2 of Ildr2 can produce a completely inactive allele. Because, the mutation is on a C3HeB/FeJ background, a C57BL/6J conditional knockout of Ildr2 can be made with or without a knockout vicinal genes. In other embodiments, the invention provides methods to characterize ILDR2 knockout mice by a number of metabolic abnormalities related to diabetes. In certain embodiments, characterization can be made by measuring the β cell response, hepatic glucose, or lipid metabolism.

ENU-mutagenized mice, as well as knockout strains which can be generated as described herein and by methods known in the art, can be characterized at various developmental stages using several parameters. Exemplary parameters are somatic growth curves, body composition, plasma glucose and insulin levels in fasted and fed states, lipid profile (triglycerides, cholesterol, FFAs), glucose tolerance tests, insulin release tests, pyruvate challenge, glucose clamps, functional, histological and immunohistochemical characterization of pancreatic islets as indicated below. Assays and techniques to carry out these characterizations are described herein and known in the art.

Non-limiting methods include calorimetry and euglycemic hyperinsulinemic clamp studies. Euglycemic hyperinsulinemic clamp studies—euglycemic clamps will be performed in conscious, unrestrained, catheterized mice as previously described (Okamoto et al, 2005, J Clin Invest 115:1314-1322). A solution of glucose (10%) will be infused at a variable rate as required to maintain euglycemia (7 mM). Mice will receive a constant infusion of HPLC-purified [3-$^3$H] and insulin (18 mU/kg body wt/min). Thereafter, plasma will be collected to determine glucose levels at times 10, 20, 30, 40, 50, 60, 70, 80, and 90 min, as well as the specific activities of [3-$^3$H] glucose and tritiated water at times 30, 40, 50, 60, 70, 80, and 90 min. Steady-state conditions can be achieved for both plasma glucose concentration and specific activity by 30 minutes in these studies. [U-$^{14}$C] lactate (5 μCi bolus/0.25 μCi/min) will be infused during the last 10 min of the study.

β-Cell "Phenotyping".

Numerous assays have been described herein and are known in the art to evaluate β-cell function in mouse models of diabetes. Ki67 immunoreactivity will be used to assess Beta cell proliferation. Detection of apoptosis can be carried out using immunohistochemistry with caspase-3. Because apoptosis occurs at specific developmental stages, time course analysis can be performed in 1 to 4 week-old mice. Islets can be isolated from mice by in vivo collagenase perfusion, and insulin release under different experimental conditions can be determined. If mutations result in developmental abnormalities, embryonic analysis can be performed by delivering embryos at various gestational stages by Caesarian section. The analysis can comprise identification of the pancreatic buds, dissection, histological or morphometric analysis of islet number, size and composition. Electron microscopy can be performed as described (Cinti et al, 1998, Diabetologia 41:171-177).

In certain embodiments, the −/−ENU mice, can be characterized by stressing the 13 cells using low dose streptozotocin, dexamethasone, dietary manipulations, etc.

Targeted Mutations

Targeted mutations in animals can be generated with ENU mice segregating on the basis of a stop codon in exon 2.

Conventional Knock-Out

A gene targeting vector, as described herein, can be designed to carry out a conventional gene inactivation experiment. The vector can be used for both ubiquitous and conditional inactivation of Ildr2. For conventional gene knockout, the sequence flanked by loxP sites can be excised in vitro, using transfections of ES cells carrying the gene-targeted allele (Bruning et al, 1998, Mol Cell 2:559-569), or by intercrossing mice carrying a floxed allele with "deleter" cre transgenics, leading to removal of the lox-flanked sequence in germ cells (Okamoto et al, 2004, J Clin Invest 114:214-223; Bruning et al, 1998, Mol Cell 2:559-569; Han et al, 2006, Cell Metab 3:257-266; Xuan et al, 2002, J Clin Invest 110:1011-1019; Okamoto et al, 2005, J Clin Invest 115:1314-1322).

Conditional Knock-Out

Cre-loxP technology known in the art can be used to introduce mutations in an organ or in a developmental stage-specific fashion. As described herein, Ildr2 ablation in β cells can affect their ability to proliferate, thus modulating diabetes susceptibility in vivo. Conditional Ildr2 knockouts can be generated at various developmental stages during endocrine pancreas differentiation using crosses of mice homozygous for a floxed Ildr2 allele with Neurogenin 3-cre, Pdx-cre and Insulin-cre transgenic mice. Each cre transgenic can cause Ildr2 inactivation at a different stage in pancreas development, and can thus provide insight into the developmental role of Ildr2 in this process.

Pdx-Cre Knock-Out

In certain embodiments, Pdx-Cre can be used to inactivate Ildr2 in pancreatic progenitors, prior to the differentiation of the endocrine, exocrine and ductal lineages. If Ildr2 plays a role in the determination of the pancreatic lineages, ablation of Ildr2 driven by this Cre mice can result in widespread alterations of exocrine and endocrine cell number, characteristics, as well as islet number, size, distribution.

Neuroenin 3-Cre Knock-Out

In other embodiments, Neurogenin 3-Cre mice can be generated to direct ablation of Ildr2 in the endocrine progenitor cell in the pancreas and entero-endocrine system, after the endocrine/exocrine split has occurred, but prior to final specification of individual islet cell types. If ILDR2 plays a role in endocrine cell differentiation, the effects of its ablation can be determined in non-β cell types (α, δ, ϵ, PP). This can also drive inactivation of ILDR2 in entero-endocrine cells and result in inactivation of Ildr2 in incretin-producing cells (K and L cells in the gut). Because incretin production is observed in diabetes, incretin response can be characterized in Neurogenin3-Cre/Ildr2 knockouts (Buteau et al, 2006, Diabetes 55:1190-1196).

Insulin-Cre Knock-Out

In other embodiments, Insulin-cre can inactivate Ildr2 in terminally differentiated Beta cells. As such, the phenotype of these mice can reflect the function of Ildr2 in daily maintenance of the phenotype/function of Beta cells. This phenotype can resemble aspects of the diabetes susceptibility seen in DD mice. In certain embodiments, stress on the Beta cell can be imposed using standard approaches such as low-dose streptozotocin, high-dose dexamethasone, high-fat, high-sucrose diet, and partial pancreatectomy.

Conditional Knock-Out in Liver

In other embodiments, Albumin-cre and α1-antitrypsin/cre mice can be used to generate Ildr2 knock out in the liver. Albumin-cre and α1-antitrypsin/cre mice have been used to ablate genes in hepatocytes, with the α1-antitrypsin/cre line being useful for earlier-onset ablation during fetal development, and the albumin-cre mice being useful for post-natal knockout (Postic et al, 2000, Genesis 26:149-150). Analyses of the knockout can be performed by protein- and mRNA-based expression assays.

The characterization of any of the knock out mice described herein, can include hepatic metabolism, hepatic glucose production (GTTs, hyperinsulinemic/euglycemic clamps, gene expression, pyruvate challenge tests) and lipid metabolism (Total and Hdl cholesterol, hepatic TG content, gene expression, ApoB levels and secretion using Triton inhibition of lipoprotein clearance; VLDL and LDL measurements by FPLC and ultracentrifugation will help identify variations in lipoprotein composition). The role of altered lipid metabolism in ILDR2 function can be examined the liver conditional Ildr2 knockout mice.

Ttr-Cre Knock-Out

In certain aspects, the invention provides unique liver/β-cell combination of expression driven by the transthyretin promoter to probe the role of the Beta cell/liver axis in metabolic control (Okamoto et al, 2004, J Clin Invest 114:214-223; Okamoto et al, 2006, J Clin Invest 116:775-782; Okamoto et al, 2005, J Clin Invest 115:1314-1322; Nakae et al, 2002, Nat Genet 32:245-253). Because Ildr2 is prominently expressed in liver and Beta cells, it can be useful to the generate of a double knockout driven by Ttr-cre to studying role the role of Ildr2 in these tissues.

Genetic and Environmental Interactions of the Ildr2 Mutation

In addition to analyzing Ildr2 mutant mice according to genetic background, the invention provides methods to determine the contribution of Ildr2 loss-of-function to other forms of insulin-resistant diabetes. In certain aspects, dietary manipulations such as high fat and "Surwit" high fat-high sucrose diets can be used to examine the contribution of Ildr2 to the environmental determinants of diabetes. The genetic component can be assessed by crossing Ildr2 knockouts with Insulin Receptor heterozygous knockouts as a model of insulin resistance (Kido et al, 2000, J Clin Invest 105:199-205), or Irs2 knockouts (Kitamura et al, 2002, J Clin Invest 110:1839-1847), as a model of β-cell failure (Accili 2004, Diabetes 53:1633-1642).

Metabolic Characterization

Metabolic characterization can be carried out for β cells, hepatocytes and other cell, tissue or organ of interest. Non-limiting examples of such tissues or organs are muscle, brain or the gut.

Conditional Activation of Ildr2

Figure 20:
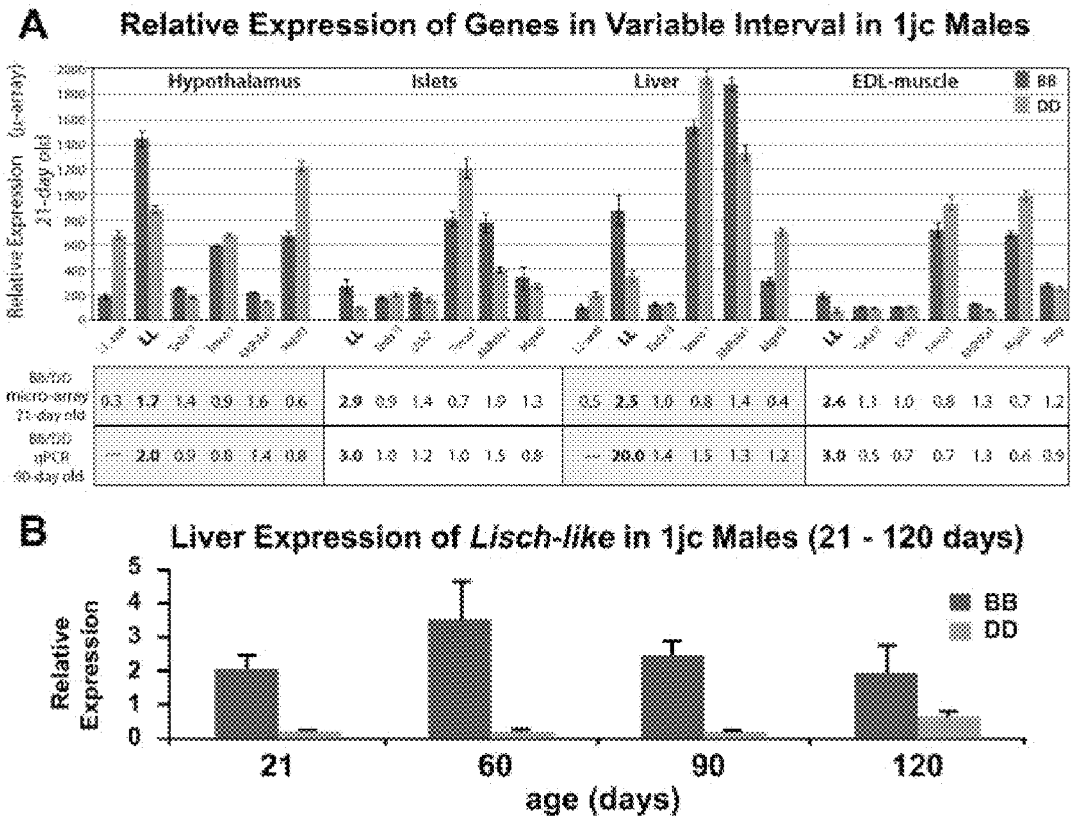
FIGS. 20A-B shows expression analysis of candidate genes and liver expression of ILDR2.
Figure 21:
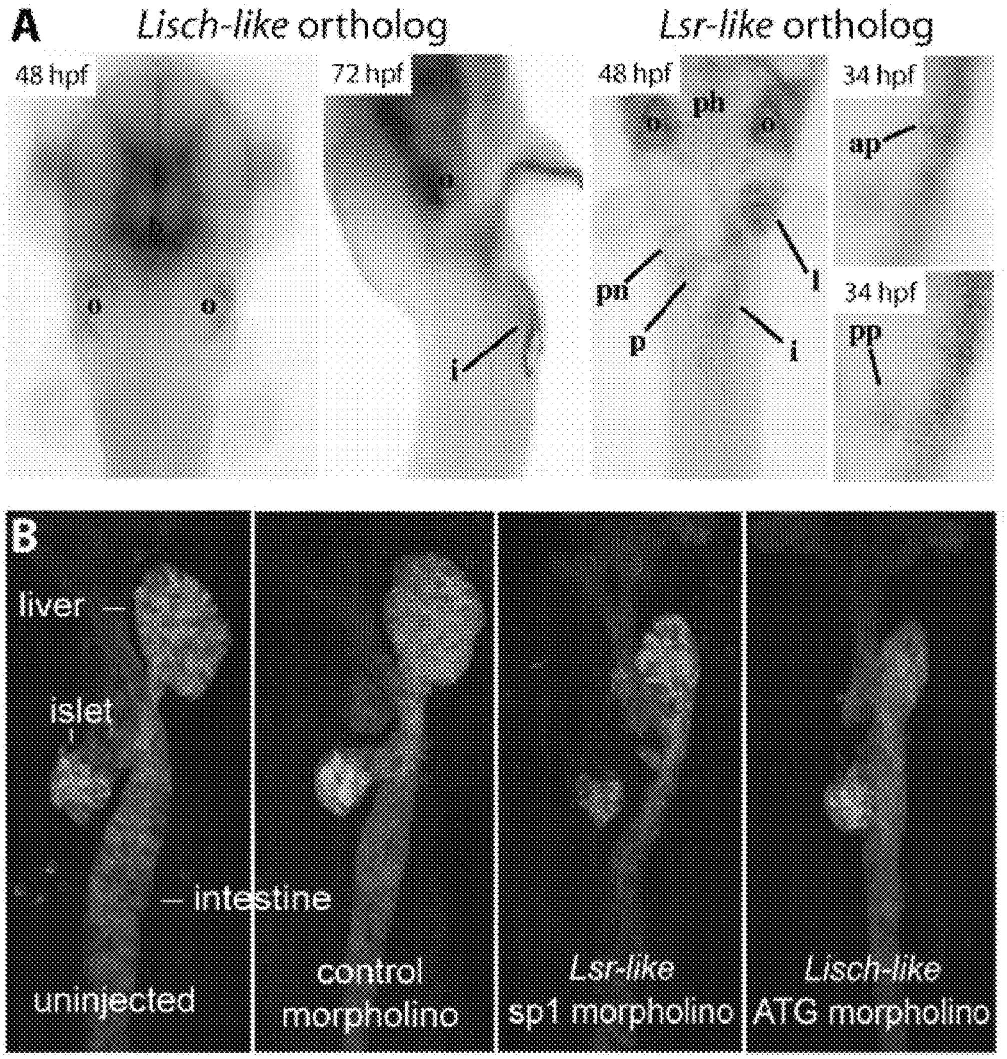
FIGS. 21A-B shows the expression patterns and morpholino knockdown in Zebrafish embryos.
Figure 22:
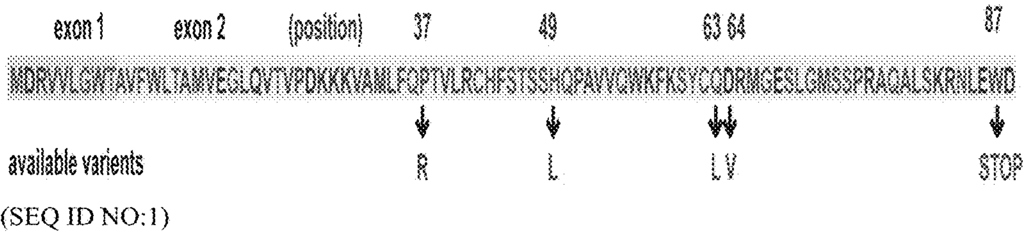
FIG. 22 shows ENU mutations in ILDR2 in C3HeB/FeJ mice. The sequence (SEQ ID NO: 1) shows the positions and changes from wild-type of the five variants available (SEQ ID NO: 151). W87* can be introgressed on the diabetes-susceptible KsJ strain.
Figure 23:
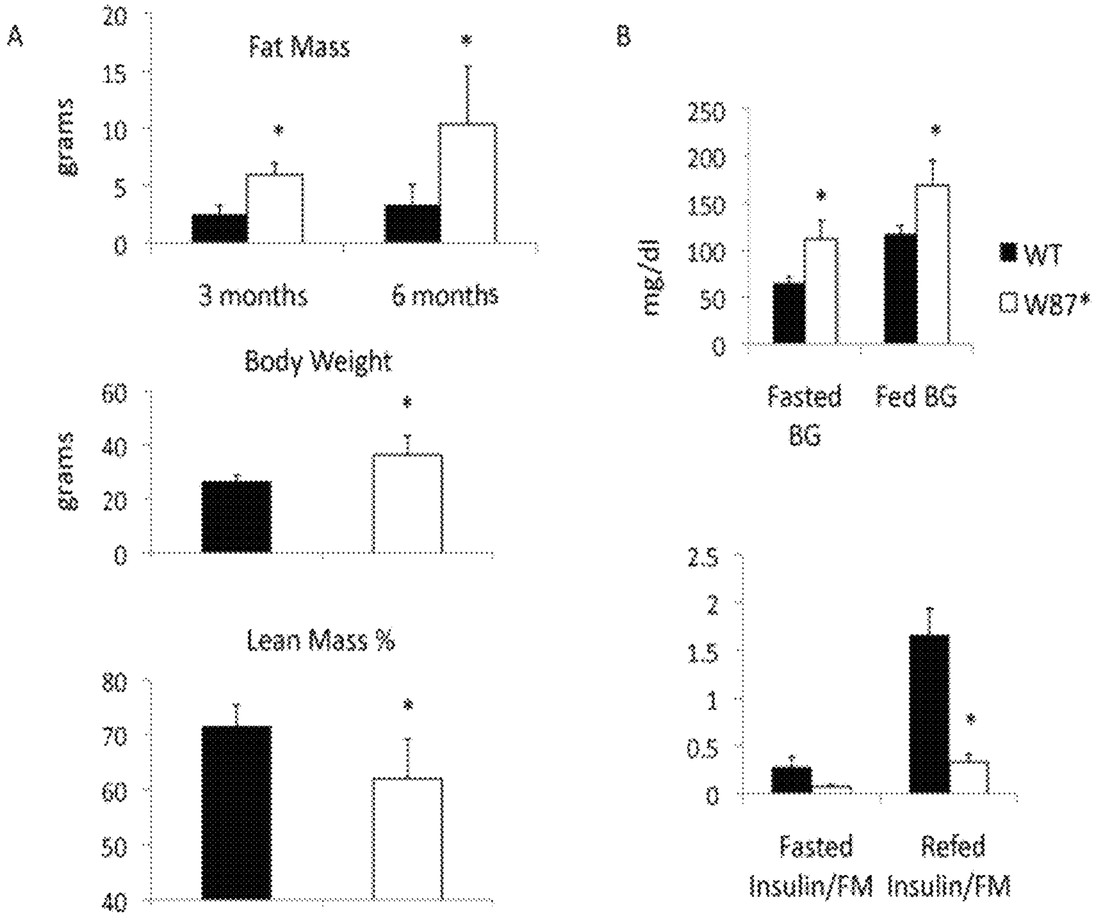
FIGS. 23A-B shows the body composition and blood chemistry in chow-fed Ildr2 W87* animals and in +1+(WT) littermates.
Figure 24:
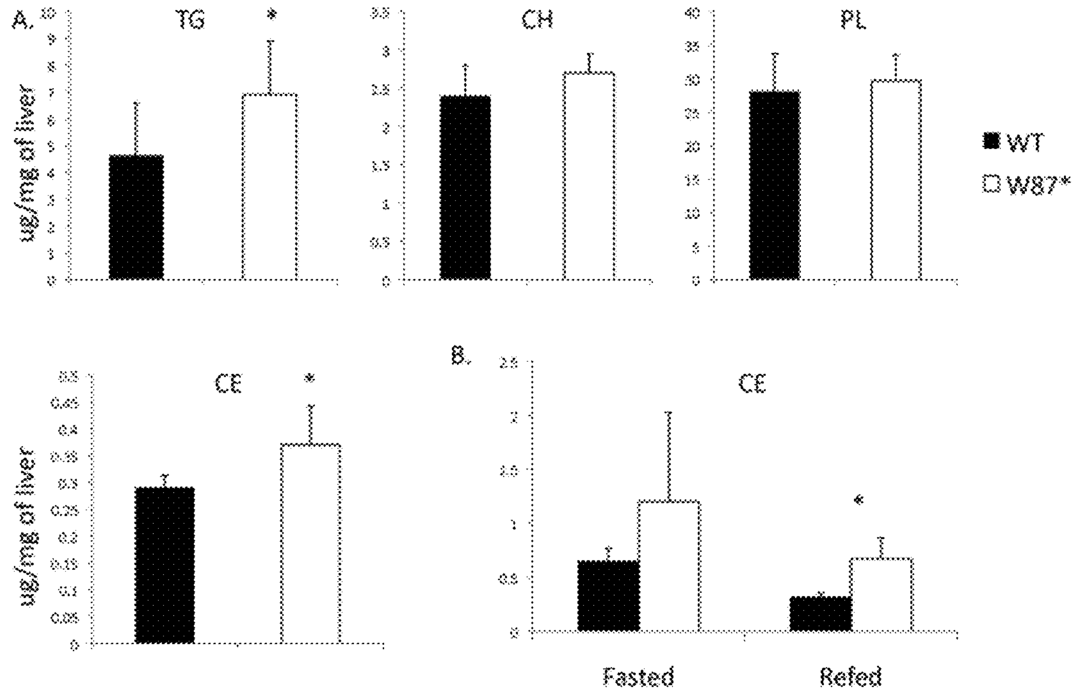
FIGS. 24A-B shows ENU-mutagenized Ildr2-null mice that encode a transcript containing a stop codon at threonine-87 (W87*) in the second exon (W87*mice) have increased hepatic triglycerides and cholesterol ester stores (FIG. 24A). The phenotype of these mice (3 months old; diet: normal chow, 4 hr fasting) were consistent with B6. DBA congenic mice. These mice were also reduced beta cell mass and persistent mild hypoinsulinemic hyperglycemia. In addition, hepatic TG and CE levels were increased in 3 month old W87 mice. (*=p<0.05; n=10 WT and 11 W87*). CE levels were measured in fasted (24 hours) and refed (12 hours) mice (FIG. 24B).
Figure 25:
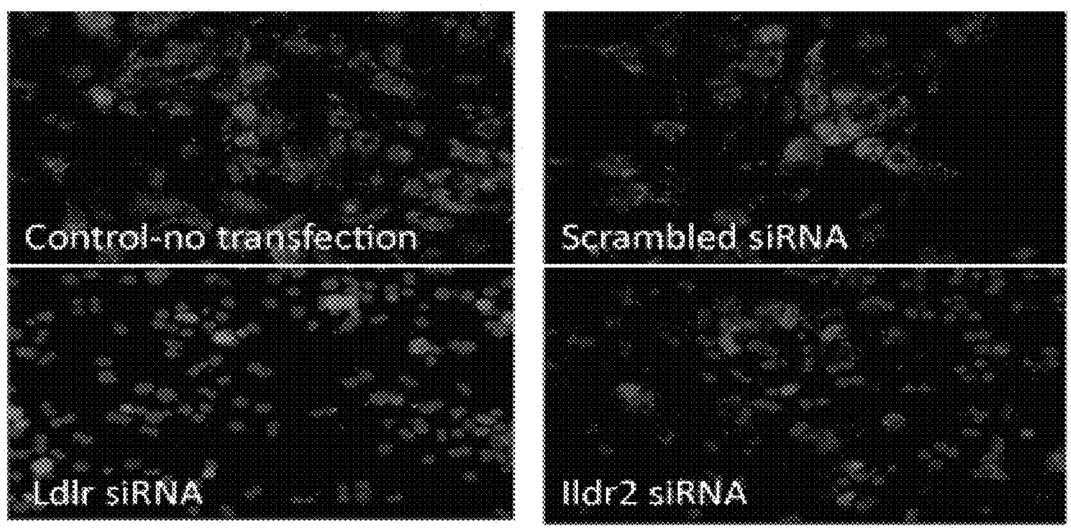
FIGS. 25A-B shows the effects of W87* and Ildr2 RNAi on LDL cholesterol uptake in isolated hepatocytes. Primary hepatocytes show reduced LDL uptake when Ildr2 is functionally reduced.
Figure 26:
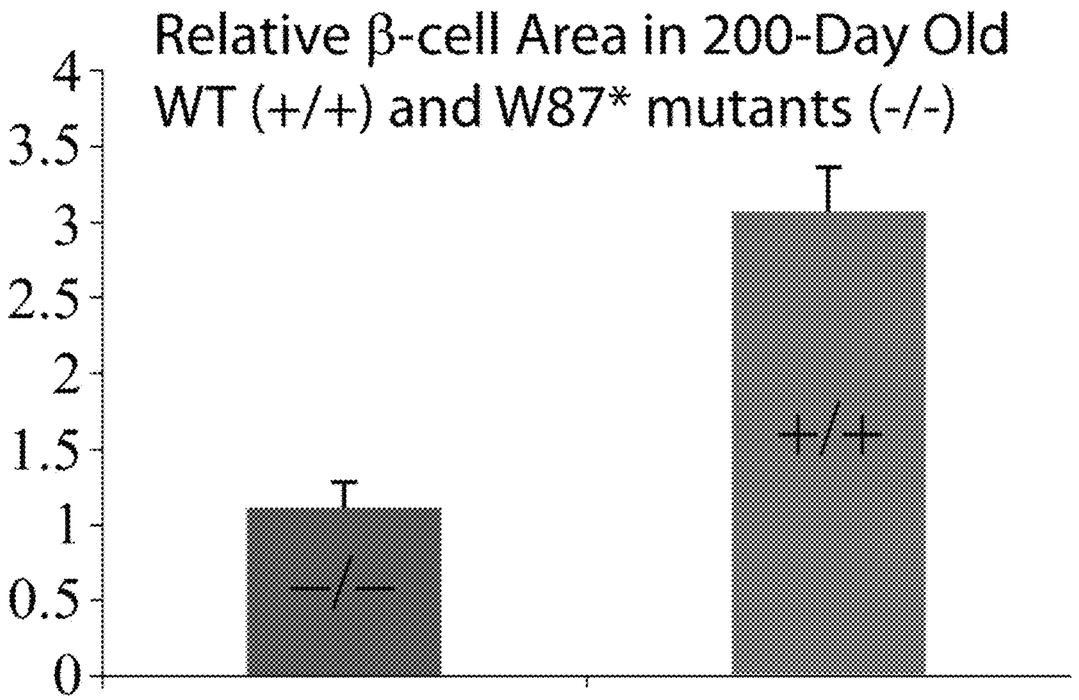
FIG. 26 shows the relative B-cell area in 200-day old WT (+1+) and W87* mutants (–/–). At 200 days, the beta cell mass of the ENU –/– is reduced by about ⅔, but the animals remain euglycemic
Figure 27:
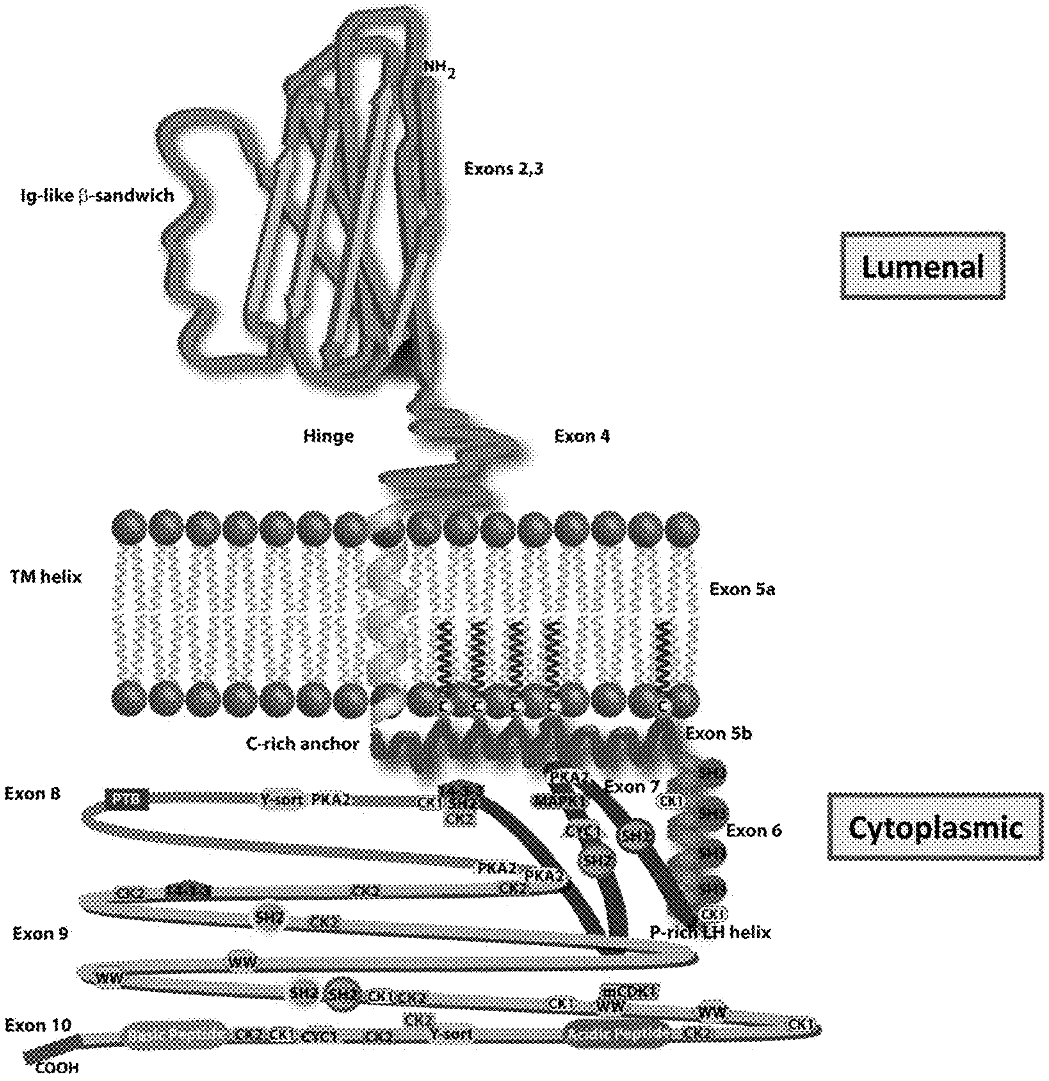
FIG. 27 shows a schematic of ILDR2. ILDR2 is a type I transmembrane protein with an immunoglobulin-like domain facing the lumen of the ER and C-terminal cytoplasmic tail. ILDR2 is highly expressed in liver, hypothalamus, fat, and islets.
Figure 30:
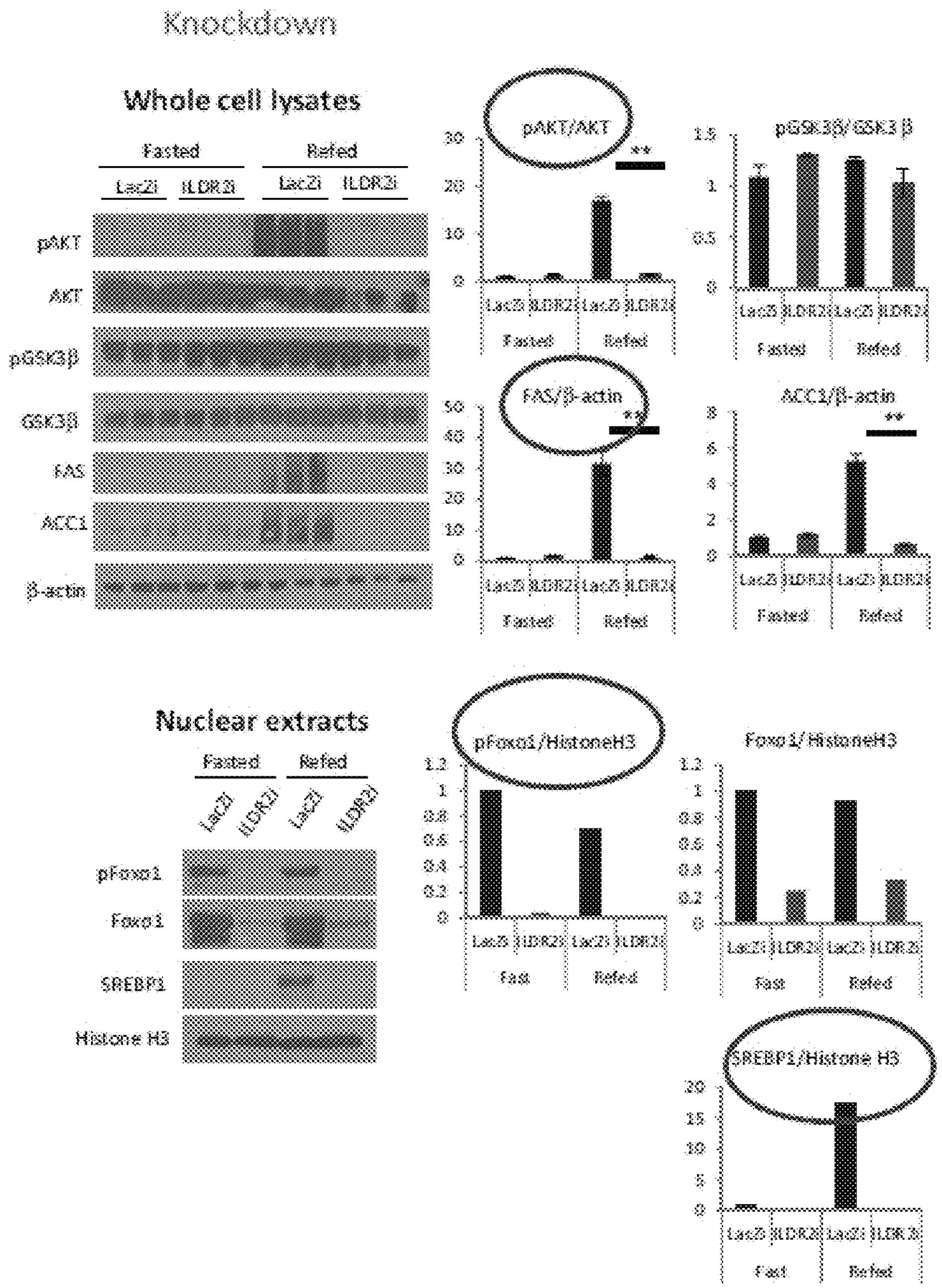
FIG. 30 shows Western Blots of 10 week knockdown C57BL/6J males, chow fed (*P<0.05, ** P<0.01). To examine levels of proteins related to lipid metabolism and insulin signaling pathway, western blots were performed. Quantification of each band is shown in the right. Phspho-Akt are decreased in refed knockdown mice. Lipogenic protein Fas and ACC were decreased. Regarding nuclear proteins, Phospho FoxO1 and FoxO1 were decreased in knockdown mice, consistent with decreased Fas and ACC, SREBP1 in refed state. In KD mice, decreased lipogenic proteins were caused by impairment of hepatic insulin signaling, suggesting that ILDR2 knockdown might induce hepatic insulin resistance.
Figure 31:
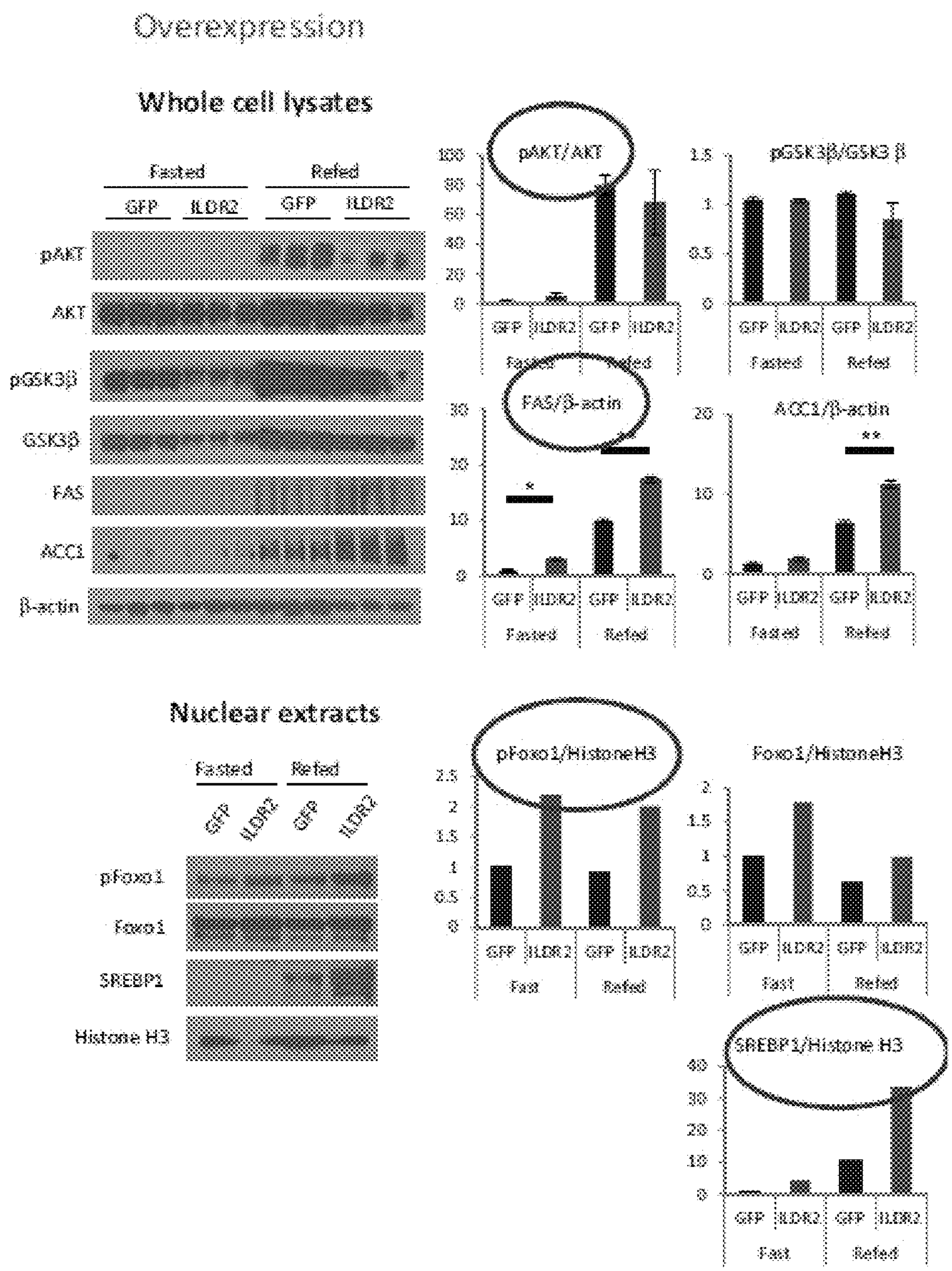
FIG. 31 shows Western Blots of 10 week overexpression C57BL/6J males, chow fed (*P<0.05,  P<0.01). To examine levels of proteins related to lipid metabolism and insulin signaling pathway, western blots were performed. Quantification of each band is shown in the right. In overexpression mice, phospho-Akt was slightly lower than control. Fas and Acc were increased. Phospho-Foxo and Foxo1 were increased. SREBP1 was also increased. These protein levels of OE mice livers were mostly opposite to KD mice (FIG. 30**).
Figure 34:
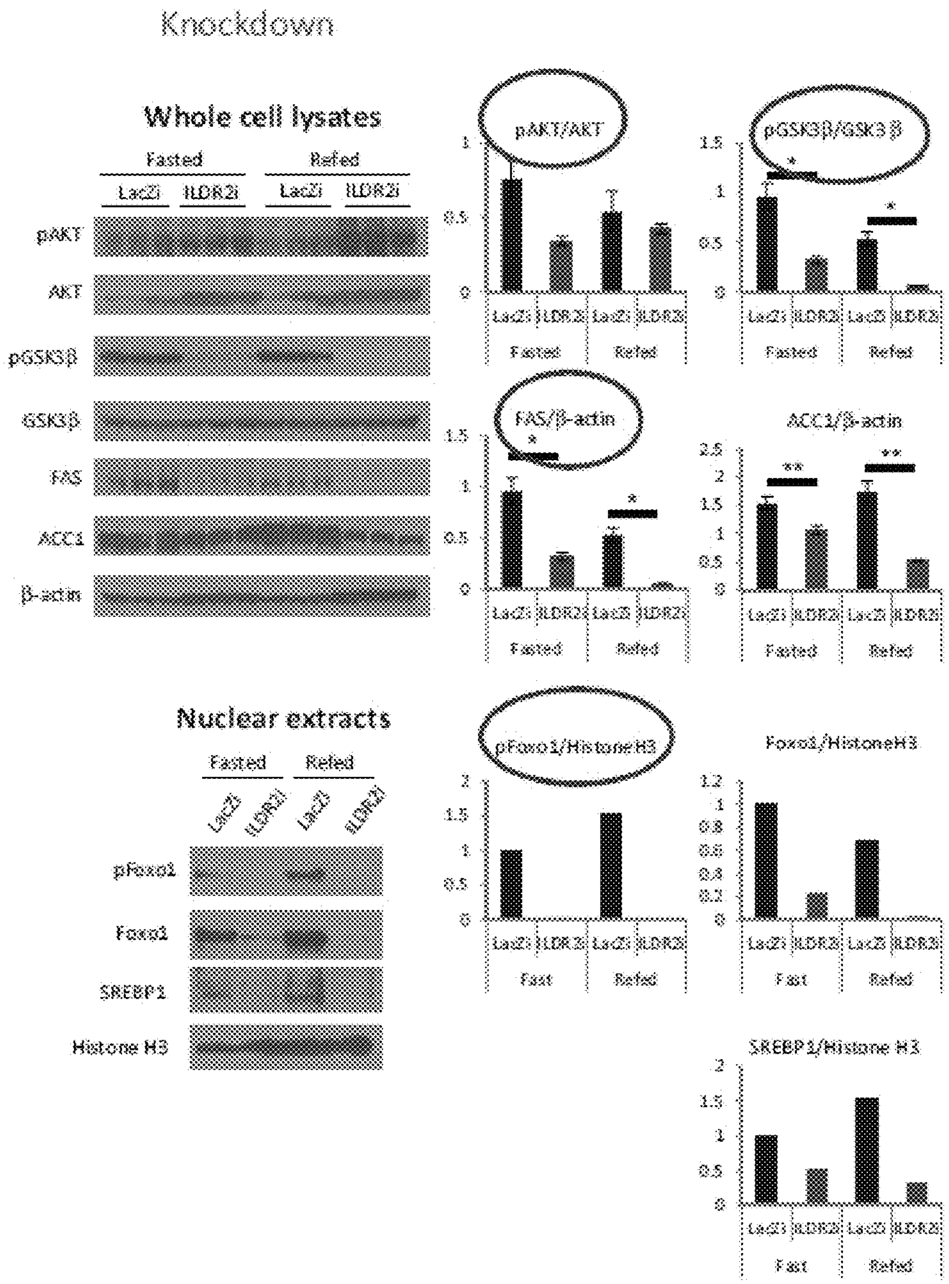
FIG. 34 shows Western Blots of 10 week knockdown ob/ob males, chow fed (*P<0.05, ** P<0.01). To examine levels of proteins related to lipid metabolism and insulin signaling pathway, western blots were performed. Quantification of each band is shown in the right. Regarding protein levels, phspho-Akt/Akt ratio in KD mice are lower than control. Fas and ACC were decreased. Phospho-FoxO1 and FoxO1 were decreased. Consistent with Fas and ACC, SREBP1 decreased in both fasted and refed state.
Figure 35:
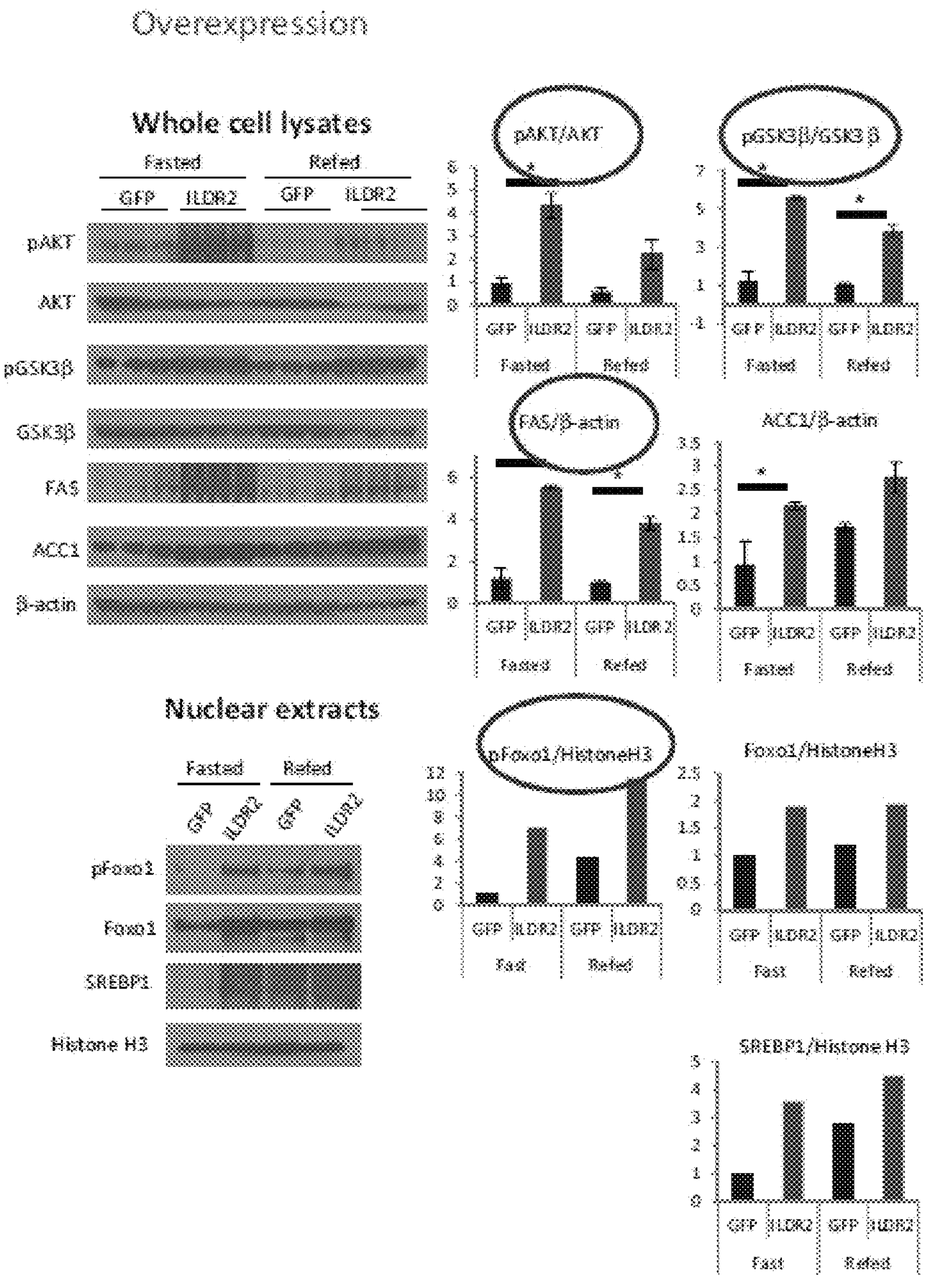
FIG. 35 shows Western Blots of 10 week overexpression ob/ob males, chow fed (*P<0.05, ** P<0.01). To examine levels of proteins related to lipid metabolism and insulin signaling pathway, western blots were performed. Quantification of each band is shown in the right. In overexpression mice, phospho-Akt was significantly increased. Fas, Acc were increased. Phospho-Foxo and Foxo1 were increased. SREBP1 was also increased. These results were mostly consistent with WT mice, suggesting that ILDR2 knockdown in ob mice induced the worse hepatic insulin resistance, and that ILDR2 overexpression in ob mice might improve hepatic insulin resistance.
Figure 36:
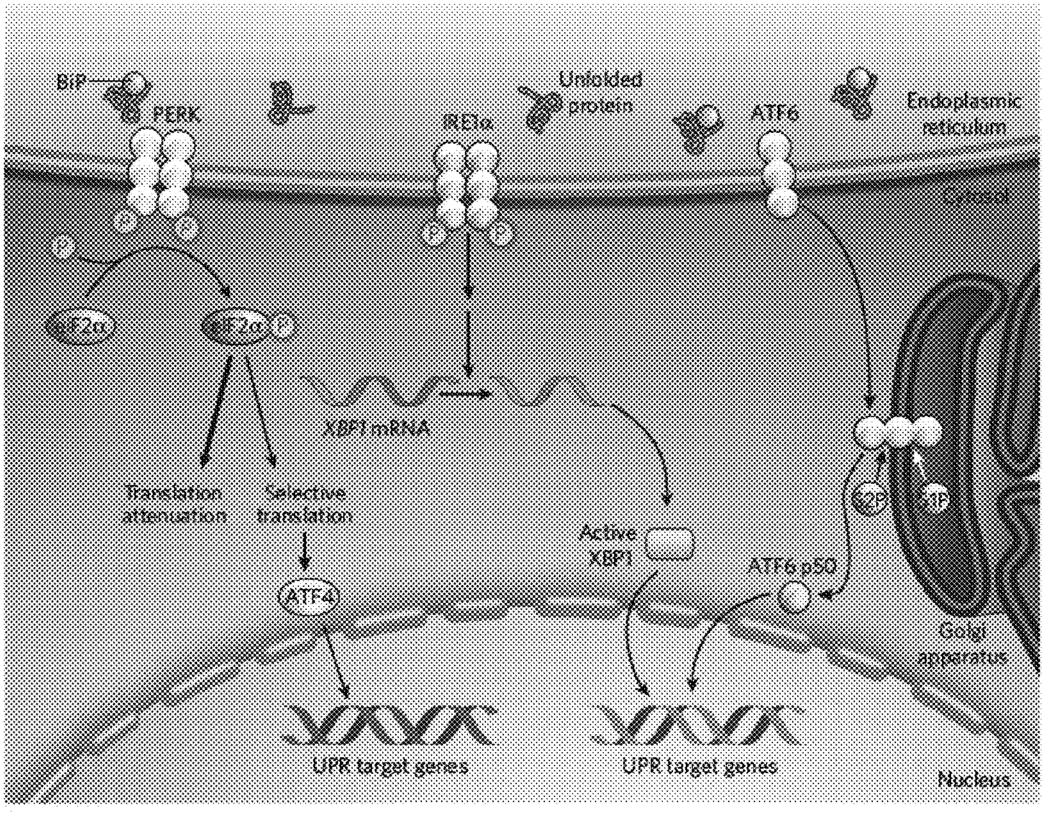
FIG. 36—Prior Art—shows a schematic of the unfolded protein response pathways (See Zhang, K and R. J. Kaufmann. Nature 454 2008).
Figure 37:
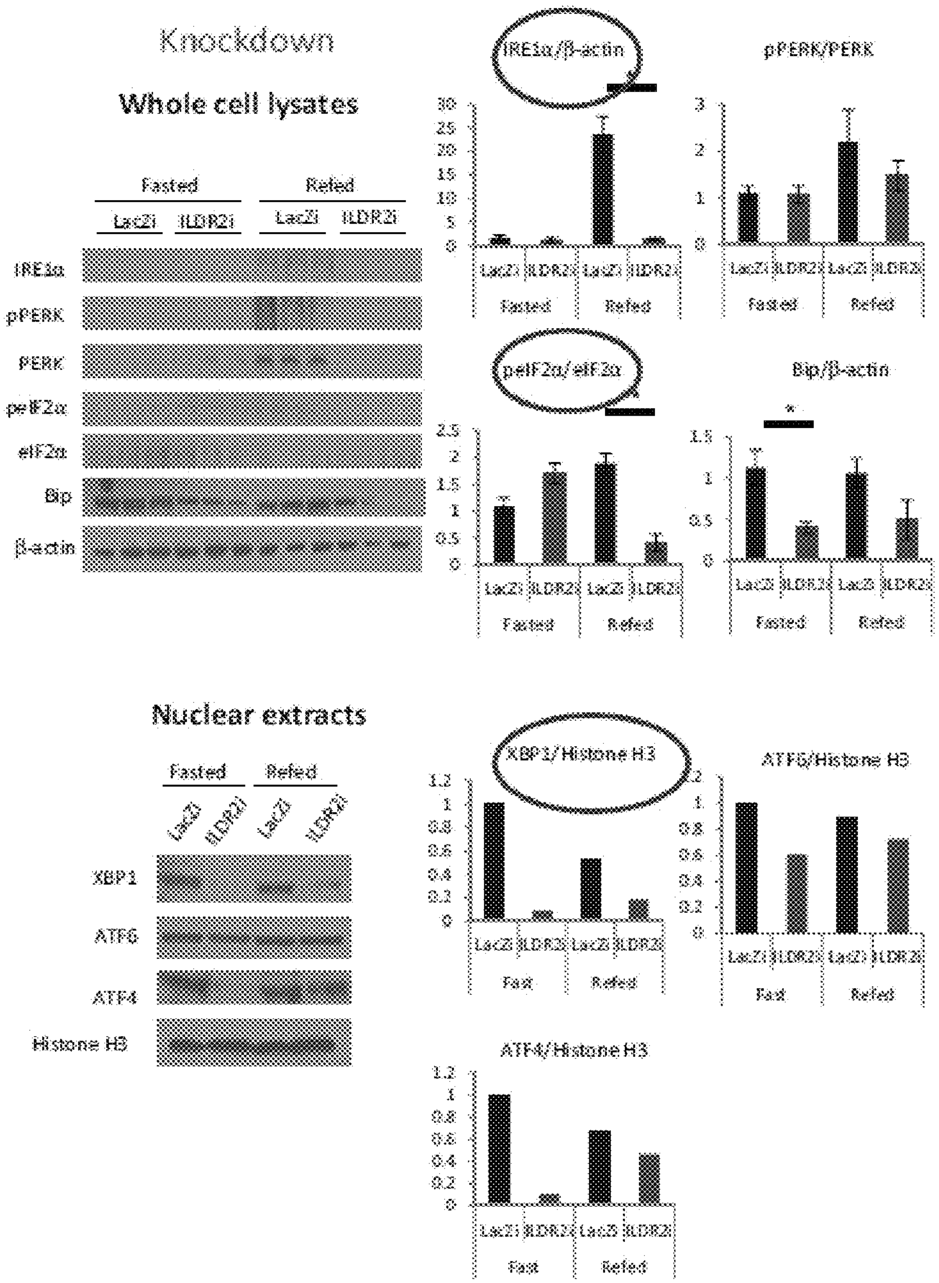
FIG. 37 shows Western Blots of 10 week knockdown C57BL/6J males, chow fed (*P<0.05, ** P<0.01). To examine levels of proteins related to ER stress response proteins, western blots were performed. Quantification of each band is shown in the right. IRE1a, phospho-eIF2a, and Bip were reduced in knockout mice. Nuclear proteins, XBP1, ATF6, and ATF4 were decreased in knockout mice.
Figure 38:
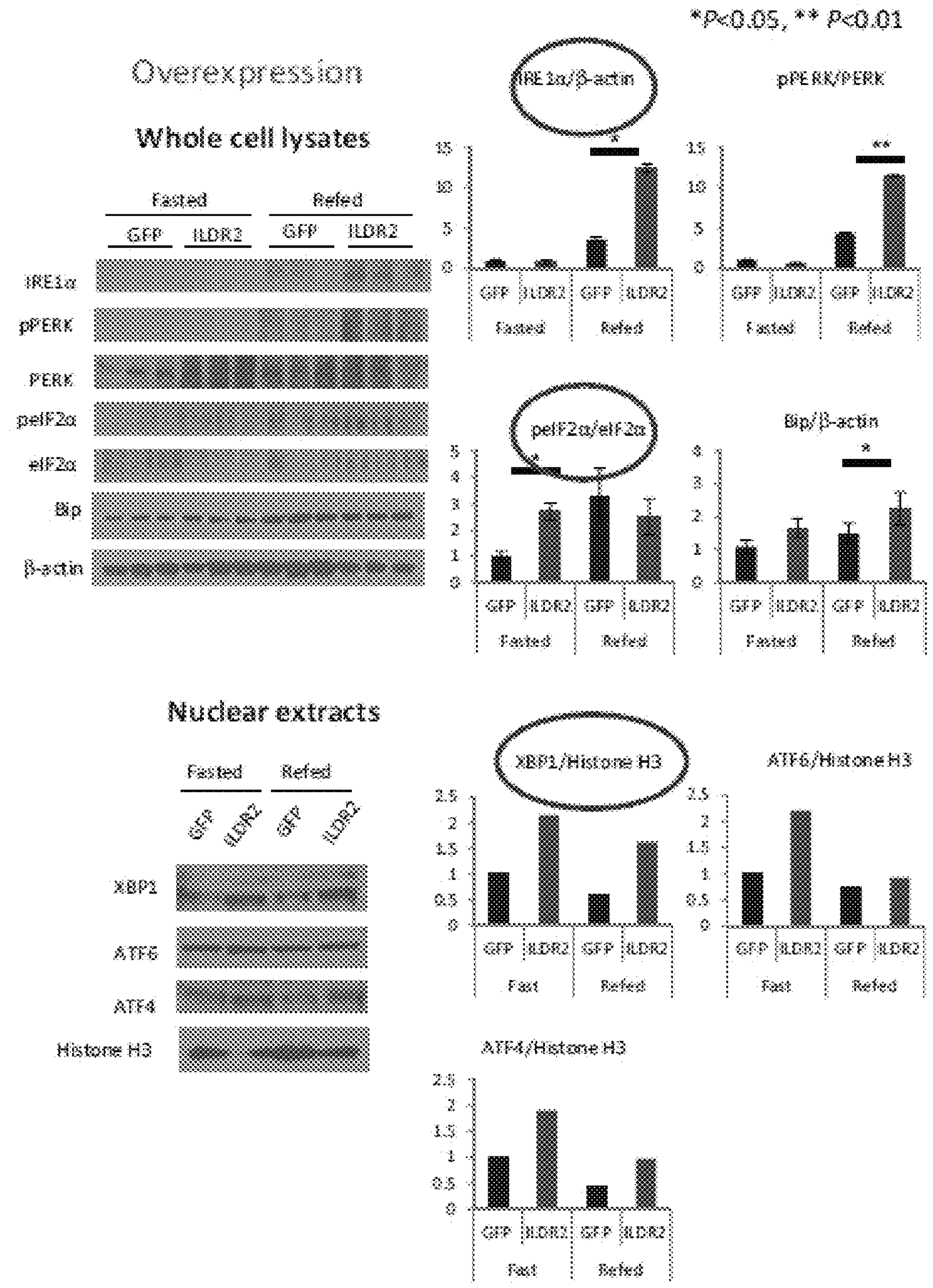
FIG. 38 shows Western Blots of 10 week overexpression C57BL/6J males, chow fed (*P<0.05, ** P<0.01). To examine levels of proteins related to ER stress response proteins, western blots were performed. Quantification of each band is shown in the right. IRE1a, phospho-PERK, phospho-eIF2a, and Bip were increased. Nuclear proteins, XBP1, ATF6, and ATF4 were also increased.
Figure 39:
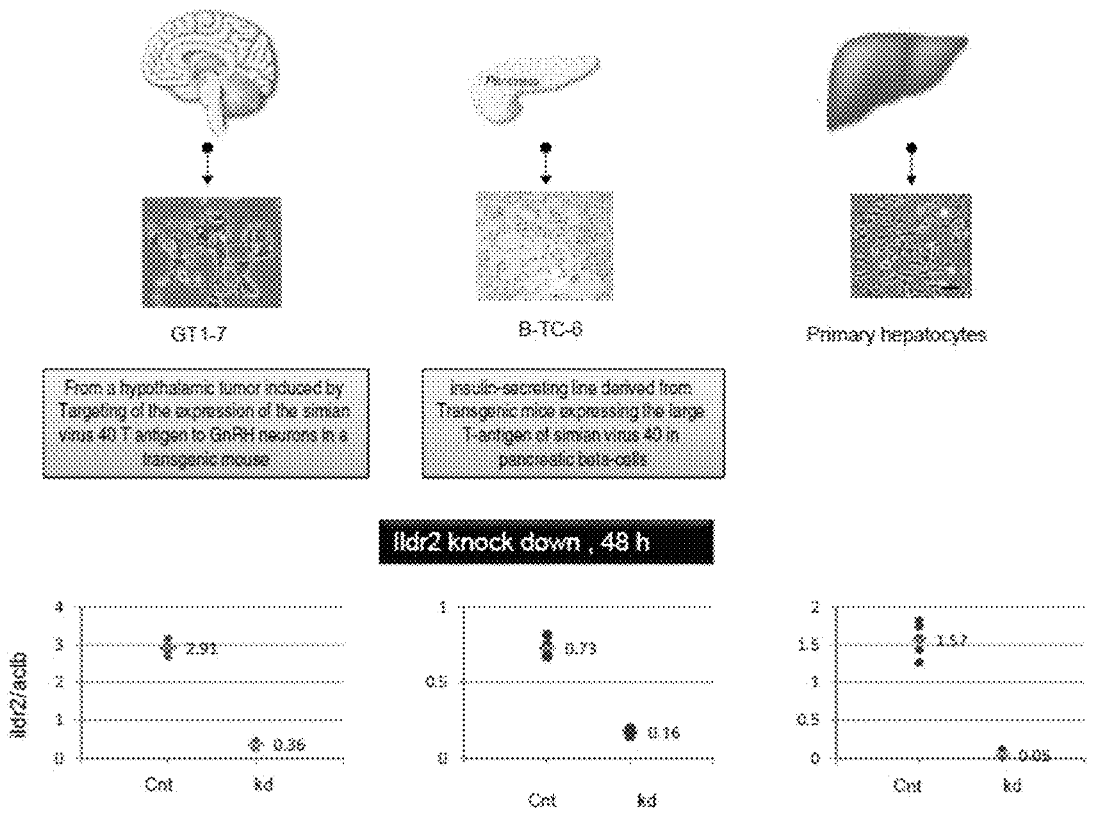
FIG. 39 shows global gene expression analysis on Affymetrix Gene Mouse 1.0 Expression Arrays. Cells were transfected (GT1-7 and BTC6) or transduced (primary hepatocytes) with RNAi for ildr2 mRNA Lower panels indicate the levels of knock down for ildr2 mRNA for the three cells types.
Figure 40:
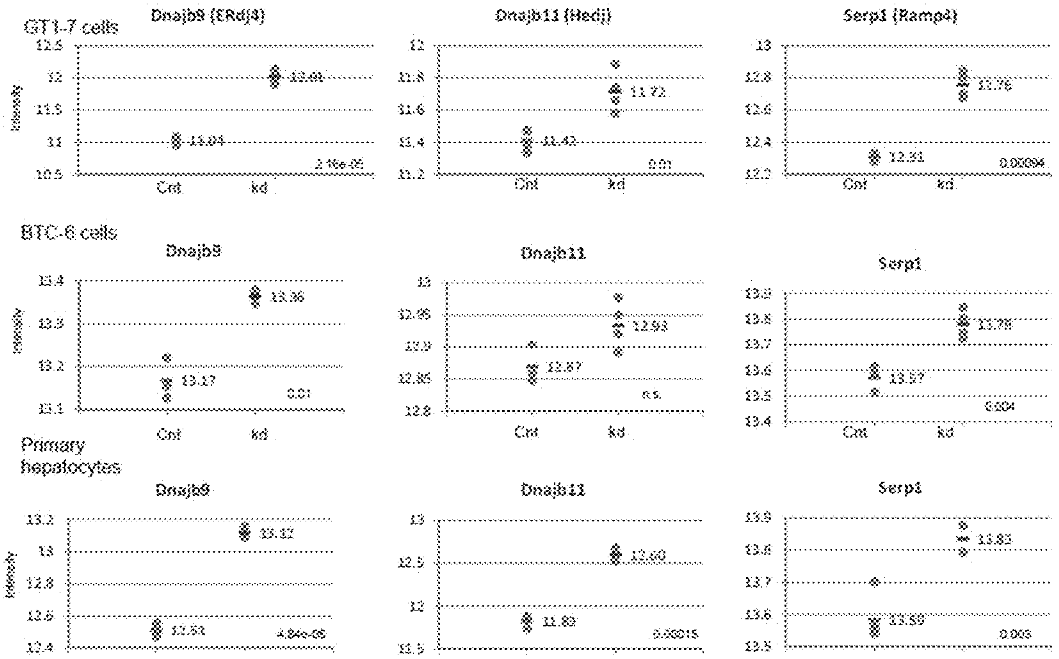
FIG. 40 shows mRNA level changes representative of the individual UPR branches (IRE1a pathway). Represented are the intensity values from the expression array data. First row: results from GT1-7 cells. Second row: results form BTC6 cells. Third row: results form primary hepatocytes.
Figure 45:
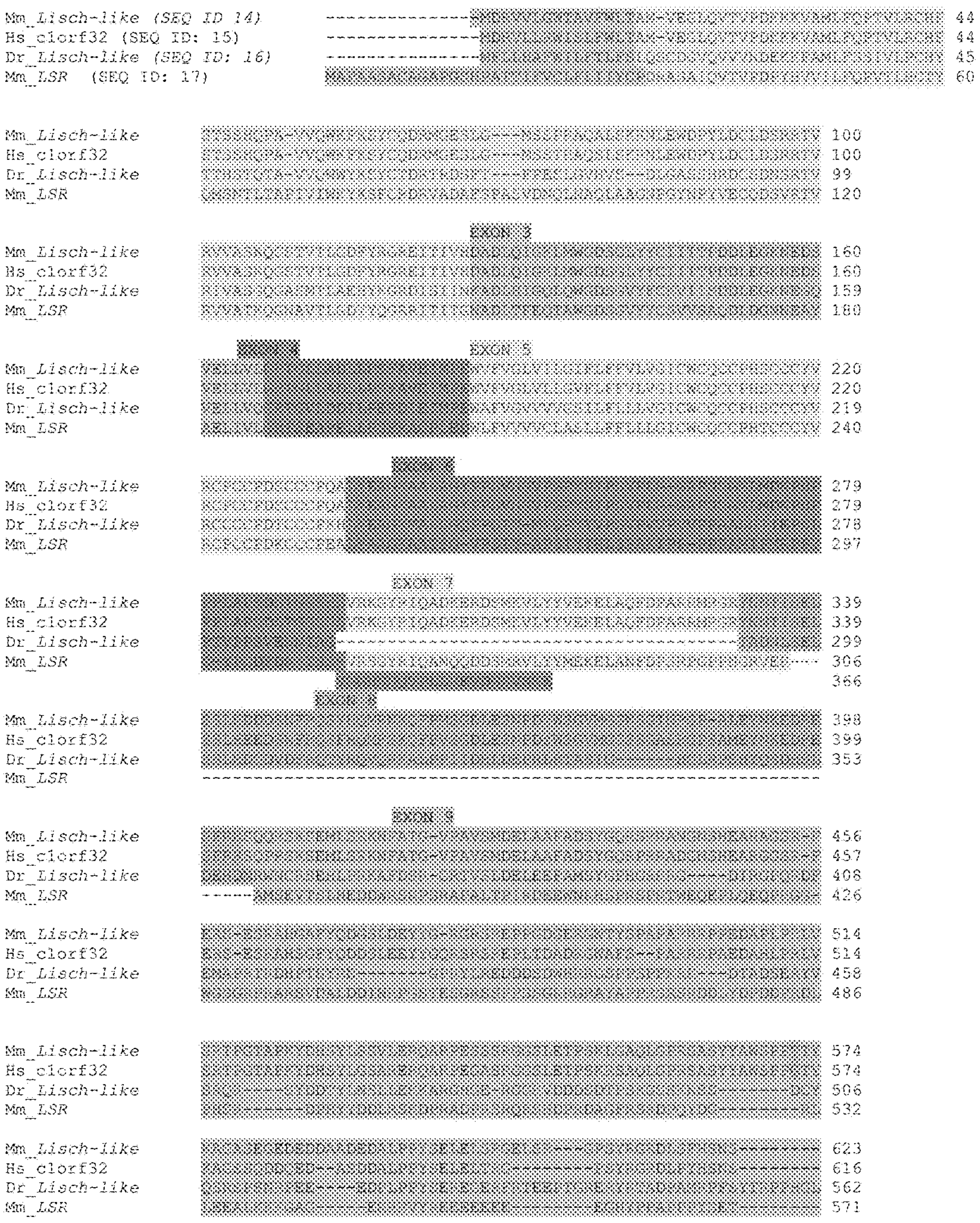
FIG. 45 shows ClustalW analysis of Ildr2(Lisch-like) homologs and the LSR protein. ClustalW analysis was performed on the EMBL-EBI server using their default settings. Display was modified to emphasize exonic alignments. Positions of non-synonymous variants in exon 9 of Ildr2 are identified by blue background. Non-homologous extension of mouse Lsr exon 6 (green background) is drawn beneath line. Abbreviations: B6, strain C57BL/6J; DBA, strain DBA/2J; ECD, extra-cellular domain; hpf, hours post-fertilization; Ig-like, immunoglobulin-like; ICD; intracellular domain; QTL, quantitative trait locus; TM, transmembrane domain; T2DM, type 2 diabetes; UTR, untranslated region. Mm_Lisch-like (mouse Ildr2) (SEQ ID NO: 14); Hs_clorf32 (humans ILDR2) (SEQ ID NO: 15); Dr_Lisch-like (SEQ ID NO: 16); Mm_LSR (SEQ ID NO: 17).

Phenotypical analysis of mice carrying the ENU amber mutation can yield preliminary insights into the developmental phenotypes of Ildr2-deficient animals. Such Ildr2-nullizygous mice can be tailored to develop normally and show increased susceptibility to diabetes at early post-natal stages. Ildr2 function can then be restored to alleviate or cure the disease. For example, if C57BL/6 Ildr2-deficient mice are viable and develop diabetes postnatally, tissue-specific reactivation of Ildr2 expression can be used to rescue the phenotype. In certain embodiments, the invention provides a conditional re-activatable Ildr2 allele generated by inserting a loxP-flanked STOP cassette consisting of an artificial splice acceptor site and a neomycin selection marker cassette into the first intron of the Ildr2 gene (FIG. 20). In this approach the presence of the STOP cassette in intron 1 can cause splicing to this artificial exon and termination of transcription by the triple SV40 polyA signal to efficiently prevent expression of the Ildr2 allele in the absence of cre (Hingorani et al, 2003, Cancer Cell 4:437-450; Ventura et al, 2007, Nature 445:661-665). Ildr2 function can then be restored in a tissue-specific manner employing the cre lines used for conditional inactivation of the gene. In other aspects, the invention provides animals carrying one or more re-activatable alleles described herein.

Methods of Treatment

The invention provides for methods of treating a metabolic disease in a subject, the method comprising administering to the subject a therapeutically effective amount of an agent which increases expression of Ildr2 mRNA or ILDR2 protein. In some embodiments, the metabolic disease is a fatty liver disease, dyslipidemia, metabolic syndrome, a cardiovascular disease, obesity, a leptin disorder, or any combination of the listed diseases. The invention provides methods for decreasing lipid levels in a subject, the method comprising administering to the subject a therapeutically effective amount of an agent which increases expression of Ildr2 mRNA or ILDR2 protein. In some embodiments, the lipid level is a cholesterol level, triglyceride level, ApoB level, LDL-cholesterol level, VLDL-cholesterol level, small LDL-particle level, small VLDL-particle level, non-HDL-cholesterol level, phospholipid level, or fatty acid level, or any combination lipid level listed herein. In one embodiment, the agent is a nucleic acid which comprises a nucleic acid sequence encoding an ILDR2 protein, an ILDR2 polypeptide, an ILDR2 isoform, or an ILDR2 functional fragment. In one embodiment, the nucleic acid is administered to the subject by an adenovirus or a adeno-associated virus. In one embodiment, the agent is an ILDR2 protein, an ILDR2 polypeptide, an ILDR2 isoform, or an ILDR2 functional fragment. In one embodiment, the agent is a peptide having SEQ ID NO: 2-9. In one embodiment, the agent is an inhibitor of PERK, IRE1a, active ATF6, or spliced XBP1. In one embodiment, the inhibitor of PERK, IRE1a, active ATF6, or spliced XBP1 is a RNAi. In one embodiment, the agent is an ER stress inhibitor.

For example, several well-established metabolic disease treatments as well as treatments for decreasing lipid levels ranging from non-pharmaceutical to pharmaceutical intervention are known in the art. Non-pharmaceutical interventions include, but are not limited to, dietary restriction, exercise, psychiatric treatment, and surgical treatments to reduce food consumption (e.g., bariatric surgery) or remove fat (e.g., liposuction). Present pharmacological interventions can induce a weight loss of between 5 to 15 kg. Appetite suppressants and energy expenditure or nutrient-modifying agents are the main focus of pharmacological intervention. Dexfenfluramine (Redux), sibutramine (Meridia), beta3-adrenergic agonists, sympathomimetic adrenergic agents (such as amphetamines (dextroamphetamine)), phentermine, benzphetamine, phendimetrazine, mazindol, diethylpropion, phenylpropanolamine, serotonin (5-HT) reuptake inhibitors (such as sibutramine), and gastrointestinal lipases (such as orlistat) are examples of such pharmacological interventions. See also, Bays, (2004) Obesity Research 12(8):1197-1211, and Klonoff et al., J Diabetes Sci Technol. 2008 September; 2(5):913-8, the contents of each which are incorporated by reference in their entireties. However, if the medication is discontinued, renewed weight gain can ensue. Surgical treatments are comparatively successful, but are complicated, expensive, and have significant risks. Surgical treatments are reserved for patients with extreme obesity and/or with serious medical complications.

The amount which will be therapeutically effective in the treatment of a particular individual's disorder or condition will depend on the symptoms and severity of the disease, and can be determined by standard clinical techniques. In vitro or in vivo assays can also be used to identify optimal dosage ranges. The precise dose to be used in the formulation will also depend on the route of administration, and the severity of the obesity or the obesity-associated disorder, and should be decided according to the judgment of a practitioner and each patient's circumstances. Effective doses can be extrapolated from dose-response curves derived from in vitro or animal model test systems, such as a db/db mouse, an ob/ob mouse, or a High-fat-diet-fed mouse model (e.g., the Diet Induced Obesity (DIO) mouse model).

In some embodiments, the subject is already suspected to have a metabolic disease. In other embodiments, the subject is being treated for a metabolic disease, before being treated according to the methods of the invention. In other embodiments, the subject is not being treated for a metabolic disease, before being treated according to the methods of the invention.

The present invention also provides a kit for treating a metabolic disease in a subject. In one embodiment, the kit for treating a metabolic disease comprises an agent which increases expression of Ildr2 mRNA or ILDR2 protein to administer to a subject and instructions of use. In one aspect, the invention provides an agent which increases expression of the Ildr2 mRNA or ILDR2 protein. In one embodiment, the agent is a nucleic acid which comprises a nucleic acid sequence encoding a ILDR2 protein, a ILDR2 polypeptide, a ILDR2 isoform, or a ILDR2 functional fragment. In another embodiment, the agent is an ILDR2 protein, a ILDR2 polypeptide, a ILDR2 isoform, or a ILDR2 functional fragment. In another embodiment, the agent is a peptide having SEQ ID NO: 2-9. In one embodiment, the agent is an inhibitor of PERK, IRE1a, active ATF6, or spliced XBP1. In one embodiment, the inhibitor of PERK, IRE1a, active ATF6, or spliced XBP1 is a RNAi. In one embodiment, the agent is an ER stress inhibitor.

The present invention also provide a method of determining the presence of, or predisposition to, a metabolic disease in a subject. In one embodiment, the presence of, or predisposition to a metabolic disease in a subject is determined by extracting a sample from a subject and detecting the presence, absence or reduction of an ILDR2 protein or nucleic acid in the sample, wherein absence, or reduction of the ILDR2 protein or nucleic acid indicates the presence of, or predisposition to, a metabolic disease. In a further embodiment, the method further comprises administering of an agent which increases expression of ILDR2 mRNA or ILDR2 protein to the subject where an ILDR2 protein or nucleic acid was not detected. In one embodiment, a reduction of an ILDR2 protein or nucleic acid in the sample comprises detecting a lower amount of an ILDR2 protein or nucleic acid in the sample than the amount of an ILDR2 protein or nucleic acid in a control sample. In one embodiment, the control sample is from a subject without a metabolic disease. In one embodiment, the ILDR2 protein or nucleic acid is detected by incubating the sample with an agent that binds to an ILDR2 protein or nucleic acid. In a further embodiment, the agent is an antibody to an ILDR2 protein.

The present invention also provides a diagnostic kit for determining the presence of, or predisposition to, a metabolic disease, the kit comprising an agent that binds to an ILDR2 protein or nucleic acid, and instructions for use. In one embodiment, the agent is an antibody to an ILDR2 protein.

In one embodiment, the subject is an animal. In another embodiment, the subject is an animal that has or is diagnosed with a disease of the digestive system. In one embodiment, the subject is a human. In other embodiments, the subject is a mammal. In one embodiment, the subject is a dog. In another embodiment, the subject is a cat. In some embodiments, the subject is a rodent, such as a mouse or a rat. In some embodiments, the subject is a cow, pig, sheep, goat, cat, horse, dog, and/or any other species of animal used as livestock or kept as pets.

Molecules of the Invention

As used herein, a "ILDR2 molecule" refers to a ILDR2 protein, or a fragment thereof. A "ILDR2 molecule" can also refer to a nucleic acid (including, for example, genomic DNA, complementary DNA (cDNA), synthetic DNA, as well as any form of corresponding RNA) which encodes a polypeptide corresponding to a ILDR2 protein, or fragment thereof. For example, an ILDR2 molecule can include the amino acid sequence shown in SEQ ID NO: 22. For example, an ILDR2 molecule can be encoded by a recombinant nucleic acid encoding a ILDR2 protein, or fragment thereof. The ILDR2 molecules of the invention can be obtained from various sources and can be produced according to various techniques known in the art. For example, a nucleic acid that encodes a ILDR2 molecule can be obtained by screening DNA libraries, or by amplification from a natural source. An ILDR2 molecule can include a fragment or portion of a ILDR2 protein. An ILDR2 molecule can include a variant of the above described examples, such as a fragment thereof. Such a variant can comprise a naturally-occurring variant due to allelic variations between individuals (e.g., polymorphisms), mutated alleles, or alternative splicing forms. In one embodiment, an ILDR2 molecule is encoded by a nucleic acid variant of the nucleic acid having the sequence shown in SEQ ID NO: 129 wherein the variant has a nucleotide sequence identity to SEQ ID NO: 129 of at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%. In another embodiment, a variant of the ILDR2 protein comprises a protein or polypeptide encoded by a ILDR2 nucleic acid sequence, such as the sequence shown in SEQ ID NO: 129.

The nucleic acid can be any type of nucleic acid, including genomic DNA, complementary DNA (cDNA), synthetic or semi-synthetic DNA, as well as any form of corresponding RNA. For example, a nucleic acid encoding a ILDR2 protein can comprise a recombinant nucleic acid encoding such a protein. The nucleic acid can be a non-naturally occurring nucleic acid created artificially (such as by assembling, cutting, ligating or amplifying sequences). It can be double-stranded or single-stranded.

The invention further provides for nucleic acids that are complementary to a ILDR2 molecule. Complementary nucleic acids can hybridize to the nucleic acid sequence described above under stringent hybridization conditions. Non-limiting examples of stringent hybridization conditions include temperatures above 30° C., above 35° C., in excess of 42° C., and/or salinity of less than about 500 mM, or less than 200 mM. Hybridization conditions can be adjusted by the skilled artisan via modifying the temperature, salinity and/or the concentration of other reagents such as SDS or SSC.

According to the invention, protein variants can include amino acid sequence modifications. For example, amino acid sequence modifications fall into one or more of three classes: substitutional, insertional or deletional variants. Insertions can include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the protein sequence. These variants ordinarily are prepared by site-specific mutagenesis of nucleotides in the DNA encoding the protein, thereby producing DNA encoding the variant, and thereafter expressing the DNA in recombinant cell culture.

In one embodiment, an ILDR2 molecule comprises a protein or polypeptide encoded by a nucleic acid sequence encoding an ILDR2 protein, such as the sequences shown in SEQ ID NO: 129. In another embodiment, the polypeptide can be modified, such as by glycosylations and/or acetylations and/or chemical reaction or coupling, and can contain one or several non-natural or synthetic amino acids. An example of an ILDR2 molecule is the polypeptide having the amino acid sequence shown in SEQ ID NO: 22. Such variants can include those having at least from about 46% to about 50% identity to SEQ ID NO: 22 or having at least from about 50.1% to about 55% identity to SEQ ID NO: 22, or having at least from about 55.1% to about 60% identity to SEQ ID NO: 22, or having from at least about 60.1% to about 65% identity to SEQ ID NO: 22, or having from about 65.1% to about 70% identity TO SEQ ID NO: 22, or having at least from about 70.1% to about 75% identity to SEQ ID NO: 22, or having at least from about 75.1% to about 80% identity to SEQ ID NO: 22, or having at least from about 80.1% to about 85% identity to SEQ ID NO: 22, or having at least from about 85.1% to about 90% identity to SEQ ID NO: 22, or having at least from about 90.1% to about 95% identity to SEQ ID NO: 22, or having at least from about 95.1% to about 97% identity to SEQ ID NO: 22, or having at least from about 97.1% to about 99% identity to SEQ ID NO: 22. In another embodiment, An ILDR2 molecule can be a fragment of a ILDR2 protein.

In one embodiment, an ILDR2 molecule, according to the methods described herein can be administered to a subject as a recombinant protein. In another embodiment, a ILDR2 molecule, can be administered to a subject as a modified recombinant protein. In a further embodiment, an ILDR2 molecule, according to the methods described herein can be administered to a subject by delivery of a nucleic acid encoding a ILDR2 protein, or fragment thereof. For example, nucleic acids can be delivered to a subject using a viral vector.

The invention provides for a nucleic acid encoding an ILDR2 protein, or fragment thereof.

For example, the polypeptide sequence of human ILDR2 is depicted in SEQ ID NO: 22. The nucleotide sequence of human ILDR2 is shown in SEQ ID NO: 129. Sequence information related to ILDR2 is accessible in public databases by GENBANK Accession numbers NP 955383.1 (protein) and NM_99351.2 (nucleic acid).

SEQ ID NO: 22 is the human wild type amino acid sequence corresponding to ILDR2 (residues 1-639):

```
  1 mdrvllrwis lfwltamveg lqvtvpdkkk vamlfqptvl rchfstsshq pavvqwkfks

 61 ycqdrmgesl gmsstraqsl skrnlewdpy ldcldsrrtv rvvaskqgst vtlgdfyrgr

121 eitivhdadl qigklmwgds glyyciittp ddlegkneds vellvlgrtg lladllpsfa

181 veimpewvfv glvllgvflf fvlvgicwcq ccphscccyv rcpccpdscc cpqalyeagk

241 aakagyppsv sgvpgpysip svplggapss gmlmdkphpp plapsdstgg shsvrkgyri
```

-continued 301 qadkerdsmk vlyyvekela qfdparrmrg rynntisels slheedsnfr qsfhqmrskq 361 fpvsgdlesn pdywsgvmgg ssgasrgpsa meynkedres frhsqprsks emlsrknfat 421 gvpavsmdel aafadsygqr prradgnshe arggsrfers esrahsgfyq ddsleeyygq 481 rsrsrepltd adrgwafspa rrrpaedahl prlvsrtpgt apkydhsylg sarergarpe 541 gasrggslet pskrsaqlgp rsasyyawsp pgtykagssq ddqedasdda lppyselelt 601 rgpsyrgrdl pyhsnsekkr kkepakktnd fptrmslvv SEQ ID NO: 129 is the human wild type nucleotide sequence corresponding to ILDR2 (nucleotides 1-508):

1 gttccagcca tttcccactt tcctcactcc gtaattcggc tgggaagttg gggaagatgg 61 atagggtctt gctgaggtgg atttctctct tctggctaac agccatggtc gaaggccttc 121 aggtcacagt gcccgacaag aagaaggtgg ccatgctctt ccagcccact gtgcttcgct 181 gccacttctc aacatcctcc catcagcctg cagttgtgca gtggaagttc aagtcctact 241 gccaggatcg catgggagaa tccttgggca tgtcctctac ccgggcccaa tctctcagca 301 agagaaacct ggaatgggac ccctacttgg attgtttgga cagcaggagg actgttcgag 361 tagtagcttc aaaacagggc tcgactgtca ccctgggaga tttctacagg ggcagagaga 421 tcacgattgt tcatgatgca gatcttcaaa ttggaaagct tatgtgggga gacagcggac 481 tctattactg tattatcacc accccagatg acctggaggg gaaaaatgag gactcagtgg 541 aactgctggt gttgggcagg acagggctgc ttgctgatct cttgcccagt tttgctgtgg 601 agattatgcc agagtgggtg tttgttggcc tggtgctcct gggcgtcttc ctcttcttcg 661 tcctggtggg gatctgctgg tgccagtgct gccctcacag ctgctgctgc tatgtccgct 721 gcccatgctg cccagattcc tgctgctgcc ctcaagcctt gtatgaagca gggaaagcag 781 caaaggccgg gtaccctccc tctgtctccg gtgtccccgg cccttactcc atcccctctg 841 tccctttggg aggagccccc tcatctggca tgctgatgga caagccgcat ccacctccct 901 tggcaccaag tgactccact ggaggaagcc acagtgttcg caaaggttac cggatccagg 961 ctgacaaaga gagagactcc atgaaggtcc tgtactatgt tgagaaggag ctggctcagt 1021 ttgatccagc cagaaggatg agaggcagat ataacaacac catctcagaa ctcagctccc 1081 tacatgagga ggacagcaat ttccgccagt ctttccatca gatgagaagc aagcagttcc 1141 ctgtgtctgg ggacttggag agcaatcctg actattggtc aggtgtcatg ggaggcagca 1201 gtggggcaag ccgcgggccc tcagccatgg agtataacaa agaggatcga gagagcttca 1261 ggcacagcca gccgcgctcc aagtcggaga tgctgtcgcg gaagaacttc gccacggggg 1321 tgccggccgt ttccatggac gagctggcgg ccttcgctga ctcctacggc cagcggcccc 1381 gccgggcaga cggcaacagt cacgaggcgc ggggcgggag ccgcttcgag cgctcggagt 1441 cgcgggcgca cagcggcttc taccaggacg actccttgga ggagtactac ggtcagcgca 1501 gccgcagccg cgagcccctg accgatgctg accgcggctg ggccttcagc cccgcgcgcc 1561 gcagacccgc cgaggacgcg cacctgccgc ggctggtgag ccgcacgcca ggcaccgcac 1621 ccaaatacga ccactcgtac ctgggcagcg cgcgggagcg ccaggcgcgg cccgagggcg 1681 ccagccgcgg tggcagcctg gagacgccat ccaagcggag cgcgcagctc ggcccgcgca 1741 gcgcctccta ctacgcttgg tcgccgcccg gcacctacaa ggccggctcg tcgcaggacg 1801 accaggagga cgcgtccgac gacgcgctgc cgccctacag cgagctggag ctgacccgcg -continued

```
1861 gcccgtccta ccgcggccgc gacctgccct accacagcaa ctcggagaag aagaggaaaa
1921 aggagcccgc caagaaaacc aatgactttc caaccaggat gtcccttgtg gtctgatgtt
1981 gtcaacattt ctctggataa tgagaaatca gacatggact acggggacaa gacacaaatc
2041 taagaaccag caggcccagg accttctctg gccatcacct tggaagattt gctgatctct
2101 gctttggcaa gggatggcag gcagccttta agggaggctg atttcaaacc tctgtgccca
2161 tctaactagt ttgagaagct taccaagaaa gcaagaatgt gtgagaacat tcctacatac
2221 agagtttctc aactatagcg tttatcctgc ccagcctcct cccttaacag aaccaggact
2281 ccatttgcaa ttctgaaaga gagttagctc tggactgcta aactccagaa attgcctatg
2341 cctacaatat gcttttctat acctcctgtg ctatacttag agacagaaga atttattact
2401 actattagaa ggccttcttc tgacaaggga agatagcttc aagtcaaaat atacctttta
2461 tccccatcac tttacagtca ctagtcaatg actgttgtta cactaaaatc aaaaggcctt
2521 tggtgagctc agtgacagtg acctctggga caatcacaga aatgacttca ctgctgttct
2581 gaatgacaat tcttaagtgg ctaggacaaa gcaaaagcga gtatacettt ttgaaaagct
2641 gtctaagtgg tatttccttt tccattctga gaacgtaaac tgctttttcc ttttctgctg
2701 cacatgtcaa tatcggagtc ttagacatta agggctcttc tcttcctccc ctctcctgga
2761 cttcccacag gttggtgcca cacacacagc cctgcctccc tctgcactct gattagattg
2821 tcattgaatg ccttgtgata aatgcttaaa atatacacat gaaagagaag agggaggaaa
2881 gaggagaaag cagtaatgca tatagaaaag aatgagaagg aatttaaaag ggaaataaca
2941 tcatctcatt atattttgaa tgtggaccat ttcacccaca aacttcactc agtcttttcc
3001 ggttttgtgc ttcacttgcc gttaattgtt tctgccatcc cagttctgcc attctaggac
3061 atgggggatg tggaacatac agcatttggc ctgactagac tgccactatg gctgctttca
3121 agagattaga gatactgctt tctcaggaag gagtacttcc tattcccacc cttgcctaaa
3181 tgatagattt tgcctaaatc ccaaagctag atctctggat tttatcgttt gtgtagatag
3241 caaaaatggc cacgaactct ttccttctca tcaagaggtg ccatcttttt tccaacccct
3301 tgaatctgga gttggctatg tgatttgatt tagccagtag cccaacaaat gtgacacaag
3361 cagagacttg aaaagttctt gtgcatgggg cttgtcctct tttgctgctc ttgggaacct
3421 tgcaactacc atcaggtgaa caagcctgga ctatcctgct gcatgacaaa agaaaagggc
3481 ccagttaccc ttgtcaccct atctgacagc ccgtcaactt ccagctgatg cagacatggg
3541 tgagtccagg tgataccaat agaagaactg cctagctgaa cccagcccaa atttctgatt
3601 cctactcgag gcgtgagaag ttggtgcatt ctttatgttc atttctcttt aagaacaaac
3661 ctgactcgtt cttgtctgaa tgttcatccc tgaacctctt aatccatcca aacttgtgtt
3721 tctcatagcc tccactattg ttgacaaatt tttatcaaag cttttcaccc tgcactcttg
3781 tggagtggag gataatgctt gactttgcta tcccttaatc cagcagtggt ttcttccctg
3841 tctatggatc cgtggacaac ctctgaagat ctcttcttta ccatcctttt ggtcttctcc
3901 agagccaccc tactggggct agaccctatt ctcaaagtac cattcctcta gtatccattt
3961 gtacttcatg acatttccaa aaaaagtcct atgtttgcaa tgaaataaga aagtggctgg
4021 gtgagggtcg gagggatgag ctggtatgtg tcattgcttg gagaattgac ctaccaaagg
4081 acttccgtgt tgctttggcc agtcccagag aaatcaggag aacagttgaa cccagtgctg
4141 gcacttccaa gggctggaag acacaagcca taaccctggt gctgagtttt agacttgctg
4201 gtgtccctgg cctctgaaag cctaggtcta gcctgtctgt ttggacccca gttcagatgg
4261 aaaagatgat aaaaaacatt tcttagtcac cagctttgga tttcaacttg ctcaggcaat
```

-continued

```
4321 tttggagaat attgggtagc tgtggtagct attatcgctt tatactgagc actgtgtcag
4381 gcttttcacc accaaagagc ctcatagcac cagctgcaga gaccaaaaat aatgtttttt
4441 taaagctacg gacgtatgat tttggtgaag gttgagggta gcaatgggaa agaaagaatt
4501 attaaaattg gaaacctgca attccaaaga caacaaaact acagatagac tgaaaagtac
4561 aaagaagata gcaggctact gaattaacct tgggagttgg gaccaggttg tcctttgtag
4621 aactggataa atcattcaga cttccaggct ttcagtagag agaaaaagca gttgtttctg
4681 ggtatatgga caggagttaa ggctgagttg acaagtcaaa acttcttgtc ctcagcaccc
4741 ctgactttcc tctatgtgtc cttttgtttc ttctcctttg aatagtgtgt cctgcacagg
4801 aaatggttat atttgttagc ttctttccta ggtcttattg gagtacaaag taaatcttgt
4861 gtaagacata atctctgtcc actaggaccc cgtaatttaa taggggaaat aagacatgct
4921 caagaaagga gattttatac atagagtatg aaatagtgct atggataaat tataataaaa
4981 ccagagattt agttttttta aaaaatgaga atactttgat attaaagtgt tgtatgtgtt
5041 tgtccatcat cttatttaaa catagacttg gtgatctgaa aagccaatac tcaaaagtct
5101 gaactgaaaa gaggtgaatt aggatcggga aagggtgagc agcaggggtc ccagggggat
5161 gatgcataag ctgctgtgct tgcctgtgag tcactactga gtcaggaaca cgctggagga
5221 gggagtgtgg atgcaggtgg cagggaggtg tcccctggta gatgagctgc ttctctaggc
5281 catgcatgga ttcattagga agttggagac aatggccatg gacctggtgc atggcagcta
5341 ttccatccaa gcacgttcac aggggagctc agcgtggctg ctcctggggc tcagttctgc
5401 ggctgtgagt gctgctgccc atattcacca acacagggca ggcctcacgg agatgctagg
5461 cctcacatcc cccttctcat gatcctcact gtgcacttga cataggatta ggcatactgg
5521 agatgagaaa aggctgccac ccaaacccaa ggcacctgac cacatctgta aatatttctg
5581 aatagtccac aaaatttcac ataggtagtc tgattagatc ttgcctttga gagaagctga
5641 agtcacagat actgttgtaa tttaccaccg cccctcaccc aatttttttt aataggtgaa
5701 gaaaccatca ctgccattaa tgaagtcaca aacctattag gtctttagac tcccaacctc
5761 tggatctttt ctgctgatta gtgtttccca aaattgccta accacaagaa ttaacttgat
5821 agctgctgtt aaaaaggtat tgttggaccc tgttttggag attgattggg tgggtctaga
5881 gccagaattc atatttttaa tatgcattcc aggagactcc tgtgatcaga tgcatttgga
5941 aatcattgca ctaagtcata cctctgggta ctccaaacag ctagtcctga ggcttccttg
6001 ggccttagaa tttttcttc aaatgtcctg gtgaggtccc tctcaatcct ttggggctgg
6061 ctgtggtgag tcactcagaa gtctggctgt gacctggatg ggctcaccag agtacgctag
6121 tggtagtggg aaaacaggca gagagaaagg agtgtcagga gcactcccag ggaggctgtt
6181 gtagatattt ccattcccag aacagtgatc tattgtgaca gtctcagaac agacaacaag
6241 aattacaggt aattttctca ttctcttgat atattttag caaaacttaa atcatgaata
6301 gaaggaaaag atgccattgg ggaaatagaa aaactcaatc attttataaa gcatacaaat
6361 cataaggatg actggccaat agcactccca ctttggtctt acctaaagtt gggtggacaa
6421 gaataataaa agtcctcatt ttatatcctt ccaaaatcag atttaaatgc tgccagcatc
6481 ttaatggaag tctgaaattg attgatagga tgtagaaatc caaattcact aaaatagggg
6541 gccagctaca taaagtccta gaaggaaaaa gtgcctcgct tttttctgcc attatcctac
6601 cccctagtca tctggggaat tgatctatga agcttgaaga aggggcattt aacatcagag
6661 tggtgcaagg gcagtgttga gatgctttaa gcagcagcct gagctttagc actatttgaa
```

```
-continued
6721 ggggagaagg ttaatactaa taatatttgt gttattttta tgatatatta ctgtttacag

6781 aacactttca tttgatccca acatcaactg ctgtgataga ggcagggcag atgttgtggt

6841 ctcattacat agaatgtaaa actgaggttg aaaaatacta agtgacttgt ctgtagtcaa

6901 atggttttta aaattataaa gccaggcctt ctgactgtct tgtctggtgt cctttccaat

6961 tccttaaata ctcatgggac tggaatctgg gtattccaga ttccagtttc tcttcacagc

7021 cagacatctg gtgagaagag ccgtagactt gatgcttgtt catatgtcat ggatgtggcg

7081 aagccatgaa gacagatact gttgctgctt catccaacta agcaccattc attcctcaaa

7141 tgctaatcta agagggagtt gtagcttcac tcaaggagag tttcgttttc tttttctttc

7201 ttttttttt ttttgagaca gggtcttgct ctgtggccca tggtgcagtg cagtgcagtg

7261 gtgctatcag ctcactgcag tctcaaactc ctagctcaag caatcctcct ccctcagcct

7321 cccaagtagg taggactaca gatatatgcc accacgtcca gcaaattttg tttgtttgta

7381 gagatggggt cttgctatat ttcccaggct tgtctcaaac tcctggcctc aagtgatcct

7441 cccaccttgg ctgcctaaag tgctggtatt acagacatga gccactgaac ccagctgaga

7501 gcctcacttt catcacctgt gctgtgaggg gtaatatatg cttcaggttt tctggagaat

7561 ccttcttgca gagaagtttc tgaatgaaac gacagattca tctggattca gaactccagg

7621 cagaagctgc ttaacagcaa aaatctggca tcttcactac attttaagat tttaggtaga

7681 actaagaggg atcagatata gaggaataag gaatgtgaga aggaaaaaga tatagtagtt

7741 tagctaaatt tttcttagag tttcttggtg gggctggcca tgaagtaact agtctgactc

7801 atttcttctg ggaaggctaa aagagacaca gatagcttct cttttacctt ggctttaagg

7861 aaaagccatt ttattaacaa aagtattaga cacgactgca taagaaattt gctgtgtgag

7921 aataaagaac aagggagtag gagggtggga cagagaaggg tgagaagttg gcttcgtgag

7981 ggccacctgt cagttgtctt tgtgccttgt gacatcaaaa ctgaaatgtt tgtattactg

8041 ttgtccatga cttttttttt ctgtgtcaga catacaaatt gaatttggtt gtaatgtttt

8101 aaacgtaata aagaattctt acctaca
```

The invention also provides for a nucleic acid encoding a PERK protein, or fragment thereof. PERK is also known as, "eukaryotic translation initiation factor 2-alpha kinase 3" ("EIF2AK3"), "PEK" and "WRS". "PERK" refers to all PERK orthologs, including, but not limited to, those found in mice and humans.

For example, the polypeptide sequence of human PERK is depicted in SEQ ID NO: 130. The nucleotide sequence of human PERK is shown in SEQ ID NO: 131. Sequence information related to PERK is accessible in public databases by GENBANK Accession numbers NP 004827.4 (protein) and NM_004836.5 (nucleic acid).

SEQ ID NO: 130 is the human wild type amino acid sequence corresponding to PERK (residues 1-1116):

```
  1 meraispgll vrallllll1 lglaartvaa grarglpapt aeaafglgaa aaptsatrvp
 61 aagavaaaev tvedaealpa aagegeprgp epddetelrp rgrslviist ldgriaaldp
121 enhgkkqwdl dvgsgslvss slskpevfgn kmiipsldga lfqwdqdres metvpftves
181 llessykfgd dvvlvggksl ttyglsaysg kvryicsalg crqwdsdeme geedilllqr
241 tqktvravgp rsgnekwnfs vghfelryip dmetragfie stfkpnente eskiisdvee
301 qeaaimdivi kvsvadwkvm afskkgghle weyqfctpia sawllkdgkv ipislfddts
361 ytsnddvled eediveaarg atensvylgm yrgglylqss vrisekfpss pkalesvtne
421 naiiplptik wkplihspsr tpvlvgsdef dkclsndkfs heeysngals ilqypydngy
481 ylpyykrern krstqitvrf ldnphynkni rkkdpvlllh wwkeivatil fciiattfiv
541 rrlfhphphr qrkesetqcq tenkydsvsg eandsswndi knsgyisryl tdfepiqclg
```

-continued

```
 601 rggfgvvfea knkvddcnya ikrirlpnre larekvmrev kalaklehpg ivryfnawle
 661 appekwgekm deiwlkdest dwplsspspm dapsvkirrm dpfatkehie iiapspqrsr
 721 sfsvgiscdq tsssesqfsp lefsgmdhed isesvdaayn lqdscltdcd vedgtmdgnd
 781 eghsfelcps easpyvrsre rtsssivfed sgcdnasske epktnrlhig nhcankltaf
 841 kptssksse atlsisspprp ttlsldltkn ttekl qpssp kvylyiqmql crkenlkdwm
 901 ngrctieere rsvclhiflq iaeaveflhs kglmhrdlkp snifftmddv vkvgdfglvt
 961 amdqdeeeqt vltpmpayar htgqvgtkly mspeqihgns yshkvdifsl glilfellyp
1021 fstqmervrt ltdvrnlkfp plftqkypce yvmvqdmlsp spmerpeain iienavfedl
1081 dfpgktvlrq rsrslsssgt khsrqsnnsh splpsn
```

SEQ ID NO: 131 is the human wild type nucleotide sequence corresponding to PERK (nucleotides 1-4665):

```
   1 ggaaagtcca ccttccccaa caaggccagc ctgggaacat ggagtggcag cggccgcagc
  61 caatgagaga gcaaacgcgc ggaaagtttg ctcaatgggc gatgtccgag ataggctgtc
 121 actcaggtgg cagcggcaga ggccgggctg agacgtggcc aggggaacac ggctggctgt
 181 ccaggccgtc ggggcggcag tagggtccct agcacgtcct tgccttcttg ggagctccaa
 241 gcggcgggag aggcaggcgt cagtggctgc gcctccatgc ctgcgcgcgg ggcgggacgc
 301 tgatggagcg cgccatcagc ccggggctgc tggtacgggc gctgctgctg ctgctgctgc
 361 tgctggggct cgcggcaagg acggtggccg cggggcgcgc ccgtggcctc ccagcgccga
 421 cggcggaggc ggcgttcggc ctcggggcgg ccgctgctcc cacctcagcg acgcgagtac
 481 cggcggcggg cgccgtggct gcggccgagg tgactgtgga ggacgctgag gcgctgccgg
 541 cagccgcggg agagcaggag cctcggggtc cggaaccaga cgatgagaca gagttgcgac
 601 cgcgcggcag gtcattagta attatcagca ctttagatgg gagaattgct gccttggatc
 661 ctgaaaatca tggtaaaaag cagtgggatt tggatgtggg atccggttcc ttggtgtcat
 721 ccagccttag caaaccagag gtatttggga ataagatgat cattccttcc ctggatggag
 781 ccctcttcca gtgggaccaa gaccgtgaaa gcatggaaac agttcctttc acagttgaat
 841 cacttcttga atcttcttat aaatttggag atgatgttgt tttggttgga ggaaaatctc
 901 tgactacata tggactcagt gcatatagtg gaaaggtgag gtatatctgt tcagctctgg
 961 gttgtcgcca atgggatagt gacgaaatgg aacaagagga agacatcctg cttctacagc
1021 gtacccaaaa aactgttaga gctgtcggac ctcgcagtgg caatgagaag tggaatttca
1081 gtgttggcca ctttgaactt cggtatattc cagacatgga aacgagagcc ggatttattg
1141 aaagcacctt taagcccaat gagaacacag aagagtctaa aattatttca gatgtggaag
1201 aacaggaagc tgccataatg gacatagtga taaaggtttc ggttgctgac tggaaagtta
1261 tggcattcag taagaaggga ggacatctgg aatgggagta ccagttttgt actccaattg
1321 catctgcctg gttacttaag gatgggaaag tcattcccat cagtcttttt gatgatacaa
1381 gttatacatc taatgatgat gttttagaag atgaagaaga cattgtagaa gctgccagag
1441 gagccacaga aaacagtgtt tacttgggaa tgtatagagg ccagctgtat ctgcagtcat
1501 cagtcagaat ttcagaaaag tttccttcaa gtcccaaggc tttggaatct gtcactaatg
1561 aaaacgcaat tattccttta ccaacaatca aatggaaacc cttaattcat tctccttcca
1621 gaactcctgt cttggtagga tctgatgaat ttgacaaatg tctcagtaat gataagtttt
1681 ctcatgaaga atatagtaat ggtgcacttt caatcttgca gtatccatat gataatggtt
```

-continued

```
1741 attatctacc atactacaag agggagagga acaaacgaag cacacagatt acagtcagat
1801 tcctcgacaa cccacattac aacaagaata tccgcaaaaa ggatcctgtt cttcttttac
1861 actggtggaa agaaatagtt gcaacgattt tgttttgtat catagcaaca acgtttattg
1921 tgcgcaggct tttccatcct catcctcaca ggcaaaggaa ggagtctgaa actcagtgtc
1981 aaactgaaaa taaatatgat tctgtaagtg gtgaagccaa tgacagtagc tggaatgaca
2041 taaaaaactc tggatatata tcacgatatc taactgattt tgagccaatt caatgcctgg
2101 gacgtggtgg ctttggagtt gtttttgaag ctaaaaacaa agtagatgac tgcaattatg
2161 ctatcaagag gatccgtctc cccaataggg aattggctcg ggaaaaggta atgcgagaag
2221 ttaaagcctt agccaagctt gaacacccgg gcattgttag atatttcaat gcctggctcg
2281 aagcaccacc agagaagtgg caagaaaaga tggatgaaat ttggctgaaa gatgaaagca
2341 cagactggcc actcagctct cctagcccaa tggatgcacc atcagttaaa atacgcagaa
2401 tggatccttt cgctacaaaa gaacatattg aaatcatagc tccttcacca caaagaagca
2461 ggtctttttc agtagggatt tcctgtgacc agacaagttc atctgagagc cagttctcac
2521 cactggaatt ctcaggaatg gaccatgagg acatcagtga gtcagtggat gcagcataca
2581 acctccagga cagttgcctt acagactgtg atgtggaaga tgggactatg gatggcaatg
2641 atgaggggca ctcctttgaa ctttgtcctt ctgaagcttc tccttatgta aggtcaaggg
2701 agagaacctc ctcttcaata gtatttgaag attctggctg tgataatgct tccagtaaag
2761 aagagccgaa aactaatcga ttgcatattg gcaaccattg tgctaataaa ctaactgctt
2821 tcaagcccac cagtagcaaa tcttcttctg aagctacatt gtctatttct cctccaagac
2881 caaccacttt aagtttagat ctcactaaaa acaccacaga aaaactccag cccagttcac
2941 caaaggtgta tctttacatt caaatgcagc tgtgcagaaa agaaaacctc aaagactgga
3001 tgaatggacg atgtaccata gaggagagag agaggagcgt gtgtctgcac atcttcctgc
3061 agatcgcaga ggcagtggag tttcttcaca gtaaaggact gatgcacagg gacctcaagc
3121 catccaacat attctttaca atggatgatg tggtcaaggt tggagacttt gggttagtga
3181 ctgcaatgga ccaggatgag gaagagcaga cggttctgac cccaatgcca gcttatgcca
3241 gacacacagg acaagtaggg accaaactgt atatgagccc agagcagatt catggaaaca
3301 gctattctca taaagtggac atcttttctt taggcctgat tctatttgaa ttgctgtatc
3361 cattcagcac tcagatggag agagtcagga ccttaactga tgtaagaaat ctcaaatttc
3421 caccattatt tactcagaaa tatccttgtg agtacgtgat ggttcaagac atgctctctc
3481 catcccccat ggaacgacct gaagctataa acatcattga aaatgctgta tttgaggact
3541 tggactttcc aggaaaaaca gtgctcagac agaggtctcg ctccttgagt tcatcgggaa
3601 caaaacattc aagacagtcc aacaactccc atagcccttt gccaagcaat tagccttaag
3661 ttgtgctagc aaccctaata ggtgatgcag ataatagcct acttcttaga atatgcctgt
3721 ccaaaattgc agacttgaaa agtttgttct tcgctcaatt tttttgtgga ctactttttt
3781 tatatcaaat ttaagctgga tttgggggca taacctaatt tgagccaact cctgagtttt
3841 gctatactta aggaaagggc tatctttgtt ctttgttagt ctcttgaaac tggctgctgg
3901 ccaagcttta tagccctcac catttgccta aggaggtagc agcaatccct aatatatata
3961 tatagtgaga actaaaatgg atatattttt ataatgcaga agaaggaaag tccccctgtg
4021 tggtaactgt attgttctag aaatatgctt tctagagata tgatgatttt gaaactgatt
4081 tctagaaaaa gctgactcca tttttgtccc tggcgggtaa attaggaatc tgcactattt
```

-continued

```
4141 tggaggacaa gtagcacaaa ctgtataacg gtttatgtcc gtagttttat agtcctattt
4201 gtagcattca atagctttat tccttagatg gttctagggt gggtttacag ctttttgtac
4261 ttttacctcc aataaaggga aaatgaagct tttatgtaa attggttgaa aggtctagtt
4321 ttgggaggaa aaaagccgta gtaagaaatg gatcatatat attacaacta acttcttcaa
4381 ctatggactt tttaagccta atgaaatctt aagtgtctta tatgtaatcc tgtaggttgg
4441 tacttccccc aaactgatta taggtaacag tttaatcatc tcacttgcta acatgttttt
4501 atttttcact gtaaatatgt ttatgtttta tttataaaaa ttctgaaatc aatccatttg
4561 ggttggtggt gtacagaaca cacttaagtg tgttaacttg tgacttcttt caagtctaaa
4621 tgatttaata aaactttttt taaattaaaa aaaaaaaaaa aaaaa
```

The invention also provides for a nucleic acid encoding a IRE1a protein, or fragment thereof. IRE1a is also known as, "endoplasmic reticulum to nucleus signaling 1" ("ERN1"), "IRE1", "IRE1P", "IRE1a", and "hIRE1p". "IRE1a" refers to all IRE1a orthologs, including, but not limited to, those found in mice and humans.

For example, the polypeptide sequence of human IRE1a is depicted in SEQ ID NO: 132. The nucleotide sequence of human IRE1a is shown in SEQ ID NO: 133. Sequence information related to IRE1 a is accessible in public databases by GENBANK Accession numbers NP 001424.3 (protein) and NM_001433.3 (nucleic acid).

SEQ ID NO: 132 is the human wild type amino acid sequence corresponding to IRE1a (residues 1-977):

```
  1 mparrlllll tlllpglgif gstvtlpe tllfvstldg slhayskrtg sikwtlkedp
 61 vlgvpthvee paflpdpndg slytlgsknn egltklpfti pelvgaspcr ssdgilymgk
121 kgdiwyvidl ltgekqqtls safadslcps tsllylgrte ytitmydtkt relrwnatyf
181 dyaaslpedd vdykmshfvs ngdglvvtvd sesgdvlwiq nyaspvvafy vwqreglrkv
241 mhinvavetl ryltfmsgev gritkwkypf pketeakskl tptlyvgkys tslyaspsmv
301 hegvavvprg stlpllegpq tdgvtigdkg ecvitpstdv kfdpglkskn klnylrnywl
361 lighhetpls astkmlerfp nnlpkhrenv ipadsekksf eevinlvdqt senapttvsr
421 dveekpahap arpeapvdsm lkdmatiils tflligwvaf iityplsmhq qqqlqhqqfq
481 kelekiqllq qqqqqlpfhp pgdtaqdgel ldtsgpyses sgtsspstsp rasnhslcsg
541 ssaskagssp sleqddgdee tsvvivgkis fcpkdvlghg aegtivyrgm fdnrdvavkr
601 ilpecfsfad revqllresd ehpnviryfc tekdrqfqyi aielcaatlq eyveqkdfah
661 lglepitllq qttsglahlh slnivhrdlk phnilismpn ahgkikamis dfglckklav
721 grhsfsrrsg vpgtegwiap emlsedcken ptytvdifsa gcvfyyvise gshpfgkslq
781 rqanillgac sldclhpekh edviarelie kmiamdpqkr psakhvlkhp ffwslekqlq
841 ffqdvsdrie kesldgpivk qlerggravv kmdwrenitv plqtdlrkfr tykggsvrdl
901 lramrnkkhh yrelpaevre tlgslpddfv cyftsrfphl lahtyramel csherlfqpy
961 yfheppepqp pvtpdal
```

SEQ ID NO: 133 is the human wild type nucleotide sequence corresponding to IRE1a (nucleotides 1-4005):

```
  1 tgcctagtca gttctgcgtc cgctgaggct cggtcaccgc ctcgctgtcg tcgcggcgcc
 61 cccgccccgt cctctgtccg taccgccccc ggagccaggg ccgagtcctc gccatgccgg
121 cccggcggct gctgctgctg ctgacgctgc tgctgcccgg cctcgggatt tttggaagta
181 ccagcacagt gacgcttcct gaaaccttgt tgtttgtgtc aacgctggat ggaagtttgc
241 atgctgtcag caagaggaca ggctcaatca aatggacttt aaaagaagat ccagtcctgc
```

-continued

```
 301 aggtcccaac acatgtggaa gagcctgcct ttctcccaga tcctaatgat ggcagcctgt
 361 atacgcttgg aagcaagaat aatgaaggcc tgacgaaact tccttttacc atcccagaat
 421 tggtgcaggc atccccatgc cgaagttcag atggaatcct ctacatgggt aaaaagcagg
 481 acatctggta tgttattgac ctcctgaccg gagagaagca gcagactttg tcatcggcct
 541 ttgcagatag tctctgccca tcaacctctc ttctgtatct tgggcgaaca gaatacacca
 601 tcaccatgta cgacaccaaa acccgagagc tccggtggaa tgccacctac tttgactatg
 661 cggcctcact gcctgaggac gacgtggact acaagatgtc ccactttgtg tccaatggtg
 721 atgggctggt ggtgactgtg gacagtgaat ctggggacgt cctgtggatc caaaactacg
 781 cctcccctgt ggtggccttt tatgtctggc agcgggaggg tctgaggaag gtgatgcaca
 841 tcaatgtcgc tgtggagacc ctgcgctatc tgaccttcat gtctggggag gtggggcgca
 901 tcacaaagtg gaagtacccg ttccccaagg agacagaggc caagagcaag ctgacgccca
 961 ctctgtatgt tgggaaatac tctaccagcc tctatgcctc tccctcaatg gtacacgagg
1021 gggttgctgt cgtgccccgc ggcagcacac ttcctttgct ggaagggccc cagactgatg
1081 gcgtcaccat tggggacaag ggggagtgtg tgatcacgcc cagcacggac gtcaagtttg
1141 atcccggact caaaagcaag aacaagctca actacttgag gaattactgg cttctgatag
1201 gacaccatga aaccccactg tctgcgtcta ccaagatgct ggagagattt cccaacaatc
1261 tacccaaaca tcgggaaaat gtgattcctg ctgattcaga gaaaaagagc tttgaggaag
1321 ttatcaacct ggttgaccag acttcagaaa acgcacctac caccgtgtct cgggatgtgg
1381 aggagaagcc cgcccatgcc cctgcccggc ccgaggcccc cgtggactcc atgcttaagg
1441 acatggctac catcatcctg agcaccttcc tgctgattgg ctgggtggcc ttcatcatca
1501 cctatcccct gagcatgcat cagcagcagc agctccagca ccagcagttc cagaaggaac
1561 tggagaagat ccagctcctg cagcagcagc agcagcagct gcccttccac cccacctggag
1621 acacggctca ggacggcgag ctcctggaca cgtctggccc gtactcagag agctcgggca
1681 ccagcagccc cagcacgtcc cccagggcct ccaaccactc gctctgctcc ggcagctctg
1741 cctccaaggc tggcagcagc ccctccctgg aacaagacga tggagatgag gaaaccagcg
1801 tggtgatagt tgggaaaatt tccttctgtc ccaaggatgt cctgggccat ggagctgagg
1861 gcacaattgt gtaccggggc atgtttgaca accgcgacgt ggccgtgaag aggatcctcc
1921 ccgagtgttt tagcttcgca gaccgtgagg tccagctgtt gcgagaatcg gatgagcacc
1981 cgaacgtgat ccgctacttc tgcacggaga aggaccggca attccagtac attgccatcg
2041 agctgtgtgc agccaccctg caagagtatg tggagcagaa ggactttgcg catctcggcc
2101 tggagcccat caccttgctg cagcagacca cctcgggcct ggcccacctc cactccctca
2161 acatcgttca cagagaccta aagccacaca acatcctcat atccatgccc aatgcacacg
2221 gcaagatcaa ggccatgatc tccgactttg gcctctgcaa gaagctggca gtgggcagac
2281 acagtttcag ccgccgatct ggggtgcctg gcacagaagg ctggatcgct ccagagatgc
2341 tgagcgaaga ctgtaaggag aaccctacct acacggtgga catcttttct gcaggctgcg
2401 tcttttacta cgtaatctct gagggcagcc acccttttgg caagtccctg cagcggcagg
2461 ccaacatcct cctgggtgcc tgcagccttg actgcttgca cccagagaag cacgaagacg
2521 tcattgcacg tgaattgata gagaagatga ttgcgatgga tcctcagaaa cgcccctcag
2581 cgaagcatgt gctcaaacac ccgttcttct ggagcctaga gaagcagctc cagttcttcc
2641 aggacgtgag cgacagaata gaaaaggaat ccctggatgg cccgatcgtg aagcagttag
2701 agagaggcgg gagagccgtg gtgaagatgg actggcggga gaacatcact gtccccctcc
```

-continued

```
2761 agacagacct gcgtaaattc aggacctata aaggtggttc tgtcagagat ctcctccgag
2821 ccatgagaaa taagaagcac cactaccggg agctgcctgc agaggtgcgg gagacgctgg
2881 ggtccctccc cgacgacttc gtgtgctact tcacatctcg cttcccccac ctcctcgcac
2941 acacctaccg ggccatggag ctgtgcagcc acgagagact cttccagccc tactacttcc
3001 acgagccccc agagccccag cccccagtga ctccagacgc cctctgagcg agggcggccc
3061 ctctgttctg gtggccccag ctgtgactga gggcctggtc accacaatta gagcttgatg
3121 cctcccggct ttgcagggag accaggcttc ccaaaccaag tgccttgagc tgcctgctct
3181 gcagcccaca gaggacagtg ctgaccccag gaagtgggag aagtggcccc tcgtgaccta
3241 cagggaactg ggaagatgct ggccccaaaa gccttacggt catgatgtct gcaaaggagg
3301 gcctcagaga cagcgcgagt agcaccccca gccatctact ggataaactt gcttcagact
3361 ttttaaattc ctgcttaatg tcagtctaca ggcctttcag gaagggagag gagggaatcg
3421 tacattttgc ttgcgtgctg ggacagctag gctgagatgc accaagtaca gccttcactg
3481 gagaccggaa ttgagaggtg ggggatgctg aggaggggga ggacggagtt cagagggtgt
3541 cgtcctgcag tgtgagattt ctcattgatc acagatgtgc ccagagtagc ccaggtcact
3601 gttaactagt gtttctgcag aggcagcagg agccatgagc atgaggtgtg gcattaggga
3661 ctggtcagct atgcatgctg gcaggtgggg ttgtgtctgc aggtctcaga aatgaagagg
3721 ctgctctgtt ctggaggcag ccgtggccca gtgccagtgg ccagaacagt ggcctttggt
3781 gggtgtgtcc cgggccatct cggggtggtg ctcaggagcg cctggggcaa gaggtaaaga
3841 gttccctggc cttcaaggag agcagcgaag acccagacag gggccagcct tcaggaccag
3901 agggaggccg ccgaatggga ccctcctggt caccaggaga aagccctggg ccagcgagta
3961 ggcagtcaaa ctccttcgtc cccaaggccg gtggaacaag aggct
```

The invention also provides for a nucleic acid encoding a ATF6 protein, or fragment thereof. ATF6 is also known as, "activating transcription factor 6" ("ATF6") and "ATF6A". "ATF6" refers to all ATF6 orthologs, including, but not limited to, those found in mice and humans.

For example, the polypeptide sequence of human ATF6 is depicted in SEQ ID NO: 134. The nucleotide sequence of human PERK is shown in SEQ ID NO: 135. Sequence information related to ATF6 is accessible in public databases by GENBANK Accession numbers NP 031374.2 (protein) and NM_007348.3 (nucleic acid).

SEQ ID NO: 134 is the human wild type amino acid sequence corresponding to ATF6 (residues 1-670):

```
  1 mgepagvagt mespfspglf hrldedwdsa lfaelgyftd tdelqleaan etyennfdnl
 61 dfdldlmpwe sdiwdinnqi ctvkdikaep qplspasssy syssprsvds ysstqhvpee
121 ldlssssqms plslygensn slssaeplke dkpvtgprnk tengltpkkk iqvnskpsiq
181 pkplllpaap ktqtnssvpa ktiiiqtvpt lmplakqqpi islqpaptkg qtvllsqptv
241 vqlqapgvlp saqpvlavag gvtqlpnhvv nvvpapsans pvngklsvtk pvlqstmrnv
301 gsdiavlrrq qrmiknresa cqsrkkkkey mlglearlka alseneqlkk engtlkrqld
361 evvsenqrlk vpspkrrvvc vmivlafiil nygpmsmleq dsrrmnpsys panqrrhllg
421 fsakeaqdts dgiiqknsyr ydhsysndka lmvlteepll yippppcqpl intteslrin
481 helrgwvhrh evertksrrm tnnqqktril qgaleqgsns qlmavqytet tssisrnsgs
541 elqvyyaspr syqdffeair rrgdtfyvvs frrdhlllpa tthnkttrpk msivlpaini
601 nenvingqdy evmmqidcqv mdtrilhiks ssvppylrdq qrnqtntffg sppaateath
661 vvstipeslq
```

SEQ ID NO: 135 is the human wild type nucleotide sequence corresponding to ATF6 (nucleotides 1-7563):

```
   1 aaaagtagtt tgtctttact aggccaccgt ctcgtcagcg ttacggagta ttttgtccgc
  61 ctgccgccgc cgtcccagat attaatcacg gagttccagg gagaaggaac ttgtgaaatg
 121 ggggagccgg ctggggttgc cggcaccatg gagtcacctt ttagcccggg actctttcac
 181 aggctggatg aagattggga ttctgctctc tttgctgaac tcggttattt cacagacact
 241 gatgagctgc aattggaagc agcaaatgag acgtatgaaa acaattttga taatcttgat
 301 tttgatttgg atttgatgcc ttgggagtca gacatttggg acatcaacaa ccaaatctgt
 361 acagttaaag atattaaggc agaacctcag ccactttctc cagcctcctc aagttattca
 421 gtctcgtctc ctcggtcagt ggactcttat tcttcaactc agcatgttcc tgaggagttg
 481 gatttgtctt ctagttctca gatgtctccc ctttccttat atggtgaaaa ctctaatagt
 541 ctctcttcag cggagccact gaaggaagat aagcctgtca ctggtcctag gaacaagact
 601 gaaaatggac tgactccaaa gaaaaaaatt caggtgaatt caaaaccttc aattcagccc
 661  aagcctttat tgcttccagc agcacccaag actcaaacaa actccagtgt tccagcaaaa
 721 accatcatta ttcagacagt accaacgctt atgccattgg caaagcagca accaattatc
 781 agtttacaac ctgcacccac taaaggccag acggttttgc tgtctcagcc tactgtggta
 841 caacttcaag cacctggagt tctgccctct gctcagccag tccttgctgt tgctgggga
 901 gtcacacagc tccctaatca cgtggtgaat gtggtaccag ccccttcagc gaatagccca
 961 gtgaatggaa aactttccgt gactaaacct gtcctacaaa gtaccatgag aaatgtcggt
1021 tcagatattg ctgtgctaag gagacagcaa cgtatgataa aaaatcgaga atccgcttgt
1081 cagtctcgca agaagaagaa agaatatatg ctagggttag aggcgagatt aaaggctgcc
1141 ctctcagaaa acgagcaact gaagaaagaa aatggaacac tgaagcggca gctggatgaa
1201 gttgtgtcag agaaccagag gcttaaagtc cctagtccaa agcgaagagt tgtctgtgtg
1261 atgatagtat tggcatttat aatactgaac tatggaccta tgagcatgtt ggaacaggat
1321 tccaggagaa tgaaccctag tgtgagccct gcaaatcaaa ggaggcacct tctaggattt
1381 tctgctaaag aggcacagga cacatcagat ggtattatcc agaaaaacag ctacagatat
1441 gatcattctg tttcaaatga caaagccctg atggtgctaa ctgaagaacc attgctttac
1501 attcctccac ctccttgtca gcccctaatt aacacaacag agtctctcag gttaaatcat
1561 gaacttcgag gatgggttca tagacatgaa gtagaaagga ccaagtcaag aagaatgaca
1621 aataatcaac agaaaacccg tattcttcag ggtgctctgg aacagggctc aaattctcag
1681 ctgatggctg ttcaatacac agaaaccact agtagtatca gcaggaactc agggagtgag
1741 ctacaagtgt attatgcttc acccagaagt tatcaagact tttttgaagc catccgcaga
1801 aggggagaca cattttatgt tgtgtcattt cgaagggatc acctgctgtt accagctacc
1861 acccataaca agaccacaag accaaaaatg tcaattgtgt taccagcaat aaacataaat
1921 gagaatgtga tcaatgggca ggactacgaa gtgatgatgc agattgactg tcaggtgatg
1981 gacaccagga tcctccatat caaaagttcg tcagttcctc cttacctccg agatcagcag
2041 aggaatcaaa ccaacacctt ctttggctcc cctcccgcag ccacagaggc aacccacgtt
2101 gtcagcacca tccctgagtc attacaatag caccctgcag ctatgctgga aaactgagcg
2161 tgggaccctg ccagactgaa gagcaggtga gcaaaatgct gctttctgcc ttggtggcag
2221 gcagagaact gtctcgtact agaattcaag gaggaaagaa gaagaaataa aagaagctgc
2281 tccatttttc atcatctacc catctatttg gaaagcactg gaattcagat gcaagagaac
```

-continued 2341 aatgtttctt cagtggcaaa tgtagccctg catcctccag tgttacctgg tgtagatttt
2401 tttttctgta cctttctaaa cctctcttcc ctctgtgatg gttttgtgtt taaacagtca
2461 tcttctttta aataatatcc acctctcctt tttgccattt cacttattga ttcataaagt
2521 gaattttatt taaagctatg ccacacatgc atgttcaaat ggtttccact gattcgattt
2581 ttcattcatt taatgcaaac ccattctgga tattgtgctt atttgagaaa acacatttca
2641 aaaccagaaa agccaaaaac actccaaaaa caagcaaaac aatttggagc tttagataaa
2701 aggaaaaact cccagttggt aaagtttatc tttacttagg atttgtggct cacacctaaa
2761 caaagggggt cagggagtgg gtacaaattt gagaaaatag aagggtaagg gaagggccag
2821 tggtggggtt tggagagagg agatagctcc attaatacac atgtttaaaa gatggaaagt
2881 tcacgcctgt aatcccagca ctttgggagg ccgaggcggg tggatcacga ggtcaggaga
2941 tcaagaccat cccggctaaa acggtgaaac cccgtctcta ctaaaaatac aaaaaattag
3001 ccgggcgtag tgacgggcgc ctgtagtccc agctacttgg gaggctgagg caggagaatg
3061 gcgtgaaccc gggaggcgga gcttgcagtg agccgagatc ccgccactgc actccagcct
3121 gggcgacaga gcgagactcc gtctcaaaaa aaaaaaaaaa aaaaaaaaaa gatggaaagt
3181 tcgatgtgac tgcagtatga gattaaagcc acaactattg tttattttgg ggactctagg
3241 ccaccaagta ttagcacaca tacttatgtt ttctctacta atctggtcca ggtcctcatg
3301 gaccacagga caaagctttc attttcattc attcttctat tgaaattata ccaaattcag
3361 ctgaggaata tggaagtaac tttagactta aacaagacaa aagttttttc actgaagaat
3421 tgacaagtat ttgctcctta aaacaacgca gattagtgaa cgtggattcc tgctgaggga
3481 gtgcatccca taatatggca ataattttca gtttctccaa cgaaaagata gtgaaggaat
3541 taaatctttt gtcctcccat ggttaaaaaa aaaaaaaaag ctgtgttcat ttttactgta
3601 ctatgcctct tttttcacca tagtagacaa ttatgtttca tttgatgaat tcatagaact
3661 ggatctcata cagcgatgtc ctctctaatg ttctaccttt cagtttctaa agtgagtctt
3721 cctccctctc ctacaaaact tttcaatttt ttgatgtaac tcatctacaa atactgtttc
3781 ttaccccagt tgacttgcct ttgtcagatt tcttcttgtt ccacactata gcaatcaatt
3841 tctcttcttc cttacaagaa agggaacgag aaattgtagc aacctctcaa ggattatatg
3901 cagctagtta gttttctgcc tgtgaaatta ggtctggctc ctaaataatt ttaaagaacc
3961 atcagcactt ctaactctct ggacaggtgc ctctttgtcc aagctagtta aatgctttcc
4021 aaggaaatca gttcaacttt tgtgagcggg gaaaagcagg gctttattgt tgtgttacct
4081 gggagtctgg agtttgaaaa gtgctaatta accttcctct ttttccacat tacaaacctt
4141 tttaagcagc gcagcactcc ccttagattt ggctatcctg ggtgattttc agacaagaac
4201 cattttctct ggggaccatt cttctgctgg gtgccaagga atataaggca aatgcccaga
4261 agaccttcag gtgactgggc agtcttatca tgggatattt cttctggccc tgccccttcc
4321 cattctgtaa tgtgaattag ccacaccaga ggctgtgacc atggctagta gacagtggca
4381 acatagtcat ccccaagatg ctaatcttct gctggaactg tcatacgtta tcatggtcaa
4441 tgtaaacctg gtttgtgtgg ggtgattata aatagagttt ccctcctctc tgtgacagaa
4501 tcacaggaga aggacccatc tcgtggcctt cttgttctta gcgcttcact tttacttcat
4561 ccctcgattc ccagcttttt ctatcatcat tttgccaact cctcagatgc aagactttgg
4621 ttatgtcata ctcaccaacg ttagtccctc tcttccaggt gaaaaggtgg gtagcggttg
4681 ggagggagtc tccactgaag agcaggaagg tggtagcagg gccggcagct ctgccacaga
4741 gctaggggtg cctgtaaggt gccgcctaga gcagcctggg agctttgcct tcttttgtct -continued 4801 ctcactagcc cttctactct ttgtcattgc ctgttcttga gtggatcttt gaaatgaggg
4861 gacaggattc tcctaagggt agagtttcag gaaatgagtg aaaggcaatt gacaaatgca
4921 aagaagtagt cactttttaa attgctggca aagctataat taatccctag gcacaattgt
4981 agtttttatt ttaatgtttg tatgcacaag gccctttagg aaatgagaag ttgccatgcc
5041 agattaattt tttttttttt ttttggtggg attgcctttt gggggttgca gccagaaatt
5101 gtgggtaatg tgtgtatttt tttatttatt aaattttaaa caggattgtg caagcttatg
5161 agacaattag ataaactcat ggaggaggca ggtcctcctg ttattagatg attttgtgct
5221 cttggggctg acaataatac actcttggga agtgatggta gagactgatg ggaatagtct
5281 ttctgcctgg ttgcaagtcc caaattttta agggttaatg gaagtaagtg gatgtttcct
5341 catgttaact actgaatcag atgttaggag cttgtccctt tggggttgac ttatgcccag
5401 cagtacaggg acacagcttc attagagtgt tagtgtaaac taactccaaa gttaggagtt
5461 aatgtgaaag gatcatcctt gaaacaaatc tgctgtttgc catgcttgta gtacagaaac
5521 ttcacatgga gttttgggtg ggatttgtgt tttcacaagt aaaaaatccc tcacgattat
5581 aaaactcaga gcatcatcta attttttttt ttaatgacta caagttccag cacaaaactg
5641 gcatttcttt gccatttctt gccagtaaga agttgacacg gaggtatttg aaagcaatgt
5701 tatgtgagtc attcttaagt gttccaagta agtttagaaa cagaaaagga acttgggatt
5761 caaattgatt tttcaaatca tttttaaaga gacatcatcc tgactaaatc ttagcctgaa
5821 ccttcctccc ctgtgtgtat tccccggtag tcaccgcagc gagatgctgg tgagactgcc
5881 gtggtggcat ttagcatcgt taaaactgga aaactctcaa gctctttgcc actttcctac
5941 tatttttga ttcttgccat tttaccaagc ttaggttgtg aaacttgaca gaaatgtatt
6001 acaggaaaaa cttataattg tatttgactt tctaacacat tgcaaagttt caaagtgact
6061 ttcactttca acaacatatt agaagtaacc actttttgctt tcacagcctg aagagttaga
6121 gcctgatctg atgccccctt tcactctgaa gtcatgggaa attttccagc catgaaagcc
6181 ctctttccac tgcatactga tgggctgact cagcttcctt cagccgactg agatcttttc
6241 atactattgg ctatttcata ccaattaacc tcttaaataa gattgtgaat tgccaaaatt
6301 gatagacact tattaccacc tgtggactcc atattcctta ccacaaatgt tattttcatc
6361 agtcctgagt cattttaact tacagaaatt aggattgttg ctgctaatat gaataccaat
6421 tataactttt agaaacaaga ataaagccta aaagagaatg aaatataaga aatgttcgtt
6481 cccaccccta ataacatttg gaagtgaata ttcccatttt cttccaccca cagggattgg
6541 gattgatttt taatttccta ggaaacaata ctagactacc caaaaagatg ttgccagaat
6601 ccaaaaggaa ctatgctcgt aaaagaaatg cagttttctc ctacctaaaa aaaagaaagt
6661 aaagtgtgtt ctgttcttat ctttttaatg actaagcttt aaacagttta ttttgggtaa
6721 gactagaact ttcggccatt tgttctaata tgtgtgttat tagatgcaat agaatttatg
6781 aaaagaagaa tgacaaaggt atctgattag aaaatttgat cttacgcatg aatccatgtc
6841 atggccagcc actgtcacat agtgggtgcc attctcaaca tattggtttg ctaactttaa
6901 gcattaggga tttagcacac taaaatactt ttaattatat taggtttggt aactaaggag
6961 taaataaatc ataatttatc atttgccaag gccaacaaac aacactattg tgctgtttgc
7021 tctcaatgaa gttgaataaa ccaggaggct tggcatatcc cctttatgtt aatcccagct
7081 agagattagt aggttgactt tcacagcaat tgtatattga tccattttaa ctcatccttg
7141 ccataatttc caggccagtc accaggacag aggagatgat ggggaaacag agctttagat -continued

```
7201 gaaaactact atgcactact agccttagag gcactggttt cctgttacca ctttggcaag
7261 tatggatggt ctaagtccag tagggcttca tccatggagc cattagaact gagggggggag
7321 tgttagagat gccatttcac caggatcttt ttgctcaggt tgtacccatg ccaattgaag
7381 aacgtgttaa agatgaggag gagagatgta ccattctctc ccttaataat gatgttggtt
7441 tgcaaaacct aaagaaataa taacaacaga ctatttcata ctttcaagca agtctttata
7501 ctacctgtta tttctctaaa attcaaataa agaattttta aacttaaaaa aaaaaaaaaa
7561 aaa
```

The invention also provides for a nucleic acid encoding a XBP1 protein, or fragment thereof. XBP1 is also known as, "X-box binding protein 1" ("XBP1"), "XBP2", "TREB5" and "XBP-1". "XBP1" refers to all XBP1 orthologs, including, but not limited to, those found in mice and humans.

For example, the polypeptide sequence of human XBP1 is depicted in SEQ ID NO: 136. The nucleotide sequence of human XBP1 is shown in SEQ ID NO: 137. Sequence information related to XBP 1 isoform XBP 1 (U) is accessible in public databases by GENBANK Accession numbers NP 005071.2 (protein) and NM_005080.3 (nucleic acid).

SEQ ID NO: 136 is the human wild type amino acid sequence corresponding to XBP1 isoform XBP1(U) (residues 1-261):

```
  1 mvvvaaapnp adgtpkvlll sgqpasaaga pagqalplmv paqrgaspea asgglpqark
 61 rqrlthlspe ekalrrklkn rvaaqtardr kkarmseleq qvvdleeenq klllenqllr
121 ekthglvven qelrqrlgmd alvaeeeaea kgnevrpvag saesaalrlr aplqqvqaql
181 splqnispwi lavltlqiqs liscwafwtt wtqscssnal pqslpawrss qrstqkdpvp
241 yqppflcqwg rhqpswkplm n
```

SEQ ID NO: 137 is the human wild type nucleotide sequence corresponding to XBP1 isoform XBP1(U) (nucleotides 1-1820):

```
   1 ggcgctgggc ggctgcggcg cgcggtgcgc ggtgcgtagt ctggagctat ggtggtggtg
  61 gcagccgcgc cgaacccggc cgacgggacc cctaaagttc tgcttctgtc ggggcagccc
 121 gcctccgccg ccggagcccc ggccggccag gccctgccgc tcatggtgcc agcccagaga
 181 ggggccagcc cggaggcagc gagcgggggg ctgccccagg cgcgcaagcg acagcgcctc
 241 acgcacctga gccccgagga gaaggcgctg aggaggaaac tgaaaaacag agtagcagct
 301 cagactgcca gagatcgaaa gaaggctcga atgagtgagc tggaacagca agtggtagat
 361 ttagaagaag agaaccaaaa acttttgcta gaaaatcagc ttttacgaga gaaaactcat
 421 ggccttgtag ttgagaacca ggagttaaga cagcgcttgg ggatggatgc cctggttgct
 481 gaagaggagg cggaagccaa ggggaatgaa gtgaggccag tggccgggtc tgctgagtcc
 541 gcagcactca gactacgtgc acctctgcag caggtgcagg cccagttgtc acccctccag
 601 aacatctccc catggattct ggcggtattg actcttcaga ttcagagtct gatatcctgt
 661 tgggcattct ggacaacttg gacccagtca tgttcttcaa atgcccttcc ccagagcctg
 721 ccagcctgga ggagctccca gaggtctacc cagaaggacc cagttcctta ccagcctccc
 781 tttctctgtc agtggggacg tcatcagcca agctggaagc cattaatgaa ctaattcgtt
 841 ttgaccacat atataccaag cccctagtct tagagatacc ctctgagaca gagagccaag
 901 ctaatgtggt agtgaaaatc gaggaagcac ctctcagccc ctcagagaat gatcaccctg
 961 aattcattgt ctcagtgaag gaagaacctg tagaagatga cctcgttccg gagctgggta
1021 tctcaaatct gctttcatcc agccactgcc caaagccatc ttcctgccta ctggatgctt
1081 acagtgactg tggatacggg ggttcccttt ccccattcag tgacatgtcc tctctgcttg
1141 gtgtaaacca ttcttgggag gacacttttg ccaatgaact ctttccccag ctgattagtg
```

-continued

```
1201 tctaaggaat gatccaatac tgttgccctt ttccttgact attacactgc ctggaggata
1261 gcagagaagc ctgtctgtac ttcattcaaa aagccaaaat agagagtata cagtcctaga
1321 gaattcctct atttgttcag atctcataga tgacccccag gtattgtctt ttgacatcca
1381 gcagtccaag gtattgagac atattactgg aagtaagaaa tattactata attgagaact
1441 acagctttta agattgtact tttatcttaa aagggtggta gttttcccta aaatacttat
1501 tatgtaaggg tcattagaca aatgtcttga agtagacatg gaatttatga atggttcttt
1561 atcatttctc ttcccccttt ttggcatcct ggcttgcctc cagttttagg tcctttagtt
1621 tgcttctgta agcaacggga acacctgctg agggggctct ttccctcatg tatacttcaa
1681 gtaagatcaa gaatcttttg tgaaattata gaaatttact atgtaaatgc ttgatggaat
1741 tttttcctgc tagtgtagct tctgaaaggt gctttctcca tttatttaaa actacccatg
1801 caattaaaag gtacaatgca
```

Sequence information related to XBP1 isoform XBP1(S) (also known as "spliced XBP 1" and "sXBP 1") is accessible in public databases by GENBANK Accession numbers NP 001073007.1 (protein) and NM_001079539.1 (nucleic acid).

SEQ ID NO: 138 is the human wild type amino acid sequence corresponding to XBP1 isoform XBP1(S) (residues 1-376):

```
  1mvvvaaapnp adgtpkvlll sgqpasaaga pagqalplmv paqrgaspea asgglpqark
 61rqrlthlspe ekalrrklkn rvaaqtardr kkarmseleq qvvdleeenq klllenqllr
121ekthglvven qelrqrlgmd alvaeeeaea kgnevrpvag saesaagagp vvtppehlpm
181dsggidssds esdillgild nldpvmffkc pspepaslee lpevypegps slpaslslsv
241gtssakleai nelirfdhiy tkplvleips etesqanvvv kieeaplsps endhpefivs
301vkeepveddl vpelgisnll ssshcpkpss clldaysdcg yggslspfsd mssllgvnhs
361wedtfanelf pqlisv
```

SEQ ID NO: 139 is the human wild type nucleotide sequence corresponding to XBP1 isoform XBP1(S) (nucleotides 1-1810):

```
  1 ggcgctgggc ggctgcggcg cgcggtgcgc ggtgcgtagt ctggagctat ggtggtggtg
 61 gcagccgcgc cgaacccggc cgacgggacc cctaaagttc tgcttctgtc ggggcagccc
121 gcctccgccg ccggagcccc ggccggccag gccctgccgc tcatggtgcc agcccagaga
181 ggggccagcc cggaggcagc gagcgggggg ctgccccagg cgcgcaagcg acagcgcctc
241 acgcacctga gccccgagga gaaggcgctg aggaggaaac tgaaaaacag agtagcagct
301 cagactgcca gagatcgaaa gaaggctcga atgagtgagc tggaacagca agtggtagat
361 ttagaagaag agaaccaaaa acttttgcta gaaaatcagc ttttacgaga gaaaactcat
421 ggccttgtag ttgagaacca ggagttaaga cagcgcttgg ggatggatgc cctggttgct
481 gaagaggagg cggaagccaa ggggaatgaa gtgaggccag tggccgggtc tgctgagtcc
541 gcagcaggtg caggcccagt tgtcacccct ccagaacatc tccccatgga ttctggcggt
601 attgactctt cagattcaga gtctgatatc ctgttgggca ttctggacaa cttggaccca
661 gtcatgttct tcaaatgccc ttccccagag cctgccagcc tggaggagct cccagaggtc
721 tacccagaag gacccagttc cttaccagcc tccctttctc tgtcagtggg gacgtcatca
```

-continued

```
781 gccaagctgg aagccattaa tgaactaatt cgttttgacc acatatatac caagcccccta
841 gtcttagaga taccctctga gacagagagc caagctaatg tggtagtgaa aatcgaggaa
901 gcacctctca gcccctcaga gaatgatcac cctgaattca ttgtctcagt gaaggaagaa
961 cctgtagaag atgacctcgt tccggagctg ggtatctcaa atctgctttc atccagccac
1021 tgcccaaagc catcttcctg cctactggat gcttacagtg actgtggata cgggggttcc
1081 ctttccccat tcagtgacat gtcctctctg cttggtgtaa accattcttg ggaggacact
1141 tttgccaatg aactctttcc ccagctgatt agtgtctaag gaatgatcca atactgttgc
1201 ccttttcctt gactattaca ctgcctggag gatagcagag aagcctgtct gtacttcatt
1261 caaaaagcca aaatagagag tatacagtcc tagagaattc ctctatttgt tcagatctca
1321 tagatgaccc ccaggtattg tcttttgaca tccagcagtc caaggtattg agacatatta
1381 ctggaagtaa gaaatattac tataattgag aactacagct tttaagattg tacttttatc
1441 ttaaaagggt ggtagttttc cctaaaatac ttattatgta agggtcatta gacaaatgtc
1501 ttgaagtaga catggaattt atgaatggtt ctttatcatt tctcttcccc ctttttggca
1561 tcctggcttg cctccagttt taggtccttt agtttgcttc tgtaagcaac gggaacacct
1621 gctgaggggg ctctttccct catgtatact tcaagtaaga tcaagaatct tttgtgaaat
1681 tatagaaatt tactatgtaa atgcttgatg gaatttttc ctgctagtgt agcttctgaa
1741 aggtgctttc tccatttatt taaaactacc catgcaatta aaaggtacaa tgcaaaaaaa
1801 aaaaaaaaaa
```

A ILDR2, PERK, IRE1a, ATF6 or XBP1 molecule can also encompass ortholog genes, which are genes conserved among different biological species such as humans, dogs, cats, mice, and rats, that encode proteins (for example, homologs (including splice variants), mutants, and derivatives) having biologically equivalent functions as the human-derived protein. Orthologs of a ILDR2, PERK, IRE1a, ATF6 or XBP1 protein include any mammalian ortholog inclusive of the ortholog in humans and other primates, experimental mammals (such as mice, rats, hamsters and guinea pigs), mammals of commercial significance (such as horses, cows, camels, pigs and sheep), and also companion mammals (such as domestic animals, e.g., rabbits, ferrets, dogs, and cats). A ILDR2, PERK, IRE1a, ATF6 or XBP1 molecule can comprise a protein encoded by a nucleic acid sequence homologous to the human nucleic acid, wherein the nucleic acid is found in a different species and wherein that homolog encodes a protein similar to a ILDR2, PERK, IRE1a, ATF6 or XBP1 protein.

The invention utilizes conventional molecular biology, microbiology, and recombinant DNA techniques available to one of ordinary skill in the art. Such techniques are well known to the skilled worker and are explained fully in the literature. See, e.g., Maniatis, Fritsch & Sambrook, "DNA Cloning: A Practical Approach," Volumes I and II (D. N. Glover, ed., 1985); "Oligonucleotide Synthesis" (M. J. Gait, ed., 1984); "Nucleic Acid Hybridization" (B. D. Hames & S. J. Higgins, eds., 1985); "Transcription and Translation" (B. D. Hames & S. J. Higgins, eds., 1984); "Animal Cell Culture" (R. I. Freshney, ed., 1986); "Immobilized Cells and Enzymes" (IRL Press, 1986): B. Perbal, "A Practical Guide to Molecular Cloning" (1984), and Sambrook, et al., "Molecular Cloning: a Laboratory Manual" (2001).

One skilled in the art can obtain ILDR2, PERK, IRE1a, ATF6 and XBP1 molecule in several ways, which include, but are not limited to, isolating the protein via biochemical means or expressing a nucleotide sequence encoding the protein of interest by genetic engineering methods.

The invention provides for ILDR2, PERK, IRE1a, ATF6 and XBP1 molecules that are encoded by nucleotide sequences. The ILDR2, PERK, IRE1a, ATF6 and XBP1 molecules can be a polypeptide encoded by a nucleic acid (including genomic DNA, complementary DNA (cDNA), synthetic DNA, as well as any form of corresponding RNA). For example, a ILDR2, PERK, IRE1a, ATF6 and XBP1 molecule can be encoded by a recombinant nucleic acid encoding a human ILDR2, PERK, IRE1a, ATF6 and XBP1 protein, or fragment thereof. The ILDR2, PERK, IRE1a, ATF6 and XBP1 molecules of the invention can be obtained from various sources and can be produced according to various techniques known in the art. For example, a nucleic acid that encodes a ILDR2, PERK, IRE1a, ATF6 and XBP1 molecule can be obtained by screening DNA libraries, or by amplification from a natural source. The ILDR2, PERK, IRE1a, ATF6 and XBP1 molecules of the invention can be produced via recombinant DNA technology and such recombinant nucleic acids can be prepared by conventional techniques, including chemical synthesis, genetic engineering, enzymatic techniques, or a combination thereof. A ILDR2, PERK, IRE1a, ATF6 and XBP1 molecule of this invention can also encompasses variants of the human ILDR2, PERK, IRE1a, ATF6 and XBP1 proteins. The variants can comprise naturally-occurring variants due to allelic variations between individuals (e.g., polymorphisms), mutated alleles, or alternative splicing forms.

In one embodiment, a fragment of a nucleic acid sequence that comprises a ILDR2, PERK, IRE1a, ATF6 and XBP1 molecule can encompass any portion of at least about 8 consecutive nucleotides of SEQ ID NO: 129, 131, 133, 135, 137, or 139. In one embodiment, the fragment can comprise at least about 10 nucleotides, at least about 15 nucleotides, at least about 20 nucleotides, or at least about 30 nucleotides of SEQ ID NO: 129, 131, 133, 135, 137, or 139. Fragments include all possible nucleotide lengths between about 8 and about 100 nucleotides, for example, lengths between about 15 and about 100 nucleotides, or between about 20 and about 100 nucleotides.

A ILDR2, PERK, IRE1a, ATF6 and XBP1 molecule, can be a fragment of a ILDR2, PERK, IRE1a, ATF6 and XBP1 protein. For example, the ILDR2, PERK, IRE1a, ATF6 and XBP1 protein fragment can encompass any portion of at least about 8 consecutive amino acids of SEQ ID NO: 22, 130, 132, 134, 136, or 138. The fragment can comprise at least about 10 consecutive amino acids, at least about 20 consecutive amino acids, at least about 30 consecutive amino acids, at least about 40 consecutive amino acids, a least about 50 consecutive amino acids, at least about 60 consecutive amino acids, at least about 70 consecutive amino acids, at least about 80 consecutive amino acids, at least about 90 consecutive amino acids, at least about 100 consecutive amino acids, at least about 110 consecutive amino acids, or at least about 120 consecutive amino acids of SEQ ID NOS: 22, 130, 132, 134, 136, or 138. Fragments include all possible amino acid lengths between about 8 and 80 about amino acids, for example, lengths between about 10 and about 80 amino acids, between about 15 and about 80 amino acids, between about 20 and about 80 amino acids, between about 35 and about 80 amino acids, between about 40 and about 80 amino acids, between about 50 and about 80 amino acids, or between about 70 and about 80 amino acids.

Metabolic Disease

In one embodiment, the invention provides a method of treating a metabolic disease. In one embodiment, the metabolic disease is a fatty liver disease. In another embodiment, the metabolic disease is dyslipidemia. In another embodiment, the metabolic disease is metabolic syndrome. In another embodiment, the metabolic disease is a cardiovascular disease. In another embodiment, the metabolic disease is obesity. In another embodiment, the metabolic disease is a leptin disorder.

Metabolic syndrome is a name for a group of risk factors the occur together and increase the risk for coronary artery disease, stroke and type II diabetes. Risk factors for metabolic syndrome include, but are not limited to, extra weight around the midsection and upper parts of the body ("central obesity"), insulin resistance, aging, hormone changes, a genetic predisposition, lack of exercise, excess blood clotting, increased levels of inflammatory markers. A subject can be diagnosed with metabolic syndrome if they are diagnosed with three or more of the following conditions, including, but not limited to, blood pressure equal or higher than 130/85 mm/Hg, fasting blood sugar (glucose) equal to or higher than 100 mg/dL, large waist circumference of 40 inches or more for men and 35 inches or more for women, low HDL cholesterol of under 40 mg/dL for men and under 50 mg/dL for women, and triglycerides equal to or higher than 150 mg/dL.

Fatty liver disease involves large vacuoles of fat accumulation in liver cells. Fatty liver disease can be diagnosed by a variety of tests, including but not limited to liver function tests, liver biochemistry tests, serum alanine transaminase levels, serum aspartate transaminase levels, imaging studies, and histology.

In one embodiment, the fatty liver disease is hepatic steatosis. In another embodiment, the fatty liver disease is non-alcoholic steatohepatitis. In another embodiment, the fatty liver disease is non-alcoholic fatty liver disease. In another embodiment, the fatty liver disease is elevated liver cholesterol levels. In another embodiment, the fatty liver disease is elevated liver triglyceride levels. In another embodiment, the fatty liver disease is elevated liver fatty acid levels. In another embodiment, the fatty liver disease is elevated liver LDL-cholesterol levels. In another embodiment, the fatty liver disease is elevated liver VLDL cholesterol levels. In another embodiment, the fatty liver disease is elevated liver non-HDL cholesterol levels.

Dyslipidemia involves an abnormal amount of lipids in the blood. In one embodiment, the dyslipidemia is hyperlipidemia. In another embodiment, the dyslipidemia is mixed dyslipidemia. In another embodiment, the dyslipidemia is hypercholesterolemia. In another embodiment, the dyslipidemia is polygenic hypercholesterolemia. In another embodiment, the dyslipidemia is hypertriglyceridemia. In another embodiment, the dyslipidemia is hyperfattyacidemia. In another embodiment, the dyslipidemia is elevated ApoB. In another embodiment, the dyslipidemia is elevated cholesterol. In another embodiment, the dyslipidemia is elevated LDL-cholesterol. In another embodiment, the dyslipidemia is elevated VLDL-cholesterol. In another embodiment, the dyslipidemia is elevated non-HDL cholesterol.

In one embodiment, the cardiovascular disease is coronary heart disease. In another embodiment, the cardiovascular disease is acute coronary syndrome. In another embodiment, the cardiovascular disease is early onset coronary heart disease. In another embodiment, the cardiovascular disease is atherosclerosis.

In one embodiment, the leptin disorder is hyperleptinemia. In another embodiment, the leptin disorder is tissue leptin resistance.

In one embodiment, the treatment improves cardiovascular outcome. In another embodiment, the treatment results in slowed progression and/or amelioration of the metabolic disease. In one embodiment, in addition to a metabolic disease, the subject has type II diabetes or insulin resistance.

In one aspect the invention provides a method of decreasing lipid levels in a subject, the method comprising administering to the subject a therapeutically effective amount of an agent which increases expression of Ildr2 mRNA or ILDR2 protein. In one embodiment, the lipid level is a cholesterol level. In another embodiment, the lipid level is a triglyceride level. In another embodiment, the lipid level is a ApoB level. In another embodiment, the lipid level is a LDL-cholesterol level. In another embodiment, the lipid level is a VLDL-cholesterol level. In another embodiment, the lipid level is a small LDL-particle level. In another embodiment, the lipid level is a small VLDL-particle level. In another embodiment, the lipid level is a non-HDL-cholesterol level. In another embodiment, the lipid level is a phospholipid level. In another embodiment, the lipid level is a or fatty acid level.

In one embodiment, the lipid level is the concentration in blood plasma. In another embodiment, the lipid level is the concentration in liver. In one embodiment the lipid level is decreased relative to a lipid level in the subject before administrating the therapeutically effective amount of an agent which increases expression of Ildr2 mRNA or ILDR2 protein. Methods of measuring lipid levels in the blood and liver are known to one of skill in the art.

In one embodiment, the expression of Ildr2 mRNA or ILDR2 protein is increased in liver tissue. In another embodiment, the expression of Ildr2 mRNA or ILDR2 protein is increased in hepatocytes.

In one aspect, the invention provides a method of increasing expression of Ildr2 mRNA or ILDR2 protein in a hepatocyte, the method comprising contacting the cell with an agent which increases expression of the Ildr2 mRNA or ILDR2 protein.

In one aspect, the invention provides an agent which increases expression of the Ildr2 mRNA or ILDR2 protein. In one embodiment, the agent is a nucleic acid which comprises a nucleic acid sequence encoding a ILDR2 protein, a ILDR2 polypeptide, a ILDR2 isoform, or a ILDR2 functional fragment. In another embodiment, the agent is an ILDR2 protein, a ILDR2 polypeptide, a ILDR2 isoform, or a ILDR2 functional fragment. In another embodiment, the agent is a peptide having SEQ ID NO: 2-9.

In one embodiment, the expression of ILDR2 protein in a subject is measured using an antibody. In another embodiment, the antibody specifically binds to a peptide having SEQ ID NOs: 2-9, or an ILDR2 protein, a ILDR2 polypeptide, a ILDR2 isoform, or any fragment thereof In one embodiment, the subject has a reduced level of expression of Ildr2 mRNA or ILDR2 protein compared to the level of expression of Ildr2 mRNA or ILDR2 protein in a subject without a metabolic disease. In another embodiment, the level of expression is determined before administrating to the subject the therapeutically effective amount of an agent which increases expression of Ildr2 mRNA or ILDR2 protein. In one embodiment, the expression of ILDR2 protein in a subject is measured using an antibody. In another embodiment, the antibody specifically binds to a peptide having SEQ ID NOs: 2-9, or an ILDR2 protein, a ILDR2 polypeptide, a ILDR2 isoform, or any fragment thereof. Other methods of measuring the level of expression of Ildr2 mRNA or ILDR2 protein in a subject are known to one of skill in the art.

The invention provides methods to modify and measure expression of Ildr2 mRNA or ILDR2 protein in a subject. In one embodiment, the subject is a human or a non-human animal. Non-limiting examples of non-human animals include primates (such as monkeys), rodents, (such as mice, rats and rabbits), ovine species (such as sheep and goats), bovine species (such as cows), porcine species, equine species, feline species and canine species. In a particular embodiment, the subject is a human. The method can comprise detecting in a sample from the subject the expression of Ildr2 mRNA or ILDR2 protein. The expression of Ildr2 mRNA or ILDR2 protein in the sample can be measured through amplification, gene expression analysis, or a combination thereof.

In another embodiment, the method can comprise detecting the expression of Ildr2 mRNA or ILDR2 protein. RNA expression includes the presence of an RNA sequence, the presence of an RNA splicing or processing, or the presence of a quantity of RNA. These can be detected by various techniques known in the art, including by sequencing all or part of the Ildr2 RNA, or by selective hybridization or selective amplification of all or part of the RNA. In a further embodiment, the method can comprise detecting the presence of a Ildr2 polypeptide expression. Polypeptide expression includes the presence of a Ildr2 polypeptide sequence, or the presence of an decreased quantity Ildr2 polypeptide as compared to a sample from a subject without a metabolic disease. These can be detected by various techniques known in the art, including by sequencing and/or binding to specific ligands (such as antibodies).

Various techniques known in the art can be used to detect or quantify DNA expression, RNA expression, or nucleic acid sequences, which include, but are not limited to, hybridization, sequencing, amplification, and/or binding to specific ligands (such as antibodies). Other suitable methods include allele-specific oligonucleotide (ASO), oligonucleotide ligation, allele-specific amplification, Southern blot (for DNAs), Northern blot (for RNAs), single-stranded conformation analysis (SSCA), PFGE, fluorescent in situ hybridization (FISH), gel migration, clamped denaturing gel electrophoresis, denaturing HLPC, melting curve analysis, heteroduplex analysis, RNase protection, chemical or enzymatic mismatch cleavage, ELISA, radio-immunoassays (RIA) and immuno-enzymatic assays (IEMA). Some other approaches are based on specific hybridization between nucleic acids from the subject and a probe specific for wild type gene or RNA. The probe can be in suspension or immobilized on a substrate. The probe can be labeled to facilitate detection of hybrids. Some of these approaches are suited for assessing a polypeptide sequence or expression level, such as Northern blot, ELISA and RIA. These latter require the use of a ligand-specific for the polypeptide, for example, the use of a specific antibody.

Sequencing.

Sequencing can be carried out using techniques well known in the art, using automatic sequencers. The sequencing can be performed on the complete gene or on specific domains thereof, such as those known or suspected to carry deleterious mutations or other alterations.

Amplification.

Amplification is based on the formation of specific hybrids between complementary nucleic acid sequences that serve to initiate nucleic acid reproduction. Amplification can be performed according to various techniques known in the art, such as by polymerase chain reaction (PCR), ligase chain reaction (LCR), strand displacement amplification (SDA) and nucleic acid sequence based amplification (NASBA). These techniques can be performed using commercially available reagents and protocols. Useful techniques in the art encompass real-time PCR, allele-specific PCR, or PCR-SSCP. Amplification usually requires the use of specific nucleic acid primers, to initiate the reaction. For example, nucleic acid primers useful for amplifying sequences from the gene or locus of Ildr2 are able to specifically hybridize with a portion of the gene locus that flanks a target region of the locus, wherein the target region is present in subjects having or are at risk of developing prostate cancer.

The invention provides for a nucleic acid primer, wherein the primer can be complementary to and hybridize specifically to a portion of a coding sequence (e.g., gene or RNA) of Ildr2 that is present in subjects having or at risk of developing prostate cancer. Primers of the invention are specific for sequences in a gene or RNA of Ildr2. By using such primers, the detection of an amplification product indicates the presence of the Ildr2 gene or the absence of such. Examples of primers of this invention can be single-stranded nucleic acid molecules of about 5 to 60 nucleotides in length, or about 8 to about 25 nucleotides in length. The sequence can be derived directly from the sequence of Ildr2. Perfect complementarity is useful, to ensure high specificity. However, certain mismatch can be tolerated. For example, a nucleic acid primer or a pair of nucleic acid primers as described herein can be used in a method for detecting the presence of or a predisposition to prostate cancer in a subject.

Amplification methods include, e.g., polymerase chain reaction, PCR (PCR PROTOCOLS, A GUIDE TO METHODS AND APPLICATIONS, ed. Innis, Academic Press, N.Y., 1990 and PCR STRATEGIES, 1995, ed. Innis, Academic Press, Inc., N.Y., ligase chain reaction (LCR) (see, e.g., Wu, Genomics 4:560, 1989; Landegren, Science 241: 1077, 1988; Barringer, Gene 89:117, 1990); transcription amplification (see, e.g., Kwoh, Proc. Natl. Acad. Sci. USA 86:1173, 1989); and, self-sustained sequence replication (see, e.g., Guatelli, Proc. Natl. Acad. Sci. USA 87:1874, 1990); Q Beta replicase amplification (see, e.g., Smith, J. Clin. Microbiol. 35:1477-1491, 1997), automated Q-beta replicase amplification assay (see, e.g., Burg, Mol. Cell. Probes 10:257-271, 1996) and other RNA polymerase mediated techniques (e.g., NASBA, Cangene, Mississauga, Ontario); see also Berger, Methods Enzymol. 152:307-316, 1987; Sambrook; Ausubel; U.S. Pat. Nos. 4,683,195 and 4,683,202; Sooknanan, Biotechnology 13:563-564, 1995. All the references stated above are incorporated by reference in their entireties.

Hybridization.

Hybridization detection methods are based on the formation of specific hybrids between complementary nucleic acid sequences that serve to detect nucleic acid sequences. A detection technique involves the use of a nucleic acid probe specific for wild type gene or RNA. The probe can be in suspension or immobilized on a substrate or support (for example, as in nucleic acid array or chips technologies). For example, a sample from the subject can be contacted with a nucleic acid probe specific for wild type Ildr2. According to the invention, a probe can be a polynucleotide sequence which is complementary to and specifically hybridizes with a, or a target portion of a, Ildr2 gene or RNA. Useful probes are those that are complementary to the Ildr2 gene, RNA, or target portion thereof. Probes can comprise single-stranded nucleic acids of between 8 to 1000 nucleotides in length, for instance between 10 and 800, between 15 and 700, or between 20 and 500. Longer probes can be used as well. A useful probe of the invention is a single stranded nucleic acid molecule of between 8 to 500 nucleotides in length, which can specifically hybridize to a region of a gene or RNA.

The sequence of the probes can be derived from the sequences of Ildr2 genes. Nucleotide substitutions can be performed, as well as chemical modifications of the probe. Such chemical modifications can be accomplished to increase the stability of hybrids (e.g., intercalating groups) or to label the probe. Some examples of labels include, without limitation, radioactivity, fluorescence, luminescence, and enzymatic labeling.

A guide to nucleic acid hybridization is found in e.g., Sambrook, ed., Molecular Cloning: A Laboratory Manual ($3^{rd}$ Ed.), Vols. 1-3, Cold Spring Harbor Laboratory, 2001; CURRENT PROTOCOLS IN MOLECULAR BIOLOGY, Ausubel, ed. John Wiley & Sons, Inc., New York, 1997; LABORATORY TECHNIQUES IN BIOCHEMISTRY AND MOLECULAR BIOLOGY: HYBRIDIZATION WITH NUCLEIC ACID PROBES, PART I. Theory and Nucleic Acid Preparation, Tijssen, ed. Elsevier, N.Y., 1993.

Specific Ligand Binding.

As indicated herein, the presence of a Ildr2 gene locus or Ildr2 expression can also be detected. Different types of ligands can be used, such as specific antibodies. In one embodiment, the sample is contacted with an antibody specific for a Ildr2 and the formation of an immune complex is subsequently determined. Various methods for detecting an immune complex can be used, such as ELISA, radioimmunoassays (RIA) and immuno-enzymatic assays (IEMA).

These methods utilize a sample from a subject in order to assess the status of the Ildr2 gene locus. The sample can be any biological sample derived from a subject, which contains nucleic acids or polypeptides. Examples of such samples include, but are not limited to, fluids, tissues, cell samples, organs, or tissue biopsies. The sample can be collected according to conventional techniques and used directly for diagnosis or stored. The sample can be treated prior to performing the method, in order to render or improve availability of nucleic acids or polypeptides for testing. Treatments include, for instance, lysis (e.g., mechanical, physical, or chemical), centrifugation. Also, the nucleic acids and/or polypeptides can be pre-purified or enriched by conventional techniques, and/or reduced in complexity. Nucleic acids and polypeptides can also be treated with enzymes or other chemical or physical treatments to produce fragments thereof. In one embodiment, the sample is contacted with reagents, such as probes, primers, or ligands, in order to assess the presence of Ildr2. Contacting can be performed in any suitable device, such as a plate, tube, well, or glass. In specific embodiments, the contacting is performed on a substrate coated with the reagent, such as a nucleic acid array or a specific ligand array. The substrate can be a solid or semi-solid substrate such as any support comprising glass, plastic, nylon, paper, metal, or polymers. The substrate can be of various forms and sizes, such as a slide, a membrane, a bead, a column, or a gel. The contacting can be made under any condition suitable for a complex to be formed between the reagent and the nucleic acids or polypeptides of the sample.

Identifying a polypeptide, RNA or DNA of Ildr2 in the sample can be correlated to the presence, predisposition or stage of progression of metabolic disease. For example, an individual expressing reduced levels of Ildr2 may have an increased risk of developing a metabolic disease. The determination of the expression of Ildr2 in a subject also allows the design of appropriate therapeutic intervention, which is more effective and customized. Also, this determination at the pre-symptomatic level allows a preventive regimen to be applied.

The standard dose(s) of an agent which increases expression of Ildr2 mRNA or ILDR2 protein to be administered according to the methods described herein can vary, for example, depending upon the identity, size, and condition of the subject being treated and can further depend upon the route by which an agent according to the methods described herein, is to be administered, if applicable, and the effect which the practitioner desires the agent according to the invention to have upon the target of interest. These amounts can be readily determined by one of skill in the art. Any of the therapeutic applications described herein can be applied to any subject in need of such therapy, including, for example, a mammal such as a human.

Appropriate dosing regimens can also be determined by one of skill in the art without undue experimentation, in order to determine, for example, whether to administer the agent in one single dose or in multiple doses, and in the case of multiple doses, to determine an effective interval between doses.

In certain embodiments, an agent which increases expression of Ildr2 mRNA or ILDR2 protein administered according to the methods described herein can be administered alone, or in combination with other drugs, therapies, small molecules, biologically active or inert compounds, or other additive intended to enhance the delivery, efficacy, tolerability, or function of the agent. In one embodiment, the agent is administered with a lipid lowering therapy. In another embodiment the lipid lowring therapy is a therapeutic lifestyle change, a HMG-CoA reductase inhibitor, niacin, a fibrate, a cholesterol absorption inhibitor, a MTP inhibitor, or any combination thereof.

Therapy dose and duration will depend on a variety of factors, such as the disease type, patient age, therapeutic index of the drugs, patient weight, and tolerance of toxicity. The skilled clinician using standard pharmacological approaches can determine the dose of a particular therapeutic and duration of therapy for a particular patient in view of the above stated factors.

Methods of Administering

The invention provides methods for treating a metabolic disease in a subject. In one embodiment, the method can comprise administering to the subject an agent which increases expression of Ildr2 mRNA or ILDR2 protein, including, but not limited to an ILDR2 molecule (e.g, an ILDR2 polypeptide or an ILDR2 polynucleotide).

Various approaches can be carried out to increasing an ILDR2 gene expression level or activity and can be accomplished through gene or protein therapy A eukaryotic expression vector can be introduced into cells in order to increase the expression or produce proteins (for example, ILDR2) encoded by nucleotide sequences of the vector. Cells can harbor an expression vector (for example, one that contains a gene encoding ILDR2) via introducing the expression vector into an appropriate host cell via methods known in the art. A nucleic acid encoding an ILDR2 molecule can be introduced into the cells of a subject. For example, the wild-type gene (or fragment thereof) can also be introduced into the cells of the subject in need thereof using a vector as described herein. The vector can be a viral vector or a plasmid. The gene can also be introduced as naked DNA. The gene can be provided so as to integrate into the genome of the recipient host cells, or to remain extra-chromosomal. Integration can occur randomly or at precisely defined sites, such as through homologous recombination. For example, a functional copy of an ILDR2 molecule can be inserted in replacement of an altered version in a cell, through homologous recombination. Further techniques include gene gun, liposome-mediated transfection, or cationic lipid-mediated transfection. Gene therapy can be accomplished by direct gene injection, or by administering ex vivo prepared genetically modified cells expressing a functional polypeptide.

A eukaryotic expression vector can be introduced into cells in order to decrease the expression of proteins (for example, ILDR2, PERK, IRE1a, ATF6, or XBP1). Cells can harbor an expression vector encoding an interfering RNA molecule (for example, one that encode a RNAi to ILDR2, PERK, IRE1a, ATF6, or XBP1) via introducing the expression vector into an appropriate host cell via methods known in the art.

Inhibition of RNA encoding a PERK, IRE1a, ATF6, or XBP1 molecule can effectively modulate the expression of the PERK, IRE1a, ATF6, or XBP1 gene from which the RNA is transcribed. Without being bound by theory, inhibition of RNA encoding a PERK, IRE1a, ATF6, or XBP1 molecule can effectively modulate the expression of ILDR2. An agent which increases expression of Ildr2 mRNA or ILDR2 protein can be selected from the group comprising: siRNA, interfering RNA or RNAi; dsRNA; RNA Polymerase III transcribed DNAs; shRNAs; ribozymes; and antisense nucleic acid, which can be RNA, DNA, or artificial nucleic acid.

Antisense oligonucleotides, including antisense DNA, RNA, and DNA/RNA molecules, act to directly block the translation of mRNA by binding to targeted mRNA and preventing protein translation. For example, antisense oligonucleotides of at least about 15 bases and complementary to unique regions of the DNA sequence encoding a PERK, IRE1a, ATF6, or XBP1 polypeptide can be synthesized, e.g., by conventional phosphodiester techniques (Dallas et al., (2006) Med. Sci. Monit. 12(4):RA67-74; Kalota et al., (2006) Handb. Exp. Pharmacol. 173:173-96; Lutzelburger et al., (2006) Handb. Exp. Pharmacol. 173:243-59; each herein incorporated by reference in its entirety).

siRNA comprises a double stranded structure containing from about 15 to about 50 base pairs, for example from about 21 to about 25 base pairs, and having a nucleotide sequence identical or nearly identical to an expressed target gene or RNA within the cell. Antisense nucleotide sequences include, but are not limited to: morpholinos, 2'-O-methyl polynucleotides, DNA, RNA and the like. RNA polymerase III transcribed DNAs contain promoters, such as the U6 promoter. These DNAs can be transcribed to produce small hairpin RNAs in the cell that can function as siRNA or linear RNAs that can function as antisense RNA. The PERK, IRE1a, ATF6, or XBP1 modulating compound can contain ribonucleotides, deoxyribonucleotides, synthetic nucleotides, or any suitable combination such that the target RNA and/or gene is inhibited. In addition, these forms of nucleic acid can be single, double, triple, or quadruple stranded. See for example Bass (2001) Nature, 411, 428 429; Elbashir et al., (2001) Nature, 411, 494 498; and PCT Publication Nos. WO 00/44895, WO 01/36646, WO 99/32619, WO 00/01846, WO 01/29058, WO 99/07409, WO 00/44914; each of which are herein incorporated by reference in its entirety.

siRNA can be produced chemically or biologically, or can be expressed from a recombinant plasmid or viral vector (for example, see U.S. Pat. No. 7,294,504; U.S. Pat. No. 7,148,342; and U.S. Pat. No. 7,422,896; the entire disclosures of which are herein incorporated by reference). Exemplary methods for producing and testing dsRNA or siRNA molecules are described in U.S. Patent Application Publication No. 2002/0173478 to Gewirtz, and in U.S. Patent Application Publication No. 2007/0072204 to Hannon et al., the entire disclosures of which are herein incorporated by reference.

An agent which increases expression of Ildr2 mRNA or ILDR2 protein can additionally be a short hairpin RNA (shRNA). The hairpin RNAs can be synthesized exogenously or can be formed by transcribing from RNA polymerase III promoters in vivo. Examples of making and using such hairpin RNAs for gene silencing in mammalian cells are described in, for example, Paddison et al., 2002, Genes Dev, 16:948-58; McCaffrey et al., 2002, Nature, 418:38-9; McManus et al., 2002, RNA, 8:842-50; Yu et al., 2002, Proc Natl Acad Sci USA, 99:6047-52; each herein incorporated by reference in its entirety. Such hairpin RNAs are engineered in cells or in an animal to ensure continuous and stable suppression of a desired gene. It is known in the art that siRNAs can be produced by processing a hairpin RNA in the cell.

When a nucleic acid such as RNA or DNA is used that encodes a protein or peptide of the invention, it can be delivered into a cell in any of a variety of forms, including as naked plasmid or other DNA, formulated in liposomes, in an expression vector, which includes a viral vector (including RNA viruses and DNA viruses, including adenovirus, lentivirus, alphavirus, and adeno-associated virus), by biocompatible gels, via a pressure injection apparatus such as the Powderject™ system using RNA or DNA, or by any other convenient means. Again, the amount of nucleic acid needed to sequester an Id protein in the cytoplasm can be readily determined by those of skill in the art, which also can vary with the delivery formulation and mode and whether the nucleic acid is DNA or RNA. For example, see Manjunath et al., (2009) Adv Drug Deliv Rev. 61(9):732-45; Singer and Verma, (2008) Curr Gene Ther. 8(6):483-8; and Lundberg et al., (2008) Curr Gene Ther. 8(6):461-73; each herein incorporated by reference in its entirety.

An agent which increases expression of Ildr2 mRNA or ILDR2 protein can also be a small molecule that binds to ILDR2, PERK, IRE1a, ATF6, or XBP and disrupts its function, or conversely, enhances its function. Suppression of ILDR2 could also be reduced by ER stress inhibitors, including, but not limited to TUDCA and 4PBA. Small molecules are a diverse group of synthetic and natural substances having low molecular weights. They can be isolated from natural sources (for example, plants, fungi, microbes and the like), are obtained commercially and/or available as libraries or collections, or synthesized. Candidate small molecules that modulate ILDR2, PERK, IRE1a, ATF6, or XBP can be identified via in silico screening or high-throughput (HTP) screening of combinatorial libraries.

An exogenous nucleic acid can be introduced into a cell via a variety of techniques known in the art. For example, a retrovirus can be used to introduce a nucleotide sequence into cells (such as hepatocytes). In one embodiment, the retrovirus is an adenovirus. Other viral vectors known in the art can be used to introduce a nucleotide sequence, including, but not limited to a lentivirus, or an adeno-associated virus.

In one embodiment, a retrovirus can be used to introduce a nucleotide sequence into hepatocytes, in order to produce proteins encoded by said nucleotide sequences or to introduce RNAi to reduce protein levels (for example, ILDR2). A eukaryotic expression vector can be used to transfect cells in order to produce proteins encoded by nucleotide sequences or to introduct RNAi to reduce protein levels (for example, ILDR2). Mammalian cells (such as hepatocytes) can harbor an expression vector via introducing the expression vector into an appropriate host cell via methods known in the art.

An exogenous nucleic acid can be introduced into a cell via a variety of techniques known in the art, such as lipofection, microinjection, calcium phosphate or calcium chloride precipitation, DEAE-dextrin-mediated transfection, or electroporation. Other methods used to transfect cells can also include calcium phosphate precipitation, modified calcium phosphate precipitation, polybrene precipitation, microinjection liposome fusion, and receptor-mediated gene delivery.

A nucleic acid encoding a gene of interest or a functional part thereof can be introduced into the cells of a subject. For example, the wild-type gene (or a functional part thereof) can also be introduced into the cells of the subject in need thereof using a vector as described herein. The vector can be a viral vector or a plasmid. The gene can also be introduced as naked DNA. The gene can be provided so as to integrate into the genome of the recipient host cells, or to remain extra-chromosomal. Integration can occur randomly or at precisely defined sites, such as through homologous recombination. For example, a functional copy of the gene can be inserted in replacement of an altered version in a cell, through homologous recombination. Further techniques include gene gun, liposome-mediated transfection, or cationic lipid-mediated transfection. Gene therapy can be accomplished by direct gene injection, or by administering ex vivo prepared genetically modified cells expressing a functional polypeptide.

Delivery of nucleic acids into viable cells can be effected ex vivo, in situ, or in vivo by use of vectors, and more specifically viral vectors (e.g., lentivirus, adenovirus, adeno-associated virus, or a retrovirus), or ex vivo by use of physical DNA transfer methods (e.g., liposomes or chemical treatments). Non-limiting techniques suitable for the transfer of nucleic acid into mammalian cells in vitro include the use of liposomes, electroporation, microinjection, cell fusion, DEAE-dextran, and the calcium phosphate precipitation method (see, for example, Anderson, Nature, supplement to vol. 392, no. 6679, pp. 25-20 (1998)). Introduction of a nucleic acid or a gene encoding a polypeptide of the invention can also be accomplished with extrachromosomal substrates (transient expression) or artificial chromosomes (stable expression). Cells can also be cultured ex vivo in the presence of therapeutic compositions of the present invention in order to proliferate or to produce a desired effect on or activity in such cells. Treated cells can then be introduced in vivo for therapeutic purposes.

Nucleic acids can be inserted into vectors and used as gene therapy vectors. A number of viruses have been used as gene transfer vectors, including papovaviruses, e.g., SV40 (Madzak et al., 1992), adenovirus (Berkner, 1992; Berkner et al., 1988; Gorziglia and Kapikian, 1992; Quantin et al., 1992; Rosenfeld et al., 1992; Wilkinson et al., 1992; Stratford-Perricaudet et al., 1990), vaccinia virus (Moss, 1992), adeno-associated virus (Muzyczka, 1992; Ohi et al., 1990), herpesviruses including HSV and EBV (Margolskee, 1992; Johnson et al., 1992; Fink et al., 1992; Breakfield and Geller, 1987; Freese et al., 1990), and retroviruses of avian (Biandyopadhyay and Temin, 1984; Petropoulos et al., 1992), murine (Miller, 1992; Miller et al., 1985; Sorge et al., 1984; Mann and Baltimore, 1985; Miller et al., 1988), and human origin (Shimada et al., 1991; Helseth et al., 1990; Page et al., 1990; Buchschacher and Panganiban, 1992). Non-limiting examples of in vivo gene transfer techniques include transfection with viral (e.g., retroviral) vectors (see U.S. Pat. No. 5,252,479, which is incorporated by reference in its entirety) and viral coat protein-liposome mediated transfection (Dzau et al., Trends in Biotechnology 11:205-210 (1993), incorporated entirely by reference). For example, naked DNA vaccines are generally known in the art; see Brower, Nature Biotechnology, 16:1304-1305 (1998), which is incorporated by reference in its entirety. Gene therapy vectors can be delivered to a subject by, for example, intravenous injection, local administration (see, e.g., U.S. Pat. No. 5,328,470) or by stereotactic injection (see, e.g., Chen, et al., 1994. Proc. Natl. Acad. Sci. USA 91: 3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

For reviews of gene therapy protocols and methods see Anderson et al., Science 256:808-813 (1992); U.S. Pat. Nos. 5,252,479, 5,747,469, 6,017,524, 6,143,290, 6,410,010 6,511,847; and U.S. Application Publication Nos. 2002/0077313 and 2002/00069, which are all hereby incorporated by reference in their entireties. For additional reviews of gene therapy technology, see Friedmann, Science, 244: 1275-1281 (1989); Verma, Scientific American: 68-84 (1990); Miller, Nature, 357: 455-460 (1992); Kikuchi et al., J Dermatol Sci. 2008 May; 50(2):87-98; Isaka et al., Expert Opin Drug Deliv. 2007 September; 4(5):561-71; Jager et al., Curr Gene Ther. 2007 August; 7(4):272-83; Waehler et al., Nat Rev Genet. 2007 August; 8(8):573-87; Jensen et al., Ann Med. 2007; 39(2):108-15; Herweijer et al., Gene Ther. 2007 January; 14(2):99-107; Eliyahu et al., Molecules, 2005 Jan. 31; 10(1):34-64; and Altaras et al., Adv Biochem Eng Biotechnol. 2005; 99:193-260, all of which are hereby incorporated by reference in their entireties.

Protein replacement therapy can increase the amount of protein by exogenously introducing wild-type or biologically functional protein by way of infusion. A replacement polypeptide can be synthesized according to known chemical techniques or can be produced and purified via known molecular biological techniques. Protein replacement therapy has been developed for various disorders. For example, a wild-type protein can be purified from a recombinant cellular expression system (e.g., mammalian cells or insect cells-see U.S. Pat. No. 5,580,757 to Desnick et al.; U.S. Pat. Nos. 6,395,884 and 6,458,574 to Selden et al.; U.S. Pat. No. 6,461,609 to Calhoun et al.; U.S. Pat. No. 6,210,666 to Miyamura et al.; U.S. Pat. No. 6,083,725 to Selden et al.; U.S. Pat. No. 6,451,600 to Rasmussen et al.; U.S. Pat. No. 5,236,838 to Rasmussen et al. and U.S. Pat. No. 5,879,680 to Ginns et al.), human placenta, or animal milk (see U.S. Pat. No. 6,188,045 to Reuser et al.), or other sources known in the art. After the infusion, the exogenous protein can be taken up by tissues through non-specific or receptor-mediated mechanism.

Indications, dosage and methods of administration of the drugs of the present invention are known to one of skill in the art. In some embodiments, a drug of the present invention can be supplied in the form of a pharmaceutical composition, comprising an isotonic excipient prepared under sufficiently sterile conditions for human administration. Choice of the excipient and any accompanying elements of the composition will be adapted in accordance with the route and device used for administration. In some embodiments, a composition comprising a drug of the present invention can also comprise, or be accompanied with, one or more other ingredients that facilitate the delivery or functional mobilization of the drugs of the present invention.

These methods described herein are by no means all-inclusive, and further methods to suit the specific application is understood by the ordinary skilled artisan. Moreover, the effective amount of the compositions can be further approximated through analogy to compounds known to exert the desired effect.

According to the invention, a pharmaceutically acceptable carrier can comprise any and all solvents, dispersion media, coatings, antibacterial and antifungal agents, isotonic and absorption delaying agents, and the like, compatible with pharmaceutical administration. The use of such media and agents for pharmaceutically active substances is well known in the art. Any conventional media or agent that is compatible with the active compound can be used. Supplementary active compounds can also be incorporated into the compositions.

Pharmaceutical compositions for use in accordance with the invention can be formulated in conventional manner using one or more physiologically acceptable carriers or excipients. The therapeutic compositions of the invention can be formulated for a variety of routes of administration, including systemic and topical or localized administration. Techniques and formulations generally can be found in Remmington's Pharmaceutical Sciences, Meade Publishing Co., Easton, Pa. ($20^{th}$ ed., 2000), the entire disclosure of which is herein incorporated by reference.

Any of the therapeutic applications described herein can be applied to any subject in need of such therapy, including, for example, a mammal such as a dog, a cat, a cow, a horse, a rabbit, a monkey, a pig, a sheep, a goat, or a human.

Administration of a drug of the present invention is not restricted to a single route, but may encompass administration by multiple routes. Multiple administrations may be sequential or concurrent. Other modes of application by multiple routes will be apparent to one of skill in the art.

The compositions of this invention can be formulated and administered to reduce the symptoms associated with a metabolic disease by any means that produce contact of the active ingredient with the agent's site of action in the body of a human or non-human subject. They can be administered by any conventional means available for use in conjunction with pharmaceuticals, either as individual therapeutic active ingredients or in a combination of therapeutic active ingredients. They can be administered alone, but are generally administered with a pharmaceutical carrier selected on the basis of the chosen route of administration and standard pharmaceutical practice.

Pharmaceutical compositions for use in accordance with the invention can be formulated in conventional manner using one or more physiologically acceptable carriers or excipients. The therapeutic compositions of the invention can be formulated for a variety of routes of administration, including systemic and topical or localized administration. Techniques and formulations generally can be found in Remmington's Pharmaceutical Sciences, Meade Publishing Co., Easton, Pa. (20th ed., 2000), the entire disclosure of which is herein incorporated by reference. For systemic administration, an injection is useful, including intramuscular, intravenous, intraperitoneal, and subcutaneous. For injection, the therapeutic compositions of the invention can be formulated in liquid solutions, for example in physiologically compatible buffers, such as PBS, Hank's solution, or Ringer's solution. In addition, the therapeutic compositions can be formulated in solid form and redissolved or suspended immediately prior to use. Lyophilized forms are also included. Pharmaceutical compositions of the present invention are characterized as being at least sterile and pyrogen-free. These pharmaceutical formulations include formulations for human and veterinary use.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EM™ (BASF, Parsippany, N.J.) or phosphate buffered saline (PBS). The composition must be sterile and fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, a pharmaceutically acceptable polyol like glycerol, propylene glycol, liquid polyetheylene glycol, and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, and thimerosal. In many cases, it can be useful to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the agent which increases expression of Ildr2 mRNA or ILDR2 protein in the required amount in an appropriate solvent with one or a combination of ingredients enumerated herein, as required, followed by filtered sterilization. Dispersions are prepared by incorporating the active compound into a sterile vehicle which contains a basic dispersion medium and the required other ingredients from those enumerated herein. In the case of sterile powders for the preparation of sterile injectable solutions, examples of useful preparation methods are vacuum drying and freeze-drying which yields a powder of the active ingredient plus any additional desired ingredient from a previously sterile-filtered solution thereof.

Oral compositions include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed.

Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or sterotes; a glidant such as colloidal silicon dioxide; a sweetening agent such as sucrose or saccharin; or a flavoring agent such as peppermint, methyl salicylate, or orange flavoring.

Systemic administration can also be by transmucosal or transdermal means. For transmucosal or transdermal administration, penetrants appropriate to the barrier to be permeated are used in the formulation. Such penetrants are known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as known in the art A composition of the invention can also be formulated as a sustained and/or timed release formulation. Such sustained and/or timed release formulations can be made by sustained release means or delivery devices that are well known to those of ordinary skill in the art, such as those described in U.S. Pat. Nos. 3,845,770; 3,916,899; 3,536,809; 3,598,123; 4,008,719; 4,710,384; 5,674,533; 5,059,595; 5,591,767; 5,120,548; 5,073,543; 5,639,476; 5,354,556; and 5,733,566, the disclosures of which are each incorporated herein by reference. The pharmaceutical compositions of the invention (e.g., that have a therapeutic effect) can be used to provide slow or sustained release of one or more of the active ingredients using, for example, hydropropylmethyl cellulose, other polymer matrices, gels, permeable membranes, osmotic systems, multilayer coatings, microparticles, liposomes, microspheres, or the like, or a combination thereof to provide the desired release profile in varying proportions. Suitable sustained release formulations known to those of ordinary skill in the art, including those described herein, can be readily selected for use with the pharmaceutical compositions of the invention. Single unit dosage forms suitable for oral administration, such as, but not limited to, tablets, capsules, gel-caps, caplets, or powders, that are adapted for sustained release are encompassed by the invention.

The dosage administered can be a therapeutically effective amount of the composition sufficient to result in treatment of a metabolic disease and can vary depending upon known factors such as the pharmacodynamic characteristics of the active ingredient and its mode and route of administration; time of administration of active ingredient; age, sex, health and weight of the recipient; nature and extent of symptoms; kind of concurrent treatment, frequency of treatment and the effect desired; and rate of excretion.

In some embodiments, the effective amount of the administered an agent which increases expression of Ildr2 mRNA or ILDR2 protein is at least about 0.01 μg/kg body weight, at least about 0.025 μg/kg body weight, at least about 0.05 μg/kg body weight, at least about 0.075 μg/kg body weight, at least about 0.1 μg/kg body weight, at least about 0.25 μg/kg body weight, at least about 0.5 μg/kg body weight, at least about 0.75 μg/kg body weight, at least about 1 μg/kg body weight, at least about 5 μg/kg body weight, at least about 10 μg/kg body weight, at least about 25 μg/kg body weight, at least about 50 μg/kg body weight, at least about 75 μg/kg body weight, at least about 100 μg/kg body weight, at least about 150 μg/kg body weight, at least about 200 μg/kg body weight, at least about 250 μg/kg body weight, at least about 300 μg/kg body weight, at least about 350 μg/kg body weight, at least about 400 μg/kg body weight, at least about 450 μg/kg body weight, at least about 500 μg/kg body weight, at least about 550 μg/kg body weight, at least about 600 μg/kg body weight, at least about 650 μg/kg body weight, at least about 700 μg/kg body weight, at least about 750 μg/kg body weight, at least about 800 μg/kg body weight, at least about 850 μg/kg body weight, at least about 900 μg/kg body weight, at least about 950 μg/kg body weight, at least about 1000 μg/kg body weight, at least about 1500 μg/kg body weight, at least about 2000 μg/kg body weight, at least about 2500 μg/kg body weight, at least about 3000 μg/kg body weight, at least about 3500 μg/kg body weight, at least about 4000 μg/kg body weight, at least about 4500 μg/kg body weight, at least about 5000 μg/kg body weight, at least about 5500 μg/kg body weight, at least about 6000 μg/kg body weight, at least about 6500 μg/kg body weight, at least about 7000 μg/kg body weight, at least about 7500 μg/kg body weight, at least about 8000 μg/kg body weight, at least about 8500 μg/kg body weight, at least about 9000 μg/kg body weight, at least about 9500 μg/kg body weight, or at least about 10000 μg/kg body weight.

In one embodiment, an agent which increases expression of Ildr2 mRNA or ILDR2 protein is administered at least once daily. In another embodiment, an agent which increases expression of Ildr2 mRNA or ILDR2 protein is administered at least twice daily. In some embodiments, an agent which increases expression of Ildr2 mRNA or ILDR2 protein is administered for at least 1 week, for at least 2 weeks, for at least 3 weeks, for at least 4 weeks, for at least 5 weeks, for at least 6 weeks, for at least 8 weeks, for at least 10 weeks, for at least 12 weeks, for at least 18 weeks, for at least 24 weeks, for at least 36 weeks, for at least 48 weeks, or for at least 60 weeks. In further embodiments, an agent which increases expression of Ildr2 mRNA or ILDR2 protein is administered in combination with a second therapeutic agent.

Toxicity and therapeutic efficacy of therapeutic compositions of the present invention can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Therapeutic agents that exhibit large therapeutic indices are useful. Therapeutic compositions that exhibit some toxic side effects can be used.

Administration of an agent which increases expression of Ildr2 mRNA or ILDR2 protein is not restricted to a single route, but may encompass administration by multiple routes. Multiple administrations may be sequential or concurrent. Other modes of application by multiple routes will be apparent to one of skill in the art.

Methods of Detection

Embodiments of the invention provide for detecting expression of an ILDR2. In one embodiment, increased or reduced protein expression and/or activity can be detected. The detection can be performed at the level of the DNA, RNA, or polypeptide.

In some embodiments, the detecting comprises detecting in a biological sample whether there is a reduction in an mRNA encoding an ILDR2 protein, or a reduction in an ILDR2 protein, or a combination thereof. In further embodiments, the detecting comprises detecting in a biological sample whether there is a reduction in an mRNA encoding an ILDR2 protein, or a reduction in an ILDR2 protein, or a combination thereof.

Methods for detecting and quantifying ILDR2 molecules in biological samples are known the art. For example, protocols for detecting and measuring the expression of a polypeptide encoded by an ILDR2 molecule using either polyclonal or monoclonal antibodies specific for the polypeptide are well established. Non-limiting examples include Western blot, enzyme-linked immunosorbent assay (ELISA), radioimmunoassay (RIA), and fluorescence activated cell sorting (FACS).

In one embodiment, a biological sample comprises, a blood sample, serum, cells (including whole cells, cell fractions, cell extracts, and cultured cells or cell lines), tissues (including tissues obtained by biopsy), body fluids (e.g., urine, sputum, amniotic fluid, synovial fluid), or from media (from cultured cells or cell lines). The methods of detecting or quantifying an ILDR2 molecule include, but are not limited to, amplification-based assays with (signal amplification) hybridization based assays and combination amplification-hybridization assays. For detecting and quantifying an ILDR2 molecule, an exemplary method is an immunoassay that utilizes an antibody or other binding agents that specifically bind to an ILDR2 protein or epitope of such, for example, Western blot or ELISA assays.

Unless otherwise defined, all technical and scientific terms used herein have the same meaning as commonly understood by one of ordinary skill in the art to which this invention belongs. Exemplary methods and materials are described below, although methods and materials similar or equivalent to those described herein can also be used in the practice or testing of the present invention.

All publications and other references mentioned herein are incorporated by reference in their entirety, as if each individual publication or reference were specifically and individually indicated to be incorporated by reference. Publications and references cited herein are not admitted to be prior art.

The following examples illustrate the present invention, and are set forth to aid in the understanding of the invention, and should not be construed to limit in any way the scope of the invention as defined in the claims which follow thereafter.

EXAMPLES

Example 1

ILDR2: An Endoplasmic Reticulum Resident Molecule Mediating Hepatic Lipid Homeostasis Ildr2, a modifier of diabetes susceptibility in obese mice, is expressed in most organs, including islets and hypothalamus, with reduced levels in livers of diabetes-susceptible B6.DBA mice congenic for a 1.8 Mb interval of Chromosome 1. In hepatoma and neuronal cells, ILDR2 is primarily located in the endoplasmic reticulum membrane. Adenovirus vectors that express shRNA or are driven by the CMV promoter, respectively, were used to knockdown or overexpress Ildr2 in livers of wild type and ob/ob mice. Livers in knockdown mice were steatotic, with increased hepatic and circulating triglycerides and total cholesterol. Increased circulating VLDL, without reduction in triglyceride clearance suggests an effect of reduced hepatic ILDR2 on hepatic cholesterol clearance. In animals that overexpress Ildr2, hepatic triglyceride and total cholesterol levels were reduced, and strikingly so in ob/ob mice. There were no significant changes in body weight, energy expenditure or glucose/insulin homeostasis in knockdown or overexpressing mice. Knockdown mice showed reduced expression of genes mediating synthesis and oxidation of hepatic lipids, suggesting secondary suppression in response to increased hepatic lipid content. In Ildr2-overexpressing ob/ob mice, in association with reduced liver fat content, levels of transcripts related to neutral lipid synthesis and cholesterol were increased, suggesting “relief” of the secondary suppression imposed by lipid accumulation. Considering the fixed location of ILDR2 in the endoplasmic reticulum, the possible participation of ILDR2 in ER stress responses was investigated. In general, Ildr2 overexpression was associated with increases, and knockdown with decreases in levels of expression of molecular components of canonical ER stress pathways. Manipulation of Ildr2 expression in liver affects both lipid homeostasis and ER stress pathways. Given these reciprocal interactions, and the relatively extended timecourse over which these studies were conducted, causal primacy cannot be assigned to either the effects on hepatic lipid homeostasis or ER stress responses.

In an earlier study [1] the differential diabetes susceptibilities of mouse strains C57BL/6J (B6) and DBA/2J (DBA) [2] segregating for the obesity mutation, Lepob, were used to identify a gene that encodes a predicted single-pass, trans-membrane molecule that, in B6. DBA congenic mice (segregating a DBA haplotype in a 1.8 Mb interval on Chr1), was associated with reduced b-cell replication rates accompanied by reduced b-cell mass, and persistent mild hypoinsulinemic hyperglycemia. This gene, formerly designated "Lisch-like", has been renamed "immunoglobulin-like domain containing receptor 20" (Ildr2) [www.informatics.jax.org/mgihome/nomen/] to reflect the similarity of the conserved domain structure of the cognate protein to the two other members of this gene family: Ildr1 and Ildr3 (aka "LSR"—lipolysis stimulated receptor).

Despite their structural similarities, the three Ildr-genes exhibit widely divergent tissue-specific expression profiles, providing little evidence of significant overlap among their functions. The major isoforms of both ILDR1 and ILDR3 localize either to the plasma membrane (PM) or to the cytosol[3,4]. Although ILDR1 has been linked to neoplastic disease 2 [5] and non-syndromic deafness [6], how it functions is unknown. ILDR3, which was initially identified as a fatty acid-activated, liver-specific lipoprotein receptor [7], has since been characterized variously as a receptor for *Clostridium* toxin[8], as an hepatic receptor upregulated by leptin [9] and as a component of tri-cellular junctions in epithelial cells [10].

The Ildr2 gene is widely expressed, with 4 major isoforms that are differentially expressed in tissues relevant to the diabetic phenotype (hypothalamus, liver and islet b-cells). Expression levels of isoform 4, highest in liver, are reduced 20-fold in B6.DBA congenic animals and 30-fold in 10-week-old DBA mice versus B6 animals [1]. To assess the role of Ildr2 in the molecular physiology of normal, adult liver, adenoviruses containing overexpression or knockdown constructs was intravenously administered to study in vivo effects in liver and whole animal, and in transduced primary hepatocytes to study in vitro effects.

Described herein are results that ILDR2, in contrast to ILDR1 and ILDR3, is exclusively localized in the endoplasmic reticulum (ER), where it apparently participates in both lipoprotein physiology and the ER stress response, with consequences for hepatic lipid homeostasis.

Results

ILDR2 is Localized to the Endoplasmic Reticulum:

As previously described [1], the four major isoforms of ILDR2 (FIG. 1) contain an amino terminal immunoglobulin-like domain and long, carboxy tail. Isoforms 1, 2, and 4 also contain a single trans-membrane (TM) domain. Isoform 1 is full-length; isoform 2 lacks exon 6 (carboxy to the TM domain); isoform 4 lacks exon 4 (amino to the TM domain); isoform 3 lacks the TM domain and both flanking exons.

Figure 2A:
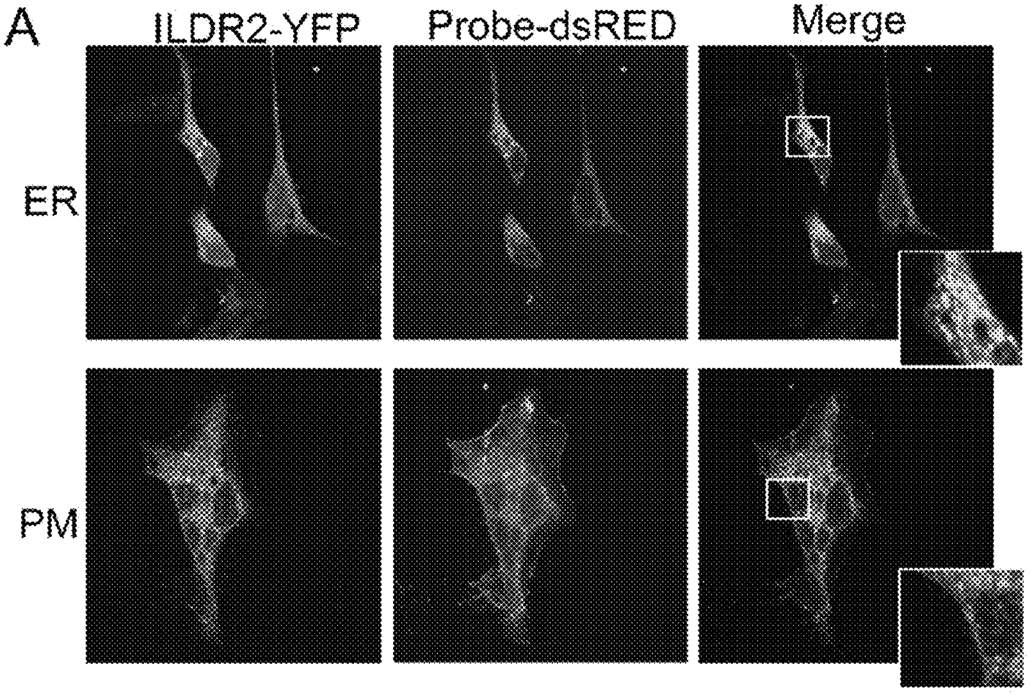
FIGS. 2A-C shows fluorescence microscopy of ILDR2 localization under basal conditions. ILDR2 fused on its C-terminus to mYFP (green) was transiently co-transduced into cell lines with DsRed-probes specific to either the ER (red) or the PM (red). The ER-specific probe is DsRed fluorescent protein attached to the ER-retention sequence KDEL (SEQ ID NO: 140). The PM-specific probe is DsRED attached to a farnesyl group that targets the protein to the inner leaflet of the PM. Cells were fixed without any further treatment 24 hr after transfection. Bar: 100 uM. Confocal images recorded at 636 magnification.
Figure 2B:
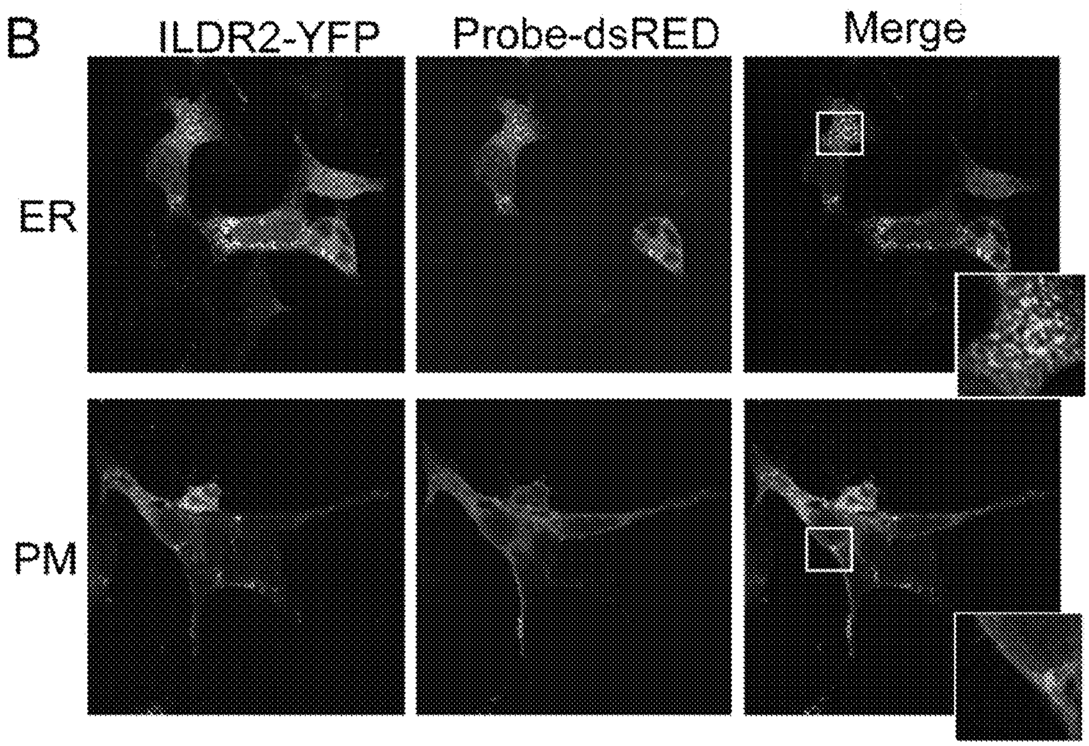
Figure 2C:
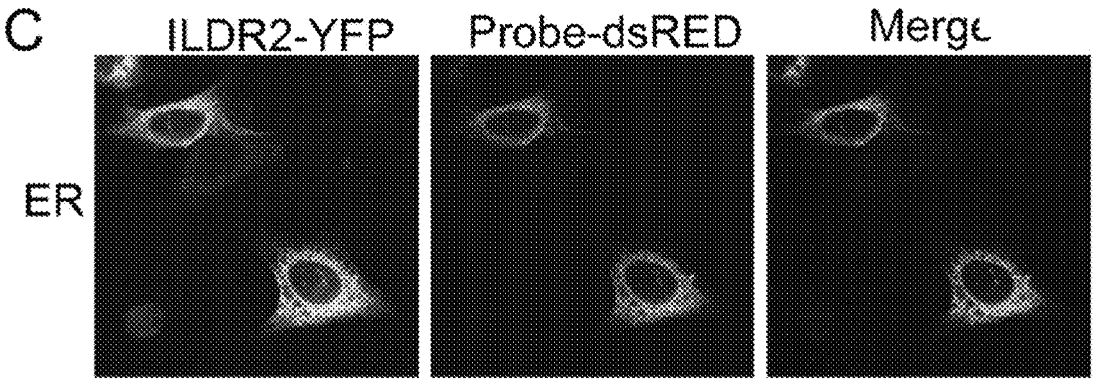
Figure 6A:
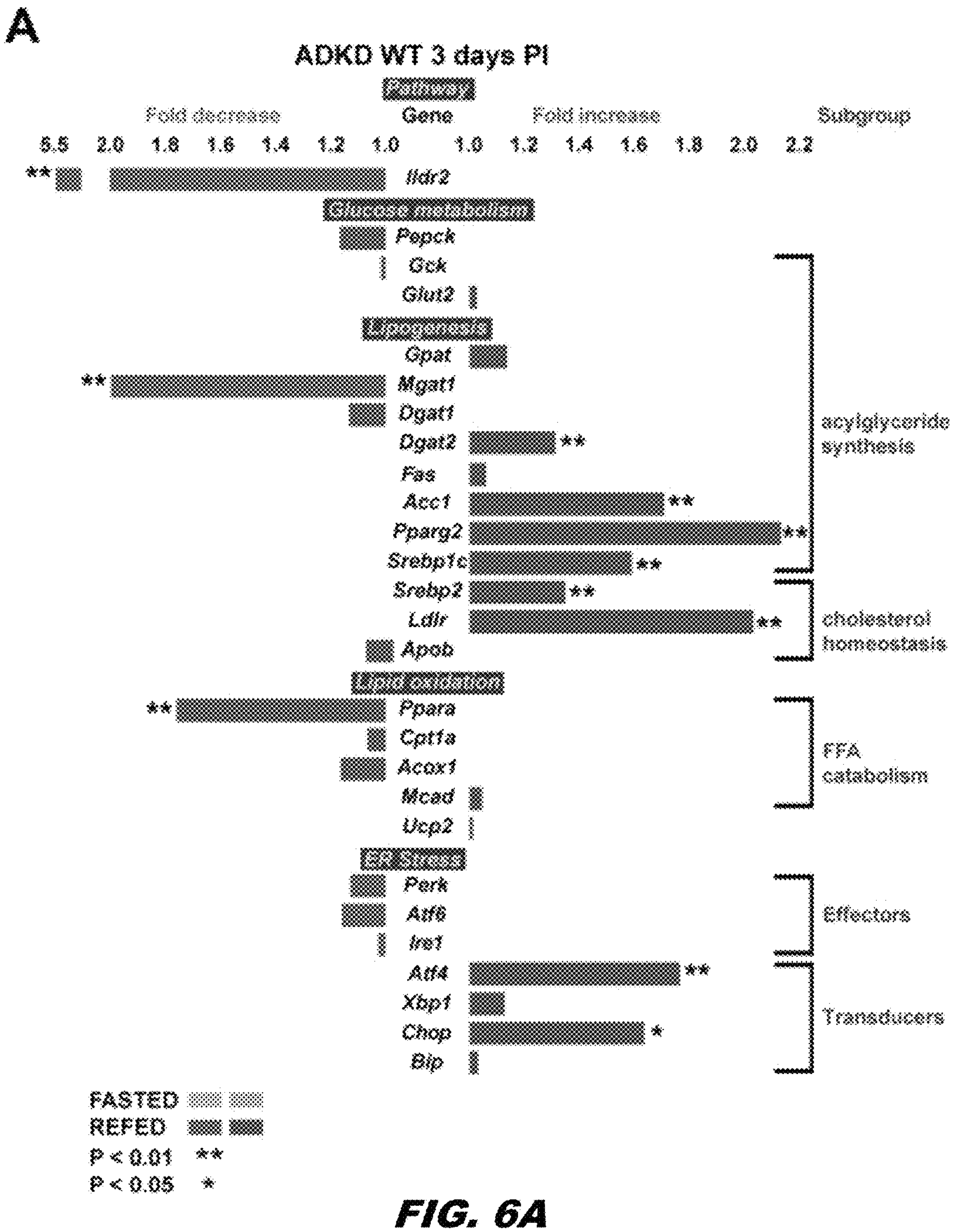
FIGS. 6A-F shows relative expression of selected genes in ADKD and ADOX WT and OB mice. 10-week-old B6 male mice were chow-fed, intravenously injected with ADKD and ADOX vectors and sacrificed at 3 days p.t, following a 12-hr fast. Expression levels were determined by qPCR normalized to expression levels of the 36B4 housekeeping gene. Fold changes are relative to the GFP control in the same state as the Ildr2 (either fasted or refed compared to fasted or refed). * indicates p,0.05;  indicates p,0.01 (2 tailed t-test).
Figure 6B:
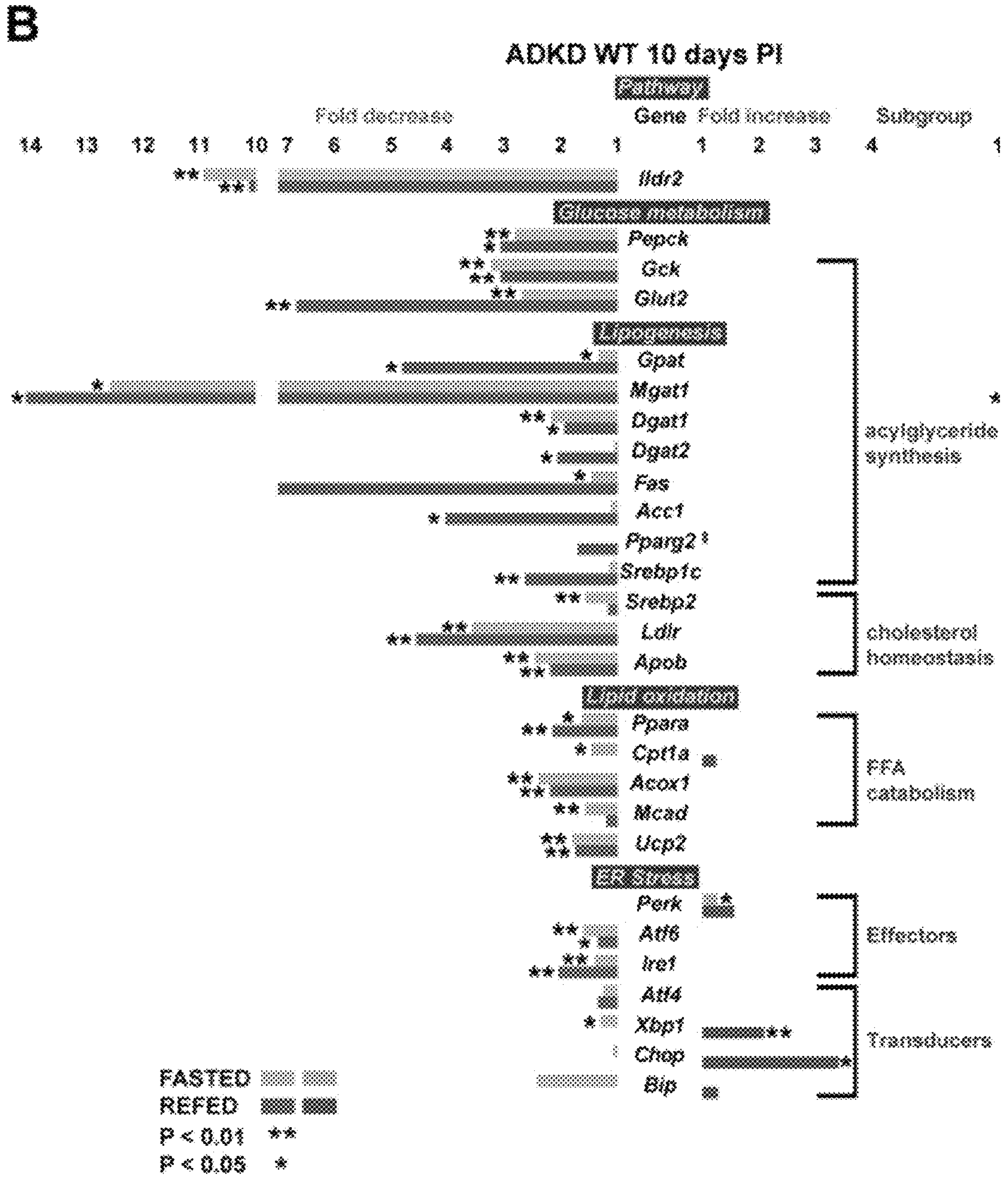
Figure 6C:
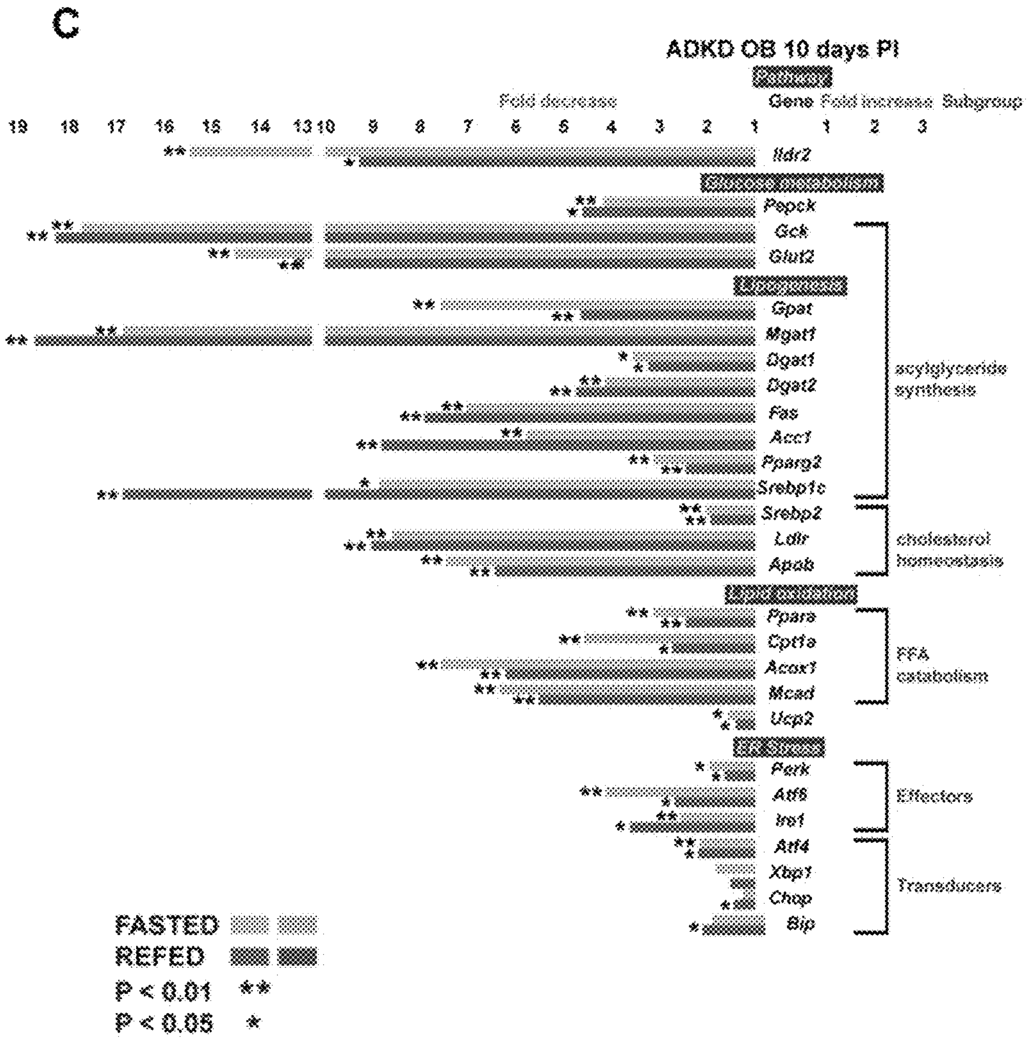
Figure 6D:
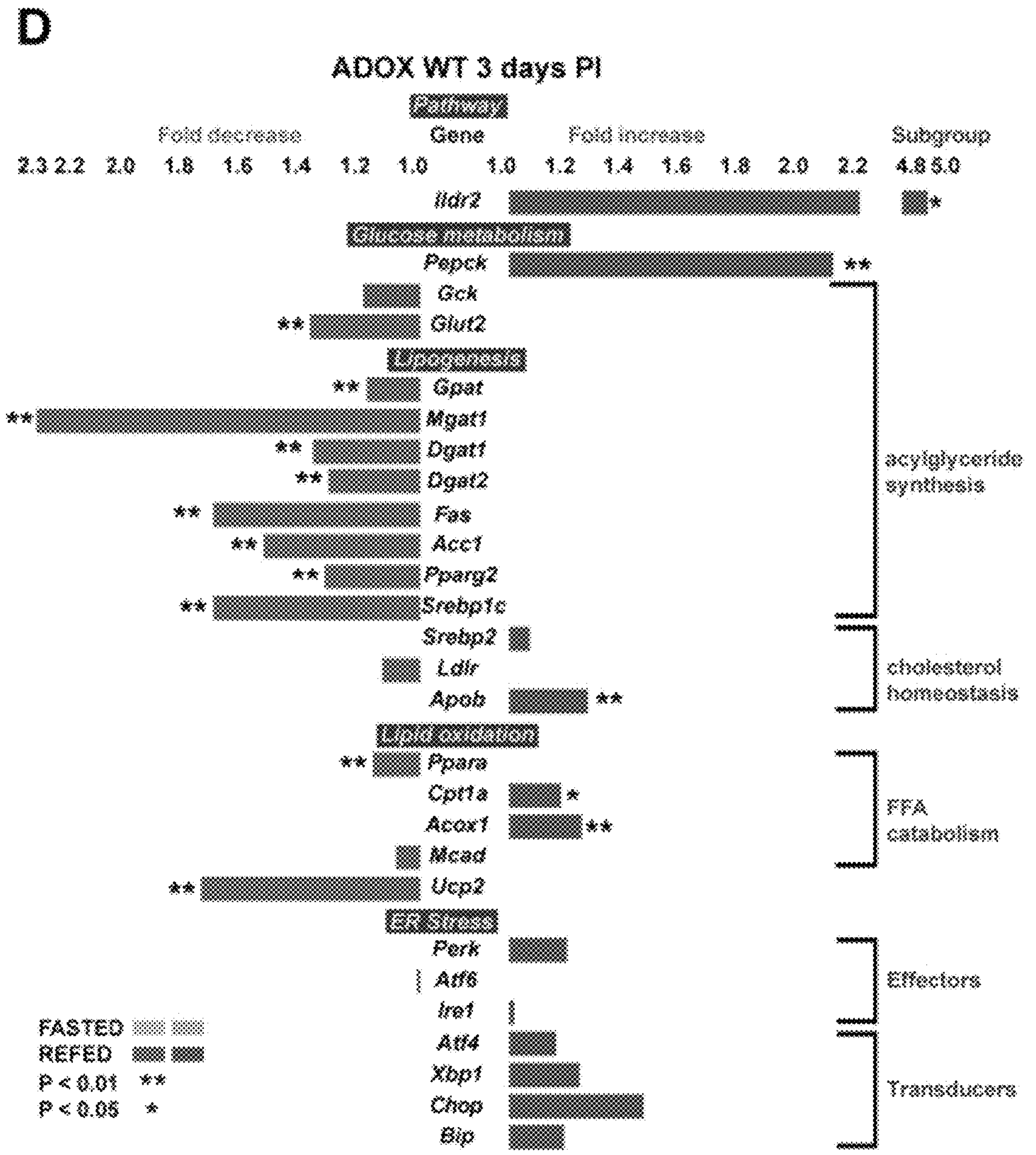
Figure 6E:
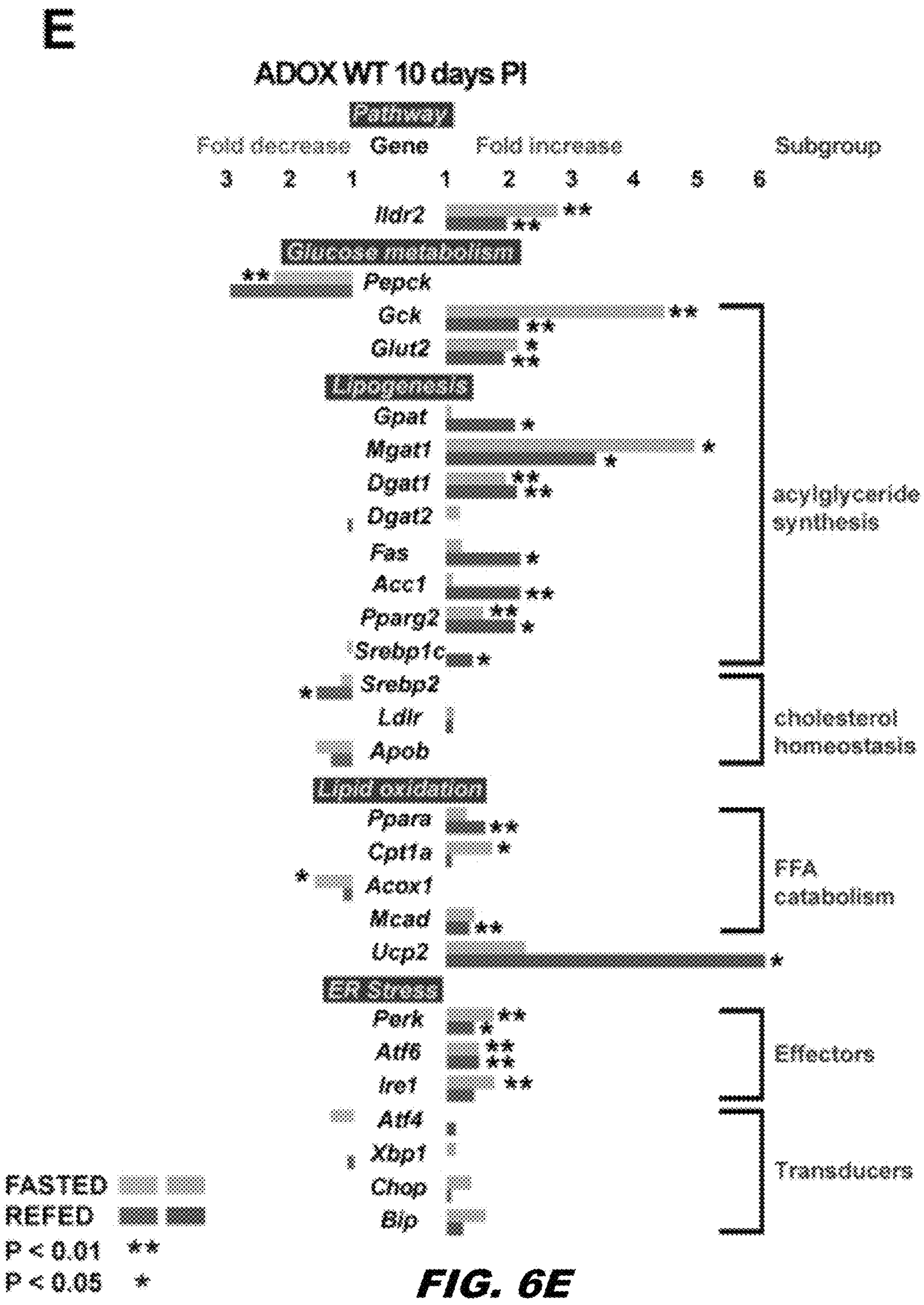
Figure 6F:
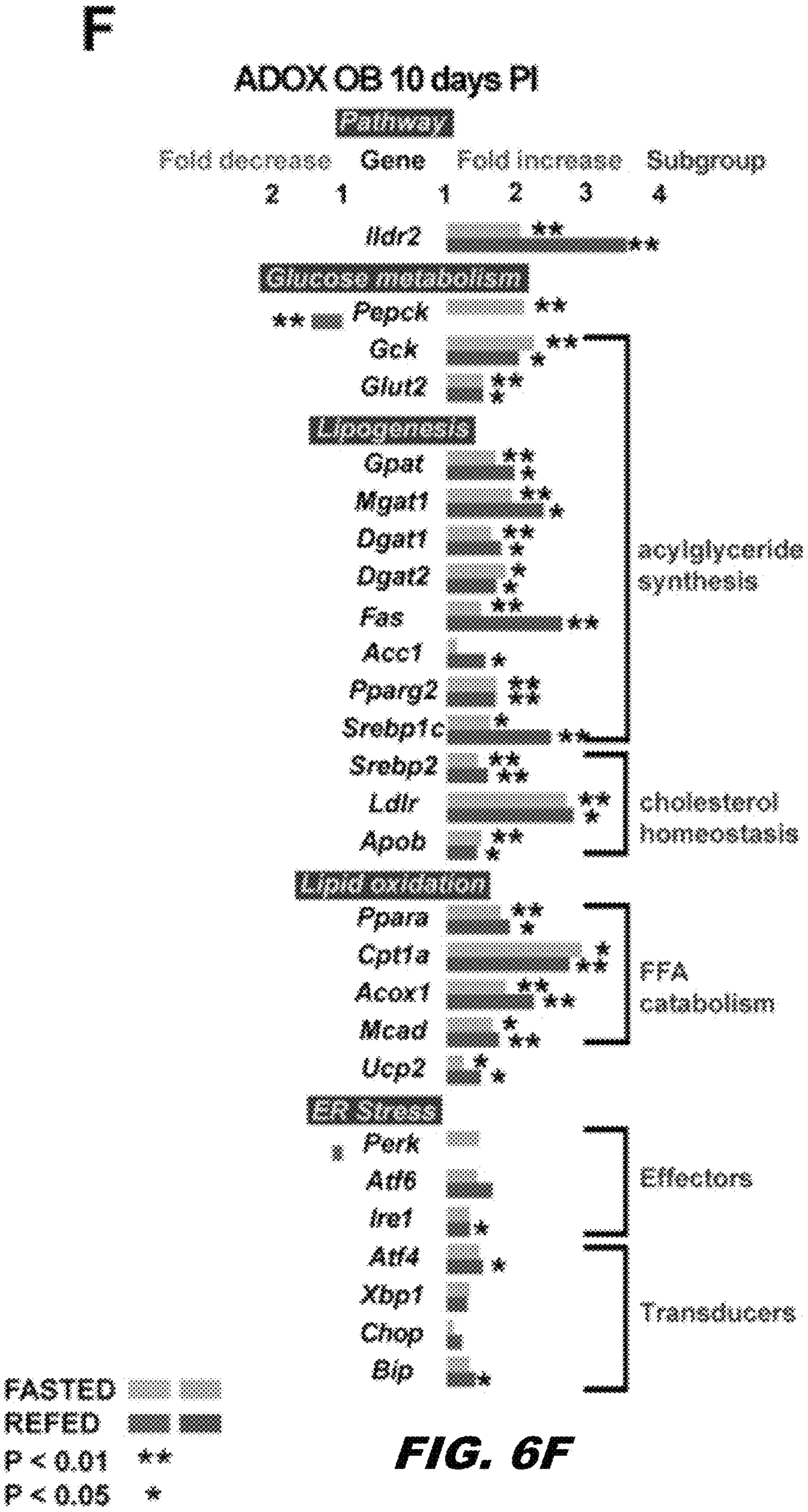
Figure 11:
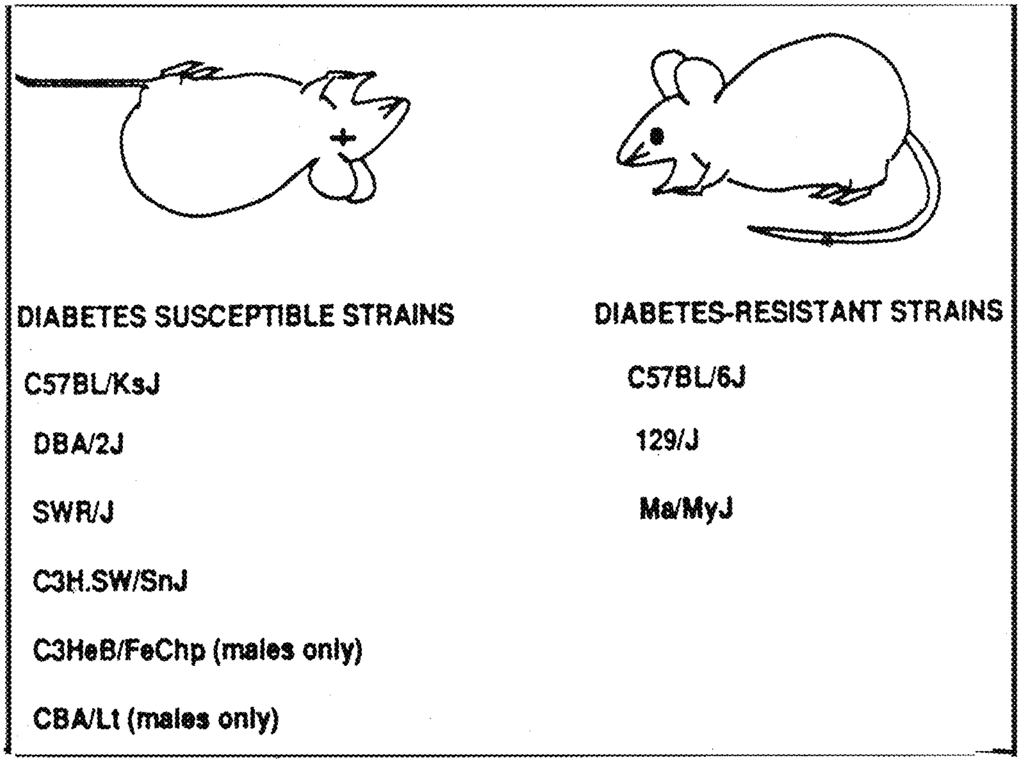
FIG. 11 shows a schematic of diabetes susceptible and diabetes-resistant mouse strains.

To determine the cellular location(s) of ILDR2, various isoforms were tagged at the C-termini with the green variant of the monomeric yellow fluorescent protein (mYFP), transiently transduced into mouse cells, and analyzed by confocal microscopy for co-localization with probes for the ER and PM (FIG. 2). Ildr2-isoform 2, predominantly expressed in the hypothalamus, was transduced into cells of the mouse hypothalamic neuronal cell line GT1-7 (FIG. 2A). Ildr2-isoform 4, the predominant isoform endogenously expressed in the liver, was transduced into cells of the mouse hepatoma cell line, Hepa1c1c7 (FIG. 2B). Both isoforms localized solely to the ER membrane, with no detectable fluorescence in the vicinity of the PM. Placement of the tagging peptide did not affect subcellular destination, since localization to the ER membrane was seen also in Hepa1c1c7 cells transduced with Ildr2-isoform 1 tagged at its N-terminus with the FLAG epitope (FIG. 2C). These results support the model depicted in FIG. 1, in which the hydrophobic, amino-terminal, immuno-globulin-like domain of isoforms 1, 2 and 4, extends into the ER lumen, and the hydrophilic carboxy-terminal tail, extends into the cytoplasm. No changes were observed in the subcellular distribution of C-terminal tagged isoform 4 in Hepa1c1c7 transfectants that were exposed to glucose, insulin, free fatty acids (FFA), and low-density lipoprotein (LDL). These results suggest that, unlike ILDR1 and ILDR3, whose final destination is the PM, ILDR2 is an integral ER trans-membrane molecule that likely does not further translocate within these cell types.

Functional analysis of Ildr2: The ER plays critical roles in protein and lipid synthesis, lipoprotein assembly and export, glucose and calcium homeostasis, and cellular responses to metabolic stress [11-15]. These protein functions affect liver [16], hypothalamus [17], and b-cells [18]. The metabolic phenotypes seen in the Ildr2 B6.DBA. congenic lines are consistent with effects on ER stress mechanisms [1]. Accessibility of the liver to in vivo and in vitro transcriptional manipulation using adenovirus vectors [19,20], led us to focus on the liver.

To examine the effects of short term changes in Ildr2 expression in liver on lipid and glucose homeostasis, 10-week-old chow-fed C57BL/6J (wild-type; WT) or B6.Cg-Lep/J (obese; OB) male mice were transduced with adenoviral expression vectors encoding shRNA ("ADKD") that knockdown Ildr2, or with adenoviral constructs driven by the CMV promoter ("ADOX") that overexpress Ildr2. To control for non-specific effects of adenoviral transduction on gene expression, mice were transduced with adenoviral expression vectors encoding shRNA that knockdown lacZ, or with adenoviral constructs driven by the CMV promoter that overexpress the green fluorescent protein (GFP). Expression levels in the hypothalamus and white adipose tissue were unaffected by transduction with either the ADKD or ADOX viral constructs (data not shown), confirming that their effects were restricted primarily to the liver. Knockdown efficiency exceeded 80% at 3 days post-transduction (p.t.) and 90% at 10 days p.t., while Ildr2 overexpression resulted in 2- to 4-fold increases in mRNA levels.

For studies of liver morphology, histology and chemistry, and for liver-specific gene expression analysis, animals were sacrificed at 3 days or 10 days p.t. To provide a general picture of the cellular/biochemical consequences of manipulations of expression of hepatic Ildr2, the livers were evaluated by visual inspection, light microscopy, chemical composition, and by quantitative expression of selected genes related to neutral lipid/cholesterol synthesis, lipid oxidation, glucose homeostasis, and ER stress. Mice were also evaluated by indirect calorimetry, ipGTT, and plasma lipid profiling. To identify very short term responses to changes in expression of Ildr2, mouse primary hepatocytes were transduced with the ADKD and ADOX constructs and analyzed responses at 24 hr p.t.

Ildr2 does not Cross-Regulate with Ildr1 or Ildr3:

Although the apparent lack of cellular colocalization of ILDR2 with other molecules of this family makes it unlikely that ILDR2 interacts directly with them, its functions could be mediated through secondary genetic effects. To test this possibility transcription levels among the ildr genes were analyzed in primary B6 mouse hepatocytes transduced with siRNAs specific to each gene (Table 1). Whereas siRNA specific to Ildr2 almost completely suppressed its own expression, it reduced expression of Ildr1 by only 3% and Ildr3 by 27%, with little effect on Ildr2 of knockdown of either Ildr1 or Ildr3. These results indicate that expression levels of Ildr genes do not significantly cross-regulate.

TABLE 1

Relative expression of Ildr-family genes transduced with Ildr-siRNAs. Genes of the Ildr-family do not significantly cross-regulate. Data for effects of Ildr1 and Ildr3 siRNAs were determined by qPCR. Data for effects of Ildr2 siRNA are from microarray. Levels of mRNA are normalized to the 36B4 ribosomal housekeeping gene, expressed relative to levels of each gene in control cells transduced with a scrambled, non-specific siRNA sequence.

| | Ildr1 siRNA (n = 3) | | Ildr2 siRNA (n = 10) | | Ildr3 siRNA (n = 3) | |
|---|---|---|---|---|---|---|
| Gene | Relative Expression | P-value | Relative Expression | P-value | Relative Expression | P-value |
| Ildr1 | 0.14 | 1.2E−03 | 0.97 | NS | ND | NA |
| Ildr2 | 0.97 | NS | 0.03 | 6.5E−06 | 1.28 | 3.3E−03 |
| Ildr3 | ND | n/a | 0.73 | 8.0E−05 | 0.03 | 3.4E−03 |

n/a: not applicable;
ND: not done; NS: not significant.

Changes in Ildr2 Expression Affect Liver Morphology and Histology:

Control WT livers (lacZ) were normal in size and appearance in WT animals at 3 and 10 days p.t. but, as expected, were enlarged and grossly steatotic in OB animals (FIG. 3). The ADKD livers (WT and OB) were enlarged and grossly steatotic, whereas the ADOX WT livers were generally normal in appearance and size as were, remarkably, the ADOX OB livers.

Control WT livers were histologically normal with the exception of occasional mild lipid vesiculation and attendant monocytic infiltration, presumably due to adenovirus transduction per se. OB control livers showed extensive large vacuolization with minimal focal lobular lymphocytic infiltration[21]. Livers of ADKD WT mice at 3 days p.t. (FIG. 3A) showed mildly increased periportal vacuolization, modest mononuclear infiltration, occasional apoptosis and autophagy. By 10 days p.t. (FIG. 3B), histologic changes were striking: smaller lipid vesicles in the periportal region progressed to larger droplets at a distance from the portal tract, with ballooning of hepatocytes, autophagy, apoptosis and periportal monocytic inflammation. Some cells showed clumped pink intermediate filaments resembling human Mallory-Denk bodies in steatohepatitis, where they signify hepatocellular oxidative stress [22]. In the fed ADKD animals, increased apoptosis and inflammation were apparent in the context of a preponderance of large droplet fat vesicles. Lobular inflammation reminiscent of human non-alcoholic steatohepatitis was also seen. The livers of ADKD OB mice at 10 days p.t. (FIG. 3C) displayed extensive lipid deposition, with micro-vesiculation accompanied by severe monocytic infiltration, and areas of fibrosis in some animals.

In ADOX WT animals, phenotypic effects were generally modest. At 3 days p.t. (FIG. 3D), livers showed mild, small droplet steatosis, but by 10 days p.t. (FIG. 3E), there were areas of increased apoptosis with minimal lipid deposition or inflam-mation, consistent with a primary effect on ER stress-related responses. In fed animals, glycogen deposition was greatly increased. ADOX OB animals at 10 days p.t. (FIG. 3F) showed substantial reduction in the severity of steatosis (mostly medium and large droplet) with virtually no inflammation or apoptosis. These changes represented a striking "rescue" of the histology seen in the OB control and KD animals.

These gross effects and microscopic characteristics indicate the importance of Ildr2 in hepatic lipid homeostasis, with reduced expression causing lipid accumulation and overexpression acting to reduce this excess in OB livers.

These effects generally increased in severity between 3 and 10 days p.t. Potential mechanisms for these effects and their molecular and physiological consequences were investigated.

Liver and Plasma Chemistry:

Hepatic triglyceride (TG) content was generally consistent with the histological effects of ADKD (Tables 2, 3, and 4) and ADOX (Tables 5, 6, and 7), whereas plasma TG, FFA, and glucose/insulin-related measurements were minimally affected. In contrast, hepatic and plasma cholesterol were greatly increased in refed 10 day ADKD animals. These phenotypes are described in more detail below.

At 3 days p.t. in ADKD WT animals (Table 2), body weight, liver weight and liver total cholesterol (TCH) content were unaffected, as were circulating concentrations of glucose, insulin, TG, TCH, and FFA. However, hepatic TG and glycogen content were significantly increased. Estimates of insulin resistance by HOMA2-IR and b-cell function by HOMA-2B % were unaffected, as were glucose excursions during IPGTT (see below). At 10 days p.t. in ADKD WT animals (Table 3), hepatic and circulating TCH and hepatic TG were increased while circulating TG was unchanged. Again, HOMA measurements were unaffected. In ADKD OB mice at 10 days p.t. (Table 4),—starting from higher baselines (as expected vs. WT animals) [21]—liver weight, TG and TCH content increased, and glycogen content decreased. Circulating concentrations of glucose, insulin, TG, TCH, and IPGTT were unaffected; circulating FFA concentrations were increased.

In ADOX WT animals at 3 days p.t. (Table 5), TG and TCH concentrations per unit wet weight of liver were higher (and glycogen lower) than in control mice. Plasma lipids were unaffected by ADOX. At 10 days p.t. in ADOX WT mice (Table 6), liver TG was lower, and glycogen content higher than in controls. Plasma TG and TCH trended higher in the ADOX animals. At 10 days p.t. in ADOX OB mice (Table 7), liver TG and TCH content were reduced without significant changes in circulating glucose, TG, TCH or FFA. Hepatic glycogen per gram wet weight was unaffected but, given the considerable reduction of TG, was probably decreased per unit liver nitrogen. Measure-ments of blood ALT and AST enzyme levels in these animals indicate that toxic effects of the adenoviral transductions on hepatocyte integrity were minimal.

TABLE 2

Liver and plasma chemistries of ADKD WT mice at 3 days p.t. Mice were chow-fed, 10-week-old B6 (WT) males, intravenously injected with ADKD vectors expressing RNAi for lacZ or Ildr2. Measurements were taken at 3 days p.t. (following a 12-hr fast).
ADKD WT 3 D
Fasted

| Phenotype (n) | lacZ (10) | Ildr2 (10) | P-value |
|---|---|---|---|
| Body weight (g) | 25.9 ± 0.5 | 25.7 ± 0.8 | 0.831 |
| Liver weight (g) | 1.2 ± 0.0 | 1.2 ± 0.0 | 0.772 |
| Hepatic TG (mg/g Liver) | 53.7 ± 5.1 | 69.2 ± 3.1 | 0.018 |
| Hepatic TCH (mg/g Liver) | 6.7 ± 0.1 | 7.2 ± 0.3 | 0.268 |
| Hepatic glycogen (mg/g Liver) | 8.6 ± 2.0 | 20.2 ± 2.9 | 0.008 |
| Plasma glucose (mg/dL) | 182 ± 10 | 216 ± 16 | 0.096 |
| Plasma insulin (μg/L) | 0.15 ± 0.04 | 0.26 ± 0.06 | 0.190 |
| Plasma TG (mg/dL) | 156.8 ± 29.7 | 157.3 ± 20.0 | 0.989 |
| Plasma TCH (mg/dL) | 67.4 ± 1.4 | 70.8 ± 2.4 | 0.250 |
| Plasma FFA (mEq/L) | 1.27 ± 0.03 | 1.29 ± 0.02 | 0.564 |
| Plasma ALT (mU/L) | 134.3 ± 10.3 | 126.2 ± 7.8 | 0.064 |
| Plasma AST (mU/L) | 125.5 ± 8.0 | 126.8 ± 7.3 | 0.707 |

TABLE 2-continued

Liver and plasma chemistries of ADKD WT mice at 3 days p.t. Mice were chow-fed, 10-week-old B6 (WT) males, intravenously injected with ADKD vectors expressing RNAi for lacZ or Ildr2. Measurements were taken at 3 days p.t. (following a 12-hr fast).
ADKD WT 3 D
Fasted

| Phenotype (n) | lacZ (10) | Ildr2 (10) | P-value |
|---|---|---|---|
| HOMA2-IR | 0.59 ± 0.17 | 1.11 ± 0.33 | 0.178 |
| HOMA2-B (%) | 14.3 ± 3.3 | 16.5 ± 2.8 | 0.598 |

n = number of animals in each study.
Data shown are mean 6 SEM;
P values were calculated by 2-tailed t test.
FFA, free fatty acids;
ALT, alanine aminotransferase;
AST, aspartate aminotransferase;
HOMA2-IR, homeostasis model assessment-estimated insulin resistance;
HOMA-2-B (%), homeostasis model assessment-b-cell function.

TABLE 3

Liver and plasma chemistries of ADKD WT mice at 10 days p.t. Mice were chow-fed, 10-week-old B6 (WT) males, intravenously injected with ADKD vectors expressing RNAi for lacZ or Ildr2. Measurements were taken at 10 days p.t. (following either a 24-hr fast "Fasted" or following a 24-hr fast and 12-hr refeeding "Refed").
ADKD WT 10 D

| | Fasted | | | Refed | | |
|---|---|---|---|---|---|---|
| Phenotype (n) | lacZ (5) | Ildr2 (6) | P-value | lacZ (5) | Ildr2 (6) | P-value |
| Body weight (g) | 25.1 | 27.5 | 0.084 | 27.5 | 27.5 | 0.983 |
| Liver weight (g) | 1.3 | 2.1 | 0.000 | 2.1 | 2.5 | 0.096 |
| Hepatic TG (mg/g Liver) | 46.4 ± 2.9 | 88.6 ± 6.5 | 0.001 | 18.6 ± 2.8 | 76.9 ± 7.0 | 0.000 |
| Hepatic TCH (mg/g Liver) | 9.8 ± 0.6 | 18.0 ± 1.7 | 0.005 | 7.6 ± 0.4 | 14.8 ± 1.4 | 0.003 |
| Hepatic glycogen (mg/g Liver) | 1.9 ± 0.2 | 3.2 ± 0.5 | 0.039 | 58.0 ± 3.6 | 37.1 ± 2.1 | 0.007 |
| Plasma glucose (mg/dL) | 81 ± 7 | 86 ± 3 | 0.619 | 187 ± 5 | 153 ± 8 | 0.009 |
| Plasma insulin (μg/L) | 0.26 ± 0.10 | 0.25 ± 0.02 | 0.903 | 4.91 ± 0.75 | 5.99 ± 1.68 | 0.576 |
| Plasma TG (mg/dL) | 114.2 ± 19.0 | 138.0 ± 17.0 | 0.362 | 203.8 ± 22.9 | 243.0 ± 27.0 | 0.275 |
| Plasma TCH (mg/dL) | 131.7 ± 4.0 | 254.0 ± 24.8 | 0.003 | 135.5 ± 8.8 | 313.3 ± 32.4 | 0.001 |
| Plasma FFA (mEq/L) | 1.52 ± 0.06 | 1.25 ± 0.13 | 0.093 | 1.05 ± 0.18 | 0.72 ± 0.03 | 0.150 |
| Plasma ALT (mU/L) | 44.5 ± 6.2 | 51.1 ± 9.3 | 0.598 | 46.6 ± 3.0 | 48.3 ± 6.0 | 0.812 |
| Plasma AST (mU/L) | 46.5 ± 6.8 | 48.8 ± 9.2 | 0.852 | 49.6 ± 3.7 | 47.5 ± 6.5 | 0.797 |
| HOMA2-IR | 0.85 ± 0.35 | 0.80 ± 0.09 | 0.901 | n/a | n/a | n/a |
| HOMA2-B (%) | 94.4 ± 22.2 | 91.0 ± 9.0 | 0.989 | n/a | n/a | n/a |

n = number of animals in each study.
n/a: not applicable.
Data shown are mean 6 SEM;
P values were calculated by 2-tailed t test.
TG, triglycerides;
TCH, total cholesterol;
FFA, free fatty acids;
ALT, alanine aminotransferase;
AST, aspartate aminotransferase;
HOMA2-IR, homeostasis model assessment-estimated insulin resistance;
HOMA-2-B (%), homeostasis model assessment-b-cell function.
Other data showed B6 mice fasted for 12 hr and not treated with adenovirus had plasma ALT of 86.0 mU/L and AST of 94.6 mU/L.

TABLE 4

Liver and plasma chemistries of ADKD OB mice at 10 days p.t. Mice were chow-fed, 10-week-old B6.V-Lepob/J (OB) males, intravenously injected with ADKD vectors expressing RNAi for lacZ or Ildr2. Measurements were taken at 10 days p.t. (following either a 24-hr fast "Fasted" or following a 24-hr fast and 12-hr refeeding "Refed").
ADKD OB 10 D

| | Fasted | | | Refed | | |
|---|---|---|---|---|---|---|
| Phenotype (n) | lacZ (3) | Ildr2 (4) | P-value | lacZ (3) | Ildr2 (4) | P-value |
| Body weight (g) | 46.7 ± 0.4 | 46.8 ± 0.9 | 0.961 | 46.4 ± 3.1 | 47.3 ± 1.9 | 0.845 |
| Liver weight (g) | 4.2 ± 0.5 | 5.8 ± 0.3 | 0.012 | 3.4 ± 0.1 | 6.4 ± 0.7 | 0.047 |

TABLE 4-continued

Liver and plasma chemistries of ADKD OB mice at 10 days p.t. Mice were chow-fed, 10-week-old B6.V-Lepob/J (OB) males, intravenously injected with ADKD vectors expressing RNAi for lacZ or Ildr2. Measurements were taken at 10 days p.t. (following either a 24-hr fast "Fasted" or following a 24-hr fast and 12-hr refeeding "Refed").

ADKD OB 10 D

| | Fasted | | | Refed | | |
|---|---|---|---|---|---|---|
| Phenotype (n) | lacZ (3) | Ildr2 (4) | P-value | lacZ (3) | Ildr2 (4) | P-value |
| Hepatic TG (mg/g Liver) | 77.5 ± 4.0 | 113.7 ± 6.8 | 0.037 | 77.0 ± 1.0 | 118.0 ± 7.3 | 0.041 |
| Hepatic TCH (mg/g Liver) | 10.6 ± 1.5 | 16.5 ± 3.4 | 0.189 | 8.9 ± 0.7 | 16.9 ± 3.6 | 0.203 |
| Hepatic glycogen (mg/g Liver) | 43.0 ± 0.4 | 14.6 ± 3.8 | 0.004 | 44.2 ± 1.9 | 5.8 ± 1.3 | 0.001 |
| Plasma glucose (mg/dL) | 175 ± 29 | 116 ± 20 | 0.215 | 379 ± 79 | 214 ± 28 | 0.233 |
| Plasma insulin (μg/L) | 18.1 ± 10.1 | 27.2 ± 19.5 | 0.707 | 77.8 ± 33.1 | 103.5 ± 5.3 | 0.576 |
| Plasma TG (mg/dL) | 97.6 ± 28.0 | 133.5 ± 16.1 | 0.395 | 121.0 ± 24.5 | 195.4 ± 24.2 | 0.135 |
| Plasma TCH (mg/dL) | 110.3 ± 2.5 | 104.0 ± 2.5 | 0.173 | 112.6 ± 9.7 | 133.7 ± 8.5 | 0.231 |
| Plasma FFA (mEq/L) | 1.23 ± 0.01 | 1.71 ± 0.08 | 0.012 | 1.31 ± 0.07 | 2.44 ± 0.16 | 0.013 |
| Plasma ALT (mU/L) | 93.2 ± 4.0 | 107.2 ± 4.1 | 0.006 | 105.9 ± 9.6 | 126.8 ± 25.3 | 0.274 |
| Plasma AST (mU/L) | 88.9 ± 2.3 | 110.0 ± 11.3 | 0.036 | 93.4 ± 10.6 | 115.8 ± 37.1 | 0.421 |

n = number of animals in each study.
Data shown are mean 6 SEM;
P values were calculated by 2-tailed t test.
TG, triglycerides;
TCH, total cholesterol;
FFA, free fatty acids;
ALT, alanine aminotransferase;
AST, aspartate aminotransferase.

TABLE 5

Liver and plasma chemistries of ADOX WT mice at 3 days p.t. Mice were chow-fed, 10-week-old B6 (WT) males, intravenously injected with ADOX vectors expressing GFP or Ildr2. Measurements were taken at 3 days p.t. (following a 12-hr fast).

ADOX WT 3 D

Fasted

| Phenotype (n) | GFP (9) | Ildr2 (9) | P-value |
|---|---|---|---|
| Body weight (g) | 25.1 ± 0.7 | 24.3 ± 0.6 | 0.439 |
| Liver weight (g) | 1.2 ± 0.0 | 1.0 ± 0.0 | 0.004 |
| Hepatic TG (mg/g Liver) | 93.0 ± 11.9 | 124.3 ± 9.6 | 0.073 |
| Hepatic TCH (mg/g Liver) | 10.7 ± 1.2 | 15.6 ± 1.6 | 0.038 |
| Hepatic glycogen (mg/g Liver) | 14.6 ± 2.2 | 6.2 ± 2.1 | 0.009 |
| Plasma glucose (mg/dL) | 159 ± 6 | 166 ± 13 | 0.637 |
| Plasma insulin (μg/L) | 0.15 ± 0.04 | 0.21 ± 0.04 | 0.316 |
| Plasma TG (mg/dL) | 127.3 ± 21.9 | 153.3 ± 14.2 | 0.338 |
| Plasma TCH (mg/dL) | 65.3 ± 0.9 | 72.1 ± 2.8 | 0.052 |
| Plasma FFA (mEq/L) | 1.28 ± 0.03 | 1.35 ± 0.09 | 0.502 |
| Plasma ALT (mU/L) | 79.5 ± 15.1 | 99.4 ± 13.1 | 0.008 |
| Plasma AST (mU/L) | 78.0 ± 20.5 | 93.3 ± 13.0 | 0.089 |

TABLE 5-continued

Liver and plasma chemistries of ADOX WT mice at 3 days p.t. Mice were chow-fed, 10-week-old B6 (WT) males, intravenously injected with ADOX vectors expressing GFP or Ildr2. Measurements were taken at 3 days p.t. (following a 12-hr fast).

ADOX WT 3 D

Fasted

| Phenotype (n) | GFP (9) | Ildr2 (9) | P-value |
|---|---|---|---|
| HOMA2-IR | 0.56 ± 0.16 | 0.79 ± 0.15 | 0.347 |
| HOMA2-B (%) | 17.7 ± 3.8 | 23.5 ± 4.7 | 0.302 |

n = number of animals in each study.
Data shown are mean ± SEM;
P values were calculated by 2-tailed t test.
TG, triglycerides;
TCH, total cholesterol;
FFA, free fatty acids;
ALT, alanine aminotransferase;
AST, aspartate aminotransferase;
HOMA2-IR, homeostasis model assessment-estimated insulin resistance;
HOMA-2-B (%), homeostasis model assessment-β-cell function.

TABLE 6

Liver and plasma chemistries of ADOX WT mice at 10 days p.t. Mice were chow-fed, 10-week-old B6 (WT) males, intravenously injected with ADOX vectors expressing GFP or Ildr2. Measurements were taken at 10 days p.t. (following either a 24-hr fast "Fasted" or following a 24-hr fast and 12-hr refeeding "Refed").

ADOX WT 10 D

| | Fasted | | | Refed | | |
|---|---|---|---|---|---|---|
| Phenotype (n) | GFP (5) | Ildr2 (6) | P-value | GFP (5) | Ildr2 (6) | P-value |
| Body weight (g) | 24.1 | 23.2 | 0.607 | 27.5 | 26.0 | 0.112 |
| Liver weight (g) | 1.0 | 1.3 | 0.011 | 1.7 | 2.2 | 0.030 |
| Hepatic TG (mg/g Liver) | 64.9 ± 6.9 | 33.0 ± 4.7 | 0.004 | 31.3 ± 5.5 | 20.0 ± 5.6 | 0.191 |
| Hepatic TCH (mg/g Liver) | 11.4 ± 0.8 | 7.4 ± 0.6 | 0.005 | 6.8 ± 0.7 | 5.4 ± 0.9 | 0.272 |
| Hepatic glycogen (mg/g Liver) | 1.1 ± 0.3 | 4.0 ± 0.9 | 0.033 | 63.0 ± 1.3 | 71.2 ± 0.4 | 0.048 |
| Plasma glucose (mg/dL) | 105 ± 4 | 92 ± 4 | 0.056 | 211 ± 4 | 155 ± 3 | 0.001 |
| Plasma insulin (μg/L) | 0.34 ± 0.09 | 0.34 ± 0.07 | 0.988 | 5.67 ± 0.09 | 4.95 ± 0.07 | 0.560 |
| Plasma TG (mg/dL) | 57.6 ± 2.5 | 98 ± 9.6 | 0.005 | 192.8 ± 23.0 | 246.1 ± 22.4 | 0.117 |
| Plasma TCH (mg/dL) | 114.6 ± 8.9 | 123.9 ± 11.6 | 0.563 | 125.7 ± 2.3 | 145.7 ± 1.2 | 0.005 |
| Plasma FFA (mEq/L) | 1.25 ± 0.16 | 1.70 ± 0.19 | 0.148 | 0.65 ± 0.18 | 0.82 ± 0.10 | 0.470 |

TABLE 6-continued

Liver and plasma chemistries of ADOX WT mice at 10 days p.t. Mice were chow-fed, 10-week-old B6 (WT) males, intravenously injected with ADOX vectors expressing GFP or Ildr2. Measurements were taken at 10 days p.t. (following either a 24-hr fast "Fasted" or following a 24-hr fast and 12-hr refeeding "Refed").

ADOX WT 10 D

| | Fasted | | | Refed | | |
|---|---|---|---|---|---|---|
| Phenotype (n) | GFP (5) | Ildr2 (6) | P-value | GFP (5) | Ildr2 (6) | P-value |
| Plasma ALT (mU/L) | 66.9 ± 5.1 | 32.1 ± 0.3 | 0.021 | 72.2 ± 6.3 | 41.1 ± 1.9 | 0.042 |
| Plasma AST (mU/L) | 65.6 ± 3.7 | 31.4 ± 0.5 | 0.012 | 68.0 ± 6.2 | 41.1 ± 2.7 | 0.028 |
| HOMA2-IR | 1.36 ± 0.25 | 1.10 ± 0.19 | 0.435 | n/a | n/a | n/a |
| HOMA2-B (%) | 86.0 ± 14.8 | 100.0 ± 18.8 | 0.570 | n/a | n/a | n/a |

n = number of animals in each study.
n/a: not applicable.
Data shown are mean ± SEM;
P values were calculated by 2-tailed t test.
TG, triglycerides;
TCH, total cholesterol;
FFA, free fatty acids;
ALT, alanine aminotransferase;
AST, aspartate aminotransferase;
HOMA2-IR, homeostasis model assessment-estimated insulin resistance;
HOMA-2-B (%), homeostasis model assessment-β-cell function.

TABLE 7

Liver and plasma chemistries of ADOX OB mice at 10 days p.t. Mice were chow-fed, 10-week-old B6.V-$Lep^{ob/J}$ (OB) males, intravenously injected with ADOX vectors expressing GFP or Ildr2. Measurements were taken at 10 days p.t. (following either a 24-hr fast "Fasted" or following a 24 hr fast and 12 hr refeeding "Refed").

ADOX OB 10 D

| | Fasted | | | Refed | | |
|---|---|---|---|---|---|---|
| Phenotype (n) | GFP (4) | Ildr2 (4) | P-value | GFP (4) | Ildr2 (4) | P-value |
| Body weight (g) | 45.1 ± 1.4 | 48.2 ± 0.6 | 0.120 | 46.9 ± 1.1 | 43.7 ± 0.8 | 0.066 |
| Liver weight (g) | 3.4 ± 0.2 | 3.9 ± 0.3 | 0.321 | 4.6 ± 0.3 | 3.4 ± 0.1 | 0.042 |
| Hepatic TG (mg/g Liver) | 49.5 ± 5.7 | 27.1 ± 3.0 | 0.019 | 56.4 ± 4.4 | 32.3 ± 4.0 | 0.007 |
| Hepatic TCH (mg/g Liver) | 7.7 ± 0.6 | 5.6 ± 0.2 | 0.038 | 6.4 ± 0.2 | 5.1 ± 0.29 | 0.015 |
| Hepatic glycogen (mg/g Liver) | 50.4 ± 4.3 | 53.5 ± 3.7 | 0.606 | 62.8 ± 101.6 | 61.3 ± 103.6 | 0.689 |
| Plasma glucose (mg/dL) | 151 ± 10 | 174 ± 24 | 0.420 | 224 ± 29 | 263 ± 20 | 0.349 |
| Plasma insulin (μg/L) | 13.6 ± 4.4 | 24.5 ± 2.5 | 0.168 | 73.9 ± 19.1 | 89.3 ± 4.0 | 0.489 |
| Plasma TG (mg/dL) | 94.3 ± 27.2 | 129.8 ± 43.4 | 0.538 | 137.6 ± 18.3 | 135.4 ± 11.7 | 0.925 |
| Plasma TCH (mg/dL) | 134.0 ± 3.5 | 129.0 ± 3.9 | 0.383 | 143.1 ± 4.8 | 130.9 ± 2.6 | 0.086 |
| Plasma FFA (mEq/L) | 1.66 ± 0.09 | 1.46 ± 0.05 | 0.119 | 2.25 ± 0.29 | 1.76 ± 0.12 | 0.206 |
| Plasma ALT (mU/L) | 115.1 ± 18.4 | 109.7 ± 15.7 | 0.668 | 108.0 ± 5.4 | 100.1 ± 15.3 | 0.386 |
| Plasma AST (mU/L) | 106.1 ± 8.8 | 101.7 ± 13.8 | 0.611 | 102.7 ± 12.7 | 98.7 ± 17.0 | 0.718 |

n = number of animals in each study.
Data shown are mean ± SEM;
P values were calculated by 2-tailed t test.
TG, triglycerides;
TCH, total cholesterol;
FFA, free fatty acids;
ALT, alanine aminotransferase;
AST, aspartate aminotransferase.

TABLE 8

Triglyceride and cholesterol content of ADKD and ADOX hepatocytes. Hepatocytes from 5, 10-week-old B6 mice were extracted, pooled and plated into individual wells and exposed for 24 hr to either the ADOX or ADKD (or empty vector control) virus in triplicate. Cells were lysed and triglyceride and total cholesterol were determined.

| | ADKD | | | ADOX | | |
|---|---|---|---|---|---|---|
| | lacZ | ILDR2 | P-value | GFP | Ildr2 | P-value |
| Triglyceride (mg/g protein) | 103.1 ± 2.3 | 119.4 ± 3.4 | 0.019 | 105.5 ± 3.9 | 92.7 ± 1.3 | 0.056 |

TABLE 8-continued

Triglyceride and cholesterol content of ADKD and ADOX hepatocytes. Hepatocytes from 5, 10-week-old B6 mice were extracted, pooled and plated into individual wells and exposed for 24 hr to either the ADOX or ADKD (or empty vector control) virus in triplicate. Cells were lysed and triglyceride and total cholesterol were determined.

| | ADKD | | | ADOX | | |
|---|---|---|---|---|---|---|
| | lacZ | ILDR2 | P-value | GFP | Ildr2 | P-value |
| Cholesterol (mg/g protein) | 7.58 ± 0.37 | 8.45 ± 0.40 | 0.083 | 8.43 ± 0.96 | 6.62 ± 0.45 | 0.081 |

TABLE 9

Area under the curve calculations for calorimetry.

| | WILD-TYPE | | | | OB/OB | | | |
|---|---|---|---|---|---|---|---|---|
| | ADKD | | ADOX | | ADKD | | ADOX | |
| AUC | lacZ | Ildr2 | GFP | Ildr2 | lacZ | Ildr2 | GFP | Ildr2 |
| 24-hr | 43.2 ± 0.6 | 40.8 ± 0.6* | 42.1 ± 0.6 | 42.0 ± 0.4 | 42.0 ± 0.8 | 40.9 ± 1.4 | 39.5 ± 0.8 | 40.3 ± 1.3 |
| Day | 20.1 ± 0.5 | 19.2 ± 0.5 | 19.6 ± 0.4 | 19.7 ± 0.2 | 19.8 ± 0.4 | 20.0 ± 0.6 | 19.1 ± 0.3 | 19.5 ± 0.6 |
| Night | 23.1 ± 0.3 | 21.6 ± 0.3** | 22.4 ± 0.2 | 22.3 ± 0.3 | 22.3 ± 0.6 | 20.9 ± 0.8 | 20.5 ± 0.5 | 20.8 ± 0.7 |

*p < 0.05;
**p < 0.01; AUC, area under the curve.

Analysis of In Vivo Lipoprotein Production and Clearance:

The increase in hepatic TG and TCH in the ADKD mice could reflect: 1. increased assembly/reduced secretion of lipoproteins; 2. increased synthesis/decreased oxidation of TG; 3. increased synthesis/decreased disposal of cholesterol. Detergents such as Triton WR1339 block clearance of TG in circulating lipoproteins by inhibiting lipoprotein lipase (LPL)-mediated lipolysis of circulating TG-rich lipoproteins [23]. When LPL is inhibited, changes in circulating concentrations of lipoprotein species reflect hepatic secretion rates of very low-density lipoprotein (VLDL). Concentrations of plasma TG were measured following LPL inhibition with Triton WR1339 in 10-week-old chow fed ADKD and ADOX WT mice at 7 days p.t. (FIG. 4). Area under the curve (AUC) analysis of hepatic lipoprotein secretion shows no significant difference in either ADKD (FIG. 4A) or ADOX mice (FIG. 4B). These results suggest that in ADKD mice, the increased hepatic lipids did not stimulate increased VLDL secretion and that, consequently, the increased plasma lipids, notably TCH, reflected reduced hepatic lipoprotein clearance. Likewise, the decreased hepatic lipids in ADOX mice were not due to increased VLDL secretion. Increased hepatic lipid synthesis in ADKD mice was not coupled to secretion or decreased hepatic fatty acid oxidation. In contrast, ADOX mice could have had decreased hepatic lipid synthesis or increased fatty acid oxidation. Finally, it is interesting to note that in these animals, glucose tolerance was normal despite severe hepatic steatosis [24].

Steady-State Lipoprotein Analysis:

Based upon the striking changes in hepatic lipid content without evidence of change in lipoprotein export, qualitative and quantitative changes in circulating lipoproteins in response to transient manipulations of Ildr2 expression were of interest. Particularly, determining if the dramatic increase in TCH in the ADKD mice represented increased TCH in VLDL or LDL, or decreased TCH in high-density lipoprotein (HDL) was of interest. In analysis by fast protein liquid chromatography (FPLC) of fasted plasma obtained prior to the Triton study (FIG. 5), VLDL cholesterol (fractions 12-16) and IDL/LDL cholesterol (fractions 17-23) were clearly higher, and HDL cholesterol (fractions 24-30) was ~20% lower in the ADKD animals (FIG. 5A, 5C). In ADOX animals (FIG. 5B, 5D), VLDL was similarly increased, LDL was not altered, and HDL was also slightly reduced. These results are consistent with the data reported in Tables 2, 3, 4, 5, 6, and 7 in which ADKD animals had higher absolute circulating TG than ADOX animals and where WT fasted and refed ADKD mice exhibited increases in plasma TCH and TG vs. controls, whereas WT ADOX mice exhibited more moderate changes.

Hepatic Gene-Expression Signatures:

To assess possible molecular bases for these changes in liver histology and lipid/glycogen chemistry with the remarkably minimal effects of these changes on systemic lipid and insulin homeostasis, hepatic expression of genes related to acylglyceride, cholesterol and glucose homeostasis and ER-resident molecules mediating responses to metabolic stress were examined (FIG. 6).

In ADKD WT animals, at 3 days p.t. (FIG. 6A), increases in transcript levels of genes involved in acylglyceride synthesis were consistent with increased TG content; however, at 10 days p.t. (FIG. 6B), transcripts of genes related to acylglyceride synthesis were reduced (where Fas expression was especially decreased in the fed animals), as were genes related to cholesterol homeostasis and FFA catabolism. Unlike the livers at 3 days p.t., those at 10 days displayed a general suppression of transcripts of genes mediating both synthesis and oxidation of hepatic lipids. The general suppression of transcripts of genes mediating both synthesis and oxidation of hepatic lipids between days 3 and 10 suggests that the accumulation of hepatic lipids due to effects of inhibition of Ildr2 transcription resulted in secondary suppression of the expression of these genes.

In ADKD OB animals at 10 days p.t. (FIG. 6C), Ildr2 knockdown greatly reduced the expression levels of all transcripts examined compared to the control (lacZ) animals. These effects were comparable, though more extensive and proportionately greater, than in the corresponding studies of WT animals, possibly reflecting, in part, the consequences of pre-existing hepatic steatosis.

In livers of ADOX WT mice at 3 days p.t. (FIG. 6D), as in the ADKD livers, in the context of an increase in TCH content (and a trend towards increased TG), transcript levels of genes mediating the synthesis of these molecules were generally reduced, although transcript levels of some fatty acid oxidation genes were slightly increased. However, at 10 days p.t. (FIG. 6E), transcript levels of genes related to glucose metabolism and acylglyceride synthesis were increased.

In livers of ADOX OB animals at 10 days p.t. (FIG. 6F), the very high levels of lipid accumulation due to the obesity of these animals were reduced by over-expression of Ildr2. In association with this reduction, levels of transcripts related to neutral lipid synthesis and cholesterol are increased, suggesting "relief" of the secondary suppression imposed by lipid accumulation as mentioned above [25].

ER Stress Pathways:

The apparent fixed location of ILDR2 in the ER (see FIG. 2) raises the possibility that the protean effects of hypomorphism for this gene might be related to a role in the mediation of ER stress responses [12]. Such a role would not be inconsistent with an independent effect on lipoprotein metabolism [26]. Accordingly, transcription rates of canonical members of the ER stress response pathways [27] were examined.

In ADKD WT animals at 3 days p.t., expression of ER stress effectors Perk, Atf6, and Ire1 was slightly reduced, while expression of transducers Atf4 and Chop was increased. In general, Ildr2 over-expression was associated with increased expression of ER stress pathway genes, while Ildr2 knockdown was associated with decreased expression. Effects were greater at 10 days than at 3 days p.t.

Increases in hepatocyte lipids activate ER stress pathways [28]-[30], and activation of ER stress pathways increases hepatic lipid deposition[31]-[33]. Given these reciprocal interactions, and the relatively extended time course over which these studies were conducted, it is not possible to assign causal primacy to either the effects on lipid synthesis or ER stress responses. The data are also consistent with the possibility that ILDR2 has primary effects on both processes. Experiments conducted in isolated hepatocytes (see FIG. 7) demonstrate that in vitro knockdown of Ildr2 modestly increases ER stress-related transcripts over a 48-hr period. Longer term, these responses may be exhausted [34], [35]. The apparent paradox of increased ER stress responses in both ADKD and ADOX hepatocytes may be due to the former's reflecting the response to increased cellular lipids, and the latter to direct interactions of the ILDR2 molecule with elements of the ER stress pathways. The increase in ER stress molecules is presumably partially protective [36]-[38].

Short-Term Effects of Ildr2 Expression on Lipid Metabolism and ER Stress Pathways in Hepatocytes:

ER stress can affect lipid metabolism and vice versa [31], [39], [40], and molecules such as XBP1 can independently affect both pathways [26]. In an effort to disarticulate—by shortening the experimental time course—possible contributions of ILDR2 to ER stress response mechanisms, C57BL/6J mouse primary hepatocytes were transduced for 24 hr with Ildr2 ADKD and ADOX adenoviral vectors and examined cellular lipid content (Table 8) and expression of genes of lipid biochemical and UPR/ER stress pathways (FIG. 7).

In the ADKD cells, TG and TCH content were increased, consistent with the changes seen in the in vivo studies. Only slight changes were seen in the transcripts analyzed, with no indication of primacy of Ildr2 knockdown effects on either lipid synthesis or ER stress genes (FIG. 7A). In the ADOX cells, TG and TCH content were reduced in the context of large, reciprocal changes in both lipogenesis, where Ldlr and Srebp1c decreased, and ER stress effectors, where Atf6 and Ire1 increased (FIG. 7B). The comparable magnitude of these changes makes it difficult to assign primacy, but is consistent with a role for Ildr2 in both pathways. If these in vitro data at 24 hr are viewed in the context of the 3 and 10 day in vivo studies, it is apparent that there are strong temporal effects of responses of the ER stress pathways, and that the responses are influenced by intercurrent processes, probably lipid deposition per se.

Effects of Feeding Status, Diet, and Ob Genotype on Ildr2 Expression:

Hepatic lipid homeostasis is strongly affected by fasting and refeeding and by diet [41]. To study their effects on Ildr2, levels of Ildr2 expression were compared in livers of WT mice fed either chow or a high-fat diet (FIG. 8). These results show that feeding status (the difference between fasted and refed mice) had little effect on Ildr2 expression, whereas obesity achieved by feeding a high-fat diet, increased Ildr2 levels by 3.6 fold (FIG. 8A). To determine if this effect was leptin-dependent, Ildr2 expression in livers of OB (leptin-deficient) mice was also analyzed. These mice showed a 3.7 fold increase in Ildr2 expression compared to age-matched WT controls (FIG. 8B). The large increases in ildr2 expression, caused by leptin deficiency and high-fat feeding are presumably secondary—at some level—to the deposition of TG in the hepatocytes under both circumstances. Given the possible dual roles of Ildr2, this effect could reflect a role of Ildr2 in ER stress responses.

Calorimetry:

To determine if there were differences in energy expenditure, physical activity, or metabolic substrate use in the mice in any of the models used (ADKD and ADOX in both WT and OB), indirect calorimetry (72-hr) was performed on chow-fed, 10-week-old WT and OB males, 4 to 5 days p.t. (FIG. 9; Table 9).

There were no differences in rates or patterns of 24-hour energy expenditure in WT mice between knockdown and control. However, in WT (FIG. 9A) and OB (FIG. 9C) ADKD mice, the nocturnal respiratory exchange ratio (RER) was 7% lower vs. controls, indicating that, at night, the ADKD mice preferentially oxidize fat to a greater extent than the WT mice. In WT (FIG. 9B) and OB (FIG. 9D) ADOX animals, the RER was not significantly different between the two groups at any time, although the OB mice had a slightly higher RER during the dark period. These data are consistent with hepatic lipid content influencing systemic fuel oxidation: higher fat content increasing fatty acid oxidation, resulting in a lower RER.

ipGTT (Intraperitoneal Glucose Tolerance Tests):

To assess systemic effects of changes in hepatic lipid and glycogen content on peripheral glucose homeostasis, ipGTT was performed on chow-fed, 10-week-old WT and OB males, 7 days p.t. with Ildr2 ADKD and ADOX constructs (FIG. 10). Surprisingly, no differences in systemic glucose tolerance were detected in ADKD or ADOX animals versus either their respective controls, or each other. Consistent with these findings, HOMA IR values based on data obtained at the time of sacrifice of ADKD and ADOX mice (at 10 days p.t.) were not significantly different (see Table 2). Thus, large changes in hepatic lipid content were not accompanied by changes in systemic glucose/insulin homeostasis. This finding has implications for the possible mechanism(s) underlying the effects of Ildr2 on hepatic lipid synthesis and handling.

Discussion.

Based upon manipulation of levels of expression of Ildr2 in liver and isolated hepatocytes using ADKD and ADOX constructs, the results described herein show ILDR2 is an ER membrane protein that participates in cellular lipid synthesis and responses to ER stress. The most salient phenotype in the ADKD mice is TG accumulation, accompanied by increased hepatic and plasma cholesterol and a mix of micro- and macro-vesicular lipid droplets in periportal hepatocytes. Overexpression of Ildr2 in ob/ob mice substantially rescued their hepatic steatosis, as Ildr2 overexpressing mice had significantly decreased hepatic TG and TCH and reduced periportal vacuolar deposition.

Despite the excess lipid in the livers at 10 days p.t., transcript levels for major lipogenic and fat-oxidative genes were reduced in ADKD mice and up-regulated in ADOX mice. At 3 days p.t., several of these genes showed changes in expression in the opposite direction, suggesting that down-regulation in ADKD mice at 10 days p.t. may have been a response to excess lipid accumulation. These changes in transcriptional profiles are likely secondary to the respective increased/decreased lipid content of the hepatocytes. Also relevant in considering the molecular pathogenesis of the steatosis in the ADKD animals is the absence of major changes of circulating TG or cholesterol in these animals, their apparently normal rates of hepatic TG secretion, and the absence of significant changes in glucose or insulin homeostasis. In ADKD mice, reduced hepatic VLDL/IDL/LDL clearance and increased circulating IDL/LDL cholesterol suggests a reduction in hepatic LDL receptor-mediated clearance of those lipoproteins, consistent with reduced expression of hepatic LDL receptor [42], [43].

Lipid accumulation in the liver is commonly associated with liver and/or systemic insulin resistance and resultant hyperglycemia. Indeed, hepatic steatosis is commonly implicated as a causative factor in these phenotypes that are aspects of the metabolic syndrome [44]-[46]. However, in the ADKD animals, large changes in hepatic lipid content were not accompanied by changes in systemic glucose/insulin homeostasis [47]. Decreased lipid droplet turnover and/or enhanced traffic of newly synthesized TG from the ER to the cytoplasmic droplets might be related to the apparent absence of effect of the increased lipid deposition on glucose/insulin homeostasis. Since neither insulin resistance nor hyperglycemia was present in the ADKD mice (similar in this regard to the phenotype of mice hypomorphic for hepatic Atgl) [24], [48], [49], other mechanisms relating Ildr2 to hepatic steatosis were investigated.

Localization of ILDR2 in the ER membrane, up-regulation of ER stress markers in the livers of ADOX mice and down-regulation in ADKD mice, along with the emerging relationship between hepatic lipid accumulation and ER stress in several metabolic disorders, including obesity, hepatic steatosis and type II diabetes [16], [31], [50], suggest that ILDR2 might have a role in cellular ER stress responses.

Three known pathways provide mechanisms whereby Ildr2 regulation of hepatocyte lipid metabolism and ER stress could be achieved:

1. ILDR2 has a primary role in ER function, where ER stress produced by Ildr2 knockdown leads to lipid accumulation. Overexpression of the ER stress chaperone BIP (GRP78) in ob/ob mice (as with Ildr2) reverses hepatic steatosis [51], and hypomorphic expression of UPR modulators Atf6, Ire1α, Chop, and Crebh in mouse models cause hepatic dyslipidemia [32], [33], [52], [53].

2. ILDR2 has a primary role in lipid metabolism, where Ildr2 knockdown leads to lipid accumulation, which causes ER stress. Excess intracellular fatty acids induce ER stress in the liver via pathways affecting ER membrane integrity and calcium homeostasis [40], [54], increasing Chop expression[55], inducing PERK signaling [28] and stimulating CREBh-induced inflammation[56], [57]. Additionally, fatty acid-binding protein-4 (aP2) has a primary role in lipid metabolism and mitigates ER stress in macrophages [39].

3. ILDR2 is independently involved in both ER function and lipid metabolism, as has been suggested for the ER stress-related gene, Xbp1, a key transcription factor and effector of the UPR which is spliced by IRE1a in response to ER stress. Xbp1 KO mice show reduced hepatic TG secretion and decreased fatty acid oxidation, along with down-regulation of key hepatic lipogenic genes [26]. Without being bound by theory, ILDR2 may be a transcription factor, by acting on downstream signaling targets, including transcription factors, it could independently affect the UPR and lipid metabolism.

The broad down-regulation of lipid metabolism and ER stress genes in the ADKD mice at 10 days p.t. is consistent with studies of pharmacologically-induced ER stress, in which expression of genes involved in lipid metabolism and ER stress initially increases and then declines. This pattern has been observed both in vitro and in vivo for spliced Xbp1, Chop, Bip, lipogenic transcription factors, lipid droplet proteins, and TG synthesis genes [34]. If Ildr2 knockdown induces ER stress in these mice, then by 10 days the decline of previously up-regulated ER stress and metabolic genes may be observed.

Since it remains uncertain, which gene expression effects are primary in the pathogenesis of the hepatic steatosis, and which may be responses to the steatosis per se, the data obtained in the 3 and 10 day adenovirus transductions should be cautiously interpreted. Absence of a clear pattern in the differential responses of the canonical UPR pathways seen in the studies reported here suggests that these variable responses may reflect differences in the timing of the responses of specific molecules and pathways coupled with secondary effects of the accumulation of hepatic lipids [58].

Ildr2-mediated effects on lipid homeostasis and ER stress responses could account for both the hepatic steatosis observed in the ADKD animals reported here, and the reduced β-cell mass and accompanying glucose intolerance in the Chr1 B6.DBA ob/ob congenic animals [1]. Perk-null mice develop ER stress specifically in the β-cell, with morphological abnormalities within the pancreatic ER leading to loss of β-cells, and hypoinsulinemic hyperglycemia [59]. Deregulation of lipid metabolism in a β-cell line impaired insulin secretion[60].

In a recent study, ILDR2, along with ILDR1 and ILDR3, was localized to tricellular junctions on the PM of mouse epithelial cells—specifically fibroblasts, mammary and retinal epithelia, and choroid plexus [61]. Without being bound by theory, these molecules can mediate macromolecular access through these "tight junctions". However, no specific effort was made to visualize ILDR2 or other ILDR molecules in the ER. As has been described for the thyrotropin-releasing hormone receptor, which is localized to the PM in pituitary cells but to the ER and Golgi in non-pituitary cells [62], ILDR2 may localize primarily to the PM in epithelial cells, and to the ER in other cell types (e.g. hepatocytes, neurons, β-cells). Alternatively, subcellular distribution of members of this family of proteins may reflect cell type-specific splicing patterns, as reported for BAT3 [63].

Materials and Methods.

Animal Care: Mice were housed in a vivarium maintained on a 12 hr-12 hr light-dark cycle, with ad libitum access to 5058 Purina PicoLab Mouse Diet 20 (9% fat) and water, unless otherwise stated. All mice were sacrificed at the same time-of-day (1000-1200 hr).

Strains: Male 9-week-old C57BL/6J (B6) (Stock number 000664) and B6.V-Lepob/J (ob/ob) (Stock number 000632) mice were obtained from Jackson Laboratories (Bar Harbor, Me.) and allowed to adjust to conditions in our local colony for 1 week prior to starting experiments. Mice used to study the effects of feeding status and diet (FIG. 8A) were fed high-fat chow (60% kcals from fat) at Jackson Laboratories from 6 weeks of age until purchase at 18 weeks of age. Mice were fed ad libitum high-fat chow (Research Diets D12492i) for 4 additional weeks.

Metabolic Parameters: Body mass and composition: Weight was measured with a Vicon Vic-212 integrating laboratory scale (Acculab). Fat and lean mass were measured with a Minispec TD-NMR Analyzer (Bruker Optics), calibrated using mouse carcasses [64].

Serum: Blood was collected at sacrifice. Plasma was analyzed for glucose using an Autokit Glucose (Wako), for TG using an L-Type TG M Color A (Wako), for TCH using Cholesterol E (Wako), for FFA using HR Series NEFA-HR (2) Color Reagent B (Wako) and insulin using an Ultra Sensitive Mouse Insulin ELISA Kit (Crystal Chem). Glucose in living mice was measured with a FreeStyle Lite portable glucose meter (Abbott) using 3 μl blood from a capillary tail bleed. IPGTT was performed in the morning after overnight fast. Blood for fasting glucose analysis was collected by tail bleed. Mice were injected with 2 mg/g of glucose using a 50 mg/ml solution in autoclaved water. Blood was collected at 5, 15, 30, 60, and 120 minutes and glucose was measured with the Autokit Glucose.

Plasma Lipid Profile and Triton Experiment: 250 μl of pooled plasma from 6 mice fasted for 5 hr was used for FPLC analysis using 2 Sepharose 6 Fast Flow columns in series (Amersham Biosciences). The buffer contained 100 mM Tris and 0.04% NaN3, pH 7.5; a flow rate of 0.7 ml/min was used. TCH and TG levels of FPLC fractions were measured using Wako enzymatic kits. To block clearance of nascent lipoproteins, these mice were then injected with Triton WR1339 (0.5 mg/g body weight; Sigma-Aldrich) via tail vein. Blood samples were collected at 0, 30, 60, and 120 min post-injection. Initial plasma samples were used for TG quantification.

Liver Glycogen: Liver fragments (0.1-0.2 g) were digested in 1 ml of 30% KOH at 95° C. for 30 min; 0.2 ml of 2% Na2SO4 and 3.2 ml of 70% ethanol were added and the mixture was centrifuged for 30 min at 6800 RCF. Pellets (containing glycogen) were washed with 70% ethanol and resuspended in 0.5 ml of 0.2 M acetate buffer; 0.1 ml of the solution was incubated for 30 min at 55° C. with 5 μl of amyloglucosidase (Sigma) and then incubated 5 min at 37° C. with Autokit Glucose (Wako Diagnostics, Richmond, Va.). Glycogen content was expressed as mg of glucose/g of wet liver.

Liver Lipids: Whole lipids were extracted by Bligh-Dyer extraction[65]. In brief, 1.5 ml of chloroform:methanol (12, v/v) with 0.4 ml of PBS was added to liver pieces (0.1-0.2 g) in a screw-capped glass test tube and mixed vigorously for 1 min. Vigorous mixing followed successive additions of 0.5 ml chloroform and 0.5 ml H2O. The mixture was centrifuged at 1800 RCF for 5 min and the lower (organic) phase, containing whole lipids, was collected and stored at −20° C. until assay. TCH and TG were determined with a colorimetric kit (Wako; Cholesterol E 439-17501; L Type TG 461-08892 and 461-09092).

HOMA-IR: HOMA2-IR (homeostasis model assessment-estimated insulin resistance) and HOMA-2-B % (homeostasis model assessment-β-cell function) were calculated using the HOMA calculator, www.dtu.ox.ac.uk/homacalculator/index.php, based on the nonlinear updated HOMA2 model [66], which takes account of variations in hepatic and peripheral glucose resistance, increases in the insulin secretion curve for plasma glucose concentrations >10 mmol/L (180 mg/dL) and the contribution of circulating proinsulin.

Energy Expenditure: Energy expenditure was measured with a LabMaster-CaloSys-calorimetry System (TSE Systems, Bad Homburg, Germany). 02 and CO2 measurements were taken every 26 min during a 72 hr period from 32, 10-week-old male mice (8 ADOX, 8 ADOX control, 8 ADKD, and 8 ADKD control). Mice were injected with the adenovirus on day 0 and placed in calorimeters from days 5-7. Because of stress related to transfer to the calorimetry chambers, only measurements taken within the last 48 hr were used to calculate total 24-hr energy expenditure (TEE; in kcal/24-hr) and respiratory exchange rate (RER=VCO2/VO2). Resting energy expenditure (REE in kcal/24-hr) was defined as the1-hr period of lowest energy expenditure. This coincided with the 1 hr of lowest total ambulatory activity (generally early afternoon), during the 48-hr period; this value was extrapolated to 24 hr. Non-resting energy expenditure (NREE) was calculated as the difference between TEE and REE (NREE=TEE−REE). Physical activity was measured by an infrared beam system integrated with the LabMaster system. Total activity (beam breaks) in X, Y, and Z axes was recorded every 26 min. The system is designed to differentiate between fine motor movement (defined as a single X or Y axis beam break), ambulatory movement (defined as the simultaneous breaking of two adjacent X or Y beams), and rearing, defined as the breaking of the Z axis infrared beam. Lights were off at night from 1900 to 0700 hr.

Adenovirus Studies: Adenoviral expression vectors: Adenoviruses were prepared and amplified with the ViraPower Adenoviral Expression System (Invitrogen). Viral titers were determined by plaque-forming assays on HEK 293A cells. PCR-amplified, full-length Ildr2-cDNA was subcloned into the pENTR/D-TOPO vector using the pENTR Directional TOPO Cloning Kit (Invitrogen). After verifying the sequence, inserts were transferred into the pAd/CMV/V5-DEST vector by the Gateway system using LR Clonase II Enzyme Mix. Sequences corresponding to the shRNAs for Ildr2 and lacZ were cloned into pBlock-it (Invitrogen). The sequence of the shRNA for Ildr2 was: 5'-cac cGT TCA AAT CCT ACT GCC Aga cgt gtg ctg tcc gtC TGG CAG TAG GAT TTG AAC-3' (SEQ ID NO: 147), where the 5' uppercase 18-nucleotide sequence corresponds to the coding strand in exon 2 for the amino acid sequence FKSYCQ (SEQ ID NO: 148).

Virus purification: To obtain virus particles, plasmids were linearized by Pac I digestion and transduced into HEK 293A cells with LIPOFECTAMINE 2000 using Opti-MEM medium. The transduced HEK 293A cells were incubated at 37° C. in a 6 cm dish until the cells started to die (about 10 days). The cells and supernatant were harvested in a 50 ml tube and subjected to 3 freeze-thaw cycles to lyse the cells. The suspension was centrifuged at 1800 RCF for 15 min to eliminate cellular debris. The supernatant was collected and used to transduce a new 10 cm dish of HEK 293A cells. This process (grow, lyse, centrifuge, transduce a larger number of cells) was repeated until 20, 15-cm dishes, were incubated simultaneously. The cells and supernatant were collected and spun at low speed (200 RCF) for 2 min. The cells and 5 ml of supernatant were then subjected to 3 freeze-thaw cycles to lyse cells, followed by centrifugation at 1800 RCF for 15 min. A CsCl step gradient was set up with a lower layer of 4 ml of 1.4 g/ml CsCl and an upper layer of 3 ml of 1.2 g/ml CsCl. 5 ml of supernatant was over-layered and ultracentrifuged at 65,000 RCF for 90 min at 4° C. The 1.2 g/ml cesium chloride layer, containing virus, was extracted and dialyzed vs. 10 mM Tris/HCL at pH 8.0. Viral concentration was determined by OD260 assay.

Injection: Recombinant viruses were administered via tail vein injection and mice were sacrificed 3 days or 10 days p.t.

Real-Time qPCR: RNA was extracted with TRIZOL acid-phenol reagent (Invitrogen) and purified with on-column DNase digestion using RNEASY Mini Kit (Qiagen). RNA integrity was verified by visual inspection of ethidium bromide stained electrophoresis gels and by OD260 nm/OD280 nm>1.9 and OD260 nm/OD230 nm>2.0. First strand cDNA synthesis was performed using 1 μg of total RNA each and the Sprint RT Complete-Random Hexamer kit (Clontech) according to the manufacturer's instructions. Reverse transcription (RT) followed by PCR was used to analyze mRNA abundance in response to treatments. Primers for genes were designed to produce an amplification product which spanned at least one exon using the Universal Probe Library Assay Design Center (www.universalprobelibrary.com, Roche Applied Sciences); primers were synthesized by Invitrogen. qPCR analysis was performed on a LIGHTCYCLER 480 (Roche) using the LIGHTCYCLER 480 SYBR Green I Mastermix (Roche).

Primers for PCR: Primers used for the PCR amplification of full-length Ildr2-cDNA. Ildr2 Forward: caccATGGATAGGGTCGTGTTGGG (SEQ ID NO: 59). Ildr2 Reverse: TCAGACTACAAGGGACATCCTGGTTGGAAAGTCACC (SEQ ID NO: 60). The first TCA in the reverse is the stop codon. The ATG in the forward is the start codon. Primers used in expression analysis are shown in Table 10.

TABLE 10

Primers used for expression analysis. PCR primers used in experiments described in Table 1, FIG. 6, and FIG. 7.

| Gene | Forward | SEQ ID NO: | Reverse | SEQ ID NO: |
|---|---|---|---|---|
| Ildr1 | TCATTGTCCTGCATTGG CTGA | 61 | CAACAGCGGGTAGGACA GCA | 62 |
| Ildr2 | ACAGGGCTCGACGGTT AC | 63 | ACACCCACTCCAACACC AGC | 64 |
| Ildr3 | TCACCATCACAGGAAAT GCTGAC | 65 | GCTTCTGAGGTCCTGCC AAGG | 66 |
| Pepck | TGTCATCCGCAAGCTGA AGA | 67 | TTCGATCCTGGCCACAT CTC | 68 |
| Gck | TCCCTGTAAGGCACGAA GACAT | 69 | ATTGCCACCACATCCAT CTCA | 70 |
| Glut2 | GGAACCTTGGCTTTCAC TGTCTT | 71 | GGAACACCCAAAACATG TCGAT | 72 |
| Gpat | GGCTACGTCCGAGTGG ATTTT | 73 | AACATCATTCGGTCTTGA AGGAA | 74 |
| Mgat1 | CTGGTTCTGTTTCCCGT TGT | 75 | GGTGAATGTTCCTGGGT GAG | 76 |
| Dgat1 | CCTCAGCCTTCTTCCAT GAG | 77 | ACTGGGGCATCGTAGTT GAG | 78 |
| Dgat2 | TCCAGCTGGTGAAGACA CAC | 79 | GATGCCTCCAGACATCA GGT | 80 |
| FAS | ATCCTGGAACGAGAACA CGATCT | 81 | AGAGACGTGTCACTCCT GGACTT | 82 |
| ACC1 | GGGCACAGACCGTGGT AGTT | 83 | CAGGATCAGCTGGGATA CTGAGT | 84 |
| Pparg2 | TTCCACTATGGAGTTCA TGCTTGT | 85 | TCCGGCAGTTAAGATCA CACCTA | 86 |
| Srebp1c | CGGCGCGGAAGCTGT | 87 | TGCAATCCATGGCTCCGT | 88 |
| Srebp2 | CTGCAGCCTCAAGTGCA AAG | 89 | CAGTGTGCCATTGGCTG TCT | 90 |
| Ldlr | TGGAGGATGAGAACCG GCT | 91 | GCACTGAAAATGGCTTC GTTTA | 92 |

TABLE 10-continued

Primers used for expression analysis. PCR primers used in experiments described in Table 1, FIG. 6, and FIG. 7.

| Gene | Forward | SEQ ID NO: | Reverse | SEQ ID NO: |
|---|---|---|---|---|
| Apob | TCACCCCCGGGATCAAG | 93 | TCCAAGGACACAGAGGG CTTT | 94 |
| Ppara | CCTCAGGGTACCACTAC GGAGT | 95 | GCCGAATAGTTCGCCGAA | 96 |
| Cpt1a | CCTGGGCATGATTGCAA AG | 97 | GGACGCCACTCACGATG TT | 98 |
| Acox1 | CGATCCAGACTTCCAAC ATGAG | 99 | CCATGGTGGCACTCTTC TTAACA | 100 |
| Mcad | TGCTTTTGATAGAACCA GACCTACAGT | 101 | CTTGGTGCTCCACTAGC AGCTT | 102 |
| Ucp2 | GACCTCATCAAAGATAC TCTCCTGAA | 103 | ATCTCGTCTTGACCACAT CAACAG | 104 |
| Rxra | GGCAAACATGGGGCTG AAC | 105 | GCTTGTCTGCTGCTTGA CAGAT | 106 |
| Fxra | TGGGCTCCGAATCCTCT TAGA | 107 | TGGTCCTCAAATAAGATC CTTGG | 108 |
| Fxrb | GGGCTTAGAAAATCCAA TTCAGATTA | 109 | CGTCCGGCACAAATCCTG | 110 |
| Perk | CCTTGGTTTCATCTAGC CTCA | 111 | ATCCAGGGAGGGGATGAT | 112 |
| Atf6 | GGACGAGGTGGTGTCA GAG | 113 | GACAGCTCTTCGCTTTG GAC | 114 |
| Ire1 | TGAAACACCCCTTCTTC TGG | 115 | CCTCCTTTTCTATTCGGT CACTT | 116 |
| Atf4 | ATGATGGCTTGGCCAGT G | 117 | CCATTTTCTCCAACATCC AATC | 118 |
| Xbp1 | TGACGAGGTTCCAGAG GTG | 119 | TGCAGAGGTGCACATAG TCTG | 120 |
| Chop | TCCCTGCCTTTCACCTT G | 121 | GCCCTGGCTCCTCTGTC A | 122 |
| Bip | CTGAGGCGTATTTGGGA AAG | 123 | TCATGACATTCAGTCCA GCAA | 124 |

Construction of Tag Protein Fusions. N-terminal 3×FLAG Ildr2 fusion construct. The Ildr2 open reading frame from exon 2 was subcloned into p3×FLAG-CMV-8 (N-terminal FLAG with PPT LS, Sigma-Aldrich # E4151-20UG). Ildr2 was amplified using a forward primer on the sequence coding for the first amino acids of exon 2 with a HindIII site (5' ATT TAC AAG CTT CAG GTC ACA GTG CCT GAC AAG AAG AAG GT3' (SEQ ID NO 125), and a reverse primer with an in-frame stop codon and EcoR1 restriction site at the end of Ildr2 last exon (5'-CAT GCA GAA TTC TCA GAC TAC AAG GGA CAT CCT G-3' SEQ ID NO: 126). The destination vector and the PCR amplified Ildr2 sequence were digested with HindIII and EcoR1 (NEBiolabs) in NEBuffer EcoR1 and BSA at 37° C. for 60 min, purified and ligated.

C-terminal-tagged ILDR2 mYFP construct. The ildr2 open reading frame from exon 1 was subcloned into pmEYFP-N1 (Clontech #6006-1). Ildr2 was amplified using a forward primer on exon 1-including Kozak sequence—with a site for the restriction enzyme NheI (5'-ATC TTG CTA GCG GTA ATG GAT AGG GTC GTG TTG G-3' SEQ ID NO: 127), and a reverse primer that bypass the stop codon and an EcoRI restriction site (5'-CAT GCA GAA TTC GGA CTA CAA GGG ACA TCC TG-3' SEQ ID NO: 128). The destination vector and the PCR-amplified Ildr2 sequence were digested with Nhe and EcoRI (NEBiolabs) in NEBuffer EcoRI+BSA at 37° C. for 60 min, purified and ligated.

Isolation of Hepatocytes: Hepatocytes were pooled from 5, 10-week-old C57BL/6J mice. The mice were anaesthetized with cocktail containing ketamine (100 mg/kg) and xylazine (20 mg/kg) and then laparotomized to expose the liver and the portal vein. A 25G winged needle attached to a 50 ml syringe filled with 37° C. EGTA-Hanks solution (Hanks Balanced Salt Solution, Gibco; EGTA final concentration 0.5 mM) was inserted into the portal vein and clipped in place with a clamp at the root of the mesentery and the needle. After cutting the inferior vena cava, the liver was perfused with 30 ml EGTA-Hanks Using a fresh syringe, the liver was then perfused with 20 ml of a solution containing collagenase (5 mM CaCl2 in Hanks with 1 mg/ml of collagenase type II Gibco #17101-015) being careful not to inject bubbles. Liver was excised and placed in a 10 cm sterile dish on ice with 2-3 ml of collagenase solution and minced with scissors to remove visible blood clots. Minced livers were pooled and incubated for 5-10 min at 37° C. and homogenized by pipetting up and down 20-30 times. Then 20 ml of RT Hanks balanced salt solution was added to the dish and mixed. The suspension was filtered through sterile gauze into a 50 ml conical tube, spun 1 min at 200 RCF at RT and aspirated to remove supernatant. Cells were resuspended in 20 ml Gibco HG medium (with 10% FBS, 1% Penicillin Streptomycin, 10 nm DEX, 100 nm insulin, and 0.1% Fungizone) and pipetted up and down 5 times. The suspension was filtered through a 100 um Nylon cell strainer (BD Falcon REF352360) and collected in 50 ml conical tube. The filtrate was centrifuged again at 200 RCF for 1 min at RT and aspirated to remove the supernatant. Cells were resuspended in 25 ml of Gibco HG medium and gently pipetted. Cells were counted with an Invitrogen Countess using trypan blue staining and then distributed at 3×106 cells per 10 cm plate and incubated overnight at 37° C. in a humidified 5% CO2 incubator before administering virus.

Cell Line Studies: Cell microscopy, image acquisition: Cell cultures were prepared and maintained according to standard cell culture procedures. Hepa1c1c7 and GT1-7 cells were maintained in Dulbecco's Modified Eagle Medium supplemented with 10% fetal calf serum using BD Falcon T75 cell culture flasks. For transient transfection, cells were harvested by Trypsin/EDTA digestion, seeded on coverslips (1×105 per coverslip) and incubated for 24 h in a cell culture incubator at 37° C. and 5% CO2. Transfection of plasmid DNA for GFP-tagged ILDR2 was performed with LIPOFECTAMINE 2000 according to the manufacturer's instructions. In brief, cells were incubated with 500 ng plasmid DNA and 1.25 μl LIPOFECTAMINE 2000 in OptiMEM (24-well plate format) over night before being analyzed. Transfection was up-scaled accordingly if other plate formats were used.

Confocal images: Transduced cells were washed with PBS, fixed in 4% paraformaldehyde at room temperature (rt) for 15 min, washed again with PBS, permeabilized with 0.1% Triton-X 100 (2 min at rt) if necessary and incubated with blocking buffer (5% normal goat serum and 0.05% Tween 20 in PBS) for 30 min. For immunostaining, cells were incubated overnight at 4° C. with the corresponding specific antibody diluted in blocking buffer, washed with PBS, incubated for 1 hr at rt with 2 μg/ml Alexa Fluor 546 goat anti-mouse secondary antibody diluted in blocking buffer washed with PBS and mounted in ProLong Gold antifade reagent with DAPI as a nuclear staining marker. Samples were analyzed with a Confocal Laser Scanning Microscope (TCS SP2, Leica, Germany). When fluorescent proteins were used, GFP was excited at 488 nm and fluorescence was detected at 500-540 nm. YFP was excited at 514 nm and fluorescence was detected at 520-560 nm. DsRed was excited at 557 nm and fluorescence was detected at 592 nm. Alexa Fluor 546 was excited with the 543 nm line of the helium laser and fluorescence was detected at 555-700 nm. Cells were imaged with a 63.0×/1.25 HCX PL APO objective lens. Images were processed with Adobe Photoshop software. Images shown are stacks of several confocal sections.

siRNA reverse transfection: RNA interference-mediated gene knockdown was achieved using custom Stealth RNAi™ siRNA designed using the BLOCK-iT™ RNAi Designer software (Invitrogen), and its correspondent controls. 10 nM RNAi duplex was diluted in OptiMEM® I Reduced Serum Medium (Invitrogen) and 5 ul of LIPOFECTAMINE RNAiMAX (Invitrogen) was added to each well containing the diluted RNAi. After mixing, the complexes were incubated for 20 min at room temperature. After incubation, approximately 0.15-0.25×$10^6$ cells per well in complete growth medium without antibiotics were added to the wells containing the siRNA-lipid complexes. Cells were then cultured in normal growth medium processed for RNA or protein extraction as indicated by experimental procedure.

Western blotting: Cells were lysed in M-PER Mammalian Protein Extraction reagent (Thermo Scientific) with protease (Calbiochem) and phosphatase inhibitor (Thermo Scientific) . Equivalent amounts of protein (100 to 400 μg) from each sample were diluted in 1×LDS sample buffer (Invitrogen) containing 100 mM DTT and incubated for 10 min at 70° C. After denaturing, the mixture was cooled at rt for at least 15 min and the protein was resolved by SDS-PAGE. The gel was transferred onto polyvinylidene fluoride (PVDF) membrane and blocked by incubation for 1 hr at rt in a solution 5% bovine serum albumin fraction V (BSA) in Tris-buffered saline with Tween (TBST) at pH 7.4, followed by overnight incubation at 4° C. with primary antibody in 5% BSA/TBST. Following 3 15-min washes with TBST, membranes were incubated for 1 hr at rt with the corresponding secondary antibody and washed 3 more times in TBST. Membranes were developed using a chemiluminescence assay system and proteins were visualized using Kodak exposure film. Membranes were stripped using Restore™ PLUS Western blot stripping buffer (Thermo Scientific) with vigorous agitation for 10 min at rt, followed by 3 TBST washes.

Statistical Analysis: Two tailed T tests were performed using Microsoft Excel.

Example 2

Generation of ILDR2 Conditional Knockout Mouse

Figure 48:
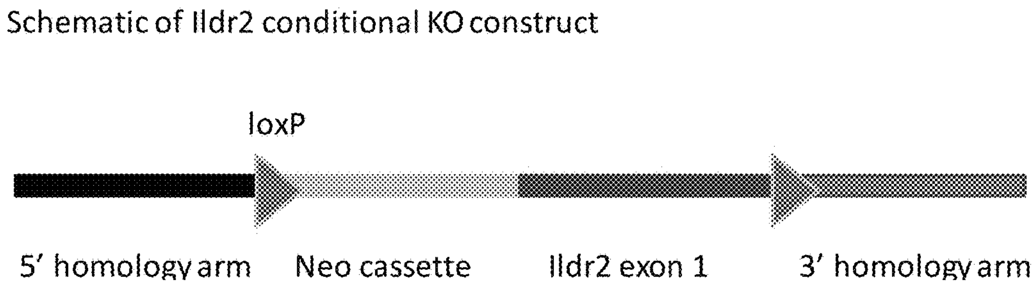
FIG. 48 shows a schematic of Ildr2 conditional knockout construct.
Figure 49E:
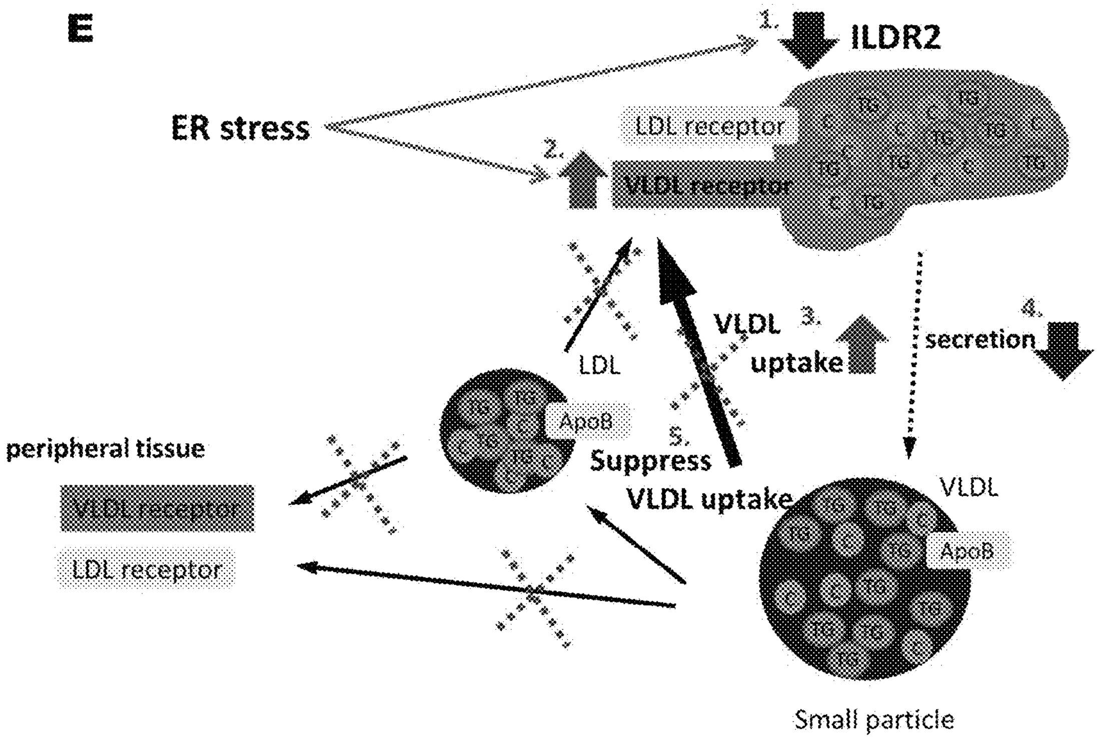

A ILDR2 conditional knock-out mouse was generated that was designed to delete exon 1 of Ildr2. A neo cassette was inserted 1.6 kb upstream of exon 1 of Ildr2. The addition of the neo cassette alone does not affect expression of ILDR2, this neo gene is in the opposite orientation to the Ildr2 gene (FIG. 48). This mouse was mated with an albumin ere mouse that expresses ere specifically in the liver. The addition of the ere excises the region between the two loxP sites; this removes the neo cassette and the first exon of Ildr2, knocking it out in the tissues where the ere is expressed. Quantification of Ildr2 expression in this mouse by qPCR, shows it has no Ildr2 expression in the liver.

REFERENCES

1. Dokmanovic-Chouinard M, Chung W K, Chevre J C, Watson E, Yonan J, et al. (2008) Positional cloning of "Lisch-Like". a candidate modifier of susceptibility to type 2 diabetes in mice. PLoS Genet 4: e1000137.
2. Clee S M, Attie A D (2007) The genetic landscape of type 2 diabetes in mice. Endocr Rev 28: 48-83.
3. Hauge H, Patzke S, Delabie J, Aasheim H C (2004) Characterization of a novel immunoglobulin-like domain containing receptor. Biochem Biophys Res Commun 323: 970-978.
4. Mesli S, Javorschi S, Berard A M, Landry M, Priddle H, et al. (2004) Distribution of the lipolysis stimulated receptor in adult and embryonic murine tissues and lethality of LSR−/− embryos at 12.5 to 14.5 days of gestation. Eur J Biochem 271: 3103-3114.
5. Zagaria A, Anelli L, Coccaro N, Casieri P, Minervini A, et al. (2012) A new recurrent chromosomal translocation t(3; 11)(q13;q14) in myelodysplastic syndromes associated with overexpression of the ILDR1 gene. Leuk Res 36: 852-856.
6. Borck G, Ur Rehman A, Lee K, Pogoda H M, Kakar N, et al. (2011) Loss-of-function mutations of ILDR1 cause autosomal-recessive hearing impairment DFNB42. Am J Hum Genet 88: 127-137.
7. Yen F T, Masson M, Clossais-Besnard N, Andre P, Grosset J M, et al. (1999) Molecular cloning of a lipolysis-stimulated remnant receptor expressed in the liver. J Biol Chem 274: 13390-13398.
8. Papatheodorou P, Wilczek C, Nolke T, Guttenberg G, Hornuss D, et al. (2012) Identification of the cellular receptor of *Clostridium* spiroforme toxin. Infect Immun 80: 1418-1423.
9. Stenger C, Hanse M, Pratte D, Mbala M L, Akbar S, et al. (2010) Up-regulation of hepatic lipolysis stimulated lipoprotein receptor by leptin: a potential lever for controlling lipid clearance during the postprandial phase. FASEB J 24: 4218-4228.
10. Masuda S, Oda Y, Sasaki H, Ikenouchi J, Higashi T, et al. (2011) LSR defines cell corners for tricellular tight junction formation in epithelial cells. J Cell Sci 124: 548-555.
11. Fagone P, Jackowski S (2009) Membrane phospholipid synthesis and endoplasmic reticulum function. J Lipid Res 50 Suppl: S311-316.
12. Hotamisligil G S (2010) Endoplasmic reticulum stress and the inflammatory basis of metabolic disease. Cell 140: 900-917.
13 Linnik K M, Herscovitz H (1998) Multiple molecular chaperones interact with apolipoprotein B during its maturation. The network of endoplasmic reticulum-resident chaperones (ERp72, GRP94, calreticulin, and BiP) interacts with apolipoprotein b regardless of its lipidation state. J Biol Chem 273: 21368-21373.
14. Stutzmann G E, Mattson M P (2011) Endoplasmic reticulum Ca(2+) handling in excitable cells in health and disease. Pharmacol Rev 63: 700-727.
15. Wang S, Kaufman R J (2012) The impact of the unfolded protein response on human disease. J Cell Biol 197: 857-867.
16. Ozcan L, Tabas I (2012) Role of endoplasmic reticulum stress in metabolic disease and other disorders. Annu Rev Med 63: 317-328.
17. Ozcan L, Ergin A S, Lu A, Chung J, Sarkar S, et al. (2009) Endoplasmic reticulum stress plays a central role in development of leptin resistance. Cell Metab 9: 35-51.
18. Back S H, Kaufman R J (2012) Endoplasmic reticulum stress and type 2 diabetes Annu Rev Biochem 81: 767-793.
19. Alemany R, Suzuki K, Curiel D T (2000) Blood clearance rates of adenovirus type 5 in mice. J Gen Virol 81: 2605-2609.
20. Worgall S, Wolff G, Falck-Pedersen E, Crystal R G (1997) Innate immune mechanisms dominate elimination of adenoviral vectors following in vivo administration. Hum Gene Ther 8: 37-44.
21. Trak-Smayra V, Paradis V, Massart J, Nasser S, Jebara V, et al. (2011) Pathology of the liver in obese and diabetic ob/ob and db/db mice fed a standard or high-calorie diet. Int J Exp Pathol 92: 413-421.
22. Strnad P, Stumptner C, Zatloukal K, Denk H (2008) Intermediate filament cytoskeleton of the liver in health and disease. Histochem Cell Biol 129: 735-749.
23. Nagata Y, Zilversmit D B (1987) Blockade of intestinal lipoprotein clearance in rabbits injected with Triton WR 1339-ethyl oleate. J Lipid Res 28: 684-692.
24. Ong K T, Mashek M T, Bu S Y, Greenberg A S, Mashek D G (2011) Adipose triglyceride lipase is a major hepatic lipase that regulates triacylglycerol turnover and fatty acid signaling and partitioning. Hepatology 53: 116-126.
25. Choi S H, Ginsberg H N (2011) Increased very low density lipoprotein (VLDL) secretion, hepatic steatosis, and insulin resistance. Trends Endocrinol Metab 22: 353-363.
26. Lee A H, Scapa E F, Cohen D E, Glimcher L H (2008) Regulation of hepatic lipogenesis by the transcription factor XBP1. Science 320: 1492-1496.
27. Ron D, Walter P (2007) Signal integration in the endoplasmic reticulum unfolded protein response. Nat Rev Mol Cell Biol 8: 519-529.
28. Cao J, Dai D L, Yao L, Yu H H, Ning B, et al. (2012) Saturated fatty acid induction of endoplasmic reticulum stress and apoptosis in human liver cells via the PERK/ATF4/CHOP signaling pathway. Mol Cell Biochem 364: 115-129.
29. Fu S, Yang L, Li P, Hofmann O, Dicker L, et al. (2011) Aberrant lipid metabolism disrupts calcium homeostasis causing liver endoplasmic reticulum stress in obesity. Nature 473: 528-531.
30. Ota T, Gayet C, Ginsberg H N (2008) Inhibition of apolipoprotein B100 secretion by lipid-induced hepatic endoplasmic reticulum stress in rodents. J Clin Invest 118: 316-332.
31. Rutkowski D T, Wu J, Back S H, Callaghan M U, Ferris S P, et al. (2008) UPR pathways combine to prevent hepatic steatosis caused by ER stress-mediated suppression of transcriptional master regulators. Dev Cell 15: 829-840.
32. Yamamoto K, Takahara K, Oyadomari S, Okada T, Sato T, et al. (2010) Induction of liver steatosis and lipid droplet formation in ATF6alpha-knockout mice burdened with pharmacological endoplasmic reticulum stress. Mol Biol Cell 21: 2975-2986.
33. Zhang K, Wang S, Malhotra J, Hassler J R, Back S H, et al. (2011) The unfolded protein response transducer IRE1alpha prevents ER stress-induced hepatic steatosis. EMBO J 30: 1357-1375.
34. Lee J S, Mendez R, Heng H H, Yang Z Q, Zhang K (2012) Pharmacological ER stress promotes hepatic lipogenesis and lipid droplet formation. Am J Transl Res 4: 102-113.
35. Lee J S, Zheng Z, Mendez R, Ha S W, Xie Y, et al. (2012) Pharmacologic ER stress induces non-alcoholic steatohepatitis in an animal model. Toxicol Lett 211: 29-38.
36. Hetz C (2012) The unfolded protein response: controlling cell fate decisions under ER stress and beyond. Nat Rev Mol Cell Biol 13: 89-102.
37. Lai E, Teodoro T, Volchuk A (2007) Endoplasmic reticulum stress: signaling the unfolded protein response. Physiology (Bethesda) 22: 193-201.
38. Xu C, Bailly-Maitre B, Reed J C (2005) Endoplasmic reticulum stress: cell life and death decisions. J Clin Invest 115: 2656-2664.
39. Erbay E, Babaev V R, Mayers J R, Makowski L, Charles K N, et al. (2009) Reducing endoplasmic reticulum stress through a macrophage lipid chaperone alleviates atherosclerosis. Nat Med 15: 1383-1391.

40. Park S W, Zhou Y, Lee J, Lee J, Ozcan U (2010) Sarco(endo) plasmic reticulum Ca2+-ATPase 2b is a major regulator of endoplasmic reticulum stress and glucose homeostasis in obesity. Proc Natl Acad Sci USA 107: 19320-19325.

41. de Meijer V E, Le H D, Meisel J A, Akhavan Sharif M R, Pan A, et al. (2010) Dietary fat intake promotes the development of hepatic steatosis independently from excess caloric consumption in a murine model. Metabolism 59: 1092-1105.

42. Biddinger S B, Hernandez-Ono A, Rask-Madsen C, Haas J T, Aleman J O, et al. (2008) Hepatic insulin resistance is sufficient to produce dyslipidemia and susceptibility to atherosclerosis. Cell Metab 7: 125-134.

43. Ishibashi S, Brown M S, Goldstein J L, Gerard R D, Hammer R E, et al. (1993) Hypercholesterolemia in low density lipoprotein receptor knockout mice and its reversal by adenovirus-mediated gene delivery. J Clin Invest 92: 883-893.

44. Bugianesi E, Moscatiello S, Ciaravella M F, Marchesini G (2010) Insulin resistance in nonalcoholic fatty liver disease. Curr Pharm Des 16: 1941-1951.

45. Kotronen A, Yki-Jarvinen H (2008) Fatty liver: a novel component of the metabolic syndrome. Arterioscler Thromb Vasc Biol 28: 27-38.

46. Lattuada G, Ragogna F, Perseghin G (2011) Why does NAFLD predict type 2 diabetes? Curr Diab Rep 11: 167-172.

47. Cantley J L, Yoshimura T, Camporez J P, Zhang D, Jornayvaz F R, et al. (2013) CGI-58 knockdown sequesters diacylglycerols in lipid droplets/ER-preventing diacylglycerol-mediated hepatic insulin resistance. Proc Natl Acad Sci USA 110: 1869-1874.

48. Wu J W, Wang S P, Alvarez F, Casavant S, Gauthier N, et al. (2011) Deficiency of liver adipose triglyceride lipase in mice causes progressive hepatic steatosis. Hepatology 54: 122-132.

49. Minehira K, Young S G, Villanueva C J, Yetukuri L, Oresic M, et al. (2008) Blocking VLDL secretion causes hepatic steatosis but does not affect peripheral lipid stores or insulin sensitivity in mice. J Lipid Res 49: 2038-2044.

50. Ozcan U, Cao Q, Yilmaz E, Lee A H, Iwakoshi N N, et al. (2004) Endoplasmic reticulum stress links obesity, insulin action, and type 2 diabetes. Science 306: 457-461.

51. Kammoun H L, Chabanon H, Hainault I, Luquet S, Magnan C, et al. (2009) GRP78 expression inhibits insulin and ER stress-induced SREBP-1c activation and reduces hepatic steatosis in mice. J Clin Invest 119: 1201-1215.

52. Maris M, Overbergh L, Gysemans C, Waget A, Cardozo A K, et al. (2012) Deletion of C/EBP homologous protein (Chop) in C57Bl/6 mice dissociates obesity from insulin resistance. Diabetologia 55: 1167-1178.

53. Zhang C, Wang G, Zheng Z, Maddipati K R, Zhang X, et al. (2012) Endoplasmic reticulum-tethered transcription factor cAMP responsive element-binding protein, hepatocyte specific, regulates hepatic lipogenesis, fatty acid oxidation, and lipolysis upon metabolic stress in mice. Hepatology 55: 1070-1082.

54. Li Y, Ge M, Ciani L, Kuriakose G, Westover E J, et al. (2004) Enrichment of endoplasmic reticulum with cholesterol inhibits sarcoplasmic-endoplasmic reticulum calcium ATPase-2b activity in parallel with increased order of membrane lipids: implications for depletion of endoplasmic reticulum calcium stores and apoptosis in cholesterol-loaded macrophages. J Biol Chem 279: 37030-37039.

55. van der Sanden M H, Houweling M, van Golde L M, Vaandrager A B (2003) Inhibition of phosphatidylcholine synthesis induces expression of the endoplasmic reticulum stress and apoptosis-related protein CCAAT/enhancer-binding protein-homologous protein (CHOP/GADD153). Biochem J 369: 643-650.

56. Gentile C L, Wang D, Pfaffenbach K T, Cox R, Wei Y, et al. (2010) Fatty acids regulate CREBh via transcriptional mechanisms that are dependent on proteasome activity and insulin. Mol Cell Biochem 344: 99-107.

57. Lee M W, Chanda D, Yang J, Oh H, Kim S S, et al. (2010) Regulation of hepatic gluconeogenesis by an ER-bound transcription factor, CREBH. Cell Metab 11: 331-339.

58. Yoshida H, Matsui T, Hosokawa N, Kaufman R J, Nagata K, et al. (2003) A time-dependent phase shift in the mammalian unfolded protein response. Dev Cell 4: 265-271.

59. Harding H P, Zeng H, Zhang Y, Jungries R, Chung P, et al. (2001) Diabetes mellitus and exocrine pancreatic dysfunction in perk−/−mice reveals a role for translational control in secretory cell survival. Mol Cell 7: 1153-1163.

60. Eto K, Yamashita T, Matsui J, Terauchi Y, Noda M, et al. (2002) Genetic manipulations of fatty acid metabolism in beta-cells are associated with dysregulated insulin secretion. Diabetes 51 Suppl 3S414-420.

61. Higashi T, Tokuda S, Kitajiri S I, Masuda S, Nakamura H, et al. (2012) Analysis of the angulin family consisting of LSR, ILDR1 and ILDR2: tricellulin recruitment, epithelial barrier function and implication in deafness pathogenesis. J Cell Sci.

62. Yu R, Hinkle P M (1997) Effect of cell type on the subcellular localization of the thyrotropin-releasing hormone receptor. Mol Pharmacol 51: 785-793.

63. Kamper N, Kessler J, Temme S, Wegscheid C, Winkler J, et al. (2012) A novel BAT3 sequence generated by alternative RNA splicing of exon 11B displays cell type-specific expression and impacts on subcellular localization. PLoS One 7: e35972.

64. Halldorsdottir S, Carmody J, Boozer C N, Leduc C A, Leibel R L (2009) Reproducibility and accuracy of body composition assessments in mice by dual energy x-ray absorptiometry and time domain nuclear magnetic resonance. Int J Body Compos Res 7: 147-154.

65. Bligh E G, Dyer W J (1959) A rapid method of total lipid extraction and purification. Can J Biochem Physiol 37: 911-917.

66. Levy J C, Matthews D R, Hermans M P (1998) Correct homeostasis model assessment (HOMA) evaluation uses the computer program. Diabetes Care 21: 2191-2192.

Example 3

Effects of ER Stress on ILDR2

Mice (WT) were transduced with adenoviral expression vectors encoding shRNA ("ADKD"). Ten day ADKD mice had hepatic steatosis and increased circulating plasma lipids. In analysis of plasma lipoprotein fractions, VLDL-TC and VLDL-TG were higher in the ADKD mice. This suggests that ILDR2 affects a change in the TG and TC content of VLDL particles.

ILDR2 binds to apoE. KYLYYVE (SEQ ID NO: 149), encoded by ILDR2 exon 7, is a critical binding site of apoE. The effects of deletion of the apoE binding sequence in mouse primary hepatocytes was investigated. A KYLYYVE (SEQ ID NO: 149) deletion adenoviral construct was used.

This construct contains the sequence of ILDR2 with the sequence encoding KYLYYVE (SEQ ID NO: 149) deleted from exon 7. ILDR2 overexpression significantly decreased TG content in primary mouse hepatocytes consistent with in vivo findings. However, overexpression of the KVLYYVE-deleted allele ("KVLYYVE" disclosed as SEQ ID NO: 150) did not markedly decrease TG content. This suggests that ILDR2 has a modulating role in the VLDL secretion cascade and may have a function in the assembly of VLDL mediated by apoE.

ER stress decreases ILDR2 expression and reduced ILDR2 levels may contribute to ER stress-dependent hepatic steatosis. Hepatic VLDLR expression is increased in response to ER stress. Increased VLDLR facilitates uptake of VLDL in liver and hepatic lipids increase. VLDLR acts as a receptor for apoE-containing lipoproteins. ApoE is an important constituent of TG-rich lipoproteins and is essential for lipoprotein uptake at LDL and VLDL receptors. ApoE-deficient mice accumulate hepatic TG and decrease rates of VLDL-TG production compared with wild-type mice. Overexpression of apoE in the liver of apoE-deficient mice increases secretion of VLDL-TG. Increased apoE expression in rat hepatoma cells increases VLDL-TG secretion. ApoE may play a role in facilitating hepatic secretion of VLDL-TG and may have a function in the assembly and/or secretion of VLDL by the liver. ILDR2 may interact with apoE in these processes, with functional impairment when ILDR2 is insufficient.

ER stress causes an increase in VLDLR which increases uptake of VLDL and accumulation of hepatic lipids. At the same time, decreased ILDR2 by ER stress impairs VLDL assembly mediated by apoE and reduces VLDL secretion, causing hepatic lipid content to be markedly increased. Reduced apoE content of circulating VLDL could reduce the efficiency of hepatic VLDL uptake, leading to an equilibrium at higher circulating concentrations of TG and cholesterol. Deficiency in ILDR2 function may, therefore, impair VLDL export from the liver, increase VLDLR at the hepatocyte surface and thereby lead to cholesterol and TG accumulation in the liver. ER stress, by reducing levels of ILDR2, could promote this process (FIGS. 49A-E).

Interaction of ER Stress-Related Proteins with ILDR2

Figure 50:
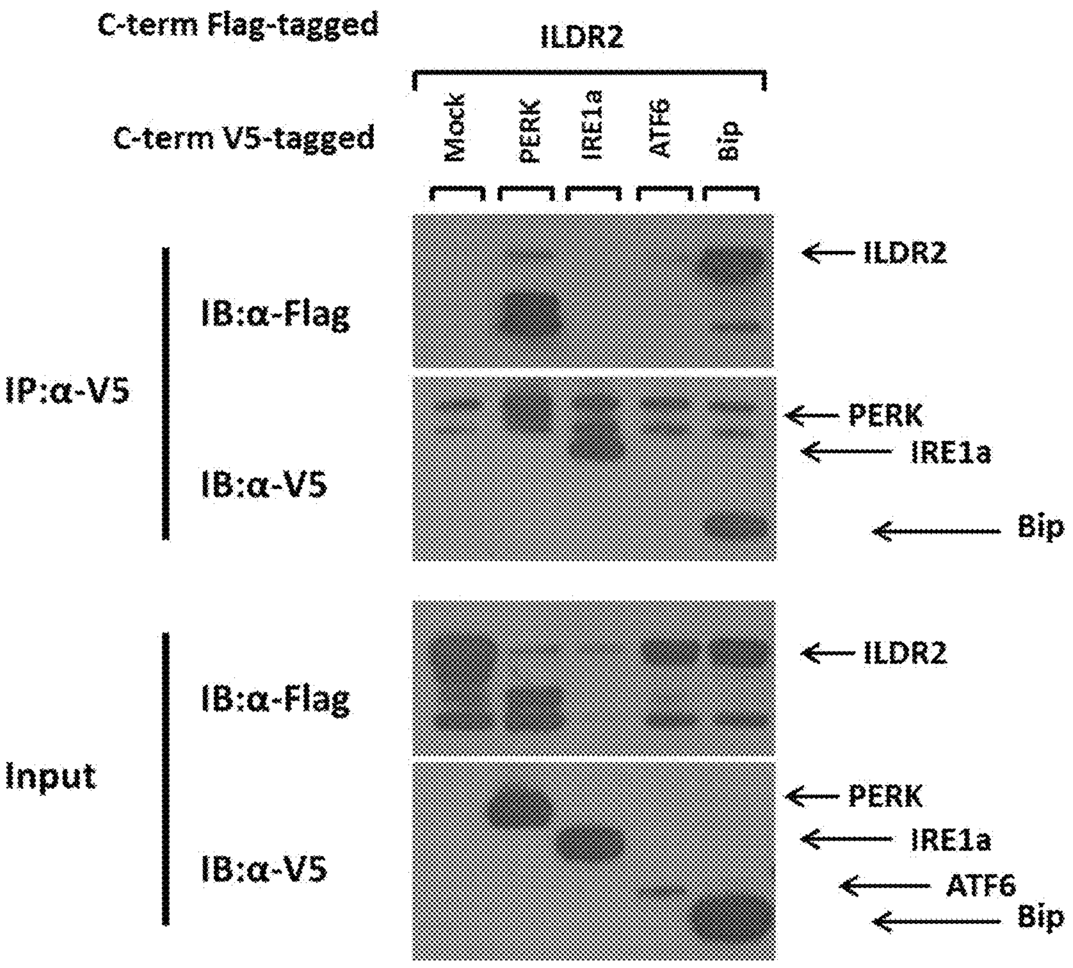
FIG. 50 shows ILDR2 interacts with ER stress-related proteins. Flag-tagged-ILDR2 vector was co-transfected with V5-tagged vectors as indicated into HEK 293 cells. Immunoprecipitation was carried out with anti-V5 antibody. Western blots were immunoblotted with either anti-Flag or anti-V5 antibody as shown.

To assess whether ER stress-related proteins interact with ILDR2, co-immunoprecipitation was performed. The results show that ILDR2 strongly binds to PERK and Bip (FIG. 50). As shown in FIG. 50, PERK binds to ILDR2 and cleaves ILDR2. Cleaved ILDR2 releases two fragments. Full length ILDR2 and cleavage of ILDR2 were decreased by co-transfection with IRE1a. IRE1a, which controls the splicing of Xbp1 mRNA, may affect the degradation of ILDR2. ILDR2 binds to Bip, a major chaperone protein that protects cells from ER stress, suggesting that ILDR2 may play a role in ER stress maintenance Interaction of PERK with ILDR2

Figure 51:
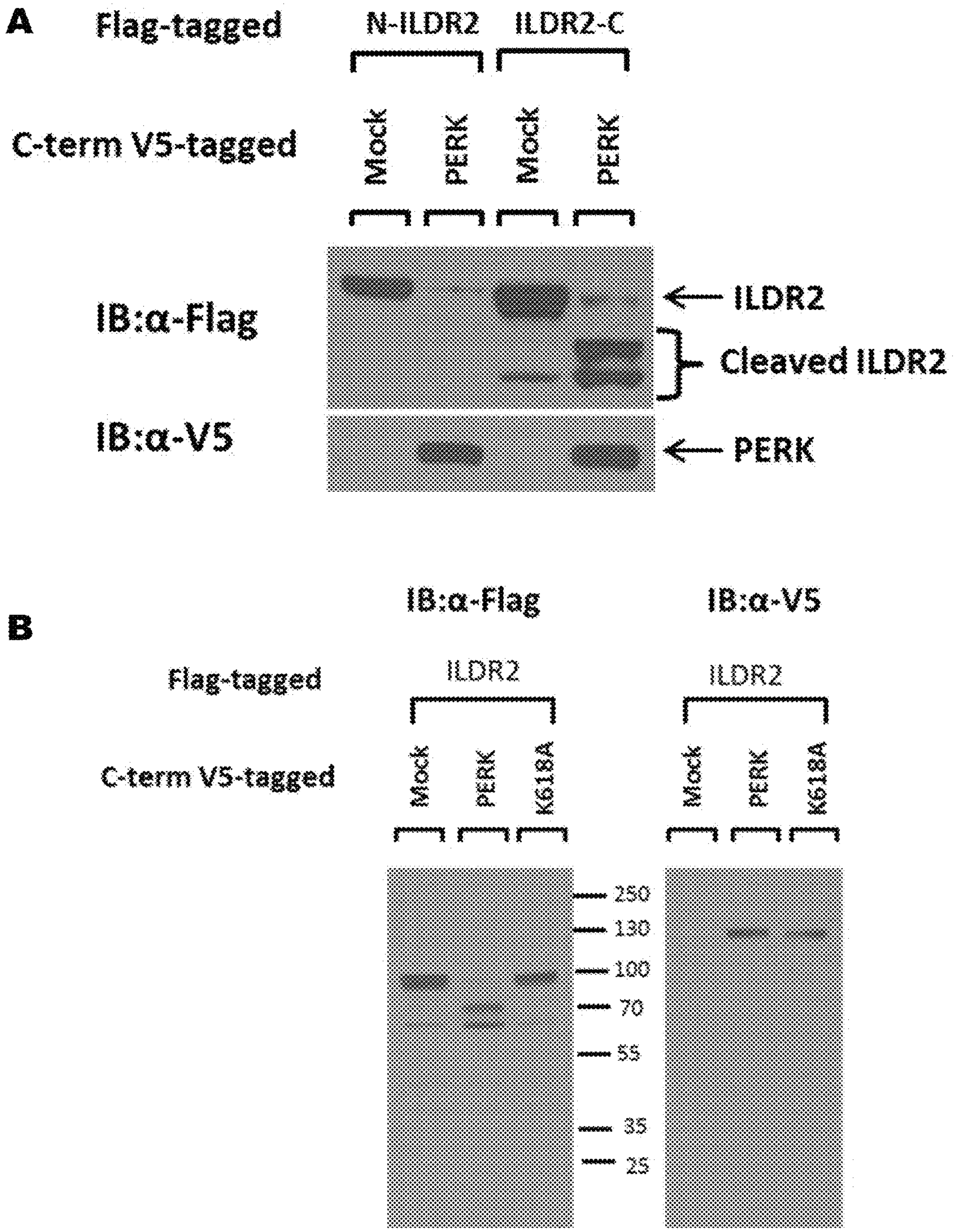
FIG. 51A shows PERK cleavage of ILDR2. Flag-tagged-ILDR2 vector was co-transfected with V5-tagged PERK vector into HEK 293 cells. Western blots were immunoblotted with either anti-Flag or anti-V5 antibody.
FIG. 51B shows PERK dominant negative did not cleave ILDR2. Flag-tagged-ILDR2 vector was co-transfected with V5-tagged PERK vector into HEK 293 cells. Western blots were immunoblotted with either anti-Flag or anti-V5 antibody.

To assess whether ILDR2 is cleaved by PERK, N-terminus tagged ILDR2 was constructed and co-transfected with PERK (FIGS. 51A-B). ILDR2 fragments were assessed by western blot. N-terminus-tagged ILDR2 was also decreased by PERK, but cleaved ILDR2 was not detected, suggesting that N-terminal ILDR2 was cleaved by PERK. The C-terminal cleaved ILDR2 fragment may be too small to be detected in this assay. PERK-K618A which is a dominant negative mutant vector did not cleave ILDR2.

IRE1a Degrades ILDR2 mRNA

Figure 52:
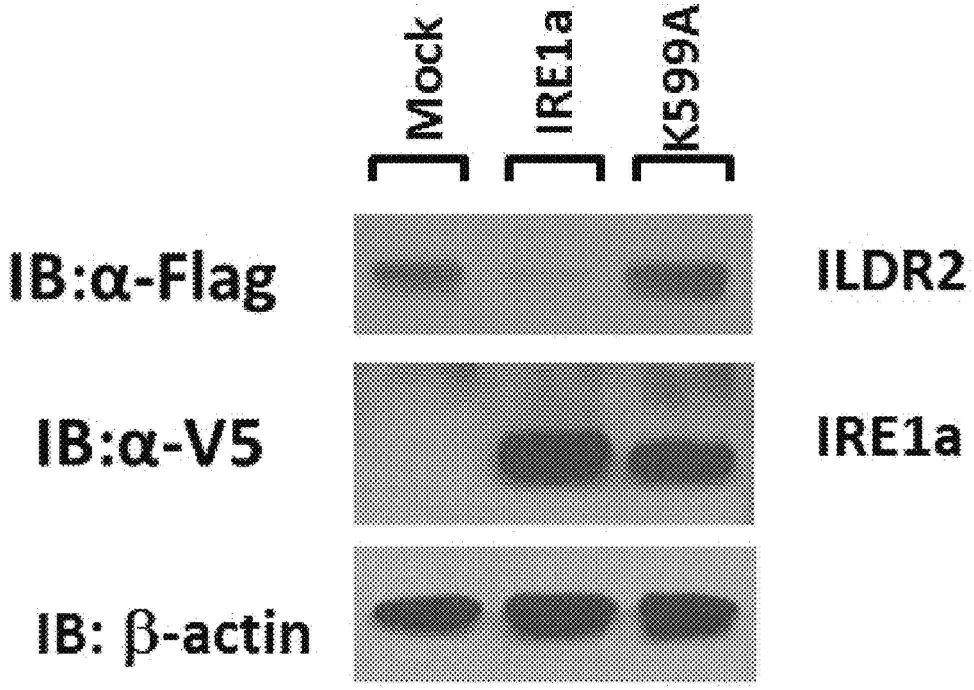
FIG. 52 shows reduction of ildr2 protein by IRE1a co-transfection (flag-tagged ILDR2; v5 tagged IRE1a). The basis for this reduction appears to be reduced levels of ildr2 mRNA.
Figure 53:
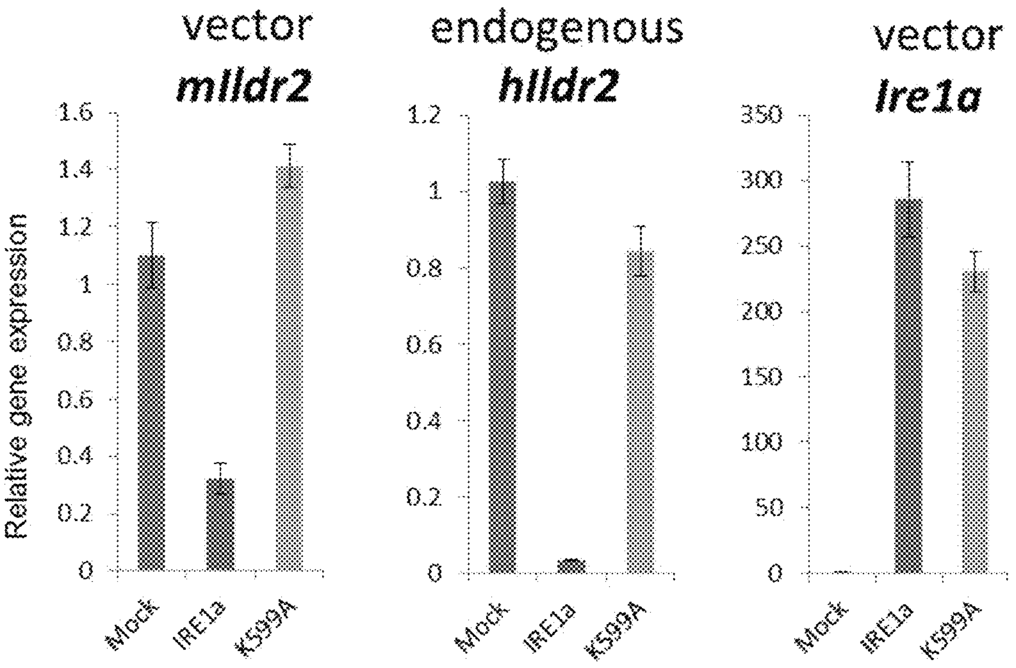
FIG. 53 shows real time PCR of ILDR2. Flag-tagged-ILDR2 were co-transfected with either V5-tagged IRE1a-WT or IRE1a-K599A expression vector into HEK 293 cells. Mouse and human ILDR2 transcript levels were markedly reduced (real time PCR) by co-transfection with IRE1a (by not the dominant-negative IRE1a isoform).
Figure 54:
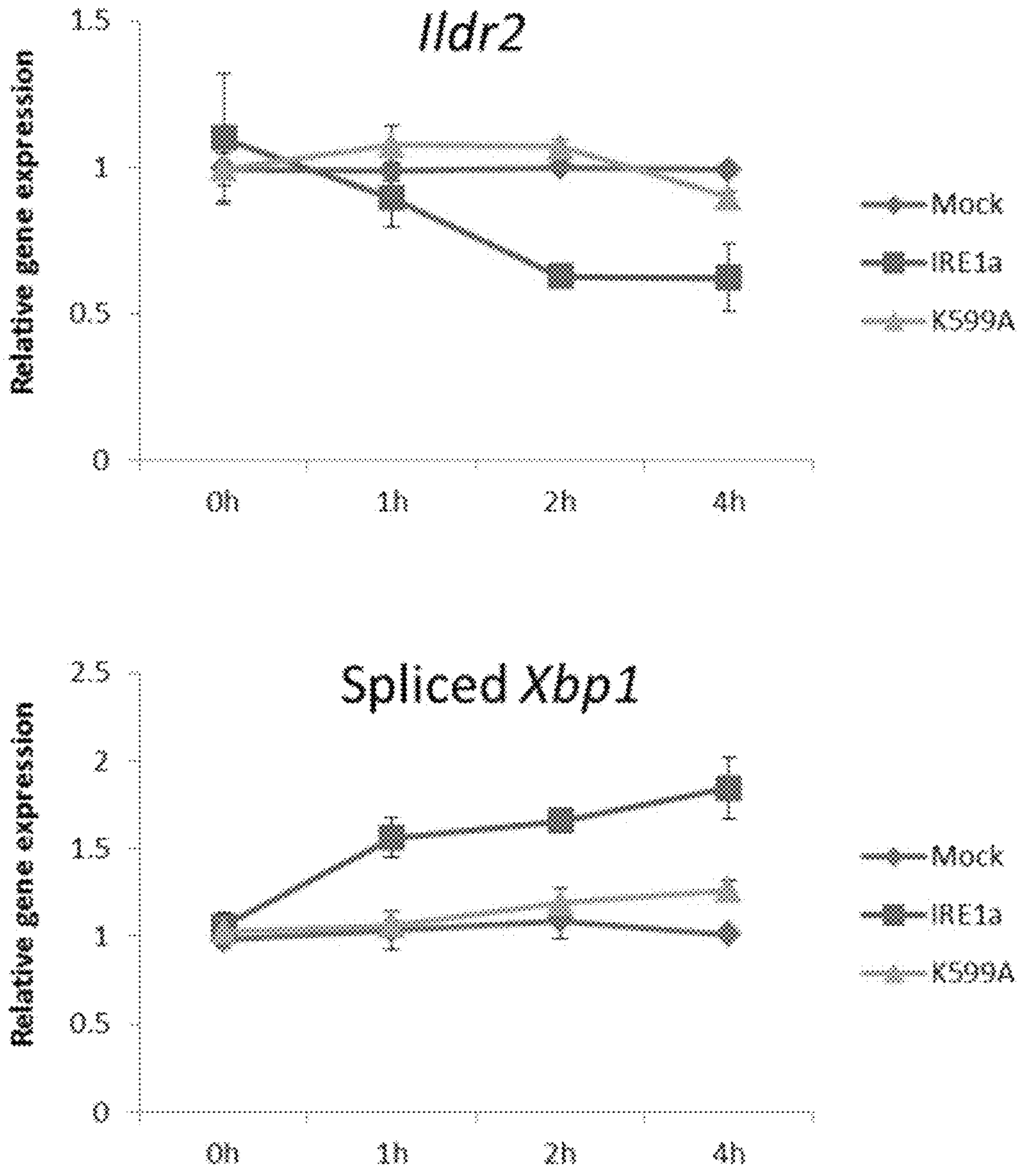
FIG. 54 shows real time PCR of endogenous ILDR2. Hepa1c1c7 cells were transfected with either IRE1a-WT or IRE1a-K599A expression vector. After overnight incubation, cells were cultured in the presence of actinomycin D (1 μg/ml) for different lengths of time. Actinomycin D blocks mRNA transcription.

When ILDR2 and IRE1 (an ER stress mediator) were co-transfected, ILDR2 protein levels were decreased (FIG. 52). To assess whether ILDR2 protein levels are decreased by IRE1a, 293 cells were co-transfected with ILDR2 vector and an IRE1a dominant-negative isoform. ILDR2 protein levels were decreased by IRE1a but not the K599A dominant negative. It ispossible that IRE1a degrades Ildr2 mRNA because IRE1a also splices Xbp1 mRNA. To assess whether IRE1a degrades Ildr2 mRNA, mRNA levels of Ildr2 were measured by real-time PCR (FIG. 53). Ildr2 mRNA levels were markedly decreased by IRE1a but not IRE1a K599A, suggesting that IRE1a degrades Ildr2 mRNA. To assess whether endogenous Ildr2 mRNA is degraded by IRE1a, Hepa1c1c cells were transfected with either IRE1a or K599A. Endogenous Ildr2 mRNA was also degraded by IRE1a in time dependent manner (FIG. 54).

ILDR2 Protein Levels were Decreased by Co-Transfection with IRE1a

Figure 55:
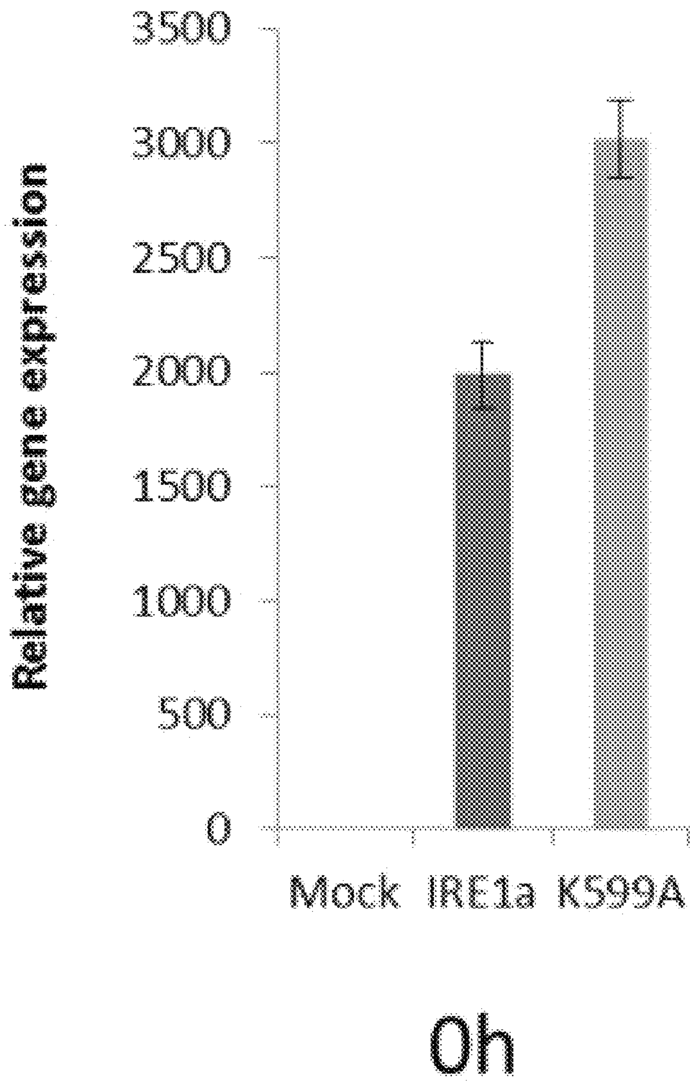

IRE1a, which controls the splicing of Xbp1 mRNA, may affect with degradation of ILDR2. To assess whether IRE1a affects ILDR2 splicing and/or degradation, an Ildr2 mRNA degradation assay was performed. Both IRE1a-WT and IRE1a-K599A were expressed in 0 h. To assess Ildr2 mRNA degradation, Actinomycin D was added in Hepa1c1c7 cells. Xbp1 was spliced by IRE1a in time dependent and spliced Xbp1 increased. Ildr2 mRNA transcription was decreased by IRE1a but not dominant negative K599A (FIG. 55).

Figure 56:
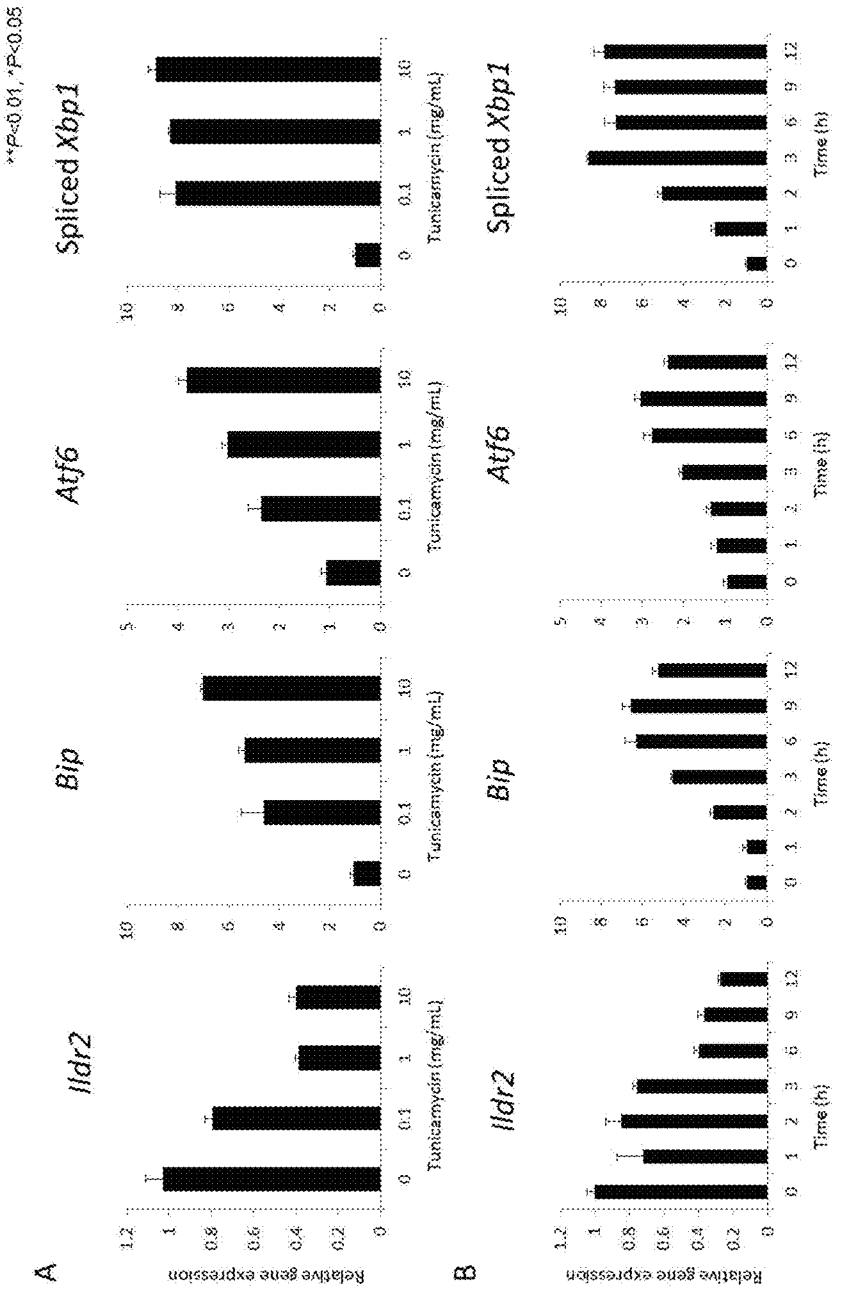
FIGS. 56A-B shows ILDR2 and ER stress protein expression levels in response to ER stress induced using tunicamycin.

To assess whether ILDR2 expression levels were affected by tunicamycin which induces ER stress, Hepa1c1c cells were treated with tunicamycin. ILDR2 expression levels were decreased by ER stress. ER stress response proteins were increased (FIGS. 56A-B).

Effects of ATF6 and XBP1 on ILDR22 Expression

Figure 57:
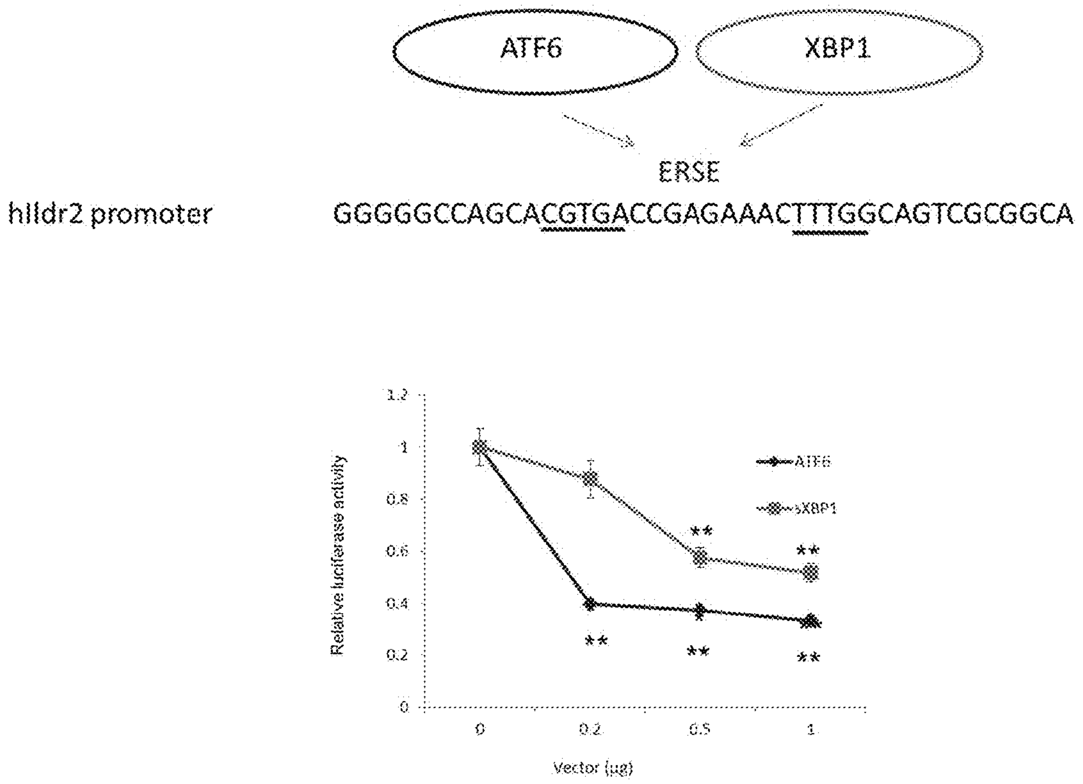
FIG. 57 shows the human ILDR2 promoter and luciferase assay. The human ILDR2 promoter (SEQ ID NO: 152) has an ERSE response element. Hepa1c1c7 cells were co-transfected with pGL4 human Ildr2 promoter vector and either the active form of ATF6 or spliced XBP1 expression vectors.

The ILDR2 promoter has an ER stress response element (ERSE)-like, suggesting that ATF6 and XBP1 may bind Ildr2 promoter and regulate transcription levels. To assess if ATF6 and XBP1 suppressed Ildr2 transcript, a luciferase assay was performed. Hepa1c1c cells were co-tranfected with the ILDR2 promoter and either ATF6 or XBP1. Both ATF6 and spliced XBP1 (sXBP1) decreased ILDR2 transcription activity in a dose dependent manner (FIG. 57)

Figure 58:
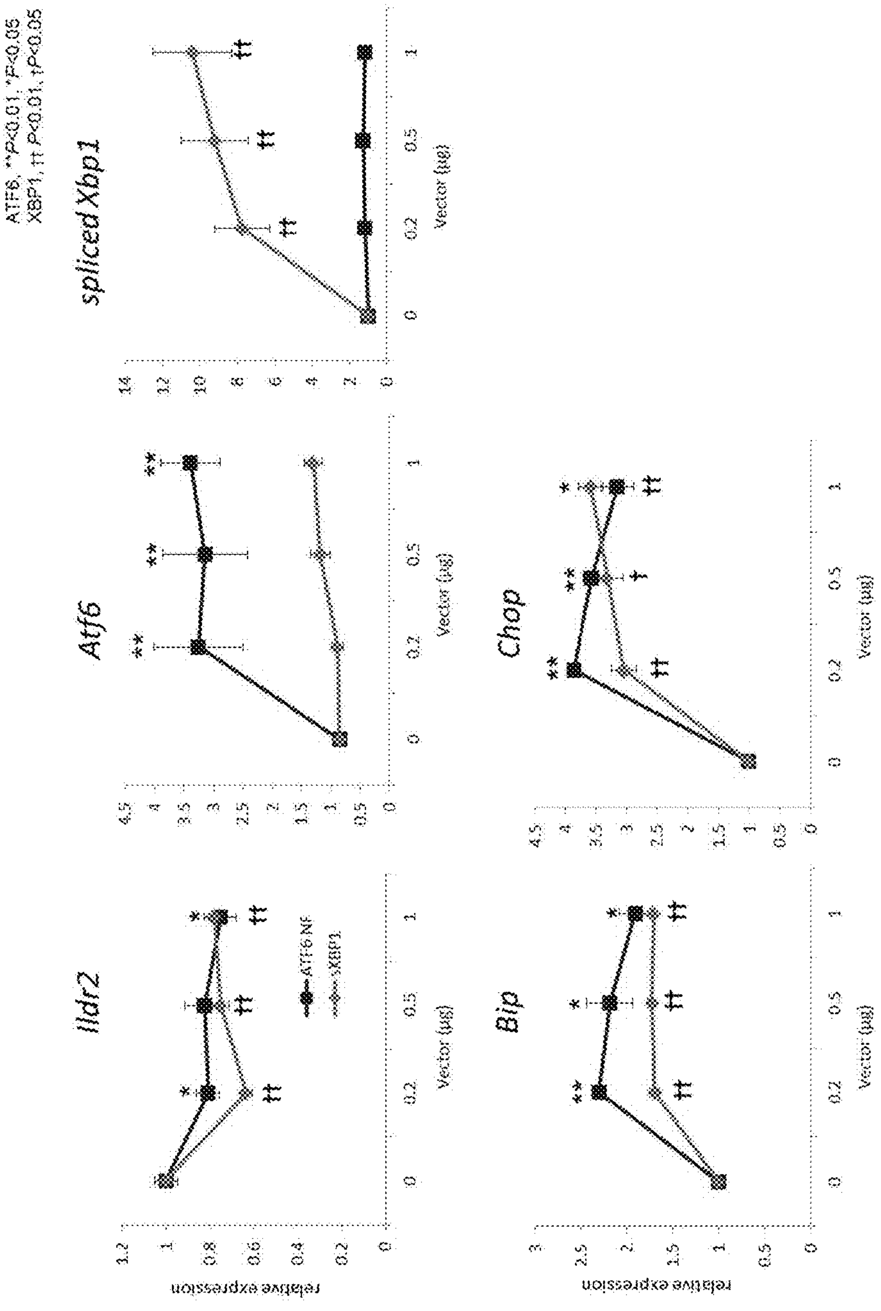
FIG. 58 shows Hepa1c1c7 cells transfected with either the active form ATF6 or spliced Xbp1 vectors of various concentrations, then harvested at 48 hrs.

To assess if ATF6 and XBP1 suppressed endogenous ILDR2 transcript levels, Hepa1c1c7 cells were transfected with either ATF6 or spliced XBP1 (sXBP1) expression vectors, When transfected with either ATF6 or sXBP1, ILDR2 mRNA levels decreased, demonstrating that ATF6 and XBP1 regulate Ildr2 transcript levels (FIG. 58).

Figure 59:
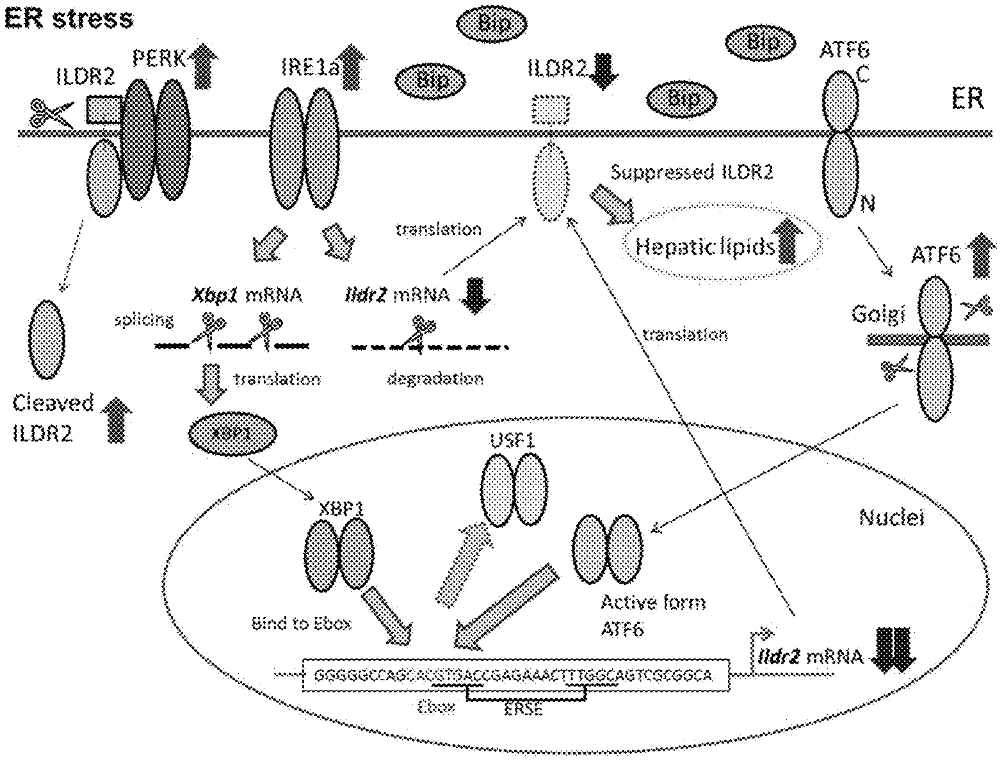
FIG. 59 shows a summary of the ER stress responses related to ILDR2 (SEQ ID NO: 152). ILDR2 binds PERK which cleaves ILDR2 (1). Transcription factors, ATF6 and XBP1 are increased by ER stress and downregulate ILDR2 transcripts by binding to its promoter region (2). IRE1a activated by ER stress degrades Ildr2 mRNA (3).

The results described herein demonstrate that ILDR2 is suppressed by ER stress (FIG. 59). Firstly, ILDR2 binds PERK which cleaves ILDR2 to an inactive form. Secondly, transcription factors, ATF6 and XBP1 are increased by ER stress and downregulate ILDR22 transcripts by binding to its promoter region. In addition, IRE1a activated by ER stress degrades Ildr2 mRNA. Suppression of ILDR2 could be reduced by ER stress inhibitors, including, but not limited to TUDCA and 4PBA. Increasing levels of cellular ILDR2 could mitigate the effects of ER stress by offsetting the decreases imposed by ER The in vivo effects of tunicamycin on liver ILDR2 (lowering), and the protective effect of overexpressing ILDR2 in liver exposed to tunicamycin were investigated. Tunicamycin (ER stress-inducer) administration (72 hrs) decreased hepatic Ildr2 expression by 45% and was associated with hepatic steatosis (tripling of TG, 50% increase in cholesterol) (FIGS. 60A-D). Conversely, over expression of Ildr2 in the livers of animals exposed to tunicamycin mitigated the steatotic effects (FIGS. 61A-D).

What is claimed is:

1. A method of treating hepatic steatosis in a subject, the method comprising administering to the subject a therapeutically effective amount of an adenoviral expression vector comprising a nucleic acid encoding full-length ILDR2, and wherein the subject has metabolic syndrome, type II diabetes, insulin resistance, or is obese, or any combination thereof.

2. A method of decreasing hepatic triglyceride level or hepatic total cholesterol level in a subject, the method comprising administering to the subject a therapeutically effective amount of an adenoviral expression vector comprising a nucleic acid encoding full-length ILDR2.

3. The method of claim 2, wherein the hepatic triglyceride level or hepatic total cholesterol level is decreased relative to a hepatic triglyceride level or hepatic total cholesterol level in the subject before administrating the therapeutically effective amount of an adenoviral expression vector comprising a nucleic acid encoding full-length ILDR2.

4. The method of claim 1 or 2, wherein the expression of Ildr2 mRNA or ILDR2 protein is increased in liver tissue.

5. The method of claim 1 or 2, wherein the expression of Ildr2 mRNA or ILDR2 protein is increased in hepatocytes.

6. The method of claim 1 or 2, wherein the subject is administered an additional therapy.

7. The method of claim 6, wherein the additional therapy is a lipid lowering therapy.

8. The method of claim 7, wherein the lipid lowering therapy is a therapeutic lifestyle change, a HMG-CoA reductase inhibitor, niacin, a fibrate, a cholesterol absorption inhibitor, a MTP inhibitor, or any combination thereof.

9. The method of claim 1 or 2, wherein expression of ILDR2 protein in the subject is measured using an antibody.

10. The method of claim 9, wherein the antibody specifically binds to a peptide selected from the group consisting of SEQ ID NOs: 2-9, an ILDR2 protein, or an ILDR2 isoform.

11. The method of claim 1, wherein the subject has a reduced level of expression of Ildr2 mRNA or ILDR2 protein compared to the level of expression of Ildr2 mRNA or ILDR2 protein in a subject without hepatic steatosis.

12. The method of claim 9, wherein the level of expression is determined before administrating to the subject the therapeutically effective amount of an adenoviral expression vector comprising a nucleic acid encoding full-length ILDR2.

13. The method of claim 11, wherein the expression of ILDR2 protein in the subject is measured using an antibody.

14. The method of claim 13, wherein the antibody specifically binds to a peptide selected from the group consisting of SEQ ID NOs: 2-9, an ILDR2 protein, or an ILDR2 isoform.

15. A method of decreasing liver fat deposits in a subject, the method comprising administering to the subject a therapeutically effective amount of an adenoviral expression vector comprising a nucleic acid encoding full-length ILDR2.

* * * * *